US008674137B2

(12) United States Patent
Scott et al.

(10) Patent No.: US 8,674,137 B2
(45) Date of Patent: Mar. 18, 2014

(54) COMPOUNDS FOR TREATING OPHTHALMIC DISEASES AND DISORDERS

(75) Inventors: Ian L. Scott, Monroe, WA (US); Vladimir Aleksandrovich Kuksa, Kenmore, WA (US); Feng Hong, Bellevue, WA (US); Ryo Kubota, Seattle, WA (US); Jennifer Gage, Kenmore, WA (US)

(73) Assignee: Acucela Inc., Bothell, WA (US)

( * ) Notice: Subject to any disclaimer, the term of this patent is extended or adjusted under 35 U.S.C. 154(b) by 0 days.

(21) Appl. No.: 12/603,025

(22) Filed: Oct. 21, 2009

(65) Prior Publication Data

US 2010/0113539 A1 May 6, 2010

Related U.S. Application Data

(60) Provisional application No. 61/197,083, filed on Oct. 22, 2008, provisional application No. 61/197,082, filed on Oct. 22, 2008, provisional application No. 61/197,081, filed on Oct. 22, 2008, provisional application No. 61/197,091, filed on Oct. 22, 2008.

(51) Int. Cl.
*C07C 215/00* (2006.01)

(52) U.S. Cl.
USPC .......................................................... 564/355

(58) Field of Classification Search
None
See application file for complete search history.

(56) References Cited

U.S. PATENT DOCUMENTS

| | | | |
|---|---|---|---|
| 2,592,364 A | 4/1952 | Weissberger et al. | |
| 3,869,442 A | 3/1975 | Weaver et al. | |
| 4,214,001 A | 7/1980 | Engelhardt et al. | |
| 4,252,951 A * | 2/1981 | Jackson et al. | 540/220 |
| 5,049,587 A | 9/1991 | Okamoto et al. | |
| 2002/0058685 A1 | 5/2002 | Hamilton | |
| 2003/0032078 A1 | 2/2003 | Travis | |
| 2003/0066140 A1 | 4/2003 | Bartolone et al. | |
| 2003/0100580 A1 | 5/2003 | Dhanak et al. | |
| 2003/0186981 A1 | 10/2003 | Hamilton et al. | |
| 2006/0069078 A1 | 3/2006 | Rando | |
| 2006/0069098 A1 | 3/2006 | Miyoshi | |
| 2006/0252107 A1 | 11/2006 | Kubota et al. | |
| 2006/0281821 A1 | 12/2006 | Palczewski et al. | |
| 2007/0037796 A1 * | 2/2007 | Barda et al. | 514/218 |

FOREIGN PATENT DOCUMENTS

| | | |
|---|---|---|
| GB | 1108577 | 4/1968 |
| NL | 6507196 A | 12/1965 |
| WO | WO-93-12075 A1 | 6/1993 |
| WO | WO-01-45694 A1 | 6/2001 |
| WO | WO-02-089785 A1 | 11/2002 |
| WO | WO-03-059872 A1 | 7/2003 |
| WO | WO 2005/054202 * | 6/2005 |
| WO | WO-2005-065050 A2 | 7/2005 |
| WO | WO-2006-004795 A2 | 1/2006 |
| WO | WO-2006-120456 A1 | 11/2006 |
| WO | WO-2010-048332 | 4/2010 |

OTHER PUBLICATIONS

Vippagunta et. al., Advanced Drug Del. Rev., 48, pp. 3-26, (2001).*
(Braga et al., "Making crystals from crystals: a green route to crystal engineering and polymorphism" ChemComm 2005, 36353645).*
Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
GB0918546.3 Search Report dated Feb. 25, 2010.
CAPLUS Abstract Accession No. 2006:732343 and Journal of Medicinal Chemistry vol. 49(17):5217-5225 (2006).
CHEMCATS Abstract Accession No. 2096297761.
CHEMCATS Abstract Accession No. 2096597704.
CHEMCATS Abstract Accession No. 2096597225.
CHEMCATS Abstract Accession No. 2096242641.
Sikazwe et al., "Binding of Sulfonyl-Containing Arylalkylamines at Human 5-HT6 Serotonin Receptors," J. Med. Chem. 49(17):5217-5225 (2006).
Washburn et al., "Arylpropanolamines: Selective beta 3 agonists arising from strategies to mitigate phase I metabolic transformations," Bioorg. Med. Chem. Ltrs. 17(15):4290-4296 (2007).
Golczak et al., "Positively charged retinoids are potent and selective inhibitors of the trans-cis isomerization in the retinoid (visual) cycle," PNAS 102(23):8162-8167 (2005).
Maeda et al., "Evaluation of the role of the retinol G protein-coupled receptor (RGR) in the vertebrate retina in vivo," J. Neurochem. 85(4):944-956 (2003).
Mata et al., "Isomerization and Oxidation of Vitamin A in Cone-Dominant Retinas: A Novel Pathway for Visual-Pigment Regeneration in Daylight;" Neuron 36:69-80 (2002).
PCT/US09/061545 Search Report and Written Opinion dated May 31, 2010.
EP09822658.2 Examination Report issued Apr. 23, 2013.
Acheson, et al. "Acidic henzothiadiazole 2,2-dioxide of iH, 3H-2,1,3-benzothiadiazole 2,2-dioxide and from trifluoro-methanesulfonanilide. A new synthesis of iH, 3H-2,1,3-benzothiadiazole 2,2-dioxide." *Journal of Medicinal Chemistry*, Nov. 1981, 24(11):1300-1304, American Chemical Society, Washington D.C.
Altenbach, et al. "Synthesis and structure-activity studies on N-(5-(1H-imidazol-4-yl)-5,6,7,8-tetrahydro-1-naplithalenyl)methanesulfonamide, an imidazole-containing alpha1A-adrenoceptor agonist." *Journal of Medicinal Chemistry*, May 11, 2004, 47(12):3220-3235, American Chemical Society, Washington D.C.

(Continued)

*Primary Examiner* — Johann R Richter
*Assistant Examiner* — Jennifer C Sawyer
(74) *Attorney, Agent, or Firm* — Wilson, Sonsini, Goodrich & Rosati

(57) ABSTRACT

Provided are compounds, pharmaceutical compositions thereof, and methods of treating ophthalmic diseases and disorders, such as age-related macular degeneration and Stargardt's Disease, using said compounds and compositions.

23 Claims, 2 Drawing Sheets

(56) References Cited

OTHER PUBLICATIONS

Banerji, K.K. "Mechanistic Study of the Oxidation of Substituted Benzylainines by N-bromoacetamide." *Bulletin of the Chemical Society of Japan*, 1988, 61(10):3717-3722, Japan Publications Trading, Tokyo, JP.

Bernstein, et al. "Mechanism of Action of Aromatic Amines that Short-circuit the Visual Cycle." *Biochemistry*, Jun. 1986, 25(11):3370-3377, American Chemical Society, Washington D.C.

Goodyer, et al. "Synthesis of N-benzyl- and N-phyny1-2-amino-4,5-dihydrothiazoles and thioureas and evaluation as modulators of the isoforms of nitric oxide synthase." *Bioorganic & Medicinal Chemistry*, Aug. 2, 2003, 11(19):4189-4206, Elsevier Science Publishers, Oxford, GB.

Hu, et al. "2,4-thiazolidinediones as potent and selective human β3 agonists." *Bioorganic & Medicinal Chemistry Letters*, Mar. 2001, 11(6):757-760, Elsevier Science Publishers, Oxford, GB.

Mannich and Dannehl. *Archiv der Pharmazie*, 1938, 276(4):206-211 (with English translation pp. 206-208).

Memetzides et al. "Synthesis of Aromatic Chloroberbines." *Heterocycles*, Feb. 1990, 31(3):341-351, Elsevier Science Publishers, Amsterdam, NL.

Mewshaw et al. "-New generation dopaminergic agents. 2.Discovery 3-OH-phenoxyethylamine and 3-OH-N<1>phenylpiperazine dopaminergic templates," *Bioorganic & Medicinal Chemistry Letters*, Feb. 3, 1998, 8(3):295-300, Elsevier Science Publishers, Oxford, GB.

Schoepfer et al. "Structure-based Design of Peptidomimetic ligands of the Grb2-SH2 domain," *Bioorganic & Medicinal Chemistry Letters*, Oct. 20, 1998, 8(20:2865-2870, Elsevier Science Publishers, Oxtbrd, GB.

Weber et al. "Diarylsulfonamides as selective, non-peptidic thrombin inhibitors," *Bioorganic & Medicinal Chemistry Letters*, Jul. 7 1998, 8(130):1613-1618, Elsevier Science Publishers, Oxford, GB.

EP09822658.2 Extended European Search Report mailed Mar. 5, 2012.

AU2009308483 Exam Report mailed Sep. 12, 2011.

\* cited by examiner

COMPOUNDS FOR TREATING OPHTHALMIC DISEASES AND DISORDERS

CROSS-REFERENCE

This application claims the benefit of U.S. Provisional Application No. 61/197,083, filed Oct. 22, 2008; U.S. Provisional Application No. 61/197,082, filed Oct. 22, 2008; U.S. Provisional Application No. 61/197,081, filed Oct. 22, 2008; and U.S. Provisional Application No. 61/197,091, filed Oct. 22, 2008, each of which is incorporated herein by reference in its entirety.

BACKGROUND OF THE INVENTION

Neurodegenerative diseases, such as glaucoma, macular degeneration, and Alzheimer's disease, affect millions of patients throughout the world. Because the loss of quality of life associated with these diseases is considerable, drug research and development in this area is of great importance.

Macular degeneration affects between ten and fifteen million patients in the United States, and it is the leading cause of blindness in aging populations worldwide. Age-related macular degeneration (AMD) affects central vision and causes the loss of photoreceptor cells in the central part of retina called the macula. Macular degeneration can be classified into two types: dry-type and wet-type. The dry-form is more common than the wet; about 90% of age-related macular degeneration patients are diagnosed with the dry-form. The wet-form of the disease and geographic atrophy, which is the end-stage phenotype of dry AMD, causes the most serious vision loss. All patients who develop wet-form AMD are believed to previously have developed dry-form AMD for a prolonged period of time. The exact causes of age-related macular degeneration are still unknown. The dry-form of AMD may result from the senescence and thinning of macular tissues associated with the deposition of pigment in the macular retinal pigment epithelium. In wet AMD, new blood vessels grow beneath the retina, form scar tissue, bleed, and leak fluid. The overlying retina can be severely damaged, creating "blind" areas in the central vision.

For the vast majority of patients who have the dry-form of macular degeneration, no effective treatment is yet available. Because the dry-form precedes development of the wet-form of macular degeneration, therapeutic intervention to prevent or delay disease progression in the dry-form AMD would benefit patients with dry-form AMD and might reduce the incidence of the wet-form.

Decline of vision noticed by the patient or characteristic features detected by an ophthalmologist during a routine eye exam may be the first indicator of age-related macular degeneration. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, factors in the disease are heredity, nutritional, traumatic, infection, or other ecologic factors.

Glaucoma is a broad term used to describe a group of diseases that causes a slowly progressive visual field loss, usually asymptotically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Current glaucoma drugs only treat intraocular pressure and are ineffective in preventing or reversing the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities Alzheimer's is a disease that affects four million people in the United States alone. It is characterized by a loss of nerve cells in areas of the brain that are vital to memory and other mental functions. Currently available drugs can ameliorate AD symptoms for a relatively period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., *J. Biol. Chem.* 277: 19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), is a very rare genetic condition affecting children shortly after birth.

SUMMARY OF THE INVENTION

A need exists in the art for an effective treatment for treating ophthalmic diseases or disorders resulting in ophthalmic disfunction including those described above. In particular, there exists a pressing need for compositions and methods for treating Stargardt's disease and age-related macular degeneration (AMD) without causing further unwanted side effects such as progressive retinal degeneration, LCA-like conditions, night blindness, or systemic vitamin A deficiency. A need also exists in the art for effective treatments for other ophthalmic diseases and disorders that adversely affect the retina.

In one embodiment is a compound of Formula (I) or tautomer, stereoisomer, geometric isomer or a pharmaceutically acceptable solvate, hydrate, salt, N-oxide or prodrug thereof:

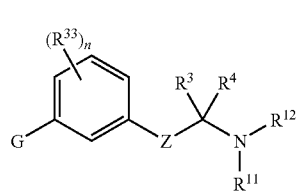

Formula (I)

wherein,

Z is a bond, $-C(R^1)(R^2)-$, $-C(R^9)(R^{10})-C(R^1)(R^2)-$, $-X-C(R^{31})(R^{32})-$, $-C(R^9)(R^{10})-C(R^1)(R^2)-C(R^{36})(R^{37})-$, $-C(R^{38})(R^{39})-X-C(R^{31})(R^{32})-$, or $-X-C(R^{31})(R^{32})-C(R^1)(R^2)-$;

X is $-O-$, $-S-$, $-S(=O)-$, $-S(=O)_2-$, $-N(R^{30})-$, $-C(=O)-$, $-C(=CH_2)-$, $-C(=N-NR^{35})-$, or $-C(=N-OR^{35})-$;

G is selected from $-N(R^{42})-SO_2-R^{40}$, $-N(R^{42})C(=O)-R^{40}$, $-N(R^{42})C(=O)-OR^{40}$, $-N(R^{42})-C(R^{42})(R^{42})-R^{40}$, $-N(R^{42})-C(=O)-N(R^{43})(R^{43})$, or $-N(R^{42})-C(=S)-N(R^{43})(R^{43})$;

$R^{40}$ is selected from $-C(R^{16})(R^{17})(R^{18})$, aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, $-OR^6$ or $-NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, $-OR^6$ or $-NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, $-C(=O)R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, $-C(=O)R^{23}$, $-C(NH)NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, SO$_2$$R^{22}$, CO$_2$$R^{22}$ or SO$_2$NR$^{26}$R$^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$, and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, OR$^{34}$, alkyl, or fluoroalkyl; and n is 0, 1, 2, 3, or 4.

In another embodiment is the compound of Formula (I) wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—($R^1$)($R^2$)—C($R^{36}$)($R^{37}$)— or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—;

$R^1$ and $R^2$ are each independently selected from hydrogen, halogen, C$_1$-C$_5$ alkyl, fluoroalkyl, —OR$^6$ or —NR$^7$R$^8$; or $R^1$ and $R^2$ together form an oxo;

$R^{31}$ and $R^{32}$ are each independently selected from hydrogen, C$_1$-C$_5$ alkyl, or fluoroalkyl;

$R^{36}$ and $R^{37}$ are each independently selected from hydrogen, halogen, C$_1$-C$_5$ alkyl, fluoroalkyl, —OR$^6$ or —NR$^7$R$^8$; or $R^{36}$ and $R^{37}$ together form an oxo;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —OR$^{19}$, —NR$^{20}$R$^{21}$ or carbocyclyl; or $R^9$ and $R^{10}$ form an oxo;

$R^{11}$ and $R^{12}$ are each independently selected from hydrogen, alkyl, carbocyclyl, —C(=O)R$^{23}$, SO$_2$R$^{23}$, CO$_2$R$^{23}$ or SO$_2$NR$^{28}$R$^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

each $R^{33}$ is independently selected from halogen, OR$^{34}$, alkyl, or fluoroalkyl; and n is 0, 1, 2, 3, or 4.

In another embodiment is the compound of Formula (I) having the structure of Formula (Ia)

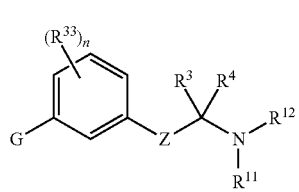

Formula (Ia)

wherein,

Z is —C($R^9$)($R^{10}$)—C($R^1$)($R^2$)— or —O—C($R^{31}$)($R^{32}$)—;

$R^1$ and $R^2$ are each independently selected from hydrogen, halogen, C$_1$-C$_5$ alkyl, fluoroalkyl, —OR$^6$ or —NR$^7$R$^8$; or $R^1$ and $R^2$ together form an oxo;

$R^{31}$ and $R^{32}$ are each independently selected from hydrogen, C$_1$-C$_5$ alkyl, or fluoroalkyl;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)R$^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —OR$^{19}$, —NR$^{20}$R$^{21}$ or carbocyclyl; or $R^9$ and $R^{10}$ together form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl or —C(=O)R$^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, OR$^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)R$^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (Ia) wherein,

Z is —C($R^9$)($R^{10}$)—C($R^1$)($R^2$)— or —O—C($R^{31}$)($R^{32}$)—;

$R^1$ and $R^2$ are each independently selected from hydrogen, halogen, C$_1$-C$_5$ alkyl, fluoroalkyl, —OR$^6$ or —NR$^7$R$^8$; or $R^1$ and $R^2$ together form an oxo;

$R^{31}$ and $R^{32}$ are each independently selected from hydrogen, C$_1$-C$_5$ alkyl, or fluoroalkyl;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)R$^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —OR$^{19}$, —NR$^{20}$R$^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (Ia) wherein, G is selected from —N($R^{42}$)—$SO_2$—$R^{40}$; $R^{40}$ is selected from —C($R^{16}$)($R^{17}$)($R^{18}$), aryl, or heteroaryl.

In another embodiment is the compound of Formula (Ia) having the structure of Formula (Ib):

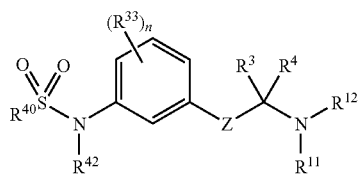

Formula (Ib)

wherein,

Z is —C($R^9$)($R^{10}$)—C($R^1$)($R^2$)— or —O—C($R^{31}$)($R^{32}$)—;

$R^{40}$ is selected from —C($R^{16}$)($R^{17}$)($R^{18}$);

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl; and each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (Ib) wherein, $R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo.

In another embodiment is the compound of Formula (Ib) having the structure of Formula (Ic):

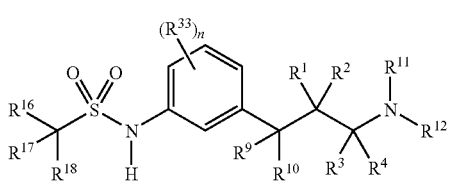

Formula (Ic)

wherein, $R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocycle;

each $R^{33}$ is independently selected from halogen, $OR^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In another embodiment is the compound of Formula (Ic) wherein n is 0 and each of $R^{11}$ and $R^{12}$ is hydrogen. In a further embodiment is the compound wherein each of $R^3$, $R^4$, $R^{14}$ and $R^{15}$ is hydrogen. In a further embodiment is the compound wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl or heterocycle; and $R^{18}$ is selected from a hydrogen, alkoxy or hydroxy.

In a further embodiment is the compound wherein $R^{16}$ and $R^{17}$, together with the carbon to which they are attached, form a cyclopropyl, cyclobutyl, cyclopentyl, cyclohexyl, cycloheptyl, or cyclooctyl, and $R^{18}$ is hydrogen or hydroxy.

In another embodiment is the compound of Formula (Ic), wherein $R^{11}$ is hydrogen and $R^{12}$ is —$C(=O)R^{23}$, wherein $R^{23}$ is alkyl. In further embodiment is the compound wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently selected from hydrogen or alkyl;

$R^{16}$ and $R^{17}$, together with the carbon atom to which they are attached, form a carbocyclyl; and $R^{18}$ is hydrogen, hydroxy or alkoxy.

In a further embodiment is the compound wherein
n is 0;

$R^{16}$ and $R^{17}$, together with the carbon atom to which they are attached, form a cyclopentyl, cyclohexyl or cyclohexyl; and $R^{18}$ is hydrogen or hydroxy.

In a further embodiment is the compound of Formula (Ic), wherein $R^1$ and $R^2$ are each independently selected from hydrogen, halogen, $C_1$-$C_5$ alkyl or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In another embodiment is the compound of Formula (Ib) having the structure of Formula (Id):

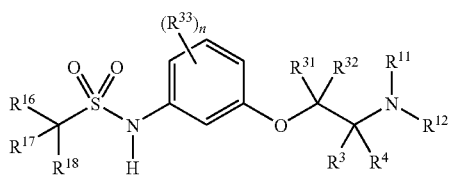

Formula (Id)

wherein, $R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —$C(=O)R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{18}$ is selected from a hydrogen, alkyl, alkoxy, hydroxy, halo or fluoroalkyl;

$R^{34}$ is hydrogen or alkyl; and each $R^{33}$ is independently selected from halogen, $OR^{34}$, alkyl, or fluoroalkyl; and n is 0, 1, 2, 3, or 4.

In another embodiment is the compound wherein n is 0 and each of $R^{11}$ and $R^{12}$ is hydrogen. In another embodiment is the compound wherein each $R^3$, $R^4$, $R^{14}$ and $R^{15}$ is hydrogen. In another embodiment is the compound wherein, $R^{31}$ and $R^{32}$ are each independently hydrogen, or $C_1$-$C_5$ alkyl; $R^{16}$ and $R^{17}$, together with the carbon atom to which they are attached, form a carbocyclyl; and $R^{18}$ is hydrogen, hydroxy, or alkoxy. In a further embodiment is the compound wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy. In a further embodiment is the compound wherein, $R^{31}$ and $R^{32}$ are each independently selected from hydrogen, or $C_1$-$C_5$ alkyl; and $R^{18}$ is hydrogen, hydroxy or alkoxy. In a further embodiment is the compound wherein, $R^{31}$ and $R^{32}$ are each independently hydrogen, or $C_1$-$C_5$ alkyl; $R^6$ and $R^{19}$ are each independently hydrogen or alkyl; $R^{16}$ and $R^{17}$ is independently selected from $C_1$-$C_{13}$ alkyl; and $R^{18}$ is hydrogen, hydroxy or alkoxy.

In another embodiment is the compound of Formula (I) wherein, Z is a bond, —X—$C(R^{31})(R^{32})$—, or —X—$C(R^{31})(R^{32})$—$C(R^1)(R^2)$—; and X is —S—, —$S(=O)$—, —$S(=O)_2$—, —$N(R^{30})$—, —$C(=O)$—, —$C(=CH_2)$—, —$C(=N—NR^{35})$—, or —$C(=N—OR^{35})$—. In a further embodiment is the compound wherein, G is selected from —$N(R^{42})$—$SO_2$—$R^{40}$; and $R^{40}$ is selected from —$C(R^{16})(R^{17})(R^{18})$, aryl, or heteroaryl.

In an additional embodiment is the compound of Formula (I) having the structure of Formula (Ie):

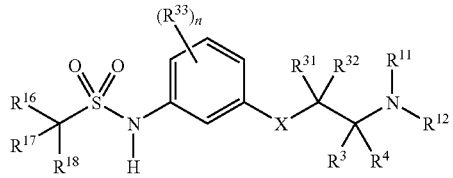

Formula (Ie)

wherein,

X is —S—, —$S(=O)$—, —$S(=O)_2$—, —$N(R^{30})$—, —$C(=O)$—, —$C(=CH_2)$—, —$C(=N—NR^{35})$—, or —$C(=N—OR^{35})$—;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —$C(=O)R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{30}$, $R^{34}$ and $R^{35}$ are each independently hydrogen or alkyl;

$R^{18}$ is selected from a hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In a further embodiment is the compound of Formula (Ie) wherein n is 0 and each $R^{11}$ and $R^{12}$ is hydrogen. In a further embodiment is the compound wherein each $R^3$, $R^4$, $R^{14}$ and $R^{15}$ is hydrogen. In a further embodiment is the compound wherein, $R^{31}$ and $R^{32}$ are each independently hydrogen, or $C_1$-$C_5$ alkyl; $R^{16}$ and $R^{17}$, together with the carbon atom to which they are attached, form a carbocyclyl or heterocycle; and $R^{18}$ is hydrogen, hydroxy, or alkoxy. In a further embodiment is the compound wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy. In a further embodiment is the compound wherein, $R^{31}$ and $R^{32}$ are each independently selected from hydrogen, or $C_1$-$C_5$ alkyl; $R^{16}$ and $R^{17}$ is independently selected from $C_1$-$C_{13}$ alkyl; and $R^{18}$ is hydrogen, hydroxy or alkoxy.

In an additional embodiment is the compound of Formula (Ia) wherein, G is selected from —N($R^{42}$)C(=O)—$R^{40}$, —N($R^{42}$)—C($R^{42}$)($R^{42}$)—$R^{40}$; $R^{40}$ is selected from —C($R^{16}$)($R^{17}$)($R^{18}$), aryl, or heteroaryl; each $R^{42}$ is independently selected from hydrogen or alkyl. In a further embodiment is the compound wherein, G is selected from —N($R^{42}$)C(=O)—$R^{40}$, —N($R^{42}$)—C($R^{42}$)($R^{42}$)—$R^{40}$; $R^{40}$ is selected from —C($R^{16}$)($R^{17}$)($R^{18}$); aryl, or heteroaryl; each $R^{42}$ is independently selected from hydrogen or alkyl. In a further embodiment is the compound wherein, $R^{42}$ is a hydrogen; $R^{40}$ is selected from —C($R^{16}$)($R^{17}$)($R^{18}$); $R^{16}$ and $R^{17}$, together with the carbon atom to which they are attached, form a carbocyclyl or heterocycle; and $R^{18}$ is hydrogen, hydroxy, or alkoxy. In a further embodiment is the compound wherein, $R^{42}$ is a hydrogen; $R^{40}$ is selected from —C($R^{16}$)($R^{17}$)($R^{18}$); $R^{16}$ and $R^{17}$, together with the carbon atom to which they are attached, form a carbocyclyl or heterocycle; and $R^{18}$ is hydrogen, hydroxy, or alkoxy.

In another embodiment is the compound of Formula (Ia) wherein,

G is selected from —N($R^{42}$)—C(=O)—N($R^{43}$)($R^{43}$), or —N($R^{42}$)—C(=S)—N($R^{43}$)($R^{43}$);

each $R^{43}$ is independently selected from hydrogen, alkyl, cycloalkyl, aralkyl, C-attached heterocyclyl, aryl, or heteroaryl; or two $R^{43}$ groups, together with the nitrogen to which they are attached, may form a heterocyclyl;

each $R^{42}$ is independently selected from hydrogen or alkyl.

In another embodiment is the compound Formula (Ia) wherein,

G is selected from —N($R^{42}$)—C(=O)—N($R^{43}$)($R^{43}$), or —N($R^{42}$)—C(=S)—N($R^{43}$)($R^{43}$);

each $R^{43}$ is independently selected from hydrogen, alkyl, cycloalkyl, aralkyl, C-attached heterocyclyl, aryl, or heteroaryl; or two $R^{43}$ groups, together with the nitrogen to which they are attached, may form a heterocyclyl; and $R^{42}$ is hydrogen.

In a further embodiment is the compound wherein, each $R^{43}$ is independently selected from hydrogen, alkyl, cycloalkyl, aralkyl, C-attached heterocyclyl, aryl, or heteroaryl; or two $R^{43}$ groups, together with the nitrogen to which they are attached, may form a heterocyclyl; and $R^{42}$ is hydrogen.

In a further embodiment is the compound wherein, $R^{40}$ is selected from —C($R^{16}$)($R^{17}$)($R^{18}$);

$R^{16}$ and $R^{17}$ are each independently selected from hydrogen, alkyl, halo, aryl, heteroaryl, aralkyl, heteroaryalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl.

In another embodiment is the compound of Formula (I) wherein one, more than one, or all of the non-exchangeable $^1H$ atoms have been substituted with $^2H$ atoms.

In a specific embodiment, the compound of Formula (I) is selected from the group consisting of:

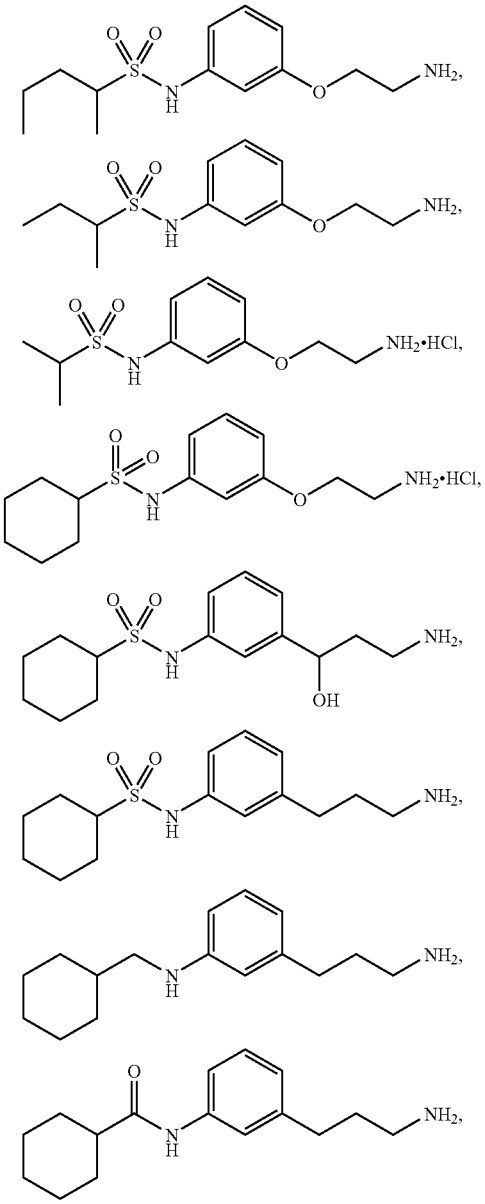

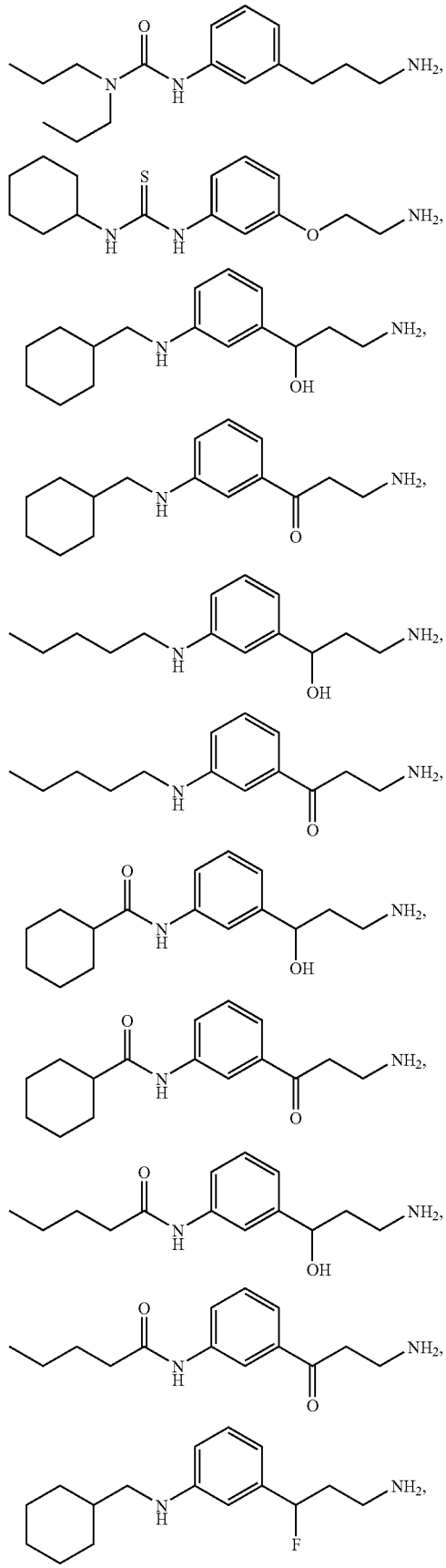
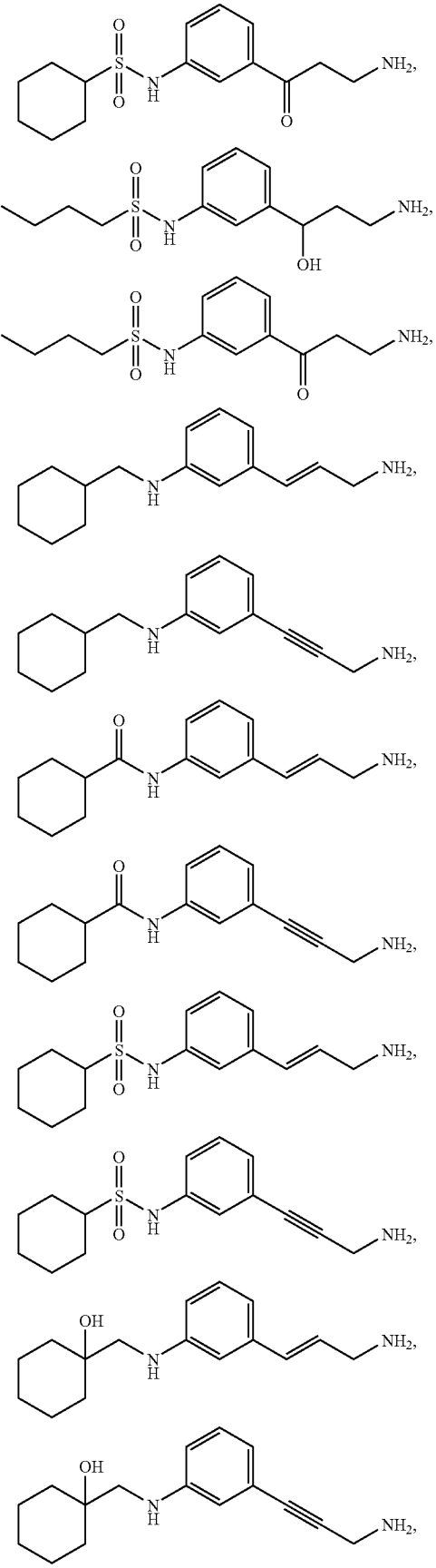

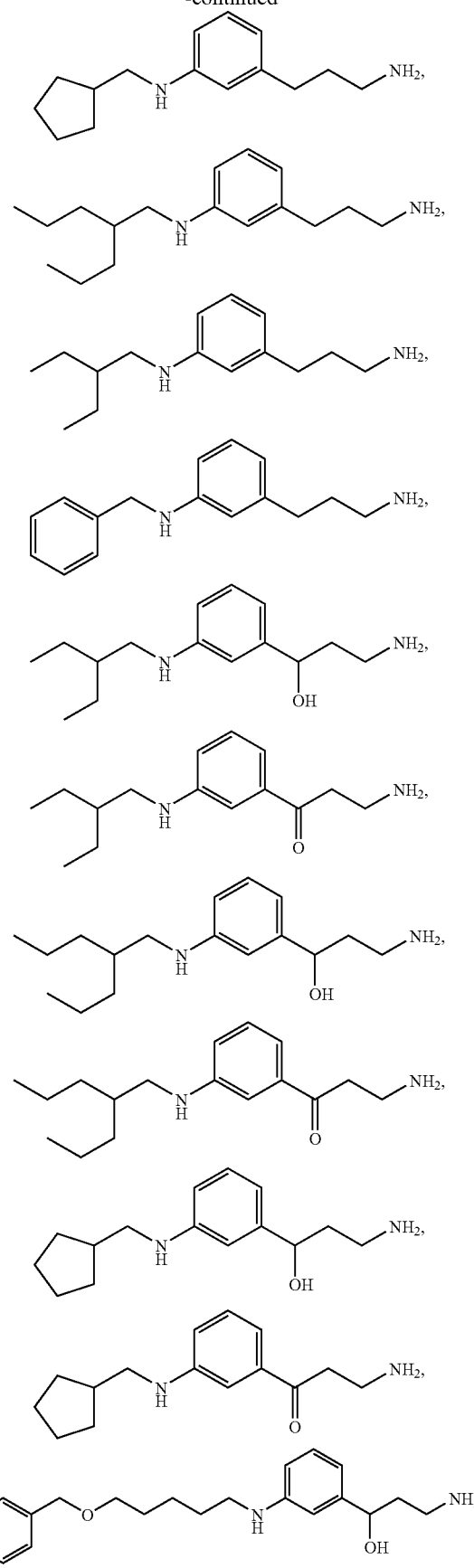
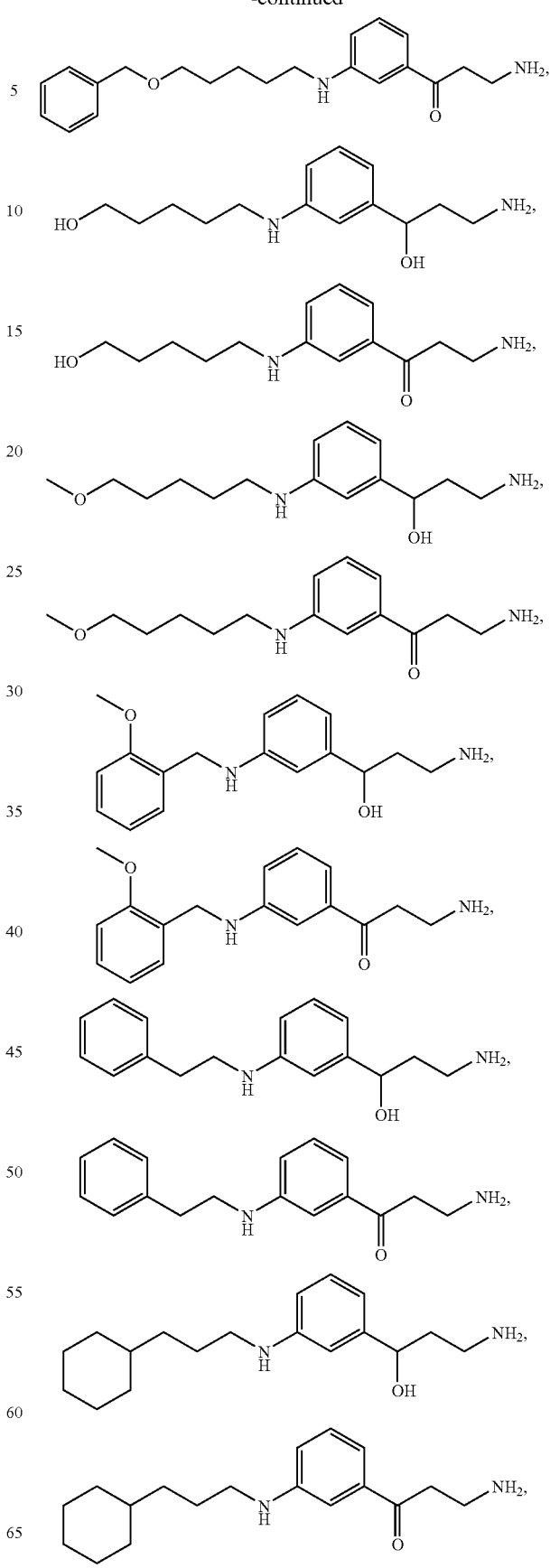

17
-continued
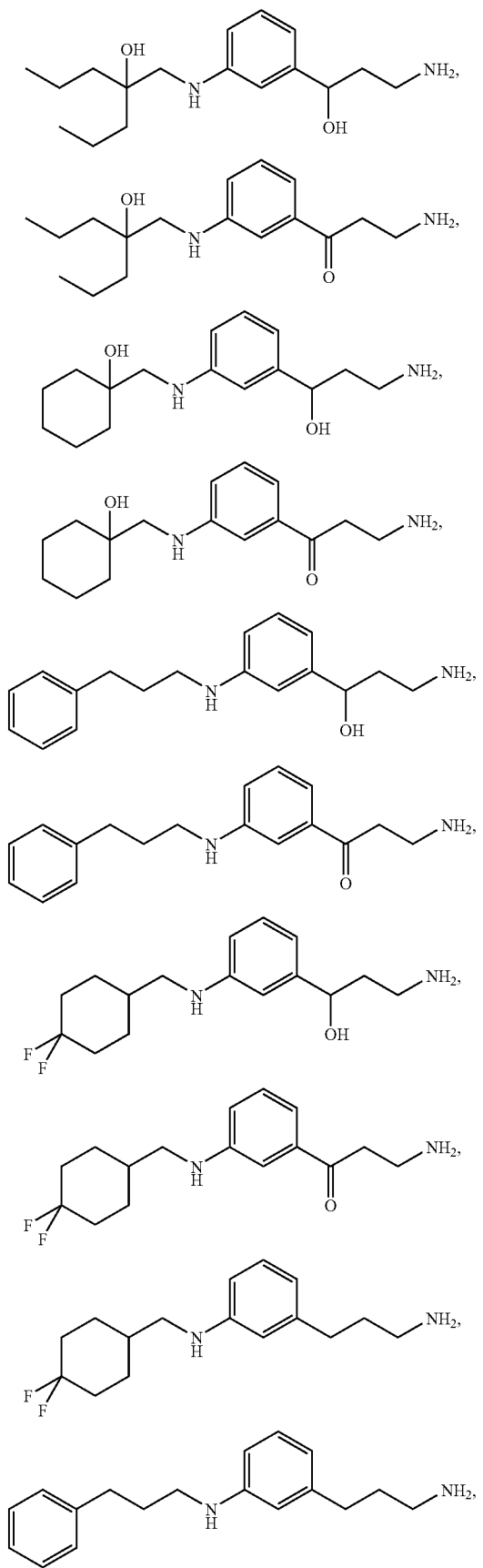
18
-continued
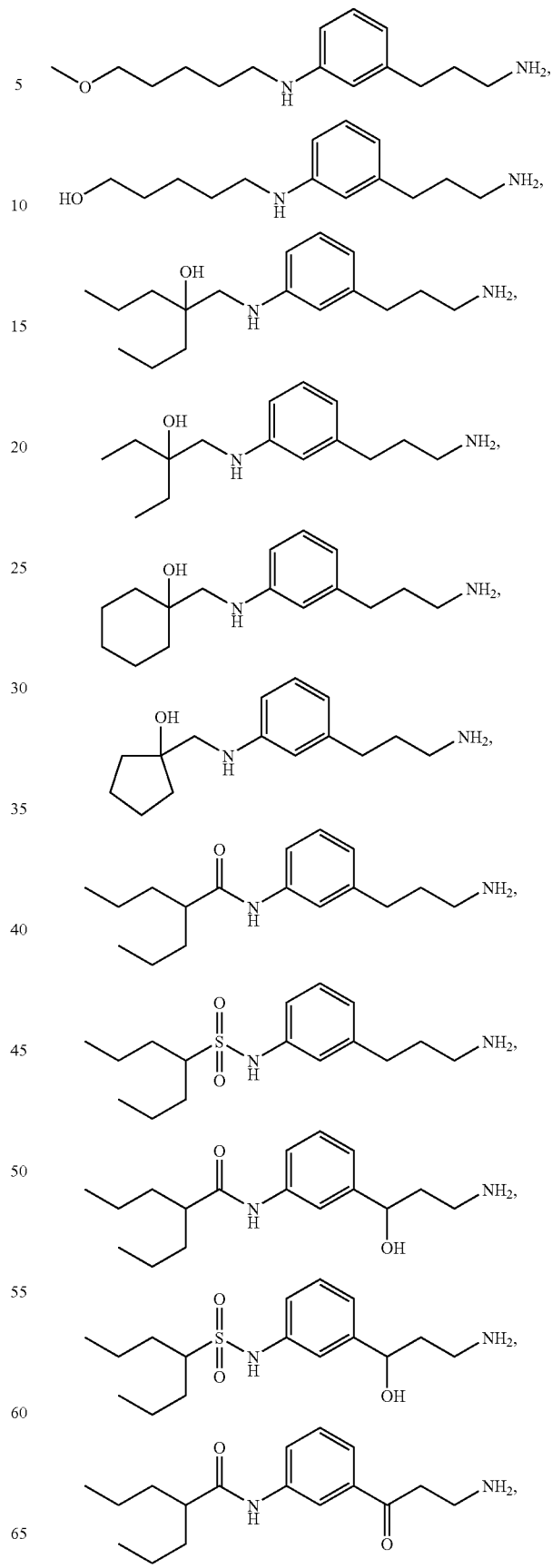

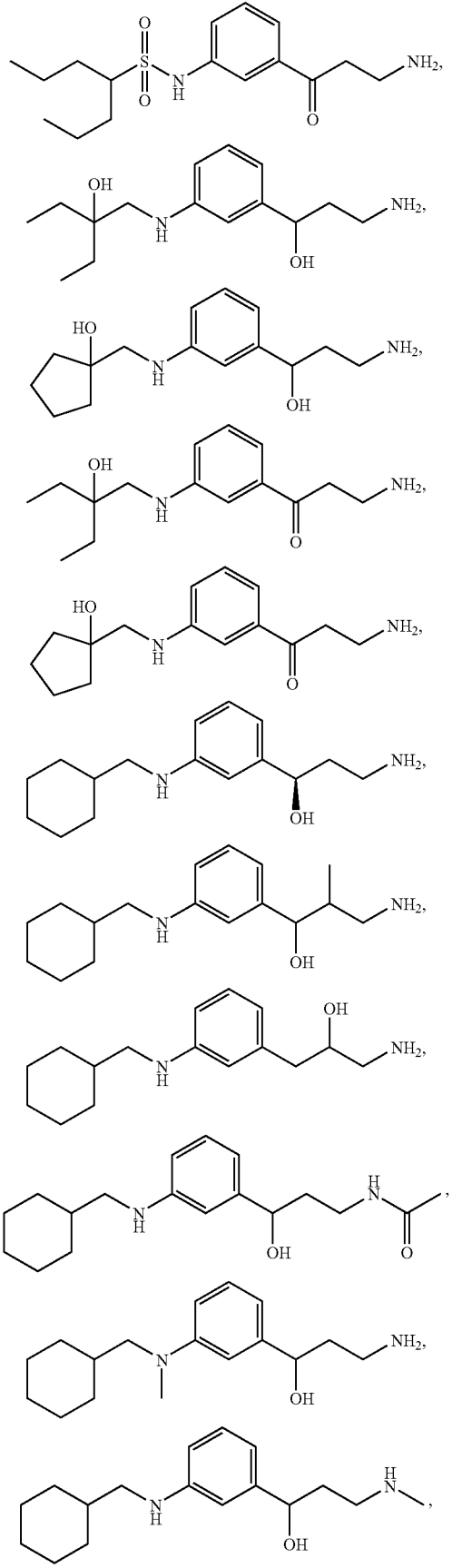
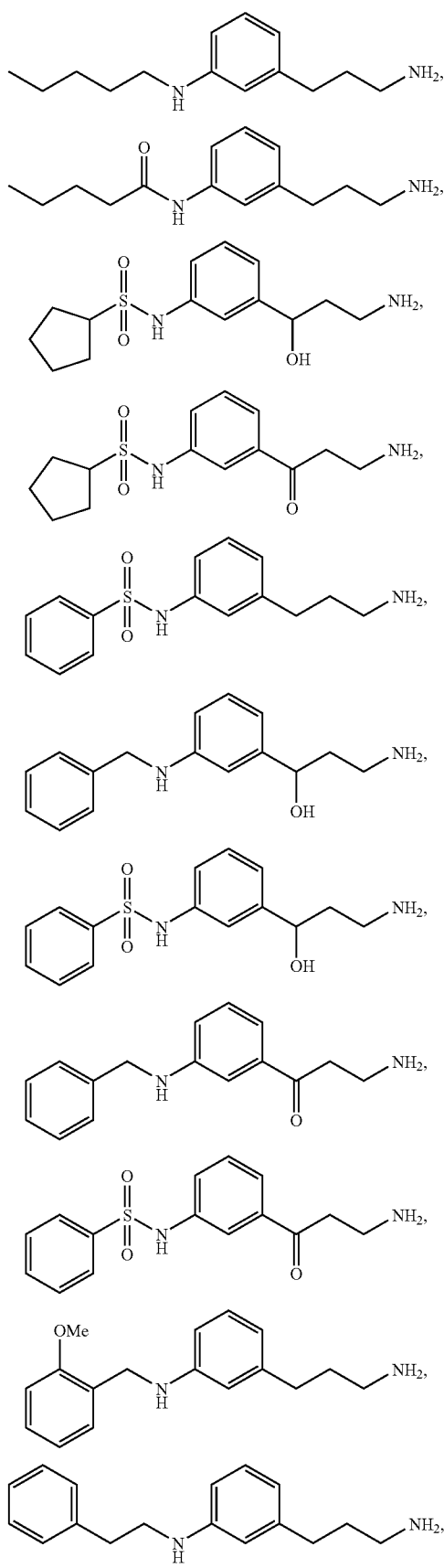

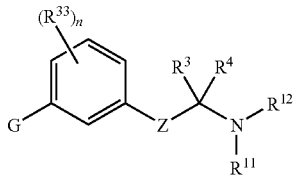

In an additional embodiment is a pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

Formula (I)

wherein,
Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)—, —C(R$^{38}$)(R$^{39}$)—X—C(R$^{31}$)(R$^{32}$)—, or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —N(R$^{42}$)—SO$_2$—R$^{40}$, —N(R$^{42}$)C(=O)—R$^{40}$, —N(R$^{42}$)C(=O)—OR$^{40}$, —N(R$^{42}$)—C(R$^{42}$)(R$^{42}$)—R$^{40}$, —N(R$^{42}$)—C(=O)—N(R$^{43}$)(R$^{43}$), or —N(R$^{42}$)—C(=S)—N(R$^{43}$)(R$^{43}$);

R$^{40}$ is selected from —C(R$^{16}$)(R$^{17}$)(R$^{18}$), aryl, or heteroaryl;
each R$^{42}$ is independently selected from hydrogen, alkyl or aryl;
each R$^{43}$ is independently selected from hydrogen, alkyl, cycloalkyl, aralkyl, alkenyl, alkynyl, C-attached heterocyclyl, aryl, or heteroaryl; or two R$^{43}$ groups, together with the nitrogen to which they are attached, may form a heterocyclyl;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^{38}$ and R$^{39}$ are each independently selected from hydrogen, C$_1$-C$_5$ alkyl, or fluoroalkyl;
R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;
R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;
R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;
R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;
each R$^{13}$, R$^{22}$ and R$^{23}$ is independently selected from alkyl, heteroalkyl, alkenyl, aryl, aralkyl, carbocyclyl, heteroaryl or heterocyclyl;
R$^6$, R$^{19}$, R$^{30}$, R$^{34}$ and R$^{35}$ are each independently hydrogen or alkyl;
R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and
each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl;
R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In an additional embodiment is a method for treating an ophthalmic disease or disorder in a subject, comprising administering to the subject a pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

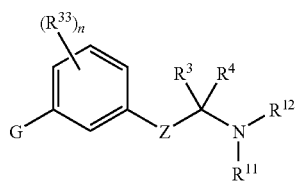

Formula (I)

wherein,

Z is a bond, $-C(R^1)(R^2)-$, $-C(R^9)(R^{10})-C(R^1)(R^2)-$, $-X-C(R^{31})(R^{32})-$, $-C(R^9)(R^{10})-C(R^1)(R^2)-C(R^{36})(R^{37})-$, $-C(R^{38})(R^{39})-X-C(R^{31})(R^{32})-$, or $-X-C(R^{31})(R^{32})-C(R^1)(R^2)-$;

X is $-O-$, $-S-$, $-S(=O)-$, $-S(=O)_2-$, $-N(R^{30})-$, $-C(=O)-$, $-C(=CH_2)-$, $-C(=N-NR^{35})-$, or $-C(=N-OR^{35})-$;

G is selected from $-N(R^{42})-SO_2-R^{40}$, $-N(R^{42})C(=O)-R^{40}$, $-N(R^{42})C(=O)-OR^{40}$, $-N(R^{42})-C(R^{42})(R^{42})-R^{40}$, $-N(R^{42})-C(=O)-N(R^{43})(R^{43})$, or $-N(R^{42})-C(=S)-N(R^{43})(R^{43})$;

$R^{40}$ is selected from $C(R^{16})(R^{17})(R^{18})$, aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, $-OR^6$ or $-NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, $-OR^6$ or $-NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, $-C(=O)R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, $-C(=O)R^{23}$, $-C(NH)NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, $-C(=O)R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In a further embodiment is the method wherein the ophthalmic disease or disorder is a retinal disease or disorder. In an additional embodiment is the method wherein the retinal disease or disorder is age-related macular degeneration or Stargardt's macular dystrophy. In an additional embodiment is the method wherein the ophthalmic disease or disorder is selected from retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS. In an additional embodiment is the method wherein the ophthalmic disease or disorder is selected from diabetic retinopathy, diabetic maculopathy, retinal blood vessel occlusion, retinopathy of prematurity, or ischemia reperfusion related retinal injury.

In an additional embodiment is the method of inhibiting at least one visual cycle trans-cis isomerase in a cell comprising contacting the cell with a compound of Formula (I) as described herein, thereby inhibiting the at least one visual cycle trans-cis isomerase. In a further embodiment is the method wherein the cell is a retinal pigment epithelial (RPE) cell.

In a further embodiment is the method of inhibiting at least one visual cycle trans-cis isomerase in a subject comprising administering to the subject the pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

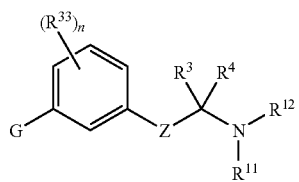

Formula (I)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—; C(R$^{36}$)(R$^{37}$)—, —C(R$^{38}$)(R$^{39}$)—X—C(R$^{31}$)(R$^{32}$)—, or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —N(R$^{42}$)—C(=O)$_2$—R$^{40}$, —N(R$^{42}$)C(=O)—R$^{40}$, —N(R$^{42}$)C(=O)—OR$^{40}$, —N(R$^{42}$)—C(R$^{42}$)(R$^{42}$)—R$^{40}$, —N(R$^{42}$)—C(=O)—N(R$^{43}$)(R$^{43}$), or —N(R$^{42}$)—C(=S)—N(R$^{43}$)(R$^{43}$);

R$^{40}$ is selected from —C(R$^{16}$)(R$^{17}$)(R$^{18}$), aryl, or heteroaryl;

each R$^{42}$ is independently selected from hydrogen, alkyl or aryl;

each R$^{43}$ is independently selected from hydrogen, alkyl, cycloalkyl, aralkyl, alkenyl, alkynyl, C-attached heterocyclyl, aryl, or heteroaryl; or two R$^{43}$ groups, together with the nitrogen to which they are attached, may form a heterocyclyl;

R$^1$ and R$^2$ are each independently selected from hydrogen, halogen, $C_1$-$C_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, $C_1$-$C_5$ alkyl, or fluoroalkyl;

R$^{38}$ and R$^{39}$ are each independently selected from hydrogen, $C_1$-$C_5$ alkyl, or fluoroalkyl;

R$^{36}$ and R$^{37}$ are each independently selected from hydrogen, halogen, $C_1$-$C_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl;

R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

R$^{18}$ is selected from hydrogen, alkyl, alkoxy, hydroxy, halo or fluoroalkyl;

each R$^{33}$ is independently selected from halogen, OR$^{34}$, alkyl, or fluoroalkyl; and n is 0, 1, 2, 3, or 4.

In a further embodiment is the method wherein the subject is human. In a further embodiment is the method wherein accumulation of lipofuscin pigment is inhibited in an eye of the subject. In a further embodiment is the method wherein the lipofuscin pigment is N-retinylidene-N-retinyl-ethanolamine (A2E). In a further embodiment is the method wherein degeneration of a retinal cell is inhibited. In a further embodiment is the method wherein the retinal cell is a retinal neuronal cell. In a further embodiment is the method wherein the retinal neuronal coil is a photoreceptor cell, an amacrine cell, a horizontal cell, a ganglion cell, or a bipolar cell. In a further embodiment is the method wherein the retinal cell is a retinal pigment epithelial (RPE) cell.

In an additional embodiment is a compound that inhibits 11-cis-retinol production with an IC$_{50}$ of about 1 µM or less when assayed in vitro, utilizing extract of cells that express RPE65 and LRAT, wherein the extract further comprises CRALBP, wherein the compound is stable in solution for at least about 1 week at room temperature. In an additional embodiment, the compound is a non-retinoid compound. In a further embodiment is the compound, wherein the compound inhibits 11-cis-retinol production with an IC$_{50}$ of about 0.1 µM or less. In a further embodiment is the compound, wherein the compound inhibits 11-cis-retinol production with an IC$_{50}$ of about 0.01 µM or less.

In an additional embodiment is a non-retinoid compound that inhibits an 11-cis-retinol producing isomerase reaction, wherein said isomerase reaction occurs in RPE, and wherein said compound has an ED$_{50}$ value of 1 mg/kg or less when administered to a subject. In a further embodiment is the non-retinoid compound wherein the ED$_{50}$ value is measured after administering a single dose of the compound to said subject for about 2 hours or longer.

In a further embodiment is the non-retinoid compound wherein the structure of the non-retinoid compound corresponds to Formula (I) or tautomer, stereoisomer, geometric isomer or a pharmaceutically acceptable solvate, hydrate, salt, N-oxide or prodrug thereof:

27

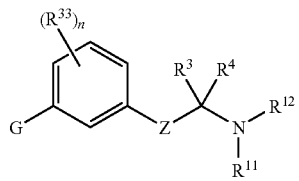

Formula (I)

wherein,

Z is a bond, —C(R¹)(R²)—, —C(R⁹)(R¹⁰)—C(R¹)(R²)—, —X—C(R³¹)(R³²)—, —C(R⁹)(R¹⁰)—C(R¹)(R²)—; C(R³⁶)(R³⁷)—, —C(R³⁸)(R³⁹)—X—C(R³¹)(R³²)—, or —X—C(R³¹)(R³²)—C(R¹)(R²)—;

X is —O—, —S—, —S(=O)—, —S(=O)₂—, —N(R³⁰)—, —C(=O)—, —C(=CH₂)—, —C(=N—NR³⁵)—, or —C(=N—OR³⁵)—;

G is selected from —N(R⁴²)—SO₂—R⁴⁰, —N(R⁴²)C(=O)—R⁴⁰, —N(R⁴²)C(=O)—OR⁴⁰, —N(R⁴²)—C(R⁴²)(R⁴²)—R⁴⁰, —N(R⁴²)—C(=O)—N(R⁴³)(R⁴³), or —N(R⁴²)—C(=S)—N(R⁴³)(R⁴³);

R⁴⁰ is selected from —C(R¹⁶)(R¹⁷)(R¹⁸), aryl, or heteroaryl;

each R⁴² is independently selected from hydrogen, alkyl or aryl;

each R⁴³ is independently selected from hydrogen, alkyl, cycloalkyl, aralkyl, alkenyl, alkynyl, C-attached heterocyclyl, aryl, or heteroaryl; or two R⁴³ groups, together with the nitrogen to which they are attached, may form a heterocyclyl;

R¹ and R² are each independently selected from hydrogen, halogen, C₁-C₅ alkyl, fluoroalkyl, —OR⁶ or —NR⁷R⁸; or R¹ and R² together form an oxo;

R³¹ and R³² are each independently selected from hydrogen, C₁-C₅ alkyl, or fluoroalkyl;

R³⁸ and R³⁹ are each independently selected from hydrogen, C₁-C₅ alkyl, or fluoroalkyl;

R³⁶ and R³⁷ are each independently selected from hydrogen, halogen, C₁-C₅ alkyl, fluoroalkyl, —OR⁶ or —NR⁷R⁸; or R³⁶ and R³⁷ together form an oxo; or optionally, R³⁶ and R¹ together form a direct bond to provide a double bond; or optionally, R³⁶ and R¹ together form a direct bond, and R³⁷ and R² together form a direct bond to provide a triple bond;

R³ and R⁴ are each independently selected from hydrogen, alkyl, alkenyl, fluoroalkyl, aryl, heteroaryl, carbocyclyl or C-attached heterocyclyl; or R³ and R⁴ together with the carbon atom to which they are attached, form a carbocyclyl or heterocyclyl; or R³ and R⁴ together form an imino;

R⁷ and R⁸ are each independently selected from hydrogen, alkyl, carbocyclyl, heterocyclyl, —C(=O)R¹³, SO₂R¹³, CO₂R¹³ or SO₂NR²⁴R²⁵; or R⁷ and R⁸ together with the nitrogen atom to which they are attached, form an N-heterocyclyl;

R⁹ and R¹⁰ are each independently selected from hydrogen, halogen, alkyl, fluoroalkyl, —OR¹⁹, —NR²⁰R²¹ or carbocyclyl; or R⁹ and R¹⁰ form an oxo; or optionally, R⁹ and R¹ together form a direct bond to provide a double bond; or optionally, R⁹ and R¹ together form a direct bond, and R¹⁰ and R² together form a direct bond to provide a triple bond;

R¹¹ and R¹² are each independently selected from hydrogen, alkyl, carbocyclyl, —C(=O)R²³, —C(NH)NH₂, SO₂R²³, CO₂R²³ or SO₂NR²⁸R²⁹; or R¹¹ and R¹², together with the nitrogen atom to which they are attached, form an N-heterocyclyl;

each R¹³, R²² and R²³ is independently selected from alkyl, heteroalkyl, alkenyl, aryl, aralkyl, carbocyclyl, heteroaryl or heterocyclyl;

28

R⁶, R¹⁹, R³⁰, R³⁴ and R³⁵ are each independently hydrogen or alkyl;

R²⁰ and R²¹ are each independently selected from hydrogen, alkyl, carbocyclyl, heterocyclyl, —C(=O)R²², SO₂R²², CO₂R²² or SO₂NR²⁶R²⁷; or R²⁰ and R²¹ together with the nitrogen atom to which they are attached, form an N-heterocyclyl; and each R²⁴, R²⁵, R²⁶, R²⁷, R²⁸, R²⁹ is independently selected from hydrogen, alkyl, alkenyl, fluoroalkyl, aryl, heteroaryl, carbocyclyl or heterocyclyl;

R¹⁶ and R¹⁷ are each independently selected from hydrogen, alkyl, halo, aryl, heteroaryl, aralkyl, heteroarylalkyl or fluoroalkyl; or R¹⁶ and R¹⁷, together with the carbon to which they are attached form a carbocyclyl or heterocycle;

R¹⁸ is selected from hydrogen, alkyl, alkoxy, hydroxy, halo or fluoroalkyl;

each R³³ is independently selected from halogen, OR³⁴, alkyl, or fluoroalkyl; and n is 0, 1, 2, 3, or 4.

In an additional embodiment is a pharmaceutical composition comprising a pharmaceutically acceptable carrier and a compound that inhibits 11-cis-retinol production with an IC₅₀ of about 1 µM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an ED₅₀ value of 1 mg/kg or less when administered to a subject.

In an additional embodiment is a method of modulating chromophore flux in a retinoid cycle comprising introducing into a subject a compound of Formula (I) as described herein. In a further embodiment is the method resulting in a reduction of lipofuscin pigment accumulated in an eye of the subject. In another embodiment is the method wherein the lipofuscin pigment is N-retinylidene-N-retinyl-ethanolamine (A2E). In yet another embodiment is the method wherein the lipofuscin pigment is N-retinylidene-N-retinyl-ethanolamine (A2E).

In an additional embodiment is a method of modulating chromophore flux in a retinoid cycle comprising introducing into a subject a compound that inhibits 11-cis-retinol production as described herein. In a further embodiment is the method resulting in a reduction of lipofuscin pigment accumulated in an eye of the subject. In another embodiment is the method wherein the lipofuscin pigment is N-retinylidene-N-retinyl-ethanolamine (A2E). In yet another embodiment is the method wherein the lipofuscin pigment is N-retinylidene-N-retinyl-ethanolamine (A2E).

In an additional embodiment is a method of modulating chromophore flux in a retinoid cycle comprising introducing into a subject a non-retinoid compound that inhibits an 11-cis-retinol producing isomerase reaction as described herein. In a further embodiment is the method resulting in a reduction of lipofuscin pigment accumulated in an eye of the subject. In another embodiment is the method wherein the lipofuscin pigment is N-retinylidene-N-retinyl-ethanolamine (A2E). In yet another embodiment is the method wherein the lipofuscin pigment is N-retinylidene-N-retinyl-ethanolamine (A2E).

In an additional embodiment is a method for treating an ophthalmic disease or disorder in a subject, comprising administering to the subject a pharmaceutical composition comprising a pharmaceutically acceptable carrier and a compound that inhibits 11-cis-retinol production with an IC₅₀ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the ophthalmic disease or disorder is age-related macular degeneration or Stargardt's macular dystrophy. In a further embodiment is the method wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method resulting in a reduction of lipofuscin pigment accumulated in an eye of the subject.

In an additional embodiment is a method for treating an ophthalmic disease or disorder in a subject, comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the ophthalmic disease or disorder is age-related macular degeneration or Stargardt's macular dystrophy. In a further embodiment is the method wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method resulting in a reduction of lipofuscin pigment accumulated in an eye of the subject.

In a further embodiment is a method of inhibiting dark adaptation of a rod photoreceptor cell of the retina comprising contacting the retina with a compound of Formula (I) as described herein.

In a further embodiment is a method of inhibiting dark adaptation of a rod photoreceptor cell of the retina comprising contacting the retina with a compound that inhibits 11-cis-retinol production as described herein.

In a further embodiment is a method of inhibiting dark adaptation of a rod photoreceptor cell of the retina comprising contacting the retina with a non-retinoid compound that inhibits an 11-cis-retinol producing isomerase reaction as described herein.

In a further embodiment is a method of inhibiting regeneration of rhodopsin in a rod photoreceptor cell of the retina comprising contacting the retina with a compound of Formula (I) as described herein.

In a further embodiment is a method of inhibiting regeneration of rhodopsin in a rod photoreceptor cell of the retina comprising contacting the retina with a compound that inhibits 11-cis-retinol production as described herein.

In a further embodiment is a method of inhibiting regeneration of rhodopsin in a rod photoreceptor cell of the retina comprising contacting the retina with a non-retinoid compound that inhibits an 11-cis-retinol producing isomerase reaction as described herein.

In a further embodiment is a method of reducing ischemia in an eye of a subject comprising administering to the subject the pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

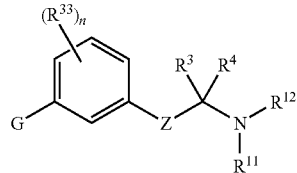

Formula (I)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)—, —C(R$^{38}$)(R$^{39}$)—X—C(R$^{31}$)(R$^{32}$)—, or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —N(R$^{42}$)—SO$_2$—R$^{40}$, —N(R$^{42}$)C(=O)—R$^{40}$, —N(R$^{42}$)C(=O)—OR$^{40}$, —N(R$^{42}$)—C(R$^{42}$)(R$^{42}$)—R$^{40}$, —N(R$^{42}$)—C(=O)—N(R$^{43}$)(R$^{43}$), or —N(R$^{42}$)—C(=S)—N(R$^{43}$)(R$^{43}$);

R$^{40}$ is selected from —C(R$^{16}$)(R$^{17}$)(R$^{18}$), aryl, or heteroaryl;

each R$^{42}$ is independently selected from hydrogen, alkyl or aryl;

each R$^{43}$ is independently selected from hydrogen, alkyl, cycloalkyl, aralkyl, alkenyl, alkynyl, C-attached heterocyclyl, aryl, or heteroaryl; or two R$^{43}$ groups, together with the nitrogen to which they are attached, may form a heterocyclyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{38}$ and R$^{39}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^7$ and R$^8$ are each independently selected from hydrogen, alkyl, carbocyclyl, heterocyclyl, —C(=O)R$^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, $-OR^{19}$, $-NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, $-C(=O)R^{23}$, $-C(NH)NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, $-C(=O)R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$, $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In another embodiment is a method of reducing ischemia in an eye of a subject comprising administering to the subject a pharmaceutical composition comprising a pharmaceutically acceptable carrier and a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the pharmaceutical composition is administered under conditions and at a time sufficient to inhibit dark adaptation of a rod photoreceptor cell, thereby reducing ischemia in the eye.

In another embodiment is a method of reducing ischemia in an eye of a subject comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the pharmaceutical composition is administered under conditions and at a time sufficient to inhibit dark adaptation of a rod photoreceptor cell, thereby reducing ischemia in the eye.

In another embodiment is a method of inhibiting neovascularization in the retina of an eye of a subject comprising administering to the subject a pharmaceutical composition comprising a pharmaceutically acceptable carrier and a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the pharmaceutical composition is administered under conditions and at a time sufficient to inhibit dark adaptation of a rod photoreceptor cell, thereby inhibiting neovascularization in the retina.

In another embodiment is a method of inhibiting neovascularization in the retina of an eye of a subject comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the pharmaceutical composition is administered under conditions and at a time sufficient to inhibit dark adaptation of a rod photoreceptor cell, thereby inhibiting neovascularization in the retina.

In another embodiment is a method of inhibiting degeneration of a retinal cell in a retina comprising contacting the retina with the compound of Formula (I) as described herein. In a further embodiment is the method wherein the retinal cell is a retinal neuronal cell. In yet another embodiment is the method wherein the retinal neuronal cell is a photoreceptor cell.

In another embodiment is a method of inhibiting degeneration of a retinal cell in a retina comprising contacting the retina with a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the retinal cell is a retinal neuronal cell. In yet another embodiment is the method wherein the retinal neuronal cell is a photoreceptor cell.

In another embodiment is a method of inhibiting degeneration of a retinal cell in a retina comprising contacting the retina with a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the retinal cell is a retinal neuronal cell. In yet another embodiment is the method wherein the retinal neuronal cell is a photoreceptor cell.

In a further embodiment is a method of reducing lipofuscin pigment accumulated in a subject's retina comprising administering to the subject a pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

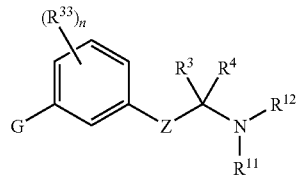

Formula (I)

wherein,

Z is a bond, $-C(R^1)(R^2)-$, $-C(R^9)(R^{10})-C(R^1)(R^2)-$, $-X-C(R^{31})(R^{32})-$, $-C(R^9)(R^{10})-C(R^1)(R^2)-C$ $(R^{36})(R^{37})$—, —$C(R^{38})(R^{39})$—X—$C(R^{31})(R^{32})$—, or —X—$C(R^{31})(R^{32})$—$C(R^1)(R^2)$—;

X is —O—, —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—;

G is selected from —N($R^{42}$)—SO$_2$—$R^{40}$, —N($R^{42}$)C(=O)—$R^{40}$, —N($R^{42}$)C(=O)—OR$^{40}$, —N($R^{42}$)—C($R^{42}$)($R^{42}$)—$R^{40}$, —N($R^{42}$)—C(=O)—N($R^{43}$)($R^{43}$), or —N($R^{42}$)—C(=S)—N($R^{43}$)($R^{43}$);

$R^{40}$ is selected from C($R^{16}$)($R^{17}$)($R^{18}$), aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, C$_1$-C$_5$ alkyl, fluoroalkyl, —OR$^6$ or —NR$^7$R$^8$; or $R^1$ and $R^2$ together form an oxo;

$R^{31}$ and $R^{32}$ are each independently selected from hydrogen, C$_1$-C$_5$ alkyl, or fluoroalkyl;

$R^{38}$ and $R^{39}$ are each independently selected from hydrogen, C$_1$-C$_5$ alkyl, or fluoroalkyl;

$R^{36}$ and $R^{37}$ are each independently selected from hydrogen, halogen, C$_1$-C$_5$ alkyl, fluoroalkyl, —OR$^6$ or —NR$^7$R$^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —OR$^{19}$, —NR$^{20}$R$^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, OR$^{34}$, alkyl, or fluoroalkyl; and n is 0, 1, 2, 3, or 4.

In a further embodiment is the method wherein the lipofuscin is N-retinylidene-N-retinyl-ethanolamine (A2E).

In another embodiment is a method of reducing lipofuscin pigment accumulated in a subject's retina comprising administering to the subject a pharmaceutical composition comprising a pharmaceutically acceptable carrier and a compound that inhibits 11-cis-retinol production with an IC$_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the lipofuscin is N-retinylidene-N-retinyl-ethanolamine (A2E).

In another embodiment is a method of reducing lipofuscin pigment accumulated in a subject's retina comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an ED$_{50}$ value of 1 mg/kg or less when administered to a subject. In a further embodiment is the method wherein the lipofuscin is N-retinylidene-N-retinyl-ethanolamine (A2E).

In one embodiment is a compound having a structure of Formula (II):

Formula (II)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:

$R^1$ and $R^2$ are each the same or different and independently hydrogen or alkyl;

$R^3$, $R^4$, $R^5$ and $R^6$ are each the same or different and independently hydrogen, halogen, nitro, —NH$_2$, —NHR$^{13}$, —N($R^{13}$)$_2$, —OR$^{12}$, alkyl or fluoroalkyl;

$R^7$ and $R^8$ are each the same or different and independently hydrogen or alkyl; or $R^7$ and $R^8$ together with the carbon atom to which they are attached, form a carbocyclyl or heterocyclyl; or $R^7$ and $R^8$ together form an imino;

$R^9$ is hydrogen, alkyl, carbocyclyl, heterocyclyl, —C(=O) R$^{13}$, —SO$_2$R$^{13}$, —CO$_2$R$^{13}$, —CONH$_2$, —CON(R$^{13}$)$_2$ or —CON(H)R$^{13}$;

$R^{10}$ is hydrogen or alkyl; or $R^9$ and $R^{10}$, together with the nitrogen atom to which they are attached, form an N-heterocyclyl;

$R^{11}$ is alkyl, alkenyl, aryl, carbocyclyl, heteroaryl or heterocyclyl;

each $R^{12}$ is independently selected from hydrogen or alkyl;

each $R^{13}$ is independently selected from alkyl, carbocyclyl, heterocyclyl, aryl or heteroaryl;

Z is a bond, Y or W—Y, wherein

W is —$C(R^{14})(R^{15})$—, —O—, —S—, —S(=O)—, —$S(=O)_2$— or —$N(R^{12})$—;

Y is —$C(R^{16})(R^{17})$— or —$C(R^{16})(R^{17})$—$C(R^{21})(R^{22})$—;

$R^{14}$ and $R^{15}$ are each the same or different and independently hydrogen, halogen, alkyl, fluoroalkyl, —$OR^{12}$, —$NR^{18}R^{19}$, carbocyclyl or heterocyclyl; or $R^{14}$ and $R^{15}$ together form an oxo, an imino, an oximo, or a hydrazino;

$R^{16}$ and $R^{17}$ are each the same or different and independently hydrogen, halogen, alkyl, fluoroalkyl, —$OR^{12}$, —$NR^{18}R^{19}$, carbocyclyl or heterocyclyl; or $R^{16}$ and $R^{17}$ together form an oxo; or optionally, $R^{14}$ and $R^{16}$ together form a direct bond to provide a double bond connecting W and Y; or optionally, $R^{14}$ and $R^{16}$ together form a direct bond, and $R^{15}$ and $R^{17}$ together form a direct bond to provide a triple bond connecting W and Y;

each $R^{18}$ and $R^{19}$ is independently selected from hydrogen, alkyl, carbocyclyl, or —$C(=O)R^{13}$, —$SO_2R^{13}$, —$CO_2R^{13}$, —$CONH_2$, —$CON(R^{13})_2$ or —$CON(H)R^{13}$; or $R^{18}$ and $R^{19}$, together with the nitrogen atom to which they are attached, form an N-heterocyclyl;

$R^{21}$ and $R^{22}$ are each the same or different and independently hydrogen, halogen, alkyl, fluoroalkyl, —$OR^{12}$, —$NR^{18}R^{19}$, carbocyclyl or heterocyclyl;

provided that when $R^{11}$ is phenyl, the compound of Formula (A) is not:

2-amino-N-[2-methoxy-5-[(1Z)-2-(3,4,5-trimethoxyphenyl) ethenyl]phenyl]acetamide; (2S,3R)-amino-3-hydroxy-N-[2-methoxy-5-[(1Z)-2-(3,4,5-trimethoxyphenyl)-ethenyl] phenyl]-butanamide;

L-glutamic acid, 1-[2-methoxy-5-[(1Z)-2-(3,4,5-trimethoxyphenyl)ethenyl]phenyl]ester; glycine, 3-hydroxy-5-[(1E)-2-(4-hydroxyphenyl)ethenyl]phenyl ester;

(2S)-2-amino-N-[2-methoxy-5-[(1Z)-2-(3,4,5-trimethoxyphenyl)ethenyl]phenyl]propanamide;

(2S)-2-amino-3-hydroxy-N-[2-methoxy-5-[(1Z)-2-(3,4,5-trimethoxyphenyl)ethenyl]phenyl]propanamide;

(2S)-2-amino-N-[2-methoxy-5-[(1Z)-2-(3,4,5-trimethoxyphenyl)ethenyl]phenyl]-4-methyl-pentanamide;

(2S)-2-amino-N-[2-methoxy-5-[(1Z)-2-(3,4,5-trimethoxyphenyl)ethenyl]phenyl]-3-methyl-butanamide; or 2-amino-N-[2-methoxy-5-[(1Z)-2-(3,4,5-trimethoxyphenyl) ethenyl]phenylbutanamide; and wherein the compound of Formula (II) is isotopically enriched.

In another embodiment is the compound of Formula (II) having one, more than one, or all of the non exchangeable $^1$H atoms are replaced with $^2$H atoms.

In another embodiment is the compound of Formula (II) having the structure of Formula (IIa):

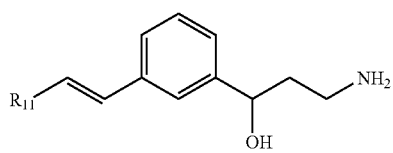

Formula (IIa)

wherein $R^{11}$ is selected from:

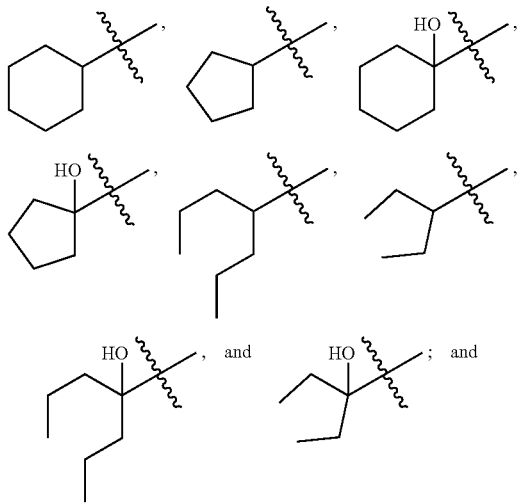

one, more than one, or all of the non-exchangeable $^1$H atoms are replaced with $^2$H atoms.

In another embodiment is the compound of Formula (IIa) selected from:

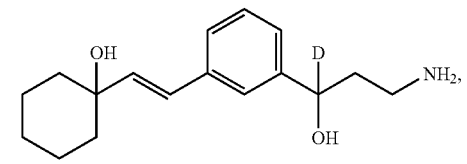

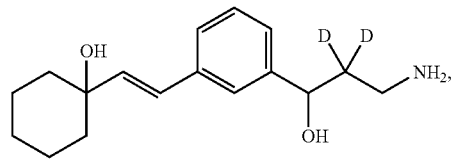

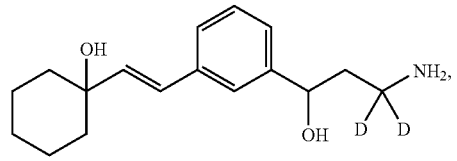

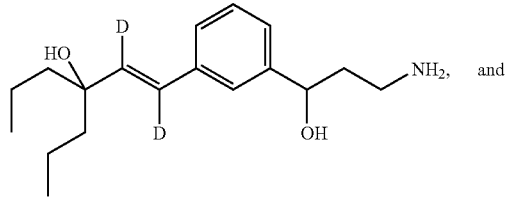

and

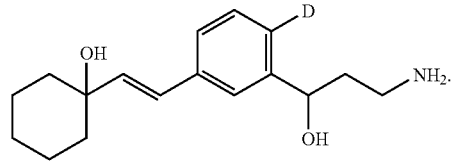

One embodiment provides a compound having a structure of Formula (III):

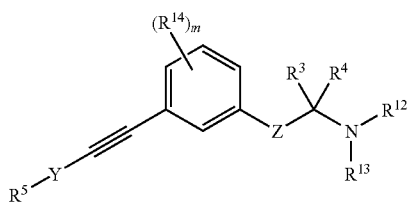

Formula (III)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

Z is a bond, —C(R$^1$)(R$^2$)—, —X—C(R$^{21}$)(R$^{22}$)—, —C(R$^{23}$)(R$^{24}$)—C(R$^1$)(R$^{26}$)—C(R$^1$)(R$^2$)—, —X—C(R$^{21}$)(R$^{22}$)—C(R$^1$)(R$^2$)—, —C(R$^{32}$)(R$^{33}$)—X—C(R$^{21}$)(R$^{22}$);

X is —O—, —S—, —S(=O)$_2$—, —N(R$^{31}$)—, —C(=O), —C(=CH$_2$)—, —C(=N—NR$^{35}$)—, or —C(=N—OR$^{35}$)—;

Y is a bond, —C(R$^{27}$)(R$^{28}$)—, or —C(R$^{27}$)(R$^{28}$)—C(R$^{29}$)(R$^{30}$)—;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{21}$, R$^{22}$, R$^{32}$ and R$^{33}$ are each independently selected from hydrogen, C$_1$-C$_5$ alkyl, or fluoroalkyl;

R$^{23}$ and R$^{24}$ are each independently selected from hydrogen, halogen, C$_1$-C$_5$ alkyl, fluoroalkyl, —OR$^6$, —NR$^7$R$^8$; or R$^{23}$ and R$^{24}$ together form an oxo; or optionally, R$^{23}$ and an adjacent R$^1$ together form a direct bond to provide a double bond; or optionally, R$^{23}$ and an adjacent R$^1$ together form a direct bond, and R$^{24}$ and an adjacent R$^2$ together form a direct bond to provide a triple bond;

R$^{25}$ and R$^{26}$ are each independently selected from hydrogen, halogen, C$_1$-C$_5$ alkyl, fluoroalkyl, —OR$^6$ or —NR$^7$R$^8$; or R$^{25}$ and R$^{26}$ together form an oxo;

R$^3$ and R$^4$ are each independently selected from hydrogen, alkyl, heteroalkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is alkyl, heteroalkyl, alkenyl, heteroalkenyl, aryl, carbocyclyl, heteroaryl or heterocyclyl;

each R$^6$ is the same or different and independently hydrogen or C$_1$-C$_5$ alkyl;

each R$^7$ and each R$^8$ are each the same or different and independently hydrogen, alkyl, carbocyclyl, heteroalkyl, heterocycloalkyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or R$^7$ and R$^8$, together with the nitrogen atom to which they are attached, form an N-heterocyclyl;

each R$^9$ is the same or different and each is independently alkyl, alkenyl, aryl, carbocyclyl, heteroaryl or heterocyclyl;

R$^{12}$ and R$^{13}$ are the same or different and independently hydrogen, alkyl, heteroalkyl, carbocyclyl, heterocyclyl, aryl, heteroaryl, —C(=O)R$^9$, SO$_2$R$^9$, CO$_2$R$^9$, SO$_2$NH$_2$, SO$_2$NHR$^9$ or SO$_2$N(R$^9$)$_2$; or R$^{12}$ and R$^{13}$ together with the nitrogen atom to which they are attached, form an N-heterocyclyl; and each R$^{14}$ is the same or different and independently alkyl, halo, fluoroalkyl or —OR$^6$;

each R$^{27}$, R$^{28}$, R$^{29}$ and R$^{31}$ are the same or different and independently hydrogen, alkyl or OR$^6$; and R$^{30}$ and R$^{35}$ are each independently hydrogen or C$_1$-C$_5$ alkyl; and wherein the compound of Formula (III) is isotopically enriched.

Another embodiment provides the compound of Formula (III) having one, more than one or all of the non-exchangeable $^1$H atoms replaced with $^2$H atoms.

Another embodiment provides the compound of Formula (IIIa):

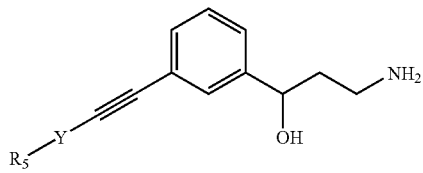

Formula (IIIa)

wherein Y is a bond;

R$^5$ is selected from:

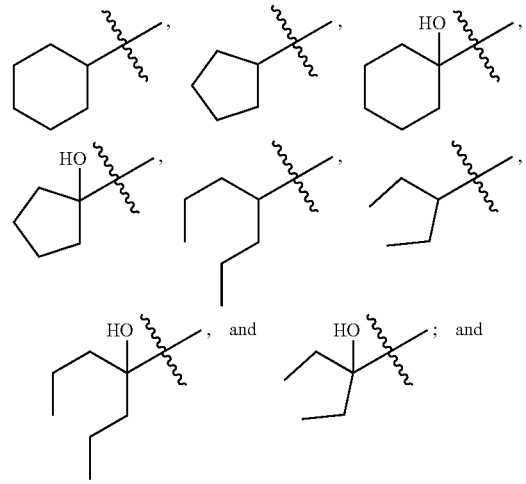

one, more than one, or all of the non-exchangeable $^1$H atoms are replaced with $^2$H atoms.

Another embodiment provides the compound of Formula (III) selected from:

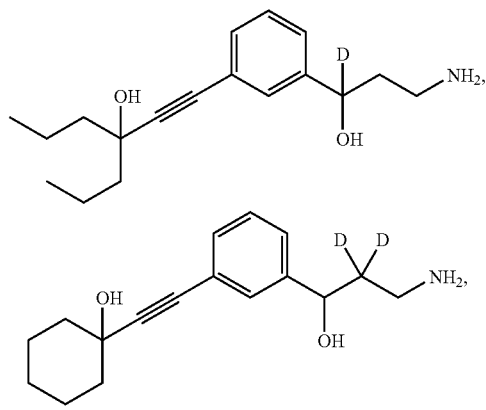

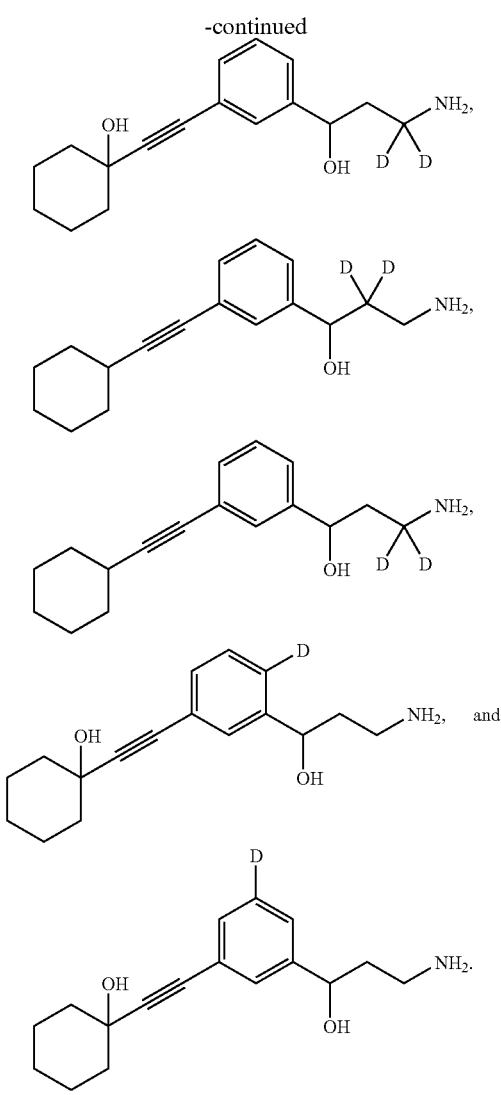

One embodiment provides a compound of Formula (IV) or tautomer, stereoisomer, geometric isomer or a pharmaceutically acceptable solvate, hydrate, salt, N-oxide or prodrug thereof:

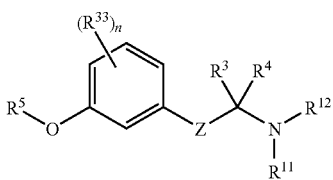

Formula (IV)

wherein,

Z is —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)— or —X—C($R^{31}$)($R^{32}$)—C($R^1$)($R^2$)—;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is $C_5$-$C_{15}$ alkyl or carbocyclyalkyl;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

X is —O—, —S—, —S(=O)—, —S(=O)$_2$—, —N($R^{30}$)—, —C(=O)—, —C(=CH$_2$)—, —C(=N—$NR^{35}$)—, or —C(=N—$OR^{35}$)—;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$, $R^{29}$ is independently selected from hydrogen, alkyl, alkenyl, fluoroalkyl, aryl, heteroaryl, carbocyclyl or heterocyclyl;

each $R^{33}$ is independently selected from halogen, $OR^{34}$, alkyl, or fluoroalkyl; and n is 0, 1, 2, 3, or 4; with the provision that $R^5$ is not 2-(cyclopropyl)-1-ethyl or an unsubstituted normal alkyl; and wherein the compound of Formula (IV) is isotopically enriched.

Another embodiment provides the compound of Formula (IV) has one, more than one or all of the non-exchangeable $^1$H atoms replaced with $^2$H atoms.

Another embodiment provides the compound having the structure of Formula (IVa):

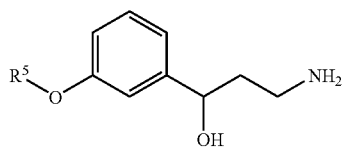

Formula (IVa)

wherein Y is a bond;

$R^5$ is selected from:

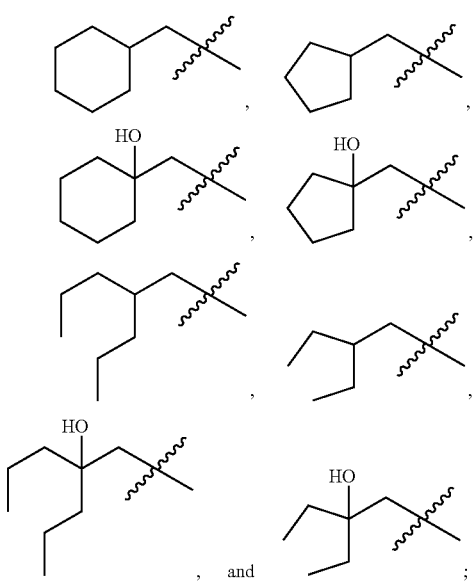

and one, more than one, or all of the non-exchangeable $^1H$ atoms are replaced with $^2H$ atoms.

Another embodiment provides the compound selected from:

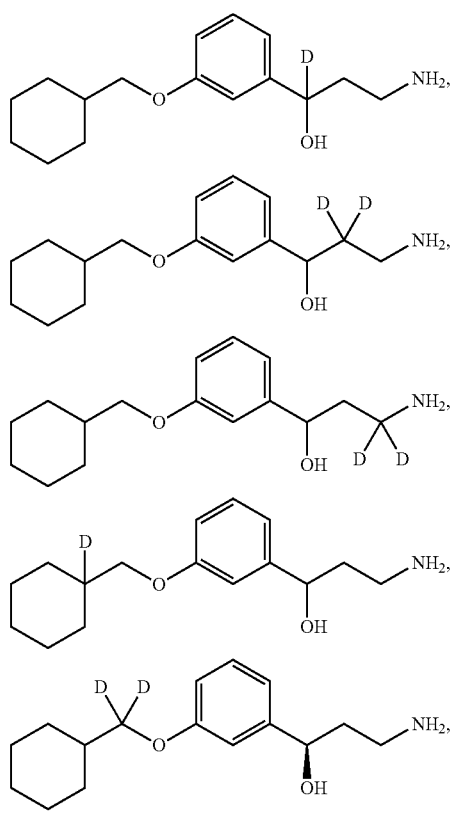

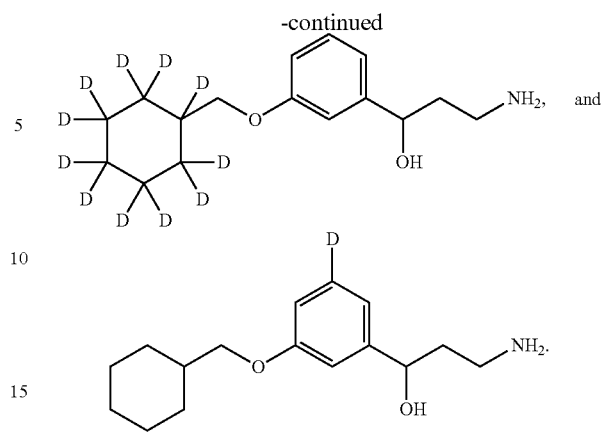

One embodiment provides a method for treating an ophthalmic disease or disorder in a subject, comprising administering to the subject a compound of Formula (II), (IIa), (III), (IIIa), (IV), or (IVa) as described herein, or tautomer, stereoisomer, geometric isomer or a pharmaceutically acceptable solvate, hydrate, salt, N-oxide or prodrug thereof. Another embodiment provides a method for treating an ophthalmic disease or disorder wherein the ophthalmic disease or disorder is age-related macular degeneration or Stargardt's macular dystrophy.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
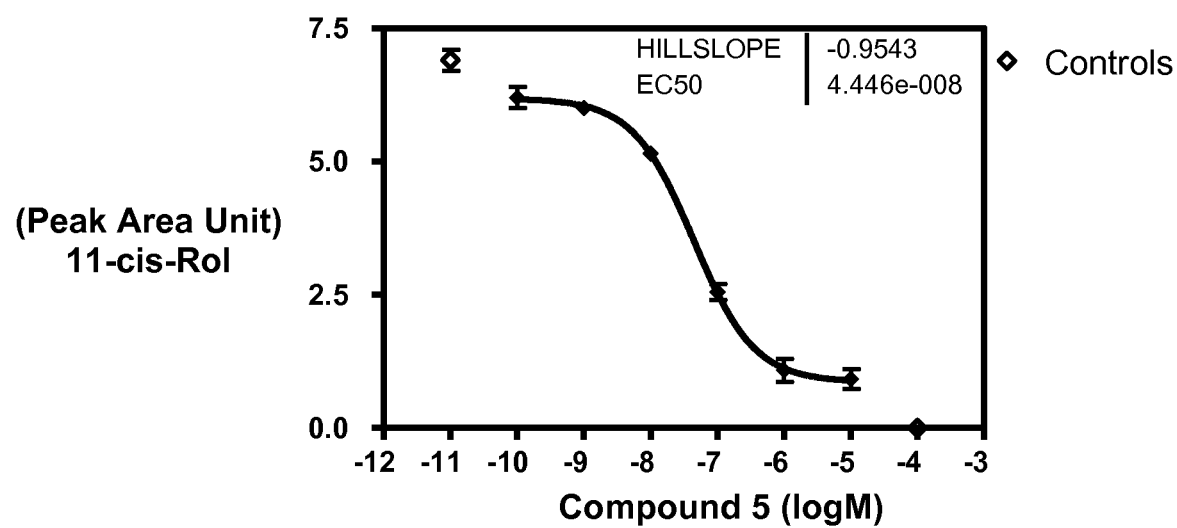
FIG. 1 depicts dose-dependent inhibition of 11-cis-retinol production (as assayed by a human in vitro isomerase assay) by the compound of Example 5 (Compound 5).

Compounds are described herein that inhibit an isomerization step of the retinoid cycle. These compounds and compositions comprising these compounds are useful for inhibiting degeneration of retinal cells or for enhancing retinal cell survival. The compounds described herein are, therefore, useful for treating ophthalmic diseases and disorders, including retinal diseases or disorders, such as age related macular degeneration and Stargardt's disease.

Nitrogen-Linked Compounds

In one embodiment is a compound of Formula (I) or tautomer, stereoisomer, geometric isomer or a pharmaceutically acceptable solvate, hydrate, salt, N-oxide or prodrug thereof:

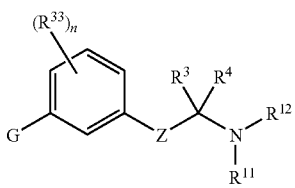

Formula (I)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)—, —C(R$^{38}$)(R$^{39}$)—X—C(R$^{31}$)(R$^{32}$)—, or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —N(R$^{42}$)—SO$_2$—R$^{40}$, —N(R$^{42}$)C(=O)—R$^{40}$, —N(R$^{42}$)C(=O)—OR$^{40}$, —N(R$^{42}$)—C(R$^{42}$)(R$^{42}$)—R$^{40}$, —N(R$^{42}$)—C(=O)—N(R$^{43}$)(R$^{43}$), or —N(R$^{42}$)—C(=S)—N(R$^{43}$)(R$^{43}$);

R$^{40}$ is selected from —C(R$^{16}$)(R$^{17}$)(R$^{18}$), aryl, or heteroaryl;

each R$^{42}$ is independently selected from hydrogen, alkyl or aryl;

each R$^{43}$ is independently selected from hydrogen, alkyl, cycloalkyl, aralkyl, alkenyl, alkynyl, C-attached heterocyclyl, aryl, or heteroaryl; or two R$^{43}$ groups, together with the nitrogen to which they are attached, may form a heterocyclyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{38}$ and R$^{39}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl;

R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

R$^{18}$ is selected from hydrogen, alkyl, alkoxy, hydroxy, halo or fluoroalkyl;

each R$^{33}$ is independently selected from halogen, OR$^{34}$, alkyl, or fluoroalkyl; and n is 0, 1, 2, 3, or 4.

In another embodiment is the compound of Formula (I) wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$) or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo;

R$^{11}$ and R$^{12}$ are each independently selected from hydrogen, alkyl, carbocyclyl, —C(=O)R$^{23}$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$, R$^{29}$ is independently selected from hydrogen, alkyl, alkenyl, fluoroalkyl, aryl, heteroaryl, carbocyclyl or heterocyclyl;

each R$^{33}$ is independently selected from halogen, OR$^{34}$, alkyl, or fluoroalkyl; and n is 0, 1, 2, 3, or 4.

In another embodiment is the compound of Formula (I) having the structure of Formula (Ia)

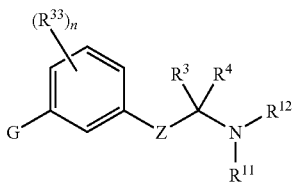

Formula (Ia)

wherein,
Z is —C(R$^9$)(R$^{10}$)—C(R$^1$)(R$^2$)— or —O—C(R$^{31}$)(R$^{32}$)—;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^3$ and R$^4$ are each independently selected from hydrogen or alkyl; or R$^3$ and R$^4$ together form an imino;
R$^7$ and R$^8$ are each independently selected from hydrogen, alkyl, carbocyclyl or —C(=O)R$^{13}$; or R$^7$ and R$^8$, together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ together form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;
R$^{11}$ and R$^{12}$ are each independently selected from hydrogen, alkyl, carbocyclyl or —C(=O)R$^{23}$; or R$^{11}$ and R$^{12}$, together with the nitrogen atom to which they are attached, form an N-heterocyclyl; and
each R$^{13}$, R$^{22}$ and R$^{23}$ is independently selected from alkyl, alkenyl, aryl, aralkyl, carbocyclyl, heteroaryl or heterocyclyl;
R$^6$, R$^{19}$, and R$^{34}$ are each independently hydrogen or alkyl;
each R$^{33}$ is independently selected from halogen, OR$^{34}$, alkyl, or fluoroalkyl; and n is 0, 1, 2, 3, or 4;
R$^{20}$ and R$^{21}$ are each independently selected from hydrogen, alkyl, carbocyclyl, —C(=O)R$^{22}$; or R$^{20}$ and R$^{21}$, together with the nitrogen atom to which they are attached, form an N-heterocyclyl; and
each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl.

In another embodiment is the compound of Formula (Ia) wherein,
Z is —C(R$^9$)(R$^{10}$)—C(R$^1$)(R$^2$)— or —O—C(R$^{31}$)(R$^{32}$)—;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^3$ and R$^4$ are each independently selected from hydrogen or alkyl; or R$^3$ and R$^4$ together form an imino;
R$^7$ and R$^8$ are each independently selected from hydrogen, alkyl, carbocyclyl or —C(=O)R$^{13}$; or R$^7$ and R$^8$, together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ together form an oxo;
R$^{11}$ and R$^{12}$ are each independently selected from hydrogen, alkyl, carbocyclyl or —C(=O)R$^{23}$; or R$^{11}$ and R$^{12}$, together with the nitrogen atom to which they are attached, form an N-heterocyclyl; and
each R$^{13}$, R$^{22}$ and R$^{23}$ is independently selected from alkyl, alkenyl, aryl, aralkyl, carbocyclyl, heteroaryl or heterocyclyl;
R$^6$, R$^{19}$, and R$^{34}$ are each independently hydrogen or alkyl;
each R$^{33}$ is independently selected from halogen, OR$^{34}$, alkyl, or fluoroalkyl; and n is 0, 1, 2, 3, or 4;
R$^{20}$ and R$^{21}$ are each independently selected from hydrogen, alkyl, carbocyclyl, —C(=O)R$^{22}$; or R$^{20}$ and R$^{21}$, together with the nitrogen atom to which they are attached, form an N-heterocyclyl; and
each R$^{24}$, R$^{25}$, R$^{26}$, R$^{27}$, R$^{28}$ and R$^{29}$ is independently selected from hydrogen, alkyl, alkenyl, fluoroalkyl, aryl, heteroaryl, carbocyclyl or heterocyclyl.

In another embodiment is the compound of Formula (Ia) wherein, G is selected from —N(R$^{42}$)—SO$_2$—R$^{40}$; R$^{40}$ is selected from —C(R$^{16}$)(R$^{17}$)(R$^{18}$), aryl, or heteroaryl.

In another embodiment is the compound of Formula (Ia) having the structure of Formula (Ib)

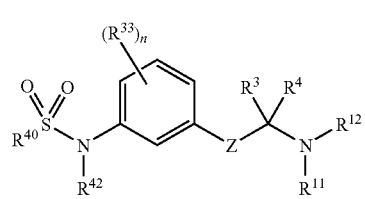

Formula (Ib)

wherein,
Z is —C(R$^9$)(R$^{10}$)—C(R$^1$)(R$^2$)— or —O—C(R$^{31}$)(R$^{32}$)—;
R$^{40}$ is selected from —C(R$^{16}$)(R$^{17}$)(R$^{18}$);
R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;
R$^{18}$ is selected from hydrogen, alkyl, alkoxy, hydroxy, halo or fluoroalkyl;
R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;
R$^{31}$ and R$^{32}$ are each independently selected from hydrogen, C$_1$-C$_5$ alkyl, or fluoroalkyl;
R$^3$ and R$^4$ are each independently selected from hydrogen or alkyl; or R$^3$ and R$^4$ together form an imino;
R$^7$ and R$^8$ are each independently selected from hydrogen, alkyl, carbocyclyl or —C(=O)R$^{13}$; or R$^7$ and R$^8$, together with the nitrogen atom to which they are attached, form an N-heterocyclyl;
R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ together form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;
R$^{11}$ and R$^{12}$ are each independently selected from hydrogen, alkyl, carbocyclyl or —C(=O)R$^{23}$; or R$^{11}$ and R$^{12}$, together with the nitrogen atom to which they are attached, form an N-heterocyclyl; and
each R$^{13}$, R$^{22}$ and R$^{23}$ is independently selected from alkyl, alkenyl, aryl, aralkyl, carbocyclyl, heteroaryl or heterocyclyl;

$R^6$, $R^{19}$, and $R^{34}$ are each independently hydrogen or alkyl;

each $R^{33}$ is independently selected from halogen, $OR^{34}$, alkyl, or fluoroalkyl; and n is 0, 1, 2, 3, or 4;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl.

In another embodiment is the compound of Formula (Ib) wherein, $R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo.

In another embodiment is the compound of Formula (Ib) having the structure of Formula (Ic):

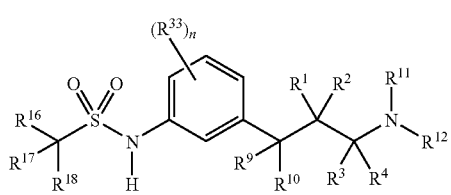

Formula (Ic)

wherein, $R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^3$ and $R^4$ are each independently selected from hydrogen or alkyl; or $R^3$ and $R^4$ together form an imino;

$R^7$ and $R^8$ are each independently selected from hydrogen, alkyl, carbocyclyl or —C(=O)$R^{13}$; or $R^7$ and $R^8$, together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ together form an oxo;

$R^{11}$ and $R^{12}$ are each independently selected from hydrogen, alkyl, carbocyclyl or —C(=O)$R^{23}$; or $R^{11}$ and $R^{12}$, together with the nitrogen atom to which they are attached, form an N-heterocyclyl;

each $R^{13}$, $R^{22}$ and $R^{23}$ is independently selected from alkyl, alkenyl, aryl, aralkyl, carbocyclyl, heteroaryl or heterocyclyl;

$R^6$, $R^{19}$ and $R^{34}$ are each independently hydrogen or alkyl;

$R^{20}$ and $R^{21}$ are each independently selected from hydrogen, alkyl, carbocyclyl, —C(=O)$R^{22}$; or $R^{20}$ and $R^{21}$, together with the nitrogen atom to which they are attached, form an N-heterocyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon to which they are attached form a carbocyclyl or heterocycle;

each $R^{33}$ is independently selected from halogen, $OR^{34}$, alkyl, or fluoroalkyl; and n is 0, 1, 2, 3, or 4; and $R^{18}$ is selected from a hydrogen, alkyl, alkoxy, hydroxy, halo or fluoroalkyl.

In another embodiment is the compound of Formula (Ic) wherein n is 0 and each of $R^{11}$ and $R^{12}$ is hydrogen. In a further embodiment is the compound wherein each of $R^3$, $R^4$, $R^{14}$ and $R^{15}$ is hydrogen. In a further embodiment is the compound wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$, together with the carbon to which they are attached form a carbocyclyl or heterocycle; and $R^{18}$ is selected from a hydrogen, alkoxy or hydroxy.

In a further embodiment is the compound wherein $R^{16}$ and $R^{17}$, together with the carbon to which they are attached, form a cyclopropyl, cyclobutyl, cyclopentyl, cyclohexyl, cycloheptyl, or cyclooctyl, and $R^{18}$ is hydrogen or hydroxy.

In another embodiment is the compound of Formula (Ic), wherein $R^{11}$ is hydrogen and $R^{12}$ is —C(=O)$R^{23}$, wherein $R^{23}$ is alkyl. In further embodiment is the compound wherein, $R^1$ and $R^2$ are each independently selected from hydrogen, halogen, $C_1$-$C_5$ alkyl, or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently selected from hydrogen or alkyl;

$R^{16}$ and $R^{17}$, together with the carbon atom to which they are attached, form a carbocyclyl; and $R^{18}$ is hydrogen, hydroxy or alkoxy.

In a further embodiment is the compound wherein n is 0;

$R^{16}$ and $R^{17}$, together with the carbon atom to which they are attached, form a cyclopentyl, cyclohexyl or cyclohexyl; and $R^{18}$ is hydrogen or hydroxy.

In a further embodiment is the compound of Formula (Ic), wherein $R^1$ and $R^2$ are each independently selected from hydrogen, halogen, $C_1$-$C_5$ alkyl or —$OR^6$;

$R^9$ and $R^{10}$ are each independently selected from hydrogen, halogen, alkyl, or —$OR^{19}$; or $R^9$ and $R^{10}$ together form an oxo;

$R^6$ and $R^{19}$ are each independently hydrogen or alkyl;

$R^{16}$ and $R^{17}$ is independently selected from $C_1$-$C_{13}$ alkyl; and $R^{18}$ is hydrogen, hydroxy or alkoxy.

In another embodiment is the compound of Formula (Ib) having the structure of Formula (Id):

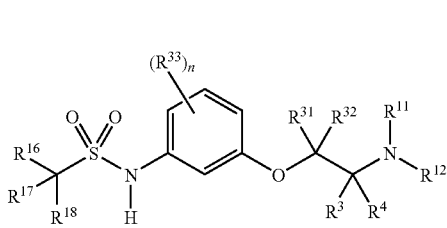

Formula (Id)

wherein, $R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{14}$ and $R^{15}$ are each independently selected from hydrogen or alkyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{18}$ is selected from a hydrogen, alkyl, alkoxy, hydroxy, halo or fluoroalkyl;

$R^{34}$ is hydrogen or alkyl; and each $R^{33}$ is independently selected from halogen, $OR^{34}$, alkyl, or fluoroalkyl; and n is 0, 1, 2, 3, or 4.

In another embodiment is the compound wherein n is 0 and each of $R^{11}$ and $R^{12}$ is hydrogen. In another embodiment is the compound wherein each $R^3$, $R^4$, $R^{14}$ and $R^{15}$ is hydrogen. In another embodiment is the compound wherein, $R^{31}$ and $R^{32}$ are each independently hydrogen, or $C_1$-$C_5$ alkyl; $R^{16}$ and $R^{17}$, together with the carbon atom to which they are attached, form a carbocyclyl; and $R^{18}$ is hydrogen, hydroxy, or alkoxy. In a further embodiment is the compound wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy. In a further embodiment is the compound wherein, $R^{31}$ and $R^{32}$ are each independently selected from hydrogen, or $C_1$-$C_5$ alkyl; and $R^{18}$ is hydrogen, hydroxy or alkoxy. In a further embodiment is the compound wherein $R^{31}$ and $R^{32}$ are each independently hydrogen, or $C_1$-$C_5$ alkyl; $R^6$ and $R^{19}$ are each independently hydrogen or alkyl; $R^{16}$ and $R^{17}$ is independently selected from $C_1$-$C_{13}$ alkyl; and $R^{18}$ is hydrogen, hydroxy or alkoxy.

In another embodiment is the compound of Formula (I) wherein, Z is a bond, —X—C($R^{31}$)($R^{32}$)—, or —X—C($R^{31}$)($R^{32}$)—C($R^1$)($R^2$)—; and X is —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—. In a further embodiment is the compound wherein, G is selected from —N($R^{42}$)—SO$_2$—$R^{40}$; and $R^{40}$ is selected from —C($R^{16}$)($R^{17}$)($R^{18}$), aryl, or heteroaryl.

In an additional embodiment is the compound of Formula (I) having the structure of Formula (Ie):

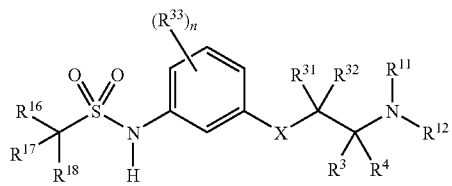

Formula (Ie)

wherein,

X is —S—, —S(=O)—, —S(=O)$_2$—, —N($R^{30}$)—, —C(=O)—, —C(=CH$_2$)—, —C(=N—NR$^{35}$)—, or —C(=N—OR$^{35}$)—;

$R^{31}$ and $R^{32}$ are each independently selected from hydrogen, $C_1$-$C_5$ alkyl, or fluoroalkyl;

$R^3$ and $R^4$ are each independently selected from hydrogen or alkyl; or $R^3$ and $R^4$ together form an imino;

$R^{11}$ and $R^{12}$ are each independently selected from hydrogen, alkyl, carbocyclyl, or —C(=O)$R^{23}$; or $R^{11}$ and $R^{12}$, together with the nitrogen atom to which they are attached, form an N-heterocyclyl;

$R^{23}$ is selected from alkyl, alkenyl, aryl, carbocyclyl, heteroaryl or heterocyclyl;

$R^{16}$ and $R^{17}$ are each independently selected from hydrogen, $C_1$-$C_{13}$ alkyl, halo or fluoroalkyl; or $R^{16}$ and $R^{17}$, together with the carbon atom to which they are attached, form a carbocyclyl or heterocycle;

$R^{30}$, $R^{34}$ and $R^{35}$ are each independently hydrogen or alkyl;

$R^{18}$ is selected from a hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In a further embodiment is the compound of Formula (Ie) wherein n is 0 and each $R^{11}$ and $R^{12}$ is hydrogen. In a further embodiment is the compound wherein each $R^3$, $R^4$, $R^{14}$ and $R^{15}$ is hydrogen. In a further embodiment is the compound wherein, $R^{31}$ and $R^{32}$ are each independently hydrogen, or $C_1$-$C_5$ alkyl; $R^{16}$ and $R^{17}$, together with the carbon atom to which they are attached, form a carbocyclyl or heterocycle; and $R^{18}$ is hydrogen, hydroxy, or alkoxy. In a further embodiment is the compound wherein $R^{16}$ and $R^{17}$, together with the carbon atom to which they are attached form a cyclopropyl, cyclobutyl, cyclopentyl, cyclohexyl, cycloheptyl or cyclooctyl and $R^{18}$ is hydrogen or hydroxy. In a further embodiment is the compound wherein, $R^{31}$ and $R^{32}$ are each independently selected from hydrogen, or $C_1$-$C_5$ alkyl; $R^{16}$ and $R^{17}$ is independently selected from $C_1$-$C_{13}$ alkyl; and $R^{18}$ is hydrogen, hydroxy or alkoxy.

In an additional embodiment is the compound of Formula (Ia) wherein, G is selected from —N($R^{42}$)C(=O)—$R^{40}$, —N($R^{42}$)—C($R^{42}$)($R^{42}$)—$R^{40}$; $R^{40}$ is selected from —C($R^{16}$)($R^{17}$)($R^{18}$), aryl, or heteroaryl; each $R^{42}$ is independently selected from hydrogen or alkyl. In a further embodiment is the compound wherein, G is selected from —N($R^{42}$)C(=O)—$R^{40}$, —N($R^{42}$)—C($R^{42}$)—$R^{40}$; $R^{40}$ is selected from —C($R^{16}$)($R^{17}$)($R^{18}$), aryl, or heteroaryl; each $R^{42}$ is independently selected from hydrogen or alkyl. In a further embodiment is the compound wherein, $R^{42}$ is a hydrogen; $R^{40}$ is selected from —C($R^{16}$)($R^{17}$)($R^{18}$); $R^{16}$ and $R^{17}$ together with the carbon atom to which they are attached, form a carbocyclyl or heterocycle; and $R^{18}$ is hydrogen, hydroxy, or alkoxy. In a further embodiment is the compound wherein, $R^{42}$ is a hydrogen; $R^{40}$ is selected from —C($R^{16}$)($R^{17}$)($R^{18}$); $R^{16}$ and $R^{17}$, together with the carbon atom to which they are attached, form a carbocyclyl or heterocycle; and $R^{18}$ is hydrogen, hydroxy, or alkoxy.

In another embodiment is the compound of Formula (Ia) wherein,

G is selected from —N($R^{42}$)—C(=O)—N($R^{43}$)($R^{43}$), or —N($R^{42}$)—C(=S)—N($R^{43}$)($R^{43}$);

each $R^{43}$ is independently selected from hydrogen, alkyl, cycloalkyl, aralkyl, C-attached heterocyclyl, aryl, or heteroaryl; or two $R^{43}$ groups, together with the nitrogen to which they are attached, may form a heterocyclyl;

each $R^{42}$ is independently selected from hydrogen or alkyl.

In another embodiment is the compound Formula (Ia) wherein,

G is selected from —N($R^{42}$)—C(=O)—N($R^{43}$)($R^{43}$), or —N($R^{42}$)—C(=S)—N($R^{43}$)($R^{43}$);

each $R^{43}$ is independently selected from hydrogen, alkyl, cycloalkyl, aralkyl, C-attached heterocyclyl, aryl, or heteroaryl; or two $R^{43}$ groups, together with the nitrogen to which they are attached, may form a heterocyclyl; and $R^{42}$ is hydrogen.

In a further embodiment is the compound wherein, each $R^{43}$ is independently selected from hydrogen, alkyl, cycloalkyl, aralkyl, C-attached heterocyclyl, aryl, or heteroaryl; or two $R^{43}$ groups, together with the nitrogen to which they are attached, may form a heterocyclyl; and $R^{42}$ is hydrogen.

In a further embodiment is the compound wherein, $R^{40}$ is selected from —$C(R^{16})(R^{17})(R^{18})$;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl.

In another embodiment is the compound of Formula (I) wherein one, more than one, or all of the non-exchangeable $^1H$ atoms have been substituted with $^2H$ atoms.

In a specific embodiment, the compound of Formula (I) is selected from the group consisting of:

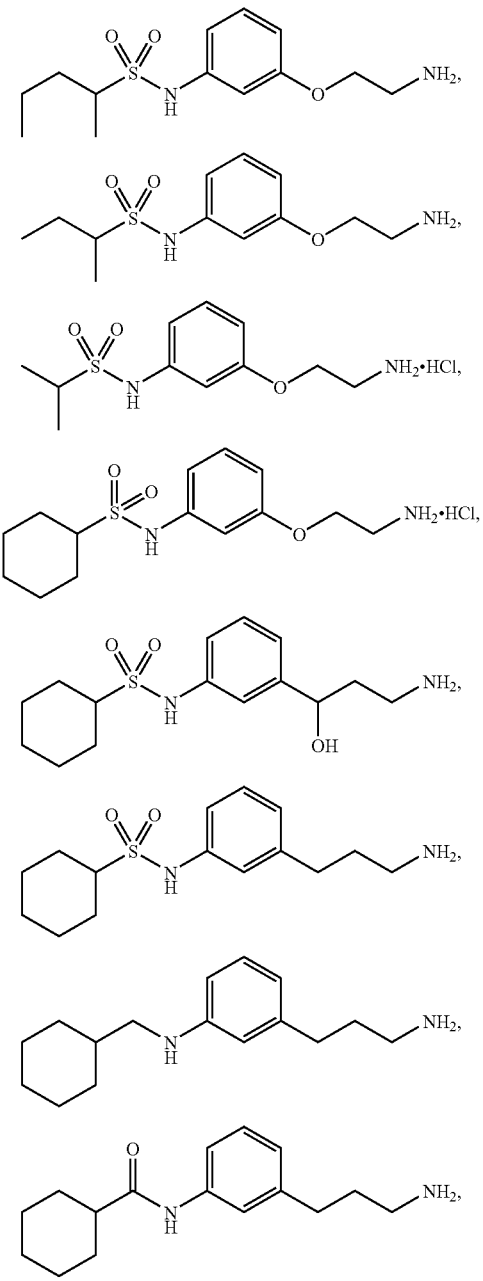

-continued

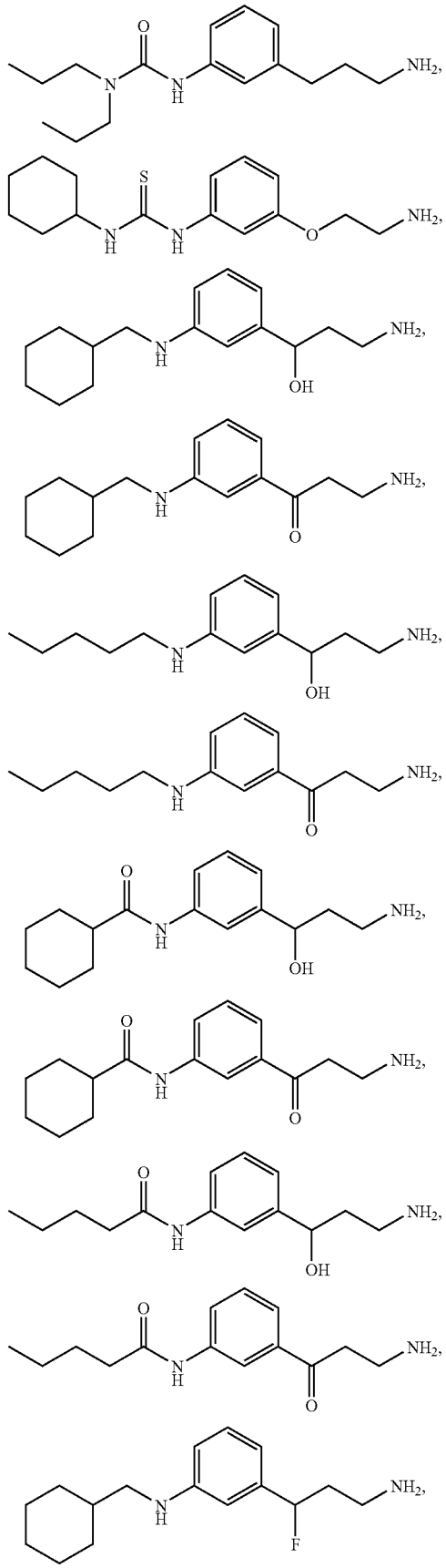

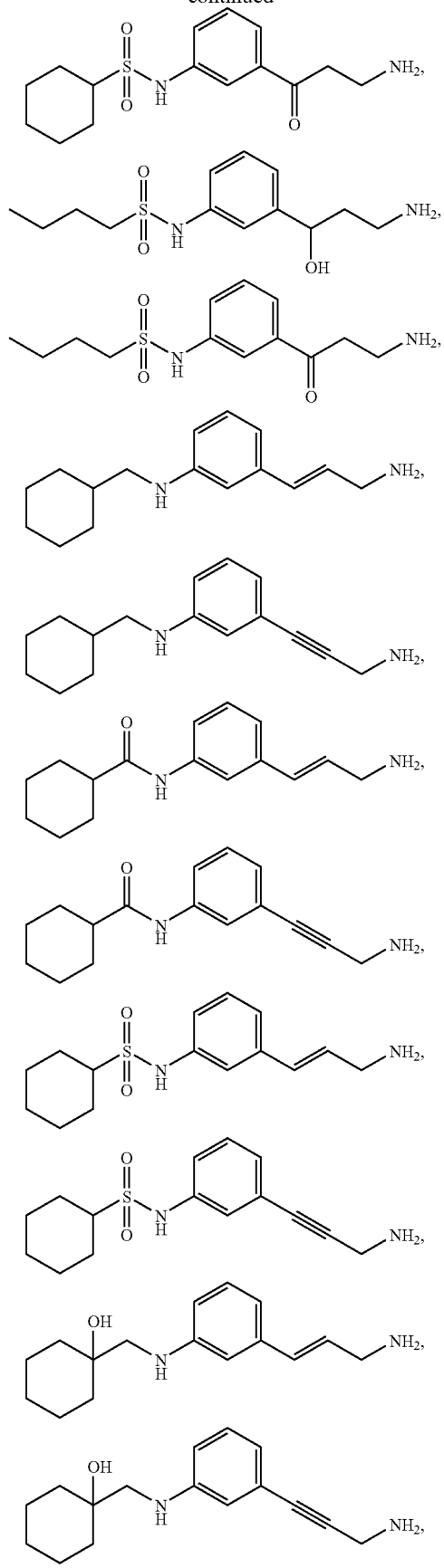
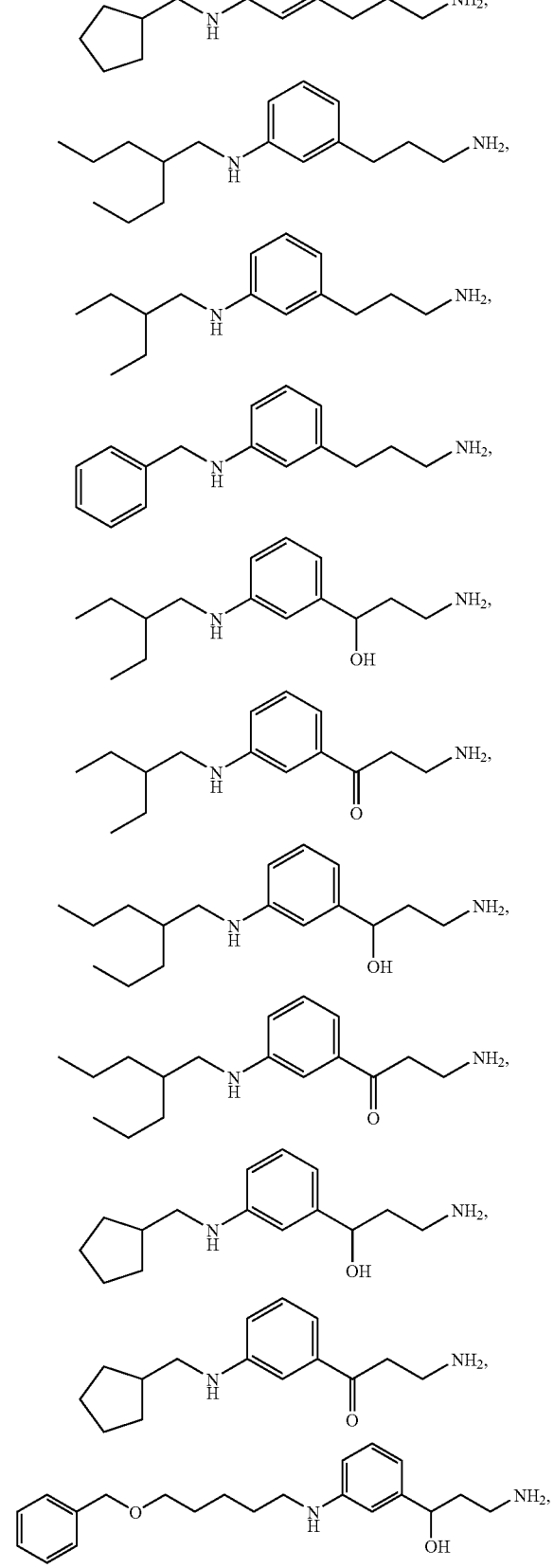

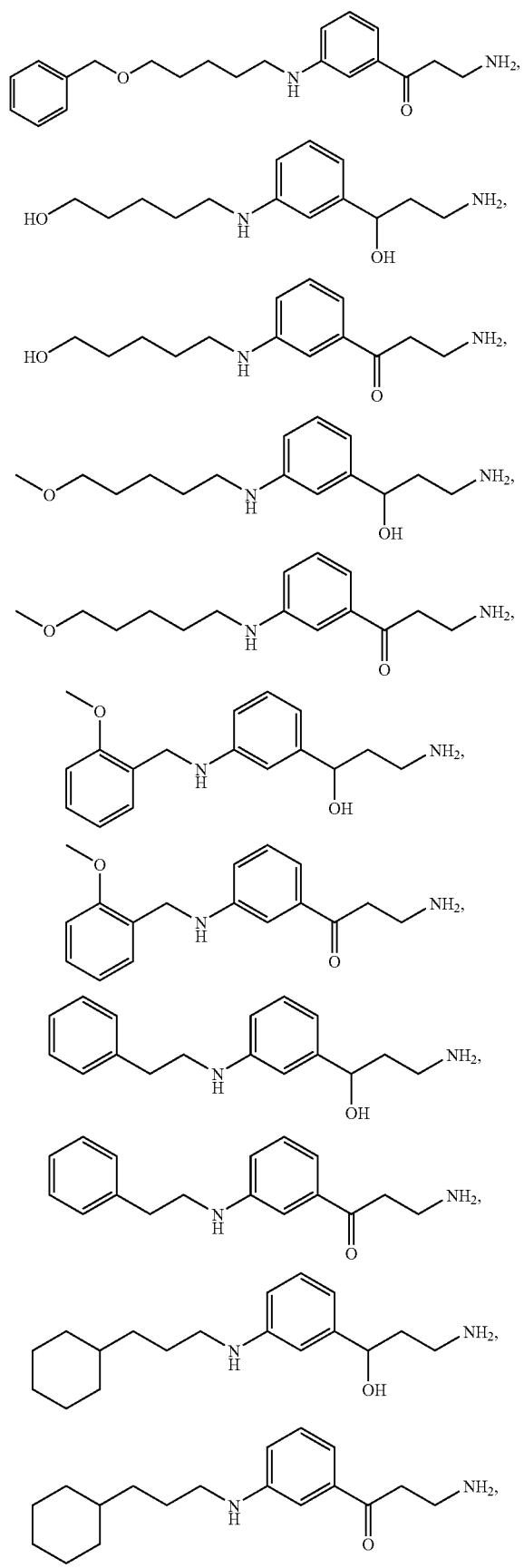
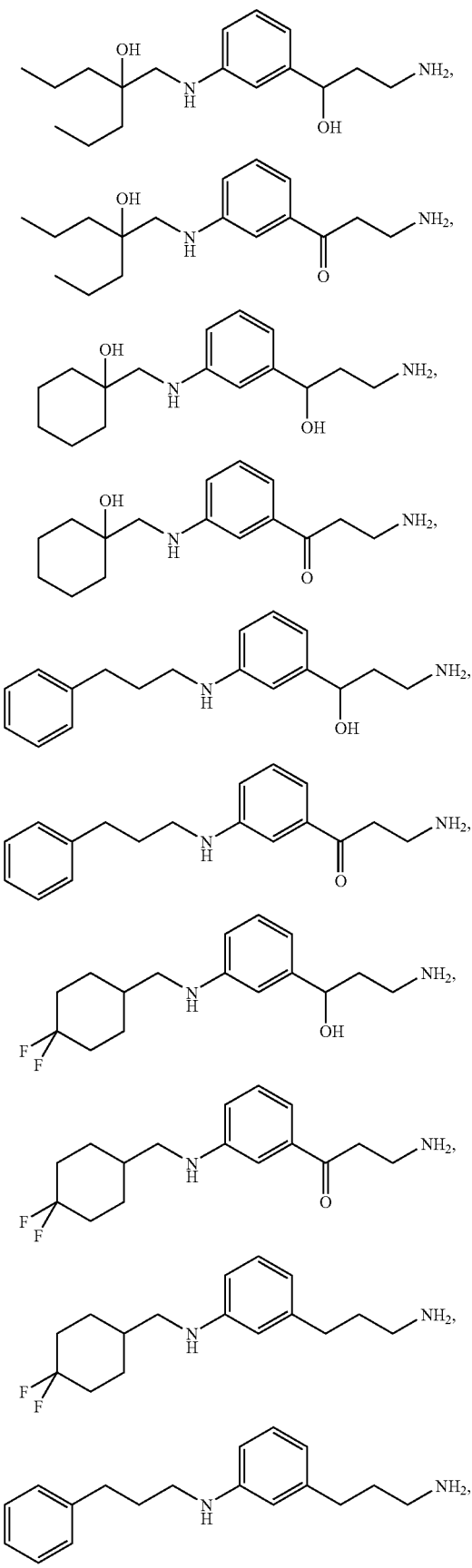

57
-continued
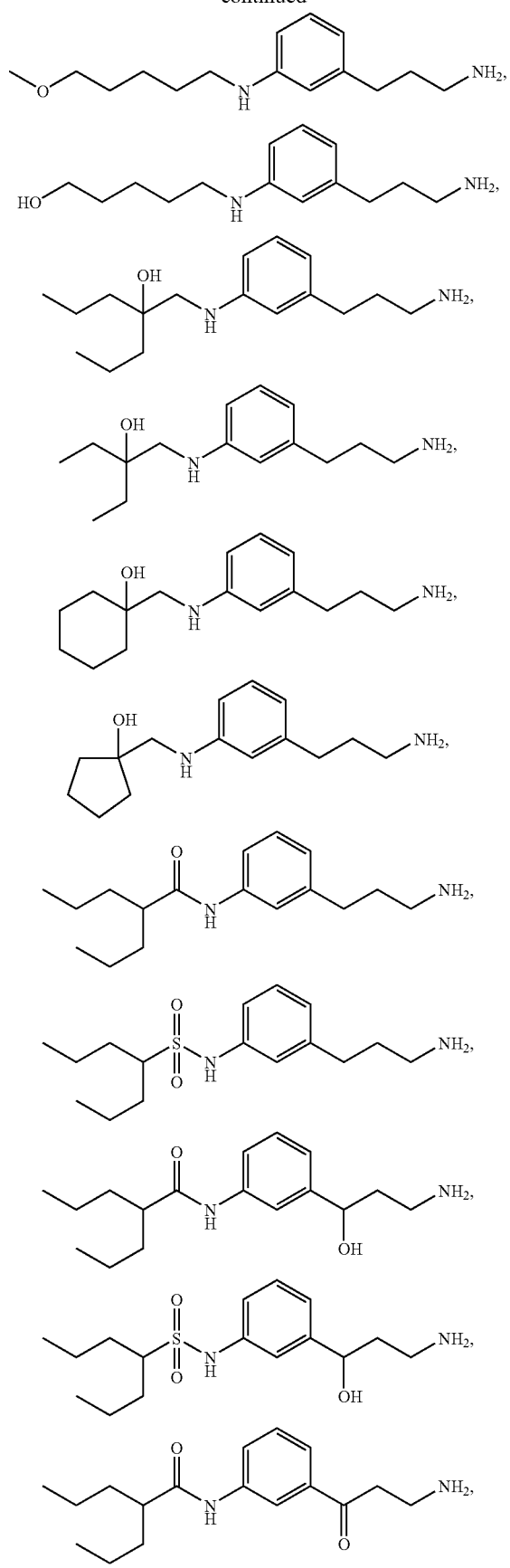
58
-continued
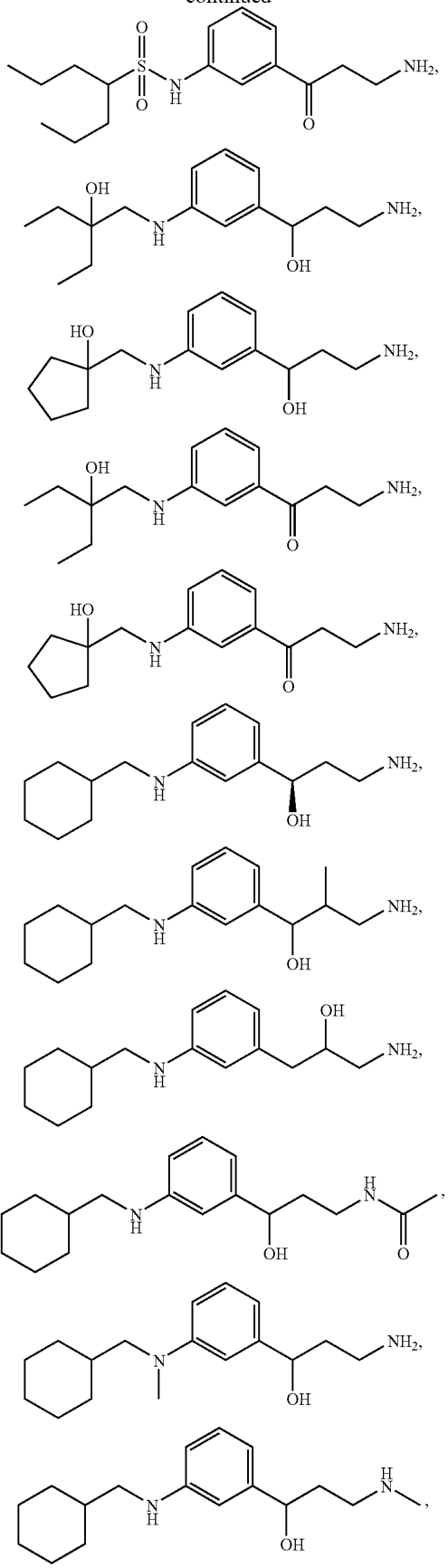

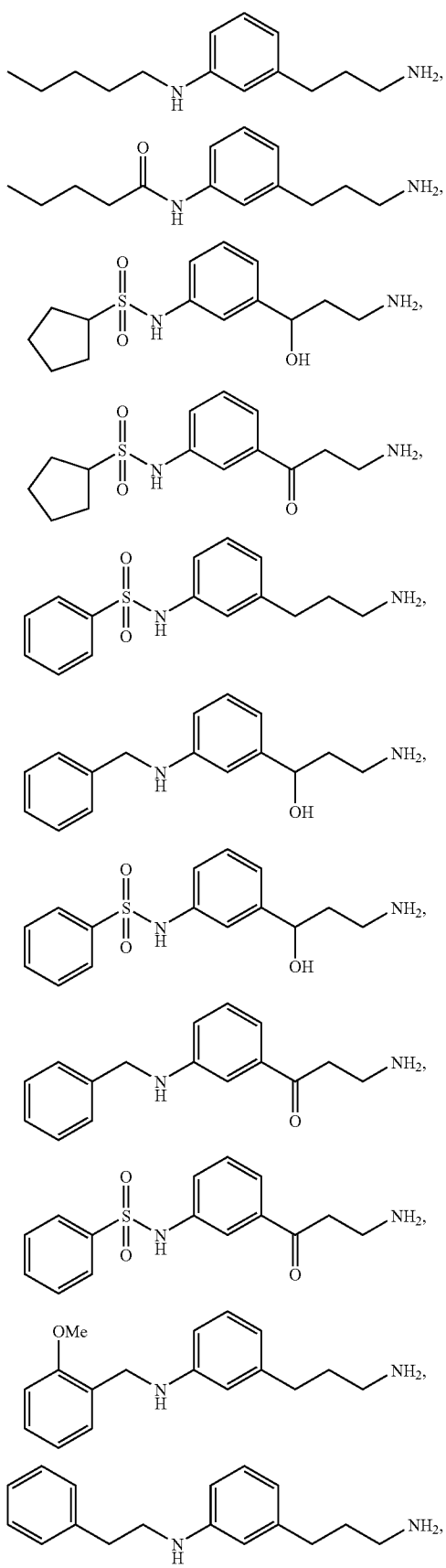

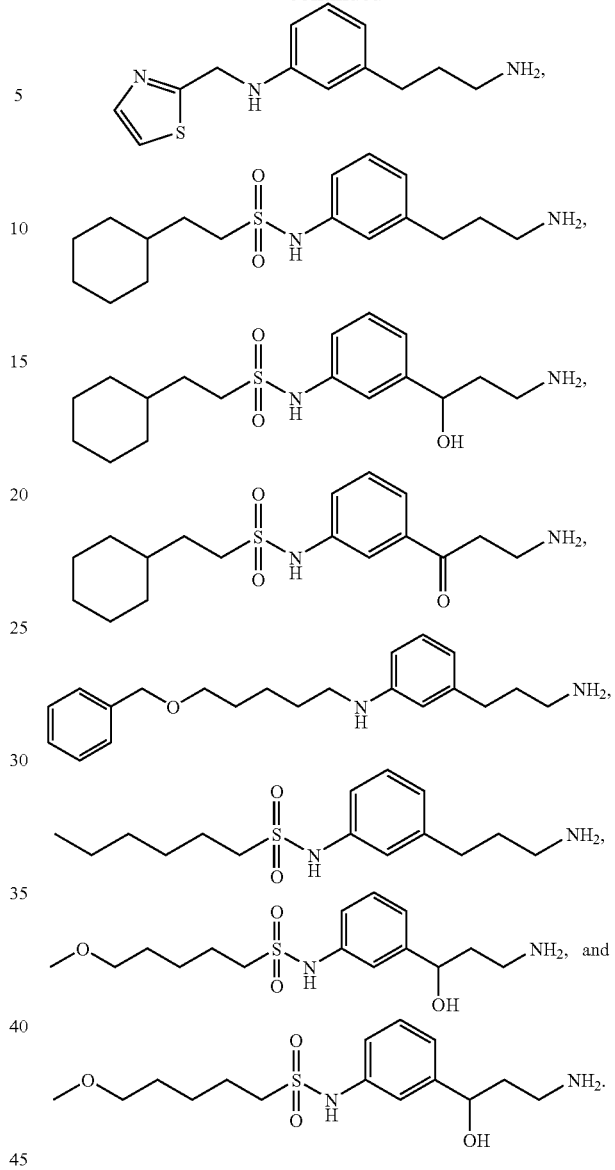

Additional Compounds of the Invention

In one embodiment is a compound having a structure of Formula (II):

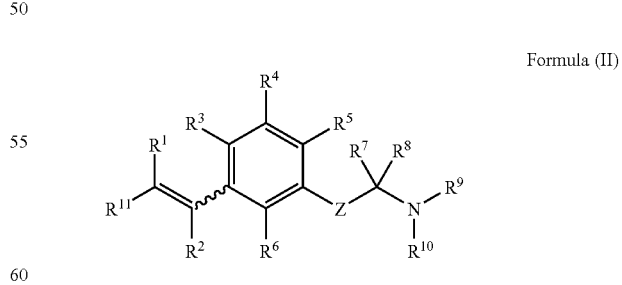

Formula (II)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:

$R^1$ and $R^2$ are each the same or different and independently hydrogen or alkyl;

$R^3$, $R^4$, $R^5$ and $R^6$ are each the same or different and independently hydrogen, halogen, nitro, —$NH_2$, —$NHR^{13}$, —$N(R^{13})_2$, —$OR^{12}$, alkyl or fluoroalkyl;

$R^7$ and $R^8$ are each the same or different and independently hydrogen or alkyl; or $R^7$ and $R^8$ together with the carbon atom to which they are attached, form a carbocyclyl or heterocyclyl; or $R^7$ and $R^8$ together form an imino;

$R^9$ is hydrogen, alkyl, carbocyclyl, heterocyclyl, —C(=O)$R^{13}$, —$SO_2R^{13}$, —$CO_2R^{13}$, —$CONH_2$, —$CON(R^{13})_2$ or —CON(H)$R^{13}$;

$R^{10}$ is hydrogen or alkyl; or $R^9$ and $R^{10}$, together with the nitrogen atom to which they are attached, form an N-heterocyclyl;

$R^{11}$ is alkyl, alkenyl, aryl, carbocyclyl, heteroaryl or heterocyclyl;

each $R^{12}$ is independently selected from hydrogen or alkyl;

each $R^{13}$ is independently selected from alkyl, carbocyclyl, heterocyclyl, aryl or heteroaryl;

Z is a bond, Y or W—Y, wherein
W is —$C(R^{14})(R^{15})$—, —O—, —S—, —S(=O)—, —S(=O)$_2$— or —N($R^{12}$)—;
Y is —$C(R^{16})(R^{17})$— or —$C(R^{16})(R^{17})$—$C(R^{21})(R^{22})$—;
$R^{14}$ and $R^{15}$ are each the same or different and independently hydrogen, halogen, alkyl, fluoroalkyl, —$OR^{12}$, —$NR^{18}R^{19}$, carbocyclyl or heterocyclyl; or $R^{14}$ and $R^{15}$ together form an oxo, an imino, an oximo, or a hydrazino;
$R^{16}$ and $R^{17}$ are each the same or different and independently hydrogen, halogen, alkyl, fluoroalkyl, —$OR^{12}$, —$NR^{18}R^{19}$, carbocyclyl or heterocyclyl; or $R^{16}$ and $R^{17}$ together form an oxo; or
optionally, $R^{14}$ and $R^{16}$ together form a direct bond to provide a double bond connecting W and Y; or optionally, $R^{14}$ and $R^{16}$ together form a direct bond, and $R^{15}$ and $R^{17}$ together form a direct bond to provide a triple bond connecting W and Y;
each $R^{18}$ and $R^{19}$ is independently selected from hydrogen, alkyl, carbocyclyl, or —C(=O)$R^{13}$, —$SO_2R^{13}$, —$CO_2R^{13}$, —$CONH_2$, —$CON(R^{13})_2$ or —CON(H)$R^{13}$; or $R^{18}$ and $R^{19}$, together with the nitrogen atom to which they are attached, form an N-heterocyclyl;
$R^{21}$ and $R^{22}$ are each the same or different and independently hydrogen, halogen, alkyl, fluoroalkyl, —$OR^{12}$, —$NR^{18}R^{19}$, carbocyclyl or heterocyclyl;
provided that when $R^{11}$ is phenyl, the compound of Formula (A) is not:
2-amino-N-[2-methoxy-5-[(1Z)-2-(3,4,5-trimethoxyphenyl)ethenyl]phenyl]acetamide;
(2S,3R)-amino-3-hydroxy-N-[2-methoxy-5-[(1Z)-2-(3,4,5-trimethoxyphenyl)-ethenyl]phenyl]-butanamide;
L-glutamic acid, 1-[2-methoxy-5-[(1Z)-2-(3,4,5-trimethoxyphenyl)ethenyl]phenyl]ester; glycine, 3-hydroxy-5-[(1E)-2-(4-hydroxyphenyl)ethenyl]phenyl ester;
(2S)-2-amino-N-[2-methoxy-5-[(1Z)-2-(3,4,5-trimethoxyphenyl)ethenyl]phenyl]propanamide;
(2S)-2-amino-3-hydroxy-N-[2-methoxy-5-[(1Z)-2-(3,4,5-trimethoxyphenyl)ethenyl]phenyl]propanamide;
(2S)-2-amino-N-[2-methoxy-5-[(1Z)-2-(3,4,5-trimethoxyphenyl)ethenyl]phenyl]-4-methyl-pentanamide;
(2S)-2-amino-N-[2-methoxy-5-[(1Z)-2-(3,4,5-trimethoxyphenyl)ethenyl]phenyl]-3-methyl-butanamide; or
2-amino-N-[2-methoxy-5-[(1Z)-2-(3,4,5-trimethoxyphenyl)ethenyl]phenylbutanamide; and wherein
the compound of Formula (II) is isotopically enriched.

In another embodiment is the compound of Formula (II) having one, more than one, or all of the non exchangeable $^1H$ atoms are replaced with $^2H$ atoms.

In another embodiment is the compound of Formula (II) having the structure of Formula (IIa):

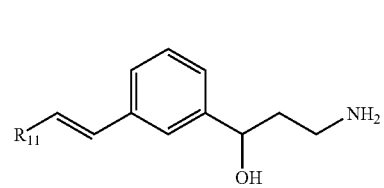

Formula (IIa)

wherein $R^{11}$ is selected from:

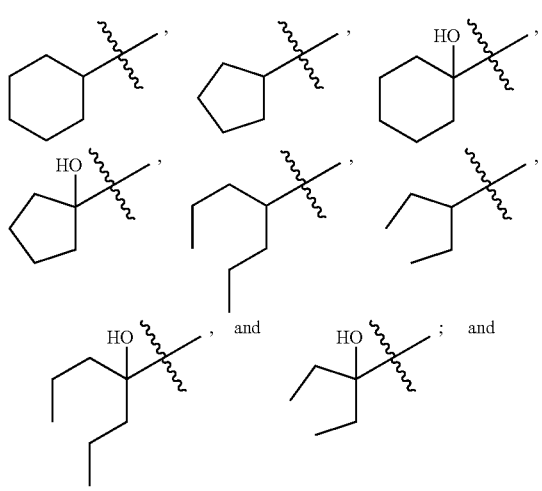

one, more than one, or all of the non-exchangeable $^1H$ atoms are replaced with $^2H$ atoms.

In another embodiment is the compound of Formula (IIa) selected from:

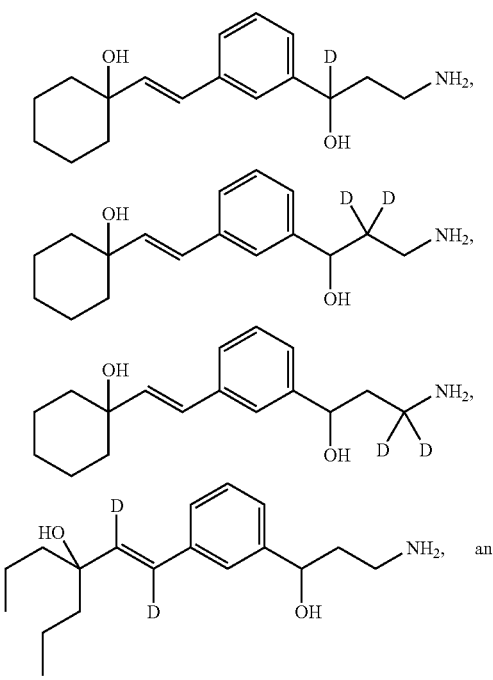

-continued

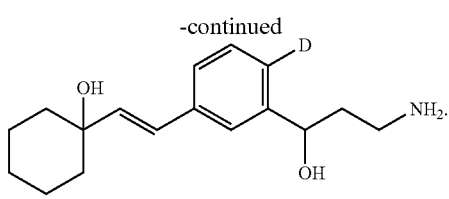

One embodiment provides a compound having a structure of Formula (IIa):

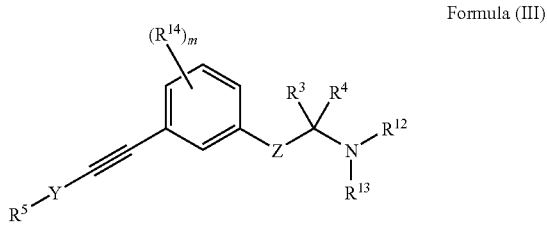

Formula (III)

as a tautomer or a mixture of tautomers, or as a pharmaceutically acceptable salt, hydrate, solvate, N-oxide, stereoisomer, geometric isomer or prodrug thereof, wherein:

m is 0, 1, 2 or 3;

Z is a bond, —C($R^1$)($R^2$)—, —X—C($R^{21}$)($R^{22}$)—, —C($R^{23}$)($R^{24}$)—C($R^1$)($R^2$)— or —C($R^{23}$)($R^{24}$)—C($R^{25}$)($R^{26}$)—C($R^1$)($R^2$)—, —X—C($R^{21}$)($R^{22}$)—C($R^1$)($R^2$)—, —C($R^{32}$)($R^{33}$)—X—C($R^{21}$)($R^{22}$)—;

X is —O—, —S—, —S(=O)—, —S(=O)$_2$—, —C($R^{31}$)—, —C(=O)—, —C(=CH$_2$)—, —C(=N—N$R^{35}$)—, or —C(=N—O$R^{35}$)—;

Y is a bond, —C($R^{27}$)($R^{28}$)—, or —C($R^{27}$)($R^{28}$)—C($R^{29}$)($R^{30}$)—;

$R^1$ and $R^2$ are each independently selected from hydrogen, halogen, $C_1$-$C_5$ alkyl, fluoroalkyl, —O$R^6$ or —N$R^7R^8$; or $R^1$ and $R^2$ together form an oxo;

$R^{21}$, $R^{22}$, $R^{32}$ and $R^{33}$ are each independently selected from hydrogen, $C_1$-$C_5$ alkyl, or fluoroalkyl;

$R^{23}$ and $R^{24}$ are each independently selected from hydrogen, halogen, $C_1$-$C_5$ alkyl, fluoroalkyl, —O$R^6$, —N$R^7R^8$; or $R^{23}$ and $R^{24}$ together form an oxo; or optionally, $R^{23}$ and an adjacent $R^1$ together form a direct bond to provide a double bond; or optionally, $R^{23}$ and an adjacent $R^1$ together form a direct bond, and $R^{24}$ and an adjacent $R^2$ together form a direct bond to provide a triple bond;

$R^{25}$ and $R^{26}$ are each independently selected from hydrogen, halogen, $C_1$-$C_5$ alkyl, fluoroalkyl, —O$R^6$ or —N$R^7R^8$; or $R^{25}$ and $R^{26}$ together form an oxo;

$R^3$ and $R^4$ are each independently selected from hydrogen, alkyl, heteroalkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^5$ is alkyl, heteroalkyl, alkenyl, heteroalkenyl, aryl, carbocyclyl, heteroaryl or heterocyclyl;

each $R^6$ is the same or different and independently hydrogen or $C_1$-$C_5$ alkyl;

each $R^7$ and each $R^8$ are each the same or different and independently hydrogen, alkyl, carbocyclyl, heteroalkyl, heterocycloalkyl, aryl, heteroaryl, —C(=O)$R^9$, SO$_2R^9$, CO$_2R^9$, SO$_2$NH$_2$, SO$_2$NH$R^9$ or SO$_2$N($R^9$)$_2$; or $R^7$ and $R^8$, together with the nitrogen atom to which they are attached, form an N-heterocyclyl;

each $R^9$ is the same or different and each is independently alkyl, alkenyl, aryl, carbocyclyl, heteroaryl or heterocyclyl;

$R^{12}$ and $R^{13}$ are the same or different and independently hydrogen, alkyl, heteroalkyl, carbocyclyl, heterocyclyl, aryl, heteroaryl, —C(=O)$R^9$, SO$_2R^9$, CO$_2R^9$, SO$_2$NH$_2$, SO$_2$NH$R^9$ or SO$_2$N($R^9$)$_2$; or $R^{12}$ and $R^{13}$ together with the nitrogen atom to which they are attached, form an N-heterocyclyl; and each $R^{14}$ is the same or different and independently alkyl, halo, fluoroalkyl or —O$R^6$;

each $R^{27}$, $R^{28}$, $R^{29}$ and $R^{31}$ are the same or different and independently hydrogen, alkyl or —O$R^6$; and $R^{30}$ and $R^{35}$ are each independently hydrogen or $C_1$-$C_5$ alkyl; and wherein the compound of Formula (III) is isotopically enriched.

Another embodiment provides the compound of Formula (III) having one, more than one or all of the non-exchangeable $^1$H atoms replaced with $^2$H atoms.

Another embodiment provides the compound of Formula (IIIa):

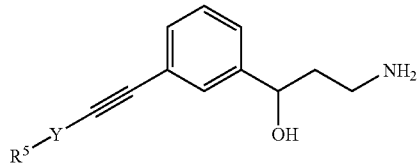

Formula (IIIa)

wherein Y is a bond;

$R^5$ is selected from:

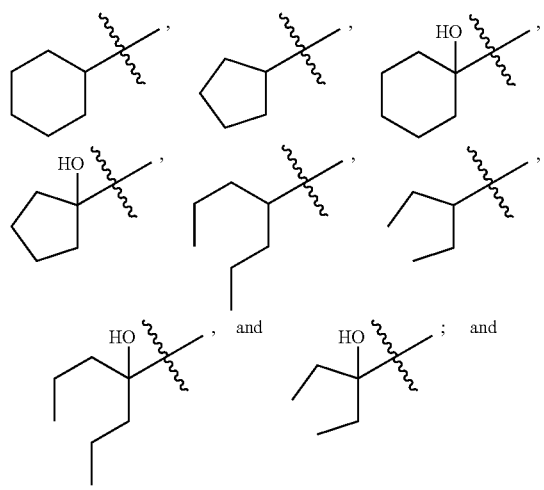

one, more than one, or all of the non-exchangeable $^1$H atoms are replaced with $^2$H atoms.

Another embodiment provides the compound of Formula (III) selected from:

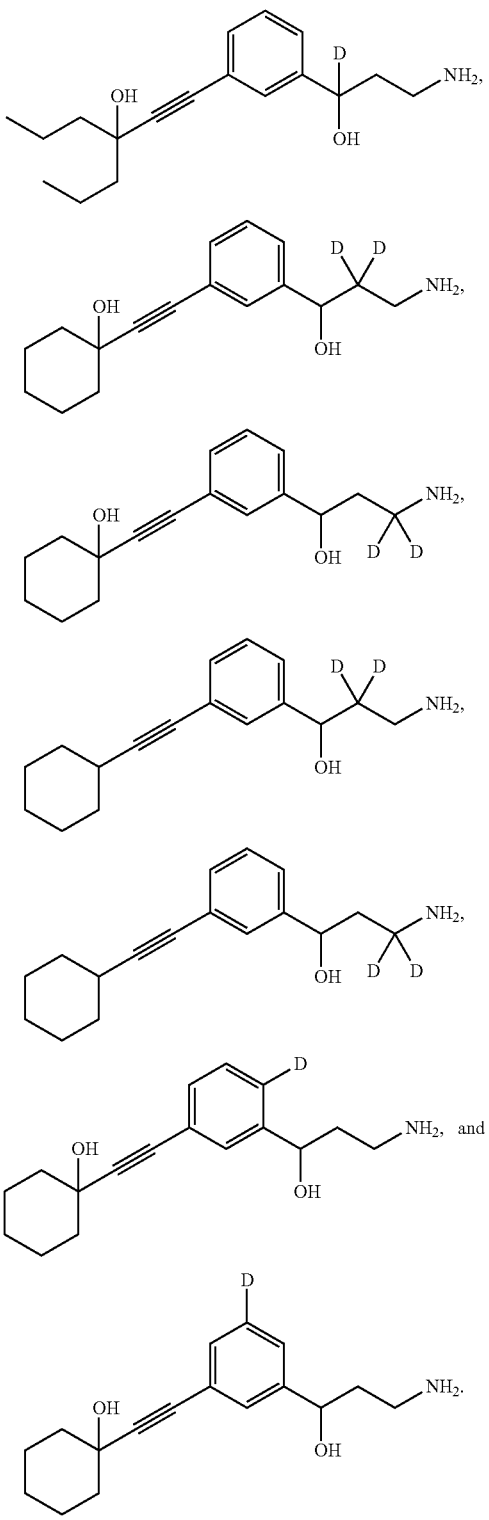

One embodiment provides a compound of Formula (IV) or tautomer, stereoisomer, geometric isomer or a pharmaceutically acceptable solvate, hydrate, salt, N-oxide or prodrug thereof:

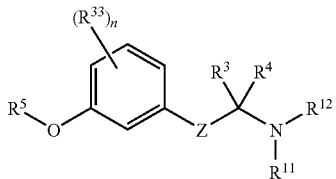

wherein,

Z is —C(R$^9$)(R$^{10}$)—C(R$^1$)(R$^2$)—, —C(R$^{31}$)(R$^{32}$)—, —C(R$^9$)(R$^{10}$)—C(R$^1$)(R$^2$)—C(R$^{36}$)(R$^{37}$)— or —X—C(R$^{31}$)(R$^{32}$)—C(R$^1$)(R$^2$)—;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^5$ is C$_5$-C$_{15}$ alkyl or carbocyclyalkyl;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$, R$^{29}$ is independently selected from hydrogen, alkyl, alkenyl, fluoroalkyl, aryl, heteroaryl, carbocyclyl or heterocyclyl;

each R$^{33}$ is independently selected from halogen, OR$^{34}$, alkyl, or fluoroalkyl; and n is 0, 1, 2, 3, or 4; with the provision that R$^5$ is not 2-(cyclopropyl)-1-ethyl or an unsubstituted normal alkyl; and wherein the compound of Formula (IV) is isotopically enriched.

Another embodiment provides the compound of Formula (IV) has one, more than one or all of the non-exchangeable $^1$H atoms replaced with $^2$H atoms.

Another embodiment provides the compound having the structure of Formula (IVa):

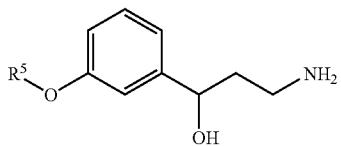

Formula (IVa)

wherein Y is a bond;
R$^5$ is selected from:

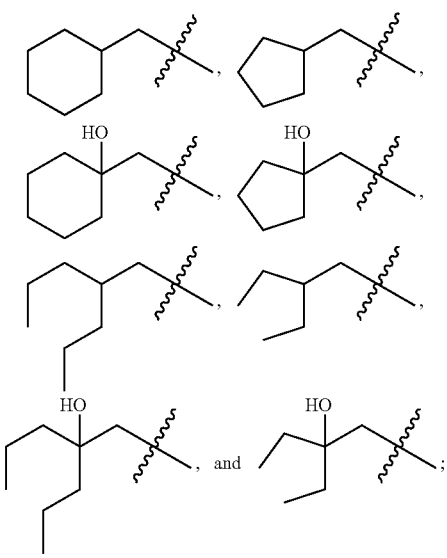

and one, more than one, or all of the non-exchangeable $^1$H atoms are replaced with $^2$H atoms.

Another embodiment provides the compound selected from:

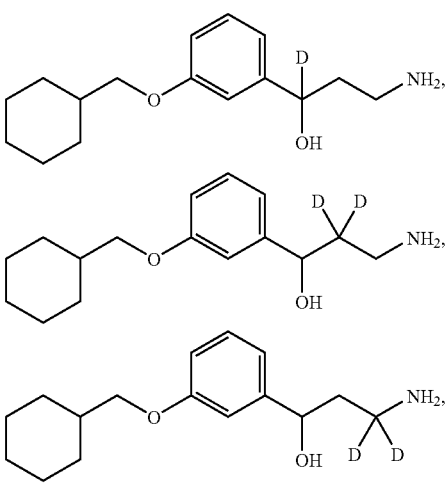

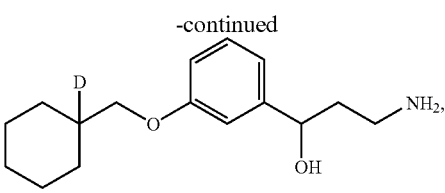

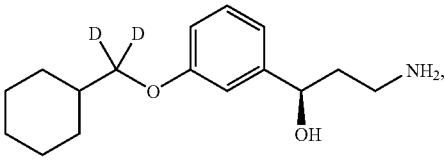

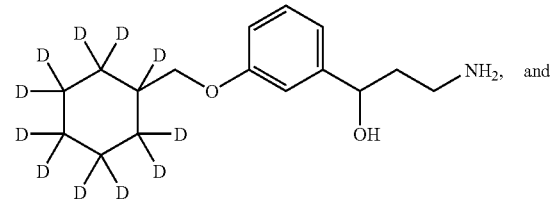

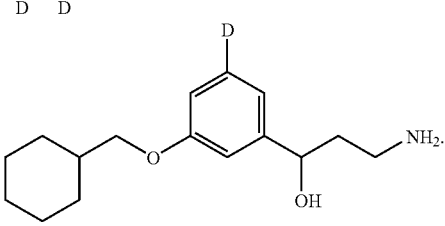

One embodiment provides a method for treating an ophthalmic disease or disorder in a subject, comprising administering to the subject a compound of Formula (I) or tautomer, stereoisomer, geometric isomer or a pharmaceutically acceptable solvate, hydrate, salt, N-oxide or prodrug thereof:

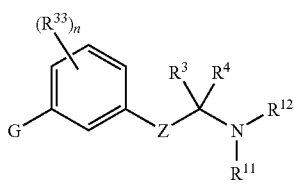

Formula (I)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)—, —C(R$^{38}$)(R$^{39}$)—X—C(R$^{31}$)(R$^{32}$)—, or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —N(R$^{42}$)—SO$_2$—R$^{40}$, —N(R$^{42}$)C(=O)—R$^{40}$, —N(R$^{42}$)C(=O)—OR$^{40}$, —N(R$^{42}$)—C(R$^{42}$)(R$^{42}$)—R$^{40}$, —N(R$^{42}$)—C(=O)—N(R$^{43}$)(R$^{43}$), or —N(R$^{42}$)—C(=S)—N(R$^{43}$)(R$^{43}$);

R$^{40}$ is selected from —C(R$^{16}$)(R$^{17}$)(R$^{18}$), aryl, or heteroaryl;

each R$^{42}$ is independently selected from hydrogen, alkyl or aryl;

each R$^{43}$ is independently selected from hydrogen, alkyl, cycloalkyl, aralkyl, alkenyl, alkynyl, C-attached heterocyclyl, aryl, or heteroaryl; or two R$^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)$NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

Another embodiment provides a method for treating an ophthalmic disease or disorder wherein the ophthalmic disease or disorder is age-related macular degeneration or Stargardt's macular dystrophy.

In a further embodiment is the method wherein the ophthalmic disease or disorder is a retinal disease or disorder. In an additional embodiment is the method wherein the retinal disease or disorder is age-related macular degeneration or Stargardt's macular dystrophy. In an additional embodiment is the method wherein the ophthalmic disease or disorder is selected from retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS. In an additional embodiment is the method wherein the ophthalmic disease or disorder is selected from diabetic retinopathy, diabetic maculopathy, retinal blood vessel occlusion, retinopathy of prematurity, or ischemia reperfusion related retinal injury.

One embodiment provides a method for treating an ophthalmic disease or disorder in a subject, comprising administering to the subject a compound of Formula (II), (IIa), (III), (IIIa), (IV), or (IVa) as described herein, or tautomer, stereoisomer, geometric isomer or a pharmaceutically acceptable solvate, hydrate, salt, N-oxide or prodrug thereof. Another embodiment provides a method for treating an ophthalmic disease or disorder wherein the ophthalmic disease or disorder is age-related macular degeneration or Stargardt's macular dystrophy.

In an additional embodiment is the method of inhibiting at least one visual cycle trans-cis isomerase in a cell comprising contacting the cell with a compound of Formula (I) as described herein, thereby inhibiting the at least one visual cycle trans-cis isomerase. In a further embodiment is the method wherein the cell is a retinal pigment epithelial (RPE) cell.

In a further embodiment is the method of inhibiting at least one visual cycle trans-cis isomerase in a subject comprising administering to the subject the pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

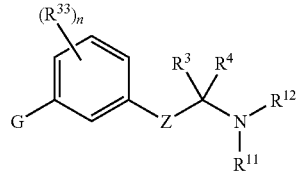

Formula (I)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)—, —C($R^{38}$)($R^{39}$)—X—C($R^{31}$)($R^{32}$)—, or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=$CH_2$)—, —C(=N—$NR^{35}$)—, or —C(=N—$OR^{35}$)—;

G is selected from —N($R^{42}$)—$SO_2$—$R^{40}$, —N($R^{42}$)C(=O)—$R^{40}$, —N($R^{42}$)C(=O)—$OR^{40}$, —N($R^{42}$)—C($R^{42}$)($R^{42}$)—$R^{40}$, —N($R^{42}$)—C(=O)—N($R^{43}$)($R^{43}$), or —N($R^{42}$)—C(=S)—N($R^{43}$)($R^{43}$);

$R^{40}$ is selected from —C($R^{16}$)($R^{17}$)($R^{18}$), aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —$C(=O)R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —$C(=O)R^{23}$, —$C(NH)NH_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —$C(=O)R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$, $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In a further embodiment is the method wherein the subject is human. In a further embodiment is the method wherein accumulation of lipofuscin pigment is inhibited in an eye of the subject. In a further embodiment is the method wherein the lipofuscin pigment is N-retinylidene-N-retinyl-ethanolamine (A2E). In a further embodiment is the method wherein degeneration of a retinal cell is inhibited. In a further embodiment is the method wherein the retinal cell is a retinal neuronal cell. In a further embodiment is the method wherein the retinal neuronal coil is a photoreceptor cell, an amacrine cell, a horizontal cell, a ganglion cell, or a bipolar cell. In a further embodiment is the method wherein the retinal cell is a retinal pigment epithelial (RPE) cell.

In an additional embodiment is a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In an additional embodiment, the compound is a non-retinoid compound. In a further embodiment is the compound, wherein the compound inhibits 11-cis-retinol production with an $IC_{50}$ of about 0.1 µM or less. In a further embodiment is the compound, wherein the compound inhibits 11-cis-retinol production with an $IC_{50}$ of about 0.01 µM or less.

In an additional embodiment is a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the non-retinoid compound wherein the $ED_{50}$ value is measured after administering a single dose of the compound to said subject for about 2 hours or longer.

In a further embodiment is the non-retinoid compound wherein the structure of the non-retinoid compound corresponds to Formula (I) or tautomer, stereoisomer, geometric isomer or a pharmaceutically acceptable solvate, hydrate, salt, N-oxide or prodrug thereof:

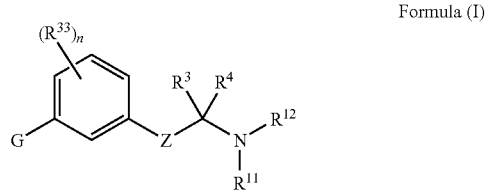

Formula (I)

wherein,

Z is a bond, —$C(R^1)(R^2)$—, —$C(R^9)(R^{10})$—$C(R^1)(R^2)$—, —X—$C(R^{31})(R^{32})$—, —$C(R^9)(R^{10})$—$C(R^1)(R^2)$—$C(R^{36})(R^{37})$—, —$C(R^{38})(R^{39})$—X—$C(R^{31})(R^{32})$—, or —X—$C(R^{31})(R^{32})$—$C(R^1)(R^2)$—;

X is —O—, —S—, —$S(=O)$—, —$S(=O)_2$—, —$N(R^{30})$—, —$C(=O)$—, —$C(=CH_2)$—, —$C(=N$—$NR^{35})$—, or —$C(=N$—$OR^{35})$—;

G is selected from —$N(R^{42})$—$SO_2$—$R^{40}$, —$N(R^{42})C(=O)$—$R^{40}$, —$N(R^{42})C(=O)$—$OR^{40}$, —$N(R^{42})$—$C(R^{42})(R^{42})$—$R^{40}$, —$N(R^{42})$—$C(=O)$—$N(R^{43})(R^{43})$, or —$N(R^{42})$—$C(=S)$—$N(R^{43})(R^{43})$;

$R^{40}$ is selected from —$C(R^{16})(R^{17})(R^{18})$, aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, —$OR^6$ or —$NR^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —$OR^6$ or —$NR^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, $SO_2R^{13}$, $CO_2R^{13}$ or $SO_2NR^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —$OR^{19}$, —$NR^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, $SO_2R^{23}$, $CO_2R^{23}$ or $SO_2NR^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, $SO_2R^{22}$, $CO_2R^{22}$ or $SO_2NR^{26}R^{27}$; or $R^{20}$ and $R^{21}$ together with the nitrogen atom to which they are attached, form an N-heterocyclyl; and each $R^{24}$, $R^{25}$, $R^{26}$, $R^{27}$, $R^{28}$ and $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, $OR^{34}$, alkyl, or fluoroalkyl; and n is 0, 1, 2, 3, or 4.

In an additional embodiment is a pharmaceutical composition comprising a pharmaceutically acceptable carrier and a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject.

In an additional embodiment is a method of modulating chromophore flux in a retinoid cycle comprising introducing into a subject a compound of Formula (I) as described herein. In a further embodiment is the method resulting in a reduction of lipofuscin pigment accumulated in an eye of the subject. In another embodiment is the method wherein the lipofuscin pigment is N-retinylidene-N-retinyl-ethanolamine (A2E). In yet another embodiment is the method wherein the lipofuscin pigment is N-retinylidene-N-retinyl-ethanolamine (A2E).

In an additional embodiment is a method of modulating chromophore flux in a retinoid cycle comprising introducing into a subject a compound that inhibits 11-cis-retinol production as described herein. In a further embodiment is the method resulting in a reduction of lipofuscin pigment accumulated in an eye of the subject. In another embodiment is the method wherein the lipofuscin pigment is N-retinylidene-N-retinyl-ethanolamine (A2E). In yet another embodiment is the method wherein the lipofuscin pigment is N-retinylidene-N-retinyl-ethanolamine (A2E).

In an additional embodiment is a method of modulating chromophore flux in a retinoid cycle comprising introducing into a subject a non-retinoid compound that inhibits an 11-cis-retinol producing isomerase reaction as described herein. In a further embodiment is the method resulting in a reduction of lipofuscin pigment accumulated in an eye of the subject. In another embodiment is the method wherein the lipofuscin pigment is N-retinylidene-N-retinyl-ethanolamine (A2E). In yet another embodiment is the method wherein the lipofuscin pigment is N-retinylidene-N-retinyl-ethanolamine (A2E).

In an additional embodiment is a method for treating an ophthalmic disease or disorder in a subject, comprising administering to the subject a pharmaceutical composition comprising a pharmaceutically acceptable carrier and a compound that inhibits 11-cis-retinol production with an $IC_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the ophthalmic disease or disorder is age-related macular degeneration or Stargardt's macular dystrophy. In a further embodiment is the method wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method resulting in a reduction of lipofuscin pigment accumulated in an eye of the subject.

In an additional embodiment is a method for treating an ophthalmic disease or disorder in a subject, comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the ophthalmic disease or disorder is age-related macular degeneration or Stargardt's macular dystrophy. In a further embodiment is the method wherein the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS. In a further embodiment is the method resulting in a reduction of lipofuscin pigment accumulated in an eye of the subject.

In a further embodiment is a method of inhibiting dark adaptation of a rod photoreceptor cell of the retina comprising contacting the retina with a compound of Formula (I) as described herein.

In a further embodiment is a method of inhibiting dark adaptation of a rod photoreceptor cell of the retina comprising contacting the retina with a compound that inhibits 11-cis-retinol production as described herein.

In a further embodiment is a method of inhibiting dark adaptation of a rod photoreceptor cell of the retina comprising contacting the retina with a non-retinoid compound that inhibits an 11-cis-retinol producing isomerase reaction as described herein.

In a further embodiment is a method of inhibiting regeneration of rhodopsin in a rod photoreceptor cell of the retina comprising contacting the retina with a compound of Formula (I) as described herein.

In a further embodiment is a method of inhibiting regeneration of rhodopsin in a rod photoreceptor cell of the retina comprising contacting the retina with a compound that inhibits 11-cis-retinol production as described herein.

In a further embodiment is a method of inhibiting regeneration of rhodopsin in a rod photoreceptor cell of the retina comprising contacting the retina with a non-retinoid compound that inhibits an 11-cis-retinol producing isomerase reaction as described herein.

In a further embodiment is a method of reducing ischemia in an eye of a subject comprising administering to the subject the pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

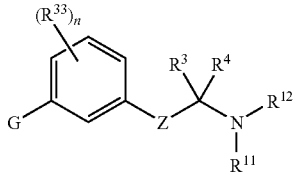

Formula (I)

wherein,

Z is a bond, —C(R$^1$)(R$^2$)—, —C(R$^9$)(R$^{10}$)—C(R$^1$)(R$^2$)—, —X—C(R$^{31}$)(R$^{32}$)—, —C(R$^9$)(R$^{10}$)—C(R$^1$)(R$^2$)—C(R$^{36}$)(R$^{37}$)—, —C(R$^{38}$)(R$^{39}$)—X—C(R$^{31}$)(R$^{32}$)—, or —X—C(R$^{31}$)(R$^{32}$)—C(R$^1$)(R$^2$)—;

X is —O—, —S—, —S(=O)—, —S(=O)$_2$—, —N(R$^{30}$)—, —C(=O)—, —C(=CH$_2$)—, —C(=N—NR$^{35}$)—, or —C(=N—OR$^{35}$)—;

G is selected from —N(R$^{42}$)—SO$_2$—R$^{40}$, —N(R$^{42}$)C(=O)—R$^{40}$, —N(R$^{42}$)C(=O)—OR$^{40}$, —N(R$^{42}$)—C(R$^{42}$)(R$^{42}$)—R$^{40}$, —N(R$^{42}$)—C(=O)—N(R$^{43}$)(R$^{43}$), or —N(R$^{42}$)—C(=S)—N(R$^{43}$)(R$^{43}$);

R$^{40}$ is selected from —C(R$^{16}$)(R$^{17}$)(R$^{18}$), aryl, or heteroaryl;

each R$^{42}$ is independently selected from hydrogen, alkyl or aryl;

each R$^{43}$ is independently selected from hydrogen, alkyl, cycloalkyl, aralkyl, alkenyl, alkynyl, C-attached heterocyclyl, aryl, or heteroaryl; or two R$^{43}$ groups, together with the nitrogen to which they are attached, may form a heterocyclyl;

R$^1$ and R$^2$ are each independently selected from hydrogen, halogen, C$_1$-C$_5$ alkyl, fluoroalkyl, —OR$^6$ or —NR$^7$R$^8$; or R$^1$ and R$^2$ together form an oxo;

R$^{31}$ and R$^{32}$ are each independently selected from hydrogen, C$_1$-C$_5$ alkyl, or fluoroalkyl;

R$^{38}$ and R$^{39}$ are each independently selected from hydrogen, C$_1$-C$_5$ alkyl, or fluoroalkyl;

R$^{36}$ and R$^{37}$ are each independently selected from hydrogen, halogen, C$_1$-C$_5$ alkyl, fluoroalkyl, —OR$^6$ or —NR$^7$R$^8$; or R$^{36}$ and R$^{37}$ together form an oxo; or optionally, R$^{36}$ and R$^1$ together form a direct bond to provide a double bond; or optionally, R$^{36}$ and R$^1$ together form a direct bond, and R$^{37}$ and R$^2$ together form a direct bond to provide a triple bond;

R$^3$ and R$^4$ are each independently selected from hydrogen, alkyl, alkenyl, fluoroalkyl, aryl, heteroaryl, carbocyclyl or C-attached heterocyclyl; or R$^3$ and R$^4$ together with the carbon atom to which they are attached, form a carbocyclyl or heterocyclyl; or R$^3$ and R$^4$ together form an imino;

R$^7$ and R$^8$ are each independently selected from hydrogen, alkyl, carbocyclyl, heterocyclyl, —C(=O)R$^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$, R$^{29}$ is independently selected from hydrogen, alkyl, alkenyl, fluoroalkyl, aryl, heteroaryl, carbocyclyl or heterocyclyl;

R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

R$^{18}$ is selected from hydrogen, alkyl, alkoxy, hydroxy, halo or fluoroalkyl;

each R$^{33}$ is independently selected from halogen, OR$^{34}$, alkyl, or fluoroalkyl; and n is 0, 1, 2, 3, or 4.

In another embodiment is a method of reducing ischemia in an eye of a subject comprising administering to the subject a pharmaceutical composition comprising a pharmaceutically acceptable carrier and a compound that inhibits 11-cis-retinol production with an $IC_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the pharmaceutical composition is administered under conditions and at a time sufficient to inhibit dark adaptation of a rod photoreceptor cell, thereby reducing ischemia in the eye.

In another embodiment is a method of reducing ischemia in an eye of a subject comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the pharmaceutical composition is administered under conditions and at a time sufficient to inhibit dark adaptation of a rod photoreceptor cell, thereby reducing ischemia in the eye.

In another embodiment is a method of inhibiting neovascularization in the retina of an eye of a subject comprising administering to the subject a pharmaceutical composition comprising a pharmaceutically acceptable carrier and a compound that inhibits 11-cis-retinol production with an $IC_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the pharmaceutical composition is administered under conditions and at a time sufficient to inhibit dark adaptation of a rod photoreceptor cell, thereby inhibiting neovascularization in the retina.

In another embodiment is a method of inhibiting neovascularization in the retina of an eye of a subject comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the pharmaceutical composition is administered under conditions and at a time sufficient to inhibit dark adaptation of a rod photoreceptor cell, thereby inhibiting neovascularization in the retina.

In another embodiment is a method of inhibiting degeneration of a retinal cell in a retina comprising contacting the retina with the compound of Formula (I) as described herein. In a further embodiment is the method wherein the retinal cell is a retinal neuronal cell. In yet another embodiment is the method wherein the retinal neuronal cell is a photoreceptor cell.

In another embodiment is a method of inhibiting degeneration of a retinal cell in a retina comprising contacting the retina with a compound that inhibits 11-cis-retinol production with an $IC_{50}$ of about 1 μM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the retinal cell is a retinal neuronal cell. In yet another embodiment is the method wherein the retinal neuronal cell is a photoreceptor cell.

In another embodiment is a method of inhibiting degeneration of a retinal cell in a retina comprising contacting the retina with a non-retinoid compound that inhibits an 11-cis-retinol producing isomerase reaction, wherein said isomerase reaction occurs in RPE, and wherein said compound has an $ED_{50}$ value of 1 mg/kg or less when administered to a subject. In a further embodiment is the method wherein the retinal cell is a retinal neuronal cell. In yet another embodiment is the method wherein the retinal neuronal cell is a photoreceptor cell.

In another embodiment is a method of reducing lipofuscin pigment accumulated in a subject's retina comprising administering to the subject a pharmaceutical composition comprising a pharmaceutically acceptable carrier and a compound of Formula (I) or tautomer, stereoisomer, geometric isomer or a pharmaceutically acceptable solvate, hydrate, salt, N-oxide or prodrug thereof:

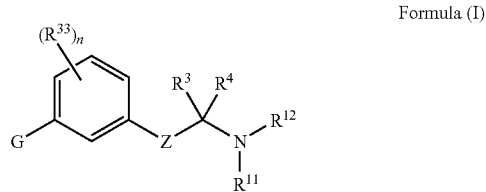

Formula (I)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)—, —C($R^{38}$)($R^{39}$)—X—C($R^{31}$)($R^{32}$)—, or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —N($R^{42}$)—SO$_2$—$R^{40}$, —N($R^{42}$)C(=O)—$R^{40}$, —N($R^{42}$)C(=O)—O$R^{40}$, —N($R^{42}$)—C($R^{42}$)($R^{42}$)—$R^{40}$, —N($R^{42}$)—C(=O)—N($R^{43}$)($R^{43}$), or —N($R^{42}$)—C(=S)—N($R^{43}$)($R^{43}$);

$R^{40}$ is selected from —C($R^{16}$)($R^{17}$)($R^{18}$), aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, —O$R^6$ or —N$R^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —O$R^6$ or —N$R^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, SO$_2$R$^{13}$, CO$_2$R$^{13}$ or SO$_2$NR$^{24}$R$^{25}$; or R$^7$ and R$^8$ together with the nitrogen atom to which they are attached, form an N-heterocyclyl;

R$^9$ and R$^{10}$ are each independently selected from hydrogen, halogen, alkyl, fluoroalkyl, —OR$^{19}$, —NR$^{20}$R$^{21}$ or carbocyclyl; or R$^9$ and R$^{10}$ form an oxo; or optionally, R$^9$ and R$^1$ together form a direct bond to provide a double bond; or optionally, R$^9$ and R$^1$ together form a direct bond, and R$^{10}$ and R$^2$ together form a direct bond to provide a triple bond;

R$^{11}$ and R$^{12}$ are each independently selected from hydrogen, alkyl, carbocyclyl, —C(=O)R$^{23}$, —C(NH)NH$_2$, SO$_2$R$^{23}$, CO$_2$R$^{23}$ or SO$_2$NR$^{28}$R$^{29}$; or R$^{11}$ and R$^{12}$, together with the nitrogen atom to which they are attached, form an N-heterocyclyl;

each R$^{13}$, R$^{22}$ and R$^{23}$ is independently selected from alkyl, heteroalkyl, alkenyl, aryl, aralkyl, carbocyclyl, heteroaryl or heterocyclyl;

R$^6$, R$^{19}$, R$^{30}$, R$^{34}$ and R$^{35}$ are each independently hydrogen or alkyl;

R$^{20}$ and R$^{21}$ are each independently selected from hydrogen, alkyl, carbocyclyl, heterocyclyl, —C(=O)R$^{22}$, SO$_2$R$^{22}$, CO$_2$R$^{22}$ or SO$_2$NR$^{26}$R$^{27}$; or R$^{20}$ and R$^{21}$ together with the nitrogen atom to which they are attached, form an N-heterocyclyl; and each R$^{24}$, R$^{25}$, R$^{26}$, R$^{27}$, R$^{28}$, R$^{29}$ is independently selected from hydrogen, alkyl, alkenyl, fluoroalkyl, aryl, heteroaryl, carbocyclyl or heterocyclyl;

R$^{16}$ and R$^{17}$ are each independently selected from hydrogen, alkyl, halo, aryl, heteroaryl, aralkyl, heteroarylalkyl or fluoroalkyl; or R$^{16}$ and R$^{17}$, together with the carbon to which they are attached form a carbocyclyl or heterocycle;

R$^{18}$ is selected from hydrogen, alkyl, alkoxy, hydroxy, halo or fluoroalkyl;

each R$^{33}$ is independently selected from halogen, OR$^{34}$, alkyl, or fluoroalkyl; and n is 0, 1, 2, 3, or 4.

In a further embodiment is the method wherein the lipofuscin is N-retinylidene-N-retinyl-ethanolamine (A2E).

In another embodiment is a method of reducing lipofuscin pigment accumulated in a subject's retina comprising administering to the subject a pharmaceutical composition comprising a pharmaceutically acceptable carrier and a compound that inhibits 11-cis-retinol production with an IC$_{50}$ of about 1 µM or less when assayed in vitro, utilizing extract of cells that express RPE65 and LRAT, wherein the extract further comprises CRALBP, wherein the compound is stable in solution for at least about 1 week at room temperature. In a further embodiment is the method wherein the lipofuscin is N-retinylidene-N-retinyl-ethanolamine (A2E).

In another embodiment is a method of reducing lipofuscin pigment accumulated in a subject's retina comprising administering to the subject a pharmaceutical composition comprising a pharmaceutically acceptable carrier and a non-retinoid compound that inhibits an 11-cis-retinol producing isomerase reaction, wherein said isomerase reaction occurs in RPE, and wherein said compound has an ED$_{50}$ value of 1 mg/kg or less when administered to a subject. In a further embodiment is the method wherein the lipofuscin is N-retinylidene-N-retinyl-ethanolamine (A2E).

Certain compounds disclosed herein have the structures shown in Table 1. The example number refers to a specific Example herein that describes the preparation of the compound having the structure/name shown.

TABLE 1

| Example No. | Structure | Name |
|---|---|---|
| 1 | 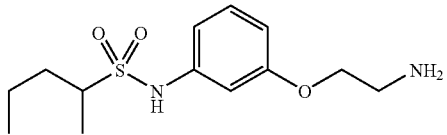 [SMILES: CCCC(C)S(=O)(=O)Nc1cccc(OCCN)c1] | N-(3-(2-Aminoethoxy)phenyl)pentane-2-sulfonamide |
| 2 | 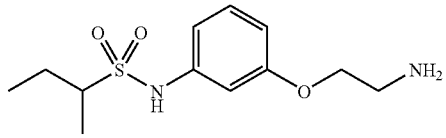 [SMILES: CCC(C)S(=O)(=O)Nc1cccc(OCCN)c1] | N-(3-(2-Aminoethoxy)phenyl)butane-2-sulfonamide |
| 3 | 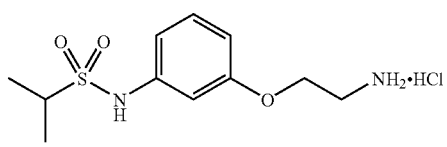 | N-(3-(2-Aminoethoxy)phenyl)propane-2-sulfonamide hydrochloride |
| 4 | 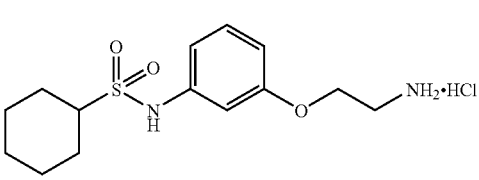 | N-(3-(2-Aminoethoxy)phenyl)cyclohexanesulfonamide hydrochloride |

TABLE 1-continued

| Example No. | Structure | Name |
|---|---|---|
| 5 | 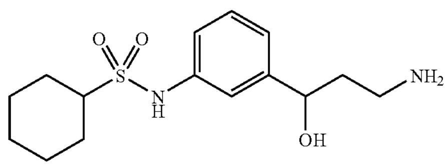 [SMILES: NCCC(O)c1cccc(NS(=O)(=O)C2CCCCC2)c1] | N-(3-(3-Amino-1-hydroxypropyl)phenyl)cyclohexanesulfonamide |
| 6 | 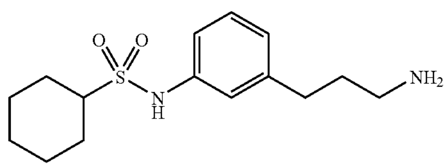 [SMILES: NCCCc1cccc(NS(=O)(=O)C2CCCCC2)c1] | N-(3-(3-Aminopropyl)phenyl)cyclohexanesulfonamide |
| 7 | 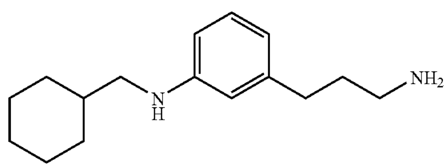 [SMILES: NCCCc1cccc(NCC2CCCCC2)c1] | 3-(3-Aminopropyl)-N-(cyclohexylmethyl)aniline |
| 8 | 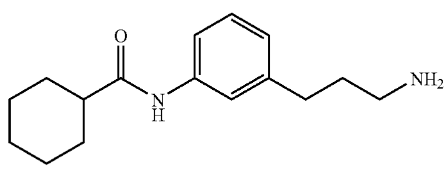 [SMILES: NCCCc1cccc(NC(=O)C2CCCCC2)c1] | N-(3-(3-Aminopropyl)phenyl)cyclohexanecarboxamide |
| 9 | 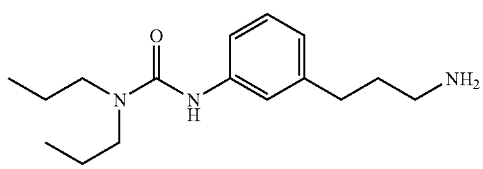 [SMILES: CCCN(CCC)C(=O)Nc1cccc(CCCN)c1] | 3-(3-(3-Aminopropyl)phenyl)-1,1-dipropylurea |
| 10 | 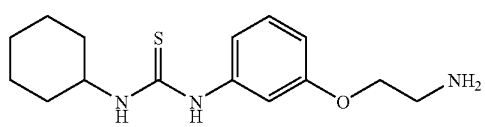 [SMILES: NCCOc1cccc(NC(=S)NC2CCCCC2)c1] | 1-(3-(2-Aminoethoxy)phenyl)-3-cyclohexylthiourea |
| 11 | 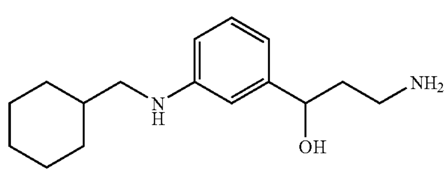 [SMILES: NCCC(O)c1cccc(NCC2CCCCC2)c1] | 3-Amino-1-(3-(cyclohexylmethylamino)phenyl)propan-1-ol |
| 12 | 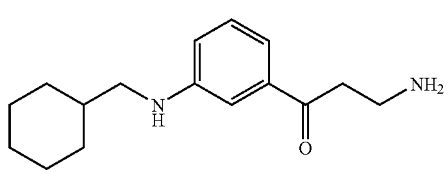 [SMILES: NCCC(=O)c1cccc(NCC2CCCCC2)c1] | 3-Amino-1-(3-(cyclohexylmethylamino)phenyl)propan-1-one |
| 13 | 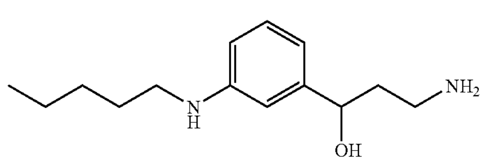 [SMILES: CCCCCNc1cccc(C(O)CCN)c1] | 3-Amino-1-(3-(pentylamino)phenyl)propan-1-ol |

TABLE 1-continued

| Example No. | Structure | Name |
|---|---|---|
| 14 | 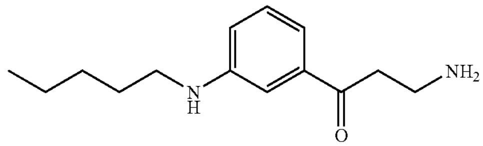 [SMILES: CCCCCNc1cccc(C(=O)CCN)c1] | 3-Amino-1-(3-(pentylamino)phenyl)propan-1-one |
| 15 | 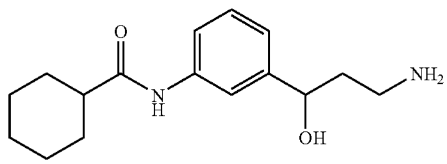 [SMILES: NCCC(O)c1cccc(NC(=O)C2CCCCC2)c1] | N-(3-(3-Amino-1-hydroxypropyl)phenyl)cyclohexanecarboxamide |
| 16 | 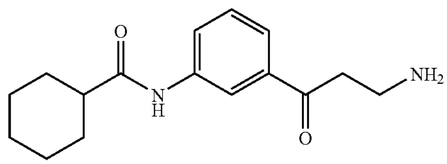 [SMILES: NCCC(=O)c1cccc(NC(=O)C2CCCCC2)c1] | N-(3-(3-Aminopropanoyl)phenyl)cyclohexanecarboxamide |
| 17 | 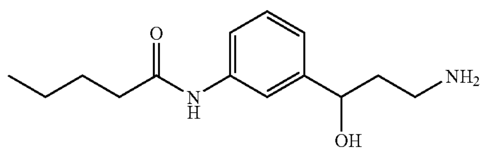 [SMILES: CCCCC(=O)Nc1cccc(C(O)CCN)c1] | N-(3-(3-Amino-1-hydroxypropyl)phenyl)pentanamide |
| 18 | 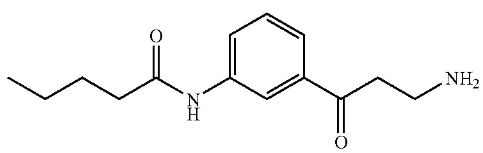 [SMILES: CCCCC(=O)Nc1cccc(C(=O)CCN)c1] | N-(3-(3-Aminopropanoyl)phenyl)pentanamide |
| 19 | 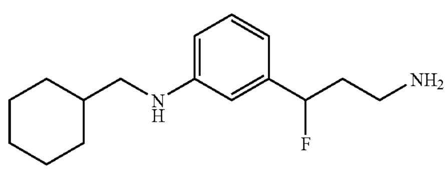 [SMILES: NCCC(F)c1cccc(NCC2CCCCC2)c1] | 3-(3-Amino-1-fluoropropyl)-N-(cyclohexylmethyl)aniline |
| 20 | 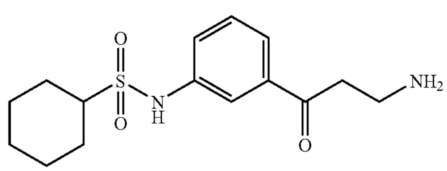 [SMILES: NCCC(=O)c1cccc(NS(=O)(=O)C2CCCCC2)c1] | N-(3-(3-Aminopropanoyl)phenyl)cyclohexanesulfonamide |
| 21 | 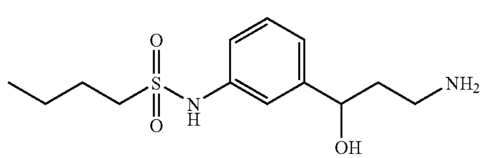 [SMILES: CCCCS(=O)(=O)Nc1cccc(C(O)CCN)c1] | N-(3-(3-Amino-1-hydroxypropyl)phenyl)butane-1-sulfonamide |
| 22 | 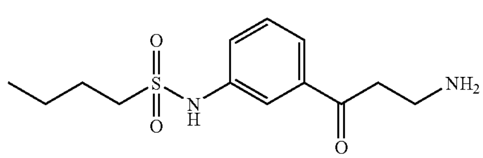 [SMILES: CCCCS(=O)(=O)Nc1cccc(C(=O)CCN)c1] | N-(3-(3-Aminopropanoyl)phenyl)butane-1-sulfonamide |

TABLE 1-continued

| Example No. | Structure | Name |
|---|---|---|
| 23 | 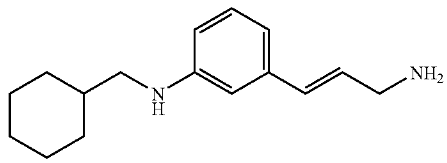 [SMILES: NC/C=C/c1cccc(NCC2CCCCC2)c1] | (E)-3-(3-Aminoprop-1-enyl)-N-(cyclohexylmethyl)aniline |
| 24 | 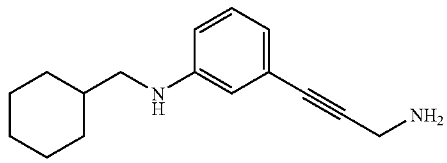 [SMILES: NCC#Cc1cccc(NCC2CCCCC2)c1] | 3-(3-Aminoprop-1-ynyl)-N-(cyclohexylmethyl)aniline |
| 25 | 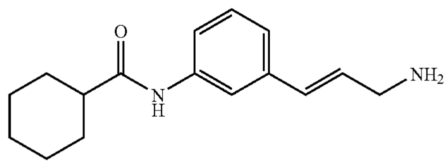 [SMILES: NC/C=C/c1cccc(NC(=O)C2CCCCC2)c1] | (E)-N-(3-(3-Aminoprop-1-enyl)phenyl)cyclohexanecarboxamide |
| 26 | 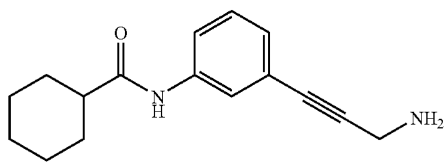 [SMILES: NCC#Cc1cccc(NC(=O)C2CCCCC2)c1] | N-(3-(3-Aminoprop-1-ynyl)phenyl)cyclohexanecarboxamide |
| 27 | 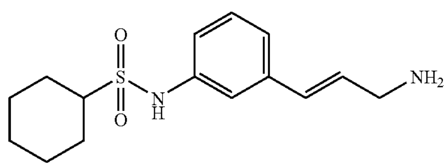 [SMILES: NC/C=C/c1cccc(NS(=O)(=O)C2CCCCC2)c1] | (E)-N-(3-(3-Aminoprop-1-enyl)phenyl)cyclohexanesulfonamide |
| 28 | 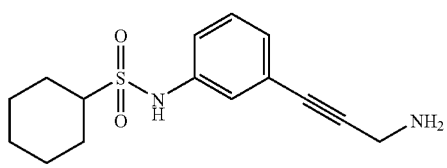 [SMILES: NCC#Cc1cccc(NS(=O)(=O)C2CCCCC2)c1] | N-(3-(3-Aminoprop-1-ynyl)phenyl)cyclohexanesulfonamide |
| 29 | 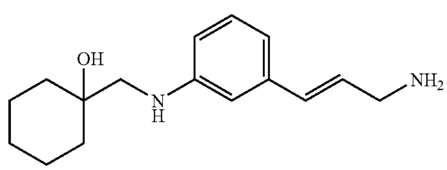 [SMILES: NC/C=C/c1cccc(NCC2(O)CCCCC2)c1] | (E)-1-((3-(3-Aminoprop-1-enyl)phenylamino)methyl)cyclohexanol |
| 30 | 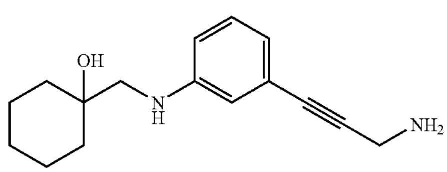 [SMILES: NCC#Cc1cccc(NCC2(O)CCCCC2)c1] | 1-((3-(3-Aminoprop-1-ynyl)phenylamino)methyl)cyclohexanol |
| 31 | 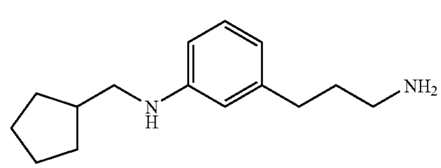 [SMILES: NCCCc1cccc(NCC2CCCC2)c1] | 3-(3-Aminopropyl)-N-(cyclopentylmethyl)aniline |

TABLE 1-continued

| Example No. | Structure | Name |
|---|---|---|
| 32 | 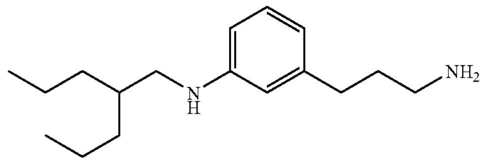 [SMILES: CCCC(CCC)CNc1cccc(CCCN)c1] | 3-(3-Aminopropyl)-N-(2-propylpentyl)aniline |
| 33 | 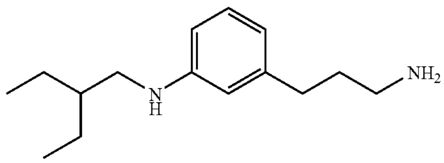 [SMILES: CCC(CC)CNc1cccc(CCCN)c1] | 3-(3-Aminopropyl)-N-(2-ethylbutyl)aniline |
| 34 | 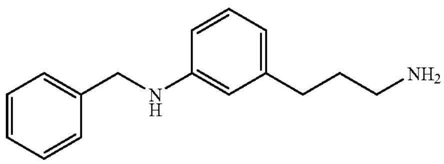 [SMILES: NCCCc1cccc(NCc2ccccc2)c1] | 3-(3-Aminopropyl)-N-benzylaniline |
| 35 | 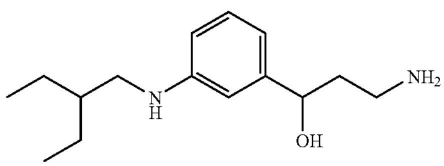 [SMILES: CCC(CC)CNc1cccc(C(O)CCN)c1] | 3-Amino-1-(3-(2-ethylbutylamino)phenyl)propan-1-ol |
| 36 | 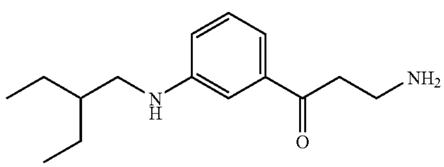 [SMILES: CCC(CC)CNc1cccc(C(=O)CCN)c1] | 3-Amino-1-(3-(2-ethylbutylamino)phenyl)propan-1-one |
| 37 | 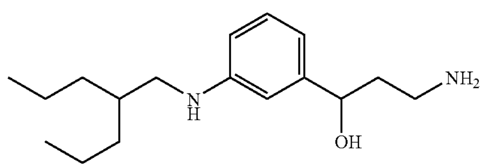 [SMILES: CCCC(CCC)CNc1cccc(C(O)CCN)c1] | 3-Amino-1-(3-(2-propylpentylamino)phenyl)propan-1-ol |
| 38 | 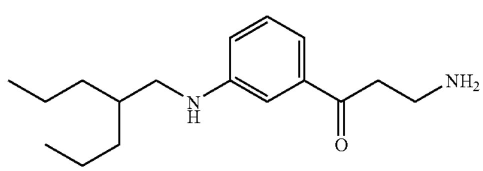 [SMILES: CCCC(CCC)CNc1cccc(C(=O)CCN)c1] | 3-Amino-1-(3-(2-propylpentylamino)phenyl)propan-1-one |
| 39 | 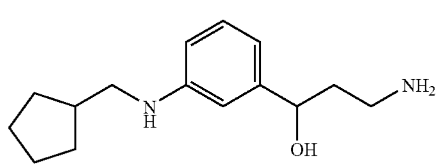 [SMILES: NCCC(O)c1cccc(NCC2CCCC2)c1] | 3-Amino-1-(3-(cyclopentylmethylamino)phenyl)propan-1-ol |
| 40 | 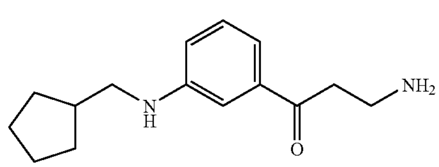 [SMILES: NCCC(=O)c1cccc(NCC2CCCC2)c1] | 3-Amino-1-(3-(cyclopentylmethylamino)phenyl)propan-1-one |

| Example No. | Structure | Name |
|---|---|---|
| 41 | 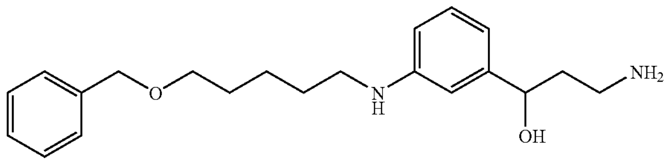 [SMILES: NCCC(O)c1cccc(NCCCCCOCc2ccccc2)c1] | 3-Amino-1-(3-(5-(benzyloxy)pentylamino)phenyl)propan-1-ol |
| 42 | 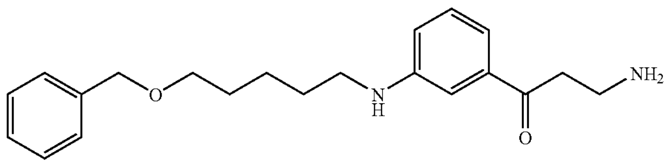 [SMILES: NCCC(=O)c1cccc(NCCCCCOCc2ccccc2)c1] | 3-Amino-1-(3-(5-(benzyloxy)pentylamino)phenyl)propan-1-one |
| 43 | 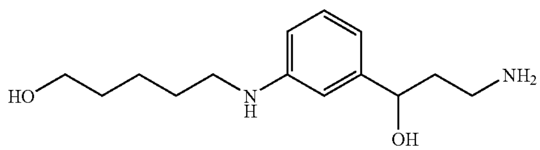 [SMILES: NCCC(O)c1cccc(NCCCCCO)c1] | 5-(3-(3-Amino-1-hydroxypropyl)phenylamino)pentan-1-one |
| 44 | 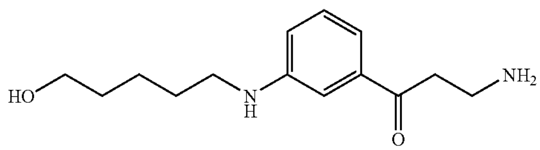 [SMILES: NCCC(=O)c1cccc(NCCCCCO)c1] | 3-Amino-1-(3-(5-hydroxypentylamino)phenyl)propan-1-one |
| 45 | 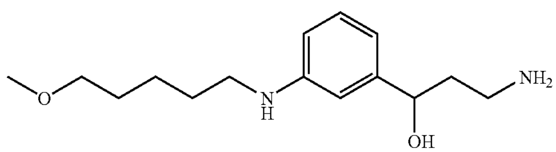 [SMILES: COCCCCCNc1cccc(C(O)CCN)c1] | 3-Amino-1-(3-(5-methoxypentylamino)phenyl)propan-1-ol |
| 46 | 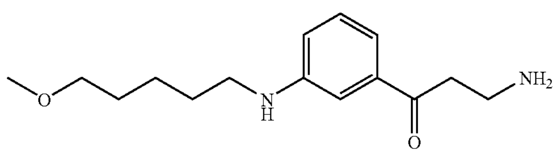 [SMILES: COCCCCCNc1cccc(C(=O)CCN)c1] | 3-Amino-1-(3-(5-methoxypentylamino)phenyl)propan-1-one |
| 47 | 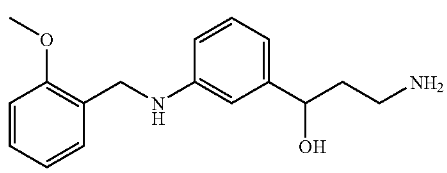 [SMILES: COc1ccccc1CNc1cccc(C(O)CCN)c1] | 3-Amino-1-(3-((2-methoxybenzyl)amino)phenyl)propan-1-ol |
| 48 | 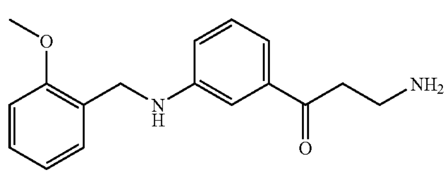 [SMILES: COc1ccccc1CNc1cccc(C(=O)CCN)c1] | 3-Amino-1-(3-(2-methoxybenzylamino)phenyl)propan-1-one |
| 49 | 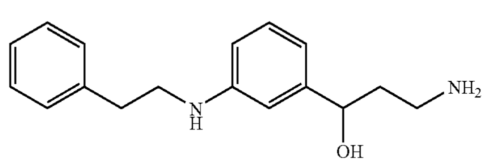 [SMILES: NCCC(O)c1cccc(NCCc2ccccc2)c1] | 3-Amino-1-(3-(phenethylamino)phenyl)propan-1-ol |

TABLE 1-continued

| Example No. | Structure | Name |
|---|---|---|
| 50 | 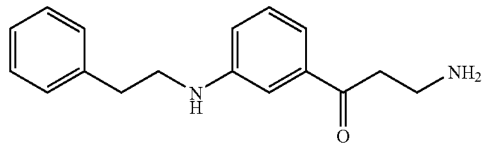 [SMILES: NCCC(=O)c1cccc(NCCc2ccccc2)c1] | 3-Amino-1-(3-(phenethylamino)phenyl)propan-1-one |
| 51 | 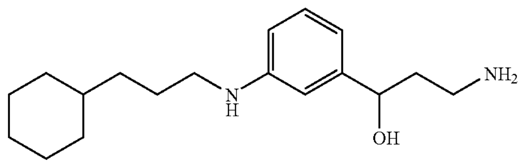 [SMILES: NCCC(O)c1cccc(NCCCC2CCCCC2)c1] | 3-Amino-1-(3-(3-cyclohexylpropylamino)phenyl)propan-1-ol |
| 52 | 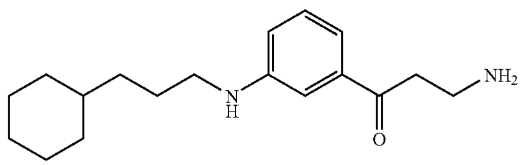 [SMILES: NCCC(=O)c1cccc(NCCCC2CCCCC2)c1] | 3-Amino-1-(3-(3-cyclohexylpropylamino)phenyl)propan-1-one |
| 53 | 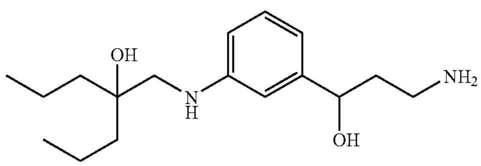 [SMILES: CCCC(O)(CCC)CNc1cccc(C(O)CCN)c1] | 4-((3-(3-Amino-1-hydroxypropyl)phenylamino)methyl)heptan-4-ol |
| 54 | 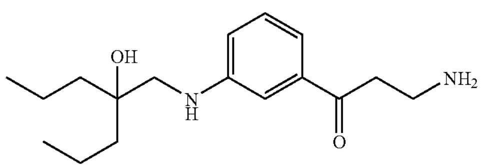 [SMILES: CCCC(O)(CCC)CNc1cccc(C(=O)CCN)c1] | 3-Amino-1-(3-(2-hydroxy-2-propylpentylamino)phenyl)propan-1-one |
| 55 | 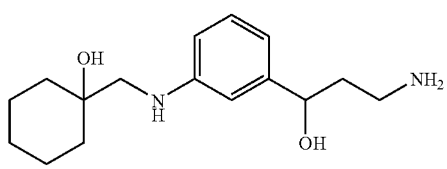 [SMILES: NCCC(O)c1cccc(NCC2(O)CCCCC2)c1] | 1-((3-(3-Amino-1-hydroxypropyl)phenylamino)methyl)cyclohexanol |
| 56 | 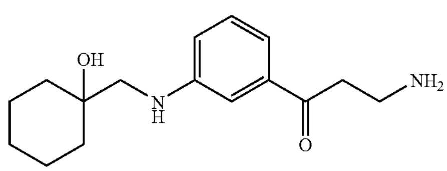 [SMILES: NCCC(=O)c1cccc(NCC2(O)CCCCC2)c1] | 3-Amino-1-(3-((1-hydroxycyclohexyl)methylamino)phenyl)propan-1-one |
| 57 | 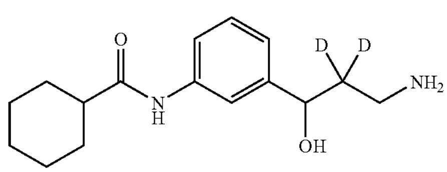 [SMILES: [2H]C([2H])(CN)C(O)c1cccc(NC(=O)C2CCCCC2)c1] | N-(3-(3-amino-2,2-dideutero-1-hydroxypropyl)phenyl)cyclohexanecarboxamide |
| 58 | 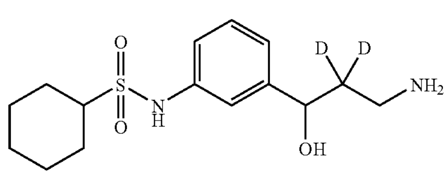 [SMILES: [2H]C([2H])(CN)C(O)c1cccc(NS(=O)(=O)C2CCCCC2)c1] | N-(3-(3-amino-2,2-dideutero-1-hydroxypropyl)phenyl)cyclohexanesulfonamide |

TABLE 1-continued

| Example No. | Structure | Name |
|---|---|---|
| 59 | 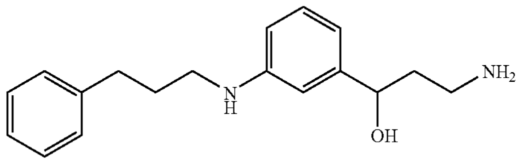 [SMILES: NCCC(O)c1cccc(NCCCc2ccccc2)c1] | 3-Amino-1-(3-(3-phenylpropylamino)phenyl)propan-1-ol |
| 60 | 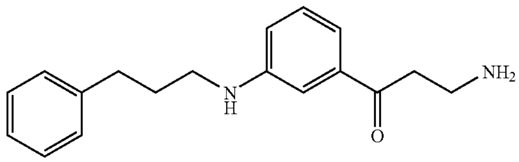 [SMILES: NCCC(=O)c1cccc(NCCCc2ccccc2)c1] | 3-Amino-1-(3-(3-phenylpropylamino)phenyl)propan-1-one |
| 61 | 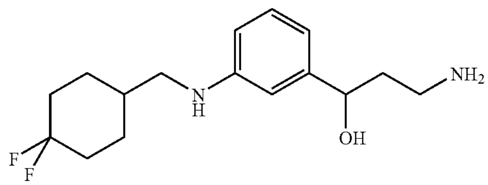 [SMILES: NCCC(O)c1cccc(NCC2CCC(F)(F)CC2)c1] | 3-Amino-1-(3-((4,4-difluorocyclohexyl)methylamino)phenyl)propan-1-ol |
| 62 | 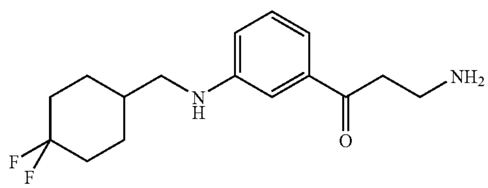 [SMILES: NCCC(=O)c1cccc(NCC2CCC(F)(F)CC2)c1] | 3-Amino-1-(3-((4,4-difluorocyclohexyl)methylamino)phenyl)propan-1-one |
| 63 | 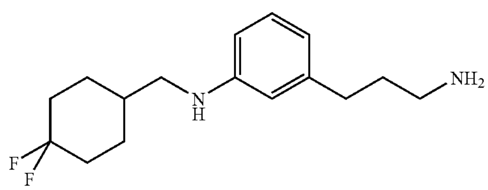 [SMILES: NCCCc1cccc(NCC2CCC(F)(F)CC2)c1] | 3-(3-Aminopropyl)-N-((4,4-difluorocyclohexyl)methyl)aniline |
| 64 | 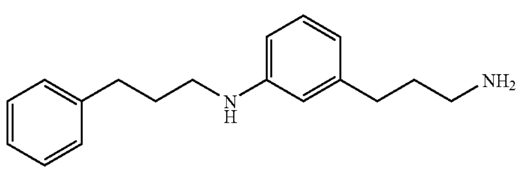 [SMILES: NCCCc1cccc(NCCCc2ccccc2)c1] | 3-(3-Aminopropyl)-N-(3-phenylpropyl)aniline |
| 65 | 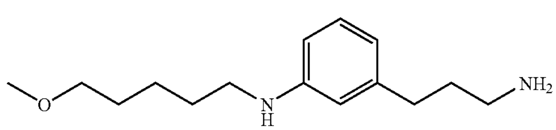 [SMILES: COCCCCCNc1cccc(CCCN)c1] | 3-(3-Aminopropyl)-N-(5-methoxypentyl)aniline |
| 66 | 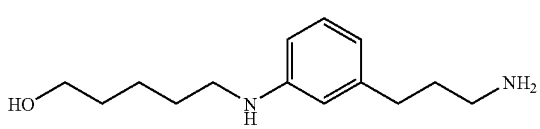 [SMILES: NCCCc1cccc(NCCCCCO)c1] | 5-(3-(3-Aminopropyl)phenylamino)pentan-1-ol |
| 67 | 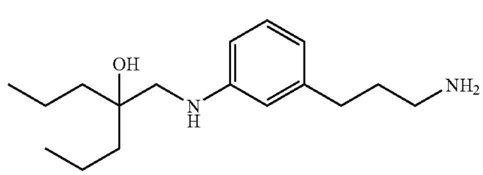 [SMILES: CCCC(O)(CCC)CNc1cccc(CCCN)c1] | 4-((3-(3-Aminopropyl)phenylamino)methyl)heptan-4-ol |

TABLE 1-continued

| Example No. | Structure | Name |
|---|---|---|
| 68 | 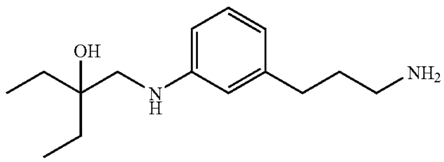 [SMILES: CCC(O)(CC)CNc1cccc(CCCN)c1] | 3-((3-(3-Aminopropyl)phenylamino)methyl)pentan-3-ol |
| 69 | 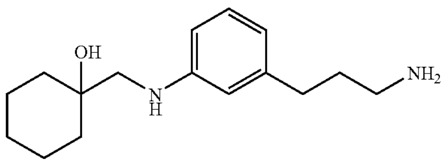 [SMILES: NCCCc1cccc(NCC2(O)CCCCC2)c1] | 1-((3-(3-Aminopropyl)phenylamino)methyl)cyclohexanol |
| 70 | 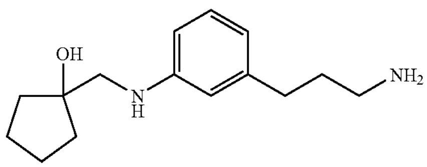 [SMILES: NCCCc1cccc(NCC2(O)CCCC2)c1] | 1-((3-(3-Aminopropyl)phenylamino)methyl)cyclopentanol |
| 71 | 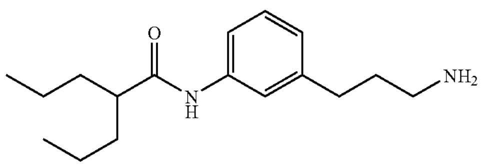 [SMILES: CCCC(CCC)C(=O)Nc1cccc(CCCN)c1] | N-(3-(3-Aminopropyl)phenyl)-2-propylpentanamide |
| 72 | 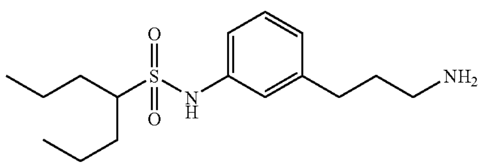 [SMILES: CCCC(CCC)S(=O)(=O)Nc1cccc(CCCN)c1] | N-(3-(3-Aminopropyl)phenyl)heptane-4-sulfonamide |
| 73 | 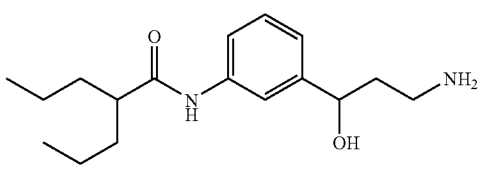 [SMILES: CCCC(CCC)C(=O)Nc1cccc(C(O)CCN)c1] | N-(3-(3-Amino-1-hydroxypropyl)phenyl)-2-propylpentanamide |
| 74 | 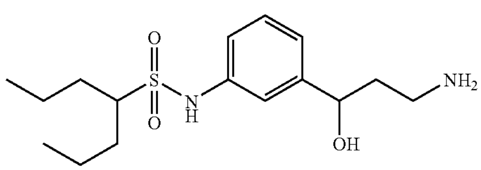 [SMILES: CCCC(CCC)S(=O)(=O)Nc1cccc(C(O)CCN)c1] | N-(3-(3-Amino-1-hydroxypropyl)phenyl)heptane-4-sulfonamide |
| 75 | 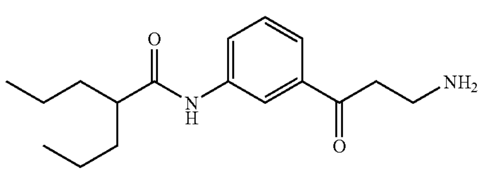 [SMILES: CCCC(CCC)C(=O)Nc1cccc(C(=O)CCN)c1] | N-(3-(3-Aminopropanoyl)phenyl)-2-propylpentanamide |
| 76 | 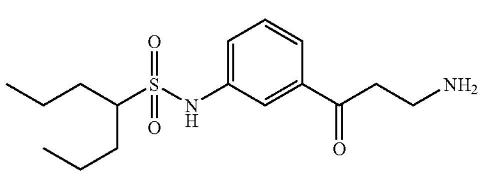 [SMILES: CCCC(CCC)S(=O)(=O)Nc1cccc(C(=O)CCN)c1] | N-(3-(3-Aminopropanoyl)phenyl)heptane-4-sulfonamide |

TABLE 1-continued

| Example No. | Structure | Name |
|---|---|---|
| 77 | 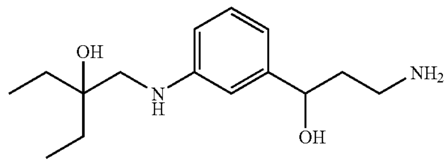 [SMILES: CCC(O)(CC)CNc1cccc(C(O)CCN)c1] | 3-((3-(3-Amino-1-hydroxypropyl)phenylamino)methyl)pentan-3-ol |
| 78 | 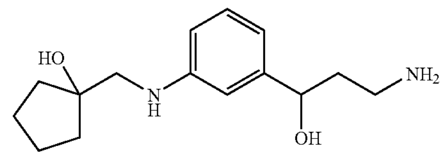 [SMILES: NCCC(O)c1cccc(NCC2(O)CCCC2)c1] | 1-((3-(3-Amino-1-hydroxypropyl)phenylamino)methyl)cyclopentanol |
| 79 | 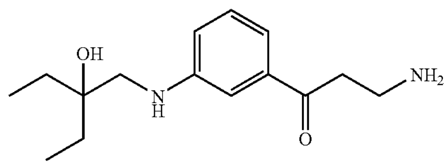 [SMILES: CCC(O)(CC)CNc1cccc(C(=O)CCN)c1] | 3-Amino-1-(3-(2-ethyl-2-hydroxybutylamino)phenyl)propan-1-one |
| 80 | 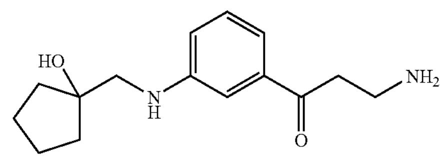 [SMILES: NCCC(=O)c1cccc(NCC2(O)CCCC2)c1] | 3-Amino-1-(3-((1-hydroxycyclopentyl)methylamino)phenyl)propan-1-one |
| 81 | 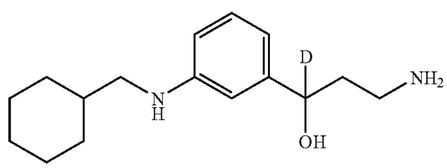 [SMILES: [2H]C(O)(CCN)c1cccc(NCC2CCCCC2)c1] | 3-Amino-1-(3-(cyclohexylmethylamino)phenyl)-1-deuteropropan-1-ol |
| 82 | 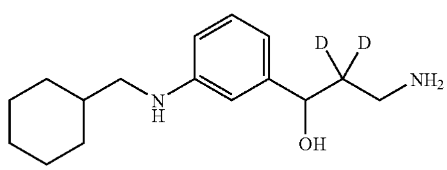 [SMILES: [2H]C([2H])(CN)C(O)c1cccc(NCC2CCCCC2)c1] | 3-Amino-1-(3-(cyclohexylmethylamino)phenyl)-2,2-dideuteropropan-1-ol |
| 83 | 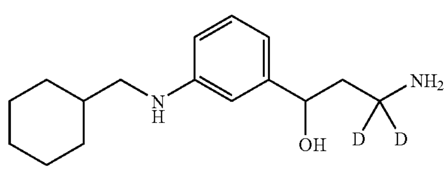 [SMILES: [2H]C([2H])(N)CC(O)c1cccc(NCC2CCCCC2)c1] | 3-Amino-1-(3-(cyclohexylmethylamino)phenyl)-3,3-dideuteropropan-1-ol |
| 84 | 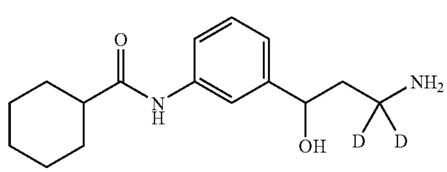 [SMILES: [2H]C([2H])(N)CC(O)c1cccc(NC(=O)C2CCCCC2)c1] | N-(3-(3-Amino-3,3-dideutero-1-hydroxypropyl)phenyl)cyclohexanecarboxamide |
| 85 | 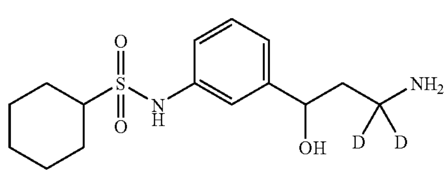 [SMILES: [2H]C([2H])(N)CC(O)c1cccc(NS(=O)(=O)C2CCCCC2)c1] | N-(3-(3-Amino-3,3-dideutero-1-hydroxypropyl)phenyl)cyclohexanesulfonamide |

TABLE 1-continued

| Example No. | Structure | Name |
|---|---|---|
| 86 | 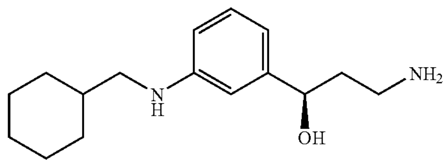 [SMILES: NCC[C@@H](O)c1cccc(NCC2CCCCC2)c1] | (R)-3-Amino-1-(3-(cyclohexylmethylamino)phenyl)propan-1-ol |
| 87 | 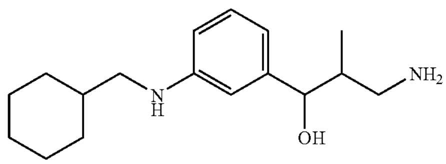 [SMILES: CC(CN)C(O)c1cccc(NCC2CCCCC2)c1] | 3-Amino-1-(3-(cyclohexylmethylamino)phenyl)-2-methylpropan-1-ol |
| 88 | 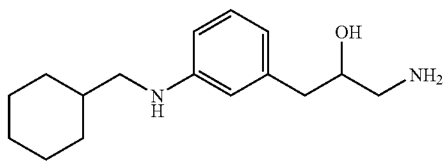 [SMILES: NCC(O)Cc1cccc(NCC2CCCCC2)c1] | 1-Amino-3-(3-(cyclohexylmethylamino)phenyl)propan-2-ol |
| 89 | 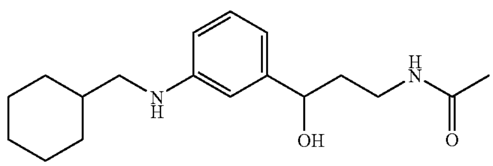 [SMILES: CC(=O)NCCC(O)c1cccc(NCC2CCCCC2)c1] | N-3(3-(3-(Cyclohexylmethylamino)phenyl)-3-hydroxypropyl)acetamide |
| 90 | 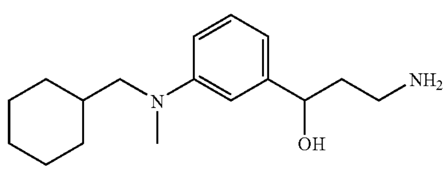 [SMILES: CN(CC1CCCCC1)c1cccc(C(O)CCN)c1] | 3-Amino-1-(3-((cyclohexylmethyl)(methyl)amino)phenyl)propan-1-ol |
| 91 | 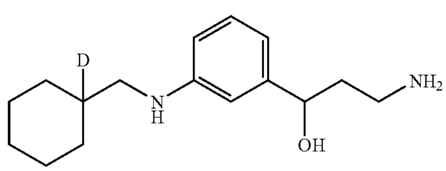 [SMILES: [2H]C1(CNc2cccc(C(O)CCN)c2)CCCCC1] | 3-Amino-1-(3-((1-deuterocyclohexyl)methylamino)phenyl)propan-1-ol |
| 92 | 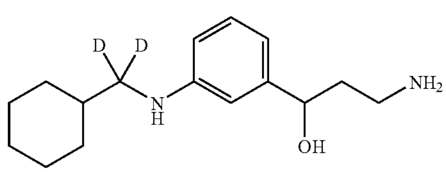 [SMILES: [2H]C([2H])(Nc1cccc(C(O)CCN)c1)C1CCCCC1] | 3-Amino-1-(3-(cyclohexyldideuteromethylamino)phenyl)propan-1-ol |
| 93 | 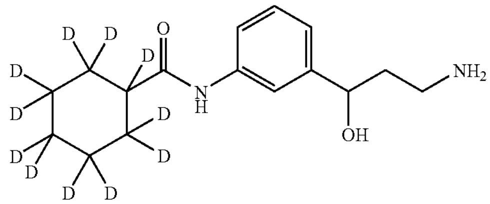 [SMILES: [2H]C1([2H])C([2H])([2H])C([2H])([2H])C([2H])(C(=O)Nc2cccc(C(O)CCN)c2)C([2H])([2H])C1([2H])[2H]] | N-(3-(3-Amino-1-hydroxypropyl)phenyl)-1,2,2,3,3,4,4,5,5,6,6-undecadeuterocyclohexanecarboxamide |
| 94 | 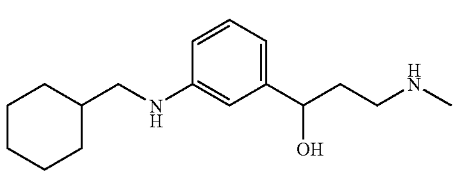 [SMILES: CNCCC(O)c1cccc(NCC2CCCCC2)c1] | 1-(3-(Cyclohexylmethylamino)phenyl)-3-(methylamino)propan-1-ol |

TABLE 1-continued

| Example No. | Structure | Name |
|---|---|---|
| 95 | 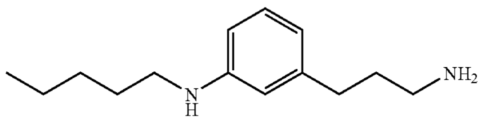 [SMILES: CCCCCNc1cccc(CCCN)c1] | 3-(3-Aminopropyl)-N-pentylaniline |
| 96 | 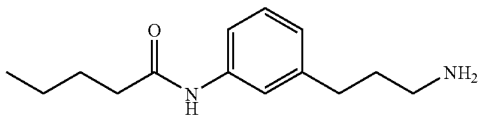 [SMILES: CCCCC(=O)Nc1cccc(CCCN)c1] | N-(3-(3-Aminopropyl)phenyl)pentanamide |
| 97 | 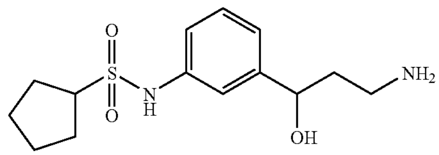 [SMILES: NCCC(O)c1cccc(NS(=O)(=O)C2CCCC2)c1] | N-(3-(3-Amino-1-hydroxypropyl)phenyl)cyclopentanesulfonamide |
| 98 | 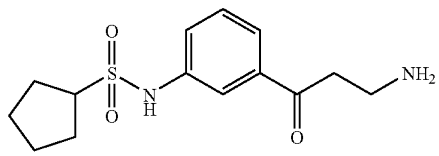 [SMILES: NCCC(=O)c1cccc(NS(=O)(=O)C2CCCC2)c1] | N-(3-(3-Aminopropanoyl)phenyl)cyclopentanesulfonamide |
| 99 | 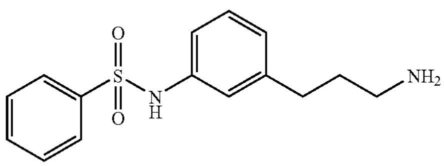 [SMILES: NCCCc1cccc(NS(=O)(=O)c2ccccc2)c1] | N-(3-(3-Aminopropyl)phenyl)benzenesulfonamide |
| 100 | 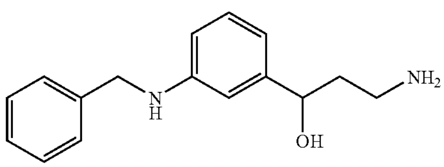 [SMILES: NCCC(O)c1cccc(NCc2ccccc2)c1] | 3-Amino-1-(3-(benzylamino)phenyl)propan-1-ol |
| 101 | 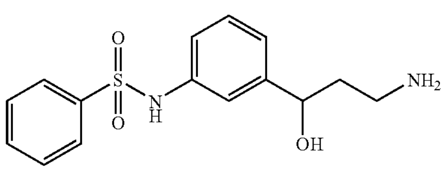 [SMILES: NCCC(O)c1cccc(NS(=O)(=O)c2ccccc2)c1] | N-(3-(3-Amino-1-hydroxypropyl)phenyl)benzenesulfonamide |
| 102 | 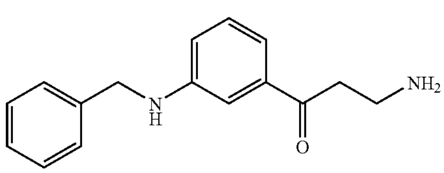 [SMILES: NCCC(=O)c1cccc(NCc2ccccc2)c1] | 3-Amino-1-(3-(benzylamino)phenyl)propan-1-one |
| 103 | 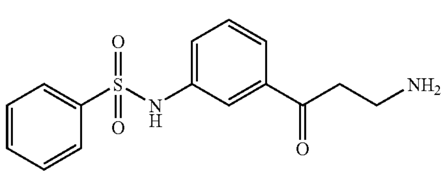 [SMILES: NCCC(=O)c1cccc(NS(=O)(=O)c2ccccc2)c1] | N-(3-(3-Aminopropanoyl)phenyl)benzenesulfonamide |

TABLE 1-continued

| Example No. | Structure | Name |
|---|---|---|
| 104 | 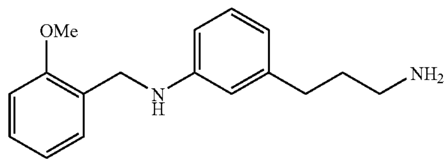 [SMILES: COc1ccccc1CNc1cccc(CCCN)c1] | 3-(3-Aminopropyl)-N-(2-methoxybenzyl)aniline |
| 105 | 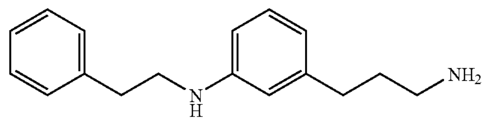 [SMILES: NCCCc1cccc(NCCc2ccccc2)c1] | 3-(3-Aminopropyl)-N-phenethylaniline |
| 106 | 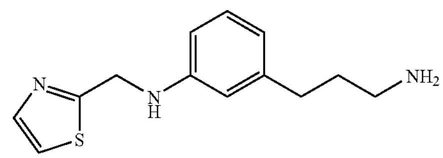 [SMILES: NCCCc1cccc(NCc2nccs2)c1] | 3-(3-Aminopropyl)-N-(thiazol-2-ylmethyl)aniline |
| 107 | 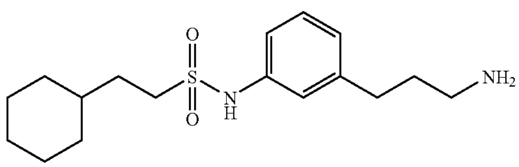 [SMILES: NCCCc1cccc(NS(=O)(=O)CCC2CCCCC2)c1] | N-(3-(3-Aminopropyl)phenyl)-2-cyclohexylethanesulfonamide |
| 108 | 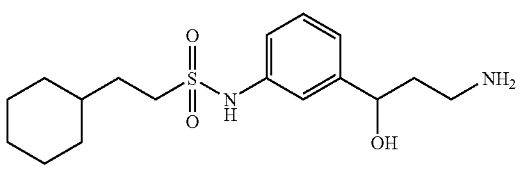 [SMILES: NCCC(O)c1cccc(NS(=O)(=O)CCC2CCCCC2)c1] | N-(3-(3-Aminopropanoyl)phenyl)-2-cyclohexylethanesulfonamide |
| 109 | 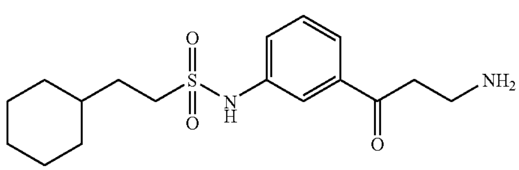 [SMILES: NCCC(=O)c1cccc(NS(=O)(=O)CCC2CCCCC2)c1] | N-(3-(3-Amino-1-hydroxypropyl)phenyl)-2-cyclohexylethanesulfonamide |
| 110 | 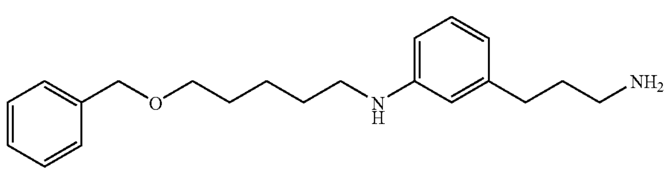 [SMILES: NCCCc1cccc(NCCCCCOCc2ccccc2)c1] | 3-(3-Aminopropyl)-N-(5-(benzyloxy)pentyl)aniline |
| 111 | 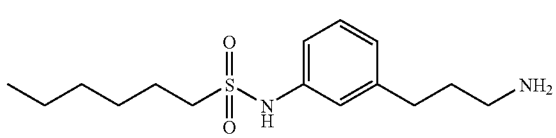 [SMILES: CCCCCCS(=O)(=O)Nc1cccc(CCCN)c1] | N-(3-(3-Aminopropyl)phenyl)-5-methoxypentane-1-sulfonamide |
| 112 | 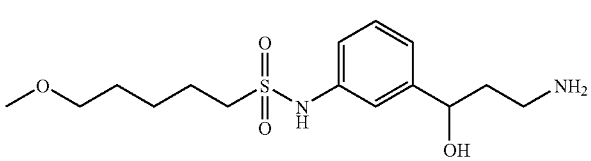 [SMILES: COCCCCCS(=O)(=O)Nc1cccc(C(O)CCN)c1] | N-(3-(3-Amino-1-hydroxypropyl)phenyl)-5-methoxypentane-1-sulfonamide |

TABLE 1-continued

| Example No. | Structure | Name |
|---|---|---|
| 113 | 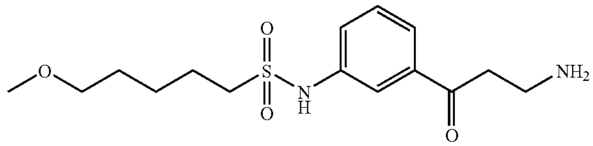 [SMILES: COCCCCCS(=O)(=O)Nc1cccc(C(=O)CCN)c1] | N-(3-(3-Aminopropanoyl)phenyl)-5-methoxypentane-1-sulfonamide |
| 114 | 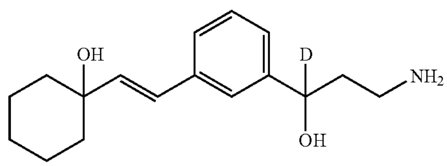 [SMILES: [2H]C(O)(CCN)c1cccc(/C=C/C2(O)CCCCC2)c1] | (E)-1-(3-(3-Amino-1-fluoro-1-hydroxypropyl)styryl)cyclohexanol |
| 115 | 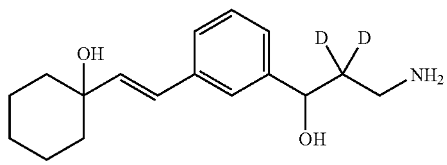 [SMILES: [2H]C([2H])(CN)C(O)c1cccc(/C=C/C2(O)CCCCC2)c1] | (E)-3-amino-1-(3-(2-cyclohexylvinyl)phenyl)-2,2-dideuteropropan-1-ol |
| 116 | 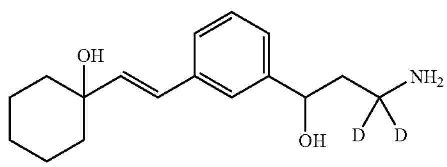 [SMILES: [2H]C([2H])(N)CC(O)c1cccc(/C=C/C2(O)CCCCC2)c1] | (E)-1-(3-(3-Amino-3,3-dideutero-1-hydroxypropyl)styryl)cyclohexanol |
| 117 | 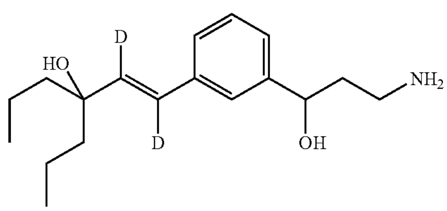 [SMILES: [2H]/C(=C(/[2H])C(O)(CCC)CCC)c1cccc(C(O)CCN)c1] | (E)-4-(2-(3-(3-Amino-1-hydroxypropyl)phenyl)-1,2-dideuterovinyl)heptan-4-ol |
| 118 | 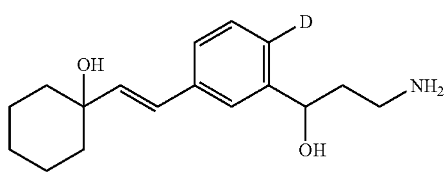 [SMILES: [2H]c1ccc(/C=C/C2(O)CCCCC2)cc1C(O)CCN] | (E)-1-(3-(3-Amino-1-hydroxypropyl)-4-deuterostyryl)cyclohexanol |
| 119 | 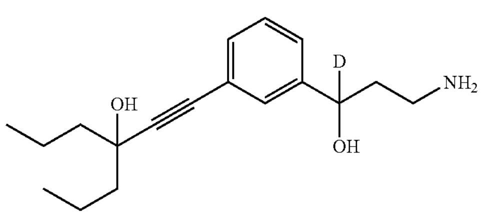 [SMILES: [2H]C(O)(CCN)c1cccc(C#CC(O)(CCC)CCC)c1] | 4-((3-(3-Amino-1-deutero-1-hydroxypropyl)phenyl)ethynyl)heptan-4-ol |
| 120 | 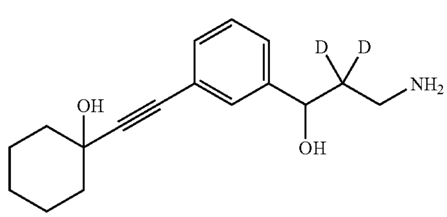 [SMILES: [2H]C([2H])(CN)C(O)c1cccc(C#CC2(O)CCCCC2)c1] | 1-((3-(3-Amino-2,2-dideutero-1-hydroxypropyl)phenyl)ethynyl)cyclohexanol |

TABLE 1-continued

| Example No. | Structure | Name |
|---|---|---|
| 121 | 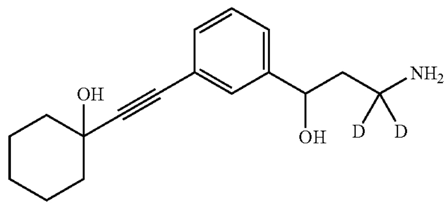 [SMILES: [2H]C([2H])(N)CC(O)c1cccc(C#CC2(O)CCCCC2)c1] | 1-((3-(3-Amino-3,3-dideutero-1-hydroxypropyl)phenyl)ethynyl)cyclohexanol |
| 122 | 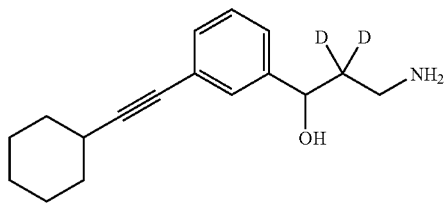 [SMILES: [2H]C([2H])(CN)C(O)c1cccc(C#CC2CCCCC2)c1] | 3-Amino-1-(3-(cyclohexylethynyl)phenyl)-2,2-dideuteropropan-1-ol |
| 123 | 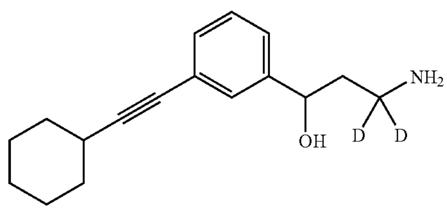 [SMILES: [2H]C([2H])(N)CC(O)c1cccc(C#CC2CCCCC2)c1] | 3-Amino-1-(3-(cyclohexylethynyl)phenyl)-3,3-dideuteropropan-1-ol |
| 124 | 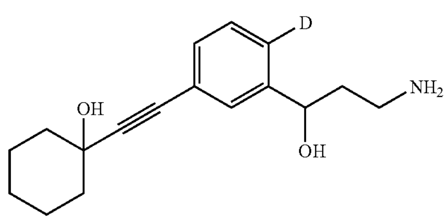 [SMILES: [2H]c1ccc(C#CC2(O)CCCCC2)cc1C(O)CCN] | 1-((3-(3-Amino-1-hydroxypropyl)-4-deuterophenyl)ethynyl)cyclohexanol |
| 125 | 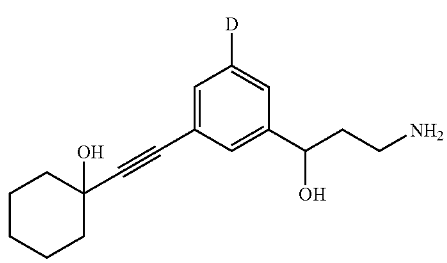 [SMILES: [2H]c1cc(C#CC2(O)CCCCC2)cc(C(O)CCN)c1] | 1-((3-(3-Amino-1-hydroxypropyl)-5-deuterophenyl)ethynyl)cyclohexanol |
| 126 | 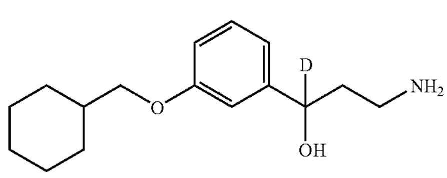 [SMILES: [2H]C(O)(CCN)c1cccc(OCC2CCCCC2)c1] | 3-Amino-1-(3-(cyclohexylmethoxy)phenyl)-1-deuteropropan-1-ol |
| 127 | 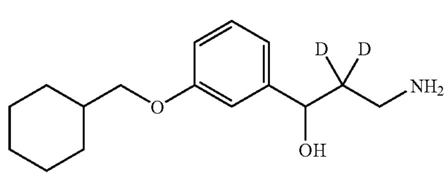 [SMILES: [2H]C([2H])(CN)C(O)c1cccc(OCC2CCCCC2)c1] | 3-Amino-1-(3-(cyclohexylmethoxy)phenyl)-2,2-dideuteropropan-1-ol |

TABLE 1-continued

| Example No. | Structure | Name |
|---|---|---|
| 128 | 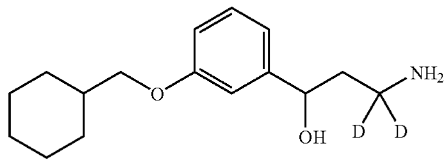 [SMILES: [2H]C([2H])(N)CC(O)c1cccc(OCC2CCCCC2)c1] | 3-Amino-1-(3-(cyclohexylmethoxy)phenyl)-3,3-dideuteropropan-1-ol |
| 129 | 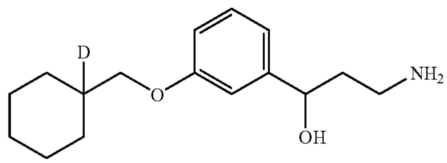 [SMILES: [2H]C1(COc2cccc(C(O)CCN)c2)CCCCC1] | 3-Amino-1-(3-((1-deuterocyclohexyl)methoxy)phenyl)propan-1-ol |
| 130 | 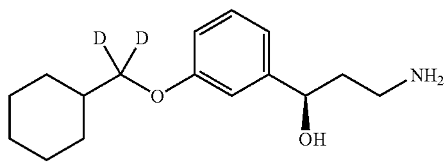 [SMILES: [2H]C([2H])(Oc1cccc([C@H](O)CCN)c1)C1CCCCC1] | (R)-3-Amino-1-(3-(cyclohexyldideuteromethoxy)phenyl)propan-1-ol |
| 131 | 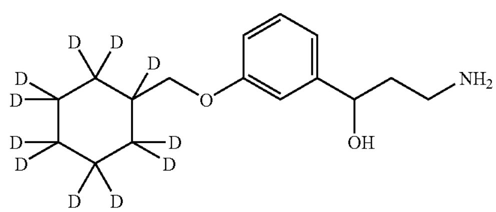 [SMILES: [2H]C1([2H])C([2H])([2H])C([2H])([2H])C([2H])(COc2cccc(C(O)CCN)c2)C([2H])([2H])C1([2H])[2H]] | 3-Amino-1-(3-((perdeuterocyclohexyl)methoxy)phenyl)propan-1-ol |
| 132 | 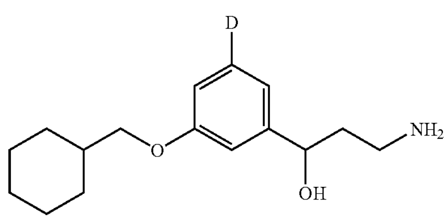 [SMILES: [2H]c1cc(OCC2CCCCC2)cc(C(O)CCN)c1] | 3-Amino-1-(3-(cyclohexylmethoxy)-5-deuterophenyl)propan-1-ol |

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Sulfanyl" refers to the —S— radical.
"Sulfinyl" refers to the —S(=O)— radical.
"Sulfonyl" refers to the —S(=O)$_2$— radical.
"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—CO(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—$C(O)R^a$, —$R^b$—$C(O)OR^a$, —$R^b$—$C(O)N(R^a)_2$, —$R^b$—O—$R^e$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, and includes fused or bridged ring systems. The heteroatom(s) in the heterocyclyl radical is optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—$N(R^a)_2$, —$R^b$—$C(O)R^a$, —$R^b$—$C(O)OR^a$, —$R^b$—C(O)N($R^a$)$_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula $R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hëckel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6] imidazo[1,2-a]pyridinyl, carbazolyl, cinnolinyl, cyclopenta [d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7] cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9, 10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9, 10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7, 8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C (O)N($R^a$)$_2$, —$R^b$—N($R^a$)C(O)O$R^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula $R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

"Stereoisomers" are compounds that have the same sequence of covalent bonds and differ in the relative disposition of their atoms in space. "Enantiomers" refers to two stereoisomers that are nonsuperimposable mirror images of one another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon are within the scope of this invention.

The compounds of the present invention may also contain unnatural proportions of atomic isotopes at one or more atoms that constitute such compounds. For example, the compounds may be labeled with isotopes, such as for example, deuterium (2H), tritium (3H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing amine derivative compounds are known in the art and include, by way of non-limiting example only, the following synthetic methods.

Deuterated starting materials, such as acid i and acid ii, are readily available and are subjected to the synthetic methods described herein for the synthesis of amine derivative compounds.

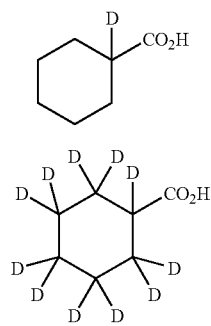

i ii

Other deuterated starting materials are also employed in the synthesis of deuterium-containing amine derivative compounds as shown, in a non-limiting example, in the scheme below. Large numbers of deuterium-containing reagents and building blocks are available commerically from chemical vendors, such as Aldrich Chemical Co.

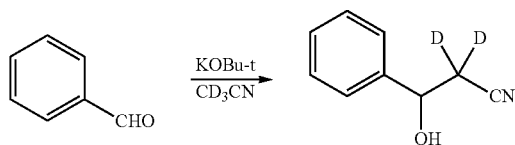 [SMILES: O=Cc1ccccc1 ; "CD3CN" ; [2H]C([2H])(C#N)C(O)c1ccccc1]

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

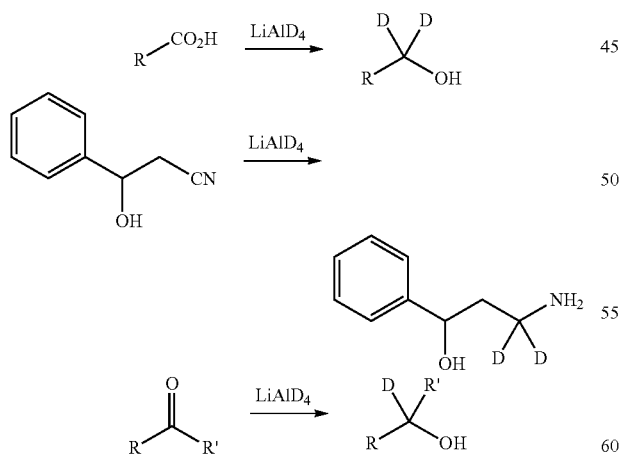

Deuterium gas and palladium catalyst are employed to reduce unsaturated carbon-carbon linkages and to perform a reductive substitution of aryl carbon-halogen bonds as illustrated, by way of example only, in the reaction schemes below.

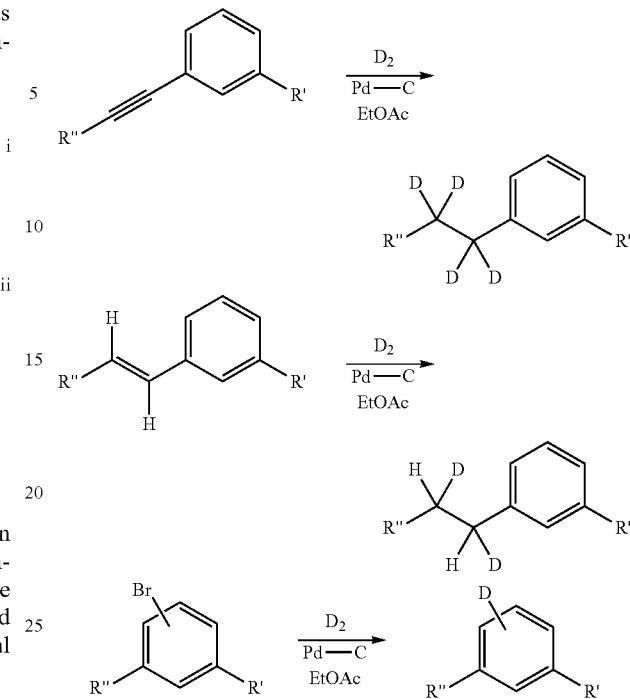

In one embodiments, the compounds disclosed herein contain one deuterium atom. In another embodiment, the compounds disclosed herein contains two deuterium atoms. In another embodiment, the compounds disclosed herein contains three deuterium atoms. In another embodiment, the compounds disclosed herein contains four deuterium atoms. In another embodiment, the compounds disclosed herein contains five deuterium atoms. In another embodiment, the compounds disclosed herein contains six deuterium atoms. In another embodiment, the compounds disclosed herein contains more than six deuterium atoms. In another embodiment, the compounds disclosed herein is fully substituted with deuterium atoms and contains no non-exchangeable $^1$H hydrogen atoms. In one embodiment, the level of deuterium incorporation is determined by synthetic methods in which a per-deuterated synthetic building block is used as a starting material. In one embodiment, acid ii is incorporated in the compounds disclosed herein to provide a compound with eleven deuterium atoms such as, by way of example only, compound iii.

iii

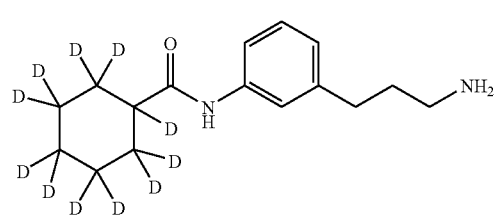

In another embodiment, is a deuterium labeled compound selected from:

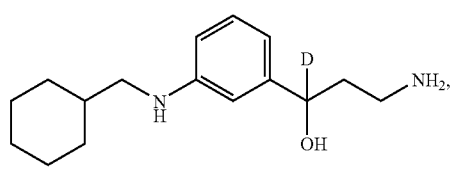
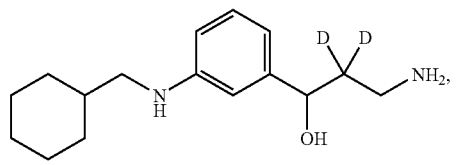
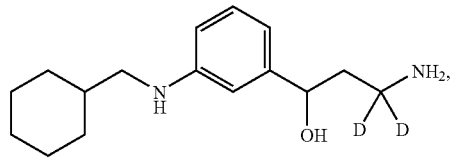
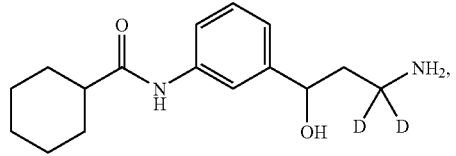
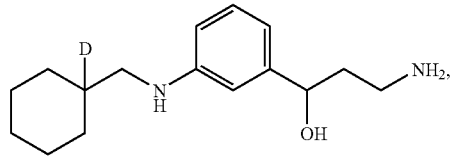
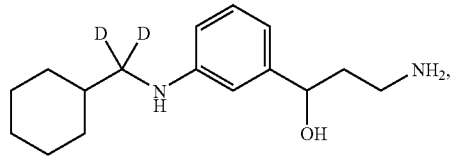
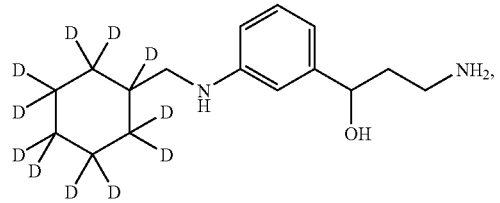
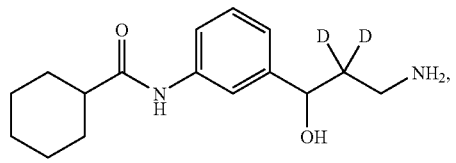
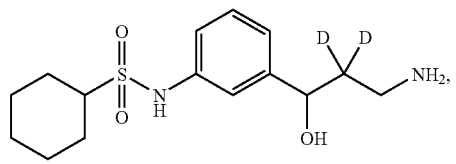
-continued
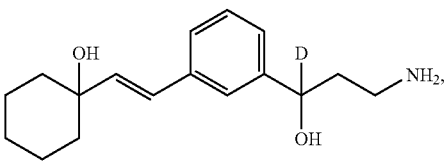
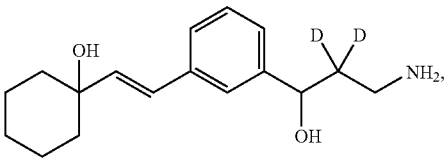
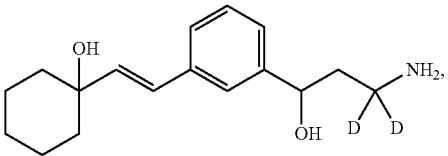
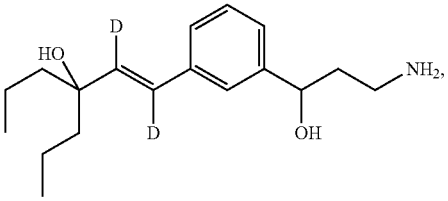
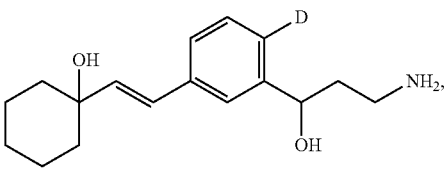
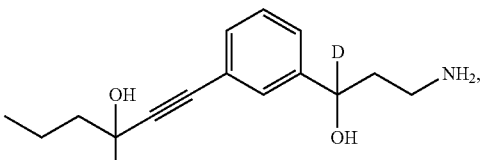
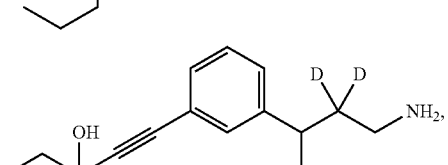
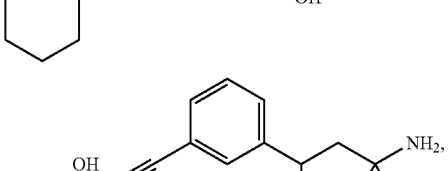
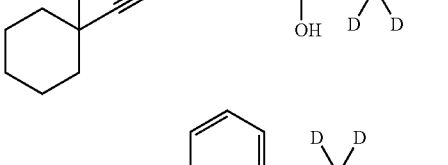
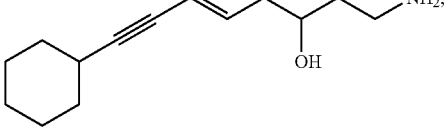

-continued

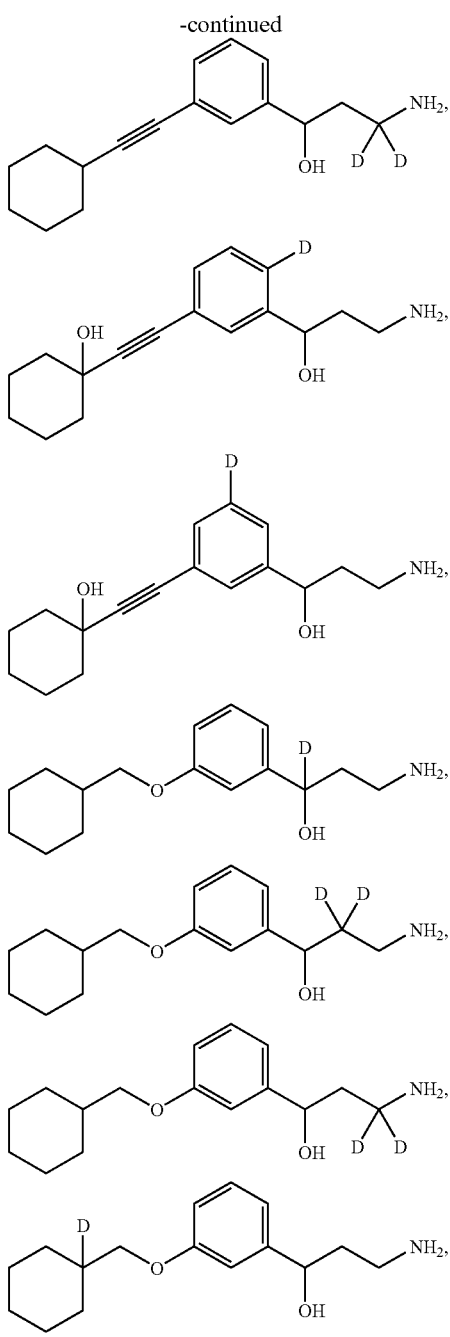

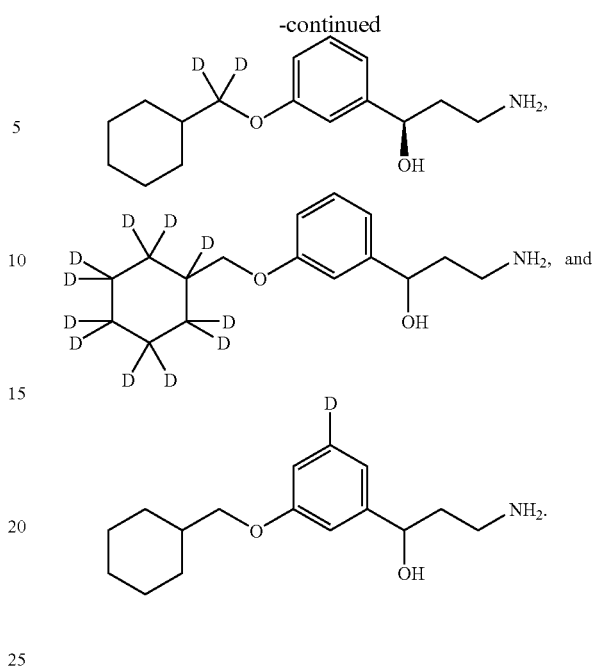

Compounds described herein optionally have a substitution of one, more than one or all of the non-exchangeable hydrogen atoms for deuterium atoms. A non-exchangeable hydrogen atom is one bound to a carbon atom. This type of deuterium substitution provides for improved pharmacokinetic and pharmacodynamic properties. As the C-D bond is stronger than the C—H bond, a metabolic process that involves breaking a C—H bond will be relatively slower for the C-D analog. Pharmacokinetic and pharmacodynamic properties modulated by deuterium substitution include bioavailability, serum half-life, clearance, drug-drug interactions, CYP inhibition and metabolite profile.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

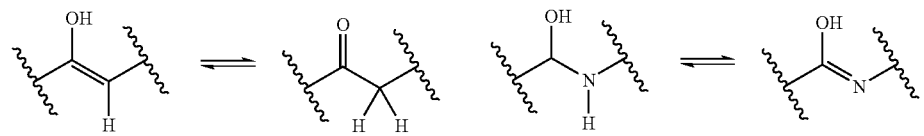

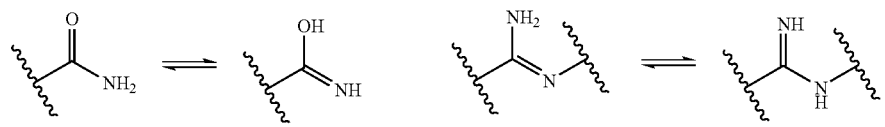

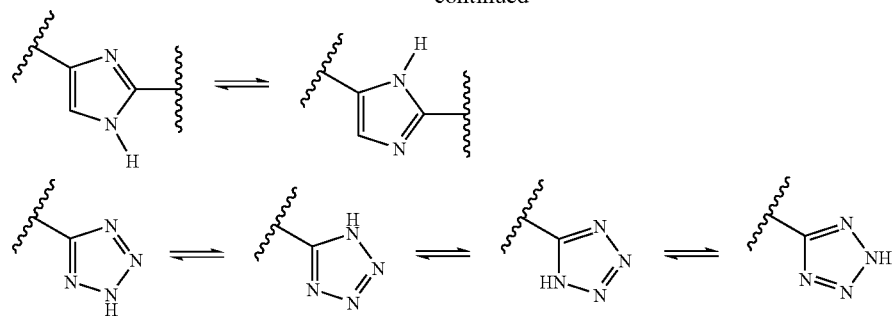

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are encompassed within the scope of the present invention.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinol amine and any derived amide, retinoic acid and any derived ester or amide. A non-retinoid compound can comprise though not require an internal cyclic group (e.g., aromatic group). A non-retinoid compound can contain though not require a nitrogen-linked group.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The compounds of the invention are synthesized by an appropriate combination of generally well known synthetic methods. Techniques useful in synthesizing the compounds of the invention are both readily apparent and accessible to those of skill in the relevant art.

The discussion below is offered to illustrate how, in principle, to gain access to the compounds claimed under this invention and to give details on certain of the diverse methods available for use in assembling the compounds of the invention. However, the discussion is not intended to define or limit the scope of reactions or reaction sequences that are useful in preparing the compounds of the present invention. The compounds of this invention may be made by the procedures and techniques disclosed in the Examples section below, as well as by known organic synthesis techniques.

I. Preparation of Compounds

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art may be identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to the following moieties.

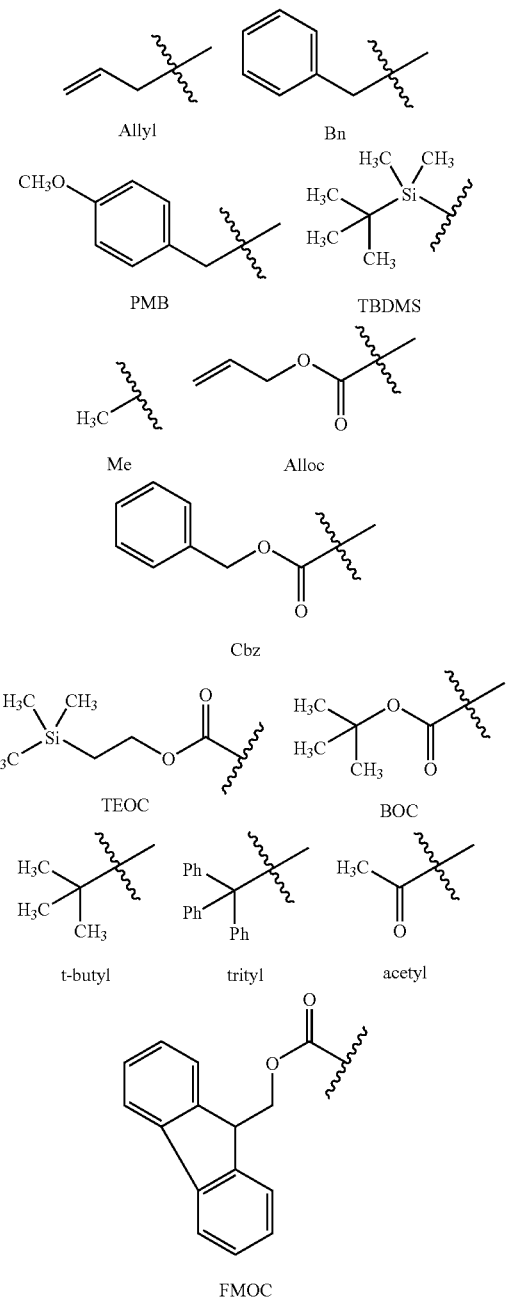

Methods for Preparing Compounds of Formula (I)

The following methods illustrate various synthetic pathways for preparing nitrogen-linked intermediates and the side chain moieties. One skilled in the art will recognize that, for example, a method for amide formation can be combined with a method for side chain formation. For example, any one of Methods A-C can be combined with any of Methods D-H, or any of Methods I-J. They can be further combined with any of Methods K-S to modify the linkage and/or the terminal nitrogen-containing moiety. In the following methods Ar is defined as an optionally substituted phenyl group.

1. N-Linkage Formation:

Methods A-E below describe the formation of the N-Linkage.

Method A below describes an approach to amide formation.

Method A illustrates the construction of a amide intermediate (A-3) through acylation of an aniline (A-2). The acylating agent (A-1) comprises a leaving group (X). This leaving group can be, for example, halogen, mesylate, acyl (as in an anhydride), alcohol (as in ester/active ester) and the like. As shown, the acylation process eliminates a molecule of HX.

A base can be used to facilitate the deprotonation of the aniline and trapping of the HX byproduct. Suitable bases are typically mild bases such as alkali carbonates (e.g., $K_2CO_3$).

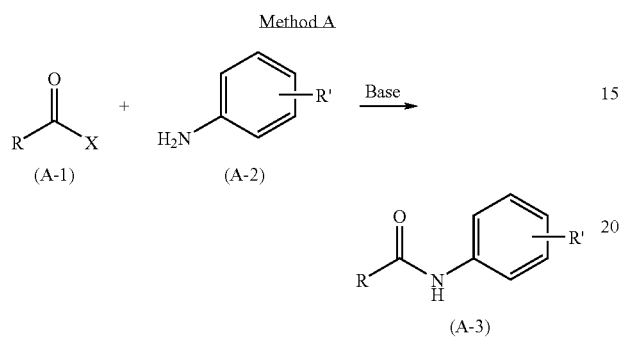

Method B shows the construction of a sulphonamide intermediate (A-5) through the coupling of a sulphonyl halide (A-4) with aniline (A-2).

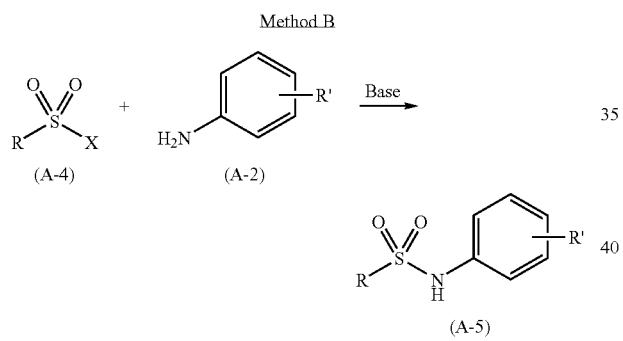

Method C shows the construction of a urea intermediate (A-7) through the coupling of aniline (A-2) with an isocyanate (A-6)

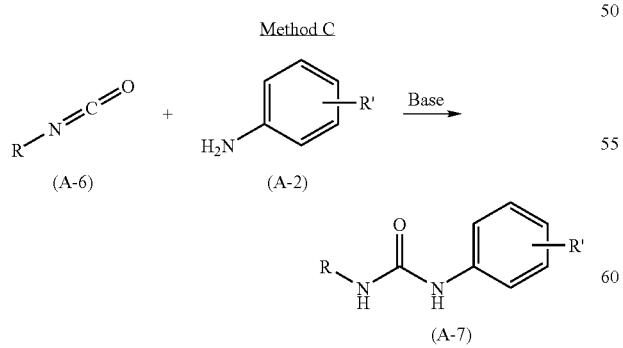

Method D shows the construction of an aniline intermediate (A-8) through the reduction of amide (A-3) with the reducing agent lithium aluminium hydride or the like.

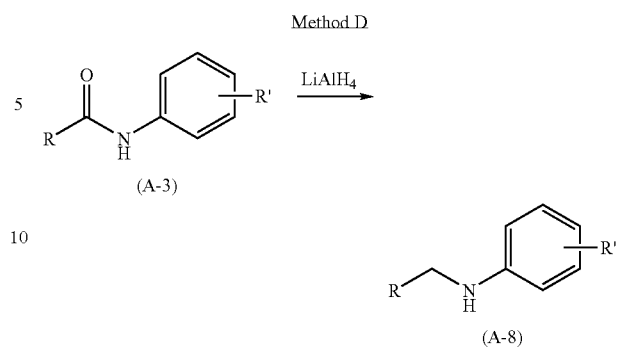

Method E shows the construction of an aniline intermediate (A-8) through the Palladium catalysed cross-coupling of an aryl halide (A-9) with an amine (A-10).

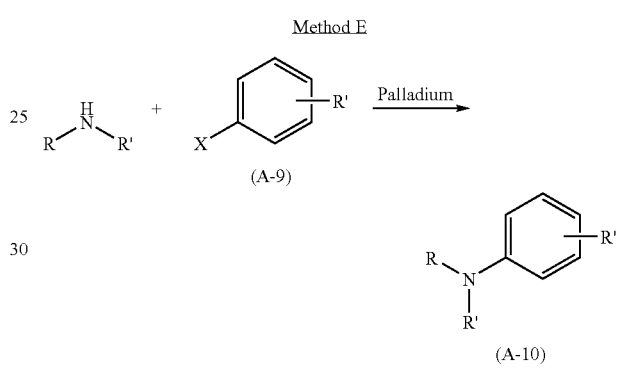

2. Side Chain Formation and Modification

Methods F-T describe methods for side chain formation and modifications.

Generally, a suitably substituted phenyl derivative can be coupled to a diverse range of side chains, which is further modified to provide the final linkages and the nitrogen-containing moieties of the compounds disclosed herein.

Methods F-I illustrate pathways to form propylene linkages of the compounds disclosed herein.

Method F illustrates an aryl halide coupling with an allyl alcohol in the presence of a palladium(0) catalyst. The terminal alcohol group of allyl alcohol has been simultaneously oxidized to an aldehyde group, which is further transformed to an amine via a reductive amination.

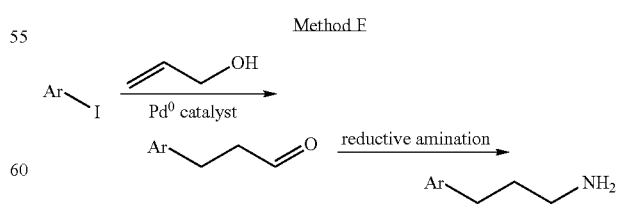

Method G illustrates a condensation between an aryl aldehyde or aryl ketone and a nitrile having at least one α-hydrogen. The resulting intermediate is further reduced to an amine.

Method G

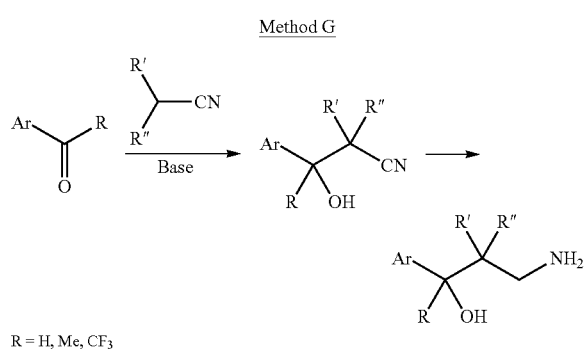

R = H, Me, CF$_3$

Method H is an acylation reaction to form a ketone-based linkage. One skilled in the art will recognize that the R' group may comprise functional groups that can be further modified.

Method H

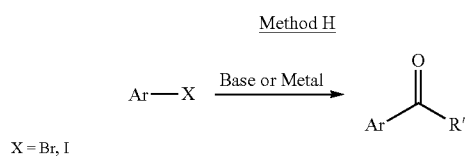

X = Br, I

Method I is an ring-opening reaction of an epoxide to form a hydroxy-substituted propylene side chain linkage.

Method I

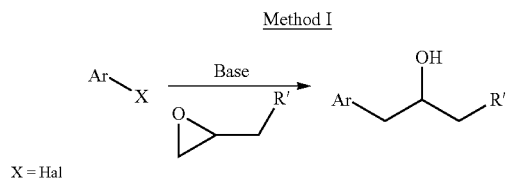

X = Hal

Method J is an attachment of side chain moieties via an oxygen atom. More specifically, a side chain precursor (R'OH) can be condensed with an aryl derivative by eliminating a molecule of H$_2$O. R' may comprise functional groups that can be further modified to prepare linkages and nitrogen-containing moieties of compounds disclosed herein.

Method J

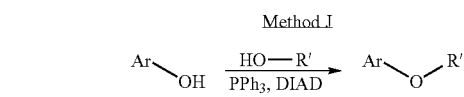

Method K is a condensation reaction that provides an oxygen linking atom. Here, a molecule of HX is eliminated as the result of the condensation.

Method K

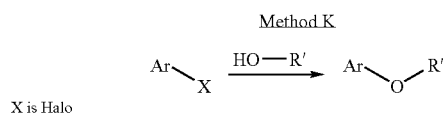

X is Halo

After attachment, the side chain moiety is optionally further modified to provide the final linkage and the terminal nitrogen-containing moiety for the compounds disclosed herein. The following methods illustrate a variety of synthetic pathways to modify the side chain moiety by reduction, oxidation, substitution, fluorination, acylation and the like. Through application of these methods, one of skill in the art recognizes that a diverse group of linkages can be synthesized.

Method L illustrates an amination process in which carboxylic acid is converted to an amine. Typically, the carboxylic acid (or ester) can be first reduced to primary alcohol, which can then be converted to an amine via mesylate, halide, azide, phthalimide, or Mitsunobu reaction and the like. Suitable reducing agents include, for example, lithium aluminum hydride (LiAlH$_4$) and the like. As shown, the resulting amine can be further functionalized, by known methods in the art.

Method L

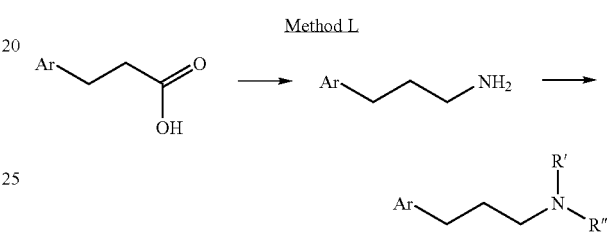

Additional or alternative modifications can be carried out according to the methods illustrated below.

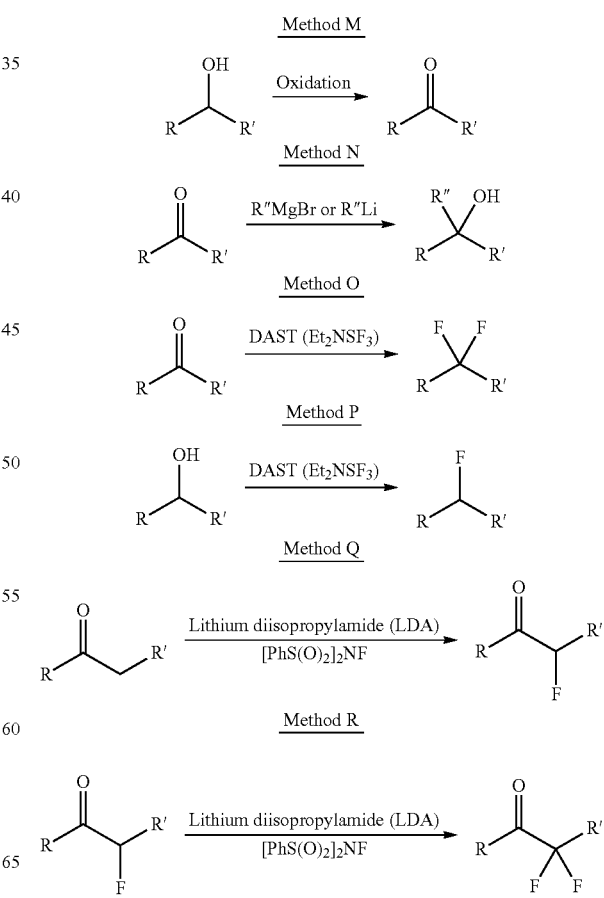

Method S

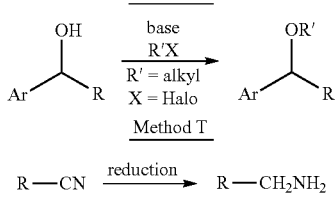

Method T

R—CN $\xrightarrow{\text{reduction}}$ R—CH$_2$NH$_2$

As a non-limiting example only, Scheme A illustrates a complete synthetic sequence for preparing a compound disclosed herein.

Scheme A

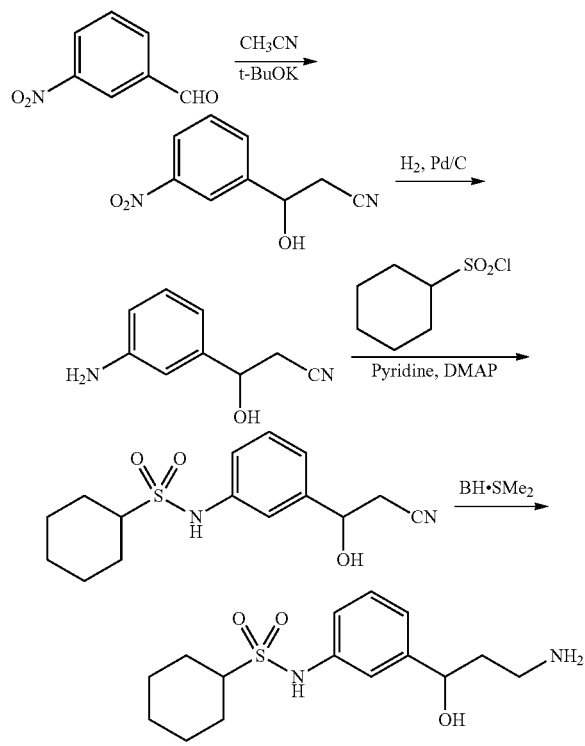

In Scheme A, the three carbon side chain is introduced through alkylation of 3-nitrobenzaldehyde with acetonitrile. The sulphonamide is introduced by a two step process involving reduction of the nitro group followed by reaction with a sulphonyl halide. Finally, reduction of the nitrile to an amine gives the target compound.

Methods for Preparing Compounds of Formula (II)

Generally speaking, the compounds disclosed herein can be prepared in a stepwise manner involving an olefin formation and a side chain formation.

In certain embodiments, an olefin intermediate can be first constructed, which forms the precursor to the styrenyl core structure. A side chain moiety, which is a precursor to the linkage and the nitrogen-containing moiety of the compounds disclosed herein, can then be attached to the olefin intermediate.

In other embodiments, the compounds disclosed herein can be prepared by first preparing a phenyl intermediate having an appropriate side chain, followed by an olefin formation to provide the styrenyl core structure.

The following Methods illustrate various synthetic pathways for preparing olefin intermediates and the side chain moieties. One skilled in the art will recognize that a method for olefin formation can be combined with a method for side chain formation to provide the compounds disclosed herein. For example, Method A can be combined with any of Method K, Methods K and U, Methods K and L, Methods K and AB, Methods T and L, Method R, Method S, Method J, Method E, Methods R and U, and the like. Similarly, Method C can be combined with Method J.

Olefin Formation:

Methods A-I below describe various approaches to olefin formation.

More specifically, Method A illustrates constructing an olefin intermediate (A-3) in a Wittig reaction. Depending on the sequence of the reactions, Ar can be a phenyl derivative compound that is already attached to a side chain moiety, or Ar may comprise a reactive group (appropriately protected), which will be coupled to a side chain moiety after the olefin formation step.

According to Method A, a phosphonium ylide reagent (or "Wittig reagent") (A-1) can be coupled to a benzaldehyde or ketone derivative (A-2) to provide the olefin intermediate (A-3) in the presence of a base. The geometry of the resulting A-3 may depend on the reactivity of the ylide reagent. Triphenylphosphonium-based ylide reagent (R is phenyl) typically produces predominantly (E) or trans-styrenes; whereas trialkylphosphonium-based ylide reagent (R is alkyl) produces predominantly (Z) or cis-styrene. The E or Z stereoisomers can be separated by, for example, chromatography or other known methods in the art.

The ylide reagent (A-1) can be prepared according to known methods in the art. For example, $R_{11}$—CH$_2$OH can be converted to the corresponding ylide reagent (A-1) in the presence of triphenylphosphine hydrobromide. The benzaldehyde or ketone derivative (A-2) may be commercially available or can be prepared by known methods in the art.

The olefin intermediate (A-3) may also be prepared by coupling a phosphonium ylide reagent derivatized from the Ar group (A-4) and an aldehyde or ketene derivative of $R_{11}$ (A-5). The ylide reagent (A-4) can be prepared from, for example, a benzyl alcohol, whereas (A-5) can be prepared by known methods in the art or can be obtained from commercial vendors.

METHOD A

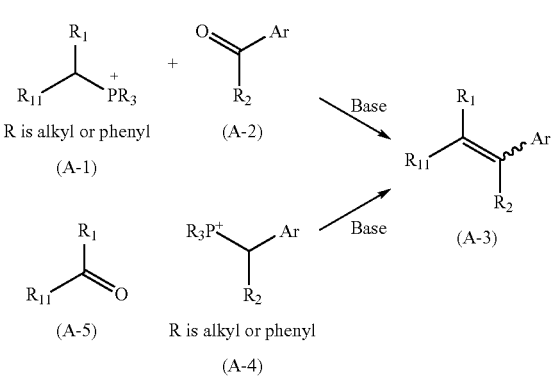

Method AE shows a coupling reaction similar to the Wittig reaction of Method A, except that a phosphorus ylide is used in place of the phosphonium ylide. The phosphorus ylide can be coupled to an aldehyde or ketone in the presence of a base (Wittig-Horner-Emmons reaction.)

METHOD AE

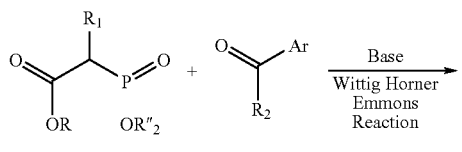

R″ is alkyl or phenyl

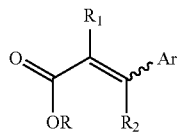

In addition, elimination reactions can be used to form olefin bonds. Methods B-D illustrate various approaches to forming alcohol precursors that can undergo alcohol dehydration in acidic conditions to produce olefin bonds. The Ar group is typically activated with a metal (e.g., Li) to facilitate the alcohol formation. Grignard reagent can also be used in place of the metal.

As discussed above in connection with Method A, the alcohol precursor in each of Methods B-D can also be prepared by using a metal activated $R_{11}$ group and an Ar group derivatized with a carbonyl group or a cyclopropyl group.

METHOD B

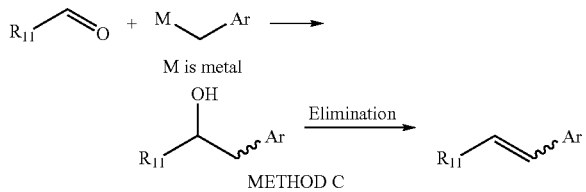

METHOD C

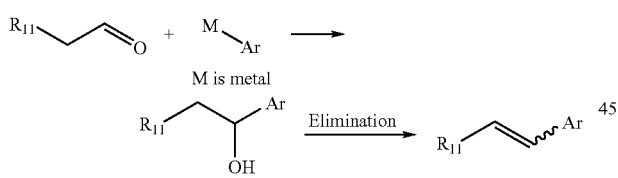

METHOD D

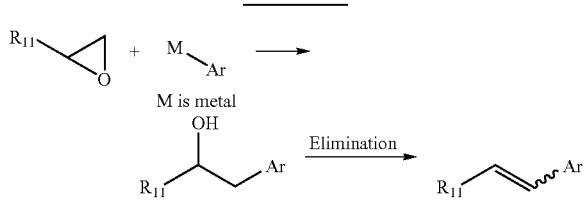

Methods E-G illustrate coupling an olefin or an activated olefin directly with an aryl halide in the presence of a palladium(0) catalyst. In certain embodiments, the olefin can be activated by a transition metal (e.g., Zn or Sn), or boronic acid (e.g., Suzuki reaction), as are known in the art. The halo substituent of the aryl group can be, for example, bromo or iodo.

Palladium catalysts suitable for coupling reactions are known to one skilled in the art. Exemplary palladium(0) catalysts include, for example, tetrakis(triphenylphosphine) palladium(0) [Pd(PPh$_3$)$_4$] and tetrakis(tri(o-tolylphosphine) palladium(0), tetrakis(dimethylphenylphosphine)palladium (0), tetrakis(tris-p-methoxyphenylphosphine)palladium(0) and the like. It is understood that a palladium (II) salt can also be used, which generates the palladium (0) catalyst in situ. Suitable palladium (II) salts include, for example, palladium diacetate [Pd(OAc)$_2$], bis(triphenylphosphine)-palladium diacetate and the like.

METHOD E

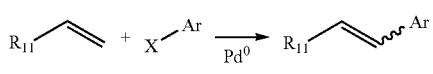

X = Halo

METHOD F

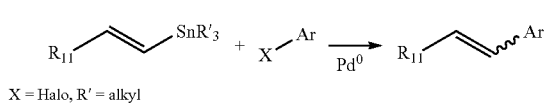

X = Halo, R′ = alkyl

METHOD G

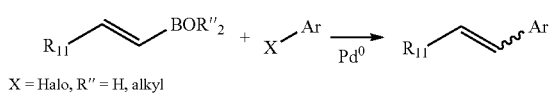

X = Halo, R″ = H, alkyl

An olefin intermediate can also be constructed from an alkyne addition/hydrogenation reaction. Depending on the reaction conditions (syn or anti addition), cis or trans configuration can be formed.

Method H illustrates a syn-addition, i.e., both hydrogens are added from one side of the alkyne molecule, which results in a cis olefin configuration. Typically, hydrogen gas can be used in the presence of a catalyst (e.g., Pd on carbon or platinum) to effect a syn addition.

METHOD H

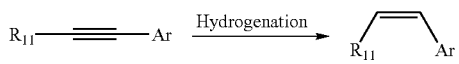

Method I illustrate an anti-addition, i.e., an adding agent is added to opposite sides of the alkyne molecule, resulting in a trans olefin configuration. The adding agent can be, for example, aluminum hydride reagents, lithium/NH$_3$ reagents and the like.

METHOD I

Side Chain Formation and Modification

Methods J-T and AA-AD below describe various approaches to side chain formation and modifications.

Generally speaking, a suitably substituted phenyl derivative can be coupled to a diverse range of side chains, which may be further modified to provide the final linkages and the nitrogen-containing moieties of the compounds disclosed herein.

Method J illustrates an aryl halide coupled with an allyl alcohol in the presence of a palladium(0) catalyst. The terminal alcohol group of allyl alcohol has been simultaneously oxidized to an aldehyde group, which can be further reduced to an amine (—NR$_9$R$_{10}$).

METHOD J

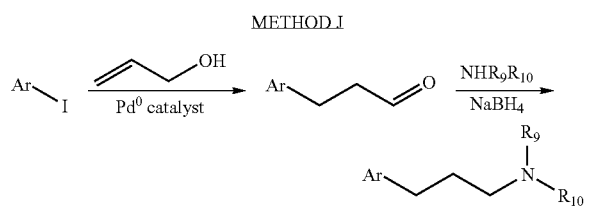

X is halo

Method K illustrates an aldol condensation between an aryl aldehyde or aryl ketone with a nitrile reagent comprising at least one α-hydrogen. The resulting condensation intermediate can be further reduced to an amine (—NR$_9$R$_{10}$).

METHOD K

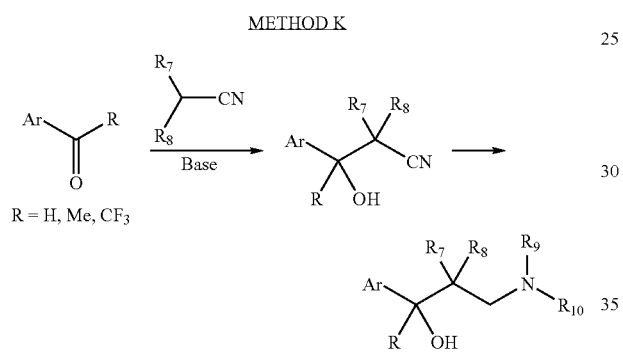

Method AA shows an acylation reaction to form a ketone-based linkage. One skilled in the art will recognize that the R' group may comprise functional groups that can be further modified.

METHOD AA

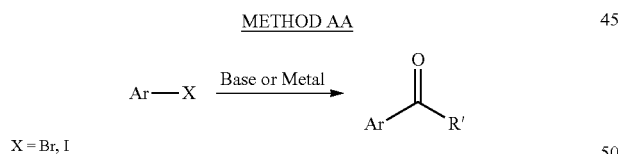

X = Br, I

Method R shows a ring-opening reaction of an epoxide reagent to form a 3-carbon side chain linkage.

METHOD R

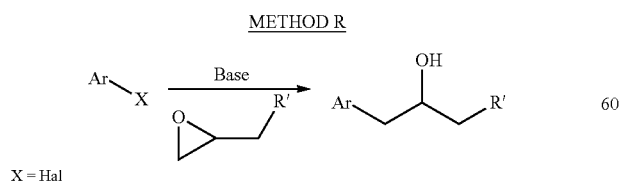

X = Hal

Method S shows the formation of a triple bond linkage based on a Sonogashira reaction. Typically, palladium(0) catalyst is used in combination with a base to couple an aryl halide with a acetylene derivative. R' can be further modified, as described herein.

METHOD S

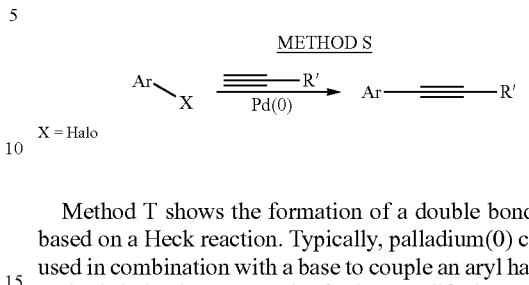

X = Halo

Method T shows the formation of a double bond linkage based on a Heck reaction. Typically, palladium(0) catalyst is used in combination with a base to couple an aryl halide with a vinyl derivative. R' can be further modified, as described herein.

METHOD T

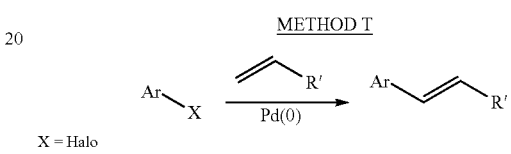

X = Halo

Methods M-P illustrate attachments of side chain moieties by heteroatoms. Method M shows a side chain precursor (R'OH) attached to an aryl derivative via an oxygen atom in a condensation reaction in which a molecule of H$_2$O is eliminated. R' may comprise functional groups that can be further modified to prepare linkages and nitrogen-containing moieties of the compounds disclosed herein.

METHOD M

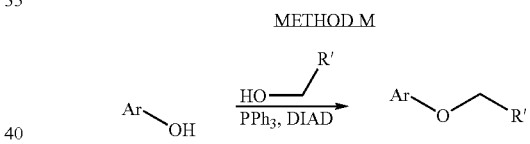

Method N shows a similar coupling reaction that provides a sulfur linking atom. Method O illustrates an oxidation step of the sulfur linking atom to provide —S(O)— or —S(O)$_2$—, depending on the degree of oxidation.

METHOD N

METHOD O

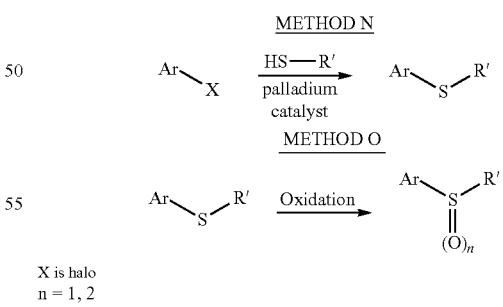

X is halo
n = 1, 2

Method P shows the formation of an amide-containing linkage, in which a aniline derivative is coupled with a carboxylic acid derivative. The carboxylic acid derivative can be activated to facilitate the amide formation. Suitable activating reagents include, for example, 1,3-dicyclohexylcarbodiimide (DCC), 1,1'-carbonyldiimidazole (CDI), 1-ethyl-3-(3-dimethylaminopropyl)carbodiimide hydrochloride (EDCL), benzotriazol-1-yl-oxy-tris(dimethylamino)phosphonium hexafluorophosphate (BOP), and 1,3-diisopropylcarbodiimide (DICD).

METHOD P

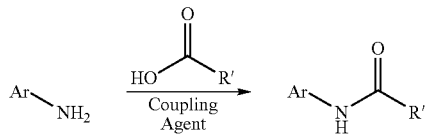

After attachment, the side chain moiety can be further modified to provide the final linkage and the terminal nitrogen-containing moiety for the compounds disclosed herein. The following methods illustrate a variety of synthetic pathways to manipulate or modify the side chain moiety by reduction, oxidation, nucleophilic or electrophilic substitution, fluorination, acylation and the like. As a result, a diverse group of linkages can be synthesized.

Method L illustrates an amination process in which carboxylic acid is converted to an amine. Typically, the carboxylic acid (or ester) can be first reduced to primary alcohol, which can then be converted to an amine via mesylate, halide, azide, phthalimide, or Mitsunobu reaction and the like. Suitable reducing agents include, for example, sodium borohydride (NaBH$_4$), sodium cyanoborohydride (NaBH$_3$CN), sodium triacetoxyborohydride (NaBH(OCOCH$_3$)$_3$), lithium aluminum hydride (LiAlH$_4$) and the like. As shown, the resulting amine can be further functionalized, by known methods in the art.

METHOD L

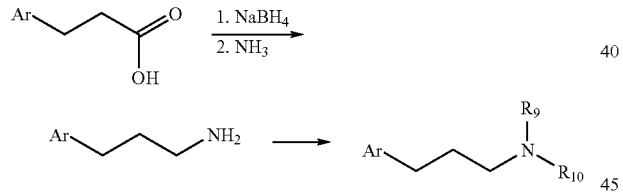

Additional or alternative modifications can be carried out according to the methods illustrated below.

METHOD Q

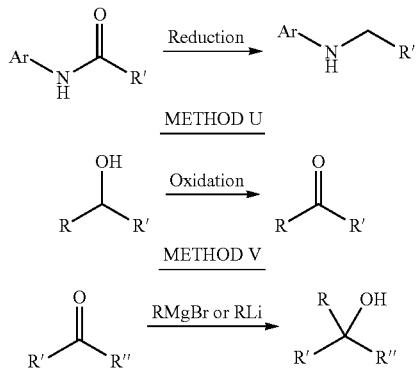

METHOD U

METHOD V

METHOD W

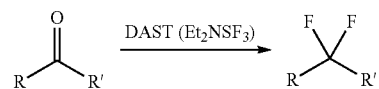

METHOD X

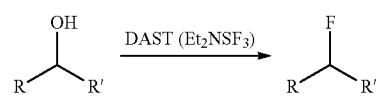

METHOD Y

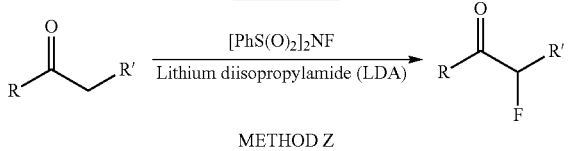

METHOD Z

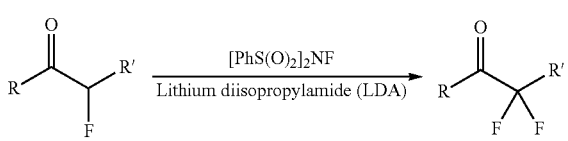

METHOD AB

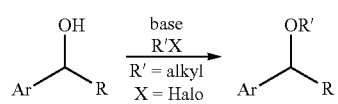

METHOD AC

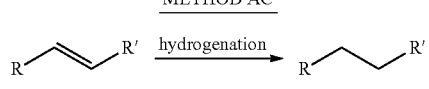

METHOD AD

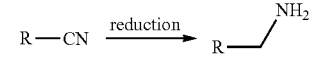

METHOD AE

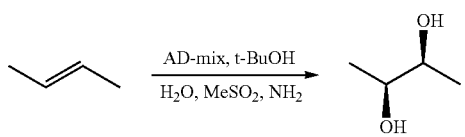

Scheme I illustrates a complete synthetic sequence for preparing one example of the compounds disclosed herein.

SCHEME I

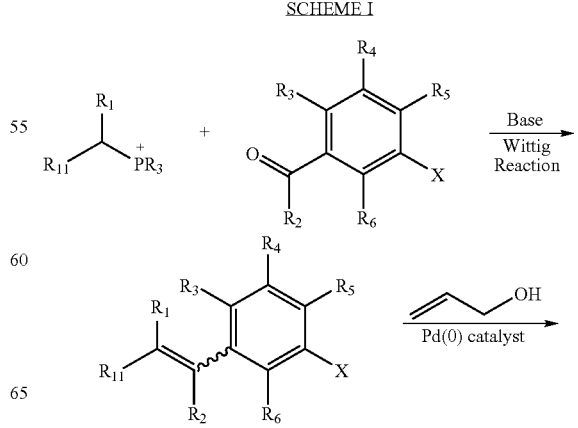

-continued

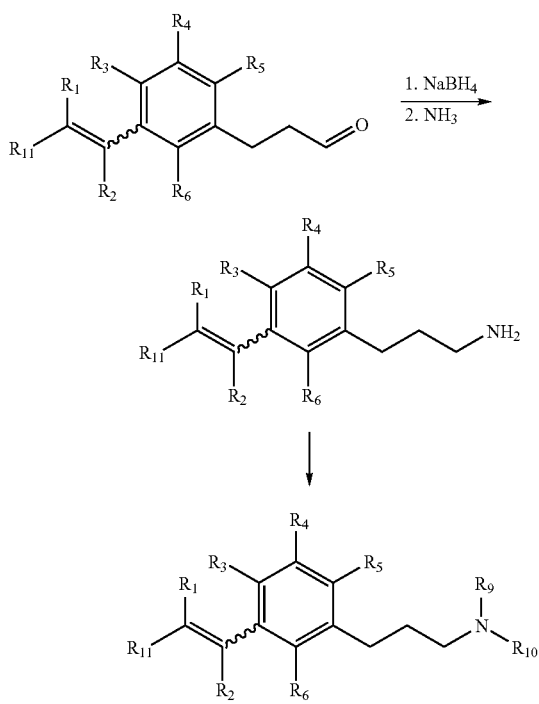

R is alkyl or phenyl
X is halogen

In Scheme I, an olefin intermediate is first constructed, followed by coupling to a side chain moiety. Further modification of the side chain moiety by reduction affords the compounds disclosed herein having a propylene linkage and a terminal amine. Other nitrogen-containing moieties can be further derived from the terminal amine, according to known methods in the art.

One skilled in the art should recognize, however, that the order of the reactions may vary. Thus, in other embodiments, as shown in Scheme II, a side chain attachment is initially performed, followed by olefin formation.

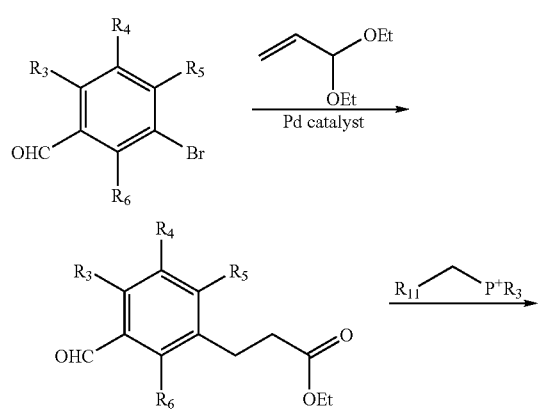

SCHEME II

-continued

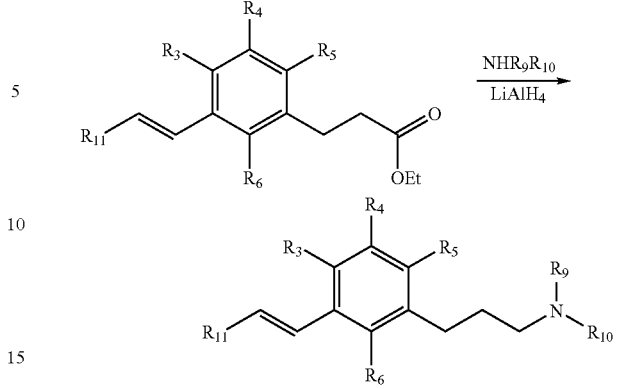

Additional methods for preparing compounds of Formula (II) are disclosed in WO 2008/131368, which is incorporated by reference in its entirety.

Methods for Preparing Compounds of Formula (III)

Generally speaking, compounds disclosed herein can be prepared in a stepwise manner involving an acetylene formation and a side chain formation of a phenyl ring. Typically, the acetylene formation can take place by attaching an acetylene precursor to a phenyl. For example, in certain embodiments, an acetylene intermediate can be first constructed, which forms the precursor to the alkynyl phenyl core structure. A side chain moiety, which is a precursor to the linkage (i.e., propylene or ethylene oxide) and the nitrogen-containing moiety of the compounds disclosed herein, can then be attached to the acetylene intermediate.

In other embodiments, the compounds disclosed herein can be prepared by first preparing a phenyl intermediate having an appropriate side chain, followed by an acetylene formation to provide the alkynyl core structure.

The following Methods illustrate various synthetic pathways for preparing acetylene intermediates and the side chain moieties. One skilled in the art will recognize that a method for acetylene formation can be combined with a method for side chain formation to provide the compounds disclosed herein. For example, any one of Methods A-D can be combined with any of Methods E-H, or any of Methods I-J. They can be further combined with any of Methods K-S to modify the linkage and/or the terminal nitrogen-containing moiety.

Acetylene Formation:

Methods A-D below describe various approaches to acetylene formation.

More specifically, Method A illustrates the construction of an acetylene intermediate (A-3) in a Sonogashira or Castro-Stephens reaction. Depending on the sequence of the reactions, Ar can be a phenyl derivative compound that is already attached to a side chain moiety, or Ar may comprise a reactive group (appropriately protected), which will be coupled to a side chain moiety after the acetylene formation step.

According to Method A, an alkyne (A-1) can be coupled to an aryl halide or a reactive equivalent (A-2) to provide the acetylene intermediate (A-3) in the presence of a copper (I) catalyst (Castro-Stephens) or a mixture of $Pd^0$ and $Cu^1$ catalysts (Sonogashira).

The alkyne (A-1) has a terminal acetylene structure that is capable of coupling to A-2. Alkynes comprising diverse $R_5$ groups can be prepared according to known methods in the art. For example, organic halides (e.g., $R_5Br$) can be converted to the corresponding alkyne (A-1) by coupling to an ethyne. The halobenzene or its reactive equivalent (A-2) may be commercially available or can be prepared by known methods in the art.

Palladium catalysts suitable for coupling reactions are known to one skilled in the art. Exemplary palladium(0) catalysts include, for example, tetrakis(triphenylphosphine) palladium(0) [Pd(PPh$_3$)$_4$] and tetrakis(tri(o-tolylphosphine) palladium(0), tetrakis(dimethylphenylphosphine)palladium (0), tetrakis(tris-p-methoxyphenylphosphine)palladium(0) and the like. It is understood that a palladium (II) salt can also be used, which generates the palladium (0) catalyst in situ. Suitable palladium (II) salts include, for example, palladium diacetate [Pd(OAc)$_2$], bis(triphenylphosphine)-palladium diacetate and the like.

Copper catalysts suitable for coupling reactions are known to one skilled in the art. Typically, the copper (I) catalyst can be copper (I) iodide.

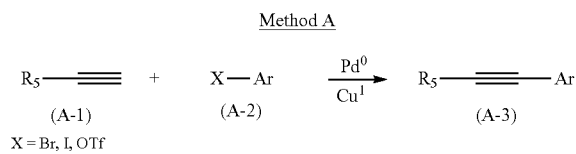

Method B shows an alternative construction of the acetylene intermediate (A-3) by coupling an organic halide (i.e., R$_5$X) with a phenyl comprising a terminal acetylene (A-5).

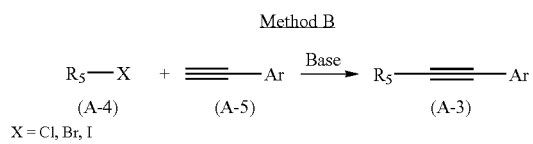

Method C shows the construction of an acetylene intermediate (A-7) through the addition of a terminal acetylene (A-5) to an aldehyde or ketone (A-6).

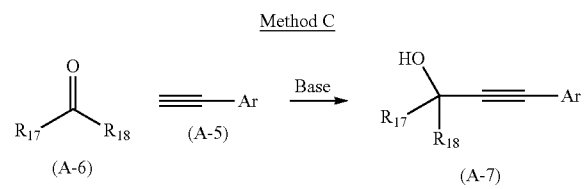

Method D shows the construction of an acetylene intermediate (A-8) through the addition of a terminal acetylene (A-5) to an epoxide (A-9).

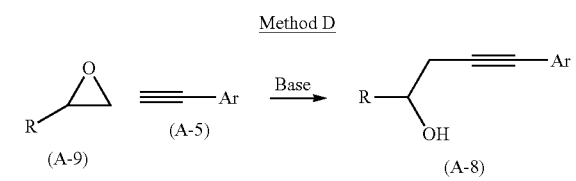

Side Chain Formation and Modification

Methods E-S below describe various approaches to side chain formation and modifications.

Generally speaking, a suitably substituted phenyl derivative can be coupled to a diverse range of side chains, which may be further modified to provide the final linkages and the nitrogen-containing moieties of the compounds disclosed herein.

Methods E-H illustrate pathways to form propylene linkages of the compounds disclosed herein.

Method E illustrates an aryl halide coupled with an allyl alcohol in the presence of a palladium(0) catalyst. The terminal alcohol group of allyl alcohol has been simultaneously oxidized to an aldehyde group, which can be further reductively aminated to an amine (—NR$_{12}$R$_{13}$).

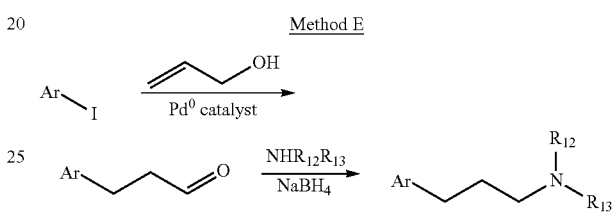

Method F illustrates an aldol condensation between an aryl aldehyde or aryl ketone with a nitrile reagent comprising at least one α-hydrogen. The resulting condensation intermediate can be further reduced to an amine (—NR$_{12}$R$_{13}$).

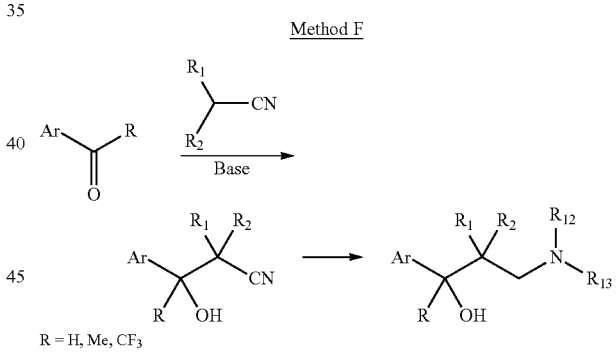

Method G shows an acylation reaction to form a ketone-based linkage (i.e., R$_{10}$ and R$_{11}$ of Formula (I) form an oxo). One skilled in the art will recognize that the R' group may comprise functional groups that can be further modified.

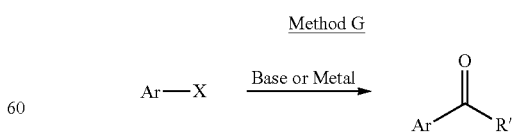

Method H shows a ring-opening reaction of an epoxide reagent to form a hydroxy-substituted propylene side chain linkage.

Method H

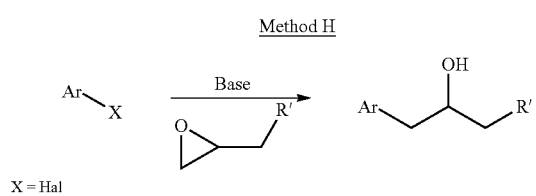

X = Hal

Method I illustrates an attachment of side chain moieties by an oxygen, which can be a precursor to an ethylene oxide linkage. More specifically, a side chain precursor (R'OH) can be condensed with an aryl derivative by eliminating a molecule of $H_2O$. R' may comprise functional groups that can be further modified to prepare linkages and nitrogen-containing moieties of compounds of Formula (III) and its substructures, including Formulae (IIIa) and (IIIb).

Method I

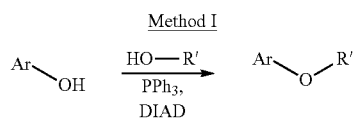

Method J shows a condensation reaction that provides an oxygen linking atom. Here, a molecule of HX is eliminated as the result of the condensation.

Method J

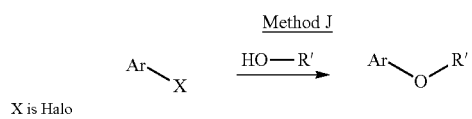

X is Halo

After attachment, the side chain moiety can be further modified to provide the final linkage and the terminal nitrogen-containing moiety for the compounds disclosed herein. The following methods illustrate a variety of synthetic pathways to manipulate or modify the side chain moiety by reduction, oxidation, nucleophilic or electrophilic substitution, fluorination, acylation and the like. As a result, a diverse group of linkages can be synthesized.

Method K illustrates an amination process in which carboxylic acid is converted to an amine. Typically, the carboxylic acid (or ester) can be first reduced to primary alcohol, which can then be converted to an amine via mesylate, halide, azide, phthalimide, or Mitsunobu reaction and the like. Suitable reducing agents include, for example, sodium borohydride ($NaBH_4$), sodium cyanoborohydride ($NaBH_3CN$), sodium triacetoxyborohydride ($NaBH(OCOCH_3)_3$), lithium aluminum hydride ($LiAlH_4$) and the like. As shown, the resulting amine can be further functionalized, by known methods in the art.

Method K

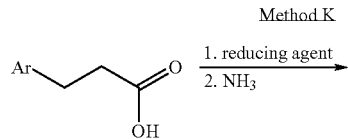

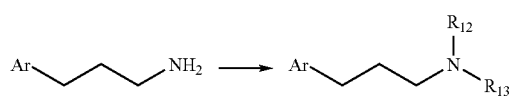

Additional or alternative modifications can be carried out according to the methods illustrated below.

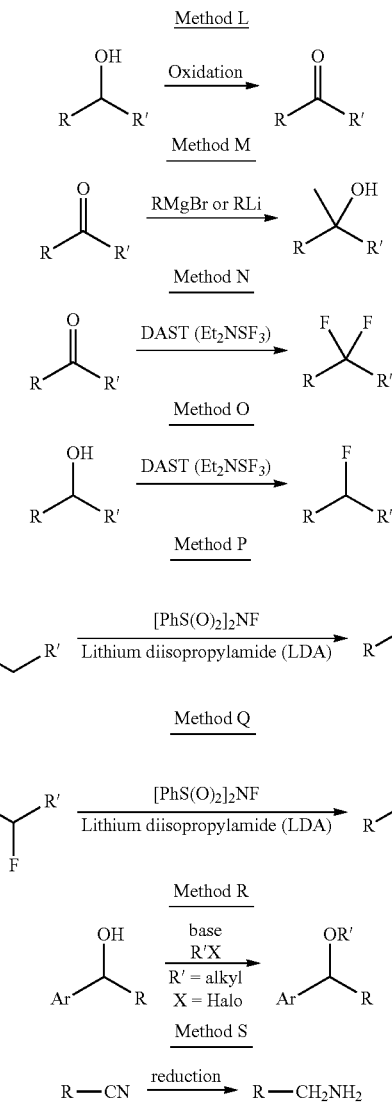

Scheme I illustrates a complete synthetic sequence for preparing a compound disclosed herein.

Scheme I

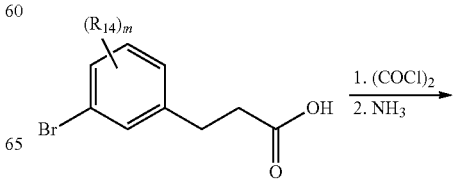

-continued

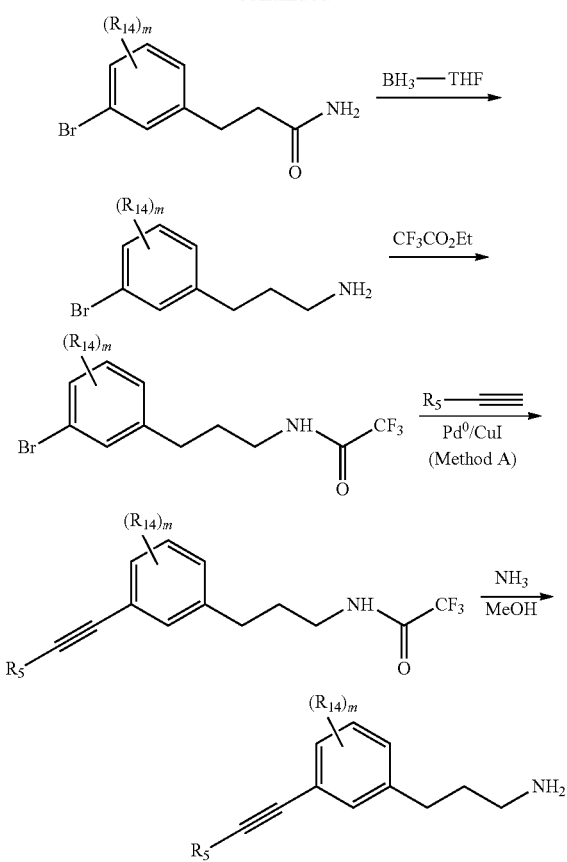

-continued

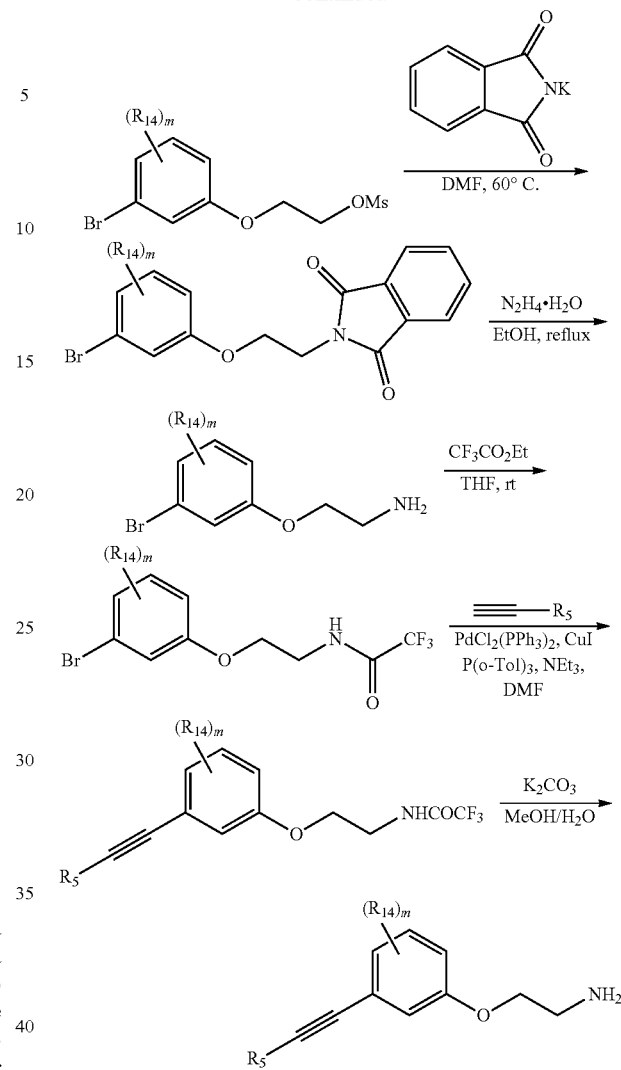

In Scheme I, the side chain moiety is first constructed and the amine protected. The acetylene moiety is then formed through coupling with a terminal acetylene according to Method A. The coupling product is then deprotected to give rise to the final alkynyl phenyl derivative compound comprising a propylene linkage terminating in a primary amine. Other nitrogen-containing moieties (—$NR_{12}R_{13}$) can be further derived from the terminal amine, according to known methods in the art.

One skilled in the art should recognize, however, that the order of the reactions may vary. Thus, in other embodiments, acetylene formation may precede the side chain attachment.

Scheme II illustrates a complete synthetic sequence for preparing a compound disclosed herein.

Scheme II

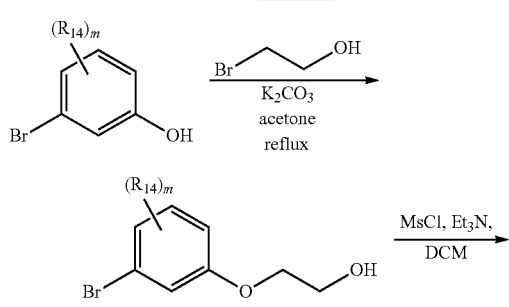

Additional methods for preparing compounds of Formula (III) are disclosed in WO 2009/005794, which is incorporated by reference in its entirety.

Methods for Preparing Compounds of Formula (IV)

Compounds disclosed herein can be prepared in a stepwise manner involving alkylation of a phenol and construction of the linker to the amine.

Alkylation:

Methods A-B below describe various approaches to alkylation.

More specifically, Method A illustrates the construction of an alkoxy intermediate (A-3) through alkylation of a phenol (A-2). The alkylating agent (A-1) comprises a moiety (X) reactive to the acidic hydrogen of phenol. X can be, for example, halogen, mesylate, tosylate, triflate and the like. As shown, the alkylation process eliminates a molecule of HX.

A base can be used to facilitate the deprotonation of the phenol. Suitable bases are typically mild bases such as alkali carbonates (e.g., $K_2CO_3$). Depending on X, other reagents (e.g., $PPh_3$ in combination with DEAD) can be used to facilitate the alkylation process.

METHOD A

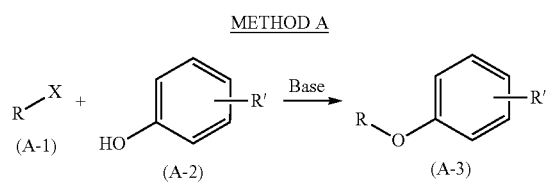

Method B shows the construction of an alkoxy intermediate (A-5) through the ring-opening of an epoxide (A-4).

METHOD B

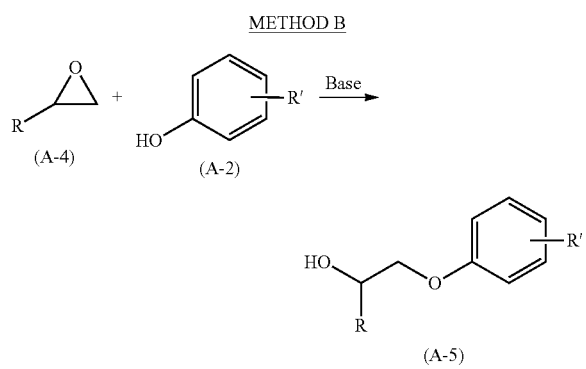

Side Chain Formation and Modification

Methods C-P below describe various approaches to side chain formation and modifications.

Generally speaking, a suitably substituted aryl derivative (e.g., alkoxyphenyl) can be coupled to a diverse range of side chains, which may be further modified to provide the final linkages and the nitrogen-containing moieties of compounds disclosed herein.

Method C illustrates an aldol condensation between an aryl aldehyde or aryl ketone with a nitrile reagent comprising at least one α-hydrogen. The resulting condensation intermediate can be further reduced to an amine (—NH$_2$).

METHOD C

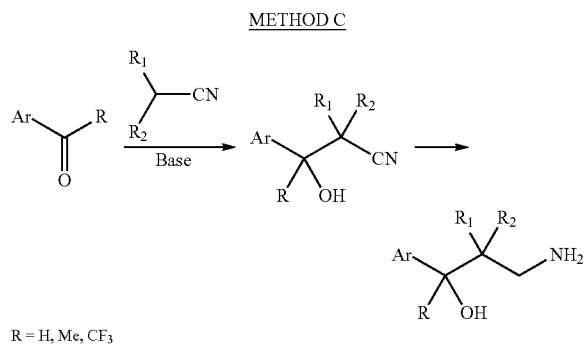

R = H, Me, CF$_3$

Method D shows an acylation reaction to form a ketone-based linkage. One skilled in the art will recognize that the R' group comprises functional groups that can be further modified.

METHOD D

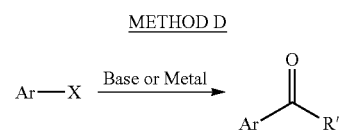

X = Br, I

Method E shows a ring-opening reaction of an epoxide reagent to form a 3-carbon side chain linkage. R' can be further modified.

METHOD E

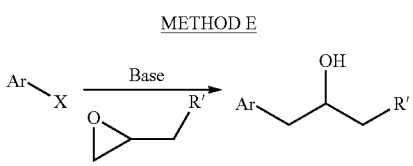

X = Hal

Method F shows the formation of a triple bond linkage based on a Sonogashira reaction. Typically, palladium(0) catalyst is used in combination with a base to couple an aryl halide with a acetylene derivative. R' can be further modified, as described herein. The acetylene linkage can also be further modified, for example, by hydrogenation to provide alkylene or alkenylene linkage.

METHOD F

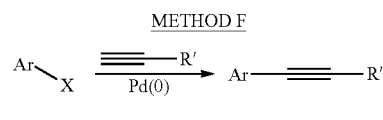

X = Halo

Palladium catalysts suitable for coupling reactions are known to one skilled in the art. Exemplary palladium(0) catalysts include, for example, tetrakis(triphenylphosphine)palladium(0) [Pd(PPh$_3$)$_4$] and tetrakis(tri-o-tolylphosphine)palladium(0), tetrakis(dimethylphenylphosphine)palladium(0), tetrakis(tris-p-methoxyphenylphosphine)palladium(0) and the like. It is understood that a palladium (II) salt can also be used, which generates the palladium (0) catalyst in situ. Suitable palladium (II) salts include, for example, palladium diacetate [Pd(OAc)$_2$], bis(triphenylphosphine)-palladium diacetate and the like.

Method G shows the formation of a double bond linkage based on a Heck reaction. Typically, palladium(0) catalyst is used in combination with a base to couple an aryl halide with a vinyl derivative. R' can be further modified, as described herein.

METHOD G

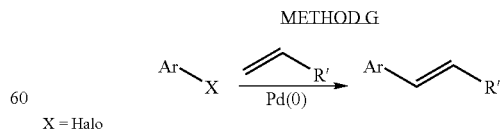

X = Halo

Methods H-P illustrate attachments of side chain moieties by heteroatoms. Method H shows a side chain precursor (R'OH) attached to an aryl derivative via an oxygen atom in a condensation reaction in which a molecule of water is eliminated. R' comprises functional groups that can be further modified to prepare linkages and nitrogen-containing moieties of the compounds disclosed herein.

METHOD H

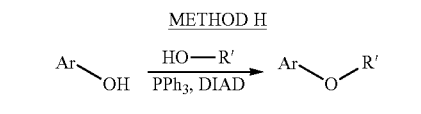

Additional or alternative modifications can be carried out according to the methods illustrated below.

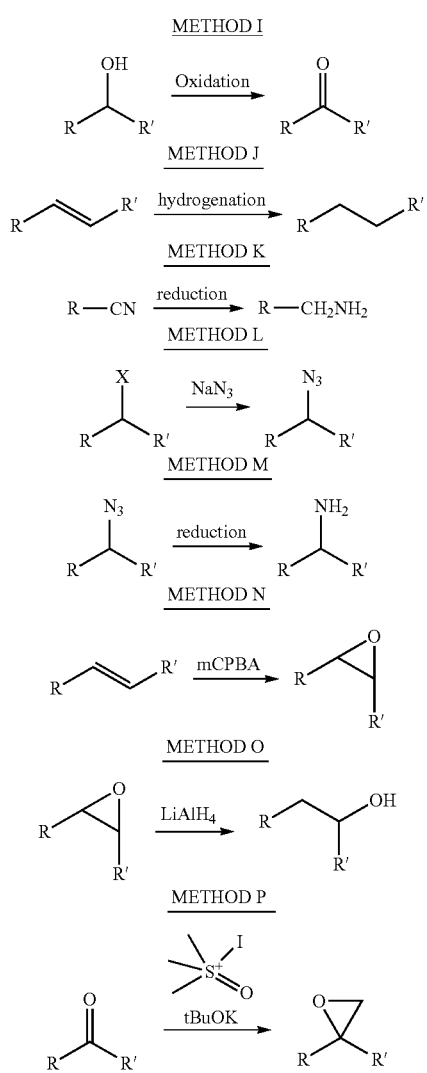

Scheme I illustrates a complete synthetic sequence for preparing a compound disclosed herein.

SCHEME I

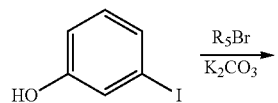

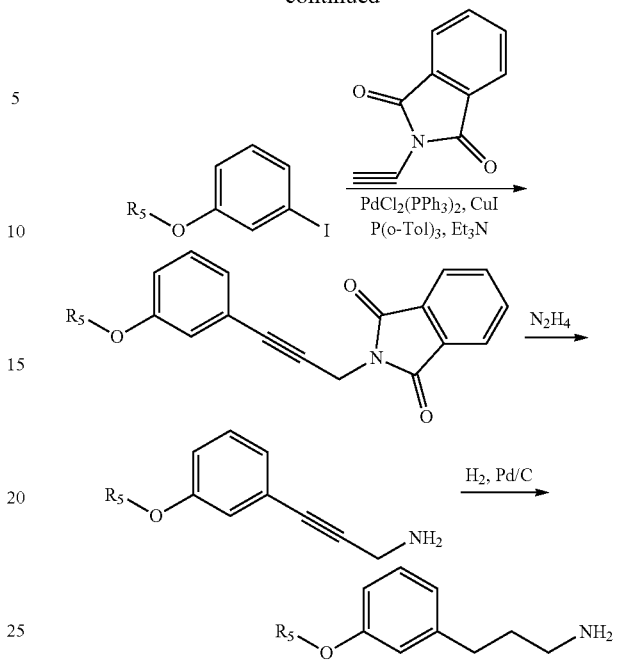

In Scheme I, the alkoxy intermediate is formed via alkylation of a phenol. The side chain is introduced through a Sonogashira coupling. Deprotection of the amine, followed by hydrogenation of the acetylene gives the target compound. Other nitrogen-containing moieties can be further derived from the terminal amine, according to known methods in the art.

Additional methods for preparing compounds of Formula (IV) are disclosed in WO 2009/045479, which is incorporated by reference in its entirety.

In addition to the generic reaction schemes and methods discussed above, other exemplary reaction schemes are also provided to illustrate methods for preparing compounds described herein or any of its subgenus structures.

II. Treatment of Ophthalmic Diseases and Disorders

Compounds as described herein, including compounds having the structure as set forth in Formula (I), (II), (IIa), (III), (IIIa), (IV), or (IVa) and substructures thereof, are useful for treating an ophthalmic disease or disorder by inhibiting one or more steps in the visual cycle. In some embodiments, the compounds disclosed herein function by inhibiting or blocking the activity of a visual cycle trans-cis isomerase. The compounds described herein, may inhibit, block, or in some manner interfere with the isomerization step in the visual cycle. In a particular embodiment, the compound inhibits isomerization of an all-trans-retinol ester; in certain embodiments, the all-trans-retinyl ester is a fatty acid ester of all-trans-retinol, and the compound inhibits isomerization of all-trans-retinol to 11-cis-retinol. The compound may bind to, or in some manner interact with, and inhibit the isomerase activity of at least one visual cycle isomerase, which may also be referred to herein and in the art as a retinal isomerase or an isomerohydrolase. The compound may block or inhibit binding of an all-trans-retinyl ester substrate to an isomerase. Alternatively, or in addition, the compound may bind to the catalytic site or region of the isomerase, thereby inhibiting the capability of the enzyme to catalyze isomerization of an all-trans-retinyl ester substrate. On the basis of scientific data to date, an at least one isomerase that catalyzes the isomerization of all-trans-retinyl esters is believed to be located in the cytoplasm of RPE cells. As discussed herein, each step, enzyme, substrate, intermediate, and product of the visual cycle is not yet elucidated (see, e.g., Moiseyev et al., *Proc. Natl. Acad. Sci. USA* 102:12413-18 (2004); Chen et al., *Invest. Opthalmol. Vis. Sci.* 47:1177-84 (2006); Lamb et al. supra).

Compounds of Formula (II), (IIa), (III), (Ma), (IV) or (IVa) as described herein, and substructures thereof, are useful for treating an ophthalmic disease or disorder by inhibiting one or more steps in the visual cycle. The compounds described herein may be useful for treating a subject who has an ophthalmic disease or disorder, particularly a retinal disease or disorder such as age-related macular degeneration or Stargardt's macular dystrophy.

A method for determining the effect of a compound on isomerase activity may be performed in vitro as described herein and in the art (Stecher et al., *J Biol Chem* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the compounds described herein to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Opthalmologica* 100:77-92 (2000)). See also Deigner et al., *Science*, 244: 968-971 (1989); Gollapalli et al., *Biochim Biophys Acta.* 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 μM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 μM; in other embodiments, the determined $IC_{50}$ level is less than about 50 μM; in other certain embodiments, the determined $IC_{50}$ level is less than about 100 μM or about 500 μM; in other embodiments, the determined $IC_{50}$ level is between about 1 μM and 10 μM; in other embodiments, the determined $IC_{50}$ level is between about 1 nM and 10 nM. When adminstered into a subject, one or more compounds of the present invention exhibits an $ED_{50}$ value of about 5 mg/kg, 5 mg/kg or less as ascertained by inhibition of an isomerase reaction that results in production of 11-cis-retinol. In some embodiments, the compounds of the present invention have $ED_{50}$ values of about 1 mg/kg when administered into a subject. In other embodiments, the compounds of the present invention have $ED_{50}$ values of about 0.1 mg/kg when administered into a subject. The $ED_{50}$ values can be measured after about 2 hours, 4 hours, 6 hours, 8 hours or longer upon administering a subject compound or a pharmaceutical composition thereof.

The compounds described herein may be useful for treating a subject who has an ophthalmic disease or disorder, particularly a retinal disease or disorder such as age-related macular degeneration or Stargardt's macular dystrophy. In one embodiment, the compounds described herein may inhibit (i.e., prevent, reduce, slow, abrogate, or minimize) accumulation of lipofuscin pigments and lipofuscin-related and/or associated molecules in the eye. In another embodiment, the compounds may inhibit (i.e., prevent, reduce, slow, abrogate, or minimize) N-retinylidene-N-retinylethanolamine (A2E) accumulation in the eye. The ophthalmic disease may result, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and a compound as described in detail herein, including a compound having the structure as set forth in Formula (I), (II), (IIa), (III), (IIIa), (IV), or (IVa) and substructures thereof, and the specific compounds described herein.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci. USA* 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed may not be enzymatically degraded. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Opthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Opthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Opthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The compounds described herein may be useful for preventing, reducing, inhibiting, or decreasing accumulation (i.e., deposition) of A2E and A2E-related and/or derived molecules in the RPE. Without wishing to be bound by theory, because the RPE is critical for the maintenance of the integrity of photoreceptor cells, preventing, reducing, or inhibiting damage to the RPE may inhibit degeneration (i.e., enhance the survival or increase or prolong cell viability) of retinal neuronal cells, particularly, photoreceptor cells. Compounds that bind specifically to or interact with A2E A2E-related and/or derived molecules or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

In other embodiments, the compounds described herein may be used for treating other ophthalmic diseases or disorders, for example, glaucoma, cone-rod dystrophy, retinal detachment, hemorrhagic or hypertensive retinopathy, retinitis pigmentosa, optic neuropathy, inflammatory retinal disease, proliferative vitreoretinopathy, genetic retinal dystrophies, traumatic injury to the optic nerve (such as by physical injury, excessive light exposure, or laser light), hereditary optic neuropathy, neuropathy due to a toxic agent or caused by adverse drug reactions or vitamin deficiency, Sorsby's fundus dystrophy, uveitis, a retinal disorder associated with Alzheimer's disease, a retinal disorder associated with multiple sclerosis; a retinal disorder associated with viral infection (cytomegalovirus or herpes simplex virus), a retinal disorder associated with Parkinson's disease, a retinal disorder associated with AIDS, or other forms of progressive retinal atrophy or degeneration. In another specific embodiment, the disease or disorder results from mechanical injury, chemical or drug-induced injury, thermal injury, radiation injury, light injury, laser injury. The subject compounds are useful for treating both hereditary and non-hereditary retinal dystrophy. These methods are also useful for preventing ophthalmic injury from environmental factors such as light-induced oxidative retinal damage, laser-induced retinal damage, "flash bomb injury," or "light dazzle", refractive errors including but not limited to myopia (see, e.g., Quinn G E et al. Nature 1999; 399:113-114; Zadnik K et al. Nature 2000; 404:143-144; Gwiazda J et al. Nature 2000; 404: 144), etc.

In other embodiments, methods are provided herein for inhibiting neovascularization (including but not limited to neovascular glycoma) in the retina using any one or more of the compounds as described in detail herein, including a compound having the structure as set forth in Formula (I), (II), (IIa), (III), (Ma), (IV), or (IVa) and substructures thereof, and the specific compounds described herein. In certain other embodiments, methods are provided for reducing hypoxia in the retina using the compounds described herein. These methods comprise administering to a subject, in need thereof, a composition comprising a pharmaceutically acceptable or suitable excipient (i.e., pharmaceutically acceptable or suitable carrier) and a compound as described in detail herein, including a compound having the structure as set forth in Formula (I), (II), (IIa), (III), (IIIa), (IV), or (IVa) and substructures thereof, and the specific compounds described herein.

Merely by way of explanation and without being bound by any theory, and as discussed in further detail herein, dark-adapted rod photoreceptors engender a very high metabolic demand (i.e., expenditure of energy (ATP consumption) and consumption of oxygen). The resultant hypoxia may cause and/or exacerbate retinal degeneration, which is likely exaggerated under conditions in which the retinal vasculature is already compromised, including, but not limited to, such conditions as diabetic retinopathy, macular edema, diabetic maculopathy, retinal blood vessel occlusion (which includes retinal venous occlusion and retinal arterial occlusion), retinopathy of prematurity, ischemia reperfusion related retinal injury, as well as in the wet form of age-related macular degeneration (AMD). Furthermore, retinal degeneration and hypoxia may lead to neovascularization, which in turn may worsen the extent of retinal degeneration. The compounds described herein that modulate the visual cycle can be administered to prevent, inhibit, and/or delay dark adaptation of rod photoreceptor cells, and may therefore reduce metabolic demand, thereby reducing hypoxia and inhibiting neovascularization.

By way of background, oxygen is a critical molecule for preservation of retinal function in mammals, and retinal hypoxia may be a factor in many retinal diseases and disorders that have ischemia as a component. In most mammals (including humans) with dual vascular supply to the retina, oxygenation of the inner retina is achieved through the intraretinal microvasculature, which is sparse compared to the choriocapillaris that supplies oxygen to the RPE and photoreceptors. The different vascular supply networks create an uneven oxygen tension across the thickness of the retina (Cringle et al., *Invest. Opthalmol. Vis. Sci.* 43:1922-27 (2002)). Oxygen fluctuation across the retinal layers is related to both the differing capillary densities and disparity in oxygen consumption by various retinal neurons and glia.

Local oxygen tension can significantly affect the retina and its microvasculature by regulation of an array of vasoactive agents, including, for example, vascular endothelial growth factor (VEGF). (See, e.g., Werdich et al., *Exp. Eye Res.* 79:623 (2004); Arden et al., *Br. J. Opthalmol.* 89:764 (2005)). Rod photoreceptors are believed to have the highest metabolic rate of any cell in the body (see, e.g., Arden et al., supra). During dark adaptation, the rod photoreceptors recover their high cytoplasmic calcium levels via cGMP-gated calcium channels with concomitant extrusion of sodium ions and water. The efflux of sodium from the cell is an ATP-dependent process, such that the retinal neurons consume up to an estimated five times more oxygen under scotopic (i.e., dark adapted), compared with photopic (i.e., light adapted) conditions. Thus, during characteristic dark adaptation of photoreceptors, the high metabolic demand leads to significant local reduction of oxygen levels in the dark-adapted retina (Ahmed et al, *Invest. Opthalmol. Vis. Sci.* 34:516 (1993)).

Without being bound by any one theory, retinal hypoxia may be further increased in the retina of subjects who have diseases or conditions such as, for example, central retinal vein occlusion in which the retinal vasculature is already compromised. Increasing hypoxia may increase susceptibility to sight-threatening, retinal neovascularization. Neovascularization is the formation of new, functional microvascular networks with red blood cell perfusion, and is a characteristic of retinal degenerative disorders, including, but not limited to, diabetic retinopathy, retinopathy of prematurity, wet AMD and central retinal vein occlusions. Preventing or inhibiting dark adaptation of rod photoreceptor cells, thereby decreasing expenditure of energy and consumption of oxygen (i.e., reducing metabolic demand), may inhibit or slow retinal degeneration, and/or may promote regeneration of retinal cells, including rod photoreceptor cells and retinal pigment epithelial (RPE) cells, and may reduce hypoxia and may inhibit neovascularization.

Methods are described herein for inhibiting (i.e., reducing, preventing, slowing or retarding, in a biologically or statistically significant manner) degeneration of retinal cells (including retinal neuronal cells as described herein and RPE cells) and/or for reducing (i.e., preventing or slowing, inhibiting, abrogating in a biologically or statistically significant manner) retinal ischemia. Methods are also provided for inhibiting (i.e., reducing, preventing, slowing or retarding, in a biologically or statistically significant manner) neovascularization in the eye, particularly in the retina. Such methods comprise contacting the retina, and thus, contacting retinal cells (including retinal neuronal cells such as rod photoreceptor cells, and RPE cells) with at least one of the compounds described herein that inhibits at least one visual cycle trans-cis isomerase (which may include inhibition of isomerization of an all-trans-retinyl ester), under conditions and at a time that may prevent, inhibit, or delay dark adaptation of a rod photoreceptor cell in the retina. As described in further detail herein, in particular embodiments, the compound that contacts the retina interacts with an isomerase enzyme or enzymatic complex in a RPE cell in the retina and inhibits, blocks, or in some manner interferes with the catalytic activity of the isomerase. Thus, isomerization of an all-trans-retinyl ester is inhibited or reduced. The compounds described herein or compositions comprising said compounds may be administered to a subject who has developed and manifested an ophthalmic disease or disorder or who is at risk of developing an ophthalmic disease or disorder, or to a subject who presents or who is at risk of presenting a condition such as retinal neovascularization or retinal ischemia.

By way of background, the visual cycle (also called retinoid cycle) refers to the series of enzyme and light-mediated conversions between the 11-cis and all-trans forms of retinol/retinal that occur in the photoreceptor and retinal pigment epithelial (RPE) cells of the eye. In vertebrate photoreceptor cells, a photon causes isomerization of the 11-cis-retinylidene chromophore to all-trans-retinylidene coupled to the visual opsin receptors. This photoisomerization triggers conformational changes of opsins, which, in turn, initiate the biochemical chain of reactions termed phototransduction (Filipek et al., *Annu. Rev. Physiol.* 65 851-79 (2003)). After absorption of light and photoisomerization of 11-cis-retinal to all-trans retinal, regeneration of the visual chromophore is a critical step in restoring photoreceptors to their dark-adapted state. Regeneration of the visual pigment requires that the chromophore be converted back to the 11-cis-configuration (reviewed in McBee et al., *Prog. Retin. Eye Res.* 20:469-52 (2001)). The chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-78 (2004)).

During the visual cycle in rod receptor cells, the 11-cis retinal chromophore within the visual pigment molecule, which is called rhodopsin, absorbs a photon of light and is isomerized to the all-trans configuration, thereby activating the phototransduction cascade. Rhodopsin is a G-protein coupled receptor (GPCR) that consists of seven membrane-spanning helices that are interconnected by extracellular and cytoplasmic loops. When the all-trans form of the retinoid is still covalently bound to the pigment molecule, the pigment is referred to as metarhodopsin, which exists in different forms (e.g., metarhodopsin I and metarhodopsin II). The all-trans-retinoid is then hydrolyzed and the visual pigment is in the form of the apoprotein, opsin, which is also called apo-rhodopsin in the art and herein. This all-trans-retinoid is transported or chaperoned out of the photoreceptor cell and across the extracellular space to the RPE cells, where the retinoid is converted to the 11-cis-isomer. The movement of the retinoids between the RPE and photoreceptors cells is believed to be accomplished by different chaperone polypeptides in each of the cell types. See Lamb et al., *Progress in Retinal and Eye Research* 23:307-80 (2004).

Under light conditions, rhodopsin continually transitions through the three forms, rhodopsin, metarhodopsin, and apo-rhodopsin. When most of the visual pigment is in the rhodopsin form (i.e., bound with 11-cis retinal), the rod photoreceptor cell is in a "dark-adapted" state. When the visual pigment is predominantly in the metarhodopsin form (i.e., bound with all-trans-retinal), the state of the photoreceptor cell is referred to as a "light-adapted," and when the visual pigment is apo-rhodopsin (or opsin) and no longer has bound chromophore, the state of the photoreceptor cell is referred to as "rhodopsin-depleted." Each of the three states of the photoreceptor cell has different energy requirements, and differing levels of ATP and oxygen are consumed. In the dark-adapted state, rhodopsin has no regulatory effect on cation channels, which are open, resulting in an influx of cations ($Na^+/K^+$ and $Ca^{2+}$). To maintain the proper level of these cations in the cell during the dark state, the photoreceptor cells actively transport the cations out of the cell via ATP-dependent pumps. Thus maintenance of this "dark current" requires a large amount of energy, resulting in high metabolic demand. In the light-adapted state, metarhodopsin triggers an enzymatic cascade process that results in hydrolysis of GMP, which in turn, closes cation-specific channels in the photoreceptor cell membrane. In the rhodopsin-depleted state, the chromophore is hydrolyzed from metarhodopsin to form the apoprotein, opsin (apo-rhodopsin), which partially regulates the cation channels such that the rod photoreceptor cells exhibit an attenuated current compared with the photoreceptor in the dark-adapted state, resulting in a moderate metabolic demand.

Under normal light conditions, the incidence of rod photoreceptors in the dark adapted state is small, in general, 2% or less, and the cells are primarily in the light-adapted or rhodopsin-depleted states, which overall results in a relatively low metabolic demand compared with cells in the dark-adapted state. At night, however, the relative incidence of the dark-adapted photoreceptor state increases profoundly, due to the absence of light adaptation and to the continued operation of the "dark" visual cycle in RPE cells, which replenishes the rod photoreceptor cells with 11-cis-retinal. This shift to dark adaptation of the rod photoreceptor causes an increase in metabolic demand (that is, increased ATP and oxygen consumption), leading ultimately to retinal hypoxia and subsequent initiation of angiogenesis. Most ischaemic insults to the retina therefore occur in the dark, for example, at night during sleep.

Without being bound by any theory, therapeutic intervention during the "dark" visual cycle may prevent retinal hypoxia and neovascularization that are caused by high metabolic activity in the dark-adapted rod photoreceptor cell. Merely by way of one example, altering the "dark" visual cycle by administering any one of the compounds described herein, which is an isomerase inhibitor, rhodopsin (i.e., 11-cis-retinal bound) may be reduced or depleted, preventing or inhibiting dark adaptation of rod photoreceptors. This in turn may reduce retinal metabolic demand, attenuating the nighttime risk of retinal ischemia and neovascularization, and thereby inhibiting or slowing retinal degeneration.

In one embodiment, at least one of the compounds described herein (i.e., a compound as described in detail herein, including a compound having the structure as set forth in Formula (I), (II), (IIa), (III), (Ma), (IV), or (IVa) and substructures thereof, and the specific compounds described herein) that, for example, blocks, reduces, inhibits, or in some manner attenuates the catalytic activity of a visual cycle isomerase in a statistically or biologically significant manner, may prevent, inhibit, or delay dark adaptation of a rod photoreceptor cell, thereby inhibiting (i.e., reducing, abrogating, preventing, slowing the progression of, or decreasing in a statistically or biologically significant manner) degeneration of retinal cells (or enhancing survival of retinal cells) of the retina of an eye. In another embodiment, the compounds described herein may prevent or inhibit dark adaptation of a rod photoreceptor cell, thereby reducing ischemia (i.e., decreasing, preventing, inhibiting, slowing the progression of ischemia in a statistically or biologically significant manner). In yet another embodiment, any one of the compounds described herein may prevent dark adaptation of a rod photoreceptor cell, thereby inhibiting neovascularization in the retina of an eye. Accordingly, methods are provided herein for inhibiting retinal cell degeneration, for inhibiting neovascularization in the retina of an eye of a subject, and for reducing ischemia in an eye of a subject wherein the methods comprise administering at least one compound described herein, under conditions and at a time sufficient to prevent, inhibit, or delay dark adaptation of a rod photoreceptor cell. These methods and compositions are therefore useful for treating an ophthalmic disease or disorder including, but not limited to, diabetic retinopathy, diabetic maculopathy, retinal blood vessel occlusion, retinopathy of prematurity, or ischemia reperfusion related retinal injury.

The compounds described herein (i.e., a compound as described in detail herein, including a compound having the structure as set forth in Formula (I), (II), (IIa), (III), (IIIa), (IV), or (IVa), and substructures thereof, and the specific compounds described herein) may prevent (i.e., delay, slow, inhibit, or decrease) recovery of the visual pigment chromophore, which may prevent or inhibit or retard the formation of retinals and may increase the level of retinal esters, which perturbs the visual cycle, inhibiting regeneration of rhodopsin, and which prevents, slows, delays or inhibits dark adaptation of a rod photoreceptor cell. In certain embodiments, when dark adaptation of rod photoreceptor cells is prevented in the presence of the compound, dark adaptation is substantially prevented, and the number or percent of rod photoreceptor cells that are rhodopsin-depleted or light adapted is increased compared with the number or percent of cells that are rhodopsin-depleted or light-adapted in the absence of the agent. Thus, in certain embodiments when dark adaptation of rod photoreceptor cells is prevented (i.e., substantially prevented), only at least 2% of rod photoreceptor cells are dark-adapted, similar to the percent or number of cells that are in a dark-adapted state during normal, light conditions. In other embodiments, at least 5-10%, 10-20%, 20-30%, 30-40%, 40-50%, 50-60%, or 60-70% of rod photoreceptor cells are dark-adapted after administration of an agent. In other embodiments, the compound acts to delay dark adaptation, and in the presence of the compound dark adaptation of rod photoreceptor cells may be delayed 30 minutes, one hour, two hours, three hours, or four hours compared to dark adaptation of rod photoreceptors in the absence of the compound. By contrast, when a compound described herein is administered such that the compound effectively inhibits isomerization of substrate during light-adapted conditions, the compound is administered in such a manner to minimize the percent of rod photoreceptor cells that are dark-adapted, for example, only 2%, 5%, 10%, 20%, or 25% of rod photoreceptors are dark-adapted (see e.g., U.S. Patent Application Publication No. 2006/0069078; Patent Application No. PCT/US2007/002330).

In the retina in the presence of at least one compound described herein, regeneration of rhodopsin in a rod photoreceptor cell may be inhibited or the rate of regeneration may be reduced (i.e., inhibited, reduced, or decreased in a statistically or biologically significant manner), at least in part, by preventing the formation of retinals, reducing the level of retinals, and/or increasing the level of retinyl esters. To determine the level of regeneration of rhodopsin in a rod photoreceptor cell, the level of regeneration of rhodopsin (which may be called a first level) may be determined prior to permitting contact between the compound and the retina (i.e., prior to administration of the agent). After a time sufficient for the compound and the retina and cells of the retina to interact, (i.e., after administration of the compound), the level of regeneration of rhodopsin (which may be called a second level) may be determined. A decrease in the second level compared with the first level indicates that the compound inhibits regeneration of rhodopsin. The level of rhodopsin generation may be determined after each dose, or after any number of doses, and ongoing throughout the therapeutic regimen to characterize the effect of the agent on regeneration of rhodopsin.

In certain embodiments, the subject in need of the treatments described herein, may have a disease or disorder that results in or causes impairment of the capability of rod photoreceptors to regenerate rhodopsin in the retina. By way of example, inhibition of rhodopsin regeneration (or reduction of the rate of rhodopsin regeneration) may be symptomatic in patients with diabetes. In addition to determining the level of regeneration of rhodopsin in the subject who has diabetes before and after administration of a compound described herein, the effect of the compound may also be characterized by comparing inhibition of rhodopsin regeneration in a first subject (or a first group or plurality of subjects) to whom the compound is administered, to a second subject (or second group or plurality of subjects) who has diabetes but who does not receive the agent.

In another embodiment, a method is provided for preventing or inhibiting dark adaptation of a rod photoreceptor cell (or a plurality of rod photoreceptor cells) in a retina comprising contacting the retina and at least one of the compounds described herein (i.e., a compound as described in detail herein, including a compound having the structure as set forth in Formula (I), (II), (IIa), (III), (Ma), (IV), or (IVa), and substructures thereof, and the specific compounds described herein), under conditions and at a time sufficient to permit interaction between the agent and an isomerase present in a retinal cell (such as an RPE cell). A first level of 11-cis-retinal in a rod photoreceptor cell in the presence of the compound may be determined and compared to a second level of 11-cis-retinal in a rod photoreceptor cell in the absence of the compound. Prevention or inhibition of dark adaptation of the rod photoreceptor cell is indicated when the first level of 11-cis-retinal is less than the second level of 11-cis-retinal.

Inhibiting regeneration of rhodopsin may also include increasing the level of 11-cis-retinyl esters present in the RPE cell in the presence of the compound compared with the level of 11-cis-retinyl esters present in the RPE cell in the absence of the compound (i.e., prior to administration of the agent). A two-photon imaging technique may be used to view and analyze retinosome structures in the RPE, which structures are believed to store retinyl esters (see, e.g., Imanishi et al., *J. Cell Biol.* 164:373-83 (2004), Epub 2004 Jan. 26). A first level of retinyl esters may be determined prior to administration of the compound, and a second level of retinyl esters may be determined after administration of a first dose or any subsequent dose, wherein an increase in the second level compared to the first level indicates that the compound inhibits regeneration of rhodopsin.

Retinyl esters may be analyzed by gradient HPLC according to methods practiced in the art (see, for example, Mata et al., *Neuron* 36:69-80 (2002); Trevino et al. *J. Exp. Biol.* 208: 4151-57 (2005)). To measure 11-cis and all-trans retinals, retinoids may be extracted by a formaldehyde method (see, e.g., Suzuki et al., *Vis. Res.* 28:1061-70 (1988); Okajima and Pepperberg, *Exp. Eye Res.* 65:331-40 (1997)) or by a hydroxylamine method (see, e.g., Groenendijk et al., *Biochim. Biophys. Acta.* 617:430-38 (1980)) before being analyzed on isocratic HPLC (see, e.g., Trevino et al., supra). The retinoids may be monitored spectrophotometrically (see, e.g., Maeda et al., *J. Neurochem.* 85:944-956 (2003); Van Hooser et al., *J. Biol. Chem.* 277:19173-82 (2002)).

In another embodiment of the methods described herein for treating an ophthalmic disease or disorder, for inhibiting retinal cell degeneration (or enhancing retinal cell survival), for inhibiting neovascularization, and for reducing ischemia in the retina, preventing or inhibiting dark adaptation of a rod photoreceptor cell in the retina comprises increasing the level of apo-rhodopsin (also called opsin) in the photoreceptor cell. The total level of the visual pigment approximates the sum of rhodopsin and apo-rhodopsin and the total level remains constant. Therefore, preventing, delaying, or inhibiting dark adaptation of the rod photoreceptor cell may alter the ratio of apo-rhodopsin to rhodopsin. In particular embodiments, preventing, delaying, or inhibiting dark adaptation by administering a compound described herein may increase the ratio of the level of apo-rhodopsin to the level of rhodopsin compared to the ratio in the absence of the agent (for example, prior to administration of the agent). An increase in the ratio (i.e., a statistically or biologically significant increase) of apo-rhodopsin to rhodopsin indicates that the percent or number of rod photoreceptor cells that are rhodopsin-depleted is increased and that the percent or number of rod photoreceptor cells that are dark-adapted is decreased. The ratio of apo-rhodopsin to rhodopsin may be determined throughout the course of therapy to monitor the effect of the agent.

Determining or characterizing the capability of compound to prevent, delay, or inhibit dark adaptation of a rod photoreceptor cell may be determined in animal model studies. The level of rhodopsin and the ratio of apo-rhodopsin to rhodopsin may be determined prior to administration (which may be called a first level or first ratio, respectively) of the agent and then after administration of a first or any subsequent dose of the agent (which may be called a second level or second ratio, respectively) to determine and to demonstrate that the level of apo-rhodopsin is greater than the level of apo-rhodopsin in the retina of animals that did not receive the agent. The level of rhodopsin in rod photoreceptor cells may be performed according to methods practiced in the art and provided herein (see, e.g., Yan et al. *J. Biol. Chem.* 279:48189-96 (2004)).

A subject in need of such treatment may be a human or may be a non-human primate or other animal (i.e., veterinary use) who has developed symptoms of an ophthalmic disease or disorder or who is at risk for developing an ophthalmic disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Also provided herein are methods for inhibiting (reducing, slowing, preventing) degeneration and enhancing retinal neuronal cell survival (or prolonging cell viability) comprising administering to a subject a composition comprising a pharmaceutically acceptable carrier and a compound described in detail herein, including a compound having any one of the structures set forth in Formula (I), (II), (IIa), (III), (Ma), (IV), or (IVa) and substructures thereof, and specific compounds recited herein. Retinal neuronal cells include photoreceptor cells, bipolar cells, horizontal cells, ganglion cells, and amacrine cells. In another embodiment, methods are provided for enhancing survival or inhibiting degeneration of a mature retinal cell such as a RPE cell or a Müller glial cell. In other embodiments, a method for preventing or inhibiting photoreceptor degeneration in an eye of a subject are provided. A method that prevents or inhibits photoreceptor degeneration may include a method for restoring photoreceptor function in an eye of a subject. Such methods comprise administering to the subject a composition comprising a compound as described herein and a pharmaceutically or acceptable carrier (i.e., excipient or vehicle). More specifically, these methods comprise administering to a subject a pharmaceutically acceptable excipient and a compound described herein, including a compound having any one of the structures set forth in Formula (I), (II), (IIa), (III), (Ma), (IV), or (IVa) or substructures thereof described herein. Without wishing to be bound by theory, the compounds described herein may inhibit an isomerization step of the retinoid cycle (i.e., visual cycle) and/or may slow chromophore flux in a retinoid cycle in the eye.

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and a compound as described in detail herein, including a compound having the structure as set forth in Formula (I), (II), (IIa), (III), (IIIa), (IV), or (IVa) or substructures thereof.

A compound described herein can be administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. Rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans-retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of a compound described herein can reduce or eliminate the requirement for endogenous retinoid. In certain embodiments, the level of endogenous retinoid may be compared before and after any one or more doses of a compound described herein is administered to a subject to determine the effect of the compound on the level of endogenous retinoids in the subject.

In another embodiment, the methods described herein for treating an ophthalmic disease or disorder, for inhibiting neovascularization, and for reducing ischemia in the retina comprise administering at least one of the compounds described herein, thereby effecting a decrease in metabolic demand, which includes effecting a reduction in ATP consumption and in oxygen consumption in rod photoreceptor cells. As described herein, consumption of ATP and oxygen in a dark-adapted rod photoreceptor cell is greater than in rod photoreceptor cells that are light-adapted or rhodopsin-depleted; thus, use of the compounds in the methods described herein may reduce the consumption of ATP in the rod photoreceptor cells that are prevented, inhibited, or delayed from dark adaptation compared with rod photoreceptor cells that are dark-adapted (such as the cells prior to administration or contact with the compound or cells that are never exposed to the compound).

The methods described herein that may prevent or inhibit dark adaptation of a rod photoreceptor cell may therefore reduce hypoxia (i.e., reduce in a statistically or biologically significant manner) in the retina. For example, the level of hypoxia (a first level) may be determined prior to initiation of the treatment regimen, that is, prior to the first dosing of the compound (or a composition, as described herein, comprising the compound). The level of hypoxia (for example, a second level) may be determined after the first dosing, and/or after any second or subsequent dosing to monitor and characterize hypoxia throughout the treatment regimen. A decrease (reduction) in the second (or any subsequent) level of hypoxia compared to the level of hypoxia prior to initial administration indicates that the compound and the treatment regiment prevent dark adaptation of the rod photoreceptor cells and may be used for treating ophthalmic diseases and disorders. Consumption of oxygen, oxygenation of the retina, and/or hypoxia in the retina may be determined using methods practiced in the art. For example, oxygenation of the retina may be determined by measuring the fluorescence of flavoproteins in the retina (see, e.g., U.S. Pat. No. 4,569,354). Another exemplary method is retinal oximetry that measures blood oxygen saturation in the large vessels of the retina near the optic disc. Such methods may be used to identify and determine the extent of retinal hypoxia before changes in retinal vessel architecture can be detected.

A biological sample may be a blood sample (from which serum or plasma may be prepared), biopsy specimen, body fluids (e.g., vitreous fluid, aqueous humor, intraocular fluid, subretinal fluid, or tears), tissue explant, organ culture, or any other tissue or cell preparation from a subject or a biological source. A sample may further refer to a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source. The subject or biological source may be a human or non-human animal, a primary cell culture (e.g., a retinal cell culture), or culture adapted cell line, including but not limited to, genetically engineered cell lines that may contain chromosomally integrated or episomal recombinant nucleic acid sequences, immortalized or immortalizable cell lines, somatic cell hybrid cell lines, differentiated or differentiable cell lines, transformed cell lines, and the like. Mature retinal cells, including retinal neuronal cells, RPE cells, and Müller glial cells, may be present in or isolated from a biological sample as described herein. For example, the mature retinal cell may be obtained from a primary or long-term cell culture or may be present in or isolated from a biological sample obtained from a subject (human or non-human animal).

3. Retinal Cells

The retina is a thin layer of nervous tissue located between the vitreous body and choroid in the eye. Major landmarks in the retina are the fovea, the macula, and the optic disc. The retina is thickest near the posterior sections and becomes thinner near the periphery. The macula is located in the posterior retina and contains the fovea and foveola. The foveola contains the area of maximal cone density and, thus, imparts the highest visual acuity in the retina. The foveola is contained within the fovea, which is contained within the macula.

The peripheral portion of the retina increases the field of vision. The peripheral retina extends anterior to the ciliary body and is divided into four regions: the near periphery (most posterior), the mid-periphery, the far periphery, and the ora serrata (most anterior). The ora serrata denotes the termination of the retina.

The term neuron (or nerve cell) as understood in the art and used herein denotes a cell that arises from neuroepithelial cell precursors. Mature neurons (i.e. fully differentiated cells) display several specific antigenic markers. Neurons may be classified functionally into three groups: (1) afferent neurons (or sensory neurons) that transmit information into the brain for conscious perception and motor coordination; (2) motor neurons that transmit commands to muscles and glands; and (3) interneurons that are responsible for local circuitry; and (4) projection interneurons that relay information from one region of the brain to another region and therefore have long axons. Interneurons process information within specific subregions of the brain and have relatively shorter axons. A neuron typically has four defined regions: the cell body (or soma); an axon; dendrites; and presynaptic terminals. The dendrites serve as the primary input of information from other neural cells. The axon carries the electrical signals that are initiated in the cell body to other neurons or to effector organs. At the presynaptic terminals, the neuron transmits information to another cell (the postsynaptic cell), which may be another neuron, a muscle cell, or a secretory cell.

The retina is composed of several types of neuronal cells. As described herein, the types of retinal neuronal cells that may be cultured in vitro by this method include photoreceptor cells, ganglion cells, and interneurons such as bipolar cells, horizontal cells, and amacrine cells. Photoreceptors are specialized light-reactive neural cells and comprise two major classes, rods and cones. Rods are involved in scotopic or dim light vision, whereas photopic or bright light vision originates in the cones. Many neurodegenerative diseases, such as AMD, that result in blindness affect photoreceptors.

Extending from their cell bodies, the photoreceptors have two morphologically distinct regions, the inner and outer segments. The outer segment lies furthermost from the photoreceptor cell body and contains disks that convert incoming light energy into electrical impulses (phototransduction). The outer segment is attached to the inner segment with a very small and fragile cilium. The size and shape of the outer segments vary between rods and cones and are dependent upon position within the retina. See Hogan, "Retina" in *Histology of the Human Eye: an Atlas and Text Book* (Hogan et al. (eds). WB Saunders; Philadelphia, Pa. (1971)); *Eye and Orbit*, $8^{th}$ Ed., Bron et al., (Chapman and Hall, 1997).

Ganglion cells are output neurons that convey information from the retinal interneurons (including horizontal cells, bipolar cells, amacrine cells) to the brain. Bipolar cells are named according to their morphology, and receive input from the photoreceptors, connect with amacrine cells, and send output radially to the ganglion cells. Amacrine cells have processes parallel to the plane of the retina and have typically inhibitory output to ganglion cells. Amacrine cells are often subclassified by neurotransmitter or neuromodulator or peptide (such as calretinin or calbindin) and interact with each other, with bipolar cells, and with photoreceptors. Bipolar cells are retinal interneurons that are named according to their morphology; bipolar cells receive input from the photoreceptors and sent the input to the ganglion cells. Horizontal cells modulate and transform visual information from large numbers of photoreceptors and have horizontal integration (whereas bipolar cells relay information radially through the retina).

Other retinal cells that may be present in the retinal cell cultures described herein include glial cells, such as Müller glial cells, and retinal pigment epithelial cells (RPE). Glial cells surround nerve cell bodies and axons. The glial cells do not carry electrical impulses but contribute to maintenance of normal brain function. Müller glia, the predominant type of glial cell within the retina, provide structural support of the retina and are involved in the metabolism of the retina (e.g., contribute to regulation of ionic concentrations, degradation of neurotransmitters, and remove certain metabolites (see, e.g., Kljavin et al., *J. Neurosci.* 11:2985 (1991))). Müller's fibers (also known as sustentacular fibers of retina) are sustentacular neuroglial cells of the retina that run through the thickness of the retina from the internal limiting membrane to the bases of the rods and cones where they form a row of junctional complexes.

Retinal pigment epithelial (RPE) cells form the outermost layer of the retina, separated from the blood vessel-enriched choroids by Bruch's membrane. RPE cells are a type of phagocytic epithelial cell, with some functions that are macrophage-like, which lies immediately below the retinal photoreceptors. The dorsal surface of the RPE cell is closely apposed to the ends of the rods, and as discs are shed from the rod outer segment they are internalized and digested by RPE cells. Similar process occurs with the disc of the cones. RPE cells also produce, store, and transport a variety of factors that contribute to the normal function and survival of photoreceptors. Another function of RPE cells is to recycle vitamin A as it moves between photoreceptors and the RPE during light and dark adaptation in the process known as the visual cycle.

Described herein is an exemplary long-term in vitro cell culture system permits and promotes the survival in culture of mature retinal cells, including retinal neurons, for at least 2-4 weeks, over 2 months, or for as long as 6 months. The cell culture system may be used for identifying and characterizing the compounds described herein that are useful in the methods described herein for treating and/or preventing an ophthalmic disease or disorder or for preventing or inhibiting accumulation in the eye of lipofuscin(s) and/or A2E. Retinal cells are isolated from non-embryonic, non-tumorigenic tissue and have not been immortalized by any method such as, for example, transformation or infection with an oncogenic virus. The cell culture system comprises all the major retinal neuronal cell types (photoreceptors, bipolar cells, horizontal cells, amacrine cells, and ganglion cells), and also may include other mature retinal cells such as retinal pigment epithelial cells and Müller glial cells.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of a compound described herein can reduce or eliminate the requirement for endogenous retinoid.

4. In Vivo and in Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Müller glial cells using the compounds described herein. Such methods comprise, in certain embodiments, administration of a compound as described herein. Such a compound is useful for enhancing retinal cell survival, including photoreceptor cell survival and retinal pigment epithelia survival, inhibiting or slowing degeneration of a retinal cell, and thus increasing retinal cell viability, which can result in slowing or halting the progression of an ophthalmic disease or disorder or retinal injury, which are described herein.

The effect of a compound described herein on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. No. 6,117,675; U.S. Pat. No. 5,736,516; WO 99/29279; WO 01/83714; WO 01/42784; U.S. Pat. No. 6,183,735; U.S. Pat. No. 6,090,624; WO 01/09327; U.S. Pat. No. 5,641,750; U.S. Patent Application Publication No. 2004/0147019; and U.S. Patent Application Publication No. 2005/0059148.

Compounds described herein that may be useful for treating an ophthalmic disease or disorder (including a retinal disease or disorder) may inhibit, block, impair, or in some manner interfere with one or more steps in the visual cycle (also called the retinoid cycle herein and in the art). Without wishing to be bound by a particular theory, a compound described herein may inhibit or block an isomerization step in the visual cycle, for example, by inhibiting or blocking a functional activity of a visual cycle trans-cis isomerase. The compounds described herein may inhibit, directly or indirectly, isomerization of all-trans-retinol to 11-cis-retinol. The compounds may bind to, or in some manner interact with, and inhibit the isomerase activity of at least one isomerase in a retinal cell. Any one of the compounds described herein may also directly or indirectly inhibit or reduce the activity of an isomerase that is involved in the visual cycle. The compound may block or inhibit the capability of the isomerase to bind to one or more substrates, including but not limited to, an all-trans-retinyl ester substrate or all-trans-retinol. Alternatively, or in addition, the compound may bind to the catalytic site or region of the isomerase, thereby inhibiting the capability of the enzyme to catalyze isomerization of at least one substrate. On the basis of scientific data to date, an at least one isomerase that catalyzes the isomerization of a substrate during the visual cycle is believed to be located in the cytoplasm of RPE cells. As discussed herein, each step, enzyme, substrate, intermediate, and product of the visual cycle is not yet elucidated. While a polypeptide called RPE65, which has been found in the cytoplasm and membrane bound in RPE cells, is hypothesized to have isomerase activity (and has also been referred to in the art as having isomerohydrolase activity) (see, e.g., Moiseyev et al., *Proc. Natl. Acad. Sci. USA* 102:12413-18 (2004); Chen et al., *Invest. Opthalmol. Vis. Sci.* 47:1177-84 (2006)), other persons skilled in the art believe that the RPE65 acts primarily as a chaperone for all-trans-retinyl esters (see, e.g., Lamb et al. supra).

Exemplary methods are described herein and practiced by persons skilled in the art for determining the level of enzymatic activity of a visual cycle isomerase in the presence of any one of the compounds described herein. A compound that decreases isomerase activity may be useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and a compound described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound may be useful for treating an ophthalmic disease or disorder, such as age-related macular degeneration or Stargardt's disease. A decrease in the level of isomerase activity in the presence of the compound compared to the level of isomerase activity in the absence of the compound indicates that the compound may also be useful in the methods described herein for inhibiting or preventing dark adaptation, inhibiting neovascularization and reducing hypoxia and thus useful for treating an ophthalmic disease or disorder, for example, diabetic retinopathy, diabetic maculopathy, retinal blood vessel occlusion, retinopathy of prematurity, or ischemia reperfusion related retinal injury.

The capability of a compound described herein to inhibit or to prevent dark adaptation of a rod photoreceptor cell by inhibiting regeneration of rhodopsin may be determined by in vitro assays and/or in vivo animal models. By way of example, inhibition of regeneration may be determined in a mouse model in which a diabetes-like condition is induced chemically or in a diabetic mouse model (see, e.g., Phipps et al., *Invest. Opthalmol. Vis. Sci.* 47:3187-94 (2006); Ramsey et al., *Invest. Opthalmol. Vis. Sci.* 47:5116-24 (2006)). The level of rhodopsin (a first level) may be determined (for example, spectrophotometrically) in the retina of animals prior to administration of the agent and compared with the level (a second level) of rhodopsin measured in the retina of animals after administration of the agent. A decrease in the second level of rhodopsin compared with the first level of rhodopsin indicates that the agent inhibits regeneration of rhodopsin. The appropriate controls and study design to determine whether regeneration of rhodopsin is inhibited in a statistically significant or biologically significant manner can be readily determined and implemented by persons skilled in the art.

Methods and techniques for determining or characterizing the effect of any one of the compounds described herein on dark adaptation and rhodopsin regeneration in rod photoreceptor cells in a mammal, including a human, may be performed according to procedures described herein and practiced in the art. For example, detection of a visual stimulus after exposure to light (i.e., photobleaching) versus time in darkness may be determined before administration of the first dose of the compound and at a time after the first dose and/or any subsequent dose. A second method for determining prevention or inhibition of dark adaptation by the rod photoreceptor cells includes measurement of the amplitude of at least one, at least two, at least three, or more electroretinogram components, which include, for example, the a-wave and the b-wave. See, for example, Lamb et al., supra; Asi et al., *Documenta Opthalmologica* 79:125-39 (1992).

Inhibiting regeneration of rhodopsin by a compound described herein comprises reducing the level of the chromophore, 11-cis-retinal, that is produced and present in the RPE cell, and consequently reducing the level of 11-cis-retinal that is present in the photoreceptor cell. Thus, the compound, when permitted to contact the retina under suitable conditions and at a time sufficient to prevent dark adaptation of a rod photoreceptor cell and to inhibit regeneration of rhodopsin in the rod photoreceptor cell, effects a reduction in the level of 11-cis-retinal in a rod photoreceptor cell (i.e., a statistically significant or biologically significant reduction). That is, the level of 11-cis-retinal in a rod photoreceptor cell is greater prior to administration of the compound when compared with the level of 11-cis-retinal in the photoreceptor cell after the first and/or any subsequent administration of the compound. A first level of 11-cis-retinal may be determined prior to administration of the compound, and a second level of 11-cis-retinal may be determined after administration of a first dose or any subsequent dose to monitor the effect of the compound. A decrease in the second level compared to the first level indicates that the compound inhibits regeneration of rhodopsin and thus inhibits or prevents dark adaptation of the rod photoreceptor cells.

An exemplary method for determining or characterizing the capability of a compound described herein to reduce retinal hypoxia includes measuring the level of retinal oxygenation, for example, by Magnetic Resonance Imaging (MRI) to measure changes in oxygen pressure (see, e.g., Luan et al., *Invest. Opthalmol. Vis. Sci.* 47:320-28 (2006)). Methods are also available and routinely practiced in the art to determine or characterize the capability of compounds described herein to inhibit degeneration of a retinal cell (see, e.g., Wenzel et al., *Prog. Retin. Eye Res.* 24:275-306 (2005)).

Animal models may be used to characterize and identify compounds that may be used to treat retinal diseases and disorders. A recently developed animal model may be useful for evaluating treatments for macular degeneration has been described by Ambati et al. (*Nat. Med.* 9:1390-97 (2003); Epub 2003 Oct. 19). This animal model is one of only a few exemplary animal models presently available for evaluating a compound or any molecule for use in treating (including preventing) progression or development of a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the compounds described herein. (See, e.g., Mata et al., *Invest. Opthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300). Other animal models include the use of mutant ELOVL4 transgenic mice to determine lipofuscin accumulation, electrophysiology, and photoreceptor degeneration, or prevention or inhibition thereof (see, e.g., Karan et al., *Proc. Natl. Acad. Sci. USA* 102:4164-69 (2005)).

The effect of any one of the compounds described herein may be determined in a diabetic retinopathy animal model, such as described in Luan et al. or may be determined in a normal animal model, in which the animals have been light or dark adapted in the presence and absence of any one of the compounds described herein. Another exemplary method for determining the capability of the agent to reduce retinal hypoxia measures retinal hypoxia by deposition of a hydroxyprobe (see, e.g., de Gooyer et al. (*Invest. Opthalmol. Vis. Sci.* 47:5553-60 (2006)). Such a technique may be performed in an animal model using Rho$^-$/Rho$^-$ knockout mice (see de Gooyer et al., supra) in which at least one compound described herein is administered to group(s) of animals in the presence and absence of the at least one compound, or may be performed in normal, wildtype animals in which at least one compound described herein is administered to group(s) of animals in the presence and absence of the at least one compound. Other animal models include models for determining photoreceptor function, such as rat models that measure elctroretinographic (ERG) oscillatory potentials (see, e.g., Liu et al., *Invest. Opthalmol. Vis. Sci.* 47:5447-52 (2006); Akula et al., *Invest. Opthalmol. Vis. Sci.* 48:4351-59 (2007); Liu et al., *Invest. Opthalmol. Vis. Sci.* 47:2639-47 (2006); Dembinska et al., *Invest. Opthalmol. Vis. Sci.* 43:2481-90 (2002); Penn et al., *Invest. Opthalmol. Vis. Sci.* 35:3429-35 (1994); Hancock et al., *Invest. Opthalmol. Vis. Sci.* 45:1002-1008 (2004)).

A method for determining the effect of a compound on isomerase activity may be performed in vitro as described herein and in the art (Stecher et al., *J. Biol. Chem.* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the compounds described herein to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem.* 85:944-956 (2003); Van Hooser et al., *J. Biol. Chem.* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.* 22 Suppl 2:315-25 (1997); Keating et al., *Documenta Opthalmologica* 100:77-92 (2000)). See also Deigner et al., *Science,* 244: 968-971 (1989); Gollapalli et al., *Biochim. Biophys. Acta* 1651: 93-101 (2003); Parish, et al., *Proc. Natl. Acad. Sci. USA* 95:14609-13 (1998); Radu et al., *Proc Natl Acad Sci USA* 101: 5928-33 (2004).

Cell culture methods, such as the method described herein, are also useful for determining the effect of a compound described herein on retinal neuronal cell survival. Exemplary cell culture models are described herein and described in detail in U.S. Patent Application Publication No. US 2005-0059148 and U.S. Patent Application Publication No. US2004-0147019 (which are incorporated by reference in their entirety), which are useful for determining the capability of a compound as described herein to enhance or prolong survival of neuronal cells, particularly retinal neuronal cells, and of retinal pigment epithelial cells, and inhibit, prevent, slow, or retard degeneration of an eye, or the retina or retinal cells thereof, or the RPE, and which compounds are useful for treating ophthalmic diseases and disorders.

The cell culture model comprises a long-term or extended culture of mature retinal cells, including retinal neuronal cells (e.g., photoreceptor cells, amacrine cells, ganglion cells, horizontal cells, and bipolar cells). The cell culture system and methods for producing the cell culture system provide extended culture of photoreceptor cells. The cell culture system may also comprise retinal pigment epithelial (RPE) cells and Müller glial cells.

The retinal cell culture system may also comprise a cell stressor. The application or the presence of the stressor affects the mature retinal cells, including the retinal neuronal cells, in vitro, in a manner that is useful for studying disease pathology that is observed in a retinal disease or disorder. The cell culture model provides an in vitro neuronal cell culture system that will be useful in the identification and biological testing of a compound described herein that is suitable for treatment of neurological diseases or disorders in general, and for treatment of degenerative diseases of the eye and brain in particular. The ability to maintain primary, in vitro-cultured cells from mature retinal tissue, including retinal neurons over an extended period of time in the presence of a stressor enables examination of cell-to-cell interactions, selection and analysis of neuroactive compounds and materials, use of a controlled cell culture system for in vitro CNS and ophthalmic tests, and analysis of the effects on single cells from a consistent retinal cell population.

The cell culture system and the retinal cell stress model comprise cultured mature retinal cells, retinal neurons, and a retinal cell stressor, which may be used for screening and characterizing a compound described herein that are capable of inducing or stimulating the regeneration of CNS tissue that has been damaged by disease. The cell culture system provides a mature retinal cell culture that is a mixture of mature retinal neuronal cells and non-neuronal retinal cells. The cell culture system comprises all the major retinal neuronal cell types (photoreceptors, bipolar cells, horizontal cells, amacrine cells, and ganglion cells), and may also include other mature retinal cells such as RPE and Müller glial cells. By incorporating these different types of cells into the in vitro culture system, the system essentially resembles an "artificial organ" that is more akin to the natural in vivo state of the retina.

Viability of one or more of the mature retinal cell types that are isolated (harvested) from retinal tissue and plated for tissue culture may be maintained for an extended period of time, for example, from two weeks up to six months. Viability of the retinal cells may be determined according to methods described herein and known in the art. Retinal neuronal cells, similar to neuronal cells in general, are not actively dividing cells in vivo and thus cell division of retinal neuronal cells would not necessarily be indicative of viability. An advantage of the cell culture system is the ability to culture amacrine cells, photoreceptors, and associated ganglion projection neurons and other mature retinal cells for extended periods of time, thereby providing an opportunity to determine the effectiveness of a compound described herein for treatment of retinal disease.

The biological source of the retinal cells or retinal tissue may be mammalian (e.g., human, non-human primate, ungulate, rodent, canine, porcine, bovine, or other mammalian source), avian, or from other genera. Retinal cells including retinal neurons from post-natal non-human primates, post-natal pigs, or post-natal chickens may be used, but any adult or post-natal retinal tissue may be suitable for use in this retinal cell culture system.

In certain instances, the cell culture system may provide for robust long-term survival of retinal cells without inclusion of cells derived from or isolated or purified from non-retinal tissue. Such a cell culture system comprises cells isolated solely from the retina of the eye and thus is substantially free of types of cells from other parts or regions of the eye that are separate from the retina, such as the ciliary body, iris, choroid, and vitreous. Other cell culture methods include the addition of non-retinal cells, such as ciliary body cell and/or stem cells (which may or may not be retinal stem cells) and/or additional purified glial cells.

The in vitro retinal cell culture systems described herein may serve as physiological retinal models that can be used to characterize aspects of the physiology of the retina. This physiological retinal model may also be used as a broader general neurobiology model. A cell stressor may be included in the model cell culture system. A cell stressor, which as described herein is a retinal cell stressor, adversely affects the viability or reduces the viability of one or more of the different retinal cell types, including types of retinal neuronal cells, in the cell culture system. A person skilled in the art would readily appreciate and understand that as described herein a retinal cell that exhibits reduced viability means that the length of time that a retinal cell survives in the cell culture system is reduced or decreased (decreased lifespan) and/or that the retinal cell exhibits a decrease, inhibition, or adverse effect of a biological or biochemical function (e.g., decreased or abnormal metabolism; initiation of apoptosis; etc.) compared with a retinal cell cultured in an appropriate control cell system (e.g., the cell culture system described herein in the absence of the cell stressor). Reduced viability of a retinal cell may be indicated by cell death; an alteration or change in cell structure or morphology; induction and/or progression of apoptosis; initiation, enhancement, and/or acceleration of retinal neuronal cell neurodegeneration (or neuronal cell injury).

Methods and techniques for determining cell viability are described in detail herein and are those with which skilled artisans are familiar. These methods and techniques for determining cell viability may be used for monitoring the health and status of retinal cells in the cell culture system and for determining the capability of the compounds described herein to alter (preferably increase, prolong, enhance, improve) retinal cell or retinal pigment epithelial cell viability or retinal cell survival.

The addition of a cell stressor to the cell culture system is useful for determining the capability of a compound described herein to abrogate, inhibit, eliminate, or lessen the effect of the stressor. The retinal cell culture system may include a cell stressor that is chemical (e.g., A2E, cigarette smoke concentrate); biological (for example, toxin exposure; beta-amyloid; lipopolysaccharides); or non-chemical, such as a physical stressor, environmental stressor, or a mechanical force (e.g., increased pressure or light exposure) (see, e.g., US 2005-0059148).

The retinal cell stressor model system may also include a cell stressor such as, but not limited to, a stressor that may be a risk factor in a disease or disorder or that may contribute to the development or progression of a disease or disorder, including but not limited to, light of varying wavelengths and intensities; A2E; cigarette smoke condensate exposure; oxidative stress (e.g., stress related to the presence of or exposure to hydrogen peroxide, nitroprusside, $Zn^{++}$, or $Fe^{++}$); increased pressure (e.g., atmospheric pressure or hydrostatic pressure), glutamate or glutamate agonist (e.g., N-methyl-D-aspartate (NMDA); alpha-amino-3-hydroxy-5-methylisoxazole-4-proprionate (AMPA); kainic acid; quisqualic acid; ibotenic acid; quinolinic acid; aspartate; trans-1-aminocyclopentyl-1,3-dicarboxylate (ACPD)); amino acids (e.g., aspartate, L-cysteine; beta-N-methylamine-L-alanine); heavy metals (such as lead); various toxins (for example, mitochondrial toxins (e.g., malonate, 3-nitroproprionic acid; rotenone, cyanide); MPTP (1-methyl-4-phenyl-1,2,3,6,-tetrahydropyridine), which metabolizes to its active, toxic metabolite MPP+ (1-methyl-4-phenylpryidine)); 6-hydroxydopamine; alpha-synuclein; protein kinase C activators (e.g., phorbol myristate acetate); biogenic amino stimulants (for example, methamphetamine, MDMA (3-4 methylenedioxymethamphetamine)); or a combination of one or more stressors. Useful retinal cell stressors include those that mimic a neurodegenerative disease that affects any one or more of the mature retinal cells described herein. A chronic disease model is of particular importance because most neurodegenerative diseases are chronic. Through use of this in vitro cell culture system, the earliest events in long-term disease development processes may be identified because an extended period of time is available for cellular analysis.

A retinal cell stressor may alter (i.e., increase or decrease in a statistically significant manner) viability of retinal cells such as by altering survival of retinal cells, including retinal neuronal cells and RPE cells, or by altering neurodegeneration of retinal neuronal cells and/or RPE cells. Preferably, a retinal cell stressor adversely affects a retinal neuronal cell or RPE cell such that survival of a retinal neuronal cell or RPE cell is decreased or adversely affected (i.e., the length of time during which the cells are viable is decreased in the presence of the stressor) or neurodegeneration (or neuron cell injury) of the cell is increased or enhanced. The stressor may affect only a single retinal cell type in the retinal cell culture or the stressor may affect two, three, four, or more of the different cell types. For example, a stressor may alter viability and survival of photoreceptor cells but not affect all the other major cell types (e.g., ganglion cells, amacrine cells, horizontal cells, bipolar cells, RPE, and Müller glia). Stressors may shorten the survival time of a retinal cell (in vivo or in vitro), increase the rapidity or extent of neurodegeneration of a retinal cell, or in some other manner adversely affect the viability, morphology, maturity, or lifespan of the retinal cell.

The effect of a cell stressor (in the presence and absence of a compound described herein) on the viability of retinal cells in the cell culture system may be determined for one or more of the different retinal cell types. Determination of cell viability may include evaluating structure and/or a function of a retinal cell continually at intervals over a length of time or at a particular time point after the retinal cell culture is prepared. Viability or long term survival of one or more different retinal cell types or one or more different retinal neuronal cell types may be examined according to one or more biochemical or biological parameters that are indicative of reduced viability, such as apoptosis or a decrease in a metabolic function, prior to observation of a morphological or structural alteration.

A chemical, biological, or physical cell stressor may reduce viability of one or more of the retinal cell types present in the cell culture system when the stressor is added to the cell culture under conditions described herein for maintaining the long-term cell culture. Alternatively, one or more culture conditions may be adjusted so that the effect of the stressor on the retinal cells can be more readily observed. For example, the concentration or percent of fetal bovine serum may be reduced or eliminated from the cell culture when cells are exposed to a particular cell stressor (see, e.g., US 2005-0059148). Alternatively, retinal cells cultured in media containing serum at a particular concentration for maintenance of the cells may be abruptly exposed to media that does not contain any level of serum.

The retinal cell culture may be exposed to a cell stressor for a period of time that is determined to reduce the viability of one or more retinal cell types in the retinal cell culture system. The cells may be exposed to a cell stressor immediately upon plating of the retinal cells after isolation from retinal tissue. Alternatively, the retinal cell culture may be exposed to a stressor after the culture is established, or any time thereafter. When two or more cell stressors are included in the retinal cell culture system, each stressor may be added to the cell culture system concurrently and for the same length of time or may be added separately at different time points for the same length of time or for differing lengths of time during the culturing of the retinal cell system. A compound described herein may be added before the retinal cell culture is exposed to a cell stressor, may be added concurrently with the cell stressor, or may be added after exposure of the retinal cell culture to the stressor.

Photoreceptors may be identified using antibodies that specifically bind to photoreceptor-specific proteins such as opsins, peripherins, and the like. Photoreceptors in cell culture may also be identified as a morphologic subset of immunocytochemically labeled cells by using a pan-neuronal marker or may be identified morphologically in enhanced contrast images of live cultures. Outer segments can be detected morphologically as attachments to photoreceptors.

Retinal cells including photoreceptors can also be detected by functional analysis. For example, electrophysiology methods and techniques may be used for measuring the response of photoreceptors to light. Photoreceptors exhibit specific kinetics in a graded response to light. Calcium-sensitive dyes may also be used to detect graded responses to light within cultures containing active photoreceptors. For analyzing stress-inducing compounds or potential neurotherapeutics, retinal cell cultures can be processed for immunocytochemistry, and photoreceptors and/or other retinal cells can be counted manually or by computer software using photomicroscopy and imaging techniques. Other immunoassays known in the art (e.g., ELISA, immunoblotting, flow cytometry) may also be useful for identifying and characterizing the retinal cells and retinal neuronal cells of the cell culture model system described herein.

The retinal cell culture stress models may also be useful for identification of both direct and indirect pharmacologic agent effects by the bioactive agent of interest, such as a compound as described herein. For example, a bioactive agent added to the cell culture system in the presence of one or more retinal cell stressors may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

In another embodiment, a compound described herein is incorporated into screening assays comprising the retinal cell culture stress model system described herein to determine whether and/or to what level or degree the compound increases or prolongs viability (i.e., increases in a statistically significant or biologically significant manner) of a plurality of retinal cells. A person skilled in the art would readily appreciate and understand that as described herein a retinal cell that exhibits increased viability means that the length of time that a retinal cell survives in the cell culture system is increased (increased lifespan) and/or that the retinal cell maintains a biological or biochemical function (normal metabolism and organelle function; lack of apoptosis; etc.) compared with a retinal cell cultured in an appropriate control cell system (e.g., the cell culture system described herein in the absence of the compound). Increased viability of a retinal cell may be indicated by delayed cell death or a reduced number of dead or dying cells; maintenance of structure and/or morphology;

lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

In certain embodiments, a method is provided for determining whether a compound described herein, enhances survival of photoreceptor cells. One method comprises contacting a retinal cell culture system as described herein with a compound described herein under conditions and for a time sufficient to permit interaction between the retinal neuronal cells and the compound. Enhanced survival (prolonged survival) may be measured according to methods described herein and known in the art, including detecting expression of rhodopsin.

The capability of a compound described herein to increase retinal cell viability and/or to enhance, promote, or prolong cell survival (that is, to extend the time period in which retinal cells, including retinal neuronal cells, are viable), and/or impair, inhibit, or impede degeneration as a direct or indirect result of the herein described stress may be determined by any one of several methods known to those skilled in the art. For example, changes in cell morphology in the absence and presence of the compound may be determined by visual inspection such as by light microscopy, confocal microscopy, or other microscopy methods known in the art. Survival of cells can also be determined by counting viable and/or non-viable cells, for instance. Immunochemical or immunohistological techniques (such as fixed cell staining or flow cytometry) may be used to identify and evaluate cytoskeletal structure (e.g., by using antibodies specific for cytoskeletal proteins such as glial fibrillary acidic protein, fibronectin, actin, vimentin, tubulin, or the like) or to evaluate expression of cell markers as described herein. The effect of a compound described herein on cell integrity, morphology, and/or survival may also be determined by measuring the phosphorylation state of neuronal cell polypeptides, for example, cytoskeletal polypeptides (see, e.g., Sharma et al., *J. Biol. Chem.* 274:9600-06 (1999); Li et al., *J. Neurosci.* 20:6055-62 (2000)). Cell survival or, alternatively cell death, may also be determined according to methods described herein and known in the art for measuring apoptosis (for example, annexin V binding, DNA fragmentation assays, caspase activation, marker analysis, e.g., poly(ADP-ribose) polymerase (PARP), etc.).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Without wishing to be bound by theory, decreased accumulation of A2E may reduce or delay degenerative processes in the RPE and retina and thus may slow down or prevent vision loss in dry AMD and Stargardt's Disease.

In another embodiment, methods are provided for treating and/or preventing degenerative diseases and disorders, including neurodegenerative retinal diseases and ophthalmic diseases, and retinal diseases and disorders as described herein. A subject in need of such treatment may be a human or non-human primate or other animal who has developed symptoms of a degenerative retinal disease or who is at risk for developing a degenerative retinal disease. As described herein a method is provided for treating (which includes preventing or prophylaxis) an ophthalmic disease or disorder by administrating to a subject a composition comprising a pharmaceutically acceptable carrier and a compound described herein (e.g., a compound having the structure of Formula (I), (II), (IIa), (III), (IIIa), (IV), or (IVa), and substructures thereof.) As described herein, a method is provided for enhancing survival of neuronal cells such as retinal neuronal cells, including photoreceptor cells, and/or inhibiting degeneration of retinal neuronal cells by administering the pharmaceutical compositions described herein comprising a compound described herein.

Enhanced survival (or prolonged or extended survival) of one or more retinal cell types in the presence of a compound described herein indicates that the compound may be an effective agent for treatment of a degenerative disease, particularly a retinal disease or disorder, and including a neurodegenerative retinal disease or disorder. Cell survival and enhanced cell survival may be determined according to methods described herein and known to a skilled artisan including viability assays and assays for detecting expression of retinal cell marker proteins. For determining enhanced survival of photoreceptor cells, opsins may be detected, for instance, including the protein rhodopsin that is expressed by rods.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD). In various embodiments, AMD can be wet- or dry-form. In AMD, vision loss primarily occurs when complications late in the disease either cause new blood vessels to grow under the macula or the macula atrophies. Without intending to be bound by any particular theory, the accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form and wet-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., *Am. J. Hum.*

*Genet.* 74:20-39 (2004) (Epub 2003 Dec. 19); Kenealy et al., *Mol. Vis.* 10:57-61 (2004); Gorin et al., *Mol. Vis.* 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., *Opthalmol. Clin. North Am.* 15:93-100, viii (2002); Weng et al., *Cell* 98:13-23 (1999)); Doyne's honeycomb retinal dystrophy (see, e.g., Kermani et al., *Hum. Genet.* 104:77-82 (1999)); Sorsby's fundus dystrophy, Malattia Levintinese, fundus flavimaculatus, and autosomal dominant hemorrhagic macular dystrophy (see also Seddon et al., *Opthalmology* 108:2060-67 (2001); Yates et al., *J. Med. Genet.* 37:83-7 (2000); Jaakson et al., *Hum. Mutat.* 22:395-403 (2003)). Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein may slow the synthesis of 11-cis-retinaldehyde (11 cRAL or retinal) and regeneration of rhodopsin by inhibiting isomerase in the visual cycle. Light activation of rhodopsin results in its release of all-trans-retinal, which constitutes the first reactant in A2E biosynthesis. Treatment with a compound described herein may inhibit lipofuscin accumulation and thus delay the onset of visual loss in Stargardt's and AMD patients without toxic effects that would preclude treatment with a compound described herein. The compounds described herein may be used for effective treatment of other forms of retinal or macular degeneration associated with lipofuscin accumulation.

Administration of a compound described herein to a subject can prevent formation of the lipofuscin pigment, A2E (and A2E related molecules), that is toxic towards retinal cells and causes retinal degeneration. In certain embodiments, administration of a compound described herein can lessen the production of waste products, e.g., lipofuscin pigment, A2E (and A2E related molecules), ameliorate the development of AMD (e.g., dry-form) and Stargardt's disease, and reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, a compound described herein is administered to a subject such as a human with a mutation in the ABCA4 transporter in the eye. The compound described herein can also be administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. Without wishing to be bound by theory, a compound described herein may be a strong inhibitor of an isomerase involved in the visual cycle. Treating patients with a compound as described herein may prevent or slow the formation of A2E (and A2E related molecules) and can have protective properties for normal vision.

In other certain embodiments, one or more of the compounds described herein may be used for treating other ophthalmic diseases or disorders, for example, glaucoma, retinal detachment, hemorrhagic retinopathy, retinitis pigmentosa, an inflammatory retinal disease, proliferative vitreoretinopathy, retinal dystrophy, hereditary optic neuropathy, Sorsby's fundus dystrophy, uveitis, a retinal injury, optical neuropathy, and retinal disorders associated with other neurodegenerative diseases such as Alzheimer's disease, multiple sclerosis, Parkinson's disease or other neurodegenerative diseases that affect brain cells, a retinal disorder associated with viral infection, or other conditions such as AIDS. A retinal disorder also includes light damage to the retina that is related to increased light exposure (i.e., overexposure to light), for example, accidental strong or intense light exposure during surgery; strong, intense, or prolonged sunlight exposure, such as at a desert or snow covered terrain; during combat, for example, when observing a flare or explosion or from a laser device, and the like. Retinal diseases can be of degenerative or non-degenerative nature. Non-limiting examples of degenerative retinal diseases include age-related macular degeneration, and Stargardt's macular dystrophy. Examples of non-degenerative retinal diseases include but are not limited hemorrhagic retinopathy, retinitis pigmentosa, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

In other certain embodiments, at least one of the compounds described herein may be used for treating, curing, preventing, ameliorating the symptoms of, or slowing, inhibiting, or stopping the progression of, certain ophthalmic diseases and disorders including but not limited to diabetic retinopathy, diabetic maculopathy, diabetic macular edema, retinal ischemia, ischemia-reperfusion related retinal injury, and retinal blood vessel occlusion (including venous occlusion and arterial occlusion).

Diabetic retinopathy is a leading cause of blindness in humans and is a complication of diabetes. Diabetic retinopathy occurs when diabetes damages blood vessels inside the retina. Non-proliferative retinopathy is a common, usually mild form that generally does not interfere with vision. Abnormalities are limited to the retina, and vision is impaired only if the macula is involved. If left untreated retinopathy can progress to proliferative retinopathy, the more serious form of diabetic retinopathy. Proliferative retinopathy occurs when new blood vessels proliferate in and around the retina. Consequently, bleeding into the vitreous, swelling of the retina, and/or retinal detachment may occur, leading to blindness.

Other ophthalmic diseases and disorders that may be treated using the methods and compositions described herein include diseases, disorders, and conditions that are associated with, exacerbated by, or caused by ischemia in the retina.

Retinal ischemia includes ischemia of the inner retina and the outer retina. Retinal ischemia can occur from either choroidal or retinal vascular diseases, such as central or branch retinal vision occlusion, collagen vascular diseases and thrombocytopenic purpura. Retinal vasculitis and occlusion is seen with Eales disease and systemic lupus erythematosus.

Retinal ischemia may be associated with retinal blood vessel occlusion. In the United States, both branch and central retinal vein occlusions are the second most common retinal vascular diseases after diabetic retinopathy. About 7% to 10% of patients who have retinal venous occlusive disease in one eye eventually have bilateral disease. Visual field loss commonly occurs from macular edema, ischemia, or vitreous hemorrhage secondary to disc or retinal neovascularization induced by the release of vascular endothelial growth factor.

Arteriolosclerosis at sites of retinal arteriovenous crossings (areas in which arteries and veins share a common adventitial sheath) causes constriction of the wall of a retinal vein by a crossing artery. The constriction results in thrombus formation and subsequent occlusion of the vein. The blocked vein may lead to macular edema and hemorrhage secondary to breakdown in the blood-retina barrier in the area drained by the vein, disruption of circulation with turbulence in venous flow, endothelial damage, and ischemia. Clinically, areas of ischemic retina appear as feathery white patches called cotton-wool spots.

Branch retinal vein occlusions with abundant ischemia cause acute central and paracentral visual field loss corresponding to the location of the involved retinal quadrants. Retinal neovascularization due to ischemia may lead to vitreous hemorrhage and subacute or acute vision loss.

Two types of central retinal vein occlusion, ischemic and nonischemic, may occur depending on whether widespread retinal ischemia is present. Even in the nonischemic type, the macula may still be ischemic. Approximately 25% central retinal vein occlusion is ischemic. Diagnosis of central retinal vein occlusion can usually be made on the basis of characteristic opthalmoscopic findings, including retinal hemorrhage in all quadrants, dilated and tortuous veins, and cotton-wool spots. Macular edema and foveal ischemia can lead to vision loss. Extracellular fluid increases interstitial pressure, which may result in areas of retinal capillary closure (i.e., patchy ischemic retinal whitening) or occlusion of a cilioretinal artery.

Patients with ischemic central retinal vein occlusion are more likely to present with a sudden onset of vision loss and have visual acuity of less than 20/200, a relative afferent pupillary defect, abundant intraretinal hemorrhages, and extensive nonperfusion on fluorescein angiography. The natural history of ischemic central retinal vein occlusion is associated with poor outcomes: eventually, approximately two-thirds of patients who have ischemic central retinal vein occlusion will have ocular neovascularization and one-third will have neovascular glaucoma. The latter condition is a severe type of glaucoma that may lead to rapid visual field and vision loss, epithelial edema of the cornea with secondary epithelial erosion and predisposition to bacterial keratitis, severe pain, nausea and vomiting, and, eventually, phthisis bulbi (atrophy of the globe with no light perception).

As used herein, a patient (or subject) may be any mammal, including a human, that may have or be afflicted with a neurodegenerative disease or condition, including an opthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms can be based on objective or subjective parameters; including the results of a physical examination. Accordingly, the term "treating" includes the administration of the compounds or agents described herein to treat pain, hyperalgesia, allodynia, or nociceptive events and to prevent or delay, to alleviate, or to arrest or inhibit development of the symptoms or conditions associated with pain, hyperalgesia, allodynia, nociceptive events, or other disorders. The term "therapeutic effect" refers to the reduction, elimination, or prevention of the disease, symptoms of the disease, or sequelae of the disease in the subject. Treatment also includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also includes prophylaxis and refers to the administration of a compound described herein to a subject to prevent degeneration or further degeneration or deterioration or further deterioration of the vertebrate visual system of the subject and to prevent or inhibit development of the disease and/or related symptoms and sequelae.

Various methods and techniques practiced by a person skilled in the medical and opthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An opthalmoscope may be used to examine the retina and vitreous. Opthalmoscopy is usually performed with dilated pupils, to allow the best view inside the eye. Two types of opthalmoscopes may be used: direct and indirect. The direct opthalmoscope is generally used to view the optic nerve and the central retina. The periphery, or entire retina, may be viewed by using an indirect opthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein can be administered. The term "vertebrate" or "mammal" includes humans and non-human primates, as well as experimental animals such as rabbits, rats, and mice, and other animals, such as domestic pets (such as cats, dogs, horses), farm animals, and zoo animals. Subjects in need of treatment using the methods described herein may be identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

III. Pharmaceutical Compositions

In certain embodiments, a compound described herein may be administered as a pure chemical. In other embodiments, the compound described herein can be combined with a pharmaceutical carrier (also referred to herein as a pharmaceutically acceptable excipient (i.e., a pharmaceutically suitable and acceptable carrier, diluent, etc., which is a non-toxic, inert material that does not interfere with the activity of the active ingredient)) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising one or more compounds described herein, or a stereoisomer, tautomer, prodrug, pharmaceutically acceptable salt, hydrate, solvate, acid salt hydrate, N-oxide or isomorphic crystalline form thereof, of a compound described herein, together with one or more pharmaceutically acceptable carriers and, optionally, other therapeutic and/or prophylactic ingredients. The carrier(s) (or excipient(s)) is acceptable or suitable if the carrier is compatible with the other ingredients of the composition and not deleterious to the recipient (i.e., the subject) of the composition. A pharmaceutically acceptable or suitable composition includes an opthalmologically suitable or acceptable composition.

Thus, another embodiment provides a pharmaceutical composition comprising a pharmaceutically acceptable excipient and a compound having a structure of Formula (I) or tautomer, stereoisomer, geometric isomer or a pharmaceutically acceptable solvate, hydrate, salt, N-oxide or prodrug thereof:

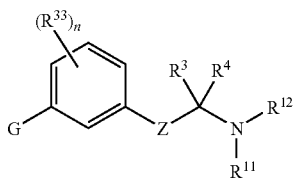

Formula (I)

wherein,

Z is a bond, —C($R^1$)($R^2$)—, —C($R^9$)($R^{10}$)—C($R^1$)($R^2$)—, —X—C($R^{31}$)($R^{32}$)—, —C($R^9$)($R^{10}$)—C($R^1$)($R^2$)—C($R^{36}$)($R^{37}$)—, —C($R^{38}$)($R^{39}$)—X—C($R^{31}$)($R^{32}$)—, or —X—C($R^{31}$)($R^{32}$)—C($R^1$)($R^2$)—;

X is —O—, —S—, —S(=O)—, —S(=O)$_2$—, —N($R^{30}$)—, —C(=O)—, —C(=CH$_2$)—, —C(=N—N$R^{35}$)—, or —C(=N—O$R^{35}$)—;

G is selected from —N($R^{42}$)—SO$_2$—$R^{40}$, —N($R^{42}$)C(=O)—$R^{40}$, —N($R^{42}$)C(=O)—O$R^{40}$, —N($R^{42}$)—C($R^{42}$)($R^{42}$)—$R^{40}$, —N($R^{42}$)—C(=O)—N($R^{43}$)($R^{43}$), or —N($R^{42}$)—C(=S)—N($R^{43}$)($R^{43}$);

$R^{40}$ is selected from —C($R^{16}$)($R^{17}$)($R^{18}$), aryl, or heteroaryl;

each $R^{42}$ is independently selected from hydrogen, alkyl or aryl;

each $R^{43}$ is independently selected from hydrogen, alkyl, cycloalkyl, aralkyl, alkenyl, alkynyl, C-attached heterocyclyl, aryl, or heteroaryl; or two $R^{43}$ groups, together with the nitrogen to which they are attached, may form a heterocyclyl;

$R^1$ and $R^2$ are each independently selected from hydrogen, halogen, $C_1$-$C_5$ alkyl, fluoroalkyl, —O$R^6$ or —N$R^7R^8$; or $R^1$ and $R^2$ together form an oxo;

$R^{31}$ and $R^{32}$ are each independently selected from hydrogen, $C_1$-$C_5$ alkyl, or fluoroalkyl;

$R^{38}$ and $R^{39}$ are each independently selected from hydrogen, $C_1$-$C_5$ alkyl, or fluoroalkyl;

$R^{36}$ and $R^{37}$ are each independently selected from hydrogen, halogen, $C_1$-$C_5$ alkyl, fluoroalkyl, —O$R^6$ or —N$R^7R^8$; or $R^{36}$ and $R^{37}$ together form an oxo; or optionally, $R^{36}$ and $R^1$ together form a direct bond to provide a double bond; or optionally, $R^{36}$ and $R^1$ together form a direct bond, and $R^{37}$ and $R^2$ together form a direct bond to provide a triple bond;

$R^3$ and $R^4$ are each independently selected from hydrogen, alkyl, alkenyl, fluoroalkyl, aryl, heteroaryl, carbocyclyl or C-attached heterocyclyl; or $R^3$ and $R^4$ together with the carbon atom to which they are attached, form a carbocyclyl or heterocyclyl; or $R^3$ and $R^4$ together form an imino;

$R^7$ and $R^8$ are each independently selected from hydrogen, alkyl, carbocyclyl, heterocyclyl, —C(=O)$R^{13}$, SO$_2R^{13}$, CO$_2R^{13}$ or SO$_2$N$R^{24}R^{25}$; or $R^7$ and $R^8$ together with the nitrogen atom to which they are attached, form an N-heterocyclyl;

$R^9$ and $R^{10}$ are each independently selected from hydrogen, halogen, alkyl, fluoroalkyl, —O$R^{19}$, —N$R^{20}R^{21}$ or carbocyclyl; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;

$R^{11}$ and $R^{12}$ are each independently selected from hydrogen, alkyl, carbocyclyl, —C(=O)$R^{23}$, —C(NH)NH$_2$, SO$_2R^{23}$, CO$_2R^{23}$ or SO$_2$N$R^{28}R^{29}$; or $R^{11}$ and $R^{12}$, together with the nitrogen atom to which they are attached, form an N-heterocyclyl;

each $R^{13}$, $R^{22}$ and $R^{23}$ is independently selected from alkyl, heteroalkyl, alkenyl, aryl, aralkyl, carbocyclyl, heteroaryl or heterocyclyl;

$R^6$, $R^{19}$, $R^{30}$, $R^{34}$ and $R^{35}$ are each independently hydrogen or alkyl;

$R^{20}$ and $R^{21}$ are each independently selected from hydrogen, alkyl, carbocyclyl, heterocyclyl, —C(=O)$R^{22}$, SO$_2R^{22}$, CO$_2R^{22}$ or SO$_2$N$R^{26}R^{27}$; or $R^{29}$ and $R^{21}$ together with the nitrogen atom to which they are attached, form an N-heterocyclyl; and each $R^{24}$, $R^{25}$, $R^{26}$, $R^{27}$, $R^{28}$, $R^{29}$ is independently selected from hydrogen, alkyl, alkenyl, fluoroalkyl, aryl, heteroaryl, carbocyclyl or heterocyclyl;

$R^{16}$ and $R^{17}$ are each independently selected from hydrogen, alkyl, halo, aryl, heteroaryl, aralkyl, heteroarylalkyl or fluoroalkyl; or $R^{16}$ and $R^{17}$, together with the carbon to which they are attached form a carbocyclyl or heterocycle;

$R^{18}$ is selected from hydrogen, alkyl, alkoxy, hydroxy, halo or fluoroalkyl;

each $R^{33}$ is independently selected from halogen, O$R^{34}$, alkyl, or fluoroalkyl; and n is 0, 1, 2, 3, or 4.

One embodiment provides a pharmaceutical composition comprising a pharmaceutically acceptable excipient and a compound of Formula (II), (IIa), (III), (IIIa), (IV), or (IVa) as described herein, or tautomer, stereoisomer, geometric isomer or a pharmaceutically acceptable solvate, hydrate, salt, N-oxide or prodrug thereof.

A pharmaceutical composition (e.g., for oral administration or delivery by injection, or combined devices, or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampules, disposable syringes or multiple dose vials made of glass or plastic. Physiological saline is commonly used as an excipient, and an injectable pharmaceutical composition or a composition that is delivered ocularly is preferably sterile.

At least one compound described herein can be administered to human or other nonhuman vertebrates. In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more compounds described herein can be administered.

A compound described herein can be delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, eye drops, intraocular injection or periocular injection. Periocular injection typically involves injection of the synthetic isomerization inhibitor, i.e., compound as described herein, under the conjunctiva or into the Tennon's space (beneath the fibrous tissue overlying the eye). Intraocular injection typically involves injection of the compound described herein into the vitreous. In certain embodiments, the administration is non-invasive, such as by eye drops or oral dosage form, or as a combined device.

A compound described herein can be formulated for administration using pharmaceutically acceptable (suitable) carriers or vehicles as well as techniques routinely used in the art. A pharmaceutically acceptable or suitable carrier includes an opthalmologically suitable or acceptable carrier. A carrier is selected according to the solubility of the compound described herein. Suitable opthalmological compositions include those that are administrable locally to the eye, such as by eye drops, injection or the like. In the case of eye drops, the formulation can also optionally include, for example, opthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to opthalmologic formulations, such as within the range of about pH 4 to 8, or pH 5 to 7, or pH 6 to 7, or pH 4 to 7, or pH 5 to 8, or pH 6 to 8, or pH 4 to 6, or pH 5 to 6, or pH 7 to 8.

In additional embodiments, the compositions described herein further comprise cyclodextrins. Cyclodextrins are cyclic oligosaccharides containing 6, 7, or 8 glucopyranose units, referred to as α-cyclodextrin, β-cyclodextrin, or γ-cyclodextrin respectively. Cyclodextrins have been found to be particularly useful in pharmaceutical formulations. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives. Some of the more common derivatives of cyclodextrin are hydroxypropyl ethers, sulfonates, and sulfoalkylethers. Shown below is the structure of β-cyclodextrin and the hydroxypropyl-β-cyclodextrin (HPβCD).

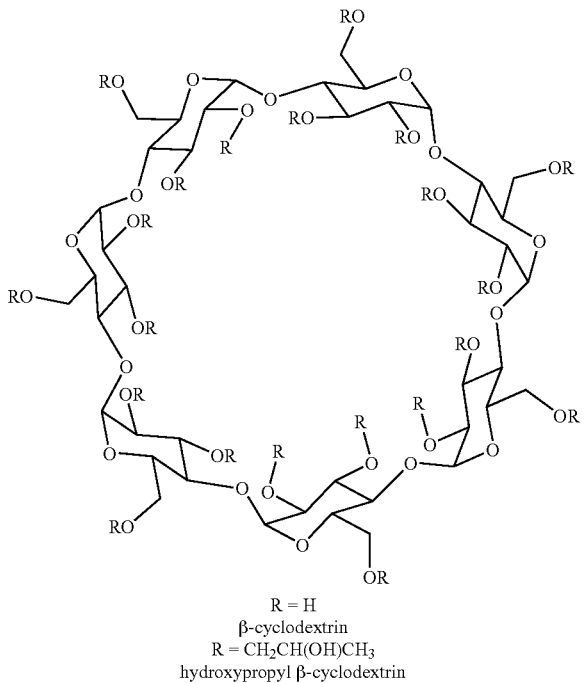

R = H
β-cyclodextrin
R = CH$_2$CH(OH)CH$_3$
hydroxypropyl β-cyclodextrin

The use of cyclodextrins in pharmaceutical compositions is well known in the art as cyclodextrins and cyclodextrin derivatives are often used to improve the solubility of a drug. Inclusion compounds are involved in many cases of enhanced solubility; however other interactions between cyclodextrins and insoluble compounds can also improve solubility. Hydroxypropyl-β-cyclodextrin (HPβCD) is commercially available as a pyrogen free product. It is a nonhygroscopic white powder that readily dissolves in water. HPIβCD is thermally stable and does not degrade at neutral pH.

Ophthalmic formulations utilizing cyclodextrins have been disclosed. For example, U.S. Pat. No. 5,227,372 discloses methods related to retaining opthalmological agents in ocular tissues. US Patent Application Publication 2007/0149480 teaches the use of cyclodextrins to prepare ophthalmic formulations of a small molecule kinase inhibitor with poor water solubility.

The concentration of the cyclodextrin used in the compositions and methods disclosed herein can vary according to the physiochemical properties, pharmacokinetic properties, side effect or adverse events, formulation considerations, or other factors associated with the therapeutically active agent, or a salt or prodrug thereof. The properties of other excipients in a composition may also be important. Thus, the concentration or amount of cyclodextrin used in accordance with the compositions and methods disclosed herein can vary. In certain compositions, the concentration of the cyclodextrin is from 10% to 25%.

For injection, the compound described herein can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

For delivery of a composition comprising at least one of the compounds described herein via a mucosal route, which includes delivery to the nasal passages, throat, and airways, the composition may be delivered in the form of an aerosol. The compound may be in a liquid or powder form for intramucosal delivery. For example, the composition may delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The compounds described herein may be formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a compound described herein is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the compounds described herein may differ, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with neurodegeneration of retinal neuronal cells and/or degeneration of other mature retinal cells such as RPE cells. Optimal doses may generally be determined using experimental models and/or clinical trials. The optimal dose may depend upon the body mass, weight, or blood volume of the patient.

The doses of the compounds described herein can be suitably selected depending on the clinical status, condition and age of the subject, dosage form and the like. In the case of eye drops, a compound described herein can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the compound described herein, one to seven times per week. In other embodiments, about 1.0 to about 30 mg of the compound described herein can be administered one to seven times per week.

Oral doses can typically range from 1.0 to 1000 mg, one to four times, or more, per day. An exemplary dosing range for oral administration is from 10 to 250 mg one to three times per day. If the composition is a liquid formulation, the composition comprises at least 0.1% active compound at particular mass or weight (e.g., from 1.0 to 1000 mg) per unit volume of carrier, for example, from about 2% to about 60%.

In certain embodiments, at least one compound described herein may be administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound may be administered at night before the subject sleeps. In other embodiments, a light stimulus may be blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the compounds that may be administered to prevent or inhibit dark adaptation of a rod photoreceptor cell can be suitably selected depending on the clinical status, condition and age of the subject, dosage form and the like. In the case of eye drops, the compound (or the composition comprising the compound) can be administered, for example, from about 0.01 mg, about 0.1 mg, or about 1 mg, to about 25 mg, to about 50 mg, to about 90 mg per single dose. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound can be administered one to seven times per week. Oral doses can typically range from about 1.0 to about 1000 mg, administered any number of days between one to seven days per week. An exemplary dosing range for oral administration is from about 10 to about 800 mg once per day prior to sleeping. In other embodiments, the composition may be delivered by intravitreal administration.

Also contemplated are compounds of the present disclosure wherein one or more atoms in the molecule are isotopically enriched. In one embodiment, the compound is enriched with deuterium. In another embodiment, the compound is enriched with an isotope selected from $^{2}H$, $^{11}C$, $^{13}C$, $^{14}C$, $^{15}C$, $^{12}N$, $^{13}N$, $^{15}C$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}S$, $^{36}S$, $^{35}S$, $^{37}Cl$, $^{79}Br$, $^{81}Br$, or $^{125}I$. In one embodiment, the enrichment is no less than 98%. In one embodiment, the enrichment is no less than 95%. In one embodiment, the enrichment is no less than 90%. In one embodiment, the enrichment is no less than 75%. In one embodiment, the enrichment is no less than 50%. In one embodiment, the enrichment is no less than 20%. In one embodiment, the enrichment is no less than 10%. In one embodiment, the enrichment is no less than 5%. In one embodiment, the enrichment is no less than 1%. Ratios of enrichment are determined by mass spectroscopy.

Isotopically enriched compounds provide improved pharmaceutical properties compared to the non-enriched compounds. In many cases this is a result of kinetic isotope effect arising during ADME processes. In one embodiment, the isotopically enriched compound of the present disclosure has improved pharmacokinetic properties compared to the non-isotopically enriched compound of the present disclosure. In one embodiment, the isotopically enriched compound of the present disclosure has an increased AUC compared to the non-isotopically enriched compound of the present disclosure. In one embodiment, the isotopically enriched compound of the present disclosure has reduced first-pass effect compared to the non-isotopically enriched compound of the present disclosure. In one embodiment, the isotopically enriched compound of the present disclosure has an increased half-life of elimination compared to the non-isotopically enriched compound of the present disclosure. In one embodiment, the isotopically enriched compound of the present disclosure has improved drug-drug interaction properties compared to the non-isotopically enriched compound of the present disclosure. In one embodiment, the isotopically enriched compound of the present disclosure has different metabolite profile compared to the non-isotopically enriched compound of the present disclosure. In one embodiment, the isotopically enriched compound of the present disclosure has a reduced rate of oxidation in vivo compared to the non-isotopically enriched compound of the present disclosure. In one embodiment, the isotopically enriched compound of the present disclosure has a reduced cytochrome p450 inhibition propensity compared to the non-isotopically enriched compound of the present disclosure. In one embodiment, the isotopically enriched compound of the present disclosure has a different cytochrome p450 inhibition profile compared to the non-isotopically enriched compound of the present disclosure. In one embodiment, the isotopically enriched compound of the present disclosure has a reduced cytochrome p450 induction propensity compared to the non-isotopically enriched compound of the present disclosure.

Also provided are methods of manufacturing the compounds and pharmaceutical compositions described herein. A composition comprising a pharmaceutically acceptable excipient or carrier and at least one of the compounds described herein may be prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Other embodiments and uses will be apparent to one skilled in the art in light of the present disclosures. The following examples are provided merely as illustrative of various embodiments and shall not be construed to limit the invention in any way.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Unless otherwise noted, reagents and solvents were used as received from commercial suppliers Anhydrous solvents and oven-dried glassware were used for synthetic transformations sensitive to moisture and/or oxygen. Yields were not optimized. Reaction times are approximate and were not optimized. Flash column chromatography and thin layer chromatography (TLC) were performed on silica gel unless otherwise noted. Proton and carbon nuclear magnetic resonance spectra were obtained with a Varian VnmrJ 400 at 400 MHz for proton and 100 MHz for carbon, or with a Bruker 400 MHz with Multi Probe/Dual Probe at 400 MHz for proton and 100 MHz for carbon, as noted. Spectra are given in ppm (δ) and coupling constants, J are reported in Hertz. For proton spectra either tetramethylsilane was used as an internal standard or the solvent peak was used as the reference peak. For carbon spectra the solvent peak was used as the reference. Mass-spectra were recorded using electrospray ionization (ES+) mode in Agilent LC/MSD SL mass-spectrometer or (ES+/ES−) mode in Waters Single Quadrupole Detector.

Chiral HPLC analysis was performed using a Chiralpak IA column (4.6×250 mm, 5μ) on an Agilent HP 1100 system with diode array detection with heptane—EtOH with 0.1% ethanesulfonic acid as an eluent.

Analytical HPLC Methods

Method 1. Column: Phenomenex Gemini (150×4.6 mm×5μ); Flow Rate: 1.0 mL/min; Detection at 220 nm using DAD; Column temperature 30° C.; Solvent A: 0.05% TFA in water, Solvent B: 0.05% TFA in acetonitrile; Run Time: 24 min; Gradient program:

| Time (min) | Solvent A (%) | Solvent B (%) |
| --- | --- | --- |
| 0 | 90 | 10 |
| 15 | 30 | 70 |
| 17 | 5 | 95 |
| 20 | 5 | 95 |
| 20.01 | 90 | 10 |
| 24 | 90 | 10 |

Method 2. Column: Phenomenex Gemini (150×4.6 mm×5μ); Flow Rate: 1.0 mL/min; Detection at 220 nm using DAD; Column temperature 30° C.; Solvent A: 0.05% TFA in water, Solvent B: 0.05% TFA in acetonitrile; Run Time: 24 min; Gradient program:

| Time (min) | Solvent A (%) | Solvent B (%) |
| --- | --- | --- |
| 0 | 90 | 30 |
| 6 | 30 | 80 |
| 9 | 5 | 95 |
| 12 | 5 | 95 |
| 13 | 90 | 30 |
| 16 | 90 | 30 |

Method 3. Column: Acquity Shield RP-18 (2.1×100 mm, 1.7 μm); Flow Rate: 0.3 mL/min; Detection at 214 nm using DAD; Column temperature 30° C.; Solvent A: 0.1% TFA in water, Solvent B: acetonitrile; Run Time: 10 min; Gradient program:

| Time (min) | Solvent A (%) | Solvent B (%) |
| --- | --- | --- |
| 0.0 | 90 | 10 |
| 1.0 | 90 | 10 |
| 2.0 | 85 | 15 |
| 4.5 | 55 | 55 |
| 6.0 | 10 | 90 |
| 8.0 | 10 | 90 |
| 9.0 | 90 | 10 |
| 10.0 | 90 | 10 |

Method 4. Column: Acquity Shield RP-18 (2.1×100 mm, 1.7 μm); Flow Rate: 0.3 mL/min; Detection at 214 nm using DAD; Column temperature 30° C.; Solvent A: 0.1% TFA in water, Solvent B: MeOH; Run Time: 10 min; Gradient program was same as for Method 3.

Method 5. Column: Waters Acquity C-8 (2.1×100 mm, 1.7 μm); Flow Rate: 0.3 mL/min; Detection at 214 nm using DAD; Column temperature 30° C.; Solvent A: 5 mM $KH_2PO_4$, Solvent B: acetonitrile; Run Time: 10 min; Gradient program was same as for Method 3.

Method 6. Column: Acquity BEH C-18 (2.1×100 mm, 1.7 μm); Flow Rate: 0.3 mL/min; Detection at 247 nm using DAD; Column temperature 30° C.; Solvent A: 5 mM Ammonium Acetate in water, Solvent B: acetonitrile; Run Time: 10 min; Gradient program was same as for Method 3.

Example 1

Preparation of N-(3-(2-aminoethoxy)phenyl)pentane-2-sulfonamide

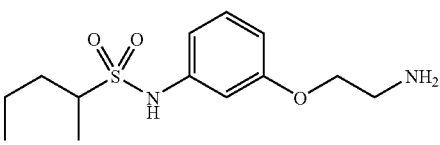 [SMILES: CCCC(C)S(=O)(=O)Nc1cccc(OCCN)c1]

N-(3-(2-Aminoethoxy)phenyl)pentane-2-sulfonamide was prepared following the method shown in Scheme 1.

SCHEME 1

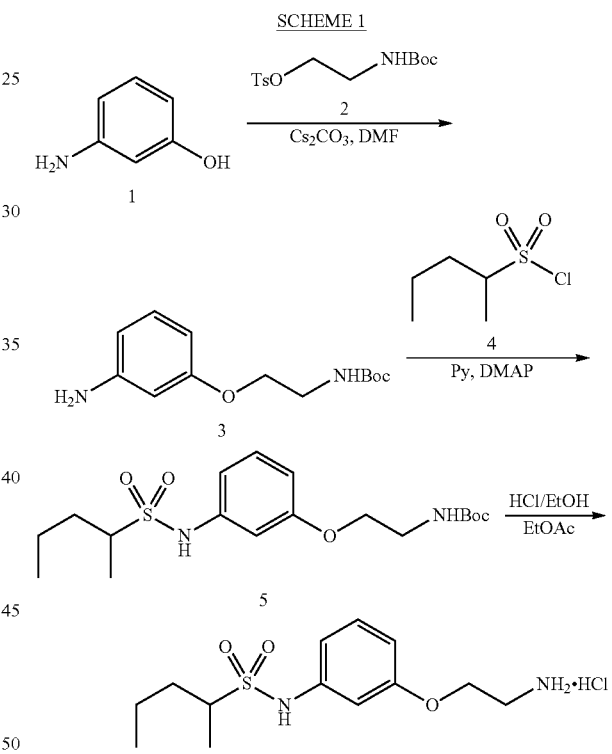

Step 1: A mixture of 1-aminophenol (1) (207 mg, 1.9 mmol), 2-(tert-butoxycarbonylamino)ethyl 4-methylbenzenesulfonate (2) (500 mg, 1.9 mmol), and cesium carbonate (770 mg, 2.2 mmol) in DMF (6 ml) was stirred at room temperature under argon for 15 hours. The mixture was concentrated under reduced pressure. The residue was partitioned between EtOAc and water. The organic layer was washed with brine, dried over $Na_2SO_4$ and concentrated under reduced pressure. Purification by flash chromatography (40 to 60% EtOAc-hexanes gradient) gave tert-butyl 2-(3-aminophenoxy)ethylcarbamate (3) as colorless oil. Yield (220 mg, 58%). $^1$H NMR (400 MHz, DMSO-$d_6$) δ 6.92 (t, J=5.2 Hz, 1H), 6.85 (t, J=8.0 Hz, 1H), 6.08-6.12 (m, 2H), 6.02-6.04 (m, 1H), 4.99 (bs, 2H), 3.79 (t, J=6.0 Hz, 2H), 3.21 (q, J=6.0 Hz, 2H), 1.36 (s, 9H).

Step 2: A mixture of tert-butyl 2-(3-aminophenoxy)ethylcarbamate (3) (210 mg, 1.1 mmol), 2-pentylsulfonyl chloride (4) (0.17 ml, 1.1 mmol) and DMAP (20 mg) in pyridine (5 ml) was stirred at room temperature under argon for 15 hours. The solvent was evaporated under reduced pressure. The residue was partitioned between EtOAc and 0.5 N HCl aq. The organic layer was washed with brine, dried over $Na_2SO_4$ and concentrated under reduced pressure. Purification by flash chromatography (40 to 60% EtOAc-hexanes gradient) gave tert-butyl 2-(3-(1-methylbutylsulfonamido)phenoxy)ethylcarbamate (5) as light yellow oil. Yield (160 mg, 46%). $^1$H NMR (400 MHz, $CDCl_3$) δ 7.20 (t, J=8.0 Hz, 1H), 6.75-6.82 (m, 1H), 6.73-6.75 (m, 1H), 6.64-6.67 (m, 1H), 6.37 (bs, 1H), 4.96 (bs, 1H), 3.99 (t, J=6.0 Hz, 2H), 3.51 (q, J=6.0 Hz, 2H), 3.11-3.18 (m, 1H), 1.91-2.0 (m, 1H), 1.53-1.60 (m, 2H), 1.44 (s, 9H), 1.23-1.37 (m, 4H), 0.88-0.91 (m, 3H).

Step 3: A mixture of tert-butyl 2-(3-(1-methylbutylsulfonamido)phenoxy)ethylcarbamate (5) (160 mg, 0.48 mmol) and HCl-EtOH (6.95 M, 3.0 ml) in ethyl acetate (5 ml) was stirred at room temperature for 15 hours. The solvent was evaporated under reduced pressure. A mixture of EtOAc-hexane (30%, 5 ml) was added and the mixture was sonicated. The solid was collected by filtration and dried to give Example 1 as a white solid. Yield (80 mg, 69%); $^1$H NMR (400 MHz, DMSO-$d_6$) δ 9.81 (s, 1H), 8.07 (bs, 3H), 7.21 (t, J=2.4 Hz, 1H), 6.81 (dd, J=8.4, 2.4 Hz, 1H), 6.56 (dd, J=8.4, 2.4 Hz, 1H), 4.09 (t, J=6.8 Hz, 2H), 3.18 (q, J=6.0 Hz, 2H), 3.01-3.09 (m, 1H), 1.74-1.83 (m, 1H), 1.33-1.46 (m, 2H), 1.18-1.28 (m, 4H), 0.79 (t, J=7.2 Hz, 3H).

Example 2

Preparation of
N-(3-(2-aminoethoxy)phenyl)butane-2-sulfonamide

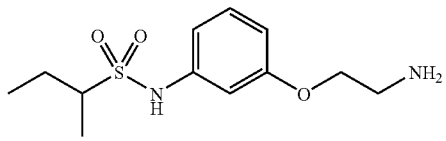 [SMILES: CCC(C)S(=O)(=O)Nc1cccc(OCCN)c1]

N-(3-(2-Aminoethoxy)phenyl)butane-2-sulfonamide was prepared following the method described in Example 1.

Step 1: Sulfonation of tert-butyl 2-(3-aminophenoxy)ethylcarbamate (3) using butane-2-sulfonyl chloride following the method described in Example 1 gave tert-butyl 2-(3-(1-methylpropylsulfonamido)phenoxy)ethylcarbamate (6) as a light yellow oil. $^1$H NMR (400 MHz, DMSO-$d_6$) δ 9.72 (s, 1H), 7.17 (t, J=8.0 Hz, 1H), 6.97 (t, J=6.0 Hz, 1H), 6.76-6.78 (m, 2H), 6.59-6.62 (m, 1H), 3.87 (t, J=5.6 Hz, 2H), 3.24 (q, J=6.4 Hz, 2H), 2.93-3.02 (m, 1H), 1.80-1.91 (m, 1H), 1.40-1.48 (m, 1H), 1.35 (s, 9H), 1.19 (d, J=6.8 Hz, 3H), 0.88 (t, J=7.2 Hz, 3H).

Step 2: Deprotection of tert-butyl 2-(3-(1-methylpropylsulfonamido)phenoxy)ethylcarbamate (6) following the method described in Example 1 gave Example 2 as a colorless oil. $^1$H NMR (400 MHz, DMSO-$d_6$) δ 7.16 (t, J=8.0 Hz, 1H), 6.75-6.77 (m, 2H), 6.59-6.62 (m, 1H), 3.83 (t, J=5.2 Hz, 2H), 2.93-3.02 (m, 1H), 2.83 (t, J=5.6 Hz, 2H), 1.80-1.91 (m, 1H), 1.38-1.48 (m, 1H), 1.19 (d, J=6.8 Hz, 3H), 0.88 (t, J=7.2 Hz, 3H).

Example 3

Preparation of
N-(3-(2-aminoethoxy)phenyl)propane-2-sulfonamide

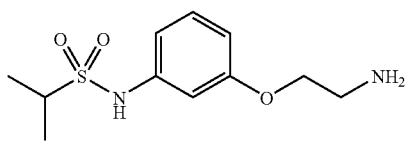 [SMILES: CC(C)S(=O)(=O)Nc1cccc(OCCN)c1]

N-(3-(2-Aminoethoxy)phenyl)propane-2-sulfonamide was prepared following the method described in Example 1.

Step 1: Sulfonation of tert-butyl 2-(3-aminophenoxy)ethylcarbamate (3) using propane-2-sulfonyl chloride following the method described in Example 1 gave tert-butyl 2-(3-(1-methylethylsulfonamido)phenoxy)ethylcarbamate (7) as a light yellow oil. $^1$H NMR (400 MHz, DMSO-$d_6$) δ 9.70 (s, 1H), 7.17 (t, J=8.0 Hz, 1H), 6.97 (t, J=6.0 Hz, 1H), 6.76-6.79 (m, 2H), 6.60-6.62 (m, 1H), 3.16-3.30 (m, 3H), 1.35 (s, 9H), 1.19 (d, J=6.8 Hz, 6H).

Step 2: Deprotection of tert-butyl 2-(3-(1-methylethylsulfonamido)phenoxy)ethylcarbamate (7) following the method described in Example 1 gave Example 3 as a white solid. $^1$H NMR (400 MHz, DMSO-$d_6$) δ 9.80 (s, 1H), 8.07 (bs, 3H), 7.21 (t, J=8.0 Hz, 1H), 6.86 (t, J=2.0 Hz, 1H), 6.81 (dd, J=8.0, 2.0 Hz, 1H), 6.66 (dd, J=8.0, 2.0 Hz, 1H), 4.10 (t, J=5.2 Hz, 2H), 3.15-3.24 (m, 3H), 1.20 (d, J=6.8 Hz, 6H).

Example 4

Preparation of
N-(3-(2-aminoethoxy)phenyl)cyclohexanesulfonamide

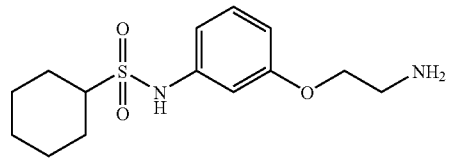 [SMILES: NCCOc1cccc(NS(=O)(=O)C2CCCCC2)c1]

N-(3-(2-Aminoethoxy)phenyl)cyclohexanesulfonamide was prepared following the method described in Example 1.

Step 1: Sulfonation of tert-butyl 2-(3-aminophenoxy)ethylcarbamate (3) using cyclohexanesulfonyl chloride (8) following the method described in Example 1 gave tert-butyl 2-(3-(cyclohexanesulfonamido)phenoxy)ethylcarbamate (9) as a light yellow oil. $^1$H NMR (400 MHz, DMSO-$d_6$) δ 9.70 (s, 1H), 7.16 (t, J=8.0 Hz, 1H), 6.97 (t, J=6.0 Hz, 1H), 6.75-6.78 (m, 2H), 6.59-6.62 (m, 1H), 3.87 (t, J=5.6 Hz, 2H), 3.24 (q, J=6.0 Hz, 2H), 2.89-2.98 (m, 1H), 1.92-2.01 (m, 2H), 1.68-1.76 (m, 2H), 1.52-1.57 (m, 1H), 1.31-42 (m, 11H), 1.05-1.22 (m, 2H).

Step 2: Deprotection of tert-butyl 2-(3-(cyclohexanesulfonamido)phenoxy)ethylcarbamate (9) following the method described in Example 1 gave Example 4 as a white solid. $^1$H NMR (400 MHz, DMSO-$d_6$) δ 9.79 (s, 1H), 8.07 (bs, 3H), 7.20 (t, J=8.0 Hz, 1H), 6.79-6.85 (m, 2H), 6.64 (d, J=7.6 Hz, 1H), 4.07 (t, J=4.8 Hz, 2H), 3.12-3.18 (m, 2H), 2.93 (t, J=7.6 Hz, 1H), 2.89-2.98 (m, 1H), 1.92-2.01 (m, 2H), 1.68-1.76 (m, 2H), 1.52-1.57 (m, 1H), 1.32-42 (m, 2H), 1.00-1.21 (m, 2H).

Example 5

Preparation of N-(3-(3-amino-1-hydroxypropyl)phenyl)cyclohexanesulfonamide

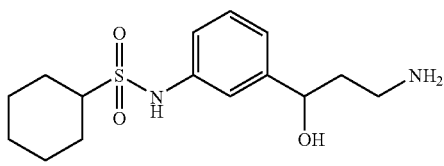 [SMILES: NCCC(O)c1cccc(NS(=O)(=O)C2CCCCC2)c1]

N-(3-(3-Amino-1-hydroxypropyl)phenyl)cyclohexanesulfonamide was prepared following the method shown in Scheme 2.

SCHEME 2

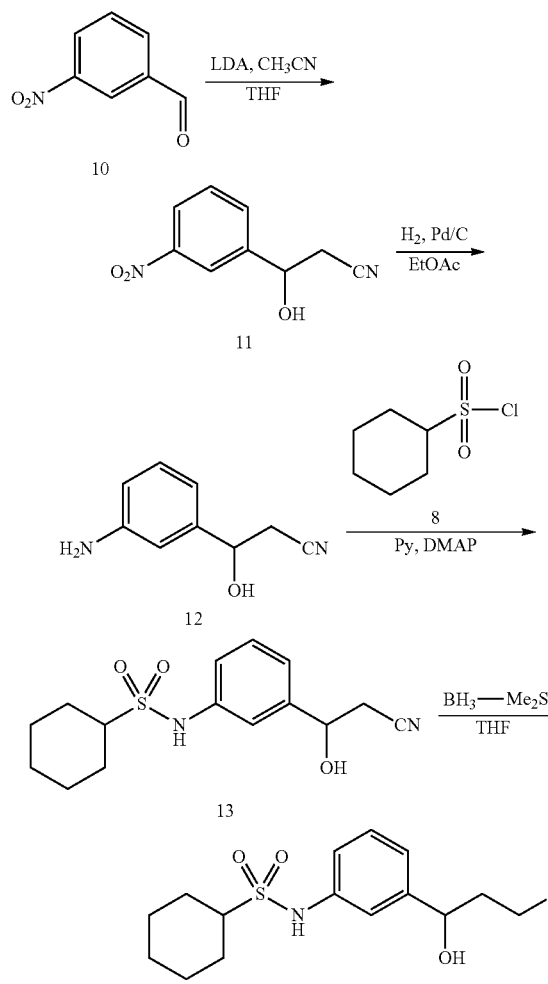

Step 1: To a solution of CH$_3$CN (0.7 ml, 16 mmol) in THF (10 ml) was added LDA (8 ml, 2M in THF, 16 mmol) at −78° C. and the mixture was stirred at this temperature for 10 min. A chilled (−78° C.) solution of nitrobenzaldehye (10) (2.0 g, 13 mmol) in THF (15 ml) was added slowly. The resulting mixture was stirred at −78° C. for 15 mins. The reaction was quenched by the addition of sat. NH$_4$Cl aq (10 ml) and the mixture allowed to warm to room temperature. The organic layer was collected and the aqueous layer was extracted with EtOAc. The combined organic layers were dried over Na$_2$SO$_4$ and concentrated under reduced pressure. Purification by flash chromatography (30 to 65% EtOAc-hexanes gradient) gave 3-hydroxy-3-(3-nitrophenyl)propanenitrile (11) as colorless oil, Yield (1.9 g, 77%); $^1$H NMR (400 MHz, CDCl$_3$) δ 8.30 (t, J=3.2 Hz, 1H), 8.21-8.24 (m, 1H), 7.76-7.80 (m, 1H), 7.71 (t, J=8.0 Hz, 1H), 5.20 (t, J=2.4 Hz, 1H), 2.22 (d, J=6.0 Hz, 2H), 1.24 (s, 1H).

Step 2: A mixture of 3-hydroxy-3-(3-nitrophenyl)propanenitrile (11) (400 mg, 2.1 mmol) and Pd/C (20 mg, 10%) in EtOAc (15 ml) was degassed vacuum/hydrogen and then stirred at room temperature under H$_2$ (balloon) for 15 hours. The mixture was filtered to remove the Pd/C and then concentrated under reduced pressure to give 3-(3-aminophenyl)-3-hydroxypropanenitrile (12) as while solid. Yield (390 mg, 99%). $^1$H NMR (400 MHz, CDCl$_3$) δ 7.15 (t, J=8.0 Hz, 1H), 6.70-6.74 (m, 2H), 6.63-6.65 (m, 1H), 4.92 (t, J=6.0 Hz, 1H), 2.72 (d, J=6.0 Hz, 2H).

Step 3: Sulfonation of 3-(3-aminophenyl)-3-hydroxypropanenitrile (12) following the method described in example Example 1 gave N-(3-(2-cyano-1-hydroxyethyl)phenyl)cyclohexanesulfonamide (13) as a light yellow oil. $^1$H NMR (400 MHz, CDCl$_3$) δ 9.74 (s, 1H), 7.23-7.29 (m, 2H), 7.04-7.11 (m, 2H), 5.94 (d, J=2.8 Hz, 1H), 4.83 (q, J=5.2 Hz, 1H), 2.92-3.01 (m, 1H), 2.72-2.86 (m, 2H), 1.91-2.02 (m, 2H), 1.63-1.73 (m, 2H), 1.50-1.57 (m, 1H), 1.31-1.42 (m, 2H), 1.02-1.22 (m, 3H).

Step 4: BH$_3$-Me$_2$S (1.2 ml, 12.7 mmol) was added under argon to a solution of N-(3-(2-cyano-1-hydroxyethyl)phenyl)cyclohexanesulfonamide (1.2 g, 3.9 mmol) in anhydrous THF. The reaction mixture was stirred at 60° C. for 18 hrs. The reaction was quenched by the addition of 2N HCl to pH 0 and stirred at room temperature for 24 hrs. The pH was then adjusted to 10 by adding 50% aq. NaOH. MTBE (40 ml) was added to the mixture and stirred. Organic layer was dried over anhydrous Na$_2$SO$_4$ and concentrated under reduced pressure to give Example 5 as a white solid. Yield (0.60 g, 49%); $^1$H MR (400 MHz, CDCl$_3$) δ 7.20-7.28 (m, 2H), 7.11-7.13 (m, 2H), 4.94 (dd, J=8.8, 2.4 Hz, 1H), 3.06-3.15 (m, 1H), 2.94-3.04 (m, 2H), 2.10-2.18 (m, 2H), 1.78-1.90 (m, 3H), 1.50-1.76 (m, 4H), 1.10-1.26 (m, 3H).

Example 6

Preparation of N-(3-(3-aminopropyl)phenyl)cyclohexanesulfonamide

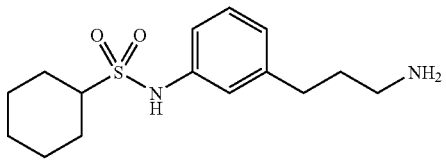

N-(3-(3-Aminopropyl)phenyl)cyclohexanesulfonamide was prepared following the method shown in Scheme 3.

SCHEME 3

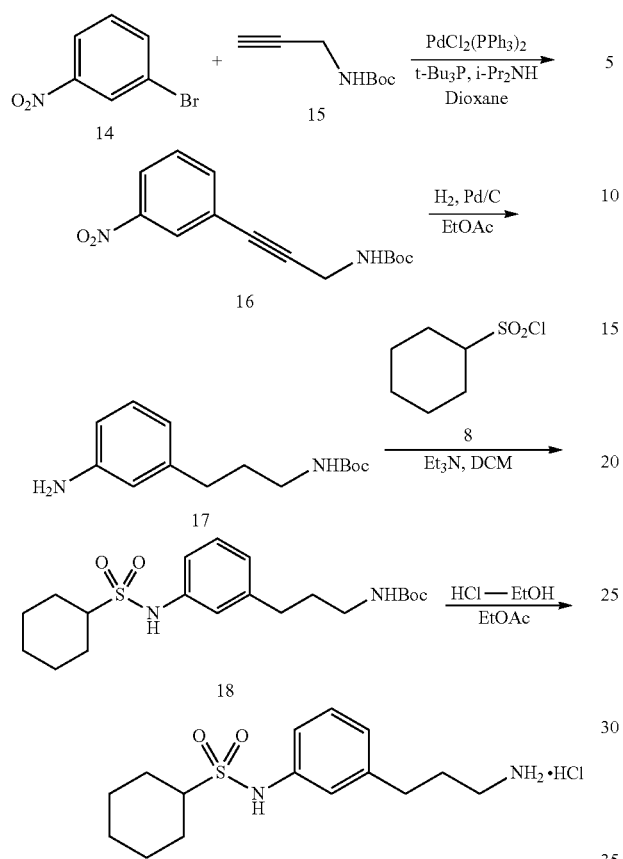

Step 1: To an oven dried, argon filed, flask was added 1-bromo-3-nitrobenzene (14) (3.09 g, 15.3 mmol), tert-butyl prop-2-ynylcarbamate (15) (2.8 g, 18.0 mmol), diisopropylamine (92.5 ml, 17.8 mmol), CuI (0.054 g, 0.18 mmol), PdCl$_2$(PPh$_3$)$_2$ (0.42 g, 0.6 mmol) and dioxane (17 ml). The resulting mixture was purged with argon three times and then a solution of t-Bu$_3$P-dioxane solution (0.9 ml, 0.9 mmol) was added. The mixture was heated at 45° C. for 15 h, cooled to room temperature, diluted with ethyl acetate, filtered through celite and the filtrate was concentrated under reduced pressure. Purification by flash chromatography (10 to 50% EtOAc-hexanes gradient) gave tert-butyl 3-(3-nitrophenyl) prop-2-ynylcarbamate (16) as colorless oil. Yield (4.98 g, 100%); $^1$H NMR (400 MHz, CDCl$_3$) δ 8.25 (t, J=1.6 Hz, 1H), 8.15 (ddd, J=8.4, 2.4, 1.2 Hz, 1H), 7.69 (dt, J=7.6, 0.8 Hz, 1H), 4.78 (br s, 1H), 4.16 (d, J=5.6 Hz, 2H), 1.47 (s, 9H).

Step 2: Hydrogenation of tert-butyl 3-(3-nitrophenyl)prop-2-ynylcarbamate (16) following method described in Example 5 gave tert-butyl 3-(3-aminophenyl)propylcarbamate (17) as a light yellow oil. Yield (2.57 g, 78%). $^1$H NMR (400 MHz, CDCl$_3$) δ 7.04-7.08 (m, 1H), 6.57-6.59 (m, 1H), 7.51-7.29 (m, 2H), 4.50 (br s, 1H), 3.13 (q, J=6.8 Hz, 2H), 2.54 (t, J=7.6 Hz, 2H), 1.73-1.81 (m, 2H), 1.43 (s, 9H).

Step 3: Sulfonation of tert-butyl 3-(3-aminophenyl)propylcarbamate (17) following the method described in Example 1 except pyridine and DMAP were used instead of TEA and DCM gave tert-butyl 3-(3-(cyclohexanesulfonamido)phenyl) propylcarbamate (18) as a colorless oil. Yield (0.2 g, 32%); $^1$H NMR (400 MHz, CDCl$_3$) δ 7.47 (s, 1H), 7.18 (t, J=8.0 Hz, 1H), 7.05-7.09 (m, 2H), 6.90 (d, J=7.6 Hz, 1H), 4.64 (br s, 1H), 3.05-3.16 (m, 2H), 2.93-3.01 (m, 1H), 2.58 (t, J=7.6 Hz, 2H), 2.12-2.15 (m, 2H), 1.72-1.83 (m, 4H), 1.48-1.64 (m, 3H), 1.42 (s, 9H), 1.10-1.24 (m, 3H).

Step 4: Deprotection of tert-butyl 3-(3-(cyclohexanesulfonamido)phenyl)propylcarbamate (18) following method described in Example 1 except that the hydrochloride salt was converted to the free amine by washing the organic solution with aqueous NaHCO$_3$ to give Example 6 as a colorless oil. Yield (0.071 g, 43%); $^1$H NMR (400 MHz, CDCl$_3$) δ 7.13-7.17 (m, 1H), 6.95-7.01 (m, 2H), 6.88-6.90 (m, 1H), 2.89-2.96 (m, 1H), 2.57 (t, J=7.6 Hz, 2H), 2.07-2.10 (m, 2H), 1.68-1.84 (m, 4H), 1.46-1.61 (m, 3H), 1.08-1.22 (m, 3H).

Example 7

Preparation of 3-(3-aminopropyl)-N-(cyclohexylmethyl)aniline

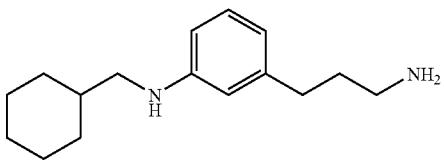 [SMILES: NCCCc1cccc(NCC2CCCCC2)c1]

3-(3-Aminopropyl)-N-(cyclohexylmethyl)aniline hydrochloride was prepared following the method shown in Scheme 4.

SCHEME 4

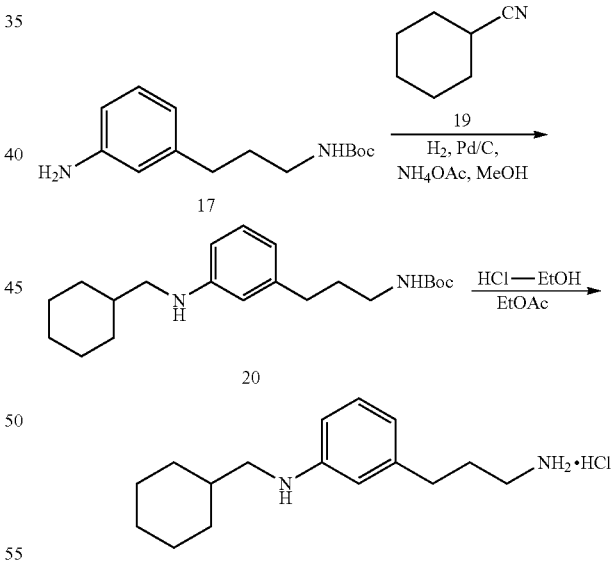

Step 1: A mixture of tert-butyl 3-(3-(cyclohexylmethylamino)phenyl)propylcarbamate (17) (0.31 g, 1.22 mmol), cyclohexanecarbonitrile (19) (0.73 ml, 6.1 mmol), ammonium acetate (0.1 g, 1.29 mmol) in MeOH (20 ml) was purged with argon. Pd/C (10%, 0.04 g) was added and the atmosphere exchange with hydrogen. The mixture was stirred under H$_2$ (balloon) for 18 h at room temperature. The Pd/C was removed by filtration through celite, and the filtrate was concentrated under reduced pressure. Purification by flash chromatography (0 to 50% EtOAc-hexanes gradient) gave tert-butyl 3-(3-(cyclohexylmethylamino)phenyl)propylcarbamate (20) as a colorless oil. Yield (0.33 g, 78%); [1]Yield (0.2 g, 32%); $^1$H NMR (400 MHz, CDCl$_3$) δ 7.06 (t, J=8.0 Hz, 1H), 6.48-6.49 (m, 1H), 6.39-6.44 (m, 2H), 4.50 (br s, 1H), 3.14 (q, J=6.8 Hz, 2H), 2.92 (d, J=6.8 Hz, 2H), 2.54 (t, J=7.6 Hz, 2H), 1.65-1.83 (m, 7H), 1.50-1.61 (m, 1H), 1.43 (s, 9H), 1.11-1.29 (m, 3H), 0.92-1.02 (m, 2H).

Step 2: Deprotection of tert-butyl 3-(3-(cyclohexylmethylamino)phenyl)propylcarbamate (20) following method described in Example 1 gave Example 7 hydrochloride salt as a white solid. Yield (0.29 g, 98%); $^1$H NMR (400 MHz, MeOD) δ 7.51 (t, J=8.0 Hz, 1H), 7.38-7.43 (m, 2H), 7.32-7.37 (m, 1H), 3.24 (d, J=6.8 Hz, 2H), 2.97 (t, J=7.6 Hz, 2H), 2.78 (t, J=7.6 Hz, 2H), 1.95-2.03 (m, 2H), 1.68-1.88 (m, 6H), 1.22-1.36 (m, 3H), 1.06-1.18 (m, 2H).

Example 8

Preparation of
N-(3-(3-aminopropyl)phenyl)cyclohexanecarboxamide Hydrochloride

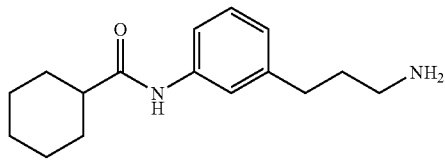 [SMILES: NCCCc1cccc(NC(=O)C2CCCCC2)c1]

N-(3-(3-Aminopropyl)phenyl)cyclohexanecarboxamide hydrochloride was prepared following the method shown in Scheme 5.

SCHEME 5

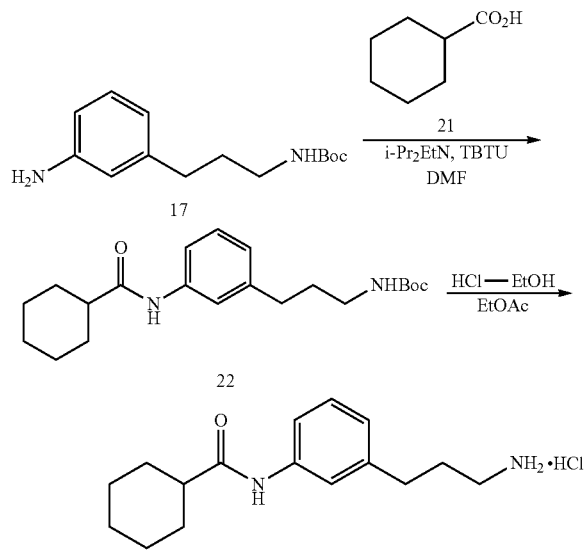

Step 1: To a mixture of cyclohexanecarboxylic acid (21) (0.23 ml, 1.79 mmol), TBTU (0.56 g, 1.74 mmol) and iPr$_2$EtN (0.33 ml, 1.89 mmol) in DMF (20 ml) was added tert-butyl 3-(3-(cyclohexylmethylamino)phenyl)propylcarbamate (17) (0.40 g, 1.59 mmol) in DMF (5 ml). The mixture was stirred at room temperature for 18 h and then diluted with water. The solution was extracted with ethyl acetate and the combined extracts were washed with water, aqueous NaHCO$_3$ and brine, dried over Na$_2$SO$_4$ and concentrated under reduced pressure. Purification by flash chromatography (5 to 50% EtOAc-hexanes gradient) gave tert-butyl 3-(3-(cyclohexanecarboxamido)phenyl)propylcarbamate (22) as a colorless oil. Yield (0.455 g, 78%); Yield (0.2 g, 32%); $^1$H NMR (400 MHz, CDCl$_3$) δ 7.43 (br s, 1H), 7.26-7.28 (m, 2H), 7.20 (t, J=7.6 Hz, 1H), 7.08 (br s, 1H), 6.89-6.91 (m, 1H), 3.12 (t, J=6.0 Hz, 2H), 2.61 (t, J=8.4 Hz, 2H), 2.17-2.23 (m, 1H), 1.93-1.96 (m, 2H), 1.74-1.86 (m, 3H), 1.65-1.72 (m, 2H), 1.48-1.59 (m, 1H), 1.31-1.42 (m, 2H), 1.43 (s, 9H), 1.22-1.38 (m, 4H).

Step 2: Deprotection of tert-butyl 3-(3-(cyclohexanecarboxamido)phenyl)propylcarbamate (22) following method described in Example 1 gave Example 8 hydrochloride salt as a white solid. Yield (0.31 g, 92%); $^1$H NMR (400 MHz, DMSO-d$_6$) δ 9.76 (s, 1H), 7.81 (br s, 3H), 7.56 (s, 1H), 7.20-7.32 (m, 1H), 7.17 (t, J=8.0 Hz, 1H), 6.83 (d, J=6.8 Hz, 1H), 2.70-2.81 (m, 2H), 2.55 (t, J=7.6 Hz, 2H), 2.26-2.34 (m, 1H), 1.61-1.83 (m, 7H), 1.13-1.41 (m, 5H).

Example 9

Preparation of
3-(3-(3-aminopropyl)phenyl)-1,1-dipropylurea

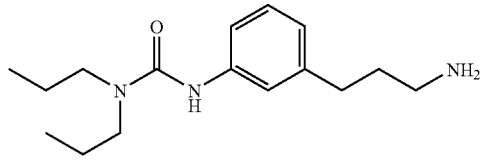 [SMILES: CCCN(CCC)C(=O)Nc1cccc(CCCN)c1]

3-(3-(3-Aminopropyl)phenyl)-1,1-dipropylurea was prepared following the method shown in Scheme 6.

SCHEME 6

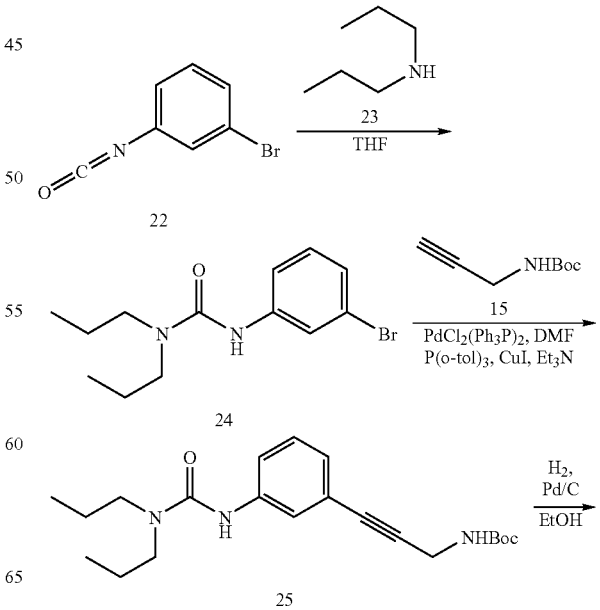

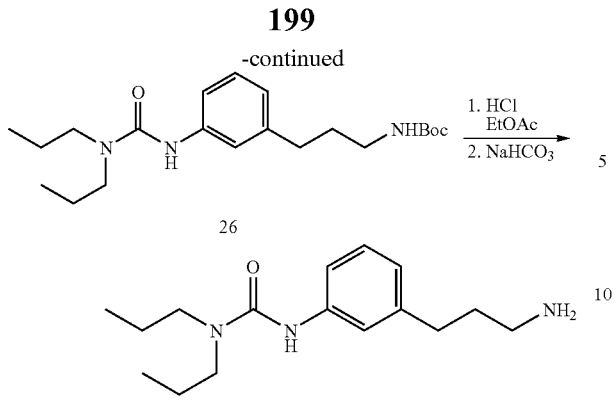

Step 1: A mixture of 1-bromo-3-isocyanatobenzene (22) (1.044 g, 5.27 mmol) and dipropylamine (23) (0.75 mL, 5.80 mmol) in anhydrous THF was stirred at room temperature for 1 hr. The mixture was concentrated under reduced pressure. Crystallization from hexanes gave 3-(3-bromophenyl)-1,1-dipropylurea (24) as a white solid. Yield (1.512 g, 96%); $^1$H NMR (400 MHz, DMSO-$d_6$) δ 8.25 (br.s, 1H), 7.76 (t, J=2.0 Hz, 1H), 7.45 (ddd, J=1.2, 2.2, 8.2 Hz, 1H), 7.14 (t, J=8.0 Hz, 1H), 7.06 (ddd, J=1.0, 2.0, 7.8 Hz, 1H), 3.21 (t, J=7.4 Hz, 4H), 1.47 (sextet, J=7.4 Hz, 4H), 0.82 (t, J=7.2 Hz, 6H).

Step 2: A solution of 3-(3-bromophenyl)-1,1-dipropylurea (24) (0.507 g, 1.70 mmol), tert-butyl prop-2-ynylcarbamate (15) (0.323 g, 2.12 mmol), tri-o-tolylphosphine (0.0342 g, 0.112 mmol) and Et$_3$N (3.0 mL) in DMF was degassed by bubbling argon for 10 min, and applying vacuum/argon 3×. PdCl$_2$(Ph$_3$P)$_2$ (0.0434 g, 0.062 mmol) followed by CuI (0.0263 g, 0.138 mmol) were added and the mixture was degassed by applying vacuum/argon 3×. The reaction mixture was stirred under argon at 70° C. for 22 hrs. The reaction mixture was concentrated under reduced pressure. Purification by flash chromatography (10% to 50% EtOAc—hexanes gradient) gave tert-butyl 3-(3-(3,3-dipropylureido)phenyl)prop-2-ynylcarbamate (25) as a pale yellow solid. Yield (0.174 g, 28%); $^1$H NMR (400 MHz, DMSO-$d_6$) δ 8.15 (br.s, 1H), 7.56 (t, J=1.8 Hz, 1H), 7.42-7.46 (m, 1H), 7.31 (br.t, 1H), 7.17 (t, J=7.8 Hz, 1H), 6.89-6.93 (m, 1H), 3.93 (d, J=5.7 Hz, 2H), 3.21 (t, J=7.6 Hz, 4H), 1.47 (sextet, J=7.4 Hz, 4H), 1.32-1.38 (m, 9H), 0.82 (t, J=7.4 Hz, 6H).

Step 3: A solution of tert-butyl 3-(3-(3,3-dipropylureido)phenyl)prop-2-ynylcarbamate (25) (0.17 g, 0.455 mmol) in EtOH (10 mL) was degassed with vacuum/Ar. Pd/C (10%, 0.0293 g) was added and the atmosphere was purged with H$_2$. The mixture was stirred under H$_2$-filled balloon at room temperature for 5 hrs. The reaction mixture was filtered through Celite and concentrated under reduced pressure. The residue was crystallized from EtOAc/hexanes to give tert-butyl 3-(3-(3,3-dipropylureido)phenyl)propylcarbamate (26) as a pale yellow solid. Yield (0.0946 g, 55%); $^1$H NMR (400 MHz, DMSO-$d_6$) δ 8.00 (s, 1H), 7.22-7.26 (m, 2H), 7.07 (t, J=7.6 Hz, 1H), 6.82 (br.t, J=5.1 Hz, 1H), 6.70-6.74 (m, 1H), 3.21 (t, J=7.4 Hz, 4H), 2.90 (q, J=6.1 Hz, 2H), 2.45 (t, J=8.0 Hz, 2H), 1.61 (m, 2H), 1.48 (sextet, J=7.4 Hz, 4H), 1.35 (s, 9H), 0.82 (t, J=7.4 Hz, 6H).

Step 4. A mixture of tert-butyl 3-(3-(3,3-dipropylureido)phenyl)propylcarbamate (26) (0.094 g, 0.249 mmol) and HCl/EtOAc (3N, 4.5 mL) in EtOAc was stirred at room temperature for 1 h. The reaction mixture was concentrated under reduced pressure and the residue was partitioned between aq. NaHCO$_3$ and MTBE. The organic layer was concentrated under reduced pressure. Purification by flash chromatography (20% 7N NH$_3$/MeOH/EtOAc) gave Example 9 as a colorless oil. Yield (0.0154 g, 22%); $^1$H NMR (400 MHz, CD$_3$OD) δ 7.20-7.22 (m, 1H), 7.12-7.18 (m, 2H), 6.84-6.89 (m, 1H), 2.58-2.69 (m, 4H), 1.78 (p, J=7.6 Hz, 2H), 1.62 (sextet, J=7.6 Hz, 4H), 0.93 (t, J=7.4 Hz, 6H); ESI MS m/z 278.60 [M+H]$^+$.

Example 10

Preparation of 1-(3-(2-aminoethoxy)phenyl)-3-cyclohexylthiourea

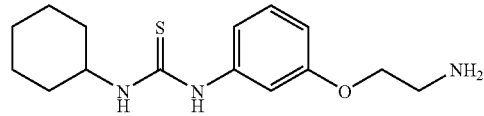

1-(3-(2-Aminoethoxy)phenyl)-3-cyclohexylthiourea was prepared following the method shown in Scheme 7.

SCHEME 7

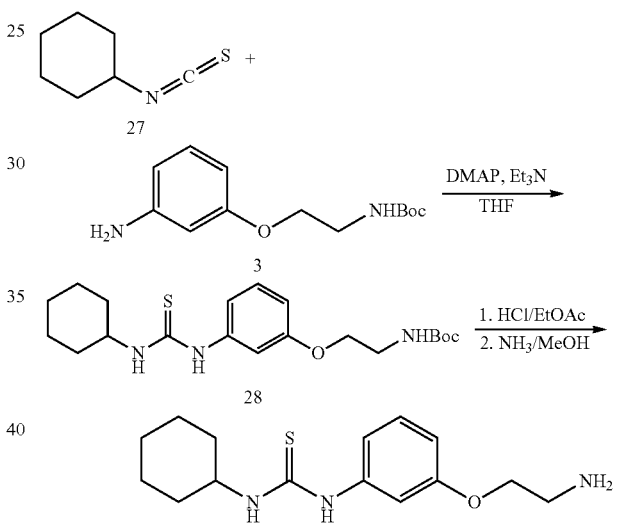

Step 1: A mixture of isothiocyanatocyclohexane (27) (0.16 mL, 1.17 mmol), tert-butyl 2-(3-aminophenoxy)ethylcarbamate (3) (0.282 g, 1.12 mmol), DMAP (0.024 g, 0.196 mmol) and Et$_3$N (0.3 mL, 2.15 mmol) in anhydrous THF was stirred under argon at 50° C. for 24 h. The mixture was concentrated under reduced pressure. Purification by flash chromatography (30% to 60% EtOAc—hexanes gradient) gave tert-butyl 2-(3-(3-cyclohexylthioureido)phenoxy)ethylcarbamate (28) as a white solid. Yield (0.1917 g, 44%); $^1$H NMR (400 MHz, DMSO-$d_6$) δ 9.29 (s, 1H), 7.59 (br.d, J=7.6 Hz, 1H), 7.15 (t, J=8.2 Hz, 1H), 6.97 (br.t, J=5.5 Hz, 1H), 6.85-6.89 (m, 1H), 6.58-6.63 (m, 1H), 4.06 (br.s, 1H), 3.88 (t, J=5.9 Hz, 2H), 3.25 (q, J=5.7 Hz, 2H), 1.82-1.90 (m, 2H), 1.60-1.70 (m, 2H), 1.47-1.57 (m, 1H), 1.36 (s, 9H), 1.07-1.34 (m, 6H).

Step 2: A mixture of tert-butyl 2-(3-(3-cyclohexylthioureido)phenoxy)ethylcarbamate (28) (0.19 g, 0.483 mmol) and HCl/EtOAc (3N, 5 mL) in EtOAc was stirred at room temperature for 24 h. A precipitate formed which was collected by filtration. The solid was dissolved in NH$_3$/MeOH (7N) and the resulting solution was concentrated under reduced pressure. Purification by flash chromatography (5% 7N NH$_3$/

MeOH/CH$_2$Cl$_2$) gave Example 10 as a white solid. Yield (0.101 g, 71%); $^1$H NMR (400 MHz, DMSO-d$_6$) δ 9.30 (s, 1H), 7.59 (br.d, J=7.6 Hz, 1H), 7.18-7.22 (m, 1H), 7.15 (t, J=8.2 Hz, 1H), 6.85-6.89 (m, 1H), 6.58-6.63 (m, 1H), 4.06 (br.s, 1H), 3.84 (t, J=5.9 Hz, 2H), 2.83 (t, J=5.7 Hz, 2H), 1.82-1.90 (m, 2H), 1.60-1.70 (m, 2H), 1.44-1.59 (m, 3H), 1.07-1.24 (m, 5H).

Example 11

Preparation of 3-amino-1-(3-(cyclohexylmethylamino)phenyl)propan-1-ol

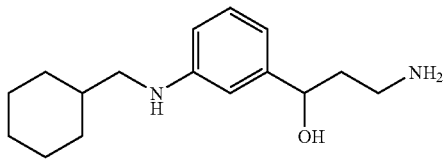 [SMILES: NCCC(O)c1cccc(NCC2CCCCC2)c1]

3-Amino-1-(3-(cyclohexylmethylamino)phenyl)propan-1-ol was prepared following the method shown in Scheme 8.

SCHEME 8

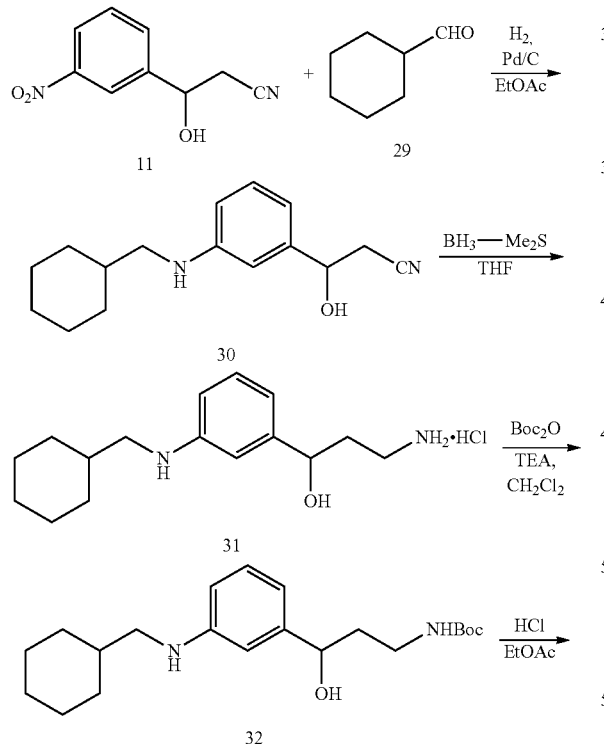

Step 1: A solution of 11 (0.8 g, 4.2 mmol) and cyclohexanecarbaldehyde (29) (0.5 ml, 4.2 mmol) in EtOAc was degassed and saturated with argon. To this solution was added 10% Pd/C (50 mg). The resulting mixture was stirred under H$_2$ at 1 atm for 18 hrs, filtered through Celite, concentrated under reduced pressure. Purification by flash chromatography (40 to 50% EtOAc-hexanes gradient) gave aniline 30 as a light yellow oil which was used in the next step without further purification. Yield (0.9 g, 70%).

Step 2: Reduction of hydroxynitrile 30 was done following the method described in Example 5 with the following exception. After the reaction was completed, it was cooled to room temperature, the excess of borane was quenched by careful addition of MeOH, followed by addition of HCl-MeOH (1.25 M, 10 ml), stirring at 60° C. for 3 hr. Concentration under reduced pressure gave amine 31 hydrochloride which was used in next step without further purification.

Step 3: A solution of Boc$_2$O (0.6 g, 2.73 mmol) in CH$_2$Cl$_2$ was added dropwise to a suspension of amine 31 (0.68 g. 2.6 mmol) and TEA (1.0 ml, 5.2 mmol) in dichloromethane at room temperature. The reaction mixture was stirred at room temperature for 2 hr, washed with HCl—NH$_4$Cl.aq (0.5 M, 50 ml), dried with Na$_2$SO$_4$ and concentrated under reduced pressure. Purification by flash chromatography (50% to 60% EtOAc—hexanes gradient) gave carbamate 32 as an off-white solid. Yield (0.8 g, 88%); $^1$H NMR (400 MHz, DMSO-d$_6$) δ 6.94 (t, J=7.6 Hz, 1H), 6.69 (t, J=4.8 Hz, 1H), 6.49 (s, 1H), 6.40 (d, J=7.6 Hz, 1H), 6.36 (dd, J=8.0, 1.6 Hz, 1H), 5.47 (bs, 1H), 4.97 (bs, 1H), 4.33-4.38 (m, 1H), 2.88-2.98 (m, 2H), 2.79 (t, J=6.0 Hz, 2H), 1.73-1.80 (m, 2H), 1.56-1.70 (m, 5H), 1.44-1.56 (m, 1H), 1.34 (s, 9H), 1.15-1.22 (m, 3H), 0.93-0.98 (m, 2H).

Step 4: Deprotection of carbamate 32 following method described in Example 1 gave Example 11 hydrochloride as a white solid. Yield (0.14 g, 92%); $^1$H NMR (400 MHz, CD$_3$OD) δ 7.51-7.58 (m, 3H), 7.38-7.41 (m, 1H), 4.92 (dd, J=8.4, 3.6 Hz, 1H), 3.26 (d, J=6.8 Hz, 2H), 3.03-3.16 (m, 2H), 1.63-2.01 (m, 8H), 1.04-1.37 (m, 5H).

Example 12

Preparation of 3-amino-1-(3-(cyclohexylmethylamino)phenyl)propan-1-one

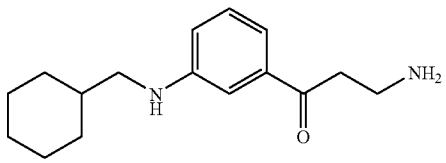 [SMILES: NCCC(=O)c1cccc(NCC2CCCCC2)c1]

3-Amino-1-(3-(cyclohexylmethylamino)phenyl)propan-1-one was prepared following the method shown in Scheme 9.

SCHEME 9

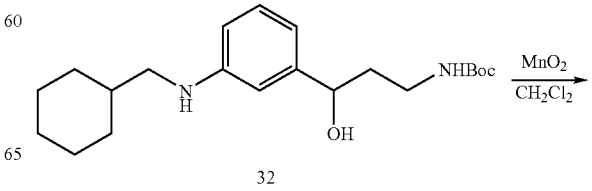

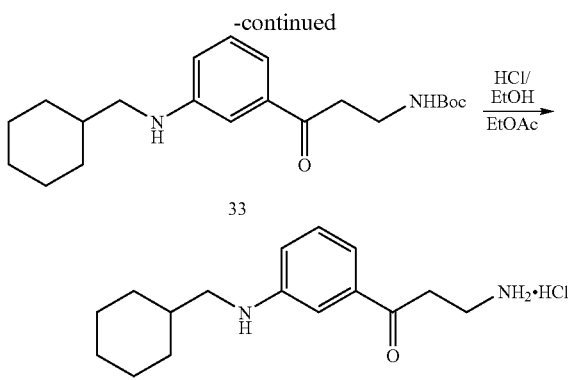

Step 1: A mixture of alcohol 32 (0.54 g. 1.32 mmol) and MnO₂ (0.35 g. 3.96 mmol) in DCM was stirred at room temperature for 18 hrs. The reaction mixture was filtered through Celite and concentrated under reduced pressure. Purification by flash chromatography (30% to 60% EtOAc—hexanes gradient) gave ketone 33 as a light yellow oil. Yield (0.27 g, 57%); $^1$H NMR (400 MHz, CDCl₃) δ 7.15 (t, J=8.0 Hz, 1H), 7.02-7.07 (m, 2H), 6.73-6.79 (m, 2H), 5.87 (t, J=5.6 Hz, 1H), 3.21 (q, J=6.0 Hz, 2H), 3.03 (t, J=6.8 Hz, 2H), 2.85 (t, J=6.0 Hz, 2H), 1.72-1.81 (m, 2H), 1.46-1.71 (m, 4H), 1.34 (s, 9H), 1.10-1.20 (m, 3H), 0.85-0.97 (m, 2H).

Step 2: Deprotection of carbamate 33 following method described in Example 1 gave Example 12 hydrochloride as a white solid. Yield (0.19 g, 94%); $^1$H NMR (400 MHz, CD₃OD) δ 8.01-8.06 (m, 2H), 7.64-7.72 (m, 2H), 3.50 (t, J=6.0 Hz, 2H), 3.35 (t, J=5.6 Hz, 2H), 3.26 (d, J=6.8 Hz, 2H), 1.67-1.90 (m, 6H), 1.20-1.36 (m, 3H), 1.05-1.16 (m, 2H).

Example 13

Preparation of 3-amino-1-(3-(pentylamino)phenyl)propan-1-ol

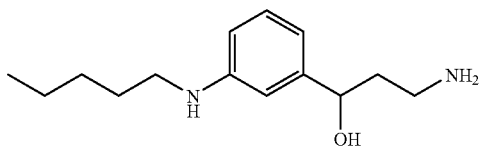 [SMILES: CCCCCNc1cccc(C(O)CCN)c1]

3-Amino-1-(3-(pentylamino)phenyl)propan-1-ol was prepared following the method used in Example 11.

Step 1: Hydrogenation of nitrobenzene 11 (0.8 g, 4.2 mmol) and pentanal (0.45 ml, 4.2 mmol) following method described in Example 11 gave 3-hydroxy-3-(3-(pentylamino)phenyl)propanenitrile as a light yellow oil. Yield (0.90 g, 77%).

Step 2: Reduction of 3-hydroxy-3-(3-(pentylamino)phenyl)propanenitrile (0.35 g, 1.51 mmol) following method described in Example 11 gave 3-amino-1-(3-(pentylamino)phenyl)propan-1-ol that was used in next reaction without further purification. Yield (0.41 g, quant.).

Step 3: Protection of 3-amino-1-(3-(pentylamino)phenyl)propan-1-ol (0.41 g, 1.51 mmol) following method described in Example 11 gave tert-butyl 3-hydroxy-3-(3-(pentylamino)phenyl)propylcarbamate as a colorless oil. Yield (0.4 g, 79%); $^1$H NMR (400 MHz, DMSO-d₆) δ 6.94 (t, J=7.6 Hz, 1H), 6.69 (t, J=4.8 Hz, 1H), 6.49 (s, 1H), 6.41 (d, J=7.6 Hz, 1H), 6.36 (dd, J=8.0, 1.2 Hz, 1H), 5.41 (t, J=6.4 Hz, 1H), 4.97 (d, J=4.4 Hz, 1H), 4.37 (q, J=4.4 Hz, 1H), 2.90-2.98 (m, 2H), 1.61 (q, J=6.8 Hz, 2H), 1.46-1.56 (m, 2H), 1.26-1.36 (m, 15H), 0.93-0.98 (m, 3H).

Step 4: Deprotection of tert-butyl 3-hydroxy-3-(3-(pentylamino)phenyl)propylcarbamate (0.15 g, 0.45 mmol) following method described in Example 1 gave Example 13 hydrochloride as a white solid. Yield (0.10 g, 95%): $^1$H NMR (400 MHz, CD₃OD) δ 7.52-7.61 (m, 3H), 7.38-7.42 (m, 1H), 4.92 (dd, J=9.2, 3.6 Hz, 1H), 3.36-3.40 (m, 2H), 3.08-3.18 (m, 2H), 1.92-2.12 (m, 2H), 1.70-1.80 (m, 2H), 1.34-1.46 (m, 4H), 0.90-0.98 (m, 3H).

Example 14

Preparation of 3-amino-1-(3-(pentylamino)phenyl)propan-1-one

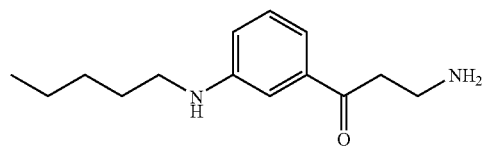 [SMILES: CCCCCNc1cccc(C(=O)CCN)c1]

3-Amino-1-(3-(pentylamino)phenyl)propan-1-one was prepared following the method used in Examples 13 and 12

Step 1: Oxidation of tert-butyl 3-hydroxy-3-(3-(pentylamino)phenyl)propylcarbamate following the method used in Example 12 gave tert-butyl 3-oxo-3-(3-(pentylamino)phenyl)propylcarbamate as a light yellow oil which was directly used in next reaction without further purification. Yield (0.05 g, 50%).

Step 2: Deprotection tert-butyl 3-oxo-3-(3-(pentylamino)phenyl)propylcarbamate (0.05 g, 0.15 mmol) following the method used in Example 12 gave Example 14 as a white solid. Yield (0.03 g, 85%); $^1$H NMR (400 MHz, CD₃OD) δ 8.14-8.19 (m, 2H), 7.73-7.82 (m, 2H), 3.53 (t, J=6.0 Hz, 2H), 3.43 (t, J=7.6 Hz, 2H), 3.36 (t, J=5.2 Hz, 2H), 1.73-1.83 (m, 2H), 1.35-1.46 (m, 4H), 0.93 (t, J=7.2 Hz, 3H).

Example 15

Preparation of N-(3-(3-amino-1-Hydroxypropyl)phenyl)cyclohexanecarboxamide

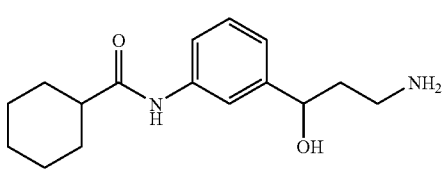 [SMILES: NCCC(O)c1cccc(NC(=O)C2CCCCC2)c1]

N-(3-(3-Amino-1-hydroxypropyl)phenyl)cyclohexanecarboxamide was prepared following the method shown in Scheme 10.

SCHEME 10

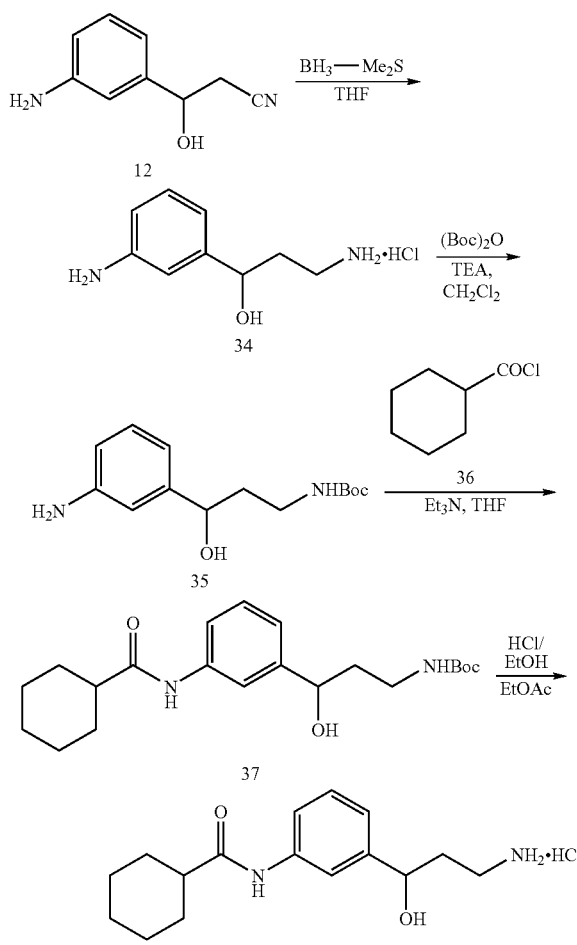

Step 1: Reduction of nitrile 12 following the method described in Example 11 gave crude amine 34 hydrochloride which was used directly in next step without further purification.

Step 2: To a suspension of crude amine salt 34 (0.94 g, 4.64 mmol) in dichloromethane (15 mL) and TEA (0.7 ml, 5.0 mmol) was added dropwise a solution of Boc$_2$O (1.0 g, 4.64 mmol) in DCM at room temperature. The reaction mixture was stirred at room temperature for 2 hr, washed with aqueous NH$_4$Cl, dried over anhydrous Na$_2$SO$_4$ and concentrated under reduced pressure. Purification by flash chromatography (65% to 75% EtOAc—hexanes gradient) gave carbamate 35 as a colorless oil. Yield (0.8 g, 64%); $^1$H NMR (400 MHz, DMSO-d$_6$) δ 6.90 (t, J=7.6 Hz, 1H), 6.69 (t, J=5.6 Hz, 1H), 6.51 (t, J=1.2 Hz, 1H), 6.36-6.41 (m, 2H), 4.97 (d, J=4.0 Hz, 1H), 4.92 (br.s, 2H), 4.34 (q, J=4.0 Hz, 1H), 2.88-2.94 (m, 2H), 1.60 (q, J=6.8 Hz, 2H), 1.34 (s, 9H).

Step 3: To a solution of carbamate 35 (0.43 g. 1.61 mmol), TEA (0.24 ml, 1.76 mmol) in THF was added dropwise a solution of cyclohexanecarbonyl chloride (36) (0.2 ml, 1.61 mmol) in THF at 0° C. The resulting mixture was allowed to warm to room temperature, stirred for 1 hr and then a mixture of 25% NH$_4$Cl-0.5N HCl (20 ml) was added. Organic layer was separated, dried over anhydrous Na$_2$SO$_4$ and concentrated under reduced pressure. Purification by flash chromatography (65 to 70% EtOAc-hexanes gradient) gave tert-butyl 3-(3-(cyclohexanecarboxamido)phenyl)-3-hydroxypropyl-carbamate (37) as a colorless oil. Yield (0.5 g, 82%); $^1$H NMR (400 MHz, DMSO-d$_6$) δ 9.72 (s, 1H), 7.54 (s, 1H), 7.44 (dd, J=8.0, 1.2 Hz, 1H), 7.17 (t, J=8.0 Hz, 1H), 6.92 (d, J=7.6 Hz, 1H), 6.72 (t, J=4.8 Hz, 1H), 5.15 (d, J=4.4 Hz, 1H), 4.47 (q, J=4.4 Hz, 1H), 2.94 (q, J=6.4 Hz, 2H), 2.24-2.33 (m, 1H), 1.50-1.79 (m, 7H), 1.14-1.93 (m, 14H).

Step 4: Deprotection of carbamate 37 following method described in Example 1 gave Example 17 hydrochloride as a white solid. Yield (0.75 g, 91%); $^1$H NMR (400 MHz, DMSO-d$_6$) δ 9.82 (s, 1H), 7.82 (m, 3H), 7.66 (s, 1H), 7.40 (d, J=7.2 Hz, 1H), 7.20 (t, J=8.0 Hz, 1H), 6.94 (d, J=7.6 Hz, 1H), 4.60 (dd, J=8.0, 4.8 Hz, 1H), 2.78-2.89 (m, 2H), 2.26-2.36 (m, 1H), 1.58-1.86 (m, 7H), 1.13-1.45 (m, 5H).

Example 16

Preparation of N-(3-(3-aminopropanoyl)phenyl)cyclohexanecarboxamide

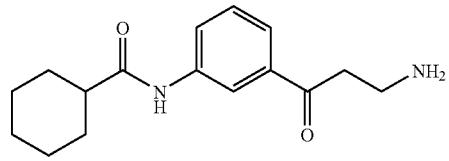 [SMILES: NCCC(=O)c1cccc(NC(=O)C2CCCCC2)c1]

N-(3-(3-Aminopropanoyl)phenyl)cyclohexanecarboxamide was prepared following the method used in Example 15.

Step 1: Oxidation of tert-butyl 3-(3-(cyclohexanecarboxamido)phenyl)-3-hydroxypropylcarbamate (37) following the method used in Example 12 except PCC was used in lieu of MnO$_2$ gave tert-butyl 3-(3-(cyclohexanecarboxamido)phenyl)-3-oxopropylcarbamate as a white solid. Yield (0.36 g, 91%); $^1$H NMR (400 MHz, DMSO-d$_6$) δ 9.97 (s, 1H), 8.15-8.18 (m, 1H), 7.82 (dd, J=1.2, 8.0 Hz, 1H), 7.57 (d, J=8.0 Hz, 1H), 7.40 (t, J=8.0 Hz, 1H), 6.79 (br.t, 1H), 3.24 (q, J=6.0 Hz, 2H), 3.08 (t, J=6.4 Hz, 2H), 2.25-2.35 (m, 1H), 1.69-1.82 (m, 4H), 1.58-1.66 (m, 1H), 1.33 (s, 9H), 1.10-1.44 (m, 5H).

Step 2: tert-Butyl 3-(3-(cyclohexanecarboxamido)phenyl)-3-oxopropylcarbamate was deprotected following the method used in Example 15 to give Example 16 hydrochloride as a white solid. Yield (0.060 g, 81%); $^1$H NMR (400 MHz, CD$_3$OD) δ 8.05-8.07 (m, 2H), 7.65-7.72 (m, 2H), 3.48 (t, J=6.0 Hz, 2H), 3.34-3.37 (m, 2H), 3.27 (t, J=6.8 Hz, 2H), 1.68-1.91 (m, 6H), 1.22-1.38 (m, 3H), 1.04-1.16 (m, 2H).

Example 17

Preparation of N-(3-(3-amino-1-Hydroxypropyl)phenyl)pentanamide

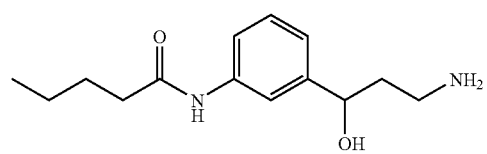 [SMILES: CCCCC(=O)Nc1cccc(C(O)CCN)c1]

N-(3-(3-Amino-1-hydroxypropyl)phenyl)pentanamide was prepared following the method described below.

Step 1: To a solution of carbamate 35 (0.43 g. 1.61 mmol), TEA (0.24 ml, 1.76 mmol) in THF (20 ml) was added pentanoyl chloride (0.19 ml, 1.55 mmol) in THF (10 ml) at 0° C.

dropwise. The resulting mixture was allowed to room temperature and stirred for 1 hr and then added NH₄Cl—HCl.aq (0.5 N, 20 ml). Layers were separated, dried over anhydrous Na₂SO₄ and concentrated under reduced pressure. Purification by flash chromatography (65 to 70% EtOAc—hexanes gradient) gave tert-butyl 3-hydroxy-3-(3-pentanamidophenyl)propylcarbamate as a colorless oil. Yield (0.5 g, 92%); ¹H NMR (400 MHz, DMSO-d₆) δ 9.79 (s, 1H), 7.51 (s, 1H), 7.45 (d, J=8.0 Hz, 1H), 7.18 (t, J=8.0 Hz, 1H), 6.92 (d, J=8.0 Hz, 1H), 6.73 (t, J=5.6 Hz, 1H), 5.16 (d, J=4.4 Hz, 1H), 4.67 (q, J=4.8 Hz, 1H), 2.94 (q, J=6.4 Hz, 2H), 2.26 (t, J=7.2 Hz, 2H), 1.63 (q, J=7.2 Hz, 2H), 1.50-1.58 (m, 2H), 1.26-1.34 (m, 11H), 0.89 (t, J=8.4 Hz, 3H).

Step 2: Deprotection of tert-butyl 3-hydroxy-3-(3-pentanamidophenyl)propylcarbamate following the method used in Example 15 gave Example 17 as a white solid. Yield (0.77 g, 95%); ¹H NMR (400 MHz, DMSO-d₆) δ 9.94 (s, 1H), 7.94 (br s, 3H), 7.62 (s, 1H), 7.44 (d, J=7.6 Hz, 1H), 7.20 (t, J=7.6 Hz, 1H), 6.95 (d, J=7.2 Hz, 1H), 4.60 (t, J=5.6 Hz, 1H), 2.28 (t, J=7.6 Hz, 2H), 2.74-2.88 (m, 2H), 1.75-1.90 (m, 2H), 1.50-1.58 (m, 2H), 1.26-1.38 (m, 2H), 0.86 (t, J=7.2 Hz, 3H).

Example 18

Preparation of N-(3-(3-aminopropanoyl)phenyl)pentanamide

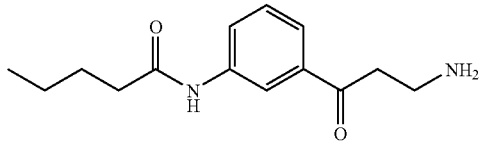 [SMILES: CCCCC(=O)Nc1cccc(C(=O)CCN)c1]

N-(3-(3-Aminopropanoyl)phenyl)pentanamide was prepared following the method used in Examples 17, 16.

Step 1: Oxidation of tert-butyl 3-hydroxy-3-(3-pentanamidophenyl)propylcarbamate following the method used in Example 16 gave tert-butyl 3-oxo-3-(3-pentanamidophenyl)propylcarbamate as a light yellow oil. Yield (0.34 g, 84%); ¹H NMR (400 MHz, DMSO-d₆) δ 10.04 (s, 1H), 8.13 (s, 1H), 7.12 (d, J=8.8 Hz, 1H), 7.58 (d, J=7.6 Hz, 1H), 7.41 (t, J=8.0 Hz, 1H), 6.79 (d, J=5.6 Hz, 1H), 3.23 (q, J=6.0 Hz, 2H), 3.09 (t, J=6.8 Hz, 2H), 2.29 (t, J=7.6 Hz, 2H), 1.52-1.60 (m, 2H), 1.26-1.36 (m, 11H), 0.87 (t, J=7.2 Hz, 3H).

Step 2: Deprotection tert-butyl 3-oxo-3-(3-pentanamidophenyl)propylcarbamate following the method used in Example 16 gave Example 18 as a white solid. Yield (0.09 g, 90%); ¹H NMR (400 MHz, DMSO-d₆) δ 10.18 (s, 1H), 8.29 (t, J=2.0 Hz, 1H), 7.78-7.82 (m, 4H), 7.60-7.63 (m, 1H), 7.46 (t, J=8.0 Hz, 1H), 3.53 (t, J=7.2 Hz, 2H), 3.12 (q, J=5.6 Hz, 2H), 3.21 (t, J=7.6 Hz, 2H), 1.52-1.60 (m, 2H), 1.26-1.36 (m, 2H), 0.88 (t, J=7.6 Hz, 3H).

Example 19

Preparation of 3-(3-amino-1-fluoropropyl)-N-(cyclohexylmethyl)aniline

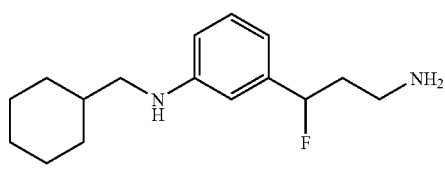 [SMILES: NCCC(F)c1cccc(NCC2CCCCC2)c1]

3-(3-Amino-1-fluoropropyl)-N-(cyclohexylmethyl)aniline is prepared following the method described below.

Step 1: A mixture of alcohol 32 and DAST are stirred at −78° C. until no starting material is seen by TLC. The reaction mixture is then quenched by addition of aqueous NH₄Cl. Layers are separated and aqueous layer is additionally extracted with EtOAc. Combined organic layers are washed with brine, dried over anhydrous MgSO₄ and concentrated under reduced pressure. Purification by flash chromatography gives 3-(3-(cyclohexylmethylamino)phenyl)-3-fluoropropanenitrile.

Step 2: 3-(3-(Cyclohexylmethylamino)phenyl)-3-fluoropropanenitrile is reduced with BH₃-Me₂S following the method used in Example 11 to give Example 19.

Example 20

Preparation of N-(3-(3-aminopropanoyl)phenyl)cyclohexanesulfonamide

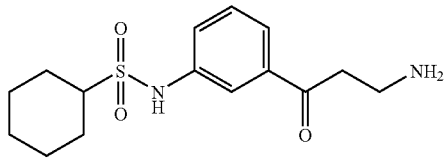 [SMILES: NCCC(=O)c1cccc(NS(=O)(=O)C2CCCCC2)c1]

N-(3-(3-Aminopropanoyl)phenyl)cyclohexanesulfonamide was prepared following the method shown in Scheme 11.

SCHEME 11

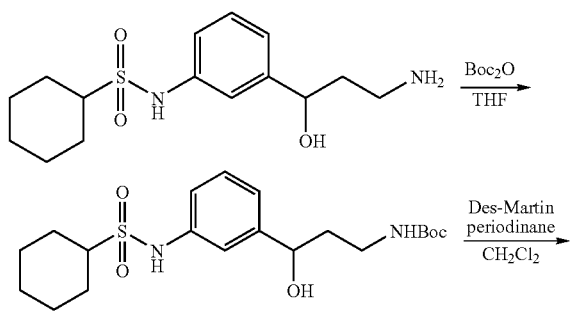

38

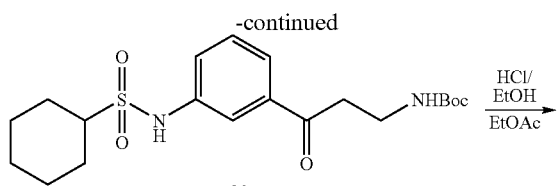

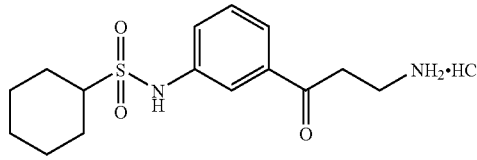

Step 1: To a solution of Example 5 (0.26 g, 0.83 mmol) in DCM (10 mL) was added Boc$_2$O (0.22 g, 1.0 mmol). The reaction mixture was stirred at room temperature for 18 hrs and concentrated under reduced pressure. Carbamate 38 was used in the next step without purification.

Step 2: To a solution of alcohol 38 (approx. 0.83 mmol) in dichloromethane (15 mL) was added Des Martin periodinane (0.4 g, 0.92 mmol). The mixture was stirred for 1 h at room temp, washed with brine and dried over anhydrous Na$_2$SO$_4$ and concentrated under reduced pressure. Purification by flash chromatography (40 to 55% EtOAc-hexanes gradient) gave ketone 39 as a light yellow oil. Yield (0.06 g, 18%); $^1$H NMR (400 MHz, CD$_3$OD) δ 7.82 (m, 1H), 7.70 (d, J=7.6 Hz, 1H), 7.41-7.50 (m, 2H), 3.42 (t, J=6.8 Hz, 2H), 3.17 (t, J=6.4 Hz, 2H), 2.08-2.16 (m, 2H), 1.80-1.88 (m, 2H), 1.61-1.69 (m, 1H), 1.46-1.58 (m, 2H), 1.41 (s, 9H), 1.15-1.30 (m, 2H).

Step 3: To a solution of ketone 39 (0.06 g. 0.14 mmol) in EtOAc was added HCl (5 ml of a 6.9 M solution in EtOH, 34.5 mmol). The reaction mixture was stirred at room temperature for 3 hrs and concentrated under reduced pressure to give a Example 20 as a white solid. Yield (0.049 g, 99%); $^1$H NMR (400 MHz, CD$_3$OD) δ 7.91 (t, J=2.0 Hz, 1H), 7.73-7.75 (m, 1H), 7.46-7.52 (m, 2H), 3.48 (t, J=6.0 Hz, 2H), 3.35 (t, J=6.0 Hz, 2H), 2.94-3.04 (m, 1H), 2.08-2.11 (m, 2H), 1.79-1.83 (m, 2H), 1.61-1.67 (m, 1H), 1.44-1.58 (m, 2H), 1.10-1.28 (m, 3H).

Example 21

Preparation of N-(3-(3-amino-1-hydroxypropyl)phenyl)butane-1-sulfonamide

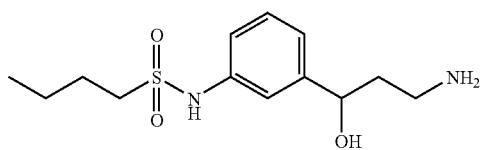 [SMILES: CCCCS(=O)(=O)Nc1cccc(C(O)CCN)c1]

N-(3-(3-Amino-1-hydroxypropyl)phenyl)butane-1-sulfonamide was prepared following the method used in Example 5.

Step 1: Coupling of aniline 12 with butane-1-sulfonyl chloride (0.47 ml, 3.5 mmol) gave N-(3-(2-cyano-1-hydroxyethyl)phenyl)butane-1-sulfonamide as a light yellow oil. Yield (0.80 g, 89%); $^1$H NMR (400 MHz, DMSO-d$_6$) δ 9.76 (s, 1H), 7.24-7.29 (m, 2H), 7.06-7.09 (m, 2H), 5.95 (d, J=4.4 Hz, 1H), 4.83 (q, J=4.4 Hz, 1H), 3.05 (t, J=8.0 Hz, 2H), 2.79 (ddd, J=24.8, 16.8, 6.4 Hz, 2H), 1.56-1.64 (m, 2H), 1.26-1.35 (m, 2H), 0.79 (t, J=8.4 Hz, 3H).

Step 2: Reduction of N-(3-(2-cyano-1-hydroxyethyl)phenyl)butane-1-sulfonamide with BH$_3$-Me$_2$S gave Example 21 as a light yellow oil. Yield (0.76 g, 93%); $^1$H NMR (400 MHz, DMSO-d$_6$) δ 7.15-7.22 (m, 2H), 6.96-7.02 (m, 2H), 4.59 (t, J=6.8 Hz, 1H), 3.00 (t, J=8.4 Hz, 2H), 2.56-21.68 (m, 2H), 1.56-1.64 (m, 4H), 1.26-1.36 (m, 2H), 0.79 (t, J=7.6 Hz, 3H).

Example 22

Preparation of N-(3-(3-aminopropanoyl)phenyl)butane-1-sulfonamide

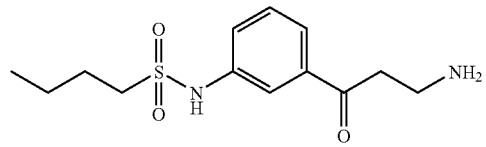 [SMILES: CCCCS(=O)(=O)Nc1cccc(C(=O)CCN)c1]

N-(3-(3-Aminopropanoyl)phenyl)butane-1-sulfonamide was prepared following the method used in Example 20.

Step 1: Protection of Example 21 with Boc$_2$O following the method used in Example 20 gave tert-butyl 3-(3-(butylsulfonamido)phenyl)-3-hydroxypropylcarbamate as a colorless oil. Yield (0.18 g, 15%); $^1$H NMR (400 MHz, DMSO-d$_6$) δ 7.30-7.38 (m, 2H), 7.18 (s, 1H), 7.06-7.10 (m, 1H), 6.76 (t, J=5.6 Hz, 1H), 5.31 (d, J=4.8 Hz, 1H), 4.57 (q, J=5.2 Hz, 1H), 3.69 (t, J=8.0 Hz, 2H), 2.90-2.98 (m, 2H), 1.60-1.78 (m, 4H), 1.34-1.45 (m, 20H), 0.90 (t, J=7.2 Hz, 3H).

Step 2: Oxidation of tert-butyl 3-(3-(butylsulfonamido)phenyl)-3-hydroxypropylcarbamate by PCC following the method used in Example 18 gave tert-butyl 3-(3-(butylsulfonamido)phenyl)-3-oxopropylcarbamate as white solid: Yield (0.18 g, 41%); $^1$H NMR (400 MHz, CD$_3$OD) δ 8.01-8.04 (m, 1H), 7.82-7.84 (m, 1H), 7.55 (t, J=8.0 Hz, 1H), 7.49-7.52 (m, 1H), 5.86-5.64 (m, 1H), 3.71-3.75 (m, 2H), 3.43 (q, J=6.0 Hz, 2H), 3.21 (t, J=6.8 Hz, 2H), 1.82-1.90 (m, 2H), 1.48-1.58 (m, 2H), 1.41-1.44 (m, 18H), 0.99 (t, J=7.2 Hz, 3H).

Step 3: Deprotection of tert-butyl 3-(3-(butylsulfonamido)phenyl)-3-oxopropylcarbamate following the method used in Example 20 gave Example 22 as a white solid. Yield (0.05 g, 97%); $^1$H NMR (400 MHz, CD$_3$OD) δ 7.92 (t, J=2.0 Hz, 1H), 7.76-7.78 (m, 1H), 7.44-7.52 (m, 2H), 3.43 (t, J=6.0 Hz, 2H), 3.30-3.38 (m, 2H), 3.07-3.11 (m, 2H), 1.70-1.79 (m, 2H), 1.36-1.46 (m, 2H), 0.88 (t, J=7.2 Hz, 3H).

Example 23

Preparation of (E)-3-(3-aminoprop-1-enyl)-N-(cyclohexylmethyl)aniline

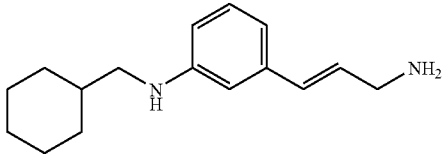 [SMILES: NC/C=C/c1cccc(NCC2CCCCC2)c1]

(E)-3-(3-Aminoprop-1-enyl)-N-(cyclohexylmethyl) aniline was prepared following the method described below.

Step 1: Cyclohexanecarbonyl chloride (0.74 g, 6.97 mmol) was added to a mixture of 3-bromoaniline (1.0 g, 5.8 mmol), TEA (1.07 mL, 7.55 mmol) and DMAP (cat.) in THF with stirring at 0° C. over 10 min. Stirring was continued for another 30 min and quenched with saturated NaHCO$_3$. The product was extracted with ethyl acetate. Combined organic layers were concentrated under reduced pressure to give a residue which was triturated with pentane to give N-(3-bromophenyl)cyclohexanecarboxamide as an off-white solid. Yield (1.3 g, 79%); $^1$H NMR (400 MHz, DMSO-d$_6$) δ 9.96 (s, 1H), 7.97 (s, 1H), 7.49 (d, J=8.0 Hz, 1H), 7.26-7.18 (m, 2H), 2.33-2.26 (m, 1H), 1.76 (t, J=14.0 Hz, 4H), 1.65 (d, J=10.4 Hz, 1H), 1.43-1.34 (m, 2H), 1.30-1.12 (m, 3H).

Step 2: Reduction of N-(3-bromophenyl)cyclohexanecarboxamide with BH$_3$-Me$_2$S following the method used in Example 11 gave 3-bromo-N-(cyclohexylmethyl)aniline as a colorless oil. Yield (1.0 g, 80%); $^1$H NMR (400 MHz, DMSO-d$_6$) δ 6.96 (t, J=8.0 Hz, 1H), 6.68 (s, 1H), 6.60 (d, J=7.6 Hz, 1H), 6.53 (d, J=8.4 Hz, 1H), 5.93 (t, J=5.6 Hz, 1H), 2.81 (t, J=6.2 Hz, 2H), 1.78 (d, J=12.8 Hz, 2H), 1.69-1.61 (m, 3H), 1.53-1.46 (m, 1H), 1.24-1.08 (m, 3H), 0.99-0.77 (m, 2H).

Step 3: Trifluoroacetic anhydride (0.75 ml, 4.49 mmol) was added to a mixture of 3-bromo-N-(cyclohexylmethyl)aniline (1.0 g, 3.74 mmol), TEA (0.8 ml) in CH$_2$Cl$_2$ at 0° C. in 10 min time. The reaction mixture was stirred for 30 min at room temperature and partitioned between saturated NaHCO$_3$ and extracted with EtOAc three times. Combined organic layers were concentrated under reduced pressure to give N-(3-bromophenyl)-N-(cyclohexylmethyl)-2,2,2-trifluoroacetamide as a colorless liquid. Yield (1.0 g, 74%); $^1$H NMR (400 MHz, CDCl$_3$) δ 7.56 (d, J=8.0 Hz, 1H), 7.39 (s, 1H), 7.31 (t, J=8.0 Hz, 1H), 7.18 (d, J=8.0 Hz, 1H), 3.61 (d, J=6.0 Hz, 2H), 1.72-1.64 (m, 5H), 1.51 (bs, 1H), 1.18-1.16 (m, 3H), 1.06-1.01 (m, 2H).

Step 4: N-(3-Bromophenyl)-N-(cyclohexylmethyl)-2,2,2-trifluoroacetamide (1.0 g, 2.74 mmol), N-allyl-2,2,2-trifluoroacetamide (0.5 g, 3.29 mmol), tri-O-tolylphosphine (0.08 g, 0.27 mmol) and triethylamine (2 mL, 13.7 mmol) was added to DMF and the mixture was flushed with argon for 15 min. Pd(OAc)$_2$ (0.06 g, 0.27 mmol) was charged to the reaction mixture which was stirred at 90° C. for 2 h. The reaction mixture was cooled and partitioned between ethyl acetate and water. Organic layer was washed thoroughly with water, dried over anhydrous sodium sulfate and concentrated under reduced pressure. Purification by column chromatography (100-200 silica mesh, 5% to 10% EtOAc in hexane) gave (E)-N-(cyclohexylmethyl)-2,2,2-trifluoro-N-(3-(3-(2,2,2-trifluoroacetamido)prop-1-enyl)phenyl)acetamide 5 as a colorless semi solid. Yield (0.4 g, 33%); $^1$H NMR (400 MHz, CDCl$_3$) δ 7.43-7.41 (m, 2H), 7.18 (s, 1H), 7.13 (d, J=6.8 Hz, 1H), 6.61 (d, J=16.0 Hz, 1H), 6.48 (bs, 1H), 6.24-6.16 (m, 1H), 4.17 (t, J=6.0 Hz, 2H), 3.62 (bs, 2H), 1.73-1.65 (m, 5H), 1.56-1.48 (m, 1H), 1.21-1.14 (m, 3H), 1.07-0.99 (m, 2H).

Step 5: A mixture of (E)-N-(cyclohexylmethyl)-2,2,2-trifluoro-N-(3-(3-(2,2,2-trifluoroacetamido)prop-1-enyl)phenyl)acetamide (0.2 g, 0.45 mmol) and K$_2$CO$_3$ (0.19 g, 1.37 mmol) in MeOH:H$_2$O was stirred at room temperature for 24 h and then at 50° C. for 16 h. The solvent was removed under reduced pressure. Purification by column chromatography (5% to 10% MeOH—CH$_2$Cl$_2$ gradient) gave 3-(3-aminoprop-1-enyl)-N-(cyclohexylmethyl)aniline as pale brown semi-solid. Yield (0.06 g, 54%); $^1$H NMR (400 MHz, DMSO-d$_6$) δ 6.99 (t, J=8.0 Hz, 1H), 6.54-6.53 (m, 2H), 6.44 (d, J=7.2 Hz, 1H), 6.42 (d, J=16.0 Hz, 1H), 6.22-6.15 (m, 1H), 5.58 (t, J=5.8 Hz, 1H), 3.34 (d, J=5.2 Hz, 2H), 2.83 (t, J=5.8 Hz, 2H), 1.80-1.77 (m, 2H), 1.70-1.56 (m, 3H), 1.54-1.49 (m, 1H), 1.18-1.12 (m, 3H), 0.97-0.91 (m, 2H); RP-HPLC (Method 4) t$_R$=5.30 min, 96.10% (AUC); ESI MS m/z 245.26 [M+H]$^+$.

Example 24

Preparation of 3-(3-aminoprop-1-ynyl)-N-(cyclohexylmethyl)aniline

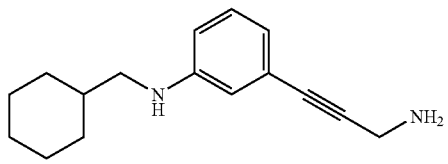 [SMILES: NCC#Cc1cccc(NCC2CCCCC2)c1]

3-(3-Aminoprop-1-ynyl)-N-(cyclohexylmethyl)aniline was prepared following the method used in Example 23 and as described below.

Step 1: Triethylamine (45 mL) was added to a mixture of N-(3-bromophenyl)-N-(cyclohexylmethyl)-2,2,2-trifluoroacetamide (3.8 g, 10.4 mmol), tert-butyl prop-2-ynylcarbamate (2.42 g, 15.6 mmol), Pd(Ph$_3$P)$_4$ (0.6 g, 0.52 mmol) and CuI (0.1 g, 0.52 mmol) and flushed for 15 min with argon. The reaction mixture was stirred for 16 h at 90° C. The reaction mixture was cooled, diluted with ethyl acetate and filtered through Celite bed and the filtrate was concentrated under reduced pressure. Purification by column chromatography (100-200 silica mesh 5% to 10% EtOAc—hexane) gave tert-butyl 3-(3-(N-(cyclohexylmethyl)-2,2,2-trifluoroacetamido)phenyl)prop-2-ynylcarbamate as a yellow semi-solid. Yield (2.1 g, 50%); $^1$H NMR (400 MHz, DMSO-d$_6$) δ 7.49-7.48 (m, 2H), 7.43-7.41 (m, 2H), 3.99 (bs, 2H), 3.58 (bs, 2H), 1.64-1.57 (m, 6H), 1.39 (s, 9H), 1.19-1.12 (m, 3H), 0.95-0.89 (m, 2H).

Step 2: A mixture of 50% CF$_3$COOH in DCM (20 mL) and tert-butyl 3-(3-(N-(cyclohexylmethyl)-2,2,2-trifluoroacetamido)phenyl)prop-2-ynylcarbamate (1.6 g, 4.67 mmol) was initially stirred at 0° C. and stirring continued at room temperature for 3 h. The reaction mixture was evaporated to dryness and triturated with pentane to give Example 24 trifluoroacetate as a brown oil. Yield (0.46 g, 54%); $^1$H NMR (400 MHz, DMSO-d$_6$) δ 8.29 (br.s, 3H), 7.08 (t, J=8.0 Hz, 1H), 6.65 (d, J=8.8 Hz, 1H), 6.60-6.59 (m, 2H), 3.98-3.96 (m, 2H), 2.83 (d, J=6.4 Hz, 2H), 1.78-1.75 (m, 2H), 1.70-1.63 (m, 3H), 1.52-1.48 (m, 1H), 1.24-1.15 (m, 3H), 0.99-0.88 (m, 2H). RP-HPLC (Method 6) t$_R$=6.17 min, 99.70% (AUC); ESI MS m/z 243.23 [M+H]$^+$.

Example 25

Preparation of (E)-N-(3-(3-aminoprop-1-enyl)phenyl)cyclohexanecarboxamide

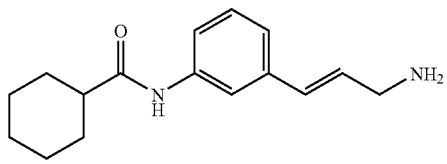 [SMILES: NC/C=C/c1cccc(NC(=O)C2CCCCC2)c1]

(E)-N-(3-(3-Aminoprop-1-enyl)phenyl)cyclohexanecarboxamide is prepared following the method used in Examples 33 and 15.

Step 1: Acylation of (E)-N-(3-(3-aminophenyl)allyl)-2,2,2-trifluoroacetamide following the method used in Example 15 gives (E)-N-(3-(3-(2,2,2-trifluoroacetamido)prop-1-enyl)phenyl)cyclohexanecarboxamide.

Step 2: Deprotection of (E)-N-(3-(3-(2,2,2-trifluoroacetamido)prop-1-enyl)phenyl)cyclohexanecarboxamide following the method used in Example 33 gives Example 25.

Example 26

Preparation of N-(3-(3-aminoprop-1-ynyl)phenyl)cyclohexanecarboxamide

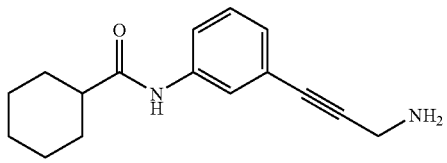 [SMILES: NCC#Cc1cccc(NC(=O)C2CCCCC2)c1]

N-(3-(3-Aminoprop-1-ynyl)phenyl)cyclohexanecarboxamide is prepared following the method used in Examples 24 and 25.

Step 1: Acylation of tert-butyl 3-(3-aminophenyl)prop-2-ynylcarbamate following the method used in Example 25 gives tert-butyl 3-(3-(cyclohexanecarboxamido)phenyl)prop-2-ynylcarbamate.

Step 2: Deprotection of tert-butyl 3-(3-(cyclohexanecarboxamido)phenyl)prop-2-ynylcarbamate following the method used in Example 24 gives Example 26 hydrochloride.

Example 27

Preparation of (E)-N-(3-(3-aminoprop-1-enyl)phenyl)cyclohexanesulfonamide

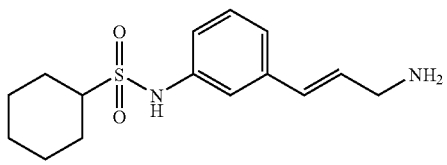 [SMILES: NC/C=C/c1cccc(NS(=O)(=O)C2CCCCC2)c1]

(E)-N-(3-(3-Aminoprop-1-enyl)phenyl)cyclohexanesulfonamide is prepared following the method used in Example 33 and 5.

Step 1: Sulfonation of (E)-N-(3-(3-aminophenyl)allyl)-2,2,2-trifluoroacetamide following the method used in Example 5 gives (E)-N-(3-(3-(cyclohexanesulfonamido)phenyl)allyl)-2,2,2-trifluoroacetamide.

Step 2: Deprotection of (E)-N-(3-(3-(cyclohexanesulfonamido)phenyl)allyl)-2,2,2-trifluoroacetamide following the method used in Example 33 gives Example 27.

Example 28

Preparation of N-(3-(3-aminoprop-1-ynyl)phenyl)cyclohexanesulfonamide

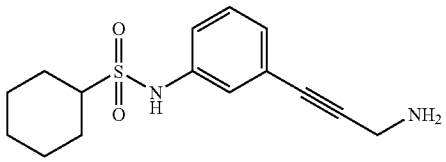 [SMILES: NCC#Cc1cccc(NS(=O)(=O)C2CCCCC2)c1]

N-(3-(3-Aminoprop-1-ynyl)phenyl)cyclohexanesulfonamide is prepared following the method used in Examples 24 and 5.

Step 1: Sulfonation of tert-butyl 3-(3-aminophenyl)prop-2-ynylcarbamate following the method used in Example 5 gives tert-butyl 3-(3-(cyclohexanesulfonamido)phenyl)prop-2-ynylcarbamate.

Step 2: Deprotection of tert-butyl 3-(3-(cyclohexanesulfonamido)phenyl)prop-2-ynylcarbamate following the method used in Example 24 gives Example 28 hydrochloride.

Example 29

Preparation of (E)-1-((3-(3-aminoprop-1-enyl)phenylamino)methyl)cyclohexanol

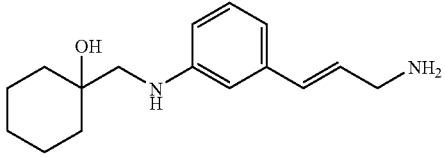 [SMILES: NC/C=C/c1cccc(NCC2(O)CCCCC2)c1]

(E)-1-((3-(3-Aminoprop-1-enyl)phenylamino)methyl)cyclohexanol was prepared following the method described below and in Example 33.

Step 1: A mixture of (E)-N-(3-(3-aminophenyl)allyl)-2,2,2-trifluoroacetamide (0.8 g, 3.28 mmol) and 1-oxaspiro[2.5]octane (0.55 g, 4.91 mmol) in EtOH:H$_2$O (9:1) was stirred under reflux for 36 hrs and concentrated under reduced pressure. Purification by column chromatography (20% to 30% EtOAc—hexanes gradient) gave (E)-2,2,2-trifluoro-N-(3-(3-((1-hydroxycyclohexyl)methylamino)phenyl)allyl)acetamide as an off-white solid. Yield (0.5 g, 43%); $^1$H NMR (400 MHz, DMSO-d$_6$) δ 9.71 (s, 1H), 7.00 (t, J=8.0 Hz, 1H), 6.67 (s, 1H), 6.55 (t, J=8.8 Hz, 2H), 6.41 (d, J=16.0 Hz, 1H), 6.61-6.09 (m, 1H), 5.22 (t, J=5.2 Hz, 1H), 4.20 (s, 1H), 3.95 (t, J=5.2 Hz, 2H), 2.94 (d, J=5.6 Hz, 2H), 1.61-1.49 (m, 5H), 1.41-1.36 (m, 4H), 1.25-1.19 (m, 1H).

Step 2: A mixture of (E)-2,2,2-trifluoro-N-(3-(3-((1-hydroxycyclohexyl)methylamino)phenyl)allyl)acetamide (0.5 g, 1.14 mmol) and potassium carbonate (0.29 g, 2.1 mmol) in methanol:water (1:1) was stirred at room temperature for 24 hrs. The solvent was evaporated under reduced pressure. Purification by column chromatography (5% to 10% MeOH—DCM gradient) gave Example 29 as an off-white solid. Yield (0.11 g, 36%); $^1$H NMR (400 MHz, DMSO-d$_6$) δ 7.72 (bs, 2H), 7.03 (t, J=7.8 Hz, 1H), 6.66 (s, 1H), 6.60-6.56 (m, 3H), 6.18-6.11 (m, 1H), 5.34 (t, J=5.8 Hz, 1H), 4.23 (s, 1H), 3.57 (d, J=6.4 Hz, 2H), 2.94 (d, J=6.0 Hz, 2H), 1.62-1.50 (m, 5H), 1.41-1.38 (m, 4H), 1.23-1.18 (m, 1H); RP-HPLC (Method 3) $t_R$=3.55 min, 99.20% (AUC); ESI MS m/z 261.29 [M+H]$^+$.

Example 30

Preparation of 1-((3-(3-aminoprop-1-ynyl)phenylamino)methyl)cyclohexanol

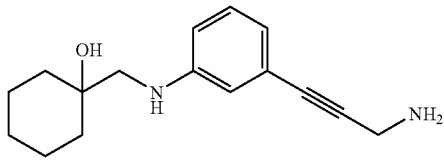 [SMILES: NCC#Cc1cccc(NCC2(O)CCCCC2)c1]

1-((3-(3-Aminoprop-1-ynyl)phenylamino)methyl)cyclohexanol is prepared following the method used in Examples 24 and 29.

Step 1: 2,2,2-Trifluoro-N-(prop-2-ynyl)acetamide (3.4 g, 22.2 mmol), 1-bromo-3-nitrobenzene (14) (3.0 g, 14.85 mmol), Pd(Ph$_3$P)$_4$ (0.85 g, 0.74 mmol) and CuI (0.14 g, 0.74 mmol) was added to triethylamine (30 mL) and the mixture was flushed with argon for 15 min. The reaction mixture was stirred at 90° C. for 16 h, cooled and diluted with ethyl acetate. The mixture was filtered through Celite and the filtrate was concentrated under reduced pressure. Purification by column chromatography (100-200 silica mesh, 15% to 20% EtOAc in hexane) gave 2,2,2-trifluoro-N-(3-(3-nitrophenyl)prop-2-ynyl)acetamide as a brown semi-solid. Yield (1.95 g, 48%); $^1$H NMR (400 MHz, DMSO-d$_6$) δ 8.22 (s, 1H), 8.16 (d, J=8.0 Hz, 1H), 1.79 (d, J=7.6 Hz, 1H), 7.66 (t, J=8.0 Hz, 1H), 7.34 (s, 1H), 4.38 (s, 2H).

Step 2: Tin(II) chloride dihydrate was added (6.5 g, 28.67 mmol) to a solution of 2,2,2-trifluoro-N-(3-(3-nitrophenyl)prop-2-ynyl)acetamide (1.95 g, 7.16 mmol) in ethanol and the reaction mixture was stirred under reflux overnight. The mixture was concentrated under reduced pressure to give dark brown viscous liquid which was partitioned between saturated aqueous NaHCO$_3$ and EtOAc. Organic layer was dried over anhydrous sodium sulfate and concentrated under reduced pressure to give N-(3-(3-aminophenyl)prop-2-ynyl)-2,2,2-trifluoroacetamide as brown oil. Yield (0.75 g, 43%); $^1$H NMR (400 MHz, DMSO-d$_6$) δ 7.28 (s, 1H), 6.94 (t, J=7.8 Hz, 1H), 6.44-6.37 (m, 3H), 5.09 (bs, 2H), 3.99 (s, 2H).

Step 3: A mixture of N-(3-(3-aminophenyl)prop-2-ynyl)-2,2,2-trifluoroacetamide (0.75 g, 3.09 mmol) and 1-oxaspiro[2.5]octane (1.2 g, 9.2 mmol) in EtOH:H$_2$O (9:1) was stirred under reflux for 36 h. The reaction mixture was concentrated under reduced pressure. Purification by column chromatography (20% to 30% EtOAc—hexanes gradient) gave 2,2,2-trifluoro-N-(3-(3-((1-hydroxycyclohexyl)methylamino)phenyl)prop-2-ynyl)acetamide as an off white solid. Yield (0.48 g, 43%); $^1$H NMR (400 MHz, DMSO-d$_6$) δ 7.28 (s, 1H), 7.00 (t, J=7.6 Hz, 1H), 6.53-6.51 (m, 2H), 6.39 (d, J=7.6 Hz, 1H), 5.28 (t, J=5.6 Hz, 1H), 4.18 (s, 1H), 4.01 (s, 2H), 2.88 (d, J=5.6 Hz, 2H), 1.60-1.47 (m, 4H), 1.39-1.34 (m, 4H), 1.22-1.14 (m, 2H).

Step 4: Deprotection of 2,2,2-trifluoro-N-(3-(3-((1-hydroxycyclohexyl)methylamino)phenyl)prop-2-ynyl)acetamide gives Example 30.

Example 31

Preparation of 3-(3-aminopropyl)-N-(cyclopentylmethyl)aniline

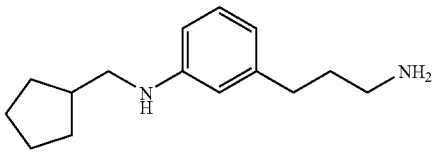 [SMILES: NCCCc1cccc(NCC2CCCC2)c1]

3-(3-Aminopropyl)-N-(cyclopentylmethyl)aniline was prepared following the method shown in Scheme 12.

SCHEME 12

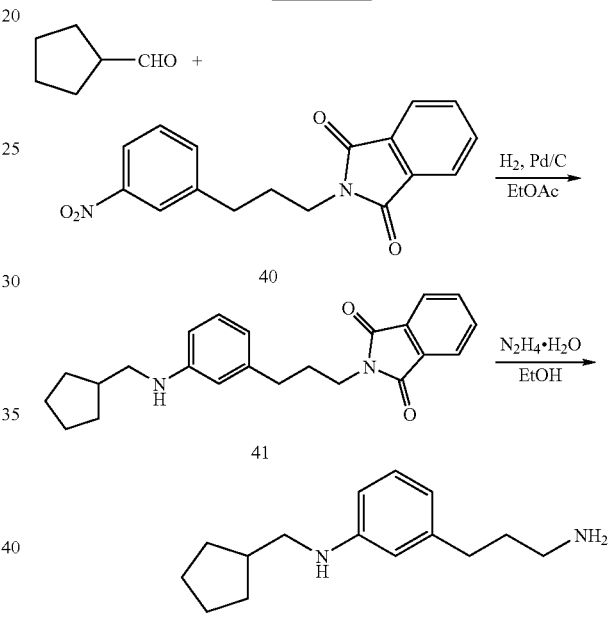

Step 1: A mixture of nitrobenzene 40 (0.5 g, 1.6 mmol) and cyclopentanecarbaldehyde (0.15 ml, 1.6 mmol) in EtOAc was degassed and saturated with argon. 10% Pd/C (0.40 g) was added to this solution and the resulting mixture was stirred under H$_2$ at 1 atm for 3 hrs. The reaction mixture was filtered through Celite, concentrated under reduced pressure. Purification by flash chromatography (40% to 50% EtOAc—hexanes gradient) gave aniline 41 as a yellow semi-solid. Yield (0.4 g, 68%); $^1$H NMR (400 MHz, DMSO-d$_6$) δ 7.86-7.80 (m, 4H), 6.90 (t, J=8.0 Hz, 1H), 6.36 (s, 1H), 6.33 (d, J=5.6 Hz, 2H), 5.40 (t, J=5.6 Hz, 1H), 3.59 (t, J=7.2 Hz, 2H), 2.86 (t, J=6.4 Hz, 2H), 2.50-2.45 (m, 2H), 2.09 (quintet, J=7.6 Hz, 1H), 1.86 (quintet, J=7.6 Hz, 2H), 1.76-1.72 (m, 2H), 1.57-1.47 (m, 4H), 1.23-1.08 (m, 2H).

Step 2: A mixture of alkylphthalimide 41 (350 mg, 0.96 mmol) and hydrazine hydrate (0.1 ml) in methanol was stirred at room temperature for 24 hours. The solvent was evaporated under reduced pressure. Purification by flash chromatography (5% to 6% MeOH—DCM gradient) gave Example 31 as a colourless semi-solid. Yield (0.16 g, 71%); $^1$H NMR (400 MHz, DMSO-d$_6$) δ 6.95 (t, J=8.0 Hz, 1H), 6.38 (bs, 2H), 6.33 (d, J=7.6 Hz, 1H), 5.47 (t, J=5.2 Hz, 1H), 3.5 (bs, 2H), 2.87 (t, J=6.4 Hz, 2H), 2.66 (t, J=7.2 Hz, 2H), 2.50-2.45 (m, 2H), 2.12

(quintet, J=7.6 Hz, 1H), 1.75-1.67 (m, 4H), 1.58-1.50 (m, 4H), 1.26-1.21 (m, 2H). RP-HPLC (Method 3) t$_R$=5.18 min, 97.03% (AUC); ESI MS m/z 233.27 [M+H]$^+$.

Example 32

Preparation of 3-(3-aminopropyl)-N-(2-propylpentyl)aniline

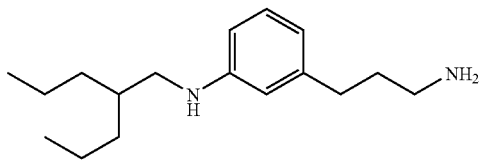 [SMILES: CCCC(CCC)CNc1cccc(CCCN)c1]

3-(3-Aminopropyl)-N-(2-propylpentyl)aniline is prepared following the method used in Example 31.

Step 1: Hydrogenation of nitrobenzene 40 and 2-propylpentanal gives 2-(3-(3-(2-propylpentylamino)phenyl)propyl)isoindoline-1,3-dione.

Step 2: Deprotection of 2-(3-(3-(2-propylpentylamino)phenyl)propyl)isoindoline-1,3-dione gives Example 32.

Example 33

Preparation of 3-(3-aminopropyl)-N-(2-ethylbutyl)aniline

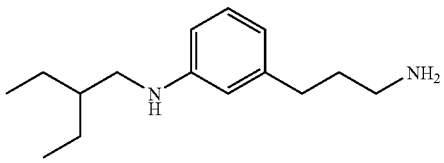 [SMILES: CCC(CC)CNc1cccc(CCCN)c1]

3-(3-Aminopropyl)-N-(2-ethylbutyl)aniline was prepared following the method below.

Step 1: Trifluoroacetic anhydride (38.58 g, 0.18 mol) was added dropwise over 10 min to a stirred solution of n-allylamine (10.0 g, 0.17 mol) in CH$_2$Cl$_2$ at 0° C. After vigorous stirring at room temperature for 15 min, the reaction mixture was quenched with saturated solution of NaHCO$_3$ and layers were separated. Aqueous layer was additionally extracted with CH$_2$Cl$_2$. Combined organic layers were washed with brine, dried over anhydrous NaSO$_4$ and concentrated under reduced pressure to give N-allyl-2,2,2-trifluoroacetamide as a yellow liquid. Yield (17.5 g, 65%); $^1$H NMR (400 MHz, DMSO-d$_6$) δ 6.52 (bs, 1H), 5.88-5.79 (m, 1H), 5.29-5.23 (m, 2H), 3.97 (t, J=5.6 Hz, 2H).

Step 2: Palladium (II) acetate (0.449 g, 0.002 mol) was added to a mixture of N-allyl-2,2,2-trifluoroacetamide (4.2 g, 0.02 mol), 1-bromo-3-nitrobenzene (5.09 g, 0.03 mol) and TBAA. The reaction mixture was flushed with argon and heated under argon at 90° C. for 4 h. The reaction mixture was partitioned between EtOAc and water. Organic layer was dried over anhydrous Na$_2$SO$_4$ and concentrated under reduced pressure to give dark brown viscous liquid. Purification by flash chromatography (5% to 30% EtOAc—hexane gradient) gave 2,2,2-trifluoro-N-(3-(3-nitrophenyl)allyl)acetamide as light yellow solid. Yield (3.5 g, 61%); $^1$H NMR (400 MHz, DMSO-d$_6$) δ 9.77 (br.s, 1H), 8.27 (s, 1H), 8.10 (d, J=8.0 Hz, 1H), 7.93 (d, J=7.6 Hz, 1H), 7.63 (t, J=8.0 Hz, 1H), 6.71 (d, J=16.0 Hz, 1H), 6.51 (dt, J=5.6, 16.0 Hz, 1H), 4.02 (t, J=5.6 Hz, 2H).

Step 3: Tin(II) chloride dihydrate (3.28 g, 14.5 mmol) was added to a solution of (E)-2,2,2-trifluoro-N-(3-(3-nitrophenyl)allyl)acetamide (1.0 g, 3.64 mmol) in ethanol. The reaction mixture was stirred under reflux overnight. The mixture was concentrated under reduced pressure to give dark brown viscous liquid. The reaction mixture was partitioned between sat NaHCO$_3$ and EtOAc and then filtered through Celite which was thoroughly washed with ethyl acetate. Organic layer was separated and concentrated under reduced pressure to give (E)-N-(3-(3-aminophenyl)allyl)-2,2,2-trifluoroacetamide as a brown liquid. Yield (0.8 g, 89%); $^1$H NMR (400 MHz, DMSO-d$_6$) δ 9.70 (bs, 1H), 6.96 (t, J=7.8 Hz, 1H), 6.51-6.60 (m, 2H), 6.45-6.48 (m, 1H), 6.39 (d, J=16.0 Hz, 1H), 6.05-6.10 (m, 1H), 5.07 (bs, 2H), 3.95 (t, J=5.6 Hz, 2H); ESI MS m/z 243.09 [M−H]$^+$.

Step 4: Hydrogenation of 2-ethylbutanal and (E)-N-(3-(3-aminophenyl)allyl)-2,2,2-trifluoroacetamide following the method used in Example 31 gave N-(3-(3-(2-ethylbutylamino)phenyl)propyl)-2,2,2-trifluoroacetamide as a colorless oil. Yield (0.5 g, 90%); $^1$H NMR (400 MHz, DMSO-d$_6$) δ 9.42 (bs, 1H), 6.94 (t, J=7.2 Hz, 1H), 6.38-6.37 (m, 2H), 6.32 (d, J=7.2 Hz, 1H), 5.40 (t, J=5.6 Hz, 1H), 3.21-3.16 (m, 2H), 2.86 (t, J=6.0 Hz, 2H), 2.43 (t, J=7.6 Hz, 2H), 1.77-1.70 (m, 2H), 1.48-1.41 (m, 1H), 1.39-1.31 (m, 4H), 0.85 (t, J=7.6 Hz, 6H).

Step 5: A mixture of N-(3-(3-(2-ethylbutylamino)phenyl)propyl)-2,2,2-trifluoroacetamide (0.500 g, 1.51 mmol) and K$_2$CO$_3$ (0.631 g, 4.53 mmol) in MeOH:water (2:1) was stirred at room temperature for 5 hr and concentrated under reduced pressure. Purification by flash column chromatography (5% to 20% of MeOH—DCM gradient) gave Example 33 as a yellow oil. Yield (0.28 g, 76%); $^1$H NMR (400 MHz, DMSO-d$_6$) δ 6.93 (t, J=7.6 Hz, 1H), 6.38-6.36 (m, 2H), 6.31 (d, J=7.6 Hz, 1H), 5.39 (t, J=5.6 Hz, 1H), 3.46 (bs, 2H), 2.86 (t, J=6.0 Hz, 2H), 2.58 (t, J=7.2 Hz, 2H), 2.43 (t, J=8.0 Hz, 2H), 1.67-1.60 (m, 2H), 1.49-1.43 (m, 1H), 1.41-1.36 (m, 2H), 1.35-1.26 (m, 2H), 0.86 (t, J=7.6 Hz, 6H); $^{13}$C NMR (100 MHz, DMSO-d$_6$) δ: 149.3, 142.3, 128.7, 115.4, 111.8, 109.3, 45.7, 40.5, 38.9, 33.4, 32.8, 23.3, 10.7; RP-HPLC (Method 3) t$_R$=3.71 min, 96.07% (AUC); ESI MS m/z 235.27 [M+H]$^+$.

Example 34

Preparation of 3-(3-aminopropyl)-N-benzylaniline

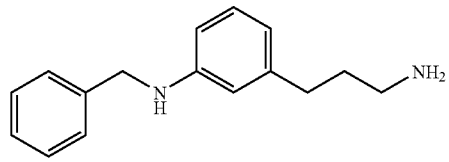 [SMILES: NCCCc1cccc(NCc2ccccc2)c1]

3-(3-Aminopropyl)-N-benzylaniline is prepared following the method used in Example 31.

Step 1: Hydrogenation of nitrobenzene 40 and benzaldehyde gives 2-(3-(3-(benzylamino)phenyl)propyl)isoindoline-1,3-dione.

Step 2: Deprotection of 2-(3-(3-(benzylamino)phenyl)propyl)isoindoline-1,3-dione gives Example 34.

Example 35

Preparation of 3-amino-1-(3-(2-ethylbutylamino)phenyl)propan-1-ol

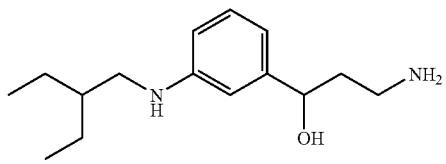 [SMILES: CCC(CC)CNc1cccc(C(O)CCN)c1]

3-Amino-1-(3-(2-ethylbutylamino)phenyl)propan-1-ol was prepared following the method used in Example 11.

Step 1: Hydrogenation of nitrobenzene 11 and 2-ethylbutanal gave (3-(3-(2-ethylbutylamino)phenyl)-3-hydroxypropanenitrile as a colorless oil. Yield (0.50 g, 78%); $^1$H NMR (400 MHz, DMSO-$d_6$) δ 7.01 (t, J=7.6 Hz, 1H), 6.61 (s, 1H), 6.50 (d, J=7.6 Hz, 1H), 6.46 (d, J=8.0 Hz, 1H), 5.77 (d, J=4.0 Hz, 1H), 5.55 (t, J=5.6 Hz, 1H), 4.72 (dd, J=4.8, 11.2 Hz, 1H), 2.88 (t, J=6.0 Hz, 2H), 2.81 (dd, J=4.8, 16.4, 1H), 2.72 (dd, J=4.8, 16.4, 1H), 1.51-1.43 (m, 1H), 1.41-1.28 (m, 4H), 0.86 (t, J=7.6 Hz, 6H).

Step 2: BH$_3$-Me$_2$S reduction of 3-(3-(2-ethylbutylamino)phenyl)-3-hydroxypropanenitrile gave Example 35 hydrochloride as a pale yellows semi-solid. Yield (0.28 g, 76%); $^1$H NMR (400 MHz, DMSO-$d_6$+5% D$_2$O) δ 7.29 (t, J=7.6 Hz, 1H), 7.08 (s, 1H), 6.99 (m, 2H), 4.64 (dd, J=4.0, 8.0 Hz, 1H), 3.04 (d, J=6.4 Hz, 2H), 2.91-2.80 (m, 2H), 1.89-1.75 (m, 2H), 1.56-1.49 (m, 1H), 1.44-1.27 (m, 4H), 0.82 (t, J=7.6 Hz, 6H); $^{13}$C NMR (100 MHz, DMSO-$d_6$) δ 147.4, 138.4, 129.9, 124.43, 120.2, 118.7, 69.4, 53.4, 37.5, 36.4, 36.3, 22.8, 10.4; RP-HPLC (Method 6) $t_R$=4.94 min, 96.74% (AUC); ESI MS m/z 251.25 [M+H]$^+$.

Example 36

Preparation of 3-amino-1-(3-(2-ethylbutylamino)phenyl)propan-1-one

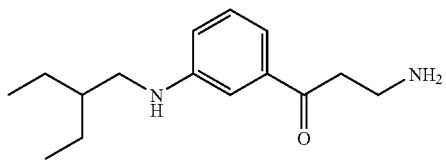 [SMILES: CCC(CC)CNc1cccc(C(=O)CCN)c1]

3-Amino-1-(3-(2-ethylbutylamino)phenyl)propan-1-one was prepared following the method used in Examples 11 and 12.

Step 1: Protection of Example 35 with Boc$_2$O following the method used in Example 11 gave tert-butyl 3-(3-(2-ethylbutylamino)phenyl)-3-hydroxypropylcarbamate as a colorless oil. Yield (0.55 g, 90%); $^1$H NMR (400 MHz, DMSO-$d_6$) δ 6.96 (t, J=8.0 Hz, 1H), 6.74 (br.s, 1H), 6.54 (s, 1H), 6.43 (d, J=7.6 Hz, 1H), 6.40 (d, J=8.0 Hz, 1H), 5.44 (t, J=5.6 Hz, 1H), 5.01 (d, J=4.0 Hz, 1H), 4.37 (m, 1H), 2.98-2.92 (m, 2H), 2.87 (t, J=6.0 Hz, 2H), 1.66-1.61 (m, 2H), 1.51-1.43 (m, 1H), 1.36 (s, 9H), 1.30-1.23 (m, 4H), 0.86 (t, J=7.6 Hz, 6H).

Step 2: Oxidation of tert-butyl 3-(3-(2-ethylbutylamino)phenyl)-3-hydroxypropylcarbamate by MnO$_2$ following the method used in Example 12 gave tert-butyl 3-(3-(2-ethylbutylamino)phenyl)-3-oxopropylcarbamate as a pale yellow oil. Yield (0.350 g, 86%); $^1$H NMR (400 MHz, DMSO-$d_6$+5% D$_2$O) δ 7.17 (t, J=7.6 Hz, 1H), 7.06 (d, J=7.6 Hz, 1H), 7.04 (s, 1H), 6.79 (d, J=7.6 Hz, 1H), 3.20 (t, J=6.4 Hz, 2H), 3.03 (t, J=6.8 Hz, 2H), 2.90 (d, J=6.0 Hz, 2H), 1.50-1.44 (m, 1H), 1.31 (s, 9H), 1.28-1.19 (m, 4H), 0.82 (t, J=7.6 Hz, 6H).

Step 3: Deprotection of tert-butyl 3-(3-(2-ethylbutylamino)phenyl)-3-oxopropylcarbamate following the method used in Example 12 gave Example 36 hydrochloride as a yellow oil. Yield (0.22 g, 90%); $^1$H NMR (400 MHz, DMSO-$d_6$+5% D$_2$O) δ 7.22 (t, J=7.6 Hz, 1H), 7.12-7.09 (m, 2H), 6.85 (d, J=7.6 Hz, 1H), 3.29 (t, J=6.4 Hz, 2H), 3.11 (t, J=6.0 Hz, 2H), 2.91 (d, J=6.0 Hz, 2H), 1.49-1.41 (m, 1H), 1.39-1.20 (m, 4H), 0.84 (t, J=7.2 Hz, 6H). RP-HPLC (Method 3) $t_R$=4.49 min, 99.38% (AUC); ESI MS m/z 249.22 [M+H]$^+$.

Example 37

Preparation of 3-amino-1-(3-(2-propylpentylamino)phenyl)propan-1-ol

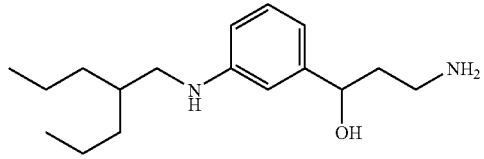 [SMILES: CCCC(CCC)CNc1cccc(C(O)CCN)c1]

3-Amino-1-(3-(2-propylpentylamino)phenyl)propan-1-ol was prepared following the method described below.

Step 1: To a stirred solution of aniline 12 (1.0 g, 6.1 mmol) in EtOH:H$_2$O (9:1) was added 2-propylpentyl 4-methylbenzenesulfonate (0.87 g, 3.08 mmol). The reaction mixture was heated under reflux for 4 days, concentrated under reduced pressure. The residue was diluted with water and extracted with EtOAc three times. Combined organic layers were dried over anhydrous sodium sulfate and concentrated under reduced pressure to dryness. Purification by flash chromatography (25% EtOAc—hexanes) gave 3-hydroxy-3-(3-(2-propylpentylamino)phenyl)propanenitrile as a colorless semi-solid. Yield (0.3 g, 18%); $^1$H NMR (400 MHz, CDCl$_3$) δ 7.17 (t, J=7.6 Hz, 1H), 6.66 (d, J=7.6 Hz, 1H), 6.62 (d, J=2.0 Hz, 1H), 6.57 (dd, J=2.0, 8.0 Hz, 1H), 4.95 (dt, J=3.2, 6.0 Hz, 1H), 3.72 (bs, 1H), 3.02 (d, J=6.0 Hz, 2H), 2.80 (d, J=6.8 Hz, 2H), 2.89 (d, J=3.2 Hz, 1H), 1.64-1.57 (m, 1H), 1.37-1.20 (m, 8H), 0.84 (t, J=6.8 Hz, 6H).

Step 2: BH$_3$-Me$_2$S reduction of 3-hydroxy-3-(3-(2-propylpentylamino)phenyl)propanenitrile following the method used in Example 11 gave Example 37. Yield (0.19 g, 62%); $^1$H NMR (400 MHz, DMSO-$d_6$) δ 6.96 (t, J=7.6 Hz, 1H), 6.55 (s, 1H), 6.42 (d, J=7.2 Hz, 1H), 6.39 (d, J=8.0 Hz, 1H), 5.42 (t, J=5.6 Hz, 1H), 4.50 (t, J=6.0 Hz, 1H), 2.843 (d, J=6.4 Hz, 2H), 2.57 (t, J=6.4 Hz, 2H), 1.78-1.60 (m, 3H), 1.39-1.15 (m, 8H), 0.831 (t, J=6.4 Hz, 6H); RP-HPLC (Method 5) $t_R$=5.67 min, 96.05% (AUC); ESI MS m/z 279.27 [M+H]$^+$.

Example 38

Preparation of 3-amino-1-(3-(2-propylpentylamino)phenyl)propan-1-one

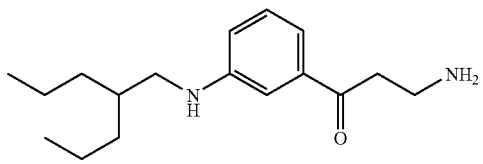 [SMILES: CCCC(CCC)CNc1cccc(C(=O)CCN)c1]

3-Amino-1-(3-(2-propylpentylamino)phenyl)propan-1-one was prepared following the method used in Examples 11 and 12.

Step 1: Protection of Example 37 with Boc$_2$O following the method used in Example 11 gave tert-butyl (3-(3-((tert-butoxycarbonyl)amino)-1-hydroxypropyl)phenyl)(2-propylpentyl)carbamate as a pale yellow semi-solid. Yield (0.6 g, 46%); $^1$H NMR (400 MHz, CDCl$_3$) δ 7.30 (t, J=8.0 Hz, 1H), 7.19-7.16 (m, 2H), 7.09 (d, J=7.2 Hz, 1H), 4.90 (bs, 1H), 4.73-4.64 (m, 1H), 3.55 (dd, J=7.2, 14.4 Hz, 2H), 3.22-3.14 (m, 2H), 3.01 (d, J=6.0 Hz, 1H), 1.87-1.81 (m, 2H), 1.45 (s, 9H), 1.43 (s, 9H), 1.33 (m, 5H), 1.21 (m, 4H), 0.89 (m, 3H), 0.81 (m, 3H).

Step 2: Oxidation of ten-butyl (3-(3-((tert-butoxycarbonyl)amino)-1-hydroxypropyl)phenyl)(2-propylpentyl)carbamate by Des-Martin periodinane following the method used in Example 40 gave tert-butyl (3-(3-((tert-butoxycarbonyl)amino)propanoyl)phenyl)(2-propylpentyl)carbamate as a pale yellow semi-solid. Yield (0.25 g, 55%); $^1$H NMR (400 MHz, CDCl$_3$) δ 7.79-7.75 (m, 2H), 7.43 (d, J=4.8 Hz, 2H), 5.13 (bs, 1H), 3.61 (d, J=7.6 Hz, 2H), 3.55-3.52 (m, 2H), 3.18 (t, J=5.6 Hz, 2H), 1.56 (s, 18H), 1.44-1.21 (m, 9H), 0.81 (t, J=6.0 Hz, 6H).

Step 3: Deprotection of tert-butyl (3-(3-((tert-butoxycarbonyl)amino)propanoyl)phenyl)(2-propylpentyl)carbamate following the method used in Example 12 gave Example 38 hydrochloride as a white solid. Yield (0.03 g, 46%); $^1$H NMR (400 MHz, DMSO-d$_6$) δ 7.85 (m, 3H), 7.24 (t, J=7.6 Hz, 1H), 7.14-7.12 (m, 2H), 6.89 (d, J=7.6 Hz, 1H), 3.32 (t, J=6.4 Hz, 2H), 3.14-3.09 (m, 2H), 2.94 (d, J=6.0, 2H), 1.62 (bs, 1H), 1.34-1.23 (m, 9H), 0.87 (t, J=6.4 Hz, 6H); RP-HPLC (Method 6) t$_R$=5.98 min, 79.55% (AUC); ESI MS m/z 277.29 [M+H]$^+$.

Example 39

Preparation of 3-amino-1-(3-(cyclopentylmethylamino)phenyl)propan-1-ol

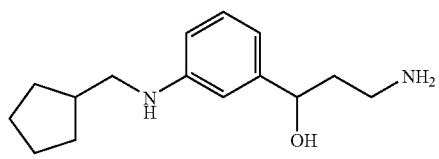 [SMILES: NCCC(O)c1cccc(NCC2CCCC2)c1]

3-Amino-1-(3-(cyclopentylmethylamino)phenyl)propan-1-ol was prepared following the method used in Example 35.

Step 1: Hydrogenation of nitrobenzene 11 and cyclopentylcarbaldehyde gave 3-(3-(cyclopentylmethylamino)phenyl)-3-hydroxypropanenitrile as a brown oil. Yield (2.42 g, 95%); $^1$H NMR (400 MHz, CDCl$_3$) δ 7.17 (t, J=7.6 Hz, 1H), 6.66 (d, J=7.6 Hz, 1H), 6.62 (s, 1H), 6.57 (dd, J=2.0, 8.0 Hz, 1H), 4.94 (t, J=6.0 Hz, 1H), 3.72 (bs, 1H), 3.02 (d, J=7.2 Hz, 2H), 2.76-2.73 (m, 2H), 2.18-2.11 (m, 1H), 1.86-1.79 (m, 2H), 1.67-1.50 (m, 4H), 1.30-1.22 (m, 2H).

Step 2: BH$_3$-Me$_2$S reduction of 3-(3-(cyclopentylmethylamino)phenyl)-3-hydroxypropanenitrile gave, after purification following the method used in Example 11, Example 39 hydrochloride as a pale yellow semi-solid. Yield (2.0 g, 81%); $^1$H NMR (400 MHz, CD$_3$OD) δ 7.54 (t, J=7.6 Hz, 2H), 7.48 (d, J=8.0 Hz, 1H), 7.37 (d, J=7.6 Hz, 1H), 4.90 (m, 1H), 3.37 (d, J=7.6 Hz, 2H), 3.14-3.09 (m, 2H), 2.25-2.21 (m, 1H), 2.07-1.98 (m, 2H), 1.96-1.87 (m, 2H), 1.75-1.67 (m, 2H), 1.65-1.62 (m, 2H), 1.37-1.30 (m, 2H); RP-HPLC (Method 6) t$_R$=4.75 min, 97.99% (AUC); ESI MS m/z 249.30 [M+H]$^+$.

Example 40

Preparation of 3-amino-1-(3-(cyclopentylmethylamino)phenyl)propan-1-one

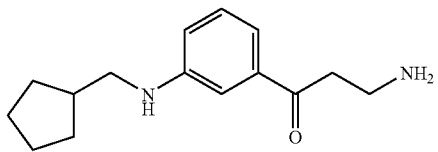 [SMILES: NCCC(=O)c1cccc(NCC2CCCC2)c1]

3-Amino-1-(3-(cyclopentylmethylamino)phenyl)propan-1-one was prepared following the method used in Examples 11 and 12.

Step 1: Protection of Example 39 hydrochloride following the method used in Example 11 gave a mixture of tert-butyl (3-(3-((cyclopentylmethyl)amino)phenyl)-3-hydroxypropyl)carbamate and tert-butyl (3-(3-((tert-butoxycarbonyl)amino)-1-hydroxypropyl)phenyl)(cyclopentylmethyl)carbamate as a pale yellow oil. Yield (2.0 g, 71%); $^1$H NMR (400 MHz, CDCl$_3$) δ 7.31 (t, J=8.0 Hz, 1H), 7.18 (m, 2H), 7.08 (d, J=6.8 Hz, 1H), 4.91 (s, 1H), 4.73 (s, 1H), 3.59 (d, J=7.6 Hz, 2H), 3.51 (d, J=5.2 Hz, 1H), 3.33 (s, 1H), 3.16 (dd, J=5.2, 14.4 Hz, 1H), 2.04-1.97 (m, 1H), 1.83 (bs, 2H), 1.59 (s, 2H), 1.45 (bs, 11H), 1.42 (s, 9H), 1.25-1.18 (m, 4H).

Step 2: To a stirred solution of the above mixture (0.6 g, 1.72 mmol) in CH$_2$Cl$_2$ was added Des-Martin periodinane (0.80 g, 1.89 mmol). After stirring at room temperature for 1 h, the reaction mixture was concentrated under reduced pressure. Purification by column chromatography (5% to 20% EtOAc—hexanes) gave a mixture of tert-butyl (3-(3-((cyclopentylmethyl)amino)phenyl)-3-oxopropyl)carbamate and tert-butyl (3-(3-((tert-butoxycarbonyl)amino)propanoyl)phenyl) (cyclopentylmethyl)carbamate as a pale yellow oil. Yield (0.55 g, 92%); $^1$H NMR (400 MHz, CDCl$_3$) δ 7.78-7.76 (m, 2H), 7.42 (d, J=4.8 Hz, 2H), 5.14 (s, 1H), 3.63 (d, J=7.6 Hz, 2H), 3.56-3.52 (m, 2H), 3.19 (t, J=5.2 Hz, 2H), 2.03-1.95 (m, 1H), 1.64-1.58 (m, 4H), 1.55-1.48 (m, 2H), 1.42 (s, 18H), 1.23-1.16 (m, 2H).

Step 3: Deprotection of the above mixture following the method used in Example 12 gave Example 40 hydrochloride as a white solid. Yield (0.17 g, 95%); $^1$H NMR (400 MHz, CD$_3$OD) δ 8.13 (s, 2H), 7.76-7.74 (m, 2H), 3.53 (t, J=6.0 Hz, 2H), 3.43 (d, J=7.2 Hz, 2H), 3.37 (t, J=6.0 Hz, 2H), 2.31-2.23 (quintet, J=7.6 Hz, 1H), 1.95-1.89 (m, 2H), 1.78-1.72 (m, 2H), 1.70-1.60 (m, 2H), 1.40-1.31 (m, 2H); $^{13}$C NMR (100 MHz, CD$_3$OD) δ 197.3, 139.2, 138.1, 132.2, 130.2, 129.0, 123.3, 58.5, 38.2, 36.8, 35.7, 31.6, 26.1; RP-HPLC (Method 6) $t_R$=5.03 min, 95.24% (AUC); ESI MS m/z 247.24 [M+H]$^+$.

Example 41

Preparation of 3-amino-1-(3-(5-(benzyloxy)pentylamino)phenyl)propan-1-ol

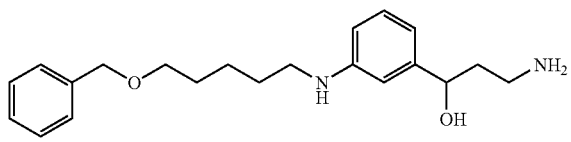 [SMILES: NCCC(O)c1cccc(NCCCCCOCc2ccccc2)c1]

3-Amino-1-(3-(5-(benzyloxy)pentylamino)phenyl)propan-1-ol was prepared following the method used in Example 11.

Step 1: Hydrogenation of nitrobenzene 11 and 5-(benzyloxy)pentanal gave 3-(3-(5-(benzyloxy)pentylamino)phenyl)-3-hydroxypropanenitrile as a colorless oil. Yield (0.90 g, 66%); $^1$H NMR (400 MHz, DMSO-d$_6$) δ 7.36-7.25 (m, 5H), 7.01 (t, J=7.6 Hz, 1H), 6.59 (s, 1H), 6.52 (d, J=7.6 Hz, 1H), 6.44 (d, J=7.6 Hz, 1H), 5.77 (d, J=4.4 Hz, 1H), 5.56 (t, J=5.2 Hz, 1H), 4.74-4.70 (m, 1H), 4.44 (s, 2H), 3.42 (t, J=6.8 Hz, 2H), 3.00-2.95 (m, 2H), 2.80 (dd, J=4.8, 16.4 Hz, 1H), 2.73 (dd, J=4.8, 16.4 Hz, 1H), 1.60-1.51 (m, 4H), 1.44-1.20 (m, 2H).

Step 2: BH$_3$-Me$_2$S reduction of 3-(3-(5-(benzyloxy)pentylamino)phenyl)-3-hydroxypropanenitrile gave Example 41 hydrochloride as a white solid. Yield (0.18 g, 66%). $^1$H NMR (400 MHz, DMSO-d$_6$) δ 7.95 (bs, 3H), 7.36-7.20 (m, 9H), 4.70-4.69 (m, 1H), 4.44 (s, 2H), 3.41 (t, J=6.4 Hz, 2H), 3.19-3.14 (m, 2H), 2.86-2.85 (m, 2H), 1.90-1.80 (m, 2H), 1.67-1.52 (m, 4H), 1.43-1.23 (m, 2H); $^{13}$CNMR (400 MHz, DMSO-d$_6$) δ 147.6, 138.9, 130.2, 130.1, 128.7, 127.9, 127.8, 125.2, 120.7, 119.1, 72.3, 69.7, 50.4, 36.7, 36.6, 36.4, 29.0, 25.8, 23.1; RP-HPLC Method 5) $t_R$=5.30 min, 94.93% (AUC); ESI MS m/z 343.30 [M+H]$^+$.

Example 42

Preparation of 3-amino-1-(3-(5-(benzyloxy)pentylamino)phenyl)propan-1-one

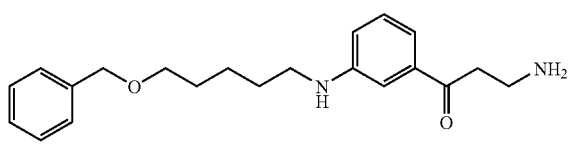 [SMILES: NCCC(=O)c1cccc(NCCCCCOCc2ccccc2)c1]

3-Amino-1-(3-(5-(benzyloxy)pentylamino)phenyl)propan-1-one was prepared following the method used in Example 38.

Step 1: Protection of Example 41 with Boc$_2$O gave a mixture of tert-butyl (3-(3-((5-(benzyloxy)pentyl)amino)phenyl)-3-hydroxypropyl)carbamate (minor component) and tert-butyl (5-(benzyloxy)pentyl)(3-(3-((tert-butoxycarbonyl)amino)-1-hydroxypropyl)phenyl)carbamate (major component) as a colorless oil. Yield (2.0 g, 98%); Major $^1$H NMR (400 MHz, CDCl$_3$) δ 7.36-7.29 (m, 4H), 7.23 (m, 1H), 7.18 (d, J=4.4 Hz, 1H), 7.14-7.12 (m, 2H), 6.64 (d, J=7.2 Hz, 1H), 4.90 (bs, 1H), 4.65 (bs, 1H), 4.50 (s, 2H), 3.62-3.60 (m, 2H), 3.48 (t, J=6.4 Hz, 2H), 3.14-3.10 (m, 2H), 1.85-1.83 (m, 2H), 1.68-1.57 (m, 6H), 1.46 (s, 9H), 1.45 (s, 9H). Minor $^1$H NMR (400 MHz, CDCl$_3$) δ 7.28-7.24 (m, 5H), 7.18-7.16 (m, 1H), 7.07-7.05 (m, 2H), 6.60 (bs, 1H), 6.50 (bs, 1H), 4.70 (bs, 1H), 4.47 (s, 2H), 3.59 (m, 2H), 3.43 (t, J=6.4 Hz, 2H), 3.17-3.14 (m, 2H), 2.90 (bs, 1H), 1.83-1.81 (m, 2H), 1.68-1.57 (m, 6H), 1.41 (s, 9H).

Step 2: Oxidation of the above mixture by Des-Martin periodinane following the method used in Example 40 gave a mixture of tert-butyl (3-(3-((5-benzyloxy)pentyl)amino)phenyl)-3-oxopropyl)carbamate (minor component) and tert-butyl (5-(benzyloxy)pentyl)(3-(3-((tert-butoxycarbonyl)amino)propanoyl)phenyl)carbamate as a colorless oil. Yield (0.3 g, 25%); $^1$H NMR (400 MHz, CDCl$_3$) δ 7.78-7.75 (m, 2H), 7.42 (d, J=5.6 Hz, 2H), 7.34-7.31 (m, 5H), 5.12 (bs, 1H), 4.47 (s, 2H), 3.65 (t, J=7.6 Hz, 2H), 3.54-3.49 (m, 2H), 3.43 (t, J=6.4 Hz, 2H), 3.17 (bs, 2H), 1.62-1.55 (m, 4H), 1.43 (s, 18H), 1.37-1.35 (m, 2H).

Step 3: Deprotection of the above mixture gave Example 42 hydrochloride as an off-white solid. Yield (0.2 g, 76%); $^1$H NMR (400 MHz, CD$_3$OD) δ 8.11 (d, J=6.8 Hz, 1H), 8.07 (s, 1H), 7.75-7.69 (m, 2H), 7.35-7.31 (m, 4H), 7.29-7.24 (m, 1H), 4.49 (s, 2H), 3.53-3.49 (m, 4H), 3.42 (t, J=7.6 Hz, 2H), 3.36-3.31 (m, 2H), 1.82-1.70 (m, 2H), 1.68-1.63 (m, 2H), 1.57-1.50 (m, 2H); RP-HPLC (Method 3) $t_R$=4.54 min, 90.10% (AUC); ESI MS m/z 341.31 [M+H]$^+$.

Example 43

Preparation of 5-(3-(3-amino-1-hydroxypropyl)phenylamino)pentan-1-ol

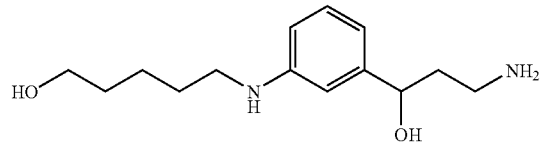 [SMILES: NCCC(O)c1cccc(NCCCCCO)c1]

5-(3-(3-Amino-1-hydroxypropyl)phenylamino)pentan-1-ol is prepared following the method described below.

Step 1: A mixture of Example 41 and Pd(OH)$_2$/C (20% wt) in absolute EtOH is stirred at room temperature under hydrogen atmosphere until no starting material is seen by TLC. The reaction mixture is filtered through Celite and concentrated under reduced pressure to give Example 43.

Example 44

Preparation of 3-amino-1-(3-(5-hydroxypentylamino)phenyl)propan-1-one

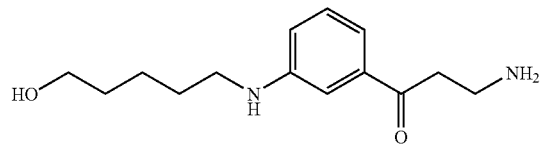 [SMILES: NCCC(=O)c1cccc(NCCCCCO)c1]

3-Amino-1-(3-(5-hydroxypentylamino)phenyl)propan-1-one is prepared following the method described below.

Step 1: Protection of Example 43 with Boc$_2$O following the method used in Example 11 gives tert-butyl 3-hydroxy-3-(3-(5-hydroxypentylamino)phenyl)propylcarbamate.

Step 2: MnO₂ oxidation of tert-butyl 3-hydroxy-3-(3-(5-hydroxypentylamino)phenyl)propylcarbamate following the method used in Example 12 gives tert-butyl 3-(3-(5-hydroxypentylamino)phenyl)-3-oxopropylcarbamate.

Step 3: Deprotection of tert-butyl 3-(3-(5-hydroxypentylamino)phenyl)-3-oxopropylcarbamate following the method used in Example 12 gives Example 44 hydrochloride.

Example 45

Preparation of 3-amino-1-(3-(5-methoxypentylamino)phenyl)propan-1-ol

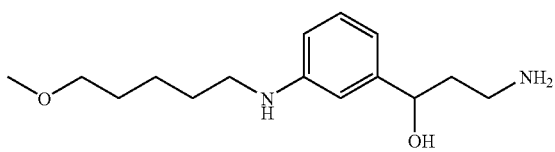 [SMILES: COCCCCCNc1cccc(C(O)CCN)c1]

3-Amino-1-(3-(5-methoxypentylamino)phenyl)propan-1-ol was prepared following the method used in Example 37.

Step 1: A mixture of 5-methoxypentanal (0.644 g, 5.54 mmol), 3-(3-aminophenyl)-3-hydroxypropanenitrile (12) (1.0 g, 6.16 mmol) and activated molecular sieves in methanol was stirred at RT for 8 hrs. NaBH₄ (0.937 g, 24.6 mmol) was added portion wise to the reaction mixture at 0° C. The reaction mixture was stirred at RT overnight. The reaction mixture was filtered through Celite and the filtrate was concentrated under reduced pressure. Purification by column chromatography (100-200 silica, 0% to 70% EtOAc—hexanes gradient) gave 3-hydroxy-3-(3-(5-methoxypentylamino)phenyl)propanenitrile as a yellow oil. Yield (0.34 g, 21%); ¹H NMR (400 MHz, CDCl₃) δ 7.17 (t, J=8.0 Hz, 1H), 6.66 (d, J=7.6 Hz, 1H), 6.62 (s, 1H), 6.56 (d, J=8.0 Hz, 1H), 4.95 (t, J=6.4 Hz, 1H), 3.39 (t, J=6.4 Hz, 2H), 3.33 (s, 3H), 3.12 (t, J=7.2 Hz, 2H), 2.75 (d, J=6.4 Hz, 2H), 1.68-1.59 (m, 4H), 1.51-1.43 (m, 2H).

Step 2: BH₃-Me₂S reduction of 3-hydroxy-3-(3-(5-methoxypentylamino)phenyl)propanenitrile following the method used in Example 11 gave Example 45 hydrochloride as a colorless oil. Yield (0.25 g, 72%); ¹H NMR (400 MHz, CD₃OD) δ 7.60-7.53 (m, 3H), 7.40 (d, J=7.6 Hz, 1H), 4.94-4.92 (m, 1H), 3.42-3.38 (m, 4H), 3.31 (s, 3H), 3.17-3.10 (m, 2H), 2.07-2.03 (m, 1H), 2.01-1.94 (m, 1H), 1.81-1.73 (m, 2H), 1.63-1.60 (m, 2H), 1.58-1.49 (m, 2H); RP-HPLC (Method 6) t_R=4.02 min, 82.18% (AUC); ESI MS m/z 267.28 [M+H]⁺.

Example 46

Preparation of 3-amino-1-(3-(5-methoxypentylamino)phenyl)propan-1-one

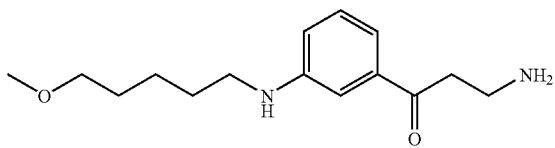 [SMILES: COCCCCCNc1cccc(C(=O)CCN)c1]

3-Amino-1-(3-(5-methoxypentylamino)phenyl)propan-1-one was prepared following the method used in Example 38.

Step 1: Protection of Example 45 with Boc₂O following the method used in Example 11 gave tert-butyl (3-(3-((tert-butoxycarbonyl)amino)propanoyl)phenyl)(5-methoxypentyl)carbamate as a colorless oil. Yield (0.22 g); ¹H NMR (400 MHz, CDCl₃) δ 7.29 (t, J=7.2 Hz, 1H), 7.19-7.17 (m, 2H), 7.08 (d, J=8.0 Hz, 1H), 4.92-4.90 (m, 1H), 4.74-4.71 (m, 1H), 3.59 (t, J=8.0 Hz, 2H), 3.57 (bs, 1H), 3.38-3.32 (m, 2H), 3.31 (s, 3H), 3.20-3.12 (m, 2H), 1.85-1.83 (m, 2H), 1.56 (s, 9H), 1.45 (m, 4H), 1.47 (s, 9H), 1.34-1.30 (m, 2H).

Step 2: Oxidation of tert-butyl (3-(3-((tert-butoxycarbonyl)amino)propanoyl)phenyl)(5-methoxypentyl)carbamate by Des-Martin periodinane following the method used in Example 40 gave tert-butyl (3-(3-((tert-butoxycarbonyl)amino)propanoyl)phenyl)(5-methoxypentyl)carbamate as a colorless oil. Yield (0.12 g, 53%); ¹H NMR (400 MHz, CDCl₃) δ 7.78-7.76 (m, 2H), 7.43-7.42 (m, 2H), 5.13 (bs, 1H), 3.65 (t, J=7.6 Hz, 2H), 3.55-3.52 (m, 2H), 3.35-3.32 (t, J=6.4 Hz, 2H), 3.30 (s, 3H), 3.20-3.17 (t, J=5.6 Hz, 2H), 1.66-1.52 (m, 4H), 1.43 (s, 9H), 1.42 (s, 9H), 1.39-1.30 (m, 2H).

Step 3: Deprotection of tert-butyl (3-(3-((tert-butoxycarbonyl)amino)propanoyl)phenyl)(5-methoxypentyl)carbamate following the method used in Example 12 gave Example 46 hydrochloride as a yellow solid. Yield (0.07 g, 70%); ¹H NMR (400 MHz, CD₃OD) δ 7.95 (d, J=7.2 Hz, 1H), 7.91 (s, 1H), 7.64 (t, J=8.0 Hz, 1H), 7.56 (d, J=6.4 Hz, 1H), 3.49 (t, J=6.0 Hz, 2H), 3.41-3.34 (m, 9H), 1.79-1.71 (m, 2H), 1.66-1.59 (m, 2H), 1.53-1.46 (m, 2H); (RP-HPLC Method 6) t_R=4.42 min, 96.0% (AUC); ESI MS m/z 265.26 [M+H]⁺.

Example 47

Preparation of 3-amino-1-(3-((2-methoxybenzyl)amino)phenyl)propan-1-ol

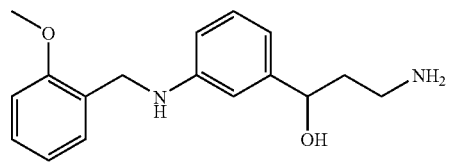 [SMILES: COc1ccccc1CNc1cccc(C(O)CCN)c1]

3-Amino-1-(3-((2-methoxybenzyl)amino)phenyl)propan-1-ol was prepared following the method used in Example 11.

Step 1: Hydrogenation of nitrobenzene 11 and 2-methoxybenzaldehyde gave 3-hydroxy-3-(3-(2-methoxybenzylamino)phenyl)propanenitrile as a yellow oil. Yield (1.4 g, 95%); ¹H NMR (400 MHz, CDCl₃) δ 7.29-7.27 (m, 1H), 7.16 (t, J=8.0 Hz, 1H), 6.94 (t, J=7.2 Hz, 1H), 6.90 (d, J=9.2 Hz, 2H), 6.68-6.67 (m, 2H), 6.61 (d, J=8.0 Hz, 1H), 4.93 (br.s, 1H), 4.69 (d, J=6.8 Hz, 1H), 4.33 (s, 2H), 3.87 (s, 3H), 2.78-2.73 (m, 2H).

Step 2: BH₃-Me₂S reduction of 3-hydroxy-3-(3-(2-methoxybenzylamino)phenyl)propanenitrile gave crude 3-amino-1-(3-(2-methoxybenzylamino)phenyl)propan-1-ol hydrochloride as a pale yellow oil. Yield (1.22 g, 86%); ¹H NMR (400 MHz, CDCl₃) δ 7.30 (dd, J=1.2, 6.4 Hz, 1H), 7.23 (dd, J=1.2, 7.6 Hz, 1H), 7.11 (t, J=8.0 Hz, 1H), 6.91-6.87 (m, 2H), 6.72 (bs, 1H), 6.66 (d, J=7.2 Hz, 1H), 6.53 (dd, J=2.0, 8.0 Hz, 1H), 4.86-4.83 (m, 1H), 4.33 (s, 2H), 4.15 (bs, 1H), 3.85 (s, 3H), 3.06-3.01 (m, 1H), 2.94-2.90 (m, 1H), 1.88-1.76 (m, 2H).

Step 3: Step 3: Boc protection of 3-amino-1-(3-(2-methoxybenzylamino)phenyl)propan-1-ol hydrochloride gave a mixture of mono- and di-Boc products which was used directly in the next step without further purification. Major component: $^1$H NMR (400 MHz, CDCl$_3$) δ 7.30 (d, J=7.6 Hz, 1H), 7.23-7.18 (m, 4H), 6.92-6.87 (m, 2H), 6.66 (d, J=7.6 Hz, 1H), 4.85 (s, 2H), 4.69-4.63 (m, 1H), 3.72 (s, 3H), 3.18-3.10 (m, 2H), 1.83-1.77 (m, 2H), 1.45 (s, 9H), 1.41 (s, 9H). Minor component: $^1$H NMR (400 MHz, CDCl$_3$) δ 7.28 (m, 1H), 7.14-7.07 (m, 4H), 6.82 (d, J=8.4 Hz, 2H), 6.68 (bs, 1H), 6.56 (d, J=9.6 Hz, 1H), 4.86-4.85 (m, 1H), 4.32 (s, 2H), 3.86 (s, 3H), 3.45-3.43 (m, 2H), 1.86-1.83 (m, 2H), 1.45 (s, 9H).

Step 4: Deprotection of the above mixture following the method used in Example 11 gave Example 47 hydrochloride as a yellow solid. Yield (0.194 g, 66%); $^1$H NMR (400 MHz, CD$_3$OD) δ 7.53-7.46 (m, 3H), 7.44-7.42 (m, 1H), 7.28-7.25 (m, 2H), 7.10 (d, J=8.0 Hz, 1H), 6.95 (t, J=7.2 Hz, 1H), 4.86 (m, 1H), 4.56 (s, 2H), 3.94 (s, 3H), 3.12-3.06 (m, 2H), 2.03-1.99 (m, 1H), 1.95-1.87 (m, 1H); $^{13}$C NMR (100 MHz, CD$_3$OD) δ 158.1, 147.4, 135.2, 131.7, 131.5, 129.9, 126.6, 121.6, 120.5, 119.9, 118.4, 110.6, 70.6, 54.8, 51.7, 37.2, 35.7; RP-HPLC (Method 6) t$_R$=4.49 min, 96.74% (AUC); ESI MS m/z 287.23 [M+H]$^+$.

Example 48

Preparation of 3-amino-1-(3-(2-methoxybenzylamino)phenyl)propan-1-one

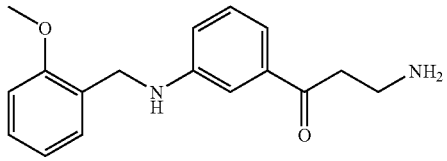 [SMILES: COc1ccccc1CNc1cccc(C(=O)CCN)c1]

3-Amino-1-(3-(2-methoxybenzylamino)phenyl)propan-1-one was prepared following the method used in Example 12.

Step 1: Protection of Example 47 with Boc$_2$O gave a mixture of tert-butyl 3-hydroxy-3-(3-(2-methoxybenzylamino)phenyl)propylcarbamate and tert-butyl tert-butylcarbonyl (3-hydroxy-3-(3-(2-methoxybenzylamino)phenyl)propyl) carbamate as a yellow oil. Yield (0.4 g, 63%); $^1$H NMR (400 MHz, CDCl$_3$) δ 7.80 (bs, 1H), 7.70 (d, J=7.2 Hz, 1H), 7.40-7.36 (m, 1H), 7.34 (t, J=7.6 Hz, 1H), 7.26-7.19 (m, 2H), 6.90 (t, J=7.2 Hz, 1H), 6.82 (d, J=8.0, 1H), 5.11 (bs, 1H), 4.89 (s, 2H), 3.71 (s, 3H), 3.51 (m, 2H), 3.12 (m, 2H), 1.42 (s, 18H).

Step 2: Oxidation of the above mixture with Des-Martin periodinane following the method used in Example 20 gave a mixture of tert-butyl 3-oxo-3-(3-(2-methoxybenzylamino) phenyl)propylcarbamate and tert-butyl tert-butylcarbonyl (3-oxo-3-(3-(2-methoxybenzylamino)phenyl)propyl)carbamate which was directly used in the next step without further purification.

Step 3: Deprotection of the above mixture following the method used in Example 12 gave Example 48 hydrochloride as an off-white solid. Yield (0.2 g, 59%); $^1$H NMR (400 MHz, CD$_3$OD) δ 8.10 (d, J=7.6 Hz, 1H), 7.99 (s, 1H), 7.69 (t, J=8.0 Hz, 1H), 7.61 (d, J=8.0 Hz, 1H), 7.43 (dt, J=1.2, 8.0 Hz, 1H), 7.29 (d, J=7.2 Hz, 1H), 7.09 (d, J=8.4 Hz, 1H), 6.95 (t, J=7.6 Hz, 1H), 4.63 (s, 2H), 3.93 (s, 3H), 3.49 (t, J=6.4 Hz, 2H), 3.37-3.34 (m, 2H); $^{13}$C NMR (100 MHz, DMSO-d$_6$) δ: 197.2, 159.5, 138.9, 137.4, 133.1, 133.0, 131.9, 130.3, 129.0, 123.5, 121.9, 119.7, 112.0, 56.3, 52.7, 36.8, 35.7; RP-HPLC (Method 6) t$_R$=4.84 min, 99.31% (AUC); ESI MS m/z 285.3 [M+H]$^+$.

Example 49

Preparation of 3-amino-1-(3-(phenethylamino)phenyl)propan-1-ol

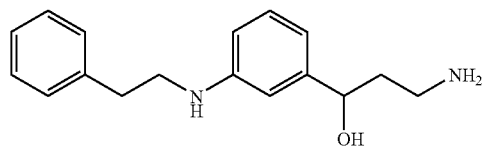 [SMILES: NCCC(O)c1cccc(NCCc2ccccc2)c1]

3-Amino-1-(3-(phenethylamino)phenyl)propan-1-ol was prepared following the method described below.

Step 1: Hydrogenation of aniline 12 and 2-phenylacetaldehyde gives 3-hydroxy-3-(3-(phenethylamino)phenyl)propanenitrile. A mixture of aniline 12 (1.00 g, 6.17 mmol), 2-phenylacetaldehyde (0.66 g, 5.55 mmol) and Å-3 molecular sieves in MeOH was stirred for 18 h and then NaBH$_4$ (1.16 g, 30.8 mmol) was added and the reaction mixture was stirred overnight. The reaction mixture was filtered through Celite, concentrated under reduced pressure. Purification by column chromatography (100-200 silica mesh, 20% EtOAc—hexane) gave 3-hydroxy-3-(3-(phenethylamino)phenyl)propanenitrile as a yellow liquid. Yield (0.432 g, 27%); $^1$H NMR (400 MHz, DMSO-d$_6$) δ 7.32-7.26 (m, 4H), 7.20 (t, J=6.4 Hz, 1H), 7.04 (t, J=7.6 Hz, 1H), 6.64 (s, 1H), 6.55 (d, J=7.2 Hz, 1H), 6.50 (d, J=8.4 Hz, 1H), 5.77 (d, J=4.4 Hz, 1H), 5.68 (t, J=5.6 Hz, 1H), 4.76-4.72 (m, 1H), 3.26-3.21 (m, 2H), 2.85-2.81 (m, 3H), 2.79-2.72 (m, 1H).

Step 2: BH$_3$-Me$_2$S reduction of 3-hydroxy-3-(3-(phenethylamino)phenyl)propanenitrile following the method used in Example 11 gave Example 49 as a yellow semi-solid. Yield (0.15 g, 38%); $^1$H NMR (400 MHz, MeOD) δ 7.31 (t, J=7.6 Hz, 2H), 7.27-7.20 (m, 4H), 6.94 (s, 1H), 6.91 (d, J=7.2 Hz, 1H), 6.82 (d, J=6.8 Hz, 1H), 4.81-4.77 (m, 1H), 3.44 (t, J=7.2 Hz, 2H), 3.10-3.02 (m, 2H), 2.93 (t, J=7.2 Hz, 2H), 1.96 (m, 2H); RP-HPLC (Method 3) t$_R$=3.42 min, 96.13% (AUC); ESI MS m/z 271.25 [M+H]$^+$.

Example 50

Preparation of 3-amino-1-(3-(phenethylamino)phenyl)propan-1-one

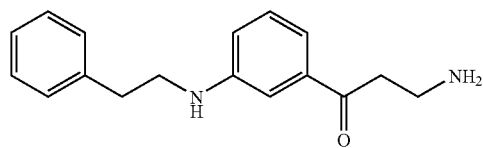 [SMILES: NCCC(=O)c1cccc(NCCc2ccccc2)c1]

3-Amino-1-(3-(phenethylamino)phenyl)propan-1-one was prepared following the method used in Example 38.

Step 1: Protection of Example 49 with Boc$_2$O gave tert-butyl (3-(3-((tert-butoxycarbonyl)amino)propanoyl)phenyl) (phenethyl)carbamate as a yellow oil. Yield (1.2 g, 98%); $^1$H NMR (400 MHz, DMSO-d$_6$) 7.29-7.23 (m, 3H), 7.21 (d, J=7.2 Hz, 1H), 7.16 (d, J=7.2 Hz, 3H), 7.10 (s, 1H), 7.04 (d, J=7.6 Hz, 1H), 6.78 (m, 1H), 5.25 (d, J=4.4 Hz, 1H), 4.54 (m, 1H), 3.79 (t, J=7.2 Hz, 2H), 2.97 (t, J=6.0 Hz, 2H), 2.77-2.71 (m, 2H), 1.70-1.66 (m, 2H), 1.42 (s, 9H), 1.34 (s, 9H).

Step 2: Oxidation of tert-butyl (3-(3-((tert-butoxycarbonyl)amino)propanoyl)phenyl)(phenethyl)carbamate by Des-Martin periodinane gave tert-butyl (3-(3-((tert-butoxycarbonyl)amino)propanoyl)phenyl)(phenethyl)carbamate as a yellow oil. Yield (0.9 g, 76%); $^1$H NMR (400 MHz, DMSO-$d_6$) δ 7.75 (d, J=7.2 Hz, 1H), 7.66 (s, 1H), 7.50-7.43 (m, 2H), 7.27 (t, J=7.6 Hz, 2H), 7.21 (d, J=7.2 Hz, 1H), 7.16 (d, J=7.6 Hz, 2H), 6.85 (bs, 1H), 3.86 (t, J=7.2 Hz, 2H), 3.26 (t, J=6.0 Hz, 2H), 3.11 (t, J=6.8 Hz, 2H), 2.78 (t, J=7.2 Hz, 2H), 1.35 (s, 18H).

Step 3: Deprotection of tert-butyl (3-(3-((tert-butoxycarbonyl)amino)propanoyl)phenyl)(phenethyl)carbamate gave Example 50 hydrochloride as a white solid. Yield (0.5 g, 94%); $^1$H NMR (400 MHz, CD$_3$OD) δ 8.05 (m, 2H), 7.73-7.69 (m, 2H), 7.35-7.24 (m, 5H), 3.69-3.65 (m, 2H), 3.51 (t, J=6.4 Hz, 2H), 3.36 (t, J=6.0 Hz, 2H), 3.07 (t, J=8.0 Hz, 2H); RP-HPLC (Method 6) $t_R$=4.93 min, 93.74% (AUC); ESI MS m/z 269.28 [M+H]$^+$.

Example 51

Preparation of 3-amino-1-(3-(3-cyclohexylpropylamino)phenyl)propan-1-ol

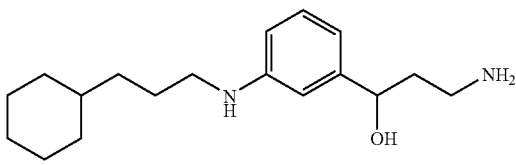

3-Amino-1-(3-(3-cyclohexylpropylamino)phenyl)propan-1-ol was prepared following the method used in Example 35.

Step 1: Hydrogenation of nitrobenzene 11 and 3-cyclohexylpropanal gave 3-(3-(3-cyclohexylpropylamino)phenyl)-3-hydroxypropanenitrile as a colorless semi-solid. Yield (0.32 g, 71%); $^1$H NMR (400 MHz, CDCl$_3$) δ 7.17 (t, J=7.6 Hz, 1H), 6.67 (d, J=7.6 Hz, 1H), 6.62 (s, 1H), 6.57 (d, J=8.0, 1H), 4.95 (t, J=6.0, 1H), 3.74-3.70 (bs, 1H), 3.09 (t, J=7.2 Hz, 2H), 2.76 (d, J=6.0 Hz, 2H), 2.23 (bs, 1H), 1.72-1.70 (m, 4H), 1.66-1.58 (m, 2H), 1.31-1.12 (m, 7H) 0.92-0.87 (m, 2H).

Step 2: BH$_3$-Me$_2$S reduction of 3-(3-(3-cyclohexylpropylamino)phenyl)-3-hydroxypropanenitrile gave Example 51 hydrochloride as a colorless semi-solid. Yield (0.250 g, 82%); $^1$H NMR (400 MHz, DMSO-$d_6$) δ 6.97 (t, J=8.0 Hz, 1H), 6.52 (s, 1H), 6.46 (d, J=7.2 Hz, 1H), 6.38 (d, J=8.0 Hz, 1H), 5.43 (t, J=4.8 Hz, 1H), 4.54-4.48 (m, 1H), 2.96-2.91 (q, J=6.4 Hz, 2H), 2.67-2.60 (m, 2H), 1.70-1.61 (m, 6H), 1.54-1.51 (m, 2H), 1.25-1.06 (m, 6H), 0.90-0.84 (m, 2H); $^{13}$C NMR (100 MHz, DMSO-$d_6$) δ 148.4, 146.5, 127.9, 112.6, 109.7, 108.9, 71.1, 42.8, 41.4, 38.37, 36.5, 34.1, 32.5, 25.8, 25.6, 25.4; RP-HPLC (Method 3) $t_R$=4.13 min, 92.02% (AUC); ESI MS m/z 291.30 [M+H]$^+$.

Example 52

Preparation of 3-amino-1-(3-(3-cyclohexylpropylamino)phenyl)propan-1-one

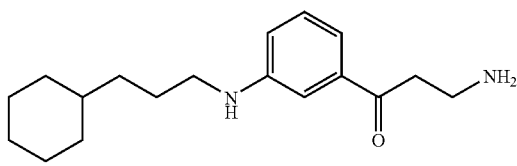 [SMILES: NCCC(=O)c1cccc(NCCCC2CCCCC2)c1]

3-Amino-1-(3-(3-cyclohexylpropylamino)phenyl)propan-1-one was prepared following the method used in Example 40.

Step 1: Protection of Example 51 hydrochloride following the method used in Example 11 gave a mixture of tert-butyl 3-(3-(3-cyclohexylpropylamino)phenyl)-3-hydroxypropylcarbamate and tert-butyl tert-butoxycarbonyloxy(3-(3-(3-cyclohexylpropylamino)phenyl)-3-hydroxypropyl)carbamate as a colorless semi-solid which was used in the next step. Yield (1.2 g, 48%); $^1$H NMR (400 MHz, DMSO-$d_6$) δ 7.29 (t, J=7.6 Hz, 1H), 7.19 (s, 2H), 7.17 (d, J=8.0 Hz, 1H), 7.14 (t, J=7.6 Hz, 1H), 7.08 (d, J=8.0 Hz, 1H), 6.64-6.61 (m, 2H), 6.51 (d, J=7.6 Hz, 1H), 4.90 (bs, 2H), 4.73-4.65 (m, 2H), 3.57 (m, 3H), 3.39 (bs, 1H), 3.19-3.15 (m, 2H), 3.09 (t, J=7.2 Hz, 2H), 2.90 (bs, 1H), 1.85-1.71 (m, 2H), 1.69-1.61 (m, 12H), 1.48 (s, 9H), 1.45 (s, 6H), 1.42-1.20 (m, 3H), 1.17-1.12 (m, 5H) 0.89-0.81 (m, 3H).

Step 2: Oxidation of the above mixture by Des-Martin periodinane following the method used in Example 20 gave a mixture of tert-butyl 3-(3-(3-cyclohexylpropylamino)phenyl)-3-oxopropylcarbamate and tert-butyl tert-butoxycarbonyloxy(3-(3-(cyclohexylpropylamino)phenyl)-3-oxopropyl)carbamate as a colorless semi-solid which was directly used in the next step. Yield (0.35 g, 70%).

Step 3: Deprotection of the above mixture following the method used in Example 12 gave Example 52 hydrochloride as a white solid. Yield (0.10 g, 36%); $^1$H NMR (400 MHz, DMSO-$d_6$+5% D$_2$O) δ 7.34-7.29 (m, 2H), 7.24 (s, 1H), 7.01 (d, J=7.2 Hz, 1H), 3.32 (t, J=6.4 Hz, 2H), 3.12 (t, J=6.4 Hz, 2H), 3.03 (t, J=7.2 Hz, 2H), 1.66-1.61 (m, 4H), 1.56-1.51 (m, 2H), 1.25-1.04 (m, 7H), 0.87-0.82 (m, 2H); RP-HPLC (Method 4) $t_R$=6.07 min, 99.37% (AUC); ESI MS m/z 289.31 [M+H]$^+$.

Example 53

Preparation of 4-(3-(3-amino-1-hydroxypropyl)phenylamino)methyl)heptan-4-ol

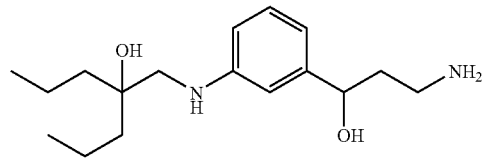 [SMILES: CCCC(O)(CCC)CNc1cccc(C(O)CCN)c1]

4-((3-(3-Amino-1-hydroxypropyl)phenylamino)methyl)heptan-4-ol was prepared following the method used in Example 67.

Step 1: Reaction between 2,2-dipropyloxirane and aniline 12 gave 3-hydroxy-3-(3-(2-hydroxy-2-propylpentylamino)phenyl)propanenitrile as a pale yellow semi-solid. Yield (1.0 g, 40%); $^1$H NMR (400 MHz, CDCl$_3$) δ 7.17 (t, J=8.0 Hz, 1H), 6.69-6.67 (m, 2H), 6.63 (d, J=8.0 Hz, 1H), 4.96-4.94 (m, 1H), 4.05 (bs, 1H), 3.08 (s, 2H), 2.76 (d, J=6.4 Hz, 2H), 2.36 (bs, 1H), 1.52 (t, J=8.4 Hz, 4H), 1.41-1.32 (m, 4H), 0.94 (t, J=7.2 Hz, 6H).

Step 2: BH$_3$-Me$_2$S reduction of 3-hydroxy-3-(3-(2-hydroxy-2-propylpentylamino)phenyl)propanenitrile gave Example 53 as a white solid. Yield (0.6 g, 60%); $^1$H NMR (400 MHz, DMSO-d$_6$) δ 6.97 (t, J=7.6 Hz, 1H), 6.59 (s, 1H), 6.48 (d, J=8.0, 2H), 4.97 (t, J=5.2 Hz, 1H), 4.52-4.49 (m, 1H), 4.20 (bs, 1H), 2.88 (d, J=5.2 Hz, 2H), 2.66-2.62 (m, 2H), 1.65-1.59 (m, 2H), 1.43-1.39 (m, 4H), 1.32-1.24 (m, 4H), 0.84 (t, J=7.2 Hz, 6H); RP-HPLC (Method 3) t$_R$=3.87 min, 96.19% (AUC); ESI MS m/z 295.38 [M+H]$^+$.

Example 54

Preparation of 3-amino-1-(3-(2-hydroxy-2-propylpentylamino)phenyl)propan-1-one

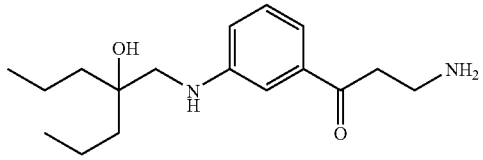 [SMILES: CCCC(O)(CCC)CNc1cccc(C(=O)CCN)c1]

3-Amino-1-(3-(2-hydroxy-2-propylpentylamino)phenyl)propan-1-one is prepared following the method used in Example 52.

Step 1: Protection of Example 53 with Boc$_2$O gives tert-butyl 3-hydroxy-3-(3-(2-hydroxy-2-propylpentylamino)phenyl)propylcarbamate.

Step 2: Oxidation of tert-butyl 3-hydroxy-3-(3-(2-hydroxy-2-propylpentylamino)phenyl)propylcarbamate following the method used in Example 12 gives tert-butyl 3-oxo-3-(3-(2-hydroxy-2-propylpentylamino)phenyl)propylcarbamate.

Step 3: Deprotection of tert-butyl 3-oxo-3-(3-(2-hydroxy-2-propylpentylamino)phenyl)propylcarbamate following the method used in Example 12 gives Example 54 hydrochloride.

Example 55

Preparation of 1-((3-(3-amino-1-hydroxypropyl)phenylamino)methyl)cyclohexanol

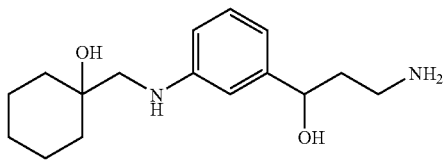 [SMILES: NCCC(O)c1cccc(NCC2(O)CCCCC2)c1]

1-((3-(3-Amino-1-hydroxypropyl)phenylamino)methyl)cyclohexanol was prepared following the method described below.

Step 1: TBDMS-Cl (2.7 g, 18.24 mmol) was added at 0° C. to a stirred solution of aniline 11 (3 g, 15.62 mmol) and TEA (1.73 g, 17.18 mmoles) in DMF and the reaction mixture was stirred at RT for 4 h. The reaction mixture was partitioned between EtOAc and water. Organic layer was washed with water 2×, dried over sodium sulfate and concentrated under reduced pressure to give 3-(tert-butyldimethylsilyloxy)-3-(3-nitrophenyl)propanenitrile as colorless liquid. Yield (4.0 g, 83%); $^1$H NMR (400 MHz, DMSO-d$_6$) δ 8.31 (s, 1H), 8.18 (d, J=7.6 Hz, 1H), 7.88 (d, J=7.6 Hz, 1H), 7.70 (t, J=7.6 Hz, 1H), 5.33 (t, J=5.6 Hz, 1H), 3.01-2.92 (m, 2H), 0.88 (s, 9H), 0.13 (s, 3H), −0.05 (s, 3H).

Step 2: Hydrogenation of 3-(tert-butyldimethylsilyloxy)-3-(3-nitrophenyl)propanenitrile following the method used in Example 11 gave 3-(3-aminophenyl)-3-(tert-butyldimethylsilyloxy)propanenitrile as a colorless oil. Yield (3.5 g, 96%); $^1$H NMR (400 MHz, DMSO-d$_6$) δ 6.97 (t, J=7.6 Hz, 1H), 6.56 (s, 1H), 6.51 (d, J=7.6 Hz, 1H), 6.46 (d, J=7.6 Hz, 1H), 5.07 (s, 2H), 4.87 (t, J=6.0 Hz, 1H), 2.82-2.70 (m, 2H), 0.86 (s, 9H), 0.07 (s, 3H), −0.06 (s, 3H).

Step 3: Epoxide ring opening of 2,2-dipropyloxirane with 3-(3-aminophenyl)-3-(tert-butyldimethylsilyloxy)propanenitrile following the method used in Example 67 gave 3-(tert-butyldimethylsilyloxy)-3-(3-((1-hydroxycyclohexyl)methylamino)phenyl)propanenitrile as a colorless oil. Yield (1.5 g, 56%); $^1$H NMR (400 MHz, DMSO-d$_6$) δ 7.01 (t, J=7.6 Hz, 1H), 6.63 (s, 1H), 6.57 (d, J=7.6 Hz, 1H), 6.52 (d, J=7.6 Hz, 1H), 5.22 (t, J=5.2 Hz, 1H), 4.91 (t, J=6.4 Hz, 1H), 4.21 (s, 1H), 2.84 (d, J=5.6 Hz, 2H), 2.78-2.75 (m, 2H), 1.77-1.39 (m, 10H), 0.87 (s, 9H), 0.05 (s, 3H), −0.05 (s, 3H).

Step 4: BH$_3$-Me$_2$S reduction of 3-(tert-butyldimethylsilyloxy)-3-(3-((1-hydroxycyclohexyl)methylamino)phenyl)propanenitrile following the method used in Example 11 gave crude 1-((3-(3-amino-1-hydroxypropyl)phenylamino)methyl)cyclohexanol hydrochloride which was taken directly into the next step.

Step 5: Boc protection of 1-((3-(3-amino-1-hydroxypropyl)phenylamino)methyl)cyclohexanol hydrochloride following the method used in Example 11 gave tert-butyl 3-hydroxy-3-(3-((1-hydroxycyclohexyl)methyl-amino)phenyl)propylcarbamate as a colorless oil. Yield (0.6 g, 29%, after two steps); $^1$H NMR (400 MHz, DMSO-d$_6$) δ 6.96 (t, J=7.6 Hz, 1H), 6.57 (s, 1H), 6.48-6.44 (m, 2H), 5.09 (t, J=5.6 Hz, 1H), 5.0 (d, J=4.4 Hz, 1H), 4.38-4.37 (m, 1H), 4.17 (s, 1H), 2.95-2.91 (m, 4H), 1.65-1.61 (m, 2H), 1.57-1.52 (m, 5H), 1.41-1.36 (m, 5H), 1.36 (s, 9H).

Step 6: tert-Butyl 3-hydroxy-3-(3-((1-hydroxycyclohexyl)methylamino)phenyl)propylcarbamate was deprotected following the method used in Example 24. Purification by column chromatography (5% NH$_4$OH/10% MeOH/CH$_2$Cl$_2$) gave Example 55 as a pale yellow oil. Yield (0.3 g, 86%); $^1$H NMR (400 MHz, CD$_3$OD) δ 7.08 (t, J=7.6 Hz, 1H), 6.69 (s, 1H), 6.61 (d, J=7.6 Hz, 1H), 6.59 (d, J=7.6 Hz, 1H), 4.76-4.66 (m, 1H), 3.07 (s, 2H), 3.05-2.97 (m, 2H), 2.03-1.96 (m, 2H), 1.68-1.61 (m, 5H), 1.59-1.49 (m, 5H); RP-HPLC (Method 6) t$_R$=4.06 min, 88.6% (AUC); ESI MS m/z 279.30 [M+H]$^+$.

Example 56

Preparation of 3-amino-1-(3-((1-hydroxycyclohexyl)methylamino)phenyl)propan-1-one

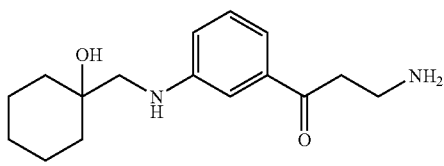 [SMILES: NCCC(=O)c1cccc(NCC2(O)CCCCC2)c1]

3-Amino-1-(3-((1-hydroxycyclohexyl)methylamino)phenyl)propan-1-one is prepared following the method used in Example 54.

Step 1: Protection of Example 55 with Boc₂O gives tert-butyl 3-hydroxy-3-(3-((1-hydroxycyclohexyl)methylamino)phenyl)propylcarbamate.

Step 2: Oxidation of tert-butyl 3-hydroxy-3-(3-((1-hydroxycyclohexyl)methylamino)phenyl)propylcarbamate following the method used in Example 12 gives tert-butyl 3-oxo-3-(3-((1-hydroxycyclohexyl)methylamino)phenyl) propylcarbamate.

Step 3: Deprotection of tert-butyl 3-oxo-3-(3-((1-hydroxycyclohexyl)methylamino)phenyl)propylcarbamate following the method used in Example 12 gives Example 56 hydrochloride.

Example 57

Preparation of N-(3-(3-amino-2,2-dideutero-1-Hydroxypropyl)phenyl)cyclhexanecarboxamide

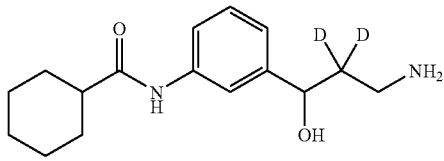

N-(3-(3-amino-2,2-dideutero-1-hydroxypropyl)phenyl) cyclohexanecarboxamide was prepared following the methods used in Examples 82, 5, 115, 15, 12.

Step 1: Hydrogenation of 2,2-dideutero-3-hydroxy-3-(3-nitrophenyl)propanenitrile was done following the method used in Example 5 for 48 hrs to give crude 3-(3-aminophenyl)-2,2-dideutero-3-hydroxypropanenitrile as a colorless oil which was directly used in the next step without further purification.

Step 2: BH₃-Me₂S reduction of crude 3-(3-aminophenyl)-2,2-dideutero-3-hydroxypropanenitrile following the method used in Example 115 gave 3-amino-1-(3-aminophenyl)-2,2-dideuteropropan-1-ol hydrochloride as a colorless oil which was directly used in the next step without further purification.

Step 3: Boc protection of 3-amino-1-(3-aminophenyl)-2,2-dideuteropropan-1-ol hydrochloride following the method used in Example 15 gave, after purification by column chromatography (66% to 75% EtOAc—hexanes gradient) tert-butyl (3-(3-aminophenyl)-2,2-dideutero-3-hydroxypropyl) carbamate as a colorless oil. Yield (0.500 g, 18% after 3 steps); ¹H NMR (400 MHz, DMSO-d₆) δ 6.90 (t, J=7.6 Hz, 1H), 6.69 (t, J=5.6 Hz, 1H), 6.50 (t, J=1.6 Hz, 1H), 6.36-6.41 (m, 2H), 4.96 (d, J=4.0 Hz, 1H), 4.94 (s, 2H), 4.33 (d, J=4.0 Hz, 1H), 2.91 (t, J=4.8 Hz, 2H), 1.32 (s, 9H).

Step 4: Reaction between tert-butyl (3-(3-aminophenyl)-2,2-dideutero-3-hydroxypropyl)carbamate and chloride 36 following the method used in Example 15 gave tert-butyl (3-(3-(cyclohexanecarboxamido)phenyl)-2,2-dideutero-3-hydroxypropyl)carbamate. Yield (0.230 g, 65%); ¹H NMR (400 MHz, DMSO-d₆) δ 9.73 (s, 1H), 7.54 (s, 1H), 7.43 (d, J=8.8 Hz, 1H), 7.16 (t, J=7.6 Hz, 1H), 6.91 (t, J=5.6 Hz, 1H), 6.73 (t, J=5.6 Hz, 1H), 5.16 (d, J=4.0 Hz, 1H), 4.44 (d, J=4.4 Hz, 1H), 2.92 (d, J=5.6 Hz, 2H), 2.24-2.32 (m, 1H), 1.58-1.80 (m, 6H), 1.30-1.41 (m, 11H), 1.12-1.28 (m, 3H).

Step 5: Deprotection of tert-butyl (3-(3-(cyclohexanecarboxamido)phenyl)-2,2-dideutero-3-hydroxypropyl)carbamate following the method used in Example 12 gave Example 57 hydrochloride as a white solid. Yield (0.170 g, 89%); ¹H NMR (400 MHz, CD₃OD) δ 7.01 (d, J=2.4 Hz, 1H), 7.26-7.33 (m, 2H), 7.09-7.11 (m, 1H), 4.78 (s, 1H), 2.99-3.11 (m, 2H), 2.31-2.40 (m, 1H), 1.81-1.84 (m, 4H), 1.68-1.76 (m, 1H), 1.46-1.57 (m, 2H), 1.22-1.42 (m, 3H).

Example 58

Preparation of N-(3-(3-amino-2,2-dideutero-1-Hydroxypropyl)phenyl)cyclohexanesulfonamide

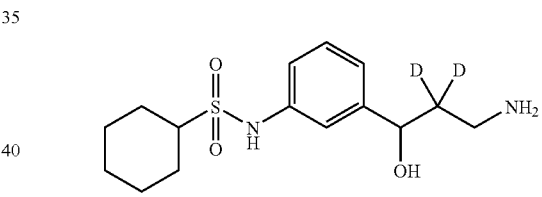

N-(3-(3-amino-2,2-dideutero-1-hydroxypropyl)phenyl) cyclohexanesulfonamide was prepared following the method used in Examples 57, 5.

Step 1: Sulfonation of tert-butyl (3-(3-aminophenyl)-2,2-dideutero-3-hydroxypropyl)carbamate by sulfonyl chloride 8 following the method used in Example 5 gave, after purification by column chromatography (EtOAc—hexanes, 2:1) tert-butyl (3-(3-(cyclohexanesulfonamido)phenyl)-2,2-dideutero-3-hydroxypropyl)carbamate as a colorless oil. Yield (0.170 g, 44%); ¹H NMR (400 MHz, DMSO-d₆) δ 9.66 (s, 1H), 7.16-7.22 (m, 2H), 6.99-7.06 (m, 1H), 6.97 (d, J=8.0 Hz, 1H), 6.73 (t, J=5.6 Hz, 1H), 5.20 (d, J=4.4 Hz, 1H), 4.47 (d, J=4.4 Hz, 1H), 2.86-2.95 (m, 3H), 1.96-1.98 (m, 2H), 1.68-1.76 (m, 2H), 1.51-1.58 (m, 1H), 1.25-1.42 (m, 11H), 1.02-1.18 (m, 3H).

Step 2: Step 3: Deprotection of tert-butyl (3-(3-(cyclohexanesulfonamido)phenyl)-2,2-dideutero-3-hydroxypropyl) carbamate following the method used in Example 57 gave Example 58 hydrochloride as a white solid. Yield (0.188 g, quant.); ¹H NMR (400 MHz, CD₃OD) δ 7.35 (t, J=2.0 Hz, 1H), 7.29 (t, J=8.0 Hz, 1H), 7.09-7.12 (m, 2H), 2.92-3.11 (m, 3H), 2.07-2.22 (m, 2H), 1.80-1.88 (m, 2H), 1.62-1.68 (m, 1H), 1.46-1.58 (m, 2H), 1.14-1.28 (m, 3H).

Example 59

Preparation of 3-amino-1-(3-(3-phenylpropylamino)phenyl)propan-1-ol

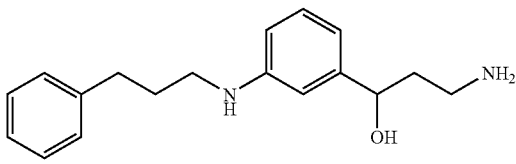 [SMILES: NCCC(O)c1cccc(NCCCc2ccccc2)c1]

3-Amino-1-(3-(3-phenylpropylamino)phenyl)propan-1-ol was prepared following the method used in Example 11.

Step 1: Hydrogenation of nitrobenzene 11 and 3-phenylpropanal gave 3-hydroxy-3-(3-(3-phenylpropylamino)phenyl)propanenitrile as a yellow oil. Yield (1.0 g, 68%); $^1$H NMR (400 MHz, CDCl$_3$) δ 7.32-7.28 (m, 2H), 7.22-7.18 (m, 3H), 7.16-7.14 (m, 1H), 6.66 (d, J=7.6 Hz, 1H), 6.57 (s, 1H), 6.53 (d, J=8.0 Hz, 1H), 4.93 (m, 1H), 3.73 (bs, 1H), 3.15 (t, J=7.2 Hz, 2H), 2.75-2.72 (m, 4H), 2.22 (d, J=3.2 Hz, 1H), 1.99-1.92 (quintet, J=7.2 Hz, 2H).

Step 2: BH$_3$-Me$_2$S reduction of 3-hydroxy-3-(3-(3-phenylpropylamino)phenyl)propanenitrile gave Example 59 hydrochloride as a yellow solid. Yield (0.85 g, 84%); $^1$H NMR (400 MHz, DMSO-d$_6$+5% D$_2$O) δ 7.38 (t, J=8.0 Hz, 1H), 7.29-7.23 (m, 3H), 7.18 (d, J=7.2 Hz, 4H), 7.13 (d, J=7.6 Hz, 1H), 4.69-4.66 (m, 1H), 3.19 (t, J=8.0 Hz, 2H), 2.85 (m, 2H), 2.65 (t, J=7.6 Hz, 2H), 1.94-1.81 (m, 4H); RP-HPLC (Method 5) $t_R$=5.04 min, 94.44% (AUC); ESI MS m/z 285.38 [M+H]$^+$.

Example 60

Preparation of 3-amino-1-(3-(3-phenylpropylamino)phenyl)propan-1-one

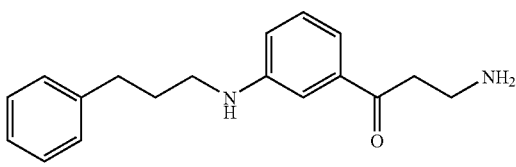 [SMILES: NCCC(=O)c1cccc(NCCCc2ccccc2)c1]

3-Amino-1-(3-(3-phenylpropylamino)phenyl)propan-1-one was prepared following the method used in Example 52.

Step 1: Protection of Example 59 with Boc$_2$O gave a mixture of tert-butyl (3-hydroxy-3-(3-((3-phenylpropyl)amino)phenyl)propyl)carbamate and tert-butyl (3-(3-((tert-butoxycarbonyl)amino)-1-hydroxypropyl)phenyl)(3-phenylpropyl)carbamate which was directly used in the next step without purification.

Step 2: Oxidation of the above mixture gave a mixture of tert-butyl (3-oxo-3-(3-((3-phenylpropyl)amino)phenyl)propyl)carbamate and tert-butyl (3-(3-((tert-butoxycarbonyl)amino)propanoyl)phenyl)(3-phenylpropyl)carbamate which was directly used in the next step without purification.

Step 3: Deprotection of the above mixture gave Example 60 hydrochloride as an off-white solid. Yield (0.30 g, 51%); $^1$H NMR (400 MHz, DMSO-d$_6$+5% D$_2$O) δ 7.61-7.59 (m, 2H), 7.48 (t, J=8.0 Hz, 1H), 7.33 (d, J=8.0 Hz, 1H), 7.28-7.25 (m, 2H), 7.20-7.15 (m, 3H), 3.37 (t, J=6.0 Hz, 2H), 3.19-3.11 (m, 4H), 2.66 (t, J=7.6 Hz, 2H), 1.93-1.87 (quintet, J=7.2 Hz, 2H). RP-HPLC (Method 5) $t_R$=4.45 min, 96.38% (AUC); ESI MS m/z 283.25 [M+H]$^+$.

Example 61

Preparation of 3-amino-1-(3-((4,4-difluorocyclohexyl)methylamino)phenyl)propan-1-ol

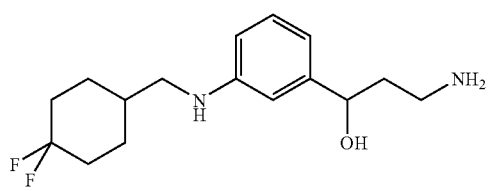 [SMILES: NCCC(O)c1cccc(NCC2CCC(F)(F)CC2)c1]

3-Amino-1-(3-((4,4-difluorocyclohexyl)methylamino)phenyl)propan-1-ol is prepared following the method used in Example 37.

Step 1: Hydrogenation of nitrobenzene 11 and 4,4-difluorocyclohexanecarbaldehyde gives 3-(3-((4,4-difluorocyclohexyl)methylamino)phenyl)-3-hydroxypropanenitrile.

Step 2: BH$_3$-Me$_2$S reduction of 3-((4,4-difluorocyclohexyl)methylamino)phenyl)-3-hydroxypropanenitrile gives Example 61.

Example 62

Preparation of 3-amino-1-(3-((4,4-difluorocyclohexyl)methylamino)phenyl)propan-1-one

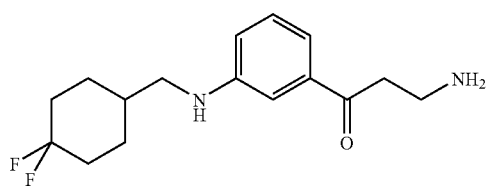 [SMILES: NCCC(=O)c1cccc(NCC2CCC(F)(F)CC2)c1]

3-Amino-1-(3-((4,4-difluorocyclohexyl)methylamino)phenyl)propan-1-one is prepared following the method used in Example 38.

Step 1: Protection of Example 61 with Boc$_2$O gives tert-butyl 3-(3-((4,4-difluorocyclohexyl)methylamino)phenyl)-3-hydroxypropylcarbamate.

Step 2: Oxidation tert-butyl 3-(3-((4,4-difluorocyclohexyl)methylamino)phenyl)-3-hydroxypropylcarbamate by MnO$_2$ gives tert-butyl 3-(3-((4,4-difluorocyclohexyl)methylamino)phenyl)-3-oxopropylcarbamate.

Step 3: Deprotection of tert-butyl 3-(3-((4,4-difluorocyclohexyl)methylamino)phenyl)-3-oxopropylcarbamate gives Example 62 hydrochloride.

Example 63

Preparation of 3-(3-aminopropyl)-N-((4,4-difluorocyclohexyl)methyl)aniline

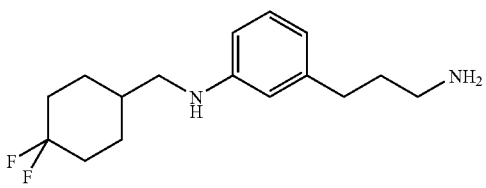 [SMILES: NCCCc1cccc(NCC2CCC(F)(F)CC2)c1]

3-(3-Aminopropyl)-N-((4,4-difluorocyclohexyl)methyl)aniline is prepared following the method used in Example 31.

Step 1: Hydrogenation of nitrobenzene 40 and 4,4-difluorocyclohexanecarbaldehyde gives 2-(3-(3-((4,4-difluorocyclohexyl)methylamino)phenyl)propyl)isoindoline-1,3-dione.

Step 2: Deprotection of 2-(3-(3-((4,4-difluorocyclohexyl)methylamino)phenyl)propyl)isoindoline-1,3-dione gives Example 63.

Example 64

Preparation of 3-(3-aminopropyl)-N-(3-phenylpropyl)aniline E

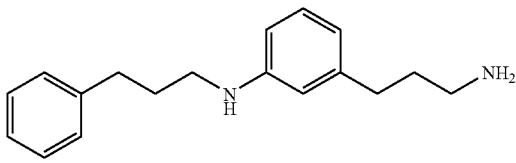 [SMILES: NCCCc1cccc(NCCCc2ccccc2)c1]

3-(3-Aminopropyl)-N-(3-phenylpropyl)aniline was prepared following the method used in Example 33.

Step 1: A mixture of 2,2,2-trifluoro-N-(3-(3-nitrophenyl)allyl)acetamide (1.0 g, 3.6 mmol) and 3-phenylpropanal (0.48 g, 3.6 mmol) in EtOAc was degassed and saturated with argon. 10% Pd/C (500 mg) was added to this solution and the resulting mixture was stirred under $H_2$ at 1 atm for 16 hrs, filtered through Celite, and concentrated under reduced pressure. Purification by flash chromatography (40% to 50% EtOAc—hexanes gradient) gave 2,2,2-trifluoro-N-(3-(3-(3-phenylpropylamino)phenyl)propyl)acetamide as a colorless semi-solid. Yield (0.54 g, 41%). $^1$H NMR (400 MHz, DMSO-$d_6$) δ 9.41 (br.s, 1H), 7.30-7.17 (m, 5H) 6.95 (t, J=7.6 Hz, 1H), 6.36-6.34 (m, 3H), 5.50 (t, J=5.6 Hz, 1H), 3.18 (q, J=6.4 Hz, 2H), 2.98 (q, J=6.4 Hz, 2H), 2.67 (t, J=8.0 Hz, 2H), 2.43 (t, J=7.6 Hz, 2H), 1.82 (quintet, J=7.6 Hz, 2H), 1.73 (quintet, J=7.6 Hz, 2H).

Step 2: A mixture of 2,2,2-trifluoro-N-(3-(3-(3-phenylpropylamino)phenyl)propyl)acetamide (0.54 g, 1.4 mmol) and $K_2CO_3$ (0.73 g, 5.3 mmol) in MeOH:$H_2O$ was stirred at room temperature for 24 hours. The solvent was removed under reduced pressure. Purification by flash chromatography (5% to 6% MeOH—$CH_2Cl_2$ gradient) gave Example 64 as a light green solid. Yield (0.22 g, 55%); $^1$H NMR (400 MHz, DMSO-$d_6$) δ 7.28-7.20 (m, 4H), 7.17 (t, J=7.2 Hz, 1H), 6.94 (t, J=7.6 Hz, 1H), 6.35-6.32 (m, 3H), 5.54 (t, J=5.6 Hz, 1H), 2.96 (q, J=6.4 Hz, 2H), 2.70-2.63 (m, 4H), 2.47-2.43 (m, 2H), 1.80 (quintet, J=7.6 Hz, 2H), 1.73 (quintet, J=7.6 Hz, 2H); RP-HPLC (Method-3) $t_R$=3.95 min, 94.30% (AUC); ESI MS m/z 269.25 [M+H]$^+$.

Example 65

Preparation of 3-(3-aminopropyl)-N-(5-methoxypentyl)aniline

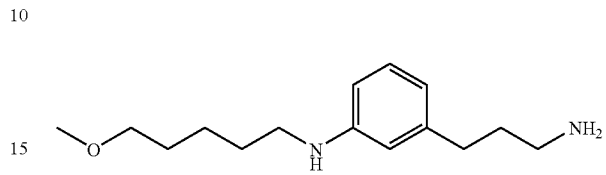

3-(3-Aminopropyl)-N-(5-methoxypentyl)aniline is prepared following the method used in Example 31.

Step 1: Hydrogenation of nitrobenzene 40 and 5-methoxypentanal gives 2-(3-(3-(5-methoxypentylamino)phenyl)propyl)isoindoline-1,3-dione.

Step 2: Deprotection of 2-(3-(3-(5-methoxypentylamino)phenyl)propyl)isoindoline-1,3-dione gives Example 65.

Example 66

Preparation of 5-(3-(3-aminopropyl)phenylamino)pentan-1-ol

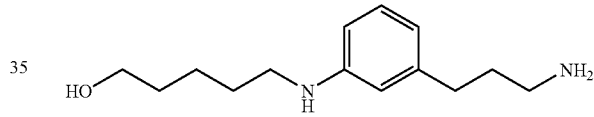

5-(3-(3-Aminopropyl)phenylamino)pentan-1-ol is prepared following the method used in Example 31.

Step 1: Hydrogenation of nitrobenzene 40 and 5-hydroxypentanal gives 2-(3-(3-(5-hydroxypentylamino)phenyl)propyl)isoindoline-1,3-dione.

Step 2: Deprotection of 2-(3-(3-(5-hydroxypentylamino)phenyl)propyl)isoindoline-1,3-dione gives Example 66.

Example 67

Preparation of 4-((3-(3-aminopropyl)phenylamino)methyl)heptan-4-ol

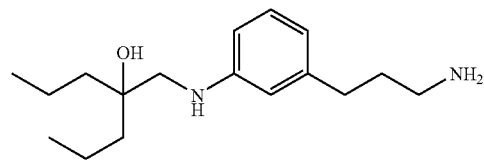 [SMILES: CCCC(O)(CCC)CNc1cccc(CCCN)c1]

4-((3-(3-Aminopropyl)phenylamino)methyl)heptan-4-ol was prepared following the method described below.

Step 1: To a stirred solution of 2-(3-(3-aminophenyl)propyl)isoindoline-1,3-dione (0.50 g, 1.78 mmol) in EtOH:$H_2O$ (9:1), 2,2-dipropyloxirane (0.45 g, 3.57 mmol) was added and the reaction mixture was stirred under reflux for 36 h. The reaction mixture was concentrated under reduced pressure.

Purification by column chromatography (20% to 30% EtOAc—hexanes gradient) gave 2-(3-(3-(2-hydroxy-2-propylpentylamino)phenyl)propyl)isoindoline-1,3-dione as a yellow semisolid. Yield (0.22 g, 30%); $^1$H NMR (400 MHz, DMSO-$d_6$) δ 7.86-7.81 (m, 4H), 6.92 (t, J=7.8 Hz, 1H), 6.45 (s, 1H), 6.41 (d, J=8.0 Hz, 1H), 6.37 (d, J=7.6 Hz, 1H), 4.89 (bs, 1H), 4.16 (s, 1H), 3.59 (t, J=7.2 Hz, 2H), 2.87 (d, J=5.2, 2H), 2.46-2.50 (m, 2H), 1.83-1.90 (quintet, J=7.2 Hz, 2H), 1.42-1.38 (m, 4H), 1.28-1.24 (m, 4H), 0.84 (t, J=7.2 Hz, 6H).

Step 2: A mixture of 2-(3-(3-(2-hydroxy-2-propylpentylamino)phenyl)propyl)isoindoline-1,3-dione (0.22 g, 0.71 mmol) and hydrazine hydrate (0.1 ml, 1.6 mmol) in ethanol was stirred at room temperature for 24 hours. The solvent was evaporated under reduced pressure. Purification by column chromatography (5% to 10% MeOH—CH$_2$Cl$_2$ gradient) gave 4-((3-(3-aminopropyl)phenylamino)methyl)heptan-4-ol as a light yellow semisolid. Yield (0.06 g, 18%); $^1$H NMR (400 MHz, DMSO-$d_6$) δ 6.93 (t, J=7.6 Hz, 1H), 6.44-6.41 (m, 2H), 6.35 (d, J=7.6 Hz, 1H), 4.92 (t, J=5.2 Hz, 1H), 4.19 (bs, 1H), 2.87 (d, J=5.2 Hz, 2H), 2.54-2.50 (m, 2H), 2.44 (t, J=7.6 Hz, 2H), 1.55-1.62 (quintet, J=7.2 Hz, 2H), 1.42-1.33 (m, 4H), 1.32-1.27 (m, 4H), 0.85 (t, J=7.2 Hz, 6H); RP-HPLC (Method 3) $t_R$=4.44 min, 97.48% (AUC); ESI MS m/z 279.31 [M+H]$^+$.

Example 68

Preparation of 3-((3-(3-aminopropyl)phenylamino)methyl)pentan-3-ol

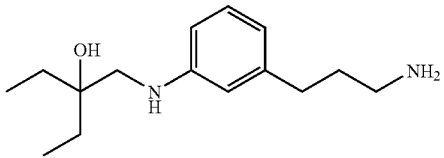 [SMILES: CCC(O)(CC)CNc1cccc(CCCN)c1]

3-((3-(3-Aminopropyl)phenylamino)methyl)pentan-3-ol is prepared following the method used in Example 67.

Step 1: Reaction between 2,2-diethyloxirane and 2-(3-(3-aminophenyl)propyl)isoindoline-1,3-dione gives 2-(3-(3-((2-ethyl-2-hydroxybutyl)amino)phenyl)propyl)isoindoline-1,3-dione.

Step 2: Deprotection of 2-(3-(3-((2-ethyl-2-hydroxybutyl)amino)phenyl)propyl)isoindoline-1,3-dione gives Example 68.

Example 69

Preparation of 1-((3-(3-aminopropyl)phenylamino)methyl)cyclohexanol

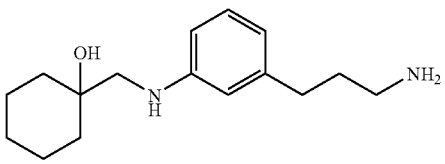 [SMILES: NCCCc1cccc(NCC2(O)CCCCC2)c1]

1-((3-(3-Aminopropyl)phenylamino)methyl)cyclohexanol was prepared following the method used in Example 29.

Step 1: Epoxide ring opening of 1-oxaspiro[2.5]octane with N-(3-(3-aminophenyl)propyl)-2,2,2-trifluoroacetamide gave 2,2,2-trifluoro-N-(3-(3-((1-hydroxycyclohexyl)methylamino)phenyl)propyl)acetamide as a colorless oil. Yield (0.8 g, 46%); $^1$H NMR (400 MHz, DMSO-$d_6$) δ 9.42 (bs, 1H), 6.94 (t, J=8.0 Hz, 1H), 6.44-6.37 (m, 2H), 6.35-6.33 (d, J=7.6 Hz, 1H), 5.07 (t, J=5.6 Hz, 1H), 4.18 (s, 1H), 3.18 (q, J=6.4 Hz, 2H), 2.91 (d, J=5.6 Hz, 2H), 2.44-2.42 (m, 2H), 1.76-1.70 (m, 2H), 1.58-1.49 (m, 6H), 1.41-1.27 (m, 4H).

Step 2: A mixture of 2,2,2-trifluoro-N-(3-(3-((1-hydroxycyclohexyl)methylamino)phenyl)propyl)acetamide 2 (0.7 g, 1.9 mmol) and K$_2$CO$_3$ (0.815 g, 5.8 mmol) in MeOH:H$_2$O (1:1) was stirred at room temperature for 16 h. The solvent was evaporated under reduced pressure. The residue was partitioned between DCM and water. Aqueous layer was extracted five times with DCM. Combined organic layers were dried over anhydrous sodium sulfate and concentrated under reduced pressure. Purification by flash chromatography (5% to 6% MeOH—DCM+5% NH$_4$OH) gave crude which was dissolved in dioxane and stirred with 4M HCl in Dioxane. The mixture was concentrated under reduced pressure and triturated with diethyl ether to give Example 69 hydrochloride as a white solid. Yield (0.32 g, 56%); $^1$H NMR (400 MHz, DMSO-$d_6$) δ 7.76 (m, 3H), 6.96 (t, J=7.6 Hz, 1H), 6.45 (m, 2H), 6.34 (d, J=7.6 Hz, 1H), 5.13 (t, J=5.6 Hz, 1H), 4.20 (s, 1H), 2.91 (d, J=5.6 Hz, 2H), 2.76 (t, J=7.6 Hz, 2H), 2.50-2.46 (m, 2H), 1.83-1.75 (m, 2H), 1.69-1.56 (m, 6H), 1.53-1.38 (m, 4H); RP-HPLC (Method 6) $t_R$=4.57 min, 92.1% (AUC); ESI MS m/z 263.2 [M+H]$^+$.

Example 70

Preparation of 1-((3-(3-aminopropyl)phenylamino)methyl)cyclopentanol

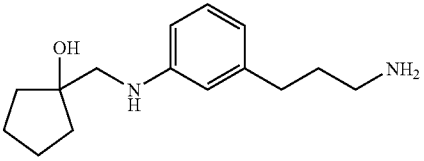 [SMILES: NCCCc1cccc(NCC2(O)CCCC2)c1]

1-((3-(3-Aminopropyl)phenylamino)methyl)cyclopentanol is prepared following the method used in Example 67.

Step 1: Reaction between 1-oxaspiro[2.4]heptane and 2-(3-(3-aminophenyl)propyl)isoindoline-1,3-dione gives 2-(3-(3-(((1-hydroxycyclopentyl)methyl)amino)phenyl)propyl)isoindoline-1,3-dione.

Step 2: Deprotection of 2-(3-(3-(((1-hydroxycyclopentyl)methyl)amino)phenyl)propyl)isoindoline-1,3-dione gives Example 68.

Example 71

Preparation of N-(3-(3-aminopropyl)phenyl)-2-propylpentanamide

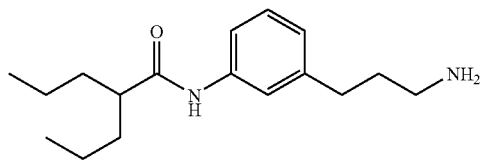 [SMILES: CCCC(CCC)C(=O)Nc1cccc(CCCN)c1]

N-(3-(3-Aminopropyl)phenyl)-2-propylpentanamide was prepared following the method described below.

Step 1: Et₃N (3.24 mL, 23.25 mmol) was added to a solution of 2-propylpentanoic acid in (2 g, 11.62 mmol) in DMF. The reaction mixture was cooled to 0° C. HATU (6.63 g, 17.4 mmol) was added to the reaction mixture which was stirred for 15 min and then 3-bromoaniline (2.5 g, 17.43 mmol) was added. The reaction mixture was stirred for 2 h at 0° C. The reaction mixture was diluted with H₂O, extracted with EtOAc, and organic layer was concentrated under reduced pressure. The residue was washed with pentane to give N-(3-bromophenyl)-2-propylpentanamide as a white solid. Yield (1.6 g, 47%); ¹H NMR (400 MHz, CDCl₃) δ 7.82 (s, 1H), 7.44 (d, J=8.0 Hz, 1H), 7.23 (d, J=7.6 Hz, 1H), 7.17 (t, J=8.0 Hz, 1H), 7.12 (bs, 1H), 2.21-2.14 (m, 1H), 1.73-1.63 (m, 2H), 1.51-1.45 (m, 2H), 1.43-1.25 (m, 4H), 0.92 (t, J=7.2 Hz, 6H).

Step 2: Et₃N (1.2 mL) was added to a solution of N-(3-bromophenyl)-2-propylpentanamide (0.6 g, 2.01 mmol), tert-butyl allylcarbamate (1.026 g, 6.55 mmol) and P(o-tol)₃ (0.06 g, 0.201 mmol) in DMF (10 mL). The reaction mixture was degassed for 30 min and then added Pd(OAc)₂ (0.09 g, 0.409 mmol) was added. The reaction mixture was again degassed for 15 min and then refluxed at 90° C. for 8 h. The reaction mixture was diluted with EtOAc, washed with H₂O, brine. The organic layer was concentrated under reduced pressure. Purification by column chromatography (100-200 mesh silica, elution 10% to 15% EtOAc in hexane) gave (E)-tert-butyl 3-(3-(2-propylpentanamido)phenyl)allylcarbamate as a yellow oil. Yield (0.7 g, 37%). ¹H NMR (400 MHz, CDCl₃) δ 7.65 (s, 1H), 7.43 (t, J=7.6 Hz, 1H), 7.24 (s, 1H), 7.08 (dd, J=1.2, 7.2 Hz, 2H), 6.48 (d, J=16.0 Hz, 1H), 6.26-6.16 (m, 1H), 4.67 (bs, 1H), 3.89 (bs, 2H), 2.17-2.04 (m, 1H), 1.73-1.64 (m, 4H), 1.48 (s, 9H), 1.45-1.14 (m, 4H), 0.91 (t, J=7.2 Hz, 6H).

Step 3: A solution of (E)-tert-butyl 3-(3-(2-propylpentanamido)phenyl)allylcarbamate (0.5 g, 1.32 mmol) in ethanol was degassed by bubbling argon for 2 min. Pd/C (10% wt, 0.5 g) was added and the reaction mixture atmosphere was changed to hydrogen by alternating between vacuum and hydrogen 2×. The reaction mixture was stirred under a H₂-filled balloon for 16 h then filtered through Celite and the filtrate was concentrated under reduced pressure. Purification by column chromatography (100-200 mesh silica, 10% to 15% EtOAc in hexane) gave compound tert-butyl 3-(3-(2-propylpentanamido)phenyl)propylcarbamate as a thick yellow oil. Yield (0.5 g, 99%); ¹H NMR (400 MHz, CDCl₃) δ 7.45 (s, 1H), 7.31 (d, J=7.6 Hz, 1H), 7.22 (t, J=8.0 Hz, 1H), 7.08 (bs, 1H), 6.93 (d, J=7.6 Hz, 1H), 4.60 (bs, 1H), 3.15-3.14 (m, 2H), 2.62 (t, J=7.2 Hz, 2H), 2.49-2.16 (m, 1H), 1.82-1.72 (m, 2H), 1.72-1.66 (m, 2H), 1.37 (s, 9H), 1.36-1.22 (m, 6H), 0.92 (t, J=7.2 Hz, 6H).

Step 4: 4M HCl/dioxane was added to a solution of tert-butyl 3-(3-(2-propylpentanamido)phenyl)propylcarbamate in DCM. The reaction mixture was stirred for 30 min. The reaction mixture was concentrated under reduced pressure to give Example 71 as a white solid. Yield (0.142 g, 41%); ¹H NMR (400 MHz, DMSO-d₆) δ 9.89 (s, 1H), 7.93 (bs, 3H), 7.58 (s, 1H), 7.39 (d, J=8.0 Hz, 1H), 7.20 (t, J=7.6 Hz, 1H), 6.88 (d, J=7.6 Hz, 1H), 2.79-2.77 (m, 2H), 2.60 (t, J=7.6 Hz, 2H), 2.42-2.38 (m, 1H), 1.83 (quintet, J=7.6 Hz, 2H), 1.56-1.48 (m, 2H), 1.37-1.19 (m, 6H), 0.86 (t, J=7.2 Hz, 6H); RP-HPLC (Method 6) t_R=5.01 min, 99.58% (AUC); ESI MS m/z 277.30 [M+H]⁺.

Example 72

Preparation of N-(3-(3-aminopropyl)phenyl)heptane-4-sulfonamide

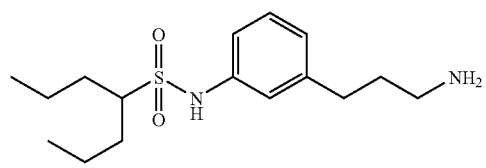 [SMILES: CCCC(CCC)S(=O)(=O)Nc1cccc(CCCN)c1]

N-(3-(3-Aminopropyl)phenyl)heptane-4-sulfonamide is prepared following the method used in Example 6.

Step 1: Sulfonation of aniline 17 by heptane-4-sulfonyl chloride following the method used in Example 6 gives tert-butyl 3-(3-(1-propylbutylsulfonamido)phenyl)propylcarbamate.

Step 2: Deprotection of tert-butyl 3-(3-(1-propylbutylsulfonamido)phenyl)propylcarbamate gave Example 72 hydrochloride.

Example 73

Preparation of N-(3-(3-amino-1-hydroxypropyl)phenyl)-2-propylpentanamide

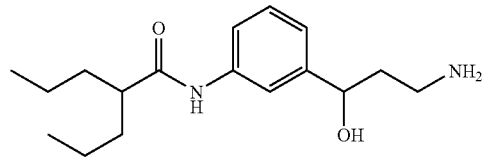 [SMILES: CCCC(CCC)C(=O)Nc1cccc(C(O)CCN)c1]

N-(3-(3-Amino-1-hydroxypropyl)phenyl)-2-propylpentanamide is prepared following the method used in Example 15.

Step 1: Acylation of aniline 35 by 2-propylpentanoyl chloride following the method used in Example 15 gives tert-butyl 3-hydroxy-3-(3-(2-propylpentanamido)phenyl)propylcarbamate.

Step 2: Deprotection of tert-butyl 3-hydroxy-3-(3-(2-propylpentanamido)phenyl)propylcarbamate gives Example 73 hydrochloride.

Example 74

Preparation of N-(3-(3-amino-1-hydroxypropyl)phenyl)heptane-4-sulfonamide

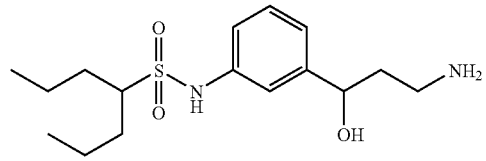 [SMILES: CCCC(CCC)S(=O)(=O)Nc1cccc(C(O)CCN)c1]

N-(3-(3-Amino-1-hydroxypropyl)phenyl)heptane-4-sulfonamide is prepared following the method used in Example 5.

Step 1: Sulfonation of aniline 35 by heptane-4-sulfonyl chloride following the method used in Example 5 gives N-(3-(2-cyano-1-hydroxyethyl)phenyl)heptane-4-sulfonamide.

Step 2: $BH_3$-$Me_2S$ reduction of N-(3-(2-cyano-1-hydroxyethyl)phenyl)heptane-4-sulfonamide following the method used in Example 5 gives Example 74.

Example 75

Preparation of N-(3-(3-aminopropanoyl)phenyl)-2-propylpentanamide

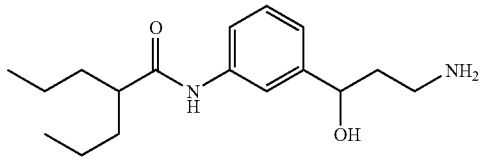

N-(3-(3-Aminopropanoyl)phenyl)-2-propylpentanamide is prepared following the method used in Examples 7316 and 12.

Step 1: Oxidation of tert-butyl 3-hydroxy-3-(3-(2-propylpentanamido)phenyl)propylcarbamate by PCC following the method used in Example 16 gives tert-butyl 3-oxo-3-(3-(2-propylpentanamido)phenyl)propylcarbamate.

Step 2: tert-Butyl 3-oxo-3-(3-(2-propylpentanamido)phenyl)propylcarbamate is deprotected following the method used in Example 12 to give Example 75 hydrochloride.

Example 76

Preparation of N-(3-(3-aminopropanoyl)phenyl)heptane-4-sulfonamide

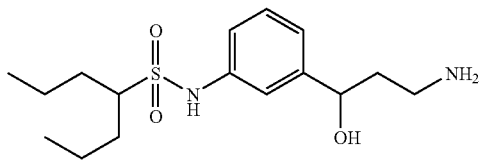

N-(3-(3-Aminopropanoyl)phenyl)heptane-4-sulfonamide is prepared following the methods used in Examples 20, 16, 12.

Step 1: Protection of Example 74 with $Boc_2O$ following the method used in Example 20 gives tert-butyl 3-hydroxy-3-(3-(1-propylbutylsulfonamido)phenyl)propylcarbamate.

Step 2: Oxidation of tert-butyl 3-hydroxy-3-(3-(1-propylbutylsulfonamido)phenyl)propylcarbamate by PCC following the method used in Example 16 gives tert-butyl 3-oxo-3-(3-(1-propylbutylsulfonamido)phenyl)propylcarbamate.

Step 3: Deprotection of tert-butyl 3-oxo-3-(3-(1-propylbutylsulfonamido)phenyl)propylcarbamate following the method used in Example 12 gives Example 76 hydrochloride.

Example 77

Preparation of 3-((3-(3-amino-1-hydroxypropyl)phenylamino)methylpentan-3-ol

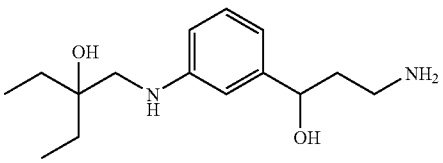 [SMILES: CCC(O)(CC)CNc1cccc(C(O)CCN)c1]

3-((3-(3-Amino-1-hydroxypropyl)phenylamino)methyl)pentan-3-ol is prepared following the method used in Example 53.

Step 1: Reaction between 2,2-diethyloxirane and aniline 12 gives 3-(3-(2-ethyl-2-hydroxybutylamino)phenyl)-3-hydroxypropanenitrile.

Step 2: $BH_3$-$Me_2S$ reduction of 3-(3-(2-ethyl-2-hydroxybutylamino)phenyl)-3-hydroxypropanenitrile gives Example 77.

Example 78

Preparation of 1-(3-(3-amino-1-hydroxypropyl)phenylamino)methyl)cyclopentanol

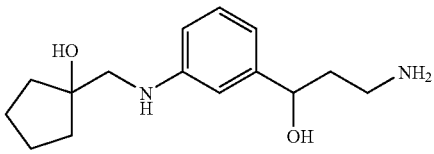 [SMILES: NCCC(O)c1cccc(NCC2(O)CCCC2)c1]

1-((3-(3-Amino-1-hydroxypropyl)phenylamino)methyl)cyclopentanol is prepared following the method used in Example 53.

Step 1: Reaction between 1-oxaspiro[2.4]heptane and aniline 12 gives 3-hydroxy-3-(3-((1-hydroxycyclopentyl)methylamino)phenyl)propanenitrile.

Step 2: $BH_3$-$Me_2S$ reduction of 3-hydroxy-3-(3-((1-hydroxycyclopentyl)methylamino)phenyl)propanenitrile gives Example 78.

Example 79

Preparation of 3-amino-1-(3-(2-ethyl-2-hydroxybutylamino)phenyl)propan-1-one

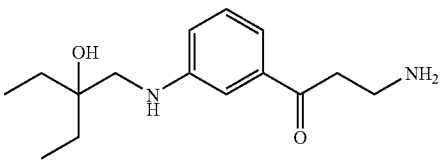 [SMILES: CCC(O)(CC)CNc1cccc(C(=O)CCN)c1]

3-Amino-1-(3-(2-ethyl-2-hydroxybutylamino)phenyl)propan-1-one is prepared following the method used in Example 40.

Step 1: Protection of Example 77 with Boc₂O gives tert-butyl 3-(3-(2-ethyl-2-hydroxybutylamino)phenyl)-3-hydroxypropylcarbamate.

Step 2: Oxidation of tert-butyl 3-(3-(2-ethyl-2-hydroxybutylamino)phenyl)-3-hydroxypropylcarbamate gives tert-butyl 3-(3-(2-ethyl-2-hydroxybutylamino)phenyl)-3-oxopropylcarbamate.

Step 3: Deprotection of tert-butyl 3-(3-(2-ethyl-2-hydroxybutylamino)phenyl)-3-oxopropylcarbamate gives Example 79 hydrochloride.

Example 80

Preparation of 3-amino-1-(3-((1-hydroxycyclopentyl)methylamino)phenyl)propan-1-one

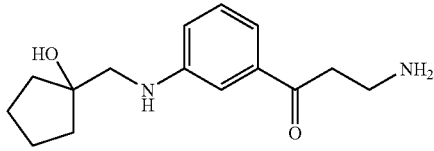 [SMILES: NCCC(=O)c1cccc(NCC2(O)CCCC2)c1]

3-Amino-1-(3-((1-hydroxycyclopentyl)methylamino)phenyl)propan-1-one is prepared following the method used in Example 40.

Step 1: Protection of Example 78 with Boc₂O gives tert-butyl 3-hydroxy-3-(3-((1-hydroxycyclopentyl)methylamino)phenyl)propylcarbamate.

Step 2: Oxidation of tert-butyl 3-hydroxy-3-(3-((1-hydroxycyclopentyl)methylamino)phenyl)propylcarbamate gives tert-butyl 3-oxo-3-(3-((1-hydroxycyclopentyl)methylamino)phenyl)propylcarbamate.

Step 3: Deprotection of tert-butyl 3-oxo-3-(3-((1-hydroxycyclopentyl)methylamino)phenyl)propylcarbamate gives Example 80 hydrochloride.

Example 81

Preparation of 3-amino-1-(3-(cyclohexylmethylamino)phenyl)-1-deuteropropan-1-ol

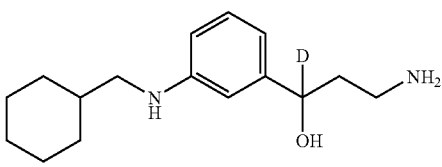

3-Amino-1-(3-(cyclohexylmethylamino)phenyl)-1-deuteropropan-1-ol was prepared following the method used in Example 20.

Step 1: NaBD₄ (0.08 g, 0.94 mmol) was added at 0° C. to a solution of ketone 33 (0.19 g. 0.47 mmol) in i-PrOH. The reaction mixture was stirred at 0° C. for 2 hr and then at room temperature for 3 hrs. The reaction mixture was partitioned between aqueous NH₄Cl and ethyl acetate, dried over anhydrous Na₂SO₄ and concentrated under reduced pressure to give tert-butyl 3-(3-(cyclohexylmethylamino)phenyl)-3-deutero-3-hydroxypropylcarbamate as a colorless oil which was used directly in the next step.

Step 2: Deprotection of tert-butyl 3-(3-(cyclohexylmethylamino)phenyl)-3-deutero-3-hydroxypropylcarbamate following the method used in Example 20 gave Example 81 as a white solid. Yield (0.14 g, quant); ¹H NMR (400 MHz, DMSO-d₆+5% D₂O) δ 7.25 (t, J=8.0 Hz, 1H), 7.12 (br. s, 1H), 6.91-6.97 (m, 2H), 2.96 (d, J=6.8 Hz, 1H), 2.78-2.86 (m, 2H), 1.42-1.86 (m, 8H), 0.88-1.18 (m, 5H).

Example 82

Preparation of 3-amino-1-(3-(cyclohexylmethylamino)phenyl)-2,2-dideuteropropan-1-ol

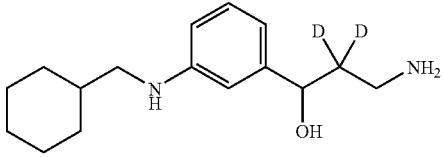 [SMILES: [2H]C([2H])(CN)C(O)c1cccc(NCC2CCCCC2)c1]

3-Amino-1-(3-(cyclohexylmethylamino)phenyl)-2,2-dideuteropropan-1-ol was prepared following the method used in Examples 5 and 11.

Step 1: Addition of CD₃CN to aldehyde 10 following the method described in Example 5 gave 2,2-dideutero-3-hydroxy-3-(3-nitrophenyl)propanenitrile as a light yellow solid. Yield (2.5 g, 39%); ¹H NMR (400 MHz, CD₃OD) δ 8.34 (t, J=1.6 Hz, 1H), 8.16-8.19 (m, 1H), 7.82-7.84 (m, 1H), 7.62 (t, J=8.0 Hz, 1H), 5.10 (s, 1H).

Step 2: Hydrogenation of 2,2-dideutero-3-hydroxy-3-(3-nitrophenyl)propanenitrile with aldehyde 29 following the method described in Example 11 gave 3-(3-(cyclohexylmethylamino)phenyl)-2,2-dideutero-3-hydroxypropanenitrile as a colorless oil. Yield (0.46 g, 68%); ¹H NMR (400 MHz, DMSO-d₆) δ 6.97 (t, J=8.0 Hz, 1H), 6.56 (t, J=1.2 Hz, 1H), 6.47 (d, J=7.6 Hz, 1H), 6.42 (dd, J=8.0, 1.6 Hz, 1H), 5.71 (d, J=4.4 Hz, 1H), 5.57 (t, J=6.0 Hz, 1H), 4.68 (d, J=4.4 Hz, 1H), 2.80 (t, J=6.0 Hz, 2H), 1.44-1.78 (m, 6H), 1.08-1.21 (m, 3H), 0.84-0.96 (m, 2H).

Step 3: BH₃-Me₂S reduction of 3-(3-(cyclohexylmethylamino)phenyl)-2,2-dideutero-3-hydroxypropanenitrile following the method described in Example 11 gave Example 82.

Example 83

Preparation of 3-amino-1-(3-(cyclohexylmethylamino)phenyl)-3,3-dideuteropropan-1-ol

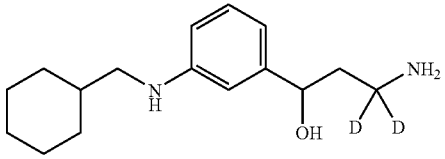 [SMILES: [2H]C([2H])(N)CC(O)c1cccc(NCC2CCCCC2)c1]

3-Amino-1-(3-(cyclohexylmethylamino)phenyl)-3,3-dideuteropropan-1-ol was prepared following the method used in Example 20.

Step 1: LiAlD₄ (0.012 g, 2.88 mmol) was added to a solution of nitrile 30 (0.5 g, 1.92 mmol) in ether was added LiAlD₄ (0.012 g, 2.88 mmol) at 0° C. The reaction mixture was stirred at ° C. for 2 hr. The reaction was quenched by slow addition of aqueous Na$_2$SO$_4$, the mixture was then diluted with MTBE, dried over MgSO$_4$ and concentrated under reduced pressure. The residue was redissolved in DCM, (Boc)$_2$O (0.6 g, 3.84 mmol) and Et$_3$N (1.0 ml) were added. The resulting mixture was stirred at room temperature for 18 hr, concentrated under reduced pressure. Purification by flash chromatography (30% to 50% EtOAc—hexanes gradient) gave tert-butyl 3-(tert-butoxycarbonyloxy)-3-(3-(cyclohexylmethylamino)phenyl)-1,1-dideuteropropylcarbamate as a colorless oil. Yield (0.23 g, 26%); $^1$H NMR (400 MHz, DMSO-d$_6$) δ 7.30 (d, J=8.0 Hz, 1H), 7.20-7.22 (m, 2H), 7.08 (d, J=7.6 Hz, 1H), 4.67 (t, J=6.4 Hz, 1H), 3.49 (d, J=7.2 Hz, 2H), 1.81 (d, J=6.4 Hz, 2H), 1.60-1.72 (m, 6H), 1.40-1.42 (m, 18H), 1.10-1.22 (m, 3H), 0.86-0.99 (m, 2H).

Step 2: Deprotection of tert-butyl 3-(tert-butoxycarbonyloxy)-3-(3-(cyclohexylmethylamino)phenyl)-1,1-dideuteropropylcarbamate following the method used in Example 20 gave Example 83 as a yellow solid. Yield (0.14 g, 90%); $^1$H NMR (400 MHz, CD$_3$OD) δ 7.48-7.60 (m, 3H), 7.38-7.42 (m, 1H), 4.91 (dd, J=9.2, 3.6 Hz, 1H), 3.24-3.33 (m, 2H), 1.66-2.08 (m, 8H), 1.24-1.36 (m, 3H), 0.96-1.06 (m, 2H).

Example 84

Preparation of N-(3-(3-Amino-3,3-dideutero-1-Hydroxypropyl)phenyl)cyclhexanecarboxamide

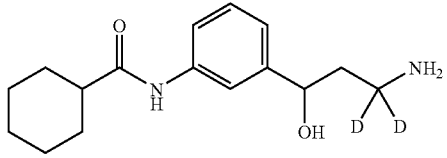 [SMILES: [2H]C([2H])(N)CC(O)c1cccc(NC(=O)C2CCCCC2)c1]

N-(3-(3-Amino-3,3-dideutero-1-hydroxypropyl)phenyl) cyclohexanecarboxamide is prepared following the method described below.

Step 1: Reduction of 3-(3-aminophenyl)-3-hydroxypropanenitrile (12) following the method used in Example 83 gives 3-amino-1-(3-aminophenyl)-3,3-dideuteropropan-1-ol.

Step 2: Protection of 3-amino-1-(3-aminophenyl)-3,3-dideuteropropan-1-ol with Boc$_2$O following the method used in Example 15 gives tert-butyl 3-(3-aminophenyl)-1,1-dideutero-3-hydroxypropylcarbamate.

Step 3: Acylation of tert-butyl 3-(3-aminophenyl)-1,1-dideutero-3-hydroxypropylcarbamate by acyl chloride 36 following the method used in Example 15 gives tert-butyl 3-(3-(cyclohexanecarboxamido)phenyl)-1,1-dideutero-3-hydroxypropylcarbamate.

Step 4: Deprotection of tert-butyl 3-(3-(cyclohexanecarboxamido)phenyl)-1,1-dideutero-3-hydroxypropylcarbamate following the method used in Example 15 gives Example 84 hydrochloride.

Example 85

Preparation of N-(3-(3-amino-3,3-dideutero-1-Hydroxypropyl)phenyl)cyclohexanesulfonamide

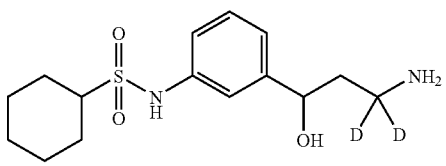 [SMILES: [2H]C([2H])(N)CC(O)c1cccc(NS(=O)(=O)C2CCCCC2)c1]

N-(3-(3-Amino-3,3-dideutero-1-hydroxypropyl)phenyl) cyclohexanesulfonamide is prepared following the method used in Examples 84, 5, and 15.

Step 1: Sulfonation of tert-butyl 3-(3-aminophenyl)-1,1-dideutero-3-hydroxypropylcarbamate by sulfonyl chloride 8 following the method used in Example 5 gives tert-butyl 3-(3-(cyclohexanesulfonamido)phenyl)-1,1-dideutero-3-hydroxypropylcarbamate.

Step 2: Deprotection of tert-butyl 3-(3-(cyclohexanesulfonamido)phenyl)-1,1-dideutero-3-hydroxypropylcarbamate following the method used in Example 15 gives Example 84 hydrochloride.

Example 86

Preparation of (R)-3-amino-1-(3-(cyclohexylmethylamino)phenyl)propan-1-ol

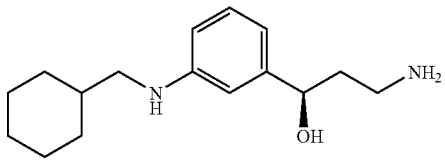 [SMILES: NCC[C@@H](O)c1cccc(NCC2CCCCC2)c1]

(R)-3-Amino-1-(3-(cyclohexylmethylamino)phenyl)propan-1-ol is prepared following the method described below.

Step 1: A mixture of aniline 33, Boc$_2$O and 4-DMAP are stirred under reflux until no starting aniline is seen by TLC. The reaction mixture partitioned between aqueous NH$_4$Cl and EtOAc and aqueous layer additionally extracted with EtOAc. Organic layer is then washed with brine, dried over anhydrous MgSO$_4$ and concentrated under reduced pressure. Purification by flash chromatography (EtOAc—hexanes gradient) gives tert-butyl 3-(3-(tert-butoxycarbonyl(cyclohexylmethyl)amino)phenyl)-3-oxopropylcarbamate.

Step 2: A mixture of tert-butyl 3-(3-(tert-butoxycarbonyl (cyclohexylmethyl)amino)phenyl)-3-oxopropylcarbamate and (+)-Ipc$_2$BCl in anhydrous THF is stirred at room temperature until no starting material is seen by TLC. The reaction is then quenched with aqueous NH$_4$Cl and stirred at room temperature. Extraction with EtOAc and drying over anhydrous MgSO$_4$ followed by flash chromatography (EtOAc—hexanes gradient) gives tert-butyl (R)-3-(3-(tert-butoxycarbonyl(cyclohexylmethyl)amino)phenyl)-3-hydroxypropylcarbamate.

Step 3: Deprotection of tert-butyl (R)-3-(3-(tert-butoxycarbonyl(cyclohexylmethyl)amino)phenyl)-3-hydroxypropylcarbamate following the method used in Example 12 gives Example 86 hydrochloride.

Example 87

Preparation of 3-amino-1-(3-(cyclohexylmethylamino)phenyl)-2-methylpropan-1-ol

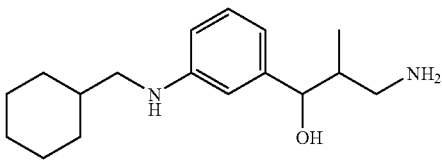

3-Amino-1-(3-(cyclohexylmethylamino)phenyl)-2-methylpropan-1-ol is prepared following the method used in Examples 5 and 11.

Step 1: Addition of propiononitrile to aldehyde 10 following the method used in Example 5 gives 3-hydroxy-2-methyl-3-(3-nitrophenyl)propanenitrile.

Step 2: Hydrogenation of the mixture of 3-hydroxy-2-methyl-3-(3-nitrophenyl)propanenitrile and aldehyde 29 following the method used in Example 11 gives 3-(3-(cyclohexylmethylamino)phenyl)-3-hydroxy-2-methylpropanenitrile.

Step 3: $BH_3$-$Me_2S$ reduction of 3-(3-(cyclohexylmethylamino)phenyl)-3-hydroxy-2-methylpropanenitrile following the method used in Example 12 gives Example 87.

Example 88

Preparation of 1-amino-3-(3-(cyclohexylmethylamino)phenyl)propan-2-ol

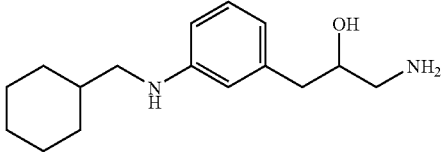 [SMILES: NCC(O)Cc1cccc(NCC2CCCCC2)c1]

1-Amino-3-(3-(cyclohexylmethylamino)phenyl)propan-2-ol is prepared following the method described below.

Step 1: A mixture of Example 23 and $Boc_2O$ in $CH_2Cl_2$ are stirred at room temperature until no starting material is seen by TLC. The reaction mixture is then concentrated under reduced pressure to give (E)-tert-butyl 3-(3-(cyclohexylmethylamino)phenyl)allylcarbamate.

Step 2: To a solution of (E)-tert-butyl 3-(3-(cyclohexylmethylamino)phenyl)allylcarbamate in $CH_2Cl_2$ is added MCPBA (77%) followed by $Na_2CO_3$. The reaction mixture is stirred at room temperature until no starting material is seen by TLC. Aqueous $NaHCO_3$ (10%) is added and the product is extracted with $CH_2Cl_2$ three times. Combined organic layers are washed with brine-$NaHCO_3$, dried over anhydrous $Na_2SO_4$ and concentrated under reduced pressure. Purification by flash chromatography (10% to 50% EtOAc—hexanes gradient) gives tert-butyl (3-(3-(cyclohexylmethylamino)phenyl)oxiran-2-yl)methylcarbamate which is used in the next step without further purification.

Step 3: A mixture of tert-butyl (3-(3-(cyclohexylmethylamino)phenyl)oxiran-2-yl)methylcarbamate, HCOOH.$Et_3N$ complex (5:2), Pd/C (10% wt) in absolute EtOH is degassed by applying vacuum/argon 3 times. The reaction mixture is stirred at room temperature until no starting material is seen by TLC, then concentrated under reduced pressure. Purification by flash chromatography (EtOAc—hexanes gradient) gives tert-butyl 3-(3-(cyclohexylmethylamino)phenyl)-2-hydroxypropylcarbamate.

Step 4: tert-Butyl 3-(3-(cyclohexylmethylamino)phenyl)-2-hydroxypropylcarbamate is deprotected following the method used in Example 12 to give Example 88 hydrochloride.

Example 89

Preparation of N-(3-(3-(cyclohexylmethylamino)phenyl)-3-hydroxypropyl)acetamide

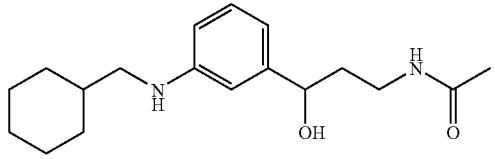 [SMILES: CC(=O)NCCC(O)c1cccc(NCC2CCCCC2)c1]

N-(3-(3-(Cyclohexylmethylamino)phenyl)-3-hydroxypropyl)acetamide is prepared following the method shown below.

Step 1: A mixture of Example 11 and 2,5-dioxopyrrolidin-1-yl acetate in $CH_2Cl_2$ are stirred at room temperature until no starting material is seen by TLC then concentrated under reduced pressure. Purification by flash chromatography (EtOAc—hexanes gradient) gives Example 89.

Example 90

Preparation of 3-amino-1-(3-((cyclohexylmethyl)(methyl)amino)phenyl)propan-1-ol

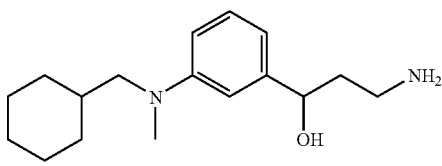 [SMILES: CN(CC1CCCCC1)c1cccc(C(O)CCN)c1]

3-Amino-1-(3-((cyclohexylmethyl)(methyl)amino)phenyl)propan-1-ol was prepared following the method described below.

Step 1: A mixture of aniline 32 (0.118 g, 0.327 mmol), DIPEA (0.060 mL) and methyl iodide (0.094 g, 0.661 mmol) in absolute EtOH was stirred at +75° C. for 28 hrs. The reaction mixture was concentrated under reduced pressure. Purification by column chromatography (30% EtOAc—hexanes) gave tert-butyl 3-(3-((cyclohexylmethyl)(methyl)amino)phenyl)-3-hydroxypropylcarbamate as a colorless oil. Yield (0.060 g, 49%); $^1H$ NMR (400 MHz, $CDCl_3$) δ 7.16 (t, J=7.8 Hz, 1H), 6.52-6.68 (m, 3H), 4.92 (br. s, 1H), 4.68 (t, J=6.3 Hz, 1H), 3.36-3.50 (m, 1H), 3.14-3.23 (m, 1H), 3.11 (d, J=6.7 Hz, 2H), 2.94 (s, 3H), 1.87 (q, J=6.7 Hz, 2H), 1.58-1.76 (m, 6H), 1.38-1.49 (m, 10H), 1.08-1.28 (m, 3H), 0.86-1.00 (m, 2H).

Step 2: Deprotection of tert-butyl 3-(3-((cyclohexylmethyl)(methyl)amino)phenyl)-3-hydroxypropylcarbamate following the method used in Example 11 gave Example 90 hydrochloride as a colorless oil. Yield (0.057 g, quant.); $^1$H NMR (400 MHz, CD$_3$OD) δ 7.75-7.79 (m, 1H), 7.54-7.63 (m, 3H), 4.94 (dd, J=3.5, 9.0 Hz, 1H), 3.40-3.60 (br. s, 1H), 3.20-3.30 (m, 2H), 3.05-3.18 (m, 5H), 2.02-2.14 (m, 1H), 1.91-2.02 (m, 1H), 1.56-1.74 (m, 4H), 1.27-1.40 (m, 1H), 0.95-1.22 (m, 5H); RP-HPLC (Method 1) t$_R$=5.10 min, 71.9% (AUC); ESI MS m/z 277.3 [M+H]$^+$.

Example 91

Preparation of 3-amino-1-(3-((1-deuterocyclohexyl)methylamino)phenyl)propan-1-ol

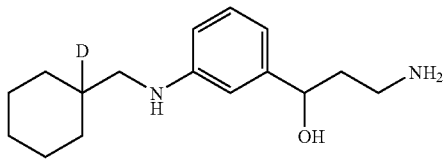

3-Amino-1-(3-((1-deuterocyclohexyl)methylamino)phenyl)propan-1-ol was prepared following the method described below.

Step 1. To a solution of 1-deuteroclohexanecarboxylic acid (5.0 g, 38.7 mmol) in anhydrous DMSO was added KOH (2.39 g, 42.6 mmol) with stirring for 5 min. Methyl iodide (6.59 g, 46.4 mmol) was added and the reaction mixture was stirred overnight at room temperature. Saturated NaHCO$_3$ and ether was added and the mixture was washed with brine, dried over Na$_2$SO$_4$ and evaporated to dryness giving methyl 1-deuterocyclohexanecarboxylate as a clear liquid. Yield (5.62 g, quant.); $^1$H NMR (400 MHz, DMSO-d$_6$) δ 3.55 (s, 3H), 1.78-1.75 (m, 2H), 1.65-1.60 (m, 2H), 1.57-1.52 (m, 1H), 1.34-1.09 (m, 5H).

Step 2. To a solution of methyl 1-deuterocyclohexanecarboxylate (5.0 g, 34.9 mmol) in anhydrous CH$_2$Cl$_2$ on an ice bath was added a solution of DIBAL-H in CH$_2$Cl$_2$ (1.0 M, 73.3 ml, 73.3 mmol) The reaction mixture was allowed to warm to room temperature over 2 hrs and quenched with Rochelle's salt (100 ml). The organic layer was dried over Na$_2$SO$_4$ and concentrated under reduced pressure to give (1-deuterocyclohexyl)methanol as a clear liquid. Yield (3.99 g, 97%); $^1$H NMR (400 MHz, DMSO-d$_6$) δ 4.27 (t, J=5.2 Hz, 1H), 3.15 (d, J=5.2 Hz, 2H), 1.66-1.56 (m, 5H), 1.21-1.20 (m, 3H), 0.84-0.78 (m, 2H).

Step 3. To a solution of (1-deuterocyclohexyl)methanol (3.0 g, 26.0 mmol) in anhydrous CH$_2$Cl$_2$ on an ice bath was added Et$_3$N (2.98 g, 28.6 mmol) and methanesulfonyl chloride (3.28 g, 28.6 mmol). The reaction mixture was warmed to room temp over 2 hr. 1N HCl was added and layers were separated. The organic layer was dried over Na$_2$SO$_4$ and concentrated under reduced pressure to give (1-deuterocyclohexyl)methyl methanesulfonate as an off white solid. Yield (4.92 g, 98%); $^1$H NMR (400 MHz, DMSO-d$_6$) δ 3.97 (s, 2H), 3.12 (s, 3H), 1.68-1.58 (m, 5H), 1.25-1.08 (m, 3H), 0.97-0.88 (m, 2H).

Step 4: A mixture of aniline 12 (0.478 g, 2.95 mmol) and (1-deuterocyclohexyl)methyl methanesulfonate (0.243 g, 1.26 mmol) in absolute EtOH was stirred under argon at +70° C. for 2 days. The reaction mixture was concentrated under reduced pressure. Purification by flash chromatography (3% of 7N NH$_3$/MeOH in CH$_2$Cl$_2$) gave 3-(3-((1-deuterocyclohexyl)methylamino)phenyl)-3-hydroxypropanenitrile as a yellow oil which crystallized on standing to off-white solid. Yield (0.157 g, 48%); $^1$H NMR (400 MHz, DMSO-d$_6$) δ 6.97 (t, J=7.8 Hz, 1H), 6.54-6.59 (m, 1H), 6.45-6.50 (m, 1H), 6.40-6.45 (m, 1H), 5.72 (d, J=4.3 Hz, 1H), 5.56 (t, J=5.7 Hz, 1H), 4.66-4.72 (m, 1H), 2.80 (d, J=5.7 Hz, 2H), 2.65-2.80 (m, 2H), 1.54-1.78 (m, 5H), 1.05-1.22 (m, 3H), 0.83-0.97 (m, 2H).

Step 5: Reduction of 3-(3-((1-deuterocyclohexyl)methylamino)phenyl)-3-hydroxypropanenitrile following the method used in Example 35 gave crude Example 91 hydrochloride as a colorless oil. This was partitioned between CH$_2$Cl$_2$ and sat. NaHCO$_3$, aqueous layer was extracted with CH$_2$Cl$_2$. Combined organic layers were washed with brine, concentrated under reduced pressure. Purification by flash chromatography (4% to 10% of 7N NH$_3$/MeOH/CH$_2$Cl$_2$—CH$_2$Cl$_2$ gradient) gave Example 91 as a colorless oil. Yield (0.0827 g, 23% over two steps); $^1$H NMR (400 MHz, CD$_3$OD) δ 7.04 (t, J=7.8 Hz, 1H), 6.61-6.63 (m, 1H), 6.55-6.59 (m, 1H), 6.49 (ddd, J=0.8, 2.3, 8.0 Hz, 1H), 4.59 (dd, J=5.5, 7.8 Hz, 1H), 2.90 (s, 2H), 2.64-2.77 (m, 2H), 1.63-1.92 (m, 7H), 1.14-1.32 (m, 3H), 0.92-1.02 (m, 2H); RP-HPLC (Method 1) t$_R$=5.20 min, 91.7% (AUC); ESI MS m/z 264.3 [M+H]$^+$.

Example 92

Preparation of 3-amino-1-(3-(cyclohexyldideuteromethylamino)phenyl)propan-1-ol

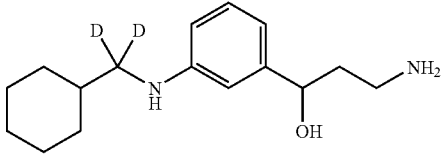 [SMILES: [2H]C([2H])(Nc1cccc(C(O)CCN)c1)C1CCCCC1]

3-Amino-1-(3-(cyclohexyldideuteromethylamino)phenyl)propan-1-ol is prepared following the method described below.

Step 1. A solution of methyl cyclohexane carboxylate (9.99 g, 70.3 mmol) was added under inert atmosphere to a cooled (0° C.) suspension of LiAlD$_4$ (2.99 g, 71.2 mmol) in anhydrous Et$_2$O. The reaction mixture was stirred at 0° C. for 3 hrs and then slowly quenched by addition of saturated Na$_2$SO$_4$ until white precipitate formed. The mixture was dried over anhydrous MgSO$_4$, filtered. The filtrate was concentrated under reduced pressure to give cyclohexyldideuteromethanol as a colorless volatile liquid. Yield (2.52 g, 32%); $^1$H NMR (400 MHz, CDCl$_3$) δ 1.63-1.78 (m, 5H), 1.40-1.50 (m, 1H), 1.10-1.35 (m, 4H), 0.86-0.99 (m, 2H).

Step 2. Mesylation of cyclohexyldideuteromethanol following the method used in Example 91 gave cyclohexyldideuteromethyl methanesulfonate as a colorless oil. Yield (4.14 g, 97%); $^1$H NMR (400 MHz, CDCl$_3$) δ 2.98 (s, 3H), 1.64-1.80 (m, 6H), 1.10-1.32 (m, 3H), 0.92-1.05 (m, 2H).

Step 3: Alkylation of aniline 12 with cyclohexyldideuteromethyl methanesulfonate following the method used in Example 91 gave 3-(3-(cyclohexyldideuteromethylamino)phenyl)-3-hydroxypropanenitrile as an off-white solid. Yield (0.128 g, 42%); $^1$H NMR (400 MHz, DMSO-d$_6$) δ 6.97 (t, J=7.8 Hz, 1H), 6.56 (t, J=1.8 Hz, 1H), 6.45-6.49 (m, 1H), 6.42 (ddd, J=0.8, 2.35, 8.0 Hz, 1H), 5.71 (d, J=4.3 Hz, 1H), 5.54 (br. s, 1H), 4.65-4.72 (m, 1H), 2.78 (ABd, J=4.9, 16.6 Hz, 1H), 2.69 (ABd, J=6.65, 6.62 Hz, 1H), 1.70-1.79 (m, 2H), 1.54-1.70 (m, 3H), 1.48 (tt, J=3.5, 11.2 Hz, 1H), 1.07-1.22 (m, 3H), 0.84-0.95 (m, 2H).

Step 4: Reduction of 3-(3-(cyclohexyldideuteromethylamino)phenyl)-3-hydroxypropanenitrile by BH$_3$-Me$_2$S following the method used in Example 91 gives Example 92.

Example 93

Preparation of N-(3-(3-amino-1-hydroxypropyl)phenyl)-1,2,2,3,3,4,4,5,5,6,6-undecadeuterocyclohexanecarboxamide

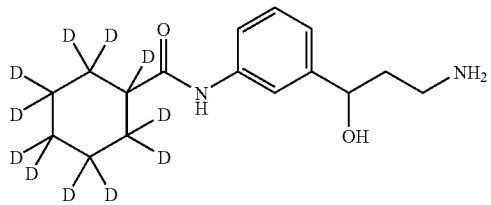 [SMILES: [2H]C1([2H])C([2H])([2H])C([2H])([2H])C([2H])(C(=O)Nc2cccc(C(O)CCN)c2)C([2H])([2H])C1([2H])[2H]]

N-(3-(3-Amino-1-hydroxypropyl)phenyl)-1,2,2,3,3,4,4,5,5,6,6-undecadeuterocyclohexanecarboxamide was prepared following the method below.

Step 1: Oxalyl chloride (0.25 mL, 2.89 mmol) was added at room temperature to a solution of perdeuterocyclohexanecarboxylic acid (0.337 g, 2.42 mmol) in anhydrous CH$_2$Cl$_2$. DMF (0.05 mL) was then added and the reaction mixture was stirred at RT for 5 min, concentrated under reduced pressure and re-dissolved in anhydrous CH$_2$Cl$_2$. This solution was then added to a stirred solution of aniline 35 (0.36 g, 1.35 mmol) in anhydrous CH$_2$Cl$_2$. After stirring overnight the mixture was concentrated under reduced pressure. Purification by flash chromatography (50% to 100% EtOAc—hexanes gradient) gave tert-butyl (3-hydroxy-3-(3-(perdeuterocyclohexanecarboxamido)phenyl)propyl)carbamate as a white solid. Yield (0.39 g, 75%); $^1$H NMR (400 MHz, DMSO-d$_6$) δ 9.71 (s, 1H), 7.52-7.56 (m, 1H), 7.41-7.46 (m, 1H), 7.17 (t, J=7.8 Hz, 1H), 6.90-6.94 (m, 1H), 6.73 (t, J=5.1 Hz, 1H), 5.15 (d, J=4.3 Hz, 1H), 4.46 (dt, J=6.5, 4.7 Hz, 1H), 2.90-2.98 (m, 2H), 1.60-1.68 (m, 2H), 1.34 (s, 9H).

Step 2: A mixture of tert-butyl (3-hydroxy-3-(3-(perdeuterocyclohexanecarboxamido)phenyl)propyl)carbamate (0.159 g, 0.41 mmol) and HCl/i-PrOH (5.5 M, 3 mL) in EtOAc was stirred at room temperature for 22 hrs, then concentrated under reduced pressure. Purification by flash chromatography (20% to 100% of 20% 7N NH$_3$/MeOH/CH$_2$Cl$_2$—CH$_2$Cl$_2$ gradient) gave Example 93 as a colorless oil. Yield (0.090 g, 64%); $^1$H NMR (400 MHz, CD$_3$OD) δ 7.54-7.57 (m, 1H), 7.45 (ddd, J=0.98, 1.96, 8.02 Hz, 1H), 7.25 (t, J=7.8 Hz, 1H), 7.05-7.10 (m, 1H), 4.70 (dd, J=5.3, 7.6 Hz, 1H), 2.68-2.81 (m, 2H), 1.77-1.94 (m, 2H); RP-HPLC (Method 1) t$_R$=6.83 min, 95.7% (AUC); ESI MS m/z 288.3 [M+H]$^+$.

Example 94

Preparation of 1-(3-(cyclohexylmethylamino)phenyl)-3-(methylamino)propan-1-ol

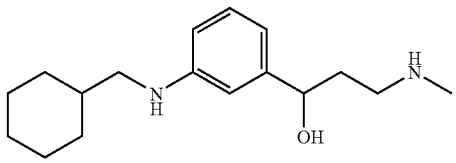 [SMILES: CNCCC(O)c1cccc(NCC2CCCCC2)c1]

1-(3-(Cyclohexylmethylamino)phenyl)-3-(methylamino)propan-1-ol is prepared following the method described below.

Step 1: A mixture of carbamate 32 and sodium bis(2-methoxyethoxy)aluminumhydride in anhydrous THF is stirred under an inert atmosphere until no starting material is seen by TLC. The reaction mixture is then quenched by slow addition of 1N NaOH and partitioned between aqueous NaHCO$_3$ and CH$_2$Cl$_2$. Organic layer is dried over anhydrous Na$_2$SO$_4$ and concentrated under reduced pressure. Purification by flash chromatography (NH$_3$/MeOH/CH$_2$Cl$_2$—CH$_2$Cl$_2$ gradient) gives Example 94.

Example 95

Preparation of 3-(3-aminopropyl)-N-pentylaniline

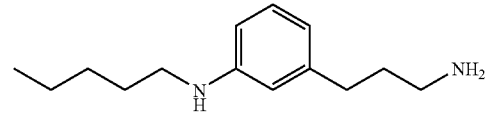 [SMILES: CCCCCNc1cccc(CCCN)c1]

3-(3-Aminopropyl)-N-pentylaniline is prepared following the method used in Example 13.

Step 1: Hydrogenation of aniline 17 and pentanal gives tert-butyl 3-(3-(pentylamino)phenyl)propylcarbamate.

Step 2: Deprotection of tert-butyl 3-(3-(pentylamino)phenyl)propylcarbamate following the method used in Example 11 gives Example 95 hydrochloride.

Example 96

Preparation of N-(3-(3-aminopropyl)phenyl)pentanamide

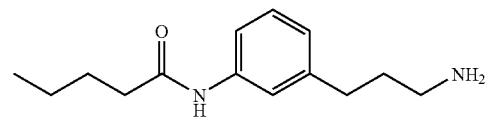 [SMILES: CCCCC(=O)Nc1cccc(CCCN)c1]

N-(3-(3-Aminopropyl)phenyl)pentanamide is prepared following the method used in Example 15.

Step 1: Acylation of aniline 17 with pentanoyl chloride gives tert-butyl 3-(3-pentanamidophenyl)propylcarbamate.

Step 2: Deprotection of tert-butyl 3-(3-pentanamidophenyl)propylcarbamate following the method used in Example 15 gives Example 96 hydrochloride.

Example 97

Preparation of N-(3-(3-amino-1-Hydroxypropyl)phenyl)cyclopentanesulfonamide

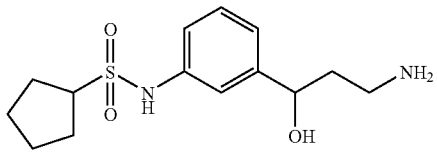 [SMILES: NCCC(O)c1cccc(NS(=O)(=O)C2CCCC2)c1]

N-(3-(3-Amino-1-hydroxypropyl)phenyl)cyclopentanesulfonamide was prepared following the method used in Example 19, 12.

Step 1: Sulfonation of aniline 35 by cyclopentanesulfonyl chloride following the method used in Example 19 gave tert-butyl 3-(3-(cyclopentanesulfonamido)phenyl)-3-hydroxypropylcarbamate as a yellow semi-solid. Yield (0.26 g, 36%). $^1$H NMR (400 MHz, DMSO-$d_6$) δ 9.74 (s, 1H), 7.30 (s, 1H), 7.28 (d, J=7.6 Hz, 1H), 7.14-7.08 (m, 2H), 5.98 (bs, 1H), 4.85 (m, 1H), 3.54-3.48 (m, 1H), 2.88 (dd, J=5.2, 16.4 Hz, 1H), 2.78 (dd, J=5.2, 16.4 Hz, 1H), 1.90-1.77 (m, 4H), 1.64-1.62 (m, 2H), 1.53-1.44 (m, 2H).

Step 2: Deprotection of tert-butyl 3-(3-(cyclopentanesulfonamido)phenyl)-3-hydroxypropylcarbamate following the method used in Example 12 gave Example 97 hydrochloride as a pale brown oil. Yield (0.14 g, 54%); $^1$H NMR (400 MHz, CD$_3$OD) δ 7.32 (s, 1H), 7.29 (t, J=8.0 Hz, 1H), 7.14 (d, J=8.0 Hz, 2H), 4.83-4.75 (t, J=6.4 Hz, 1H), 3.59-3.51 (m, 1H), 2.98-2.86 (m, 2H), 2.04-1.97 (m, 2H), 1.96-1.80 (m, 4H), 1.80-1.74 (m, 2H), 1.62-1.60 (m, 2H). RP-HPLC (Method 6) $t_R$=3.81 min, 90.65% (AUC); ESI MS m/z 299.32 [M+H]$^+$.

Example 98

Preparation of N-(3-(3-aminopropanoyl)phenyl)cyclopentanesulfonamide

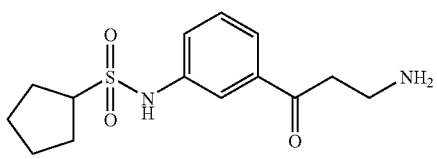 [SMILES: NCCC(=O)c1cccc(NS(=O)(=O)C2CCCC2)c1]

N-(3-(3-Aminopropanoyl)phenyl)cyclopentanesulfonamide is prepared following the method used in Example 97, 20.

Step 1: Oxidation of tert-butyl 3-(3-(cyclopentanesulfonamido)phenyl)-3-hydroxypropylcarbamate following the method used in Example 20 gives tert-butyl 3-(3-(cyclopentanesulfonamido)phenyl)-3-oxopropylcarbamate.

Step 2: Deprotection of tert-butyl 3-(3-(cyclopentanesulfonamido)phenyl)-3-oxopropylcarbamate following the method used in Example 20 gives Example 98 hydrochloride.

Example 99

Preparation of N-(3-(3-aminopropyl)phenyl)benzenesulfonamide

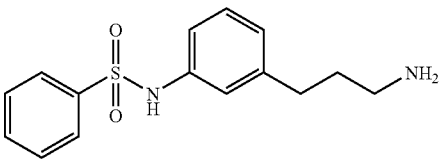 [SMILES: NCCCc1cccc(NS(=O)(=O)c2ccccc2)c1]

N-(3-(3-Aminopropyl)phenyl)benzenesulfonamide was prepared following the method described below.

Step 1: Sulfonation of 2-(3-(3-aminophenyl)propyl)isoindoline-1,3-dione by benzenesulfonyl chloride following the method used in Example 6 gave N-(3-(3-(1,3-dioxoisoindolin-2-yl)propyl)phenyl)benzenesulfonamide as a yellow semi-solid. Yield (0.80 g, 62%). $^1$H NMR (400 MHz, DMSO-$d_6$) δ 10.18 (s, 1H), 7.87-7.81 (m, 4H), 7.72 (d, J=7.6 Hz, 2H), 7.58-7.49 (m, 3H), 7.11 (t, J=8.0, 1H), 6.92 (s, 1H), 6.88-6.85 (m, 2H), 3.52 (t, J=7.2 Hz, 2H), 2.50-2.49 (m, 2H), 1.81-1.74 (m, 2H).

Step 2: Deprotection of N-(3-(3-(1,3-dioxoisoindolin-2-yl)propyl)phenyl)benzenesulfonamide following the method used in Example 31 gave Example 99 as a white solid. Yield (0.26 g, 42%); $^1$H NMR (400 MHz, DMSO-$d_6$) δ 7.23 (d, J=6.4 Hz, 2H), 7.55-7.46 (m, 3H), 7.03 (t, J=7.6 Hz, 1H), 6.86 (s, 1H), 6.82 (d, J=8.0 Hz, 1H), 6.73 (d, J=7.2 Hz, 1H), 2.56 (t, J=7.2 Hz, 2H), 2.46 (t, J=7.6 Hz, 2H), 1.60 (quintet, J=7.6 Hz, 2H). RP-HPLC (Method 6) $t_R$=4.32 min, 99.85% (AUC); ESI MS m/z 291.19 [M+H]$^+$.

Example 100

Preparation of 3-amino-1-(3-(benzylamino)phenyl)propan-1-ol

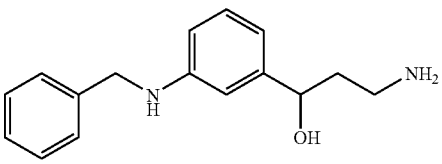 [SMILES: NCCC(O)c1cccc(NCc2ccccc2)c1]

3-Amino-1-(3-(benzylamino)phenyl)propan-1-ol was prepared following the method used in Example 11.

Step 1: NaBH(OAc)$_3$ (7.84 g, 36.99 mmol) was added to a solution of aniline 12 (2.0 g, 12.33 mmol) and benzaldehyde (1.3 g, 12.33 mmol) in DCM. The resulting mixture was stirred at RT for 5 h and quenched with saturated aqueous NaHCO$_3$. Organic layer was washed with water followed by brine and dried over anhydrous Na$_2$SO$_4$. Organic layer was concentrated under reduced pressure. Purification by flash chromatography (40% to 50% EtOAc—hexanes gradient) gave 3-(3-(benzylamino)phenyl)-3-hydroxypropanenitrile as a pale yellow oil. Yield (2.61 g, 83%); $^1$H NMR (400 MHz, DMSO-$d_6$) δ 7.36-7.29 (m, 4H), 7.23-7.19 (m, 1H), 6.99 (t, J=8.0 Hz, 1H), 6.68 (s, 1H), 6.54 (d, J=7.6 Hz, 1H), 6.44 (dd, J=1.6, 8.0 Hz, 1H), 6.27 (t, J=6.0 Hz, 1H), 5.79 (d, J=4.4 Hz, 1H), 4.72-4.68 (m, 1H), 4.25 (d, J=6.0 Hz, 2H), 2.82-2.67 (m, 2H).

Step 2: BH₃-Me₂S reduction of 3-(3-(benzylamino)phenyl)-3-hydroxypropanenitrile following the method used in Example 11 gave crude 3-amino-1-(3-(benzylamino)phenyl)propan-1-ol as an off-white semi-solid which was used directly in next step. Yield (2.0 g, 75%).

Step 3: Protection of 3-amino-1-(3-(benzylamino)phenyl)propan-1-ol with Boc₂O gave tert-butyl benzyl(3-(3-((tert-butoxycarbonyl)amino)-1-hydroxypropyl)phenyl)carbamate as an off white semi-solid. Yield (2.7 g, 84%); ¹H NMR (400 MHz, DMSO-d₆) δ 7.31-7.27 (m, 2H), 7.26-7.16 (m, 4H), 7.14 (s, 1H), 7.09 (d, J=7.6 Hz, 1H), 7.02 (d, J=8.0 Hz, 1H), 6.76 (t, J=5.2 Hz, 1H), 5.20 (d, J=4.4 Hz, 1H), 4.81 (d, J=6.0 Hz, 2H), 4.52-4.47 (m, 1H), 2.93 (q, J=6.4 Hz, 2H), 1.65-1.60 (m, 2H), 1.36 (s, 18H).

Step 4: Deprotection of tert-butyl benzyl(3-(3-((tert-butoxycarbonyl)amino)-1-hydroxypropyl)phenyl)carbamate gave Example 100 hydrochloride as a yellow solid. Yield (0.5 g, 69%); ¹H NMR (400 MHz, DMSO-d₆) δ 8.06 (bs, 3H), 7.45 (d, J=6.0 Hz, 2H), 7.36-7.24 (m, 4H), 7.19 (bs, 1H), 7.05 (bs, 2H), 4.64-4.62 (m, 1H), 4.42 (s, 2H), 2.82-2.77 (m, 2H), 1.86-1.77 (m, 2H); RP-HPLC (Method 6) $t_R$=4.48 min, 90.84% (AUC); ESI MS m/z 257.22 [M+H]⁺.

Example 101

Preparation of N-(3-(3-amino-1-Hydroxypropyl)phenyl)benzenesulfonamide

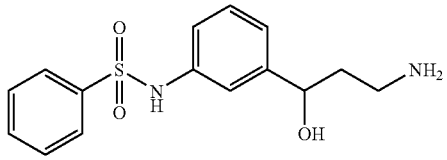 [SMILES: NCCC(O)c1cccc(NS(=O)(=O)c2ccccc2)c1]

N-(3-(3-Amino-1-hydroxypropyl)phenyl)benzenesulfonamide was prepared following the method used in Example 5.

Step 1: Sulfonation of aniline 12 by benzenesulfonyl chloride gave N-(3-(2-cyano-1-hydroxyethyl)phenyl)benzenesulfonamide as a yellow semi-solid. Yield (0.9 g, 81%); ¹H NMR (400 MHz, DMSO-d₆) δ 10.30 (s, 1H), 7.77-7.69 (m, 2H), 7.61-7.57 (m, 1H), 7.54-7.45 (m, 2H), 7.21 (d, J=4.8 Hz, 1H), 7.18 (d, J=8.0 Hz, 1H), 7.08-6.98 (m, 1H), 6.84 (d, J=8.0 Hz, 1H), 6.09 (d, J=3.6 Hz, 1H), 4.91-4.77 (m, 1H), 2.80 (dd, J=4.8, 16.8 Hz, 1H), 2.70 (dd, J=4.8, 16.8 Hz, 1H).

Step 2: BH₃-Me₂S reduction of N-(3-(2-cyano-1-hydroxyethyl)phenyl)benzenesulfonamide gives Example 101 as a white solid. Yield (0.385 g, 48%); ¹H NMR (400 MHz, DMSO-d₆) δ 7.71 (dd, J=2.0, 7.2 Hz, 2H), 7.52-7.43 (m, 3H), 7.04 (t, J=8.0 Hz, 1H), 6.98 (s, 1H), 6.81 (t, J=8.4 Hz, 2H), 4.48 (t, J=6.4 Hz, 1H), 2.60 (t, J=7.2 Hz, 2H), 1.61 (quintet, J=7.2 Hz, 2H); RP-HPLC (Method 6) $t_R$=4.02 min, 94.69% (AUC); ESI MS m/z 307.29 [M+H]⁺.

Example 102

Preparation of 3-amino-1-(3-(benzylamino)phenyl)propan-1-one

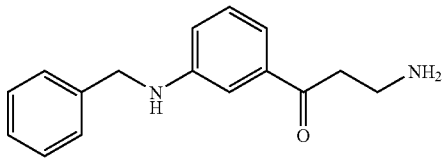 [SMILES: NCCC(=O)c1cccc(NCc2ccccc2)c1]

3-Amino-1-(3-(benzylamino)phenyl)propan-1-one was prepared following the method used in Example 100 and 12.

Step 1: Oxidation of tert-butyl benzyl(3-(3-((tert-butoxycarbonyl)amino)-1-hydroxypropyl)phenyl)carbamate with Des-Martin periodinane following the method used in Example 40 gave tert-butyl benzyl(3-(3-((tert-butoxycarbonyl)amino)propanoyl)phenyl)carbamate as a yellow oil. Yield (1.2 g, 74%); ¹H NMR (400 MHz, DMSO-d₆) δ 7.75 (s, 1H), 7.71 (d, J=6.0 Hz, 1H), 7.45-7.41 (m, 2H), 7.32-7.29 (m, 2H), 7.23-7.19 (m, 3H), 6.80 (bs, 1H), 4.89 (s, 2H), 3.24 (m, 2H), 3.15-3.09 (m, 2H), 1.38 (s, 9H), 1.35 (s, 9H).

Step 2: Deprotection of tert-butyl benzyl(3-(3-((tert-butoxycarbonyl)amino)propanoyl)phenyl)carbamate gave Example 102 hydrochloride as a yellow oil. Yield (0.8 g, yellow solid, 92%); ¹H NMR (400 MHz, DMSO-d₆) δ 8.06 (bs, 3H), 7.45 (d, J=6.4 Hz, 2H), 7.45-7.22 (m, 7H), 7.01 (bs, 1H), 4.42 (s, 2H), 3.49-3.42 (m, 2H), 3.10-3.02 (m, 2H); RP-HPLC (Method 6) $t_R$=4.72 min, 73.30% (AUC); ESI MS m/z 255.20 [M+H]⁺.

Example 103

Preparation of N-(3-(3-aminopropanoyl)phenyl)benzenesulfonamide

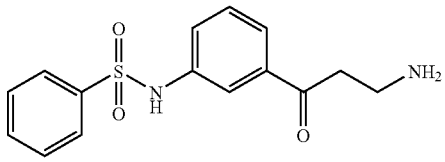 [SMILES: NCCC(=O)c1cccc(NS(=O)(=O)c2ccccc2)c1]

N-(3-(3-Aminopropanoyl)phenyl)benzenesulfonamide was prepared following the method used in Example 40.

Step 1: Protection of Example 101 following the method used in Example 40 gave tert-butyl tert-butoxycarbonyl (3-hydroxy-3-(3-(phenylsulfonamido)phenyl)propyl)carbamate as a colorless oil. Yield (0.36 g, 87%); ¹H NMR (400 MHz, CDCl₃) δ 7.98 (dd, J=1.2, 8.0 Hz, 2H), 7.66 (t, J=7.6 Hz, 1H), 7.56 (t, J=8.0 Hz, 2H), 7.42-7.38 (m, 2H), 7.29 (s, 1H), 7.16 (d, J=6.8 Hz, 1H), 4.89 (bs, 1H), 4.80-4.78 (m, 1H), 3.52 (m, 1H), 3.45 (bs, 1H), 3.21-3.13 (m, 1H), 1.91-1.81 (m, 2H), 1.39 (s, 9H), 1.33 (s, 9H).

Step 2: Oxidation of tert-butyl tert-butoxycarbonyl (3-hydroxy-3-(3-(phenylsulfonamido)phenyl)propyl)carbamate gives tert-butyl tert-butoxycarbonyl (3-oxo-3-(3-(phenylsulfonamido)phenyl)propyl)carbamate as a colorless oil. Yield (0.19 g, 76%); ¹H NMR (400 MHz, DMSO-d₆) δ 8.06 (d, J=7.2 Hz, 1H), 7.99 (d, J=7.6 Hz, 2H), 7.84-7.79 (m, 2H), 7.72 (t, J=7.6 Hz, 2H), 7.68-7.62 (m, 2H), 6.82 (m, 1H), 3.31 (m, 2H), 3.21-3.18 (m, 2H), 1.36 (s, 9H), 1.24 (s, 9H).

Step 3: Deprotection of tert-butyl 3-oxo-3-(3-(phenylsulfonamido)phenyl)propylcarbamate gives Example 103 hydrochloride as a pale yellow solid. Yield (0.12 g, 93%); $^1$H NMR (400 MHz, MeOD) δ 7.82 (s, 1H), 7.79 (d, J=7.2 Hz, 2H), 7.72 (d, J=7.6 Hz, 1H), 7.56 (t, J=7.2 Hz, 1H), 7.47 (t, J=7.6 Hz, 2H), 7.39 (t, J=8.0 Hz, 1H), 7.33 (d, J=8.0 Hz, 1H), 3.38 (t, J=6.0 Hz, 2H), 3.31 (m, 2H). RP-HPLC (Method 6) $t_R$=4.11 min, 98.36% (AUC); ESI MS m/z 305.25 [M+H]$^+$.

Example 104

Preparation of 3-(3-aminopropyl)-N-(2-methoxybenzyl)aniline

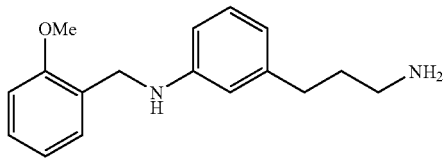 [SMILES: COc1ccccc1CNc1cccc(CCCN)c1]

3-(3-Aminopropyl)-N-(2-methoxybenzyl)aniline was prepared following the method used in Example 64.

Step 1: Hydrogenation of 2,2,2-trifluoro-N-(3-(3-nitrophenyl)allyl)acetamide and 2-methoxybenzaldehyde gave tert-butyl 3-(3-(2-methoxybenzylamino)phenyl)propylcarbamate as a colorless semi-solid. Yield (0.16 g, 16%); $^1$H NMR (400 MHz, DMSO-d$_6$) δ 9.42 (br.s, 1H), 7.23-7.18 (m, 2H), 6.97 (d, J=8.4 Hz, 1H), 6.93 (t, J=7.6 Hz, 1H), 6.86 (t, J=7.6 Hz, 1H), 6.40 (s, 1H), 6.35-6.34 (m, 2H), 5.94 (t, J=6.0 Hz, 1H), 4.18 (d, J=6.0 Hz, 2H), 3.82 (s, 3H), 3.16 (q, J=6.4, 2H), 2.41 (t, J=7.6 Hz, 2H), 1.70 (quintet, J=7.6, 2H).

Step 2: Deprotection of tert-butyl 3-(3-(2-methoxybenzylamino)phenyl)propylcarbamate following the method used in Example 95 gave Example 104 as a light green semi-solid. Yield (0.09 g, 76%); $^1$H NMR (400 MHz, DMSO-d$_6$) δ 7.23-7.19 (m, 2H), 6.98 (d, J=8.0 Hz, 1H), 6.93 (t, J=7.6 Hz, 1H), 6.87 (t, J=7.6 Hz, 1H), 6.39 (s, 1H), 6.34 (d, J=8.0 Hz, 2H), 5.95 (t, J=6.0 Hz, 1H), 4.18 (d, J=6.0 Hz, 2H), 3.83 (s, 3H), 2.62 (t, J=7.6 Hz, 2H), 2.44 (t, J=7.6 Hz, 2H), 1.65 (quintet, J=7.2 Hz, 2H); RP-HPLC (Method 6) $t_R$=4.92 min, 97.97% (AUC); ESI MS m/z 271.28 [M+H]$^+$.

Example 105

Preparation of 3-(3-aminopropyl)-N-phenethylaniline

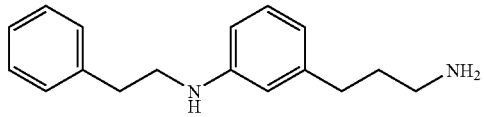 [SMILES: NCCCc1cccc(NCCc2ccccc2)c1]

3-(3-Aminopropyl)-N-phenethylaniline was prepared following the method used in Example 33 and 11.

Step 1: Hydrogenation of (E)-2,2,2-trifluoro-N-(3-(3-nitrophenyl)allyl)acetamide and 2-phenylacetaldehyde gave 2,2,2-trifluoro-N-(3-(3-(phenethylamino)phenyl)propyl)acetamide as a colorless semi-solid. Yield (0.3 g, 24%); $^1$H NMR (400 MHz, DMSO-d$_6$) δ 9.43 (bs, 1H), 7.31-7.18 (m, 5H) 6.95 (t, J=7.6 Hz, 1H), 6.49-6.36 (m, 3H), 5.56 (t, J=6.0 Hz, 1H), 3.24-3.14 (m, 4H), 2.87-2.82 (m 2H), 2.37 (t, J=7.6 Hz, 2H), 1.74 (quintet, J=7.6 Hz, 2H).

Step 2: Deprotection of 2,2,2-trifluoro-N-(3-(3-(phenethylamino)phenyl)propyl)acetamide following the method used in Example 23 gave Example 105 as a light green semi-solid. Yield (0.12 g, 55%); $^1$H NMR (400 MHz, DMSO-d$_6$) δ 7.30-7.18 (m, 5H), 6.98 (t, J=8.0 Hz, 1H), 6.41 (d, J=7.2 Hz, 2H), 6.37 (d, J=7.6 Hz, 1H), 5.57 (t, J=5.6 Hz, 1H), 3.21 (q, J=6.4, Hz, 2H), 2.82 (t, J=7.6 Hz, 2H), 2.64 (t, J=7.6 Hz, 2H), 2.50-2.46 (m, 2H), 1.69 (quintet, J=7.6, 2H); RP-HPLC (Method 6) $t_R$=5.13 min, 97.42% (AUC); ESI MS m/z 255.24 [M+H]$^+$.

Example 106

Preparation of 3-(3-aminopropyl)-N-(thiazol-2-ylmethyl)aniline

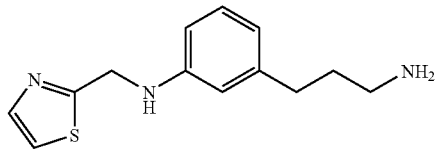 [SMILES: NCCCc1cccc(NCc2nccs2)c1]

3-(3-Aminopropyl)-N-(thiazol-2-ylmethyl)aniline was prepared following the method described below.

Step 1: Å-3 Molecular sieves were added to a solution of aniline 17 (0.4 g, 1.6 mmol) and thiazole-2-carbaldehyde (0.18 g, 1.6 mmol) in MeOH. The reaction mixture was stirred for 18 h and then NaBH$_4$ (0.121 g, 3.2 mmol) was added and the reaction mixture was stirred for overnight. The reaction mixture was filtered through Celite, concentrated under reduced pressure Purification by column chromatography (100-200 silica mesh, 20% EtOAc in hexane) gave tert-butyl 3-(3-(thiazol-2-ylmethylamino)phenyl)propylcarbamate as a brown oil. Yield (0.17 g, 31%); $^1$H NMR (400 MHz, DMSO-d$_6$) δ 7.73 (d, J=3.2 Hz, 1H), 7.56 (d, J=3.2 Hz, 1H), 6.96 (t, J=7.6 Hz, 1H), 6.80 (bs, 1H), 6.45-6.38 (m, 4H), 4.55 (d, J=6.0 Hz, 2H), 2.91 (q, J=6.4 Hz, 2H), 2.39 (t, J=7.2 Hz, 2H), 1.59 (quintet, J=7.2 Hz, 2H), 1.37 (s, 9H).

Step 2: Deprotection of tert-butyl 3-(3-(thiazol-2-ylmethylamino)phenyl)propylcarbamate following the method used in Example 11 gave Example 106 hydrochloride as a pale brown solid. Yield (0.09 g, 31%); $^1$H NMR (400 MHz, DMSO-d$_6$) δ 7.90 (m, 3H), 7.76 (d, J=3.2 Hz, 1H), 7.61 (d, J=3.2 Hz, 1H), 7.00 (t, J=7.6 Hz, 1H), 6.48-6.45 (m, 3H), 4.55 (s, 2H), 4.77 (bs, 2H), 2.73 (t, J=6.4 Hz, 2H), 2.50 (m, 2H), 1.77 (quintet, J=7.6 Hz, 2H); RP-HPLC (Method 6) $t_R$=3.92 min, 99.76% (AUC); ESI MS m/z 248.20 [M+H]$^+$.

Example 107

Preparation of N-(3-(3-aminopropyl)phenyl)-2-cyclohexylethanesulfonamide

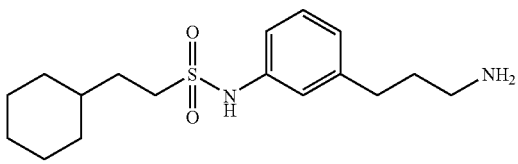 [SMILES: NCCCc1cccc(NS(=O)(=O)CCC2CCCCC2)c1]

N-(3-(3-Aminopropyl)phenyl)-2-cyclohexylethanesulfonamide is prepared following the method used in Example 6.

Step 1: Sulfonation of aniline 17 by 2-cyclohexylethanesulfonyl chloride following the method used in Example 6 gives tert-butyl 3-(3-(2-cyclohexylethylsulfonamido)phenyl)propylcarbamate.

Step 2: Deprotection of tert-butyl 3-(3-(2-cyclohexylethylsulfonamido)phenyl)propylcarbamate gives Example 107 hydrochloride.

Example 108

Preparation of N-(3-(3-aminopropanoyl)phenyl)-2-cyclohexylethanesulfonamide

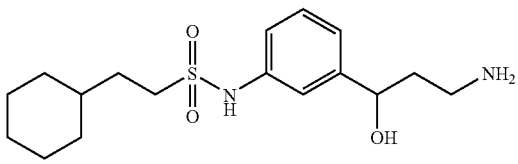 [SMILES: NCCC(O)c1cccc(NS(=O)(=O)CCC2CCCCC2)c1]

N-(3-(3-Aminopropanoyl)phenyl)-2-cyclohexylethanesulfonamide is prepared following the method used in Example 97.

Step 1: Sulfonation of aniline 35 by 2-cyclohexylethanesulfonyl chloride gives tert-butyl 3-(3-(2-cyclohexylethylsulfonamido)phenyl)-3-hydroxypropylcarbamate.

Step 2: Deprotection of tert-butyl 3-(3-(2-cyclohexylethylsulfonamido)phenyl)-3-hydroxypropylcarbamate gives Example 108 hydrochloride.

Example 109

Preparation of N-(3-(3-amino-1-hydroxypropyl)phenyl)-2-cyclohexylethanesulfonamide

N-(3-(3-Amino-1-hydroxypropyl)phenyl)-2-cyclohexylethanesulfonamide is prepared following the method used in Example 98.

Step 1: Oxidation of tert-butyl 3-(3-(2-cyclohexylethylsulfonamido)phenyl)-3-hydroxypropylcarbamate gives tert-butyl 3-(3-(2-cyclohexylethylsulfonamido)phenyl)-3-oxopropylcarbamate.

Step 2: Deprotection of tert-butyl 3-(3-(2-cyclohexylethylsulfonamido)phenyl)-3-oxopropylcarbamate gives Example 109 hydrochloride.

Example 110

Preparation of 3-(3-aminopropyl)-N-(5-(benzyloxy)pentyl)aniline

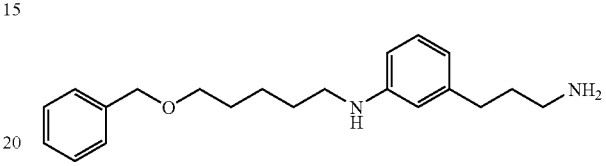

3-(3-Aminopropyl)-N-(5-(benzyloxy)pentyl)aniline is prepared following the method used in Example 95.

Step 1: Hydrogenation of aniline 17 and 5-(benzyloxy)pentanal gives tert-butyl 3-(3-(5-(benzyloxy)pentylamino)phenyl)propylcarbamate.

Step 2: Deprotection of tert-butyl 3-(3-(5-(benzyloxy)pentylamino)phenyl)propylcarbamate following the method used in Example 11 gives Example 110 hydrochloride.

Example 111

Preparation of N-(3-(3-aminopropyl)phenyl)-5-methoxypentane-1-sulfonamide

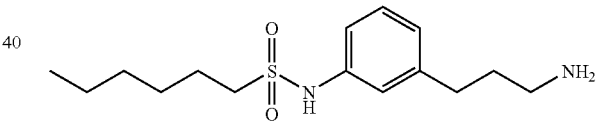

N-(3-(3-Aminopropyl)phenyl)-5-methoxypentane-1-sulfonamide is prepared following the method used in Example 6.

Step 1: Sulfonation of aniline 17 by hexane-1-sulfonyl chloride following the method used in Example 6 gives tert-butyl 3-(3-(hexylsulfonamido)phenyl)propylcarbamate.

Step 2: Deprotection of tert-butyl 3-(3-(hexylsulfonamido)phenyl)propylcarbamate gives Example 111 hydrochloride.

Example 112

Preparation of N-(3-(3-amino-1-hydroxypropyl)phenyl)-5-methoxypentane-1-sulfonamide

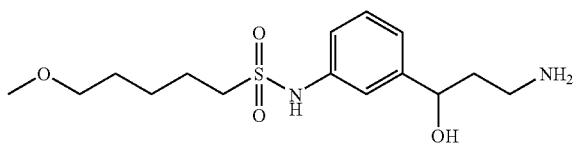 [SMILES: COCCCCCS(=O)(=O)Nc1cccc(C(O)CCN)c1]

N-(3-(3-Amino-1-hydroxypropyl)phenyl)-5-methoxypentane-1-sulfonamide is prepared following the method used in Example 97.

Step 1: Sulfonation of aniline 35 by 5-methoxypentane-1-sulfonyl chloride gives tert-butyl 3-hydroxy-3-(3-(5-methoxypentylsulfonamido)phenyl)propylcarbamate.

Step 2: Deprotection of tert-butyl 3-hydroxy-3-(3-(5-methoxypentylsulfonamido)phenyl)propylcarbamate gives Example 112 hydrochloride.

Example 113

Preparation of N-(3-(3-aminopropanoyl)phenyl)-5-methoxypentane-1-sulfonamide

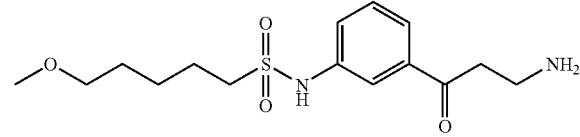 [SMILES: COCCCCCS(=O)(=O)Nc1cccc(C(=O)CCN)c1]

N-(3-(3-Aminopropanoyl)phenyl)-5-methoxypentane-1-sulfonamide is prepared following the method used in Example 98.

Step 1: Oxidation of tert-butyl 3-hydroxy-3-(3-(5-methoxypentylsulfonamido)phenyl)propylcarbamate gives tert-butyl 3-(3-(5-methoxypentylsulfonamido)phenyl)-3-oxopropylcarbamate.

Step 2: Deprotection of tert-butyl 3-(3-(5-methoxypentylsulfonamido)phenyl)-3-oxopropylcarbamate gives Example 113 hydrochloride.

Example 114

Preparation of (E)-1-(3-(3-amino-1-deutero-1-hydroxypropyl)styryl)cyclohexanol

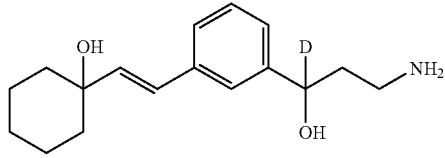 [SMILES: [2H]C(O)(CCN)c1cccc(/C=C/C2(O)CCCCC2)c1]

(E)-1-(3-(3-Amino-1-deutero-1-hydroxypropyl)styryl) cyclohexanol was prepared following the method shown in Scheme 13.

SCHEME 13

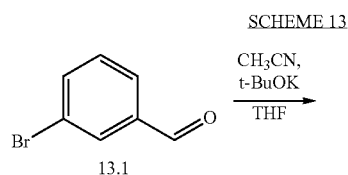

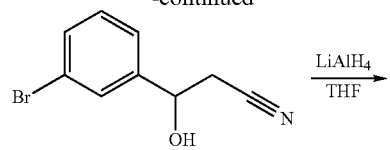

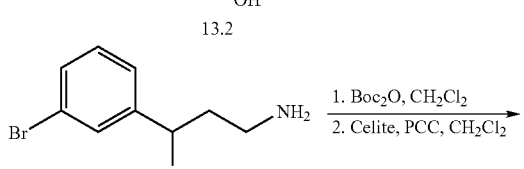

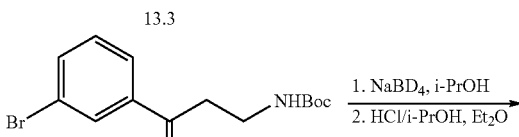

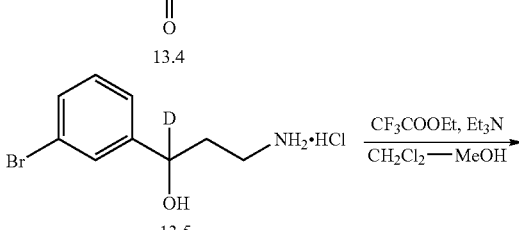

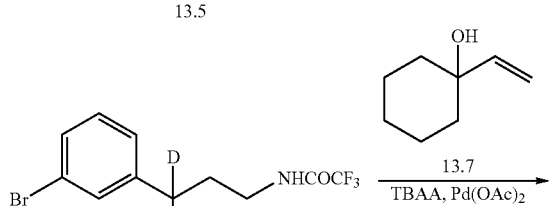

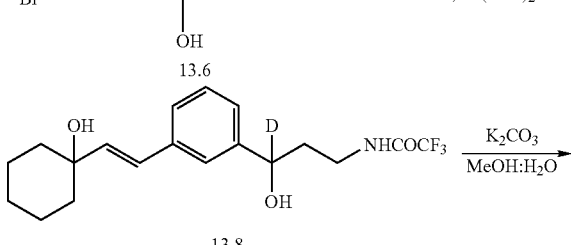

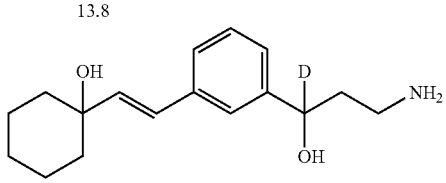

Step 1: To a cold (−50° C.) solution of t-BuO⁻K⁺ in THF (1M, 0.76 L, 760 mmol) under $N_2$ was slowly added acetonitrile (37.0 mL, 703 mmol). The reaction mixture was stirred for 25 min and then a solution of 3-bromobenzaldehyde (13.1) (75 mL, 640 mmol) in anhydrous THF was added dropwise keeping the temperature below −40° C. After addition was complete, the reaction mixture as stirred at for 45 min while slowly warming to −10° C. The reaction mixture was partitioned between THF and an aqueous solution of $NH_4Cl$ (25%), organic layer was washed with brine, dried over anhydrous $MgSO_4$ and filtered. The filtrate was concentrated under reduced pressure to give hydroxynitrile 13.2 as an amber oil. Yield (148 g, quant.); ¹H NMR (400 MHz, DMSO-d₆) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 4.87-4.92 (m, 1H), 2.94-2.80 (m, 2H).

Step 2: To an ice cold solution of 3-(3-bromophenyl)-3-hydroxypropanenitrile (13.2) (2.70 g, 11.9 mmol) in anhydrous THF under argon was added a solution of LiAlH$_4$ in THF (11.9 mL of a 2 M solution in THF, 23.8 mmol). The mixture was stirred at 0° C. for 45 min, diluted with ether (50 mL), and quenched with the dropwise addition of saturated aqueous Na$_2$SO$_4$ (approximately 2 mL). After drying over MgSO$_4$, the mixture was filtered and concentrated under reduced pressure to give amine 13.3 as a light green oil. This material was used in the next step without further purification. Yield (2.30 g, 84%); $^1$H NMR (400 MHz, DMSO-d$_6$) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 3: To a solution of amine 13.3 (5.67 g, 24.6 mmol) in anhydrous CH$_2$Cl$_2$ was added Boc$_2$O (5.69 g, 26.1 mmol). The reaction mixture was stirred at room temperature for 15 min, concentrated under reduced pressure, the residue was dissolved in CH$_2$Cl$_2$ and Celite (8.67 g) followed by pyridinium chlorochromate (7.67 g, 35.6 mmol) was added. The reaction mixture was stirred at room temperature for 17 hrs and solvent was removed under reduced pressure. Dark brown residue was suspended in EtOAc—hexanes (30%), filtered and the filtrate was concentrated under reduced pressure. Purification by flash chromatography (20% to 80% EtOAc—hexanes gradient) gave ketone 13.4 as a light yellow oil. Yield (7.2 g, 89%); $^1$H NMR (400 MHz, DMSO-d$_6$) δ 8.0-8.04 (m, 1H), 7.87-7.93 (m, 1H), 7.78-7.83)m, 1H), 7.47 (t, J=7.8 Hz, 1H), 6.78 (br. t, J=5.1 Hz, 1H), 3.25 (q, J=5.7 Hz, 2H), 3.12 (t, J=6.3 Hz, 2H), 1.33 (s, 9H).

Step 4: NaBD$_4$ (1.07 g, 25.5 mmol) was added to stirred solution of ketone 13.4 (3.30 g, 10.1 mmol) in i-PrOH. The reaction mixture was stirred at room temperature for 30 min, aqueous NH$_4$Cl (25%) was carefully added. The product was extracted with EtOAc, organic layer was washed with brine, dried over anhydrous MgSO$_4$ and concentrated under reduced pressure to give 3-amino-1-(3-bromophenyl)-1-deuteropropan-1-ol as a colorless oil. Yield (3.44 g, quant.); $^1$H NMR (400 MHz, DMSO-d$_6$) δ 7.49 (t, J=1.6 Hz, 1H), 7.39 (dt, J=1.6, 7.4 Hz, 1H), 7.23-7.32 (m, 2H), 6.75 (br. t, J=4.9 Hz, 1H), 5.30 (s, 1H), 2.87-3.00 (m, 2H), 1.65 (t, J=7.0 Hz, 2H), 1.35 (s, 9H). A mixture of 3-amino-1-(3-bromophenyl)-1-deuteropropan-1-ol (3.44 g), HCl/i-PrOH (5.5 M, 30 mL) and Et$_2$O was stirred at room temperature for 6 hrs and concentrated under reduced pressure to give amine hydrochloride 13.5 as a colorless oil. Yield (3.07 g, quant.). The product was used in the next step without purification.

Step 5: To a solution of salt 13.5 (3.07 g) in CH$_2$Cl$_2$—MeOH (2:1) was added Et$_3$N (1.8 mL, 12.9 mmol) followed by CF$_3$COOEt (3.0 mL, 25.1 mmol) and the reaction mixture was stirred at room temperature overnight. The reaction mixture was concentrated under reduced pressure, the residue was partitioned between aq. NH$_4$Cl (25%) and EtOAc. The aqueous layer was extracted with EtOAc, combined organic layers were washed with brine, dried over anhydrous MgSO$_4$, and concentrated under reduced pressure to give amide 13.6 as a light yellow oil. Yield (3.14 g, 83%); $^1$H NMR (400 MHz, DMSO-d$_6$) δ 9.32 (br. s, 1H), 7.51 (t, J=1.8 Hz, 1H), 7.38-7.42 (m, 1H), 7.23-7.33 (m, 2H), 5.43 (s, 1H), 3.16-3.29 (m, 2H), 1.70-1.85 (m, 2H).

Step 6. Tetrabutylammonium acetate (2.0 g) was added to N-(3-(3-bromophenyl)-3-deutero-3-hydroxypropyl)-2,2,2-trifluoroacetamide (13.6) (0.72 g, 2.2 mmol), 1-vinylcyclohexanol (13.7) (0.416 g, 3.3 mmol) and Pd(OAc)$_2$ (0.01 g, 0.045 mmol). This mixture was stirred under an atmosphere of argon at 90° C. overnight. H$_2$O and EtOAc were added to the reaction mixture and layers were separated. The organic layer was dried over Na$_2$SO$_4$ and concentrated under reduced pressure. Flash chromatography (30% EtOAc/hexanes) gave alkene 13.8 as a light brown oil. Yield (0.53 g, 64%); $^1$H NMR (400 MHz, DMSO-d$_6$) δ 9.31 (t, J=5.0 Hz, 1H), 7.35 (s, 1H), 7.26-7.22 (m, 2H), 7.16-7.13 (m, 1H), 6.51 (d, J=16.0 Hz, 1H), 6.35 (d, J=16.0 Hz, 1H), 5.27 (br.s, 1H), 4.39 (br.s, 1H), 3.26-3.21 (m, 2H), 1.80-1.77 (m, 2H), 1.63-1.39 (m, 9H), 1.26-1.17 (m, 1H).

Step 7. To a solution of (E)-N-(3-deutero-3-hydroxy-3-(3-(2-(1-hydroxycyclohexyl)vinyl)phenyl)propyl)-2,2,2-trifluoroacetamide (13.8) (0.26 g, 0.69 mmol) in H$_2$O/MeOH (1:4) was added K$_2$CO$_3$ (0.48 g, 3.5 mmol). This mixture was stirred at 50° C. for 3 h and then evaporated to near dryness. H$_2$O and EtOAc were added to the residue and the layers were separated. The organic layer was dried over Na$_2$SO$_4$ and concentrated under reduced pressure. Flash chromatography (10% MeOH/CH$_2$Cl$_2$) followed by (10% 7N NH$_3$ in MeOH/CH$_2$Cl$_2$) gave Example 115 as a clear oil. Yield (0.122 g, 64%); $^1$H NMR (400 MHz, DMSO-d$_6$) δ 7.35 (s, 1H), 7.29-7.15 (m, 2H), 7.14-7.11 (m, 1H), 6.50 (d, J=16.0 Hz, 1H), 6.33 (d, J=16.0 Hz, 1H), 4.40 (br.s, 1H), 2.66-2.53 (m, 2H), 1.66-1.49 (m, 4H), 1.47-1.39 (m, 7H), 1.25-1.17 (m, 1H); ESI MS m/z 277.3 [M+H]$^+$.

Example 115

Preparation of (E)-3-amino-1-(3-(2-cyclohexylvinyl)phenyl)-2,2-dideuteropropan-1-ol

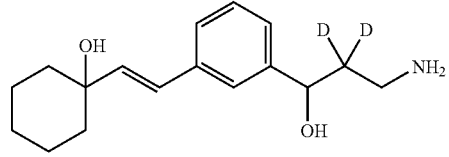 [SMILES: [2H]C([2H])(CN)C(O)c1cccc(/C=C/C2(O)CCCCC2)c1]

(E)-3-Amino-1-(3-(2-cyclohexylvinyl)phenyl)-2,2-dideuteropropan-1-ol was prepared following the method used in Example 114.

Step 1: Addition of trideuteroacetonitrile to 3-bromobenzaldehyde gave 3-(3-bromophenyl)-2,2-dideutero-3-hydroxypropanenitrile as a colorless oil. Yield (5.17 g, 95%); $^1$H NMR (400 MHz, DMSO-d$_6$) δ 7.60 (t, J=1.6 Hz, 1H), 7.46 (ddd, J=1.2, 2.0, 7.8 Hz, 1H), 7.37-7.41 (m, 1H), 7.31 (t, J=7.6 Hz, 1H), 6.05 (d, J=4.0 Hz, 1H), 4.88 (m, 1H).

Step 2: A mixture of 3-(3-bromophenyl)-2,2-dideutero-3-hydroxypropanenitrile (1.91 g, 8.37 mmol), borane-dimethylsulfide (2.0 mL, 21.1 mmol) in anhydrous THF was sritted under reflux for 15 hr. After cooling to room temperature MeOH was carefully added to the reaction mixture followed by HCl/MeOH (1.25 M, 10 mL). The mixture was stirred under reflux for 4 hrs and concentrated under reduced pressure to give 3-amino-1-(3-bromophenyl)-2,2-dideuteropropan-1-ol hydrochloride as a white foam which was used in the next step without purification. Yield (2.25 g, quant.).

Step 3: To a solution of 3-amino-1-(3-bromophenyl)-2,2-dideuteropropan-1-ol hydrochloride (2.25 g, 8.38 mmol) in CH$_2$Cl$_2$—MeOH (2:1) was added CF$_3$COOEt (3.0 mL) followed by Et$_3$N (2.0 mL, 14.3 mmol). The reaction mixture was stirred at room temperature for 1 h and concentrated under reduced pressure. The residue was suspended in EtOAc, washed with brine, dried over anhydrous MgSO$_4$ and concentrated under reduced pressure to give N-(3-(3-bromophenyl)-2,2-dideutero-3-hydroxypropyl)-2,2,2-trifluoroacetamide as a colorless oil. Yield (2.81 g, quant.); $^1$H NMR (400 MHz, DMSO-d$_6$) δ 9.32 (br.s, 1H), 7.49-7.52 (m, 1H), 7.40 (dt, J=1.6, 7.4 Hz, 1H), 7.24-7.32 (m, 2H), 5.44 (d, J=4.7 Hz, 1H), 4.56 (d, J=4.7 Hz, 1H), 3.16-3.27 (m, 2H).

Step 4. Heck coupling between N-(3-(3-bromophenyl)-2,2-dideutero-3-hydroxypropyl)-2,2,2-trifluoroacetamide and 1-vinylcyclohexanol following the method used in Example 114 gave (E)-N-(2,2-dideutero-3-hydroxy-3-(3-(2-(1-hydroxycyclohexyl)vinyl)phenyl)propyl)-2,2,2-trifluoroacetamide as a clear oil. Yield (0.32 g, 56%); $^1$H NMR (400 MHz, CD$_3$OD) δ 7.40 (s, 1H), 7.24-7.28 (m, 2H), 7.16-7.20 (m, 1H), 6.60 (d, J=16.4 Hz, 1H), 6.36 (d, J=16.4 Hz, 1H), 4.67 (s, 1H), 3.35 (s, 2H), 1.49-1.76 (m, 9H), 1.28-1.40 (m, 1H).

Step 5. (E)-N-(2,2-dideutero-3-hydroxy-3-(3-(2-(1-hydroxycyclohexyl)vinyl)phenyl)propyl)-2,2,2-trifluoroacetamide was deprotected following the method used in Example 114 to give Example 115 as a light yellow oil. Yield (0.22 g, quant.); $^1$H NMR (400 MHz, CD$_3$OD) δ 7.40 (s, 1H), 7.24-7.28 (m, 2H), 7.16-7.20 (m, 1H), 6.60 (d, J=16.4 Hz, 1H), 6.35 (d, J=16.4 Hz, 1H), 4.70 (s, 1H), 2.71 (d, J=6.0 Hz, 2H), 1.49-1.78 (m, 9H), 1.30-1.40 (m, 1H).

Example 116

Preparation of (E)-1-(3-(3-Amino-3,3-dideutero-1-hydroxypropyl)styryl)cyclohexanol

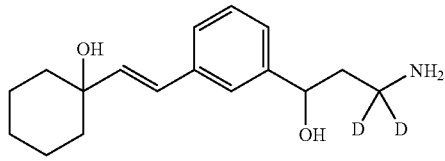 [SMILES: [2H]C([2H])(N)CC(O)c1cccc(/C=C/C2(O)CCCCC2)c1]

(E)-1-(3-(3-Amino-3,3-dideutero-1-hydroxypropyl)styryl)cyclohexanol was prepared following the method used in Example 114.

Step 1. Heck coupling between N-(3-(3-bromophenyl)-1,1-dideuteropropyl)-2,2,2-trifluoroacetamide and 1-vinylcyclohexanol following the method used in Example 114 gave (E)-N-(1,1-dideutero-3-hydroxy-3-(3-(2-(1-hydroxycyclohexyl)vinyl)phenyl)propyl)-2,2,2-trifluoroacetamide as a clear oil. Yield (0.41 g, 70%); $^1$H NMR (400 MHz, DMSO-d$_6$) δ 9.31 (s, 1H), 7.34 (s, 1H), 7.26-7.22 (m, 2H), 7.16-7.12 (m, 1H), 6.50 (d, J=16.0 Hz, 1H), 6.34 (d, J=16.0 Hz, 1H), 5.29 (d, J=4.4 Hz, 1H), 4.57-4.53 (m, 1H), 4.40 (s, 1H), 1.80-1.73 (m, 2H), 1.62-1.39 (m, 9H), 1.25-1.15 (m, 1H).

Step 2. (E)-N-(1,1-dideutero-3-hydroxy-3-(3-(2-(1-hydroxycyclohexyl)vinyl)phenyl)propyl)-2,2,2-trifluoroacetamide was deprotected following the method used in Example 114 to give Example 116 as a clear oil. Yield (0.22 g, 72%); $^1$H NMR (400 MHz, DMSO-d$_6$) δ 7.36 (m, 1H), 7.22-7.15 (m, 2H), 7.14-7.11 (m, 1H), 6.50 (d, J=16.0 Hz, 1H), 6.33 (d, J=16.0 Hz, 1H), 4.63 (t, J=5.6 Hz, 1H), 4.40 (br.s, 1H), 1.67-1.52 (m, 4H), 1.49-1.39 (m, 7H), 1.26-1.17 (m, 1H); ESI MS m/z 278.2 [M+H]$^+$.

Example 117

Preparation of (E)-4-(2-(3-(3-amino-1-Hydroxypropyl)phenyl)-1,2-dideuterovinyl)heptan-4-ol

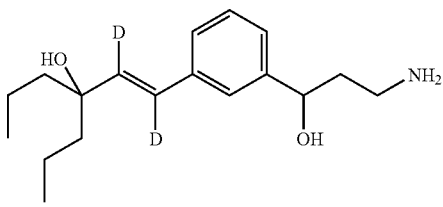 [SMILES: [2H]/C(=C(/[2H])C(O)(CCC)CCC)c1cccc(C(O)CCN)c1]

(E)-4-(2-(3-(3-Amino-1-hydroxypropyl)phenyl)-1,2-dideuterovinyl)heptan-4-ol was prepared following the method described below.

Step 1. To an ice cooled solution of 4-((3-(3-amino-1-hydroxypropyl)phenyl)ethynyl)heptan-4-ol (1.0 g, 3.46 mmol) in anhydrous ether was slowly added LiAlD$_4$ (0.436 g, 10.4 mmol) over a 2-3 min period. The solution was allowed to warm to room temp while stirring overnight. The reaction was quenched with saturated solution of anhydrous Na$_2$SO$_4$ in D$_2$O (3 ml) and stirred for 6.0 hr. MgSO$_4$ (~5 g) was added and the solution was left to stand overnight. Filtration and evaporation was followed with flash chromatography (10% 7N NH$_3$/MeOH/CH$_2$Cl$_2$) to give Example 117 as a clear oil. Yield (0.524 g, 51%); $^1$H NMR (400 MHz, DMSO-d$_6$) δ 7.32 (m, 1H), 7.23-7.18 (m, 2H), 7.14-7.10 (m, 1H), 4.64-4.61 (m, 1H), 4.31 (br.s, 1H), 2.67-2.57 (m, 2H), 1.64-1.57 (m, 2H), 1.48-1.17 (m, 8H), 0.82 (t, J=7.2 Hz, 6H).

Example 118

Preparation of (E)-1-(3-(3-amino-1-hydroxypropyl)-4-deuterostyryl)cyclohexanol

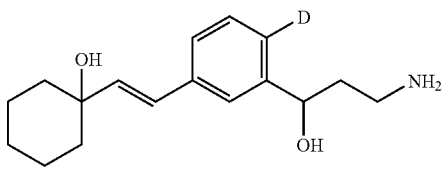 [SMILES: [2H]c1ccc(/C=C/C2(O)CCCCC2)cc1C(O)CCN]

(E)-1-(3-(3-Amino-1-hydroxypropyl)-4-deuterostyryl)cyclohexanol was prepared following the method shown in Scheme 14.

SCHEME 14

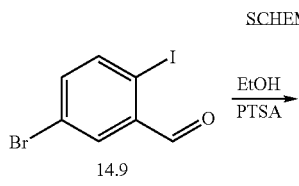

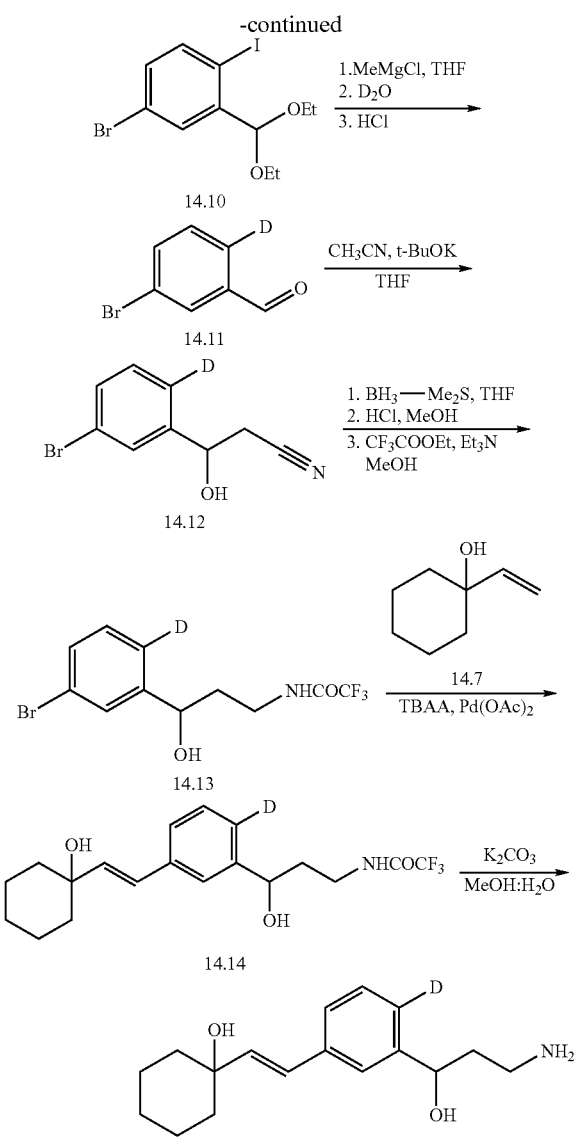

Step 1: A mixture of 5-bromo-2-iodobenzaldehyde (14.9) (1.0 g, 3.2 mmol) and PTSA (0.1 g) in ethanol was stirred under reflux for 18 hrs and concentrated under reduced pressure. The residue was dissolved in ethyl acetate and washed with saturated NaHCO$_3$, dried over anhydrous Na$_2$SO$_4$ and concentrated to give 4-bromo-2-(diethoxymethyl)-1-iodobenzene (14.10) that was directly used in next reaction without further purification.

Step 2. To a solution of 4-bromo-2-(diethoxymethyl)-1-iodobenzene (3.2 mmol) in THF was added MeMgCl (2 ml, 3M in THF) at −25° C. under argon. After stirring at −25° C. for 30 mins, the reaction mixture was warmed to 0° C. and stirred at 0° C. for 30 mins. D$_2$O (0.6 ml) was added followed by 6N HCl (5 ml) and the mixture was stirred at room temperature for 2 hrs, then extracted with ethyl acetate (8 ml). Organic portion was washed with brine, dried and concentrated to give product 3-bromo-5-deuterobenzaldehyde as a light yellow oil. Yield (0.59 g, quant.); $^1$H NMR (400 MHz, DMSO-d$_6$) δ 9.56 (s, 1H), 8.05 (d, J=2.0 Hz, 1H), 7.88 (dd, J=8.0, 2.4 Hz, 1H), 7.54 (d, J=8.0 Hz, 1H).

Step 3: Addition of acetonitrile to 3-bromo-5-deuterobenzaldehyde (14.11) gave 3-(5-bromo-2-deuterophenyl)-3-hydroxypropanenitrile as a colorless oil. Yield (0.31 g, 41%); $^1$H NMR (400 MHz, DMSO-d$_6$) δ 7.51 (d, J=2.0 Hz, 1H), 7.46 (dd, J=8.0, 2.0 Hz, 1H), 7.30 (d, J=8.0 Hz, 1H), 7.60 (t, J=1.6 Hz, 1H), 6.04 (br. s, 1H), 4.89 (br. s, 1H), 2.79-2.93 (m, 2H).

Step 4: A mixture of 3-(5-bromo-2-deuterophenyl)-3-hydroxypropanenitrile (14.12) (0.3 g, 1.32 mmol), borane-dimethylsulfide (0.5 mL, 3.9 mmol) in anhydrous THF was stirred under reflux for 18 hr. After cooling to room temperature MeOH was carefully added to the reaction mixture followed by HCl/MeOH (1.25 M, 10 mL). The mixture was stirred at 50° C. for 5 hrs and concentrated. To the residue was added CH$_2$Cl$_2$—MeOH (2:1) (30 ml), CF$_3$COOEt (5.0 mL) and Et$_3$N (2.0 mL, 14.3 mmol). The reaction mixture was stirred at 50° C. for 8 h and concentrated under reduced pressure. The residue was partitioned in EtOAc and 1N HCl. Organic portion was washed with brine, dried over anhydrous Na$_2$SO$_4$ and concentrated under reduced pressure. Purification by flash chromatography (40% to 50% EtOAc—hexanes gradient) gave N-(3-(5-bromo-2-deuterophenyl)-3-hydroxypropyl)-2,2,2-trifluoroacetamide as a colorless oil. Yield (0.21 g, 89%); $^1$H NMR (400 MHz, CD$_3$OD) δ 9.16 (br.s, 1H), 7.53 (d, J=2.4 Hz, 1H), 7.39 (dd, J=8.0, 2.0 Hz, 1H), 7.23 (d, J=8.0 Hz, 1H), 4.65 (dd, J=7.6, 5.6 Hz, 1H), 3.35-3.41 (m, 2H), 1.88-1.94 (m, 2H).

Step 5. Heck coupling between N-(3-(5-bromo-2-deuterophenyl)-3-hydroxypropyl)-2,2,2-trifluoroacetamide and 1-vinylcyclohexanol following the method used in Example 114 gave (E)-2,2,2-trifluoro-N-(3-hydroxy-3-(5-(2-(1-hydroxycyclohexyl)vinyl)-2-deuterophenyl)propyl)acetamide as a colorless oil. Yield (0.2 g, 84%); $^1$H NMR (400 MHz, CD$_3$OD) δ 7.39 (s, 1H), 7.26-7.28 (m, 2H), 6.60 (d, J=16.0 Hz, 1H), 6.36 (d, J=16.0 Hz, 1H), 4.67 (t, J=6.4 Hz, 1H), 3.37 (t, J=7.2 Hz, 2H), 1.94 (q, J=7.2 Hz, 2H), 1.49-1.76 (m, 9H), 1.26-1.40 (m, 1H).

Step 6. (E)-2,2,2-trifluoro-N-(3-hydroxy-3-(5-(2-(1-hydroxycyclohexyl)vinyl)-2-deuterophenyl)propyl)acetamide (14) was deprotected following the method used in Example 114 to give Example 118 as a light yellow oil. Yield (0.15 g, quant.); $^1$H NMR (400 MHz, CD$_3$OD) δ 7.40 (s, 1H), 7.24-7.28 (m, 2H), 6.60 (d, J=16.4 Hz, 1H), 6.35 (d, J=16.4 Hz, 1H), 4.71 (dd, J=8.0, 5.6 Hz, 1H), 2.68-2.78 (m, 2H), 1.80-1.94 (m, 2H), 1.48-1.76 (m, 9H), 1.30-1.42 (m, 1H).

Example 119

Preparation of 4-((3-(3-amino-1-deutero-1-hydroxypropyl)phenyl)ethynyl)heptan-4-ol

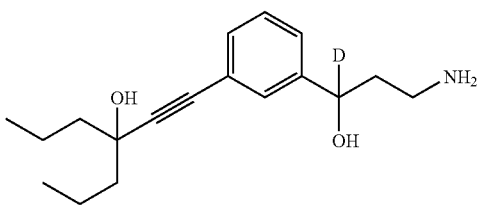 [SMILES: [2H]C(O)(CCN)c1cccc(C#CC(O)(CCC)CCC)c1]

4-((3-(3-Amino-1-deutero-1-hydroxypropyl)phenyl)ethynyl)heptan-4-ol was prepared following the method shown in Scheme 15.

SCHEME 15

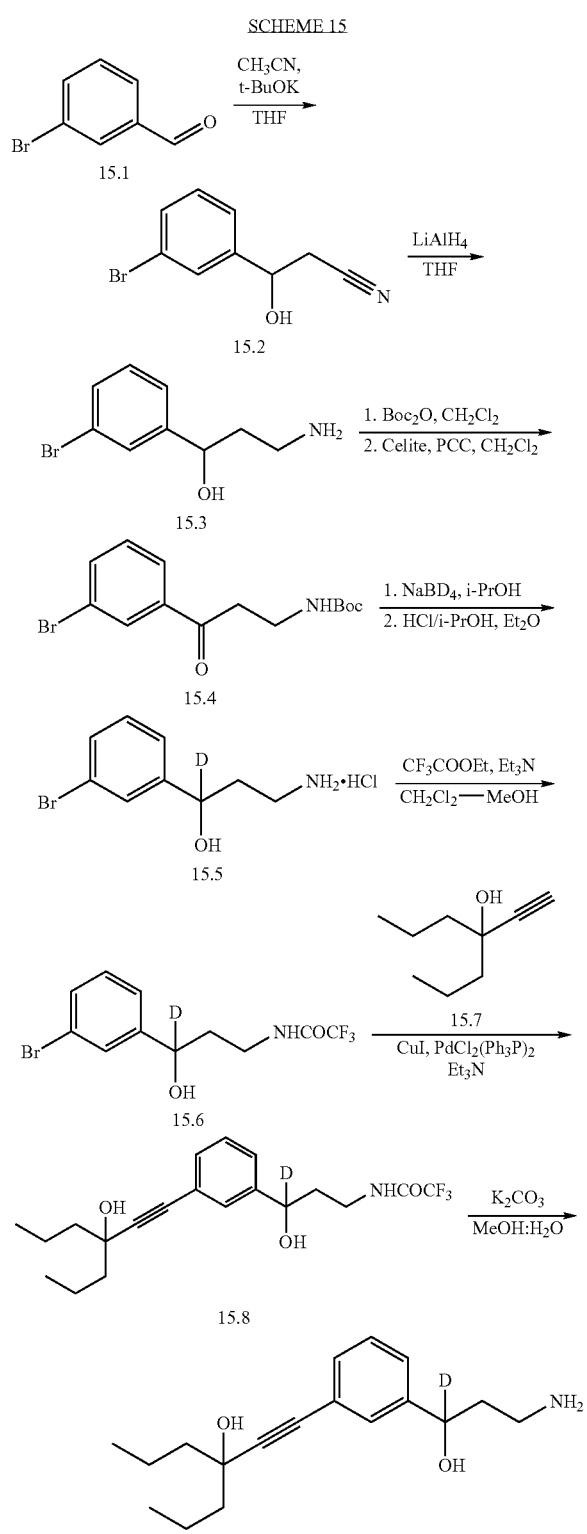

Step 1: To a cold (−50° C.) solution of t-BuO⁻K⁺ in THF (1M, 0.76 L, 760 mmol) under N₂ was slowly added acetonitrile (37.0 mL, 703 mmol). The reaction mixture was stirred for 25 min and then a solution of 3-bromobenzaldehyde (15.1) (75 mL, 640 mmol) in anhydrous THF was added dropwise keeping the temperature below −40° C. After addition was complete, the reaction mixture as stirred at for 45 min while slowly warming to −10° C. The reaction mixture was partitioned between THF and an aqueous solution of NH₄Cl (25%), organic layer was washed with brine, dried over anhydrous MgSO₄ and filtered. The filtrate was concentrated under reduced pressure to give hydroxynitrile 15.2 as an amber oil. Yield (148 g, quant.); ¹H NMR (400 MHz, DMSO-d₆) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 4.87-4.92 (m, 1H), 2.94-2.80 (m, 2H).

Step 2: To an ice cold solution of 3-(3-bromophenyl)-3-hydroxypropanenitrile (15.2) (2.70 g, 11.9 mmol) in anhydrous THF under argon was added a solution of LiAlH₄ in THF (11.9 mL of a 2 M solution in THF, 23.8 mmol). The mixture was stirred at 0° C. for 45 min, diluted with ether (50 mL), and quenched with the dropwise addition of saturated aqueous Na₂SO₄ (approximately 2 mL). After drying over MgSO₄, the mixture was filtered and concentrated under reduced pressure to give amine 15.3 as a light green oil. This material was used in the next step without further purification. Yield (2.30 g, 84%); ¹H NMR (400 MHz, DMSO-d₆) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 3: To a solution of amine 15.3 (5.67 g, 24.6 mmol) in anhydrous CH₂Cl₂ was added Boc₂O (5.69 g, 26.1 mmol). The reaction mixture was stirred at room temperature for 15 min, concentrated under reduced pressure, the residue was dissolved in CH₂Cl₂ and Celite (8.67 g) followed by pyridinium chlorochromate (7.67 g, 35.6 mmol) was added. The reaction mixture was stirred at room temperature for 17 hrs and solvent was removed under reduced pressure. Dark brown residue was suspended in EtOAc—hexanes (30%), filtered and the filtrate was concentrated under reduced pressure. Purification by flash chromatography (20% to 80% EtOAc—hexanes gradient) gave ketone 15.4 as a light yellow oil. Yield (7.2 g, 89%); ¹H NMR (400 MHz, DMSO-d₆) δ 8.0-8.04 (m, 1H), 7.87-7.93 (m, 1H), 7.78-7.83)m, 1H), 7.47 (t, J=7.8 Hz, 1H), 6.78 (br. t, J=5.1 Hz, 1H), 3.25 (q, J=5.7 Hz, 2H), 3.12 (t, J=6.3 Hz, 2H), 1.33 (s, 9H).

Step 4: NaBD₄ (1.07 g, 25.5 mmol) was added to stirred solution of ketone 15.4 (3.30 g, 10.1 mmol) in i-PrOH. The reaction mixture was stirred at room temperature for 30 min, aqueous NH₄Cl (25%) was carefully added. The product was extracted with EtOAc, organic layer was washed with brine, dried over anhydrous MgSO₄ and concentrated under reduced pressure to give 3-amino-1-(3-bromophenyl)-1-deuteropropan-1-ol as a colorless oil. Yield (3.44 g, quant.); ¹H NMR (400 MHz, DMSO-d₆) δ 7.49 (t, J=1.6 Hz, 1H), 7.39 (dt, J=1.6, 7.4 Hz, 1H), 7.23-7.32 (m, 2H), 6.75 (br. t, J=4.9 Hz, 1H), 5.30 (s, 1H), 2.87-3.00 (m, 2H), 1.65 (t, J=7.0 Hz, 2H), 1.35 (s, 9H). A mixture of 3-amino-1-(3-bromophenyl)-1-deuteropropan-1-ol (3.44 g), HCl/i-PrOH (5.5 M, 30 mL) and Et₂O was stirred at room temperature for 6 hrs and concentrated under reduced pressure to give amine hydrochloride 15.5 as a colorless oil. Yield (3.07 g, quant.). The product was used in the next step without purification.

Step 5: To a solution of salt 15.5 (3.07 g) in CH₂Cl₂—MeOH (2:1) was added Et₃N (1.8 mL, 12.9 mmol) followed by CF₃COOEt (3.0 mL, 25.1 mmol) and the reaction mixture was stirred at room temperature overnight. The reaction mixture was concentrated under reduced pressure, the residue was partitioned between aq. NH₄Cl (25%) and EtOAc. The aqueous layer was extracted with EtOAc, combined organic layers were washed with brine, dried over anhydrous MgSO₄, and concentrated under reduced pressure to give amide 15.6 as a light yellow oil. Yield (3.14 g, 83%); ¹H NMR (400 MHz, DMSO-d$_6$) δ 9.32 (br. s, 1H), 7.51 (t, J=1.8 Hz, 1H), 7.38-7.42 (m, 1H), 7.23-7.33 (m, 2H), 5.43 (s, 1H), 3.16-3.29 (m, 2H), 1.70-1.85 (m, 2H).

Step 6: A solution of alkyne 15.7 (0.657 g, 4.69 mmol) and bromide 15.6 (1.369 g, 4.18 mmol) in Et$_3$N (10 mL) was degassed for 3 min by bubbling argon. CuI (0.04 g, 0.2 mmol) and PdCl$_2$(Ph$_3$P)$_2$ (0.131 g, 0.19 mmol) were added, argon was bubbled for 2 min and the reaction mixture was stirred under argon at +80° C. for 2 hrs. The reaction mixture was concentrated under reduced pressure and the residue was purified by flash chromatography (5% to 100% EtOAc—hexanes gradient). Fractions containing product were pooled together, treated with activated charcoal, filtered and the filtrate was concentrated under reduced pressure to give alkyne 15.8 as a light yellow oil. Yield (1.35 g, 83.3%); $^1$H NMR (400 MHz, DMSO-d$_6$) δ 9.33 (br. s, 1H), 7.30-7.34 (m, 1H), 7.25-7.30 (m, 2H), 7.18-7.24 (m, 1H), 5.35 (s, 1H), 5.12 (s, 1H), 3.17-3.26 (m, 2H), 1.70-1.83 (m, 2H), 1.40-1.63 (m, 8H), 0.89 (t, J=7.0 Hz, 6H).

Step 7: A solution of amide 15.8 (0.619 g, 1.60 mmol) and K$_2$CO$_3$ (0.909 g, 6.58 mmol) in MeOH:H$_2$O (2:1, 18 mL) was stirred at room temperature for 24 hrs and the reaction mixture was concentrated under reduced pressure. Purification by flash chromatography (20% to 100% of 20% 7N NH$_3$/MeOH—CH$_2$Cl$_2$—CH$_2$Cl$_2$ gradient) gave Example 119 as a colorless oil. Yield (0.39 g, 84%); $^1$H NMR (400 MHz, CD$_3$OD) δ 7.39-7.41 (m, 1H), 7.26-7.33 (m, 3H), 2.68-2.79 (m, 2H), 1.76-1.89 (m, 2H), 1.52-1.73 (m, 8H), 0.97 (t, J=7.0 Hz, 6H); RP-HPLC (Method 1) t$_R$=9.16 min, 93.1% (AUC); ESI-MS m/z 291.2 [M+H]$^+$.

Step 3: To a solution of 3-amino-1-(3-bromophenyl)-2,2-dideuteropropan-1-ol hydrochloride (2.25 g, 8.38 mmol) in CH$_2$Cl$_2$—MeOH (2:1) was added CF$_3$COOEt (3.0 mL) followed by Et$_3$N (2.0 mL, 14.3 mmol). The reaction mixture was stirred at room temperature for 1 h and concentrated under reduced pressure. The residue was suspended in EtOAc, washed with brine, dried over anhydrous MgSO$_4$ and concentrated under reduced pressure to give N-(3-(3-bromophenyl)-2,2-dideutero-3-hydroxypropyl)-2,2,2-trifluoroacetamide as a colorless oil. Yield (2.81 g, quant.); $^1$H NMR (400 MHz, DMSO-d$_6$) δ 9.32 (br.s, 1H), 7.49-7.52 (m, 1H), 7.40 (dt, J=1.6, 7.4 Hz, 1H), 7.24-7.32 (m, 2H), 5.44 (d, J=4.7 Hz, 1H), 4.56 (d, J=4.7 Hz, 1H), 3.16-3.27 (m, 2H).

Step 4: Sonogashira coupling between N-(3-(3-bromophenyl)-2,2-dideutero-3-hydroxypropyl)-2,2,2-trifluoroacetamide and 1-ethynylcyclohexanol following the method used in Example 119 gave N-(2,2-dideutero-3-hydroxy-3-(3-((1-hydroxycyclohexyl)ethynyl)phenyl)propyl)-2,2,2-trifluoroacetamide as a light brown oil. Yield (0.99 g, 87%); $^1$H NMR (400 MHz, DMSO-d$_6$) δ 9.32 (br. t, 1H), 7.32-7.36 (m, 1H), 7.26-7.31 (m, 2H), 7.22-7.25 (m, 1H), 5.35-5.38 (m, 2H), 4.56 (d, J=4.5 Hz, 1H), 3.16-3.26 (m, 2H), 1.78-1.86 (m, 2H), 1.56-1.66 (m, 2H), 1.40-1.56 (m, 5H), 1.16-1.24 (m, 1H).

Step 5: Deprotection of N-(2,2-dideutero-3-hydroxy-3-(3-((1-hydroxycyclohexyl)ethynyl)phenyl)propyl)-2,2,2-trifluoroacetamide following the method used in Example 119 gave Example 120 as a colorless oil. Yield (0.22 g, 59%); $^1$H NMR ((400 MHz, DMSO-d$_6$) δ 7.31-7.34 (m, 1H), 7.24-7.28 (m, 2H), 7.19-7.23 (m, 1H), 5.38 (br.s, 1H), 4.63 (s, 1H), 2.58 (dt, J=8.4, 12.0 Hz, 2H), 1.76-1.85 (m, 2H), 1.56-1.66 (m, 2H), 1.40-1.56 (m, 7H), 1.16-1.24 (m, 1H).

Example 120

Preparation of 1-((3-(3-amino-2,2-dideutero-1-Hydroxypropyl)phenyl)ethynyl)cyclohexanol Example 121

Preparation of 1-((3-(3-amino-3,3-dideutero-1-Hydroxypropyl)phenyl)ethynyl)cyclohexanol

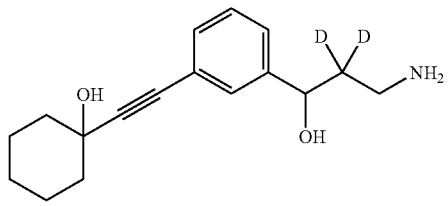 [SMILES: [2H]C([2H])(CN)C(O)c1cccc(C#CC2(O)CCCCC2)c1]

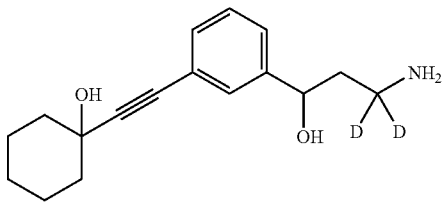 [SMILES: [2H]C([2H])(N)CC(O)c1cccc(C#CC2(O)CCCCC2)c1]

1-((3-(3-Amino-2,2-dideutero-1-hydroxypropyl)phenyl)ethynyl)cyclohexanol was prepared following the method used in Example 119.

Step 1: Addition of trideuteroacetonitrile to 3-bromobenzaldehyde gave 3-(3-bromophenyl)-2,2-dideutero-3-hydroxypropanenitrile as a colorless oil. Yield (5.17 g, 95%); $^1$H NMR (400 MHz, DMSO-d$_6$) δ 7.60 (t, J=1.6 Hz, 1H), 7.46 (ddd, J=1.2, 2.0, 7.8 Hz, 1H), 7.37-7.41 (m, 1H), 7.31 (t, J=7.6 Hz, 1H), 6.05 (d, J=4.0 Hz, 1H), 4.88 (m, 1H).

Step 2: A mixture of 3-(3-bromophenyl)-2,2-dideutero-3-hydroxypropanenitrile (1.91 g, 8.37 mmol), borane-dimethylsulfide (2.0 mL, 21.1 mmol) in anhydrous THF was stirred under reflux for 15 hr. After cooling to room temperature MeOH was carefully added to the reaction mixture followed by HCl/MeOH (1.25 M, 10 mL). The mixture was stirred under reflux for 4 hrs and concentrated under reduced pressure to give 3-amino-1-(3-bromophenyl)-2,2-dideuteropropan-1-ol hydrochloride as a white foam which was used in the next step without purification. Yield (2.25 g, quant.).

1-((3-(3-Amino-3,3-dideutero-1-hydroxypropyl)phenyl)ethynyl)cyclohexanol was prepared following the method used in Example 119.

Step 1: A solution of 3-(3-bromophenyl)-3-hydroxypropanenitrile (3.72 g, 16.5 mmol) in anhydrous Et$_2$O was added under argon to a cooled (0° C.) stirred suspension of LiAlD$_4$ (0.76 g, 18.1 mmol) in anhydrous Et$_2$O and the reaction mixture was stirred at 0° C. for 2 h. Saturated Na$_2$SO$_4$ was slowly added to the reaction mixture until white precipitate formed. The suspension was dried over anhydrous MgSO$_4$ and filtered to give a solution of 3-(3-bromophenyl)-1,1-dideuteropropan-1-amine. $^1$H NMR (400 MHz, CD$_3$OD) δ 7.54 (t, J=1.6 Hz, 1H), 7.39 (dt, J=1.2, 7.8 Hz, 1H), 7.26-7.33 (m, 1H), 7.23 (t, J=7.8 Hz, 1H), 4.66 (dd, J=5.5, 7.4 Hz, 1H), 1.85-1.95 (m, 2H). Ethyl trifluoroacetate (10 mL) was added to the solution of the amine and the mixture was stirred at room temperature for 1 h, concentrated under reduced pressure. Purification by flash chromatography (5% to 20% EtOAc—hexanes gradient) gave N-(3-(3-bromophenyl)-1,1- dideutero-3-hydroxypropyl)-2,2,2-trifluoroacetamide as a light yellow oil. Yield (3.76 g, 70%); $^1$H NMR (400 MHz, CD$_3$OD) δ 7.53 (br.t, J=1.6 Hz, 1H), 7.39 (ddd, J=1.2, 1.8, 7.8 Hz, 1H), 1.30 (m, 1H), 7.23 (t, J=7.8 Hz, 1H), 4.66 (dd, J=5.5, 7.4 Hz, 1H), 1.85-1.94 (m, 2H).

Step 2: Sonogashira coupling between N-(3-(3-bromophenyl)-1,1-dideutero-3-hydroxypropyl)-2,2,2-trifluoroacetamide and 1-ethynylcyclohexanol following the method used in Example 120 gave N-(1,1-dideutero-3-hydroxy-3-(3-((1-hydroxycyclohexyl)ethynyl)phenyl)propyl)-2,2,2-trifluoroacetamide as a light brown oil. Yield (0.84 g, 65%); $^1$H NMR (400 MHz, DMSO-d$_6$) δ 9.31 (br.s, 1H), 7.33-7.36 (m, 1H), 7.25-7.32 (m, 2H), 7.21-7.23 (m, 1H), 5.35-5.39 (m, 2H), 4.57 (dt, J=4.7, 7.8 Hz, 1H), 1.70-1.86 (m, 4H), 1.56-1.66 (m, 2H), 1.40-1.56 (m, 5H), 1.18-1.26 9m, 1H).

Step 3: Deprotection of N-(1,1-dideutero-3-hydroxy-3-(3-((1-hydroxycyclohexyl)ethynyl)phenyl)propyl)-2,2,2-trifluoroacetamide following the method used in Example 120 gave Example 121 as an off-white solid. Yield (0.097 g, 54%); $^1$H NMR (400 MHz, CD$_3$OD) δ 7.40-7.43 9m, 1H), 7.26-7.33 (m, 3H), 4.70 (dd, J=5.3, 7.8 Hz, 1H), 1.90-2.0 (m, 2H), 1.53-1.88 (m, 11H), 1.24-1.35 (m, 1H); RP-HPLC (Method 1) t$_R$=7.52 min, 96.7% (AUC); ESI-MS m/z 276.1 [M+H]$^+$.

Example 122

Preparation of 3-amino-1-(3-(cyclohexylethynyl) phenyl)-2,2-dideuteropropan-1-ol

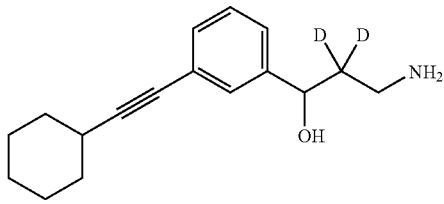 [SMILES: [2H]C([2H])(CN)C(O)c1cccc(C#CC2CCCCC2)c1]

3-Amino-1-(3-(cyclohexylethynyl)phenyl)-2,2-dideuteropropan-1-ol was prepared following the method used in Examples 119, 120.

Step 1: Sonogashira coupling between N-(3-(3-bromophenyl)-2,2-dideutero-3-hydroxypropyl)-2,2,2-trifluoroacetamide and ethynylcyclohexane following the method used in Example 119 gave N-(3-(3-(cyclohexylethynyl)phenyl)-2,2-dideutero-3-hydroxypropyl)-2,2,2-trifluoroacetamide as a clear oil. Yield (0.29 g, 54%); $^1$H NMR (400 MHz, DMSO-d$_6$) δ 9.31 (s, 1H), 7.31 (s, 1H), 7.28-7.24 (m, 2H), 7.22-7.18 (m, 1H), 5.33 (d, J=4.4 Hz, 1H), 4.53 (d, J=4.0 Hz, 1H), 3.25-3.15 (m, 2H), 2.63-2.57 (m, 1H), 1.80-1.77 (m, 2H), 1.68-1.64 (m, 2H), 1.48-1.40 (m, 3H), 1.35-1.29 (m, 3H).

Step 2: Deprotection of N-(3-(3-(cyclohexylethynyl)phenyl)-2,2-dideutero-3-hydroxypropyl)-2,2,2-trifluoroacetamide following the method used in Example 119 gave Example 122 as a colorless oil. Yield (0.14 g, 67%); $^1$H NMR (400 MHz, DMSO-d$_6$) δ 7.29 (s, 1H), 7.24-7.22 (m, 2H), 7.19-7.16 (m, 1H), 4.61 (s, 1H), 2.63-2.51 (m, 3H), 1.80-1.77 (m, 2H), 1.69-1.64 (m, 2H), 1.48-1.40 (m, 3H), 1.35-1.29 (m, 3H).

Example 123

Preparation of 3-amino-1-(3-(cyclohexylethynyl) phenyl)-3,3-dideuteropropan-1-ol

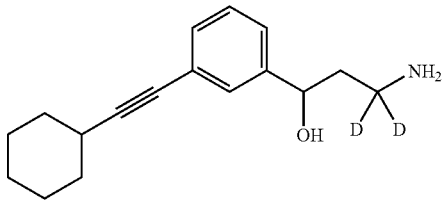 [SMILES: [2H]C([2H])(N)CC(O)c1cccc(C#CC2CCCCC2)c1]

3-Amino-1-(3-(cyclohexylethynyl)phenyl)-3,3-dideuteropropan-1-ol was prepared following the method used in Example 121, 119.

Step 1: Sonogashira coupling between N-(3-(3-bromophenyl)-1,1-dideuteropropyl)-2,2,2-trifluoroacetamide and ethynylcyclohexane following the method used in Example 119 gave N-(3-(3-(cyclohexylethynyl)phenyl)-1,1-difluoro-3-hydroxypropyl)-2,2,2-trifluoroacetamide as a clear oil. Yield (0.079 g, 15%); $^1$H NMR (400 MHz, DMSO-d$_6$) δ 9.30 (s, 1H), 7.31 (s, 1H), 7.26-7.24 (m, 2H), 7.22-7.18 (m, 1H), 5.29 (d, J=4.0 Hz, 1H), 4.56-4.52 (m, 1H), 2.63-2.53 (m, 1H), 1.80-1.29 (m, 10H).

Step 2: Deprotection of N-(3-(3-(cyclohexylethynyl)phenyl)-1,1-difluoro-3-hydroxypropyl)-2,2,2-trifluoroacetamide following the method used in Example 119 gave Example 123 as a colorless oil. Yield (0.037 g, 73%); $^1$H NMR (400 MHz, DMSO-d$_6$) δ 7.29 (s, 1H), 7.24-7.22 (m, 2H), 7.20-7.16 (m, 1H), 4.62 (t, J=6.4 Hz, 1H), 2.63-2.56 (m, 1H), 1.80-1.77 (m, 2H), 1.69-1.62 (m, 2H), 1.57 (d, J=6.8 Hz, 2H), 1.52-1.40 (m, 3H), 1.35-1.29 (m, 3H).

Example 124

Preparation of 1-((3-(3-amino-1-hydroxypropyl)-4-deuterophenyl)ethynyl)cyclohexanol

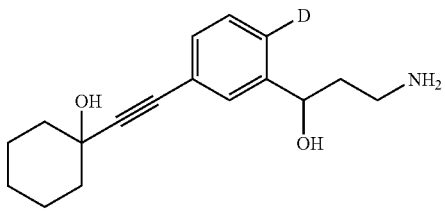 [SMILES: [2H]c1ccc(C#CC2(O)CCCCC2)cc1C(O)CCN]

1-((3-(3-Amino-1-hydroxypropyl)-4-deuterophenyl)ethynyl)cyclohexanol was prepared following the method shown in Scheme 16.

SCHEME 16

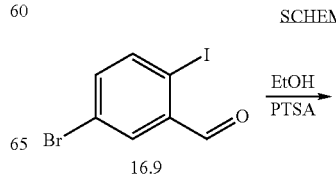

16.9

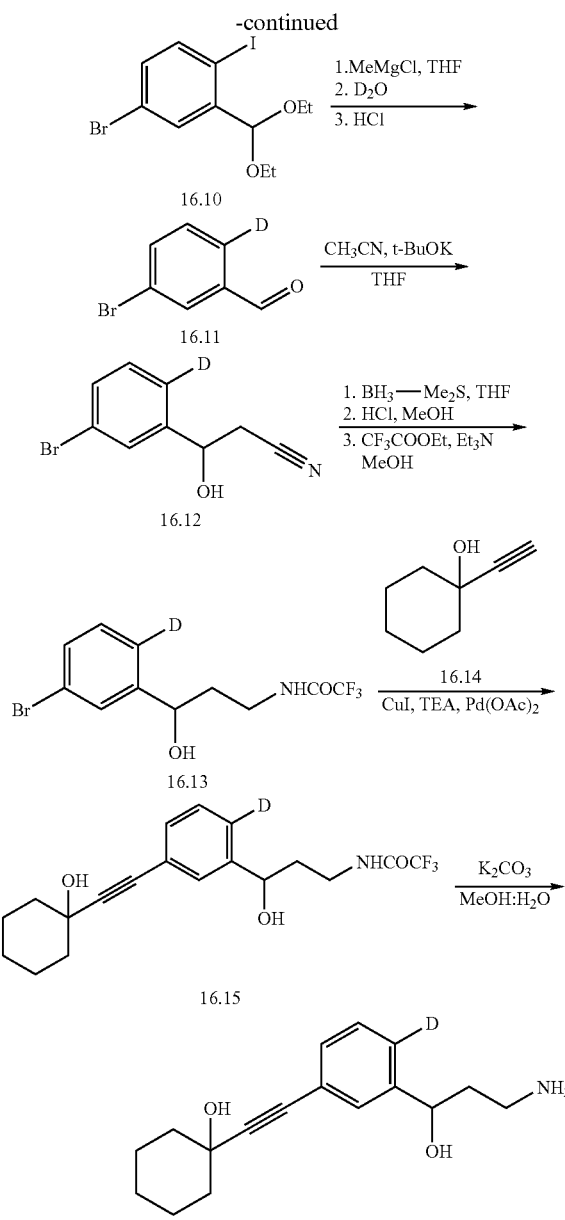

Step 1: A mixture of 5-bromo-2-iodobenzaldehyde (1.0 g, 3.2 mmol) and PTSA (0.1 g) in ethanol was stirred under reflux for 18 hrs and concentrated under reduced pressure. The residue was dissolved in ethyl acetate and washed with saturated NaHCO$_3$, dried over anhydrous Na$_2$SO$_4$ and concentrated to give 4-bromo-2-(diethoxymethyl)-1-iodobenzene (16.10) that was directly used in next reaction without further purification.

Step 2. To a solution of 4-bromo-2-(diethoxymethyl)-1-iodobenzene (3.2 mmol) in THF was added MeMgCl (2 ml, 3M in THF) at −25° C. under argon. After stirring at −25° C. for 30 mins, the reaction mixture was warmed to 0° C. and stirred at 0° C. for 30 mins. D$_2$O (0.6 ml) was added followed by 6N HCl (5 ml) and the mixture was stirred at room temperature for 2 hrs, then extracted with ethyl acetate (8 ml). Organic portion was washed with brine, dried and concentrated to give product 3-bromo-5-deuterobenzaldehyde as a light yellow oil. Yield (0.59 g, quant.); $^1$H NMR (400 MHz, DMSO-d$_6$) δ 9.56 (s, 1H), 8.05 (d, J=2.0 Hz, 1H), 7.88 (dd, J=8.0, 2.4 Hz, 1H), 7.54 (d, J=8.0 Hz, 1H).

Step 3: Addition of acetonitrile to 3-bromo-5-deuterobenzaldehyde (16.11) gave 3-(5-bromo-2-deuterophenyl)-3-hydroxypropanenitrile as a colorless oil. Yield (0.31 g, 41%); $^1$H NMR (400 MHz, DMSO-d$_6$) δ 7.51 (d, J=2.0 Hz, 1H), 7.46 (dd, J=8.0, 2.0 Hz, 1H), 7.30 (d, J=8.0 Hz, 1H), 7.60 (t, J=1.6 Hz, 1H), 6.04 (br. s, 1H), 4.89 (br. s, 1H), 2.79-2.93 (m, 2H).

Step 4: A mixture of 3-(5-bromo-2-deuterophenyl)-3-hydroxypropanenitrile (16.12) (0.3 g, 1.32 mmol), borane-dimethylsulfide (0.5 mL, 3.9 mmol) in anhydrous THF was sritted under reflux for 18 hr. After cooling to room temperature MeOH was carefully added to the reaction mixture followed by HCl/MeOH (1.25 M, 10 mL). The mixture was stirred at 50° C. for 5 hrs and concentrated. To the residue was added CH$_2$Cl$_2$—MeOH (2:1) (30 ml), CF$_3$COOEt (5.0 mL) and Et$_3$N (2.0 mL, 14.3 mmol). The reaction mixture was stirred at 50° C. for 8 h and concentrated under reduced pressure. The residue was partitioned in EtOAc and 1N HCl. Organic portion was washed with brine, dried over anhydrous Na$_2$SO$_4$ and concentrated under reduced pressure. Purification by flash chromatography (40% to 50% EtOAc—hexanes gradient) gave N-(3-(5-bromo-2-deuterophenyl)-3-hydroxypropyl)-2,2,2-trifluoroacetamide as a colorless oil. Yield (0.21 g, 89%); $^1$H NMR (400 MHz, CD$_3$OD) δ 9.16 (br.s, 1H), 7.53 (d, J=2.4 Hz, 1H), 7.39 (dd, J=8.0, 2.0 Hz, 1H), 7.23 (d, J=8.0 Hz, 1H), 4.65 (dd, J=7.6, 5.6 Hz, 1H), 3.35-3.41 (m, 2H), 1.88-1.94 (m, 2H).

Step 5. Sonogashira coupling between N-(3-(5-bromo-2-deuterophenyl)-3-hydroxypropyl)-2,2,2-trifluoroacetamide and 1-ethynylcyclohexanol following the method used in Example 120 gave 2,2,2-trifluoro-N-(3-hydroxy-3-(5-((1-hydroxycyclohexyl)ethynyl)-2-deuterophenyl)acetamide as a colorless oil. Yield (0.26 g, 88%); $^1$H NMR (400 MHz, CD$_3$OD) δ 7.41 (d, J=0.4 Hz, 1H), 7.28-7.30 (m, 2H), 4.66 (t, J=6.4 Hz, 1H), 3.37 (t, J=7.2 Hz, 2H), 1.90-1.98 (m, 4H), 1.54-1.78 (m, 7H), 1.24-1.34 (m, 1H).

Step 6. 2,2,2-Trifluoro-N-(3-hydroxy-3-(5-((1-hydroxycyclohexyl)ethynyl)-2-deuterophenyl)acetamide (16.15) was deprotected following the method used in Example 119 to give Example 124 as a light yellow oil. Yield (0.15 g, 78%); $^1$H NMR (400 MHz, DMSO-d$_6$) δ 7.32 (d, J=1.6 Hz, 1H), 7.27 (d, J=7.6 Hz, 1H), 7.19 (dd, J=7.6, 1.6 Hz, 1H), 5.37 (br s, 1H), 4.64 (t, J=6.4 Hz, 1H), 2.54-2.66 (m, 2H), 1.76-1.86 (m, 2H), 1.56-1.68 (m, 4H), 1.42-1.56 (m, 5H), 1.16-1.26 (m, 1H).

Example 125

Preparation of 1-((3-(3-amino-1-hydroxypropyl)-5-deuterophenyl)ethynyl)cyclohexanol

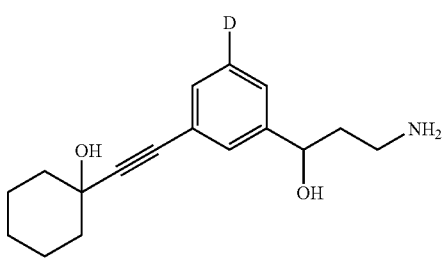 [SMILES: [2H]c1cc(C#CC2(O)CCCCC2)cc(C(O)CCN)c1]

1-((3-(3-Amino-1-hydroxypropyl)-5-deuterophenyl)ethynyl)cyclohexanol is prepared following the method described below.

Step 1: A mixture of 3-bromo-5-iodophenol (1.40 g, 4.68 mmol), benzyl bromide (0.89 g, 5.20 mmol) and anhydrous K₂CO₃ (1.44 g, 10.4 mmol) in anhydrous NMP (8 mL) was stirred under argon at +70° C. for 1 hour. The reaction mixture was partitioned between aqueous NH₄Cl and hexanes. Aqueous layer was additionally extracted with hexanes and combined organic layers were washed with 1N NaOH, brine, dried over anhydrous MgSO₄ and concentrated under reduced pressure to give 1-(benzyloxy)-3-bromo-5-iodobenzene as a colorless oil. Yield (2.14 g, 99%); ¹H NMR (400 MHz, CDCl₃) δ 7.45 (t, J=1.4 Hz, 1H), 7.32-7.40 (m, 5H), 7.26 (dd, J=1.4, 2.2 Hz, 1H), 7.09 (t, J=2.0 Hz, 1H), 5.00 (s, 2H).

Step 2: A solution of methylmagnesium chloride in THF (3N, 1.8 mL, 5.4 mmol) was added under argon to a cooled (−10° C.) solution of 1-(benzyloxy)-3-bromo-5-iodobenzene (1.82 g, 4.68 mmol) in anhydrous THF. The reaction mixture was stirred at −10° C. to 0° C. for 2 hrs after which D₂O (0.75 mL) was added to the reaction mixture. The mixture was stirred for 15 min and partitioned between NH₄Cl and THF. Organic layer was separated and concentrated under reduced pressure to give 1-(benzyloxy)-3-bromo-5-deuterobenzene as a light yellow oil. Yield (1.29 g, quant.); ¹H NMR (400 MHz, CDCl₃) δ 7.30-7.45 (m, 5H), 7.14 (dd, J=1.8, 2.3 Hz, 1H), 7.07-7.10 (m, 1H), 6.88-6.91 (m, 1H), 5.04 (s, 2H).

Step 3: A solution of n-BuLi (2.5 M/THF, 3.0 mL, 7.5 mmol) was added under argon to a cold (−78° C.) solution of 1-(benzyloxy)-3-bromo-5-deuterobenzene (1.29 g, 4.88 mmol) and the reaction mixture was stirred at −78° C. for 10 min. Anhydrous DMF (0.7 mL) was added to the reaction mixture and stirring continued for 1 hr. Reaction was quenched by adding aqueous NH₄Cl. The mixture was stirred, layers were separated. Aqueous layer was extracted with EtOAc. Combined organic layer were washed with brine and concentrated under reduced pressure. Purification by flash chromatography (1% to 20% EtOAc—hexanes gradient) gave 3-(benzyloxy)-5-deuterobenzaldehyde as a white solid. Yield (0.692 g, 67%); ¹H NMR (400 MHz, CDCl₃) δ 9.97 (s, 1H), 7.28-7.48 (m, 8H), 5.12 (s, 2H).

Step 4: Addition of acetonitrile to 3-(benzyloxy)-5-deuterobenzaldehyde following the method used in Example 6 gave 3-(3-(benzyloxy)-5-deuterophenyl)-3-hydroxypropanenitrile as a yellow oil which was used in the next step without purification. Yield (0.868 g, quant.); ¹H NMR (400 MHz, DMSO-d₆) δ 7.28-7.45 (m, 5H), 7.04-7.06 (m, 1H), 6.95-6.98 (m, 1H), 6.87-6.91 (m, 1H), 5.91 (d, J=4.5 Hz, 1H), 5.06 (s, 2H), 4.80-4.86 (m, 1H), 2.86 (ABd, J=4.9, 16.6 Hz, 1H), 2.77 (ABd, J=6.7, 16.6 Hz, 1H).

Step 5: Reduction of 3-(3-(benzyloxy)-5-deuterophenyl)-3-hydroxypropanenitrile following the method used in Example 6 gave 3-amino-1-(3-(benzyloxy)-5-deuterophenyl)propan-1-ol hydrochloride as a colorless oil which was used in the next step without further purification. Yield (1.147 g, quant.).

Step 6: A mixture of 3-amino-1-(3-(benzyloxy)-5-deuterophenyl)propan-1-ol hydrochloride (1.147 g, 3.89 mmol), Et₃N (0.6 mL, 4.66 mmol), CF₃COOEt (0.7 mL, 5.87 mmol) in EtOH was stirred at room temperature for 1 hr. The reaction mixture was concentrated under reduced pressure and the residue was resuspended in EtOAc. The resulting suspension was filtered, the filtrate was concentrated under reduced pressure to give crude N-(3-(3-(benzyloxy)-5-deuterophenyl)-3-hydroxypropyl)-2,2,2-trifluoroacetamide as a colorless oil which was used directly in the next step without purification. ¹H NMR (400 MHz, DMSO-d₆) δ 9.32 (br.t, 1H), 7.27-7.44 (m, 5H), 6.95-6.97 (m, 1H), 6.86-6.88 (m, 1H), 6.83-6.85 (m, 1H), 5.30 (d, J=4.5 Hz, 1H), 5.06 (s, 2H), 4.49-4.55 (m, 1H), 3.18-3.25 (m, 2H), 1.72-1.81 (m, 2H).

Step 7: A solution of N-(3-(3-(benzyloxy)-5-deuterophenyl)-3-hydroxypropyl)-2,2,2-trifluoroacetamide in EtOH was stirred under H₂ atmosphere in the presence of Pd(OH)₂/C (20% wt, 0.113 g) for 20 hrs. The reaction mixture was filtered through Celite and concentrated under reduced pressure. Purification by flash chromatography (20% to 100% EtOAc—hexanes gradient) gave 2,2,2-trifluoro-N-(3-(3-deutero-5-hydroxyphenyl)-3-hydroxypropyl)acetamide as a colorless oil. Yield (0.47 g, 46% over 2 steps); ¹H NMR (400 MHz, DMSO-d₆) δ 9.32 (br. s, 1H), 9.24 (s, 1H), 6.66-6.74 (m, 2H), 6.56-6.60 (m, 1H), 5.22 (d, J=4.5 Hz, 1H), 4.42-4.50 (m, 1H), 3.17-3.25 (m, 2H), 1.68-1.80 (m, 2H).

Step 8: A mixture of 2,2,2-trifluoro-N-(3-(3-deutero-5-hydroxyphenyl)-3-hydroxypropyl)acetamide, Et₃N and triflic anhydride in anhydrous CH₂Cl₂ is stirred at 0° C. until no starting phenol is seen by TLC. The reaction mixture is washed with brine, dried over anhydrous MgSO₄ and concentrated under reduced pressure. Purification by flash chromatography (EtOAc—hexanes gradient) gives 3-deurero-5-(1-hydroxy-3-(2,2,2-trifluoroacetamido)propyl)phenyl trifluoromethanesulfonate.

Step 9: Sonogashira coupling between 3-deurero-5-(1-hydroxy-3-(2,2,2-trifluoroacetamido)propyl)phenyl trifluoromethanesulfonate and alkynol 14 following the method used in Example 1 gives 2,2,2-trifluoro-N-(3-(3-deutero-5-((1-hydroxycyclohexyl)ethynyl)phenyl)-3-hydroxypropyl)acetamide.

Step 10: Deprotection of 2,2,2-trifluoro-N-(3-(3-deutero-5-((1-hydroxycyclohexyl)ethynyl)phenyl)-3-hydroxypropyl)acetamide following the method used in Example 1 gives Example 7.

Example 126

Preparation of 3-amino-1-(3-(cyclohexylmethoxy)phenyl)-1-deuteropropan-1-ol

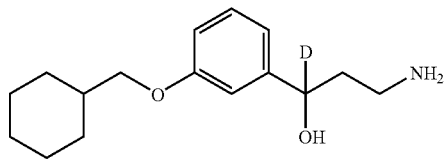 [SMILES: [2H]C(O)(CCN)c1cccc(OCC2CCCCC2)c1]

3-Amino-1-(3-(cyclohexylmethoxy)phenyl)-1-deuteropropan-1-ol was prepared following the method shown in Scheme 17.

SCHEME 17

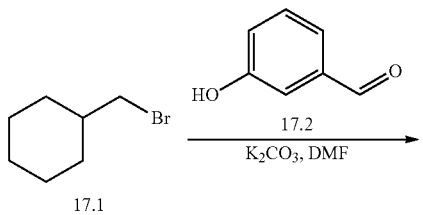

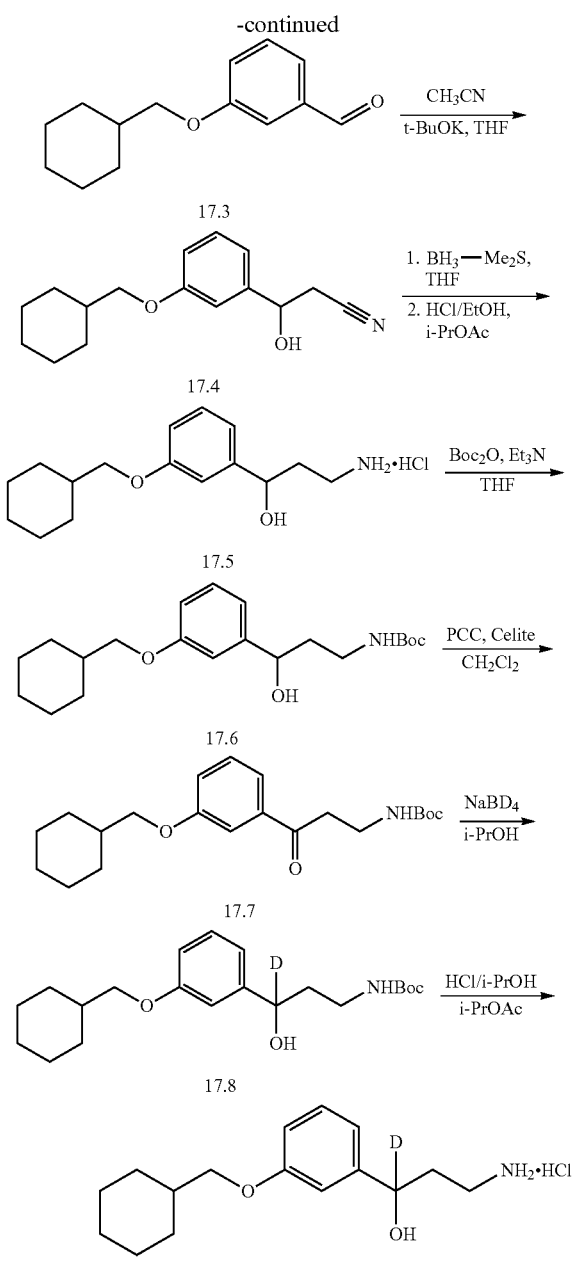

Step 1. To a mixture of 3-hydroxybenzaldehyde (545 g, 4.46 mol), $K_2CO_3$ (679 g, 4.91 mol) and NMP (0.718 L) was added bromomethylcyclohexane (718 g, 4.05 mol) and the reaction mixture was heated at +75° C. for 24 hrs. The reaction mixture was cooled to 20° C. followed by addition of aqueous NaOH (1N), water and heptane. The mixture was stirred for 15 min and layers were separated. Organic layer was washed with NaOH (1N), brine and concentrated under reduced pressure to give ether 17.3 as a pale amber oil. Yield (675 g, 76%); $^1$H NMR (400 MHz, DMSO-$d_6$) δ 9.95 (s, 1H), 7.45-7.5 (m, 2H), 7.38-7.39 (m, 1H), 7.22-7.25 (m, 1H), 3.82 (d, J=6.4 Hz, 2H), 1.74-1.81 (m, 2H), 1.58-1.73 (m, 4H), 1.10-1.28 (m, 3H), 0.98-1.08 (m, 2H).

Step 2. Acetonitrile (118 mL, 2.26 mol) was added dropwise under nitrogen to a cooled (−50° C.) solution of potassium tert-butoxide (1M/THF, 2.7 L, 2.7 mol). The reaction mixture was stirred at −50° C. for 40 mins and then a solution of aldehyde 17.3 (450 g, 2.06 mol) in anhydrous THF was added dropwise to the reaction mixture. The reaction mixture was stirred for 45 min at −45° C. and cooling bath was replaced with ice bath. The reaction mixture was stirred for 40 min after which aqueous $NH_4Cl$ (20%) was added. Layers were separated and organic layer was washed with brine, filtered and dried over anhydrous $Na_2SO_4$. The mixture was concentrated under reduced pressure to give hydroxynitrile 17.4 as amber oil. (Yield 502 g, 94%); $^1$H NMR (400 MHz, $CDCl_3$) δ 7.27-7.31 (m, 1H), 6.92-6.95 (m, 2H), 6.85-6.88 (m, 1H), 5.00 (t, J=6.4 Hz, 1H), 3.76 (d, J=6.4 Hz, 2H), 2.77 (d, J=1.6 Hz, 1H), 2.75 (s, 1H), 1.82-1.89 (m, 2H), 1.68-1.82 (m, 4H), 1.14-1.36 (m, 4H), 1.01-1.10 (m, 2H).

Step 3. Borane-dimethyl sulfide (240 mL, 2.52 mol) was added dropwise under $N_2$ atmosphere to a solution of nitrile (502 g, 3.55 mol) in anhydrous THF over 1 h while dimethylsulfide-THF (550 mL) was distilling off. The reaction mixture was heated under reflux for 3 hrs, then cooled to 10° C. and then aqueous HCl (3N, 0.65 L) was slowly added. The mixture was stirred at room temperature overnight, aqueous NaOH (50%) was added to pH 12. Water and MTBE were added, the mixture was stirred and layers were separated. Organic layer was washed with 30% NaCl, dried over anhydrous $Na_2SO_4$ and concentrated under reduced pressure Re-evaporation with absolute EtOH gave crude 3-amino-1-(3-(cyclohexylmethoxy)phenyl)propan-1-ol which was used in the next step withour further purification. Yield (504 g, 99%); $^1$H NMR (400 MHz, $CDCl_3$) δ 7.22 (t, J=8.0 Hz, 1H), 6.95 (t, J=1.6 Hz, 1H), 6.90 (d, J=7.6 Hz, 1H), 6.77 (ddd, J=8.0, 2.4, 0.8 Hz, 1H), 4.90 (dd, J=8.8, 3.2 Hz, 1H), 3.75 (d, J=6.4 Hz, 2H), 3.12 (br s, 2H), 3.06 (ddd, J=12.4, 6.0, 4.0 Hz, 1H), 2.90-2.96 (m, 1H), 1.82-1.89 (m, 3H), 1.67-1.81 (m, 6H), 1.15-1.34 (m, 3H), 0.99-1.09 (m, 2H).

To a solution of amine (504 g, 1.91 mol) in ethanol ethanolic HCl (5.8 M, 266 mL) was added dropwise so that the temperature was kept below +45° C. The white precipitate formed and the mixture was stirred at +40° C. for 20 min. The mixture was diluted with i-PrOAc and stirred for 20 min The precipitate was collected by filtration, washed with i-PrOAc and dried overnight under a stream of $N_2$. Drying in vacuum gave salt 5 as a white powder. Yield (425 g, 73%); $^1$H NMR (400 MHz, DMSO-$d_6$) δ 7.81 (br.s, 3H), 7.20 (t, J=7.8 Hz, 1H), 6.83-6.88 (m, 2H), 6.76 (ddd, J=0.8, 2.5, 8.2 Hz, 1H), 5.49 (d, J=4.1 Hz, 1H), 4.58-4.66 (m, 1H), 3.73 (d, J=6.26 Hz, 2H), 2.74-2.86 (m, 2H), 1.59-1.90 (m, 8H), 0.95-1.30 (m, 5H).

Step 4: To a suspension of amine hydrochloride 17.5 (118 g, 0.396 mol) in anhydrous THF was added $Et_3N$ (42.0 g, 0.415 mol) and $Boc_2O$ (86.3 g, 0.396 mol). The reaction mixture was stirred overnight at room temperature, concentrated under reduced pressure and partitioned between EtOAc and HCl (0.5 N). Organic layer was washed with brine, dried over $Na_2SO_4$ and concentrated under reduced pressure. Recrystallization of the residue from hexanes/EtOAc gave carbamate 17.6 as a white solid. Yield (125.4 g, 87%); $^1$H NMR (400 MHz, DMSO-$d_6$) δ 7.16 (t, J=7.8 Hz, 1H), 7.81-7.86 (m, 2H), 6.70-6.75 (m, 2H), 5.13 (d, J=4.5 Hz, 1H), 4.48 (q, J=4.9 Hz, 1H), 3.72 (d, J=6.26 Hz, 2H), 2.93 (q, J=6.8 Hz, 2H), 1.73-1.82 (m, 2H), 1.58-1.73 (m, 6H), 1.34 (s, 9H), 1.07-1.29 (m, 3H), 0.95-1.07 (m, 2H).

Step 5: To a solution of alcohol 17.6 (125.3 g, 345 mmol) in dichloromethane was added Celite (125 g) and pyridinium chlorochromate (81.8 g, 380 mmol). The mixture was stirred overnight at room temp, filtered and the filtrate was concentrated under reduced pressure. Purification by column chromatography (20% EtOAc-hexanes) gave ketone 17.7 as a white solid. Yield (102 g, 82%); $^1$H NMR (400 MHz, DMSO-$d_6$) δ 7.45-7.50 (m, 1H), 7.35-7.42 (m, 2H), 7.14-7.18 (m, 1H), 6.77 (br.t, J=5.1 Hz, 1H), 3.80 (d, J=6.26 Hz, 2H), 3.24 (q, J=6.1 Hz, 2H), 3.10 (t, J=6.5 Hz, 2H), 1.58-1.83 (m, 6H), 1.33 (s, 9H), 1.08-1.30 (m, 3H), 0.96-1.08 (m, 2H).

Step 6. Sodium borodeuteride (0.101 g, 2.41 mmol) was added to a cooled (0° C.) solution of ketone 7 (0.531 g, 1.47 mmol) in isopropanol and the reaction mixture was stirred at 0° C. for 2 hrs. Aqueous NH₄Cl (25%) was slowly added to the reaction mixture followed by EtOAc. Layers were separated and aqueous layer was additionally extracted with EtOAc. Combined organic layers were washed with brine and dried over anhydrous MgSO₄. Concentration under reduced pressure gave alcohol 17.8 as a white solid. Yield (0.455 g, 85%).

Step 7. A solution of HCl in i-PrOH (5.5N, 3.0 mL) was added to a stirred solution of carbamate 17.8 (0.454 g, 1.25 mmol) in i-PrOAc at room temperature and the reaction mixture was stirred for 20 hrs. The reaction mixture was concentrated under reduced pressure, i-PrOAc was added to the residue and the mixture was sonicated. The product was collected by filtration, washed with i-PrOAc, hexanes and dried to give Example 126 hydrochloride as a white solid. Yield (0.348 g, 93%); ¹H NMR (400 MHz, CD₃OD) δ 7.16-7.26 (m, 1H), 6.85-6.94 (m, 2H), 6.74-6.82 (m, 1H), 3.73-3.78 (m, 2H), 2.98-3.14 (m, 2H), 1.93-2.07 (m, 2H), 1.66-1.90 (m, 5H), 1.16-1.40 (m, 3H), 1.02-1.16 (m, 2H); RP-HPLC (Method 1) t$_R$=10.05 min, 91.95% (AUC); ESI-MS m/z 265.2 [M+H]⁺.

Example 127

Preparation of 3-amino-1-(3-(cyclohexylmethoxy)phenyl)-2,2-dideuteropropan-1-ol

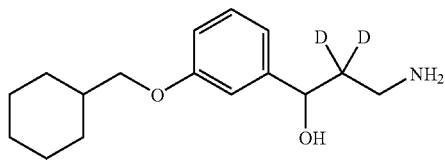 [SMILES: [2H]C([2H])(CN)C(O)c1cccc(OCC2CCCCC2)c1]

3-Amino-1-(3-(cyclohexylmethoxy)phenyl)-2,2-dideuteropropan-1-ol was prepared following the method shown in Scheme 18.

SCHEME 18

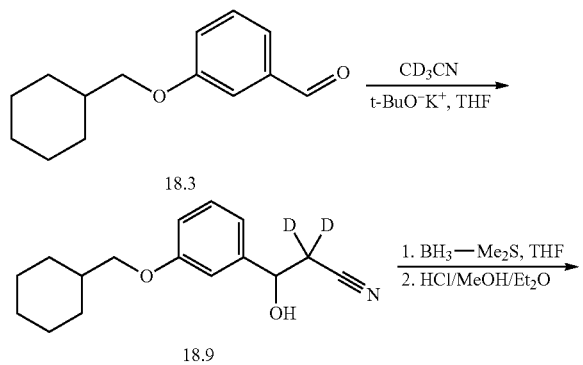

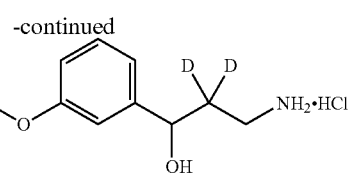

Step 1. Addition of trideuteroacetonitrile to aldehyde 18.3 following the procedure shown in Example 126 gave hydroxynitrile 18.9 as a yellow oil. Yield (4.05 g, 85%); ¹H NMR (400 MHz, DMSO-d₆) δ 7.21 (t, J=8.0 Hz, 1H), 6.90-6.96 (m, 2H), 6.80 (ddd, J=0.8, 2.4, 8.4 Hz, 1H), 5.88 (br. d, J=4.0 Hz, 1H), 4.81-4.82 (m, 1H), 3.74 (d, J=6.8 Hz, 2H), 1.58-1.83 (m, 6H), 1.09-1.29 (m, 3H), 0.95-1.07 (m, 2H).

Step 2. Reduction of hydroxynitrile 18.9 was done following the procedure shown in Example 126 with the following exceptions. Methanolic HCl (1.25 M, 3.68 mL, 4.6 mmol) was added to a cooled solution (0° C.) of free amine in Et₂O. After stirring for 15 min at 0° C. the precipitate was collected by filtration, washed with Et₂O and dried to give Example 127 hydrochloride as a white solid. Yield (2.81 g, 61%); ¹H NMR (400 MHz, DMSO-d₆) δ 7.95 (br.s, 3H), 7.20 (t, J=7.6 Hz, 1H), 6.83-6.88 (m, 2H), 6.76 (ddd, J=1.2, 2.4, 8.4 Hz, 1H), 5.49 (d, J=4.0 Hz, 1H), 4.62 (d, J=4.0 Hz, 1H), 3.73 (d, J=6.0 Hz, 2H), 2.54-2.57 (m, 2H), 1.58-1.82 (m, 6H), 1.08-1.28 (m, 3H), 0.95-1.07 (m, 2H); RP-HPLC (Method 1) t$_R$=10.04 min, 91.95% (AUC); ESI-MS m/z 266.2 [M+H]⁺.

Example 128

Preparation of 3-amino-1-(3-(cyclohexylmethoxy)phenyl)-3,3-dideuteropropan-1-ol

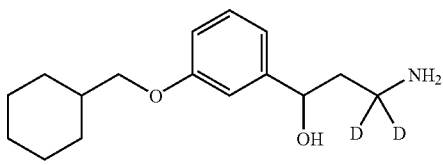 [SMILES: [2H]C([2H])(N)CC(O)c1cccc(OCC2CCCCC2)c1]

3-Amino-1-(3-(cyclohexylmethoxy)phenyl)-3,3-dideuteropropan-1-ol was prepared following the method shown in Scheme 19.

SCHEME 19

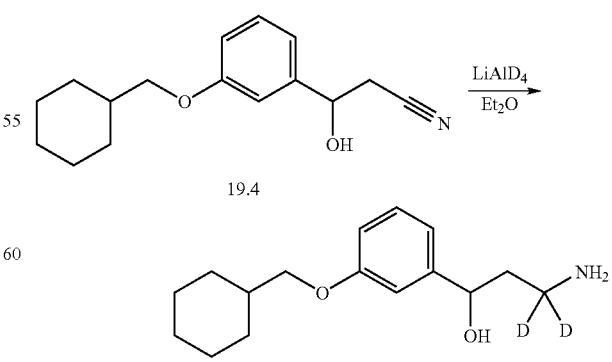

Step 1. LiAlD₄ was added under argon to a cooled (0° C.) solution of hydroxynitrile 19.4 (0.54 g, 2.08 mmol) in anhydrous Et$_2$O. The reaction mixture was stirred at 0° C. for 40 min and quenched by slow addition of saturated aqueous Na$_2$SO$_4$ until white precipitate formed. Anhydrous MgSO$_4$ was then added to the mixture which was stirred and filtered. The filtrate was concentrated under reduced pressure, and purification of the residue by flash column chromatography (10%±100% of 20% 7N NH$_3$/MeOH/CH$_2$Cl$_2$—CH$_2$Cl$_2$ gradient) gave pure amine as a colorless oil. Yield (0.346 g, 63%). The amine was dissolved in i-PrOAc, cooled to 0° C., and HCl/i-PrOH (5.5 N, 1 mL) was added to the reaction mixture. The precipitate was collected by filtration, washed with i-PrOAc, hexanes and dried to give Example 128 hydrochloride as a white solid. Yield (0.359 g, 91%); $^1$H NMR (400 MHz, DMSO-d$_6$) δ 7.23 (t, J=7.8 Hz, 1H), 6.89-6.94 (m, 2H), 6.79 (ddd, J=0.8, 2.4, 8.4 Hz, 1H), 4.79 (dd, J=4.4, 8.0 Hz, 1H), 3.76 (d, J=6.4 Hz, 2H), 1.90-2.04 (m, 2H), 1.82-1.90 (m, 2H), 1.66-1.80 (m, 4H), 1.16-1.38 (m, 3H), 1.02-1.14 (m, 2H); RP-HPLC (Method 1) $t_R$=10.06 min, 97.5% (AUC); ESI-MS m/z 266.2 [M+H]$^+$.

Example 129

Preparation of 3-amino-1-(3-((1-deuterocyclohexyl)methoxy)phenyl)propan-1-ol

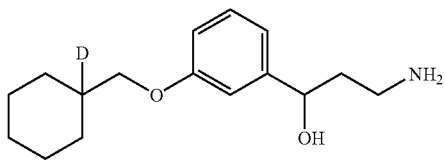 [SMILES: [2H]C1(COc2cccc(C(O)CCN)c2)CCCCC1]

3-Amino-1-(3-((1-deuterocyclohexyl)methoxy)phenyl)propan-1-ol was prepared following the method shown in Scheme 20.

SCHEME 20

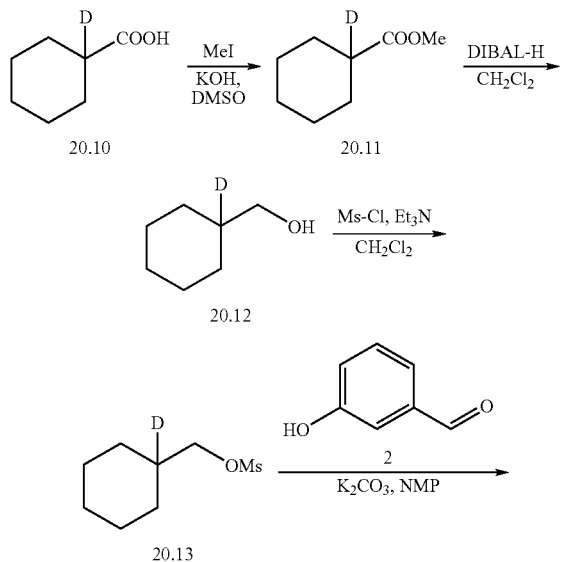

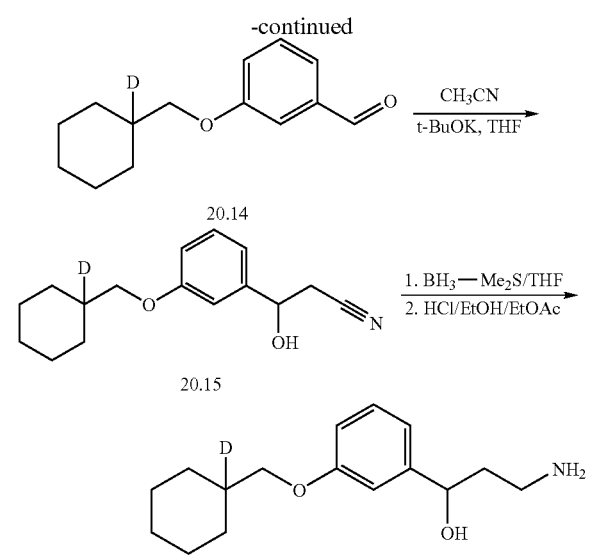

Step 1. To a solution of 1-deuteroclohexanecarboxylic acid (20.10) (5.0 g, 38.7 mmol) in anhydrous DMSO was added KOH (2.39 g, 42.6 mmol) with stirring for 5 min. Methyl iodide (6.59 g, 46.4 mmol) was added and the reaction mixture was stirred overnight at room temperature. Saturated NaHCO$_3$ and ether was added and the mixture was washed with brine, dried over Na$_2$SO$_4$ and evaporated to dryness giving methyl 1-deuterocyclohexanecarboxylate (20.11) as a clear liquid. Yield (5.62 g, quant.); $^1$H NMR (400 MHz, DMSO-d$_6$) δ 3.55 (s, 3H), 1.78-1.75 (m, 2H), 1.65-1.60 (m, 2H), 1.57-1.52 (m, 1H), 1.34-1.09 (m, 5H).

Step 2. To a solution of ester 20.11 (5.0 g, 34.9 mmol) in anhydrous CH$_2$Cl$_2$ on an ice bath was added a solution of DIBAL-H in CH$_2$Cl$_2$ (1.0 M, 73.3 ml, 73.3 mmol) The reaction mixture was allowed to warm to room temperature over 2 hrs and quenched with Rochelle's salt (100 ml). The organic layer was dried over Na$_2$SO$_4$ and concentrated under reduced pressure to give (1-deuterocyclohexyl)methanol (20.12) as a clear liquid. Yield (3.99 g, 97%); $^1$H NMR (400 MHz, DMSO-d$_6$) δ 4.27 (t, J=5.2 Hz, 1H), 3.15 (d, J=5.2 Hz, 2H), 1.66-1.56 (m, 5H), 1.21-1.20 (m, 3H), 0.84-0.78 (m, 2H).

Step 3. To a solution of alcohol 20.12 (3.0 g, 26.0 mmol) in anhydrous CH$_2$Cl$_2$ on an ice bath was added TEA (2.98 g, 28.6 mmol) and methanesulfonyl chloride (3.28 g, 28.6 mmol). The reaction mixture was warmed to room temp over 2 hr. 1N HCl was added and layers were separated. The organic layer was dried over Na$_2$SO$_4$ and concentrated under reduced pressure to give (1-deuterocyclohexyl)methyl methanesulfonate (20.13) as an off white solid. Yield (4.92 g, 98%); $^1$H NMR (400 MHz, DMSO-d$_6$) δ 3.97 (s, 2H), 3.12 (s, 3H), 1.68-1.58 (m, 5H), 1.25-1.08 (m, 3H), 0.97-0.88 (m, 2H).

Step 4. Alkylation of 3-hydroxybenzaldehyde (20.2) by mesylate 20.13 following the method shown in Example 126 gave 3-((1-deuterocyclohexyl)methoxy)benzaldehyde (20.14) as a colorless oil. Yield (0.47 g, 55%); $^1$H NMR (400 MHz, DMSO-d$_6$) δ 9.94 (s, 1H), 7.50-7.44 (m, 2H), 7.39-7.38 (m, 1H), 7.24 (dt, J=6.8, 2.4 Hz, 1H), 3.82 (s, 2H), 1.79-1.61 (m, 5H), 1.23-0.91 (m, 5H).

Step 5. Acetonitrile addition to aldehyde following the method shown in Example 126 gave 3-(3-((1-deuterocyclohexyl)methoxy)phenyl)-3-hydroxypropanenitrile (20.15) as a colorless oil. Yield (0.53 g, 96%); $^1$H NMR (400 MHz, DMSO-d$_6$) δ 7.21 (t, J=7.8 Hz, 1H), 6.94-6.91 (m, 2H), 6.80

(ddd, J=8.4, 2.4, 0.8 Hz, 1H), 5.88, (d, J=4.4 Hz, 1H), 4.84-4.80 (m, 1H), 3.73 (s, 2H), 2.85 (Abd, J=16.8, 4.8 Hz, 1H), 2.77 (Abd, J=16.4, 5.2 Hz, 1H), 1.79-1.61 (m, 5H), 1.28-0.94 (m, 5H).

Step 6. Hydroxynitrile reduction following the method shown in Example 126 gave free amine as a colorless oil. Amine was converted into HCl salt following the method shown in Example 126 to give Example 129 hydrochloride as a white solid. Yield (0.27 g, 44%); $^1$H NMR (400 MHz, DMSO-$d_6$) δ 7.91 (br.s, 3H), 7.20 (t, J=7.8 Hz, 1H), 6.86-6.84 (m, 2H), 6.76 (m, 1H), 5.50, (d, J=4.4 Hz, 1H), 4.65-4.60 (m, 1H), 3.72 (s, 2H), 2.78-2.80 (m, 2H), 1.89-1.61 (m, 7H), 1.27-0.94 (m, 5H); RP-HPLC (Method 1) $t_R$=10.04 min, 96.9% (AUC); ESI-MS m/z 265.2 [M+H]$^+$.

Example 130

Preparation of (R)-3-amino-1-(3-(cyclohexyldideuteromethoxy)phenyl)propan-1-ol

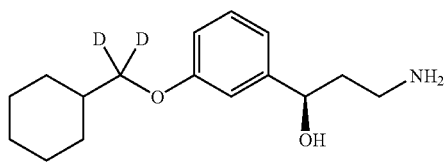 [SMILES: [2H]C([2H])(Oc1cccc([C@H](O)CCN)c1)C1CCCCC1]

(R)-3-Amino-1-(3-(cyclohexyldideuteromethoxy)phenyl)propan-1-ol was prepared following the method shown in Schemes 21a and 21b.

SCHEME 21a

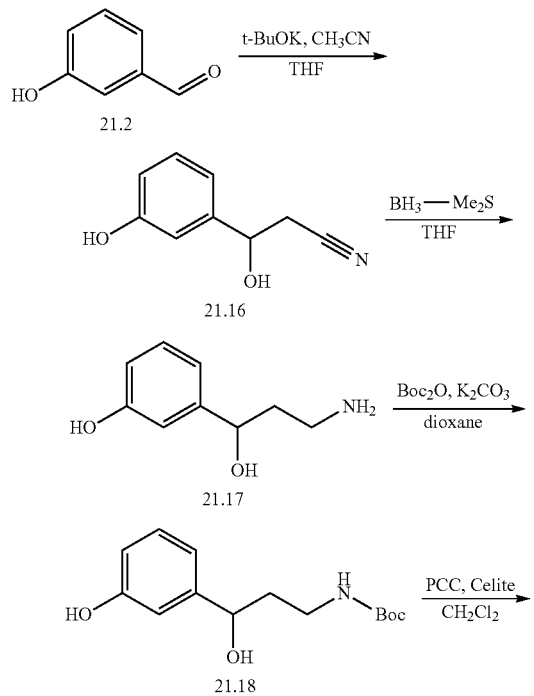

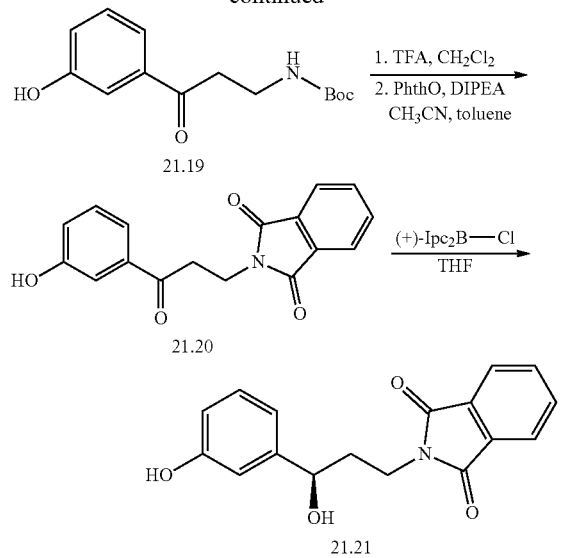

Step 1: To a stirred suspension of t-BuO$^-$K$^+$ (68.5 g, 614 mmol) in THF, cooled to −50° C., was added acetonitrile (30.3 mL, 540 mmol), dropwise over a period of 5 min. The resulting mixture was stirred at −50° C. for 30 min following which a solution of 3-hydroxybenzaldehyde (21.2) (30.0 g, 244 mmol) in THF was added slowly, over a period of 10 min. This was then allowed to warm to 0° C. and stirred for another 3 h during which the reaction was complete. The reaction was quenched by slow addition of ice-water followed by extraction with EtOAc. The combined organics were washed with water, brine and dried over Na$_2$SO$_4$. The solution was concentrated under reduced pressure to give 3-hydroxy-3-(3-hydroxyphenyl)propanenitrile (21.16) as yellow oil which was purified by flash column chromatography (0 to 20% EtOAc hexanes gradient). Yield (25.0 g, 62%); $^1$H NMR (400 MHz, CDCl$_3$) δ 7.27 (s, 1H), 6.95 (d, J=7.6 Hz, 1H), 6.90-6.93 (m, 1H), 6.82 (dd, J=8.0, 2.4 Hz, 1H), 4.91-5.03 (m, 1H), 2.76 (d, J=6.4 Hz, 2H).

Step 2: To a stirred solution of the nitrile 21.16 (25.0 g, 153 mmol) in THF, cooled to 0° C., was added BH$_3$-DMS (49.5 mL, 460 mmol), following which the cooling bath was removed. The resulting mixture was boiled under reflux overnight, cooled in an ice-bath and quenched by the slow addition of large excess of MeOH. After stirring at room temperature for 2 h, the excess solvent was removed under reduced pressure. The residue was again treated with MeOH and evaporated. The process was repeated three times. The brown oil was then applied onto a flash silica gel column and eluted (0 to 15% (9:1 MeOH—NH$_3$)-DCM gradient) to give 3-(3-amino-1-hydroxypropyl)phenol (21.17) as a brown solid. Yield (25.0 g, 97%); $^1$H NMR (400 MHz, DMSO-$d_6$) δ 7.04-7.09 (m, 1H), 6.74 (s, 1H), 6.70 (d, J=7.6 Hz, 1H), 6.58 (dd, J=8.0, 2.0 Hz, 1H), 4.55 (dd, J=7.2, 5.6 Hz, 1H), 2.57-2.66 (m, 2H), 1.56-1.62 (m, 2H).

Step 3: To a solution of amine 21.17 (25.0 g, 0.149 mol) in 1,4-dioxane was added K$_2$CO$_3$ (20.6 g, 150 mmol) followed by the slow addition of Boc$_2$O (36 mL, 150 mmol). The mixture was stirred at room temperature for 2 h during which the reaction was found to be complete. This mixture was then quenched by the addition of water and extracted with ethyl acetate. The organic layer was washed with water and brine. This was dried over anhydrous Na$_2$SO$_4$, filtered and concentrated under reduced pressure. Purification by flash chromatography (0 to 20% EtOAc-hexanes gradient) afforded crude tert-butyl 3-hydroxy-3-(3-hydroxyphenyl)propylcarbamate (21.18) as off white solid. Yield (35.0 g, quant); $^1$H NMR (400 MHz, CDCl$_3$) δ 7.05-7.10 (m, 1H), 6.70-6.76 (m, 2H), 6.59 (dd, J=8.0, 1.6 Hz, 1H), 5.11 (d, J=4.4 Hz, 1H), 4.42-4.47 (m, 1H), 3.57 (s, 1H), 2.92-2.98 (m, 2H), 1.61-1.67 (m, 2H), 1.37 (s, 9H).

Step 4: A stirred suspension of PCC (42.3 g, 196 mmol) and Celite (43 g) in DCM (300 mL) was cooled to 0° C. Alcohol 21.18 (35.0 g, 131 mmol) was slowly added to the reaction mixture over a period of 15 min. The reaction mixture was allowed to stir at room temperature for 2 h. The reaction mixture was then filtered through a pad of Celite and the filter bed was washed with DCM. Concentration of the filtrate gave a black tarry mass which was purified by flash chromatography (30-50% ethyl acetate-hexanes gradient) to give tert-butyl 3-(3-hydroxyphenyl)-3-oxopropylcarbamate 21.19 as pale yellow solid. Yield (20.3 g, 58%); $^1$H NMR (400 MHz, CDCl$_3$) δ 9.78 (s, 1H), 7.27-7.40 (m, 2H), 7.01 (dd, J=8.0, 1.6 Hz, 1H), 6.80-6.83 (m, 1H), 3.22-3.27 (m, 2H), 3.08 (t, J=6.8 Hz, 2H), 1.36 (s, 9H).

Step 5: To a stirred solution of TFA (80 mL) and DCM at 0° C. was slowly added ketone (20 g, 75 mmol). The resulting reaction mixture was allowed to stir at room temperature for 2 h. After the reaction was complete, the solvent was removed under reduced pressure and the residue was triturated with toluene. The complete removal of the solvent gave the TFA salt of amine. The crude mass was directly utilized for the next transformation without purification. Yield (21.0 g, crude); MS 166 [M+H]$^+$.

DIPEA (23 mL, 179 mmol) was added to a cooled to 0° C. solution of crude amine (21.0 g, 72 mmol) in a mixture of acetonitrile:toluene (1:3). The resulting mixture was stirred at room temperature for 10 min. This was followed by the addition of phthalic anhydride (10.6 g, 72 mmol). The reaction mixture was then refluxed for 2 h using a Dean-Stark assembly. After completion of the reaction the solvent was distilled off under reduced pressure and the reaction mass was treated with DCM. The organic layer was washed with water and saturated NH$_4$Cl, followed by saturated NaHCO$_3$, dried over anhydrous Na$_2$SO$_4$, filtered and concentrated under reduced pressure to give phthalimidophenol 21.20 as an off-white solid. Yield (14 g, 62%); $^1$H NMR (400 MHz, CDCl$_3$) δ 9.79 (s, 1H), 7.82-7.88 (m, 4H), 7.38 (d, J=8.0 Hz, 1H), 7.31 (d, J=7.6 Hz, 1H), 7.28 (s, 1H), 7.01 (dd, J=8.0, 2.0 Hz, 1H), 3.91 (t, J=7.2 Hz, 2H), 3.37 (t, J=7.2 Hz, 2H). MS: 296 [M+1]$^+$.

Step 6: A solution of (+)-diisopinocampheylchloroborane ((+)-Ipc$_2$B—Cl) in hexanes (1.5 M, 14 mL, 21 mmol) was added under inert atmosphere to a solution of ketone 21.20 (3.02 g, 10.2 mmol) in anhydrous THF at room temperature. The reaction mixture was stirred for 3.5 hrs and partitioned between 25% NH$_4$Cl and THF. Aqueous layer was additionally extracted with EtOAc, combined organic layers were washed with brine, dried over anhydrous MgSO$_4$, and concentrated under reduced pressure. Purification by flash chromatography (15% to 60% EtOAc—hexanes gradient) gave (R)-alcohol 21.21 as a white solid. Yield (2.78 g, 92%); $^1$H NMR (400 MHz, DMSO-d$_6$) δ 9.23 (s, 1H), 7.75-7.84 (m, 4H), 7.04 (t, J=7.6 Hz, 1H), 6.67-6.73 (m, 2H), 6.54 (ddd, J=1.0, 2.3, 8.0 Hz, 1H), 5.22 (d, J=4.3 Hz, 1H), 4.49 (dt, J=4.5, 6.3 Hz, 1H), 3.55-3.69 (m, 2H), 1.85 (q, J=7.4 Hz, 2H).

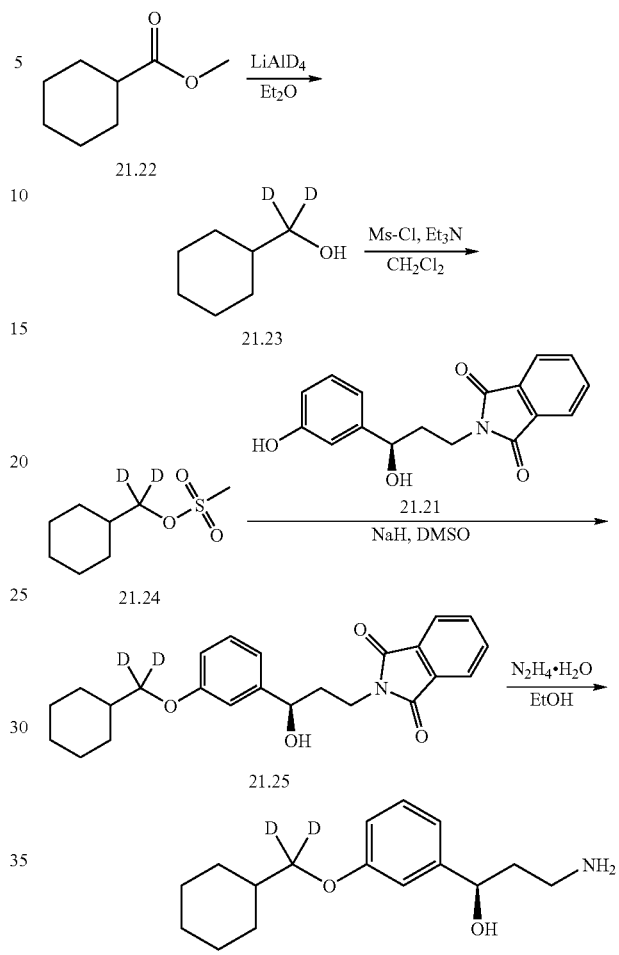

SCHEME 21b

Step 7. A solution of ester 21.22 (9.99 g, 70.3 mmol) was added under inert atmosphere to a cooled (0° C.) suspension of LiAlD$_4$ (2.99 g, 71.2 mmol) in anhydrous Et$_2$O. The reaction mixture was stirred at 0° C. for 3 hrs and then slowly quenched by addition of saturated Na$_2$SO$_4$ until white precipitate formed. The mixture was dried over anhydrous MgSO$_4$, filtered. The filtrate was concentrated under reduced pressure to give alcohol 21.23 as a colorless volatile liquid. Yield (2.52 g, 32%); $^1$H NMR (400 MHz, CDCl$_3$) δ 1.63-1.78 (m, 5H), 1.40-1.50 (m, 1H), 1.10-1.35 (m, 4H), 0.86-0.99 (m, 2H).

Step 8. Mesylation of alcohol 21.23 following the method used in Example 129 gave mesylate 22.24 as a colorless oil. Yield (4.14 g, 97%); $^1$H NMR (400 MHz, CDCl$_3$) δ 2.98 (s, 3H), 1.64-1.80 (m, 6H), 1.10-1.32 (m, 3H), 0.92-1.05 (m, 2H).

Step 9. NaH (60% suspension in mineral oil, 0.98 g, 2.45 mmol) was added to a stirred solution of phenol 21.21 (0.756 g, 2.54 mmol) in anhydrous DMSO. The mixture was stirred at room temperature until all NaH dissolved. Mesylate 21.24 was added to the resulting yellow solution of phenolate and the reaction mixture was stirred at +90° C. under argon for 2 days. The reaction mixture was partitioned between EtOAc and 25% NH$_4$Cl, aqueous layer was extracted with EtOAc. Combined organic layers were washed with brine, dried over anhydrous MgSO$_4$ and concentrated under reduced pressure. Purification by flash chromatography (5% to 50% EtOAc— hexanes gradient) gave ether 21.25 as a colorless oil. Yield (0.25 g, 27%); ¹H NMR (400 MHz, DMSO-d₆) δ 7.81 (m, 4H), 7.15 (t, J=8.0 Hz, 1H), 6.80-6.90 (m, 2H), 6.65-6.73 (m, 1H), 5.25-5.29 (m, 1H), 4.52-4.60 (m, 1H), 3.56-3.73 (m, 2H), 1.84-1.94 (m, 2H), 1.57-1.84 (m, 6H), 1.10-1.30 (m, 3H), 0.96-1.08 (m, 2H).

Step 10. A mixture of phthalimide 21.25 (0.24 g, 0.607 mmol), N₂H₄·H₂O (0.15 mL) in EtOH was stirred at room temperature for 26 hrs. The reaction mixture was concentrated under reduced pressure; the residue was resuspended in CH₂Cl₂, filtered. The filtrate was dissolved in i-PrOAc (20 mL), cooled to 0° C. and HCl/i-PrOH (5.5M, 0.4 mL) was added. The precipitate was collected by filtration to give Example 130 hydrochloride as a white solid. Yield (0.126 g, 69%); ¹H NMR (400 MHz, CD₃OD) δ 7.23 (t, J=7.8 Hz, 1H), 6.88-6.95 (m, 2H), 6.77-6.82 (m, 1H), 4.79 (dd, J=4.5, 7.6 Hz, 1H), 2.97-3.11 (m, 2H), 1.91-2.03 (m, 2H), 1.81-1.90 (m, 2H), 1.66-1.80 (m, 4H), 1.161-1.37 (m, 3H), 1.02-1.14 (m, 2H); RP-HPLC (Method 1) t$_R$=9.96 min, 90.7% (AUC); ESI-MS m/z 266.2 [M+H]⁺.

Example 131

Preparation of 3-amino-1-(3-((perdeuterocyclohexyl)methoxy)phenyl)propan-1-ol

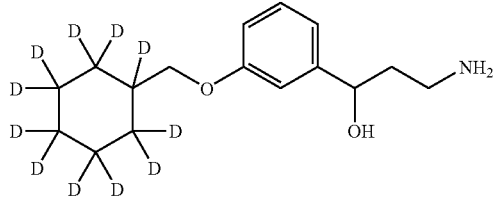 [SMILES: [2H]C1([2H])C([2H])([2H])C([2H])([2H])C([2H])(COc2cccc(C(O)CCN)c2)C([2H])([2H])C1([2H])[2H]]

3-Amino-1-(3-((perdeuterocyclohexyl)methoxy)phenyl)propan-1-ol was prepared following the method used in Example 129.

Step 1. Reaction between perdeuterocyclohexylcarboxylic acid and MeI gave methyl perdeuterocyclohexanecarboxylate as a clear liquid. Yield (2.26 g, quant.); ¹H NMR (400 MHz, DMSO-d₆) δ 3.55 (s).

Step 2. Reduction of methyl perdeuterocyclohexanecarboxylate with DIBAL-H gave (perdeuterocyclohexyl)methanol as a clear oil. Yield (1.86 g, quant.); ¹H NMR (400 MHz, DMSO-d₆) δ 4.26 (t, J=5.2 Hz, 1H), 3.15 (d, J=5.2 Hz, 2H).

Step 3. Mesylation of (perdeuterocyclohexyl)methanol gave (perdeuterocyclohexyl)methyl methanesulfonate as a pale yellow liquid. Yield (3.02 g, quant.); ¹H NMR (400 MHz, DMSO-d₆) δ 3.97 (s, 2H), 3.12 (s, 3H).

Step 4. 3-((Perdeuterocyclohexyl)methoxy)benzaldehyde was prepared following the method used in Example 4. Yield (1.32 g, 40%); ¹H NMR (400 MHz, DMSO-d₆) δ 9.94 (s, 1H), 7.50-7.44 (m, 2H), 7.39-7.38 (m, 1H), 7.23 (dt, J=2.4, 6.8 Hz, 1H), 3.81 (s, 2H).

Step 5. 3-(3-((Perdeuterocyclohexyl)methoxy)phenyl)-3-hydroxypropanenitrile was prepared following the method used in Example 129. Yield (1.47 g, 96%); ¹H NMR (400 MHz, DMSO-d₆) δ 7.21 (t, J=7.8 Hz, 1H), 6.94-6.91 (m, 2H), 6.80 (ddd, J=8.4, 2.4, 0.8 Hz, 1H), 5.88, (d, J=4.4 Hz, 1H), 4.84-4.80 (m, 1H), 3.73 (s, 2H), 2.85 (ABd, J=16.8, 4.8 Hz, 1H), 2.77 (ABd, J=16.4, 5.2 Hz, 1H).

Step 6. Hydroxynitrile reduction following the method used in Example 129 gave, after column chromatography purification (10% MeOH/CH₂Cl₂ followed by 10% 7N NH₃/MeOH/CH₂Cl₂) 3-amino-1-(3-((perdeuterocyclohexyl)methoxy)phenyl)propan-1-ol as a colorless oil. Yield (1.06 g, 71%). The amine was dissolved in Et₂O, cooled on ice bath and HCl/MeOH (1.25M, 3.7 mL, 4.6 mmol) was added. The mixture was stirred for 15 min, the precipitate was collected by filtration to give Example 131 hydrochloride as a white solid. Yield (0.72 g, 61%); m.p. 165-166° C.; ¹H NMR (400 MHz, DMSO-d₆) δ 7.20 (t, J=7.8 Hz, 1H), 6.87-6.84 (m, 2H), 6.76 (m, 1H), 5.88, (d, J=4.4 Hz, 1H), 4.64-4.61 (m, 1H), 3.72 (s, 2H), 2.85-2.74 (m, 2H), 1.91-1.76 (m, 2H); RP-HPLC (Method 2) t$_R$=4.29 min, 99.4% (AUC); ESI-MS m/z 275.3 [M+H]⁺; Elemental analysis: C, 61.7%, H, 8.32%, N, 4.57%, Cl 11.42%.

Example 132

Preparation of 3-amino-1-(3-(cyclohexylmethoxy)-5-deuterophenyl)propan-1-ol

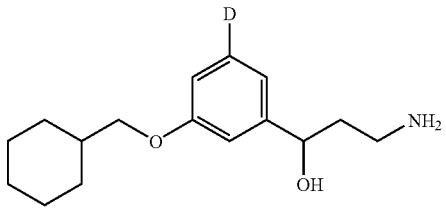 [SMILES: [2H]c1cc(OCC2CCCCC2)cc(C(O)CCN)c1]

3-Amino-1-(3-(cyclohexylmethoxy)-5-deuterophenyl)propan-1-ol was prepared following the method shown in Scheme 23.

SCHEME 23

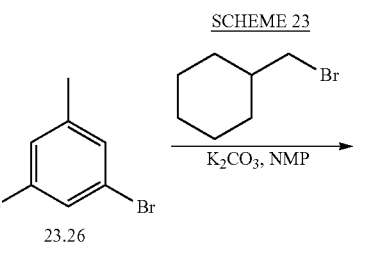

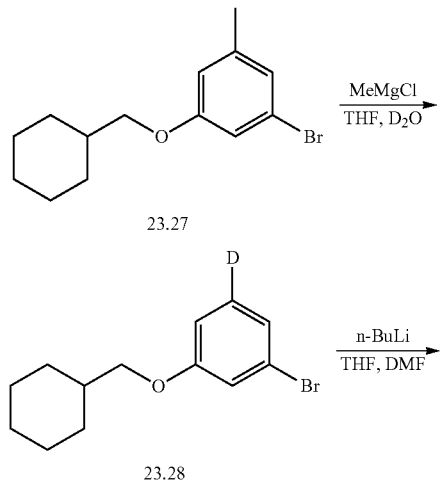

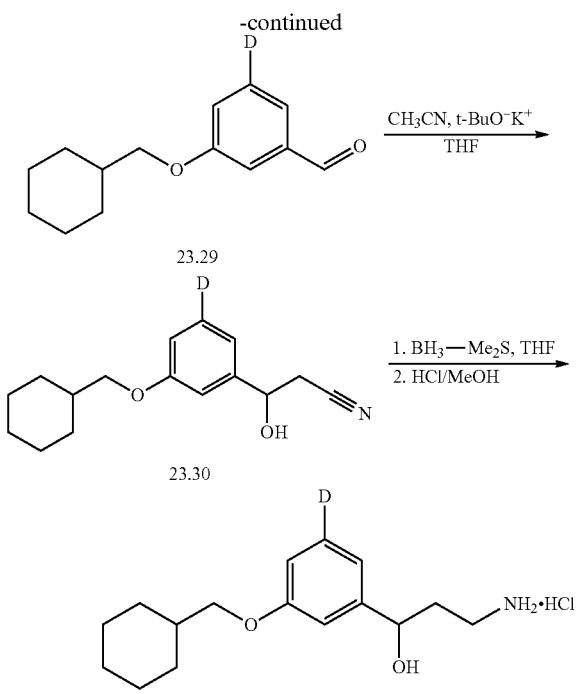

Step 1. Alkylation of 3-bromo-5-iodophenol (23.26) with bromomethylcyclohexane following the method used in Example 126 gave ether 23.27 as a colorless oil. Yield (2.30 g, 87%); $^1$H NMR (400 MHz, CDCl$_3$) δ 7.40 (t, J=1.6 Hz, 1H), 7.16 (dd, J=1.4, 2.2 Hz, 1H), 6.99 (dd, J=1.8, 2.2 Hz, 1H), 3.68 (d, J=6.26 Hz, 2H), 1.66-1.86 (m, 6H), 1.16-1.37 (m, 3H), 0.96-1.10 (m, 2H).

Step 2. To a cold (−25° C.) solution of iodide 23.27 (1.95 g, 4.94 mmol) under argon was added a solution of MeMgCl in THF (3N, 2.0 mL, 6.0 mmol) and the reaction mixture was slowly warmed to 0° C. D$_2$O (0.6 mL) was added to the reaction mixture which was stirred for additional 20 min while warming to room temperature. The mixture was partitioned between aqueous NH$_4$Cl (25%) and THF. Aqueous layer was extracted with EtOAc, combined organic layers were washed with brine, dried over anhydrous MgSO$_4$ and concentrated under reduced pressure to give deuteride 23.28 as a colorless oil. Yield (1.56 g, quant.); $^1$H NMR (400 MHz, CDCl$_3$) δ 7.11 (t, J=8.2 Hz, 1H), 7.02-7.06 9m, 2H), 3.72 (d, J=6.3 Hz, 2H), 1.65-1.88 (m, 6H), 1.12-1.35 (m, 3H), 0.97-1.09 (m, 2H).

Step 3. To a cold (−78° C.) solution of 1-bromo-3-(cyclohexylmethoxy)-5-deuterobenzene (23.28) (1.56 g, 5.77 mmol) under argon in anhydrous THF (10 mL) was added a solution of n-BuLi in hexanes (2.5 M, 3.0 mL, 7.5 mmol) and the reaction mixture was stirred at −78° C. for 20 min. DMF (1.0 mL, 23 mmol) was added, the reaction mixture was allowed to warm to −20° C. and partitioned between aqueous NH$_4$Cl (25%, mL) and EtOAc. Aqueous layer was extracted with EtOAc, combined organic layers were washed with brine, dried over anhydrous MgSO$_4$, and concentrated under reduced pressure. The residue was purified to give 3-(cyclohexylmethoxy)-5-deuterobenzaldehyde (23.29) as a colorless oil. Yield (0.97 g, 77%); $^1$H NMR (400 MHz, CDCl$_3$) δ 10.01 (s, 1H), 7.41-7.44 (m, 1H), 7.37 (dd, J=1.4, 2.7 Hz, 1H), 7.15-7.17 (m, 1H), 3.80 (d, J=6.3 Hz, 2H), 1.66-1.90 (m, 6H), 1.14-1.36 (m, 3H), 1.00-1.11 (m, 2H).

Step 4. Acetonitrile addition to aldehyde 23.29 following the method used in Example 126 gave hydroxypropanenitrile 23.30 as a colorless oil. Yield (1.09 g, 95%); $^1$H NMR (400 MHz, DMSO-d$_6$) δ 6.90-6.96 (m, 2H), 6.77-6.81 (m, 1H), 5.88 (d, J=4.5 Hz, 1H), 4.80-4.85 (m, 1H), 3.74 (d, J=6.3 Hz, 2H), 2.86 (ABd, J=4.9, 16.8 Hz, 1H), 2.77 (ABd, J=6.8, 16.8 Hz, 1H), 1.60-1.82 (m, 6H), 1.10-1.30 (m, 3H), 0.95-1.08 (m, 2H).

Step 5. 3-(3-(Cyclohexylmethoxy)-5-deuterophenyl)-3-hydroxypropanenitrile (23.30) was reduced with borane following the method used in Example 126 except the following. After the reduction was complete as judged by TLC (50% EtOAc—hexanes), MeOH was slowly added to the reaction mixture until a gas formation ceased, followed by HCl/MeOH (1.25 M, 8 mL). The mixture was heated under reflux for 1.5 hrs and concentrated under reduced pressure. The residue was crystallized from i-PrOH/EtOAc (1:2) to give Example 132 hydrochloride as a white solid. Yield (0.96 g, 79%); $^1$H NMR (400 MHz, CD$_3$OD) δ 6.90-6.94 (m, 2H), 6.78-6.81 (m, 1H), 4.79 (dd, J=4.7, 7.4 Hz, 1H), 3.76 (d, J=6.3 Hz, 2H), 2.96-3.11 (m, 2H), 1.90-2.04 (m, 2H), 1.82-1.90 (m, 2H), 1.66-1.81 (m, 4H), 1.16-1.38 (m, 3H), 1.02-1.13 (m, 2H); RP-HPLC (Method 1) t$_R$=10.07 min, 97.8% (AUC); ESI-MS m/z 265.2 [M+H]$^+$.

Example 133

In Vitro Isomerase Inhibition Assay

The capability of compounds described herein to inhibit the activity of a visual cycle isomerase was determined in vitro either in a human or bovine-based assay system. The isomerase inhibition reactions were performed essentially as described (Stecher et al., *J. Biol. Chem.* 274:8577-85 (1999); see also Golczak et al., *Proc. Natl. Acad. Sci. USA* 102:8162-67 (2005), reference 3), either using a human cell line or a bovine retinal pigment epithelium (RPE) microsome membranes as the source of visual enzymes.

Isolation of Human Apo Cellular Retinaldehyde-Binding Protein (CRALBP)

Recombinant human apo cellular retinaldehyde-binding protein (CRALBP) was cloned and expressed according to standard methods in the molecular biology art (see Crabb et al., *Protein Science* 7:746-57 (1998); Crabb et al., *J. Biol. Chem.* 263:18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., *J. Biol. Chem.* 263:18688-92 (1988); Intres, et al., *J. Biol. Chem.* 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6×His-tagged human CRALBP was expressed in One Shot TOP 10 chemically competent *E. coli* cells (Invitrogen), and the recombinant polypeptide was isolated from *E. coli* cell lysates by nickel affinity chromatography using nickel (Ni) Sepharose XK16-20 columns for HPLC (Amersham Bioscience, Pittsburgh, Pa.; catalog no. 17-5268-02). The purified 6×His-tagged human CRALBP was dialyzed against 10 mM bis-tris-Propane (BTP) and analyzed by SDS-PAGE. The molecular weight of the recombinant human CRALBP was approximately 39 kDal.

Human In Vitro Isomerase Inhibition Reaction

Figure 2:
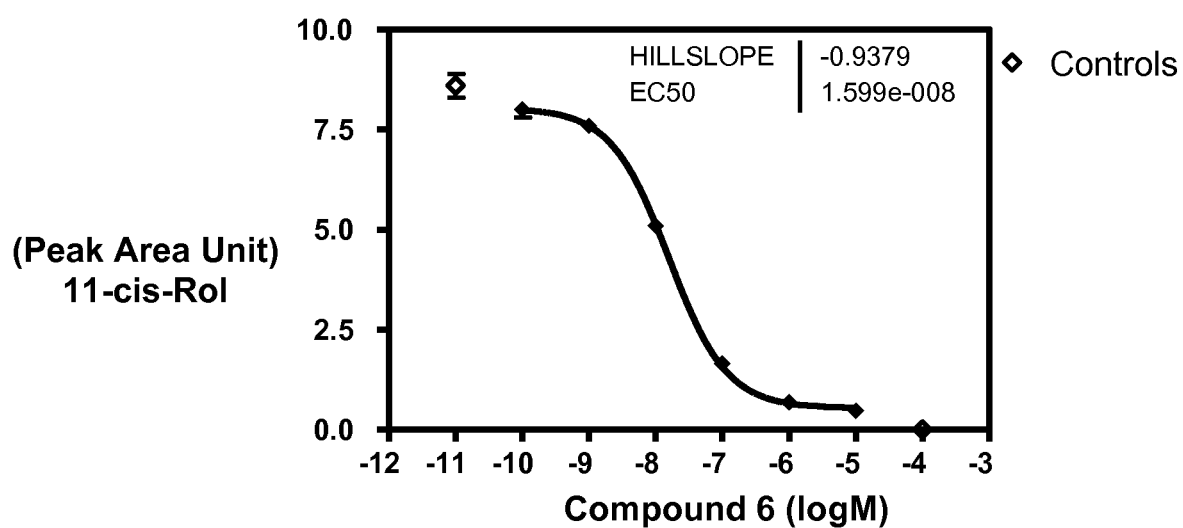
FIG. 2 depicts dose-dependent inhibition of 11-cis-retinol production (as assayed by a human in vitro isomerase assay) by the compound of Example 6 (Compound 6).

The concentration dependent effect of the compounds disclosed herein on the retinol isomerization reaction was evaluated with a recombinant human enzyme system. In particular, the in vitro isomerase assay was performed essentially as in Golczak et al. 2005 (*Proc. Natl. Acad. Sci. USA* 102:8162-67 (2005), reference 3). A homogenate of HEK293 cell clone expressing recombinant human RPE65 and LRAT were the source of the visual enzymes, and exogenous all-trans-retinol (about 20µ4) was used as the substrate. Recombinant human CRALBP (about 80 ug/mL) was added to enhance the formation of 11-cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 µL methanol. The amount of reaction product, 11-cis-retinol, was measured by HPLC analysis following Heptane extraction of the reaction mixture. The Peak Area Units (PAUs) corresponding to 11-cis-retinol in the HPLC chromatograms were recorded and concentration dependent curves analyzed by GraphPad Prism for $IC_{50}$ values. The ability of the compounds disclosed herein to inhibit isomerization reaction was quantified and the respective $IC_{50}$ value was determined. Table 2 summarizes the $IC_{50}$ values of several of the compounds of the present disclosure. FIGS. 1 and 2 depict dose-dependent curves for the inhibition of the accumulation of 11-cis-retinol in the human in vitro assay by the compounds of Example 5 and Example 6 (Compound 5 and Compound 6).

TABLE 2

Human in vitro Inhibition Data

| $IC_{50}$ (nM) | Compound/Example Number |
|---|---|
| >1 to ≤10 nM | 35, 37, 81, 91, 117, 120, 121, 122, 123, 126, 127, 128, 129, 130, 131, 132 |
| >10 to ≤100 nM | 5, 11, 12, 13, 14, 15, 33, 39, 40, 41, 47, 48, 49, 51, 58, 82, 83, 90, 93, 114, 115, 116, 118, 119, 124 |
| >100 to ≤1000 nM | 4, 6, 7, 8, 16, 17, 18, 20, 21, 22, 31, 52, 57, 60 |
| >1000 nM | 1, 2, 3, 9, 10, 64, 99 |

Bovine In Vitro Isomerase Inhibition Reaction

Bovine RPE microsome membrane extracts are prepared according to methods described (Golczak et al., *Proc. Natl. Acad. Sci. USA* 102:8162-67 (2005)) and stored at about −80° C. Crude RPE microsome extracts are thawed in a 37° C. water bath, and then immediately placed on ice. About 50 ml crude RPE microsomes are placed into a 50 ml Teflon-glass homogenizer (Fisher Scientific, catalog no. 0841416M) on ice, powered by a hand-held DeWalt drill, and homogenized about ten times up and down on ice under maximum speed. This process is repeated until the crude RPE microsome solution is homogenized. The homogenate is then subjected to centrifugation (50.2 Ti rotor (Beckman, Fullerton, Calif.), about 13,000 RPM; about 15360 Rcf) for about 15 minutes at 4° C. The supernatant is collected and subjected to centrifugation at about 42,000 RPM (about 160,000 Rcf; 50.2 Ti rotor) for about 1 hour at 4° C. The supernatant is removed, and the pellets are suspended in about 12 ml (final volume) cold 10 mM MOPS buffer, pH 7.0. The resuspended RPE membranes in about 5 ml aliquots are homogenized in a glass-to-glass homogenizer (Fisher Scientific, catalog no. K885500-0021) to high homogeneity. Protein concentration is quantified using the BCA protein assay according to the manufacturer's protocol (Pierce, Rockford, Ill.). The homogenized RPE preparations are stored at −80° C.

Compounds described herein and control compounds are reconstituted in ethanol to about 0.1 M. Ten-fold serial dilutions ($10^{-1}$, $10^{-2}$, $10^{-3}$, $10^{-4}$, $10^{-5}$, $10^{-6}$, $10^{-7}$ M) in ethanol of each compound are prepared for analysis in the isomerase assay.

The isomerase assay is performed in about 10 mM bis-tris-propane (BTP) buffer, pH ~7.5, ~0.5% BSA (diluted in BTP buffer), about 1 mM sodium pyrophosphate, about 20 µM all-trans-retinol (in ethanol), and about 6 µM apo-CRALBP. The test compounds (~2 µl) (final 1/15 dilution of serial dilution stocks) are added to the above reaction mixture to which RPE microsomes are added. The same volume of ethanol is added to the control reaction (absence of test compound). Bovine RPE microsomes (~9 µl) (see above) are then added, and the mixtures transferred to 37° C. to initiate the reaction (total volume=~150 µl). The reactions are stopped after about 30 minutes by adding methanol (about 300 µl). Heptane is added (300 µl) and mixed into the reaction mixture by pipetting. Retinoid is extracted by agitating the reaction mixtures, followed by centrifugation in a microcentrifuge. The upper organic phase is transferred to HPLC vials and then analyzed by HPLC using an Agilent 1100 HPLC system with normal phase column: SILICA (Agilent Technologies, dp 5µ, 4.6 mm×, 25CM; running method has a flow rate of 1.5 ml/min; injection volume about 100 µl). The solvent components are about 20% of about 2% isopropanol in EtOAc and about 80% of 100% hexane.

The area under the $A_{318}$ nm curve represents the 11-cis-retinol peak, which is calculated by Agilent Chemstation software and recorded manually. The $IC_{50}$ values (concentration of compound that gives 50% inhibition of 11-cis-retinol formation in vitro) are calculated using GraphPad Prism® 4 Software (Irvine, Calif.). All tests are performed in at least duplicate and it is expected that the compounds of the present disclosure show concentration dependent effects on the retinol isomerization reaction, as compared to control compounds.

Example 134

In Vivo Murine Isomerase Assay

The capability of compounds described herein to inhibit isomerase was determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo. Delayed recovery, as represented by lower 11-cis-retinal oxime levels, indicates inhibition of isomerization reaction. Procedures were performed essentially as described by Golczak et al., *Proc. Natl. Acad. Sci. USA* 102:8162-67 (2005). See also Deigner et al., *Science*, 244: 968-71 (1989); Gollapalli et al., *Biochim Biophys Acta.* 1651: 93-101 (2003); Parish, et al., *Proc. Natl. Acad. Sci. USA,* 14609-13 (1998); Radu, et al., *Proc Natl Acad Sci USA* 101: 5928-33 (2004).

About six-week old dark-adapted CD-1 (albino) male mice were orally gavaged with compound (0.01-25 mg/kg) dissolved in an appropriate amount of oil (about 100 µl corn oil containing 10% ethanol, at least five animals per group). Mice were gavaged with the compounds described in the present disclosure. After about 2-24 hours in the dark, the mice were exposed to photobleaching of about 5,000 lux of white light for 10 minutes. The mice were allowed to recover for about 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and red filtered flashlights for spot illumination as needed) (see, e.g., Maeda et al., *J. Neurochem* 85:944-956, 2003; Van Hooser et al., *J Biol Chem* 277:19173-82, 2002). After the mice were sacrificed, the eyes were immediately removed and placed in liquid nitrogen for storage.

The eyes were placed in about 500 µL of bis-tris propane buffer (10 mM, pH ~7.3) and about 20 µL of 0.8M hydroxylamine (pH ~7.3). The eyes were cut up into small pieces with small iris scissors and then thoroughly homogenized at 30000 rpm with a mechanical homogenizer (Polytron PT 1300 D) in the tube until no visible tissue remains. About 500 µL of methanol and about 500 µL of heptane was added to each tube. The tubes were attached to a vortexer so that the contents are mixed thoroughly for about 15 minutes in room temperature. The organic phase was separated from the aqueous phase by centrifugation for about 10 min at 13K rpm, 4° C. 240 µL of the solution from the top layer (organic phase) was removed and transferred to clean 300 µl glass inserts in HPLC vials using glass pipette and the vials were crimped shut tightly.

The samples were analyzed on an Agilent 1100 HPLC system with normal phase column: SILICA (Beckman Coutlier, dp 5 µm, 4.6 mM×250 mM). The running method has a flow rate of 1.5 ml/min; solvent components are 15% solvent 1 (1% isopropanol in ethyl acetate), and 85% solvent 2 (100% hexanes). Loading volume for each sample was about 100 µl; detection wavelength is 360 nm. The area under the curve for 11-cis-retinal oxime was calculated by Agilent Chemstation software and recorded manually. Data processing was performed using Prizm software.

Positive control mice (no compound administered) were sacrificed fully dark-adapted and the eye retinoids analyzed. Light (bleached) control mice (no compound administered) were sacrificed and retinoids isolated and analyzed immediately after light treatment.

A time course study was also performed to determine the isomerase inhibitory activity of compounds of the present disclosure. Female or male mice (such as Balb/c mice) (at least 4/group) received 0 to about 5 mg of compounds (in water) per kg bodyweight orally, by gavage. The animals were then "photo-bleached" (about 5000 Lux white light for about 10 minutes) at about 2, 4, 8, 16 and 24 hours after dosing, and returned to darkness to allow recovery of the 11-cis-retinal content of the eyes. Mice were sacrificed about 2 hours after bleaching, eyes were enucleated, and retinoid content was analyzed by HPLC.

A dose response in vivo isomerase inhibition study is performed with compounds of the present disclosure. Male or female mice (such as Balb/c mice) (at least about 8/group) are dosed orally with about 0.01 to 25 mg/kg of the compounds of HCl salts of the compounds in sterile water as solution, and photobleached about 4 hours after dosing. Recovery and retinoid analysis is performed as described above. Dark control mice are vehicle-only treated, sacrificed fully dark adapted without light treatment, and analyzed. The concentration-dependent inhibition of isomerase activity at about 4 hours post dosing of the compounds, inhibition of 11-cis-retinal (oxime) recovery for and estimates of $ED_{50}$s (dose of compound that gives 50% inhibition of 11-cis-retinal (oxime) recovery) are calculated. Table 3 provides the in vivo inhibition data.

TABLE 3

In vivo Inhibition Data

| Example Number | % Inibition 1 mg/kg, 24 h | % Inibition 1 mg/kg, 4 h |
|---|---|---|
| 5 | Not tested | −11.7 ± 4.36 |
| 6 | 48.70 ± 2.71 | −11.93 ± 18.17 |
| 15 | Not tested | −0.003 ± 19.4 |
| 11 | Not tested | 95.27 ± 2.7 |
| 13 | Not tested | 1.979 ± 6.016 |
| 131 | Not tested | 97.9 ± 11.8 |
| 126 | Not tested | 91.75 ± 2.7 |
| 128 | Not tested | 98.0 ± 0.99 |
| 121 | Not tested | 27.5 ± 9.6 |
| 129 | Not tested | 97.23 ± 1.5 |
| 130 | Not tested | 100.9 ± 0.955 |
| 132 | Not tested | 100.8 ± 1.2 |
| 117 | Not tested | 97.9 ± 1.5 |
| 123 | Not tested | 91.4 ± 2.5 |
| 122 | Not tested | 84.9 ± 4.5 |
| 35 | Not tested | 95.25 ± 1.41 |
| 33 | Not tested | 4.32 ± 7.88 |
| 40 | Not tested | 1.24 ± 9.74 |
| 39 | Not tested | 69.94 ± 6.85 |
| 57 | Not tested | 2.01 ± 1.3 |
| 31 | Not tested | 9.52 ± 4.6 |
| 47 | Not tested | 4.08 ± 4.84 |
| 58 | Not tested | 6.94 ± 5.15 |
| 16 | Not tested | 17.08 ± 5.32 |
| 14 | Not tested | 8.12 ± 16.18 |
| 12 | Not tested | 9.16 ± 9.41 |
| 93 | Not tested | −0.53 ± 4.53 |
| 83 | Not tested | 89.46 ± 2.09 |
| 81 | Not tested | 84.98 ± 3.06 |
| 90 | Not tested | 3.17 ± 4.97 |
| 91 | Not tested | 95.49 ± 1.07 |
| 82 | Not tested | 75.08 ± 8.03 |
| 60 | Not tested | −1.33 ± 5.20 |
| 48 | Not tested | 0.21 ± 8.88 |
| 41 | Not tested | −0.34 ± 6.12 |
| 99 | Not tested | −3.83 ± 5.52 |
| 37 | Not tested | 101.56 ± 0.49 |
| 64 | Not tested | 3.83 ± 3.83 |
| 49 | Not tested | 4.54 ± 6.31 |
| 73 | Not tested | −1.24 ± 4.43 |
| 59 | Not tested | 4.24 ± 12.99 |
| 36 | Not tested | −1.4 ± 2.78 |
| 103 | Not tested | −2.77 ± 6.53 |
| 101 | Not tested | 1.82 ± 10.54 |

A single dose study of any compound is also performed at various dosages, a various time points post dosing. The experiments can be carried out in CD1 male mice, by way of example. Results are analyzed by HPLC. It is expected that the compounds of the present disclosure will exhibit different profiles of activity at different times and dosages, with different compounds also exhibiting different recovery patterns.

Example 135

Preparation of Retinal Neuronal Cell Culture System

This example describes methods for preparing a long-term culture of retinal neuronal cells. All compounds and reagents can be obtained from Sigma Aldrich Chemical Corporation (St. Louis, Mo.) or other suitable vendors.

Retinal Neuronal Cell Culture

Porcine eyes are obtained from Kapowsin Meats, Inc. (Graham, Wash.). Eyes are enucleated, and muscle and tissue are cleaned away from the orbit. Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing about 25 µg/ml of insulin, about 100 µg/ml of transferrin, about 60 µM putrescine, about 30 nM selenium, about 20 nM progesterone, about 100 U/ml of penicillin, about 100 µg/ml of streptomycin, about 0.05 M Hepes, and about 10% FBS. Dissociated primary retinal cells are plated onto Poly-D-lysine- and Matrigel- (BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis

The retinal neuronal cells are cultured for about 1, 3, 6, and 8 weeks, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted about 1:500; Chemicon, Temecula, Calif.). An antibody to midweight neurofilament (NFM rabbit polyclonal, diluted about 1:10,000, Chemicon) is used to identify ganglion cells; an antibody to β3-tubulin (G7121 mouse monoclonal, diluted about 1:1000, Promega, Madison, Wis.) is used to generally identify interneurons and ganglion cells, and antibodies to calbindin (AB1778 rabbit polyclonal, diluted about 1:250, Chemicon) and calretinin (AB5054 rabbit polyclonal, diluted about 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for about 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4′,6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Survival of mature retinal neurons after varying times in culture is indicated by the histochemical analyses. Photoreceptor cells are identified using a rhodopsin antibody; ganglion cells are identified using an NFM antibody; and amacrine and horizontal cells are identified by staining with an antibody specific for calretinin.

Cultures are analyzed by counting rhodopsin-labeled photoreceptors and NFM-labeled ganglion cells using an Olympus IX81 or CZX41 microscope (Olympus, Tokyo, Japan). Twenty fields of view are counted per coverslip with a 20× objective lens. Six coverslips are analyzed by this method for each condition in each experiment. Cells that are not exposed to any stressor are counted, and cells exposed to a stressor are normalized to the number of cells in the control. It is expected that compounds presented in this disclosure promote dose-dependent and time-dependent survival of mature retinal neurons.

Example 136

Effect of Compounds on Retinal Cell Survival

This Example describes the use of the mature retinal cell culture system that comprises a cell stressor for determining the effects of a compound on the viability of the retinal cells.

Retinal cell cultures are prepared as described in Example 135. A2E is added as a retinal cell stressor. After culturing the cells for 1 week, a chemical stress, A2E, is applied. A2E is diluted in ethanol and added to the retinal cell cultures at concentration of about 0, 10 µM, 20 µM, and 40 µM. Cultures are treated for about 24 and 48 hours. A2E is obtained from Dr. Koji Nakanishi (Columbia University, New York City, N.Y.) or is synthesized according to the method of Parish et al. (*Proc. Natl. Acad. Sci. USA* 95:14602-13 (1998)). A compound described herein is then added to the culture. To other retinal cell cultures, a compound described herein is added before application of the stressor or is added at the same time that A2E is added to the retinal cell culture. The cultures are maintained in tissue culture incubators for the duration of the stress at 37° C. and 5% $CO_2$. The cells are then analyzed by immunocytochemistry as described in Example 135

Apoptosis Analysis

Retinal cell cultures are prepared as described in Example 135 and cultured for about 2 weeks and then exposed to white light stress at about 6000 lux for about 24 hours followed by about a 13-hour rest period. A device was built to uniformly deliver light of specified wavelengths to specified wells of the 24-well plates. The device contains a fluorescent cool white bulb (GE P/N FC12T9/CW) wired to an AC power supply. The bulb is mounted inside a standard tissue culture incubator. White light stress is applied by placing plates of cells directly underneath the fluorescent bulb. The $CO_2$ levels are maintained at about 5%, and the temperature at the cell plate is maintained at 37° C. The temperature is monitored by using thin thermocouples. The light intensities for all devices is measured and adjusted using a light meter from Extech Instruments Corporation (P/N 401025; Waltham, Mass.). A compound described herein is added to wells of the culture plates prior to exposure of the cells to white light and is added to other wells of the cultures after exposure to white light. To assess apoptosis, TUNEL is performed as described herein.

Apoptosis analysis is also performed after exposing retinal cells to blue light. Retinal cell cultures are cultured as described in Example 135. After culturing the cells for about 1 week, a blue light stress is applied. Blue light is delivered by a custom-built light-source, which consists of two arrays of 24 (4×6) blue light-emitting diodes (Sunbrite LED P/N SSP-01TWB7UWB12), designed such that each LED is registered to a single well of a 24 well disposable plate. The first array is placed on top of a 24 well plate full of cells, while the second one is placed underneath the plate of cells, allowing both arrays to provide a light stress to the plate of cells simultaneously. The entire apparatus is placed inside a standard tissue culture incubator. The $CO_2$ levels are maintained at about 5%, and the temperature at the cell plate is maintained at about 37° C. The temperature is monitored with thin thermocouples. Current to each LED is controlled individually by a separate potentiometer, allowing a uniform light output for all LEDs. Cell plates are exposed to about 2000 lux of blue light stress for about either 2 hours or 48 hours, followed by about a 14-hour rest period. A compound described herein is added to wells of the culture plates prior to exposure of the cells to blue light and is added to other wells of the cultures after exposure to blue light. To assess apoptosis, TUNEL is performed as described herein.

To assess apoptosis, TUNEL is performed according to standard techniques practiced in the art and according to the manufacturer's instructions. Briefly, the retinal cell cultures are first fixed with 4% paraformaldehyde and then ethanol, and then rinsed in DPBS. The fixed cells are incubated with TdT enzyme (0.2 units/μfinal concentration) in reaction buffer (Fermentas, Hanover, Md.) combined with Chroma-Tide Alexa568-5-dUTP (0.1 μM final concentration) (Molecular Probes) for about 1 hour at 37° C. Cultures are rinsed with DPBS and incubated with primary antibody either overnight at 4° C. or for about 1 hour at 37° C. The cells are then rinsed with DPBS, incubated with Alexa 488-conjugated secondary antibodies, and rinsed with DPBS. Nuclei are stained with DAPI, and the cultures are rinsed with DPBS before removing the glass coverslips and mounting them with Fluoromount-G on glass slides for viewing and analysis.

Cultures are analyzed by counting TUNEL-labeled nuclei using an Olympus IX81 or CZX41 microscope (Olympus, Tokyo, Japan). Twenty fields of view are counted per coverslip with a 20× objective lens. Six coverslips are analyzed by this method for each condition. Cells that are not exposed to a compound described herein are counted, and cells exposed to the antibody are normalized to the number of cells in the control. Data are analyzed using the unpaired Student's t-test. It is expected that compounds described herein reduce A2E-induced apoptosis and cell death in retinal cell cultures in a dose-dependent and time-dependent manner.

The cells are assessed for cell death using Sytox green nucleic acid stain assay (Sytox, Molecular Probes, Eugene, Oreg.). Sytox is a DNA-binding dye that penetrates only dying cells in which the plasma membrane is compromised. The green nucleic acid stain assay is added at 1 μM to 96-well plates and incubated for 30 minutes at 37° C. Fluorescence is determined using a plate reader with excitation fluorescence at 485 nm and emission fluorescence at 528 nm.

Example 137

In Vivo Light Mouse Model

This Example describes the effect of a compound in an in vivo light damage mouse model.

Exposure of the eye to intense white light can cause photodamage to the retina. The extent of damage after light treatment can be evaluated by measuring cytoplasmic histone-associated-DNA-fragment (mono- and oligonucleosomes) content in the eye (see, e.g., Wenzel et al., *Prog. Retin. Eye Res.* 24:275-306 (2005)).

Dark adapted mice (for example, male Balb/c (albino, 10/group)) are gavaged with the compounds of the present disclosure at various doses (about 0.01-25 mg/kg) or vehicle only is administered. About six hours after dosing, the animals are subjected to light treatment (8,000 lux of white light for 1 hour). Mice are sacrificed after about 40 hours of recovery in dark, and retinas are dissected. A cell death detection ELISA assay is performed according to the manufacturer's instructions (ROCHE APPLIED SCIENCE, Cell Death Detection ELISA plus Kit). Contents of fragmented DNA in the retinas are measured to estimate the retinal-protective activity of the compounds. It is expected that compounds of the present disclosure mitigate or inhibit photo-damage to the retina.

Example 138

Electroretinographic (ERG) Study

This example describes determining the effect of a compound that is a visual cycle modulator on the magnitude of the ERG response in the eyes of mice after oral dosing of the animals with the compound. The level of ERG response in the eyes is determined after administering the compound to the animals (for example at 18 and 66 hours post administration).

Three groups of about nine-week old mice (19-25 grams), both genders (strain C5 7BL/6, Charles River Laboratories, Wilmington, Mass.) are housed at room temperature, 72±4° F., and relative humidity of approximately 25%. Animals are housed in a 12-hour light/dark cycle environment, have free access to feed and drinking water and are checked for general health and well-being prior to use and during the study. Body weights are determined for a representative sample of mice prior to initiation of dosing. The average weight determined from this sampling is used to establish the dose for all mice in the study.

Each test compound is dissolved in the control solvent (EtOH), and diluted 1:10 (90 ml/900 ml) in the appropriate oil (for example corn oil (Crisco Pure Corn Oil, J. M. Smucker Company, Orrville, Ohio)) to the desired dose (mg/kg) in the desired volume (about 0.1 mL/animal). The control vehicle is ethanol: oil (about 1:10 (0.9 ml/9 ml)). An example of treatment designations and animal assignments are described in Table 4.

TABLE 4

| Group | Route | Treatment | Dose (mg/kg) | Animals |
| --- | --- | --- | --- | --- |
| Test | oral | test compound | (~0.01-~25 mg/kg) | >4 |
| Control | oral | Vehicle | None | >4 |

Animals are dosed once orally by gavage, with the assigned vehicle control or test compounds during the light cycle (between about 30 min and about 3 hours 30 min after the beginning of the light cycle). The volume of the administered dose usually does not exceed about 10 mL/kg.

ERG recordings are made on dark-adapted and, subsequently (during the course of the same experiment), on light-adapted states. For the dark-adapted response, animals are housed in a dark-adapted environment for at least about 1 hour prior to the recording, commencing at least about 30 minutes after the start of the light cycle.

At about eighteen and about sixty six hours after dosing, the mice are anesthetized with a mixture of Ketamine and Xylazine (100 mg/kg and 20 mg/kg, respectively) and placed on a heating pad to maintain stable core body temperature during the course of the experiment. Pupils are dilated by placing a 5 microliter drop of mydriatic solution (tropicamide 0.5%) in the recorded eye. A mouse corneal monopolar contact lens electrode (Mayo Corporation, Inazawa, Aichi, Japan) is placed on the cornea, and a subcutaneous reference low profile needle 12 mm electrode (Grass Telefactor, W Warwick, R.I.) is placed medial from the eye. A ground needle electrode is placed in the tail. Data collection is obtained using an Espion $E^2$ (Diagnosys LLC, Littleton, Mass.) ERG recording system with Color Dome Ganzfeld stimulator. Full dark-adapted intensity-response function is determined following a brief white flash stimuli of about 14 intensities ranging from about 0.0001 cd.s/m² to about 333 cd.s/m². Subsequently, full light-adapted intensity-response function is determined following a brief white flash stimuli of about 9 intensities ranging from about 0.33 cd.s/m² to about 333 cd.s/m². Analysis of the obtained responses is done off-line. Intensity-response function determination is done by fitting a sigmoid function to the data (Naka K I, Rushton Wash., 1966; Naka K I, Rushton Wash., 1967). It is expected that compounds of the present disclosure will depress or suppress the dark-adapted ERG responses (measured at about 0.01 cd.s/m²) while minimally affecting the photopic, light-adapted $V_{max}$ values when compared to control compounds.

Example 139

Effect of a Compound on Recovery of Rod B-Wave Response after Light Bleach

ERG studies with a test compound that is a visual cycle modulator will examine the recovery of scotopic, rod-dominated b-wave response (measured 0 to 30 minutes with white flash stimuli at about 0.01 cd.s/m²) in Balb/c mice after photo-bleach (60 cd.s/m², 45 seconds) as a biomarker for suppression of rod activity. The recovery curve at different times after single oral dosing with 0.3 mg/kg compound is compared to vehicle. The slope of the scotopic rod ERG b-wave recovery curve (0-30 minutes) is calculated by linear regression and normalized to the vehicle group. The effect on rod ERG recovery varies with time after dosing, the greatest effect is expected to be observed at 8 hours, and returning to near vehicle control levels at 24 hours. The effects on ERG recovery of a range of compound doses (0.03, 0.1, 0.3 and 1 mg/kg, by oral gavage) are also studied at the 8 hour interval. The effect of the compound on rod ERG is calculated by linear regression as above and is expected to be dose dependent.

Example 140

Effect of a Compound on Reduction of Lipofuscin Fluorophores

This example describes testing the capability of a test compound to reduce the level of existing bis-retinoid, N-retinylidene-N-retinylethanolamine (A2E) and lipofuscin fluorophores in the retina of mice as well as prevention of the formation of A2E and lipofuscin fluorophores. A2E is the major fluorophore of toxic lipofuscin in ocular tissues.

The eyes of abca-4-null (abca-4−/−) mutant mice (see, e.g., Weng et al., Cell 98:13-23 (1999) have an increased accumulation of lipofuscin fluorophores, such as A2E (see, e.g., Karan et al., *Proc. Natl. Acad. Sci. USA* 102:4164-69 (2005)). Compounds (about 1 mg/kg) or vehicle are administered daily for about three months by oral gavage to abca4$^{-/-}$ mice that are about 2 months old. Mice are sacrificed after about three months of treatment. Retinas and RPE are extracted for A2E analysis.

A similar experiment is performed with aged balb/c mice (at least about 10 months old). The test mice are treated with about 1 mg/kg/day of compounds for about three months and the control mice are treated with vehicle.

Briefly, under dim red light, each pair of eye balls are harvested, homogenized in a mixture of PBS buffer and methanol and the A2E extracted into chloroform. The samples are dried down and reconstituted in a water/acetonitrile mix for HPLC analysis. The amount of A2E present is determined by comparison of the area under the curve (AUC) of the A2E peak in the sample with an A2E concentration/AUC curve for an A2E reference standard measuring at 440 nm.

It is expected that A2E levels are reduced upon treatment with one or more compounds disclosed herein.

Example 141

Effect of a Compound on Retinoid Nuclear Receptor Activity

Retinoid nuclear receptor activity is associated with transduction of the non-visual physiologic, pharmacologic, and toxicologic retinoid signals that affect tissue and organ growth, development, differentiation, and homeostasis.

The effect of one or more compounds disclosed herein and the effect of a retinoic acid receptor (RAR) agonist (E-4-[2-(5,6,7,8-tetrahydro-5,5,8,8-tetramethyl-2-naphthylenyl)-1-propenyl]benzoic acid) (TTNPB), and of all-trans-retinoic acid (at-RA), which is an RAR and retinoid X receptor (RXR) agonist, are studied on RAR and RXR receptors essentially as described by Achkar et al. (*Proc. Natl. Acad. Sci. USA* 93:4879-84 (1996)). It is expected that the compounds of the present disclosure do not show significant effects on retinoid nuclear receptors (RAR and RXR). By contrast, TTNPB and at-RA activated the $RXR_\alpha$, $RAR_\alpha$, $RAR_\beta$ and RAR receptors as expected (Table 5).

TABLE 5

| Compound | RARα EC$_{50}$ (nM) | RARβ EC$_{50}$ (nM) | RARγ EC$_{50}$ (nM) | RXRα EC$_{50}$ (nM) |
|---|---|---|---|---|
| TTNPB | 5.5 +/− 4.5 | 0.3 +/− 0.1 | 0.065 +/− 0.005 | N/A |
| at-RA | N/A | N/A | N/A | 316 +/− 57 |

N/A = Not applicable

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. A compound of Formula (V) or tautomer, stereoisomer, geometric isomer or a pharmaceutically acceptable salt, or N-oxide thereof:

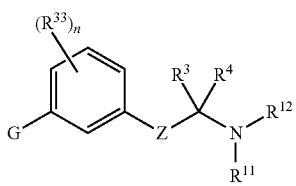

Formula (V)

wherein,
Z is —C($R^9$)($R^{10}$)—C($R^1$)($R^2$)—;
G is selected from —N($R^{42}$)C(=O)—$R^{40}$, or —N($R^{42}$)—C($R^{42}$)($R^{42}$)—$R^{40}$;
$R^{40}$ is selected from —C($R^{16}$)($R^{17}$)($R^{18}$);
each $R^{42}$ is independently selected from hydrogen, or alkyl;
$R^1$ and $R^2$ are each independently selected from hydrogen, halogen, $C_1$-$C_5$ alkyl, fluoroalkyl, —$OR^6$; or $R^1$ and $R^2$ together form an oxo;
$R^3$ and $R^4$ are each hydrogen;
$R^9$ and $R^{10}$ are each independently selected from hydrogen, halogen, alkyl, fluoroalkyl, or —$OR^{19}$; or $R^9$ and $R^{10}$ form an oxo; or optionally, $R^9$ and $R^1$ together form a direct bond to provide a double bond; or optionally, $R^9$ and $R^1$ together form a direct bond, and $R^{10}$ and $R^2$ together form a direct bond to provide a triple bond;
$R^{11}$ and $R^{12}$ are each independently selected from hydrogen, $CH_3$, —C(=O)$R^{23}$, or $CO_2R^{23}$;
$R^{23}$ is alkyl;
$R^6$ and $R^{19}$ are each independently hydrogen or alkyl;
$R^{16}$ and $R^{17}$, together with the carbon to which they are attached form a carbocyclyl;
$R^{18}$ is selected from hydrogen, alkyl, alkoxy, hydroxy, halo or fluoroalkyl;
each $R^{33}$ is independently selected from halogen, hydroxyl, alkoxy, alkyl, or fluoroalkyl; and n is 0, 1, 2, 3, or 4.

2. The compound of claim 1 wherein,
$R^9$ and $R^{10}$ are each independently selected from hydrogen, halogen, alkyl, fluoroalkyl, —$OR^{19}$; or $R^9$ and $R^{10}$ form an oxo.

3. The compound of claim 1 wherein,
$R^{11}$ and $R^{12}$ are each independently selected from hydrogen, $CH_3$, or —C(=O)$R^{23}$.

4. The compound of claim 3 wherein,
$R^9$ and $R^{10}$ are each independently selected from hydrogen, halogen, —OH; or $R^9$ and $R^{10}$ together form an oxo.

5. The compound of claim 3 wherein,
G is selected from —N($R^{42}$)C(=O)—$R^{40}$; and $R^{11}$ and $R^{12}$ are each hydrogen.

6. The compound of claim 3 wherein,
G is selected from —N($R^{42}$)—C($R^{42}$)($R^{42}$)—$R^{40}$; and $R^{11}$ and $R^{12}$ are each hydrogen.

7. The compound of claim 4 wherein,
G is selected from —N($R^{42}$)C(=O)—$R^{40}$; and $R^{11}$ and $R^{12}$ are each hydrogen.

8. The compound of claim 4 wherein,
G is selected from —N($R^{42}$)—C($R^{42}$)($R^{42}$)—$R^{40}$; and $R^{11}$ and $R^{12}$ are each hydrogen.

9. The compound of claim 3 wherein,
$R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

10. The compound of claim 9 wherein,
$R^{16}$ and $R^{17}$, together with the carbon to which they are attached, form a cyclopentyl, cyclohexyl, or cycloheptyl; and
n is 0, 1, or 2.

11. The compound of claim 4 wherein, $R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

12. The compound of claim 5 wherein,
$R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

13. The compound claim 6 wherein,
$R^{16}$ and $R^{17}$ together with the carbon to which they are attached, form a cyclopropyl, cyclobutyl, cyclopentyl, cyclohexyl, cycloheptyl, or cyclooctyl; and
n is 0, 1, or 2.

14. The compound of claim 7 wherein,
$R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

15. The compound of claim 8 wherein,
$R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

16. The compound of claim 4 wherein,
G is selected from —N($R^{42}$)C(=O)—$R^{40}$; and $R^{11}$ is hydrogen and $R^{12}$ is C(=O)$R^{23}$.

17. The compound of claim 4 wherein,
G is selected from —N($R^{42}$)—C($R^{42}$)($R^{42}$)—$R^{40}$; and $R^{11}$ is hydrogen and $R^{12}$ is C(=O)$R^{23}$.

18. The compound of claim 16 wherein,
$R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

19. The compound of claim 17 wherein,
$R^{16}$ and $R^{17}$, together with the carbon to which they are attached, form a cyclopropyl, cyclobutyl, cyclopentyl, cyclohexyl, cycloheptyl, or cyclooctyl; and
n is 0, 1, or 2.

20. The compound of claim 1 selected from the group consisting of:

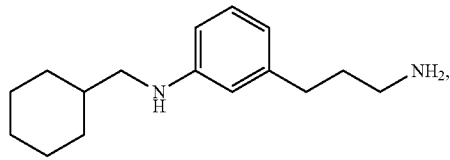

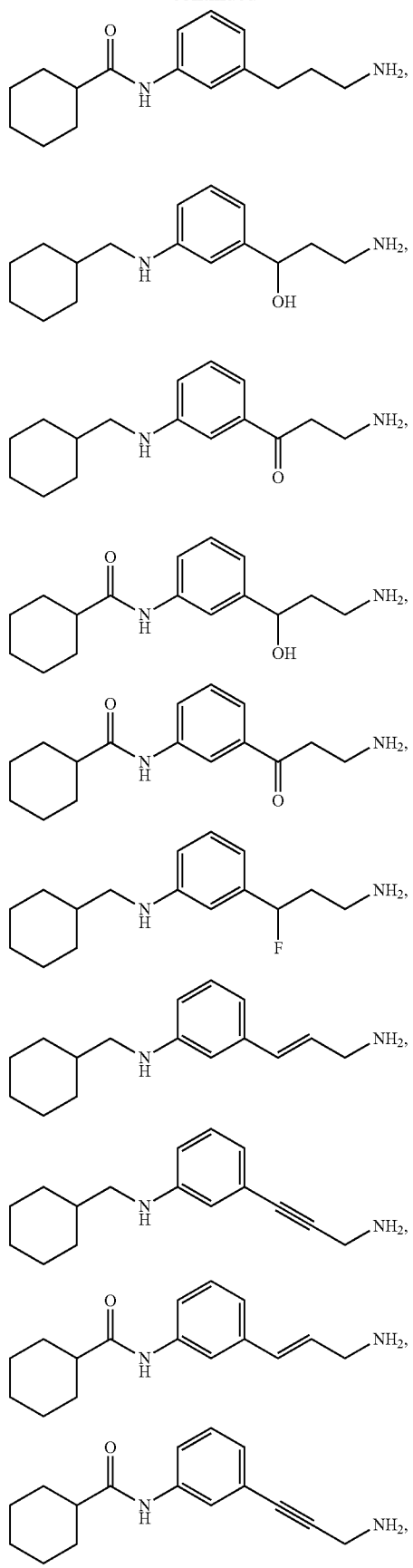
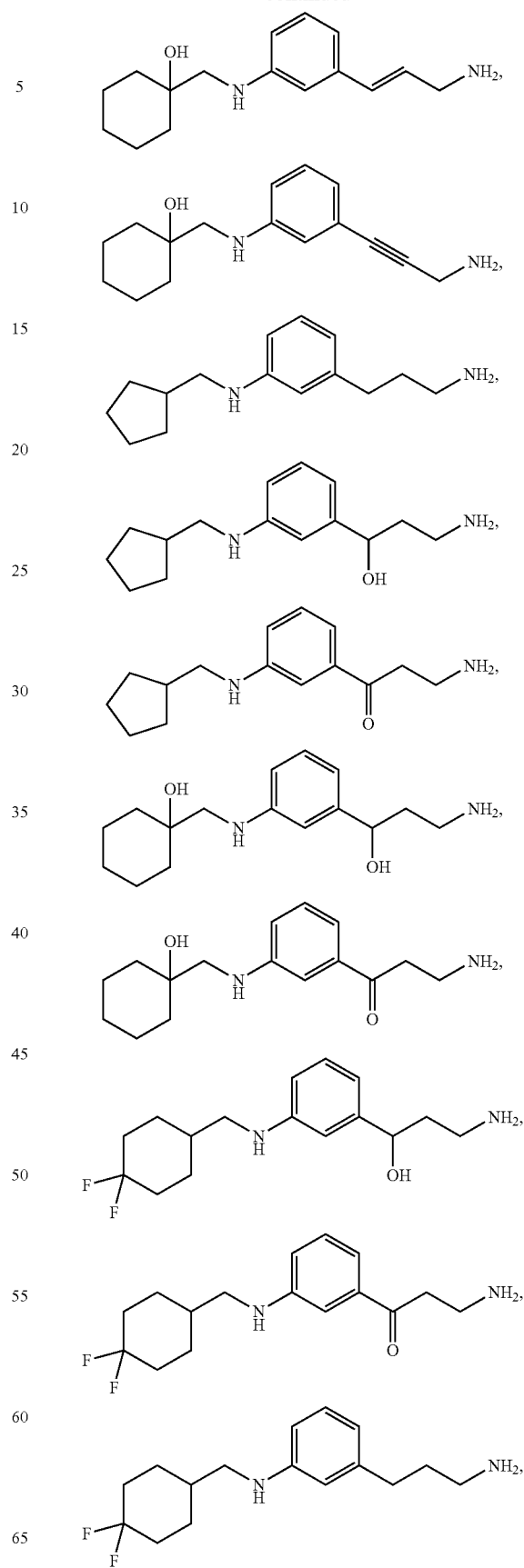

21. A compound selected from:
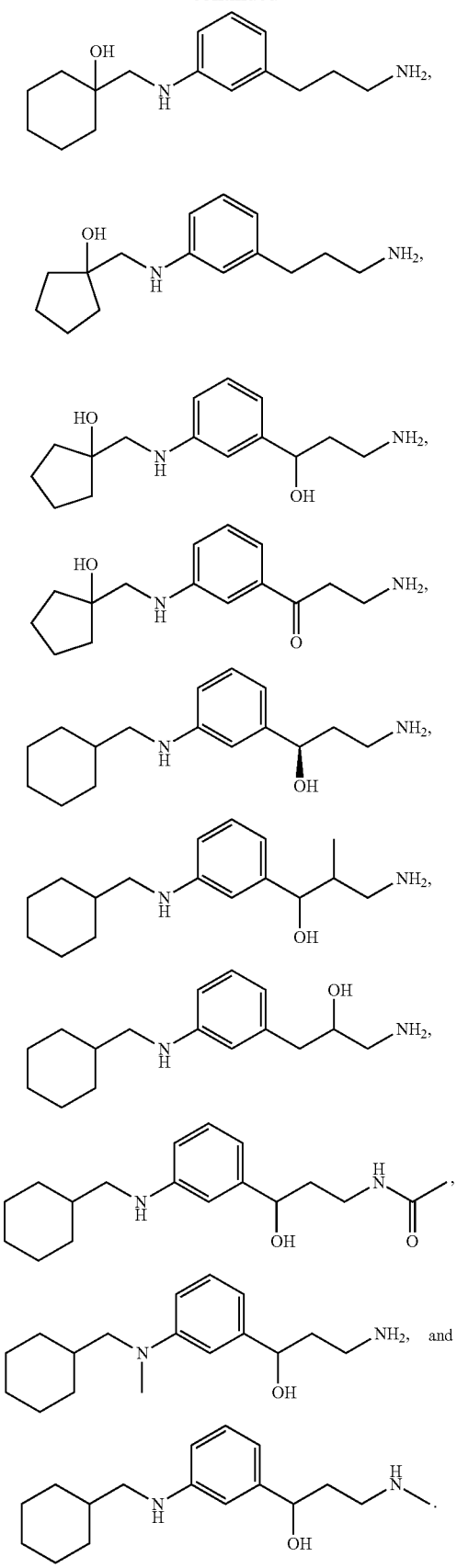

-continued

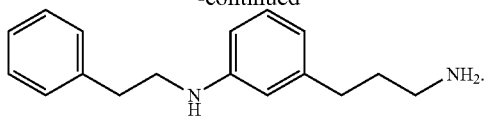

22. A pharmaceutical composition comprising a pharmaceutically acceptable carrier and a compound of Formula (V) of claim 1 or tautomer, stereoisomer, geometric isomer, or pharmaceutically acceptable salt, or N-oxide thereof.

23. A pharmaceutical composition comprising a pharmaceutically acceptable carrier and a compound as provided in claim 21 or tautomer, stereoisomer, geometric isomer, or pharmaceutically acceptable salt, or N-oxide thereof.

* * * * *